US010160798B2

(12) United States Patent
Hotamisligil et al.

(10) Patent No.: US 10,160,798 B2
(45) Date of Patent: Dec. 25, 2018

(54) ANTI-AP2 ANTIBODIES AND ANTIGEN BINDING AGENTS TO TREAT METABOLIC DISORDERS

(71) Applicants: President and Fellows of Harvard College, Cambridge, MA (US); UCB Biopharma SPRL, Brussels (BE)

(72) Inventors: Gökhan S. Hotamisligil, Wellesley, MA (US); Mehmet F. Burak, Watertown, MA (US); Feyza Engin, Madison, WI (US); Scott B. Widenmaier, Brighton, MA (US); Elisabeth Helen Roberts, Slough (GB); Adrian Richard Moore, Slough (GB); Carl Brendan Doyle, Slough (GB); Ralph Adams, Slough (GB); Karine Jeannine Madeleine Hervé, Vancouver (CA); Shauna Mhairi Wales, Slough (GB); Kerry Louise Tyson, Slough (GB)

(73) Assignees: President and Fellows of Harvard College, Cambridge, MA (US); UCB Biopharma SPRL, Brussels (BE)

( * ) Notice: Subject to any disclaimer, the term of this patent is extended or adjusted under 35 U.S.C. 154(b) by 0 days.

(21) Appl. No.: 15/143,162

(22) Filed: Apr. 29, 2016

(65) Prior Publication Data
US 2016/0319003 A1 Nov. 3, 2016

Related U.S. Application Data

(60) Provisional application No. 62/268,257, filed on Dec. 16, 2015, provisional application No. 62/232,148, filed on Sep. 24, 2015, provisional application No. 62/155,217, filed on Apr. 30, 2015.

(51) Int. Cl.
*C07K 16/18* (2006.01)
*A61K 39/00* (2006.01)

(52) U.S. Cl.
CPC .............. *C07K 16/18* (2013.01); *A61K 39/00* (2013.01); *A61K 2039/505* (2013.01); *A61K 2039/507* (2013.01); *A61K 2039/6018* (2013.01); *C07K 2317/24* (2013.01); *C07K 2317/55* (2013.01); *C07K 2317/565* (2013.01); *C07K 2317/70* (2013.01); *C07K 2317/76* (2013.01); *C07K 2317/92* (2013.01)

(58) Field of Classification Search
CPC ................... C07K 16/18; C07K 16/26; C07K 16/00–16/468
See application file for complete search history.

(56) References Cited

U.S. PATENT DOCUMENTS

| 5,858,366 | A | 1/1999 | Sodroski et al. |
| 6,548,529 | B1 | 4/2003 | Robl et al. |
| 7,390,824 | B1 | 6/2008 | Robl et al. |
| 7,906,117 | B2* | 3/2011 | Smith ................. C07K 16/248 424/133.1 |
| 8,846,413 | B2 | 9/2014 | Ruzicka |
| 9,062,104 | B2* | 6/2015 | Garcia-Martinez .... C07K 16/22 |
| 2002/0035064 | A1 | 3/2002 | Robl et al. |
| 2003/0040516 | A1 | 2/2003 | Sulsky et al. |
| 2004/0010119 | A1 | 1/2004 | Guo et al. |
| 2009/0022659 | A1* | 1/2009 | Olson ................. A61K 47/4843 424/1.49 |
| 2012/0134998 | A1 | 5/2012 | Hotamisligil et al. |
| 2015/0093769 | A1 | 4/2015 | Ruzicka |
| 2016/0297874 | A1 | 10/2016 | Hotamisligil et al. |

FOREIGN PATENT DOCUMENTS

| CN | 103665139 A | 3/2014 |
| WO | 00/15230 A1 | 3/2000 |
| WO | WO 2000/15229 A1 | 3/2000 |
| WO | 00/47734 A1 | 8/2000 |
| WO | 03/043624 A1 | 5/2003 |
| WO | 2010/102171 A2 | 9/2010 |

OTHER PUBLICATIONS

Almagro & Fransson, Frontiers in Bioscience 2008; 13:1619-33.*
De Genst et al., Dev Comp Immunol 2006; 30:187-98.*
PCT/US2016/030303, Invitation to pay additional fees and, where applicable, protest fee, mailed Sep. 12, 2016.
Banaszak et al. "Lipid-binding proteins: a family of fatty acid and retinoid transport proteins" Adv. Protein Chem., 1994; 45: 89-151.
Boord et al. "Adipocyte Fatty Acid-Binding Protein, aP2, Alters Late Atherosclerotic Lesion Formation in Severe Hypercholesterolemia" Arterioscler. Thromb. Vasc. Biol., Oct. 2002; 22(10): 1686-1691.
Cabre et al. "Fatty acid binding protein 4 is increased in metabolic syndrome and with thiazolidinedione treatment in diabetic patients" Atherosclerosis, 2007; 195: e150-e158.

(Continued)

*Primary Examiner* — Jessica H Roark
(74) *Attorney, Agent, or Firm* — Knowles Intellectual Property Strategies, LLC

(57) ABSTRACT

This invention is in the area of improved anti-aP2 antibodies and antigen binding agents, and compositions thereof, which target the lipid chaperone aP2/FABP4 (referred to as "aP2") for use in treating disorders such as diabetes, obesity, cardiovascular disease, fatty liver disease, and/or cancer, among others. In one aspect, improved treatments for aP2 mediated disorders are disclosed in which serum aP2 is targeted and the biological activity of aP2 is neutralized or modulated using low-binding affinity aP2 monoclonal antibodies, providing lower fasting blood glucose levels, improved systemic glucose metabolism, increased systemic insulin sensitivity, reduced fat mass, reduced liver steatosis, reduced cardiovascular disease and/or a reduced risk of developing cardiovascular disease.

48 Claims, 71 Drawing Sheets
Specification includes a Sequence Listing.

(56) References Cited

OTHER PUBLICATIONS

Cai et al. "Benzbromarone, an old uricosuric drug, inhibits human fatty acid binding protein 4 in vitro and lowers the blood glucose level in db/db mice" Acta Pharmacologica Sinica, 2013; 34: 1397-1402.
Cao et al. "Regulation of Metabolic Responses by Adipocyte/Macrophage Fatty Acid-Binding Proteins in Leptin-Deficient Mice" Diabetes, Jul. 2006; 55: 1915-1922.
DeFronzo "Insulin resistance, lipotoxicity, type 2 diabetes and atherosclerosis: the missing links. The Claude Brenard Lecture 2009" Diabetologia, 2010; 53: 1270-1287.
Distel et al. "Fatty Acid Regulation of Gene Expression: Transcriptional and Post-Transcriptional Mechanisms" The Journal of Biological Chemistry, Mar. 25, 1992; 267(9): 5937-5941.
Erbay et al. "Reducing endoplasmic reticulum stress through a macrophage lipid chaperone alleviates atherosclerosis" Nature Medicine, Dec. 2009; 15(12): 1383-1391.
Ertunc et al. "Secretion of fatty acid binding protein aP2 from adipocytes through a nonclassical pathway in response to adipocyte lipase activity" Journal of Lipid Research, 2015; 56: 423-434.
Fu et al. "Oxidized LDL induces the expression of ALBP/aP2 mRNA and protein in human THP-1 macrophages" Journal of Lipid Research, 2000; 41: 2017-2023.
Furuhashi et al. "Serum Fatty Acid-Binding Protein 4 Is a Predictor of Cardiovascular Events in End-Stage Renal Disease" PLOS One, Nov. 2011; 6(11): e27356.
Hall et al. "USP7 Attenuates Hepatic Gluconeogenesis Through Modulation of FoxO1 Gene Promoter Occupancy" Mol. Endocrinol., Jun. 2014; 28(6): 912-924.
Hertzel et al. "The Mammalian Fatty Acid-binding Protein Multigene Family: Molecular and Genetic Insights into Function" Trends in Endocrinology & Metabolism, 2000; 11(5): 175-180.
Hoo et al. "Pharmacological inhibition of adipocyte fatty acid binding protein alleviates both acute liver injury and non-alcoholic steatohepatitis in mice" Journal of Hepatology, 2013; 58: 358-364.
Hotamisligil et al. "Uncoupling of Obesity from Insulin Resistance Through a Targeted Mutation in aP2, the Adipocyte Fatty Acid Binding Protein" Science, Nov. 22, 1996; 274(5291): 1377-1379.
Hunt et al. "Adipocyte P2 gene: Developmental expression and homology of 5'-flanking sequences among fat cell-specific genes" PNAS, Jun. 1986; 83: 3786-3790.
Ishimura et al. "Circulating Levels of Fatty Acid-Binding Protein Family and Metabolic Phenotype in the General Population" PLOS One, Nov. 2013; 8(11): e81318.
Jack et al. "C-terminal binding protein: A metabolic sensor implicated in regulating adipogenesis" The International Journal of Biochemistry & Cell Biology, 2011; 43: 693-696.
Kaess et al. "Cardiometabolic Correlates and Heritability of Fetuin-A, Retinol-Binding Protein 4, and Fatty-Acid Binding Protein 4 in the Framingham Heart Study" J. Clin. Endocrinol. Metab., Oct. 2012; 97(10): e1943-e1947.
Kajimura et al. "Regulation of the brown and white fat gene programs through a PRDM16/CtBP transcriptional complex" Genes & Development, 2008; 22: 1397-1409.
Karakas et al. "Serum fatty acid binding protein 4, free fatty acids, and metabolic risk markers" Metabolism Clinical and Experimental, 2009; 58: 1002-1007.
Kashima et al. "Diagnostic utility of aP2/FABP4 expression in soft tissue tumours" Virchows Archiv., Apr. 2013; 462(4): 465-472.
Layne et al. "Role of macrophage-expressed adipocyte fatty acid binding protein in the development of accelerated atherosclerosis in hypercholesterolemic mice" The FASEB Journal, Dec. 2001; 15: 2733-2735.
Lin et al. "Hormonal Regulation of Hepatic Glucose Production in Health and Disease" Cell Metabolism, Jul. 6, 2011; 14: 9-19.
Makowski et al. "The Fatty Acid-binding Protein, aP2, Coordinates Macrophage Cholesterol Trafficking and Inflammatory Activity" The Journal of Biological Chemistry, Apr. 1, 2005; 280(13): 12888-12895.

Melki et al. "Expression of the adipocyte fatty acid-binding protein streptozotocin-diabetes: effects of insulin deficiency and supplementation" Journal of Lipid Research, 1993; 34: 1527-1534.
Miao et al. "The mAb against adipocyte fatty acid-binding protein 2E4 attenuates the inflammation in the mouse model of high-fat diet-induced obesity via toll-like receptor 4 pathway" Molecular and Cellular Endocrinology, 2015; 403: 1-9.
Nardini et al. "CtBP/BARS: a dual-function protein involved in transcription co-repression and Golgi membrane fission" The EMBO Journal, 2003; 22(12): 3122-3130.
Ozcan et al. "Chemical Chaperones Reduce ER Stress and Restore Glucose Homeostasis in a Mouse Model of Type 2 Diabetes" Science, Aug. 25, 2006; 313(5790): 1137-1140.
Saksi et al. "Low-Expression Variant of Fatty Acid-Binding Protein 4 Favors Reduced Manifestations of Atherosclerotic Disease and Increased Plaque Stability" Circ. Cardiovasc. Genet., 2014; 7: 588-598.
Suh et al. "Serum AFBP levels are elevated in patients with nonalcoholic fatty liver disease" Scandinavian Journal of Gastroenterology, 2014; 49(8): 979-985.
Tuncman et al. "A genetic variant at the fatty acid-binding protein aP2 locus reduces the risk for hypertriglyceridemia, type 2 diabetes, and cardiovascular disease" PNAS, May 2, 2006; 103(18): 6970-6975.
Uysal et al. "Improved Glucose and Lipid Metabolism in Genetically Obese Mice Lacking aP2" Endocrinology, 2000; 141: 3388-3396.
Vemochet et al. "C/EBPalpha and the Corepressors CtBP1 and CtBP2 Regulate Repression of Select Visceral White Adipose Genes during Induction of the Brown Phenotype in White Adipocytes by Peroxisome Proliferator-Activated Receptor gamma Agonists" Molecular and Cellular Biology, Sep. 2009; 29(17): 4714-4728.
von Eynatten et al. "Circulating Adipocyte Fatty Acid-Binding Protein Levels and Cardiovascular Morbidity and Mortality in Patients With Coronary Heart Disease—A 10-year Prospective Study" Arterioscler. Thromb. Vasc. Biol., Sep. 2012; 32: 2327-2335.
Won et al. "Oligopeptide complex for targeted non-viral gene delivery to adipocytes" Nature Materials, Dec. 2014; 13: 1157-1164.
Yoo et al. "Serum Adipocyte Fatty Acid-Binding Protein Is Associated Independently with Vascular Inflammation: Analysis with 18F-Fluorodeoxyglucose Positron Emission Tomography" J. Clin. Endocrinol. Metab., Mar. 2011; 96(3): E488-E492.
Barf et al. "N-Benzyl-indolo carboxylic acids: Design and synthesis of potent and selective adipocyte fatty-acid binding protein (A-FABP) inhibitors" Bioorganic and Medicinal Chemistry Letters, Mar. 15, 2009; 19(6): 1745-1748.
Baxa et al. "Human adipocyte lipid-binding protein: purification of the protein and cloning of its complementary DNA" Biochemistry, 1989; 28: 8683-8690.
Cao et al. "Identification of a Lipokine, a Lipid Hormone Linking Adipose Tissue to Systemic Metabolism" Cell, Sep. 19, 2008; 134:933-944.
Cao et al. "Adipocyte lipid chaperone aP2 is a secreted adipokine regulating hepatic glucose production" Cell Metabolism, May 2013; 17(5); 768-778.
Cayman Chemical FABP4 Polyclonal Antibody product sheet (5 pages) downloaded on Sep. 30, 2015.
Furuhashi et al. "Treatment of diabetes and atherosclerosis by inhibiting fatty-acid-binding protein aP2" Nature, 2007; 447(21): 959-965.
Furuhashi et al. "Adipocyte/Macrophage Fatty Acid-Binding Proteins Contribute to Metabolic Deterioration Through Actions in Both Macrophages and Adipocytes in Mice" J. Clin. Invest., Jul. 2008; 118(7):2640-2650.
Gillilan et al. "Structural Basis for Activation of Fatty Acid-binding Protein 4" J. Mol. Biol., 2007; 372:1246-1260.
Girona et al. "FABP4 Induces Vascular Smooth Muscle Cell Proliferation and Migration through a MAPK—Dependent Pathway" PLoS One, Nov. 2013; 8(11): e81914.
Gorbenko et al. "Generation and Characterization of Monoclonal Antibodies against FABP4" Hybridoma, 2006; 25(2):86-90.

(56) References Cited

OTHER PUBLICATIONS

Hecker et al. "Heat shock proteins as biomarkers for the rapid detection of brain and spinal cord ischemia: a review and comparison to other methods of detection in thoracic aneurysm repair" Cell Stress and Chaperones, 2011; 16: 119-131.

Hellberg et al. "X-ray crystallographic analysis of adipocyte fatty acid binding protein (aP2) modified with 4-hydroxy-2-nonenal" Protein Science, 2010; 19: 1480-1489.

Hertzel et al. "Identification and characterization of a small molecule inhibitor of Fatty Acid binding proteins" Journal of Medicinal Chemistry, Oct. 8, 2009; 52(19): 6024-6031.

Hunter-Lavin et al. "Hsp70 release from peripheral blood mononuclear cells" Biochemical and Biophysical Research Communications, Nov. 12, 2004; 324(2): 511-517.

LaLonde et al. "X-ray Crystallographic Structures of Adipocyte Lipid-Binding Protein Complexed with Palmitate and Hexadecanesulfonic Acid. Properties of Cavity Binding Sites" Biochemistry, 1994; 33: 4885-4895.

Lan et al. "Small-molecule inhibitors of FABP4/5 ameliorate dyslipidemia but not insulin resistance in mice with diet-induced obesity" Journal of Lipid Research, Apr. 2011; 52(4): 646-656.

Lehmann et al. "Discovery of inhibitors of human adipocyte fatty acid-binding protein, a potential type 2 diabetes target" Bioorganic and Medicinal Chemistry Letters, Sep. 6, 2004; 14(17):4445-4448.

Maeda et al. "Adipocyte/Macrophage Fatty-Acid Bonding Proteins Control Integrated Metabolic Responses in Obesity and Diabetes" Cell Metab., Feb. 2005; 1:107-119.

Makowski et al. "Lack of Macrophage Fatty-Acid-Binding Protein aP2 Protects Mice Deficient in Apolipoprotein E Aqainst Atherosclerosis" Nat. Med., Jun. 2001; 7(6):699-705.

Ringom et al. "Substituted benzylamino-6-(trufluoromethyl)pyramidin-4(1 H)-ones: a novel class of selective human A-FABP inhibitors" Bioorganic and Medicinal Chemistry Letters, 2004; 14: 4449-4452.

Rosen et al. "Adipocytes as Regulators of Energy Balance and Glucose Homeostasis" Nature, Dec. 14, 2006; 444:847-853.

Storch et al. "Structural and functional analysis of fatty acid-binding proteins" Journal of Lipid Research, 2009; 50: S126-S131.

Sulsky et al. "Potent and selective biphenyl azole inhibitors of adipocyte fatty acid binding protein (aFABP)" Bioorganic and Medicinal Chemistry Letters, Jun. 15, 2007; 17(12): 3511-3515.

van Dongen et al. "Structure-based screening as applied to human FABP4: a highly efficient alternative to HTS for hit generation" Journal of the American Chemical Society, Oct. 9, 2002; 124(40): 11874-11880.

Xu et al. "The adipocyte lipid-binding protein at 1.6-A resolution. Crystal structures of the apoprotein and with bound saturated and unsaturated fatty acids" Journal of Biological Chemistry, 1993; 268: 7874-7884.

Xu et al. "Adipocyte Fatty Acid-Binding Protein Is a Plasma Biomarker Closely Associated with Obesity and Metabolic Syndrome" Clinical Chemistry, 2006; 52(3): 405-413.

Xu et al. "Circulating Adipocyte—Fatty Acid Binding Protein Levels Predict the Development of the Metabolic Syndrome—A 5-Year Prospective Study" Circulation, 2007, 115:1537-1543.

Zhang et al. "Exosomes" a novel pathway of local and distant intercellular communication that facilitates the growth and metastasis of neoplastic lesions "American Journal of Pathology, Jan. 2014; 184(1)" 28-41.

Burak, M.F., et al, "Development of a therapeutic monoclonal antibody targeting secreted aP2 to treat type 2 diabetes;" PDB:5D8J deposited on Aug. 17, 2015 and released on Jan. 13, 2016, available at: //www.resb.org/pdb/explore/explore.do?structureId=5D8J.

Burak, M.F., et al., "Chain L, Development of a Therapeutic Monoclonal Antibody Targeting Secreted Ap2 to Treat Type 2 Diabetes." PDB:5D8J_L deposited on Aug. 17, 2015 and released on Aug. 2, 2017, available at: //www.ncbi.nlm.nih.gov/protein/5D8J_L.

Burak, M.F., et al., "Chain D, Development of a Monoclonal Antibody Targeting Secreted Ap2 to Treat Diabetes and Fatty Liver Disease," PDB:5C0N_D deposited on Jun. 12, 2015 and released on Jan. 13, 2016, available at: //www.ncbi.nlm.nih.gov/protein/5C0N_D.

Burak, M.F., et al., "Development of a monoclonal antibody targeting secreted aP2 to treat diabetes and fatty liver disease," PDB:5CON deposited on Jun. 12, 2015 and released on Jun. 24, 2015, available at: //www.resb.org/pdb/explore/explore.do?structureId=5CON.

PK Office Action dated Sep. 26, 2017, for Pakistan application No. 246/2016.

* cited by examiner

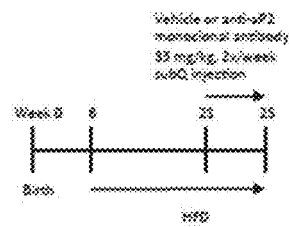
FIG. 1A
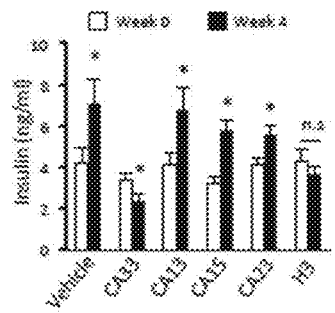
FIG. 1B
FIG. 1C
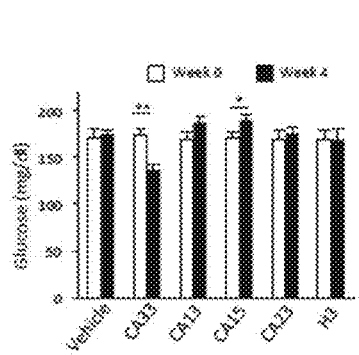
FIG. 1D
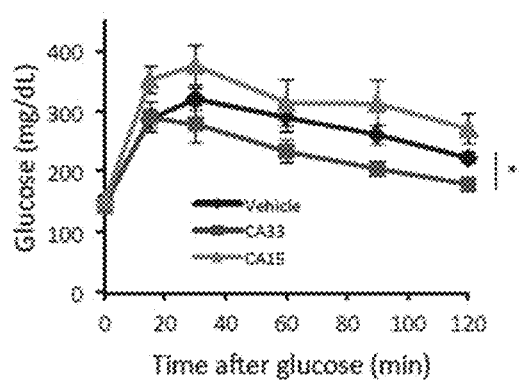
FIG. 1E
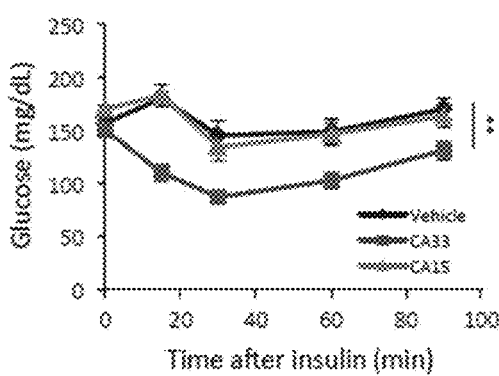
FIG. 1F
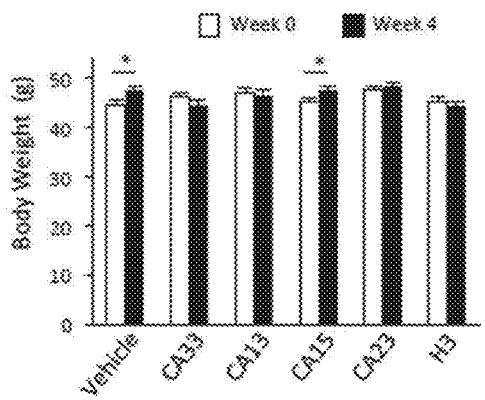
FIG. 1G

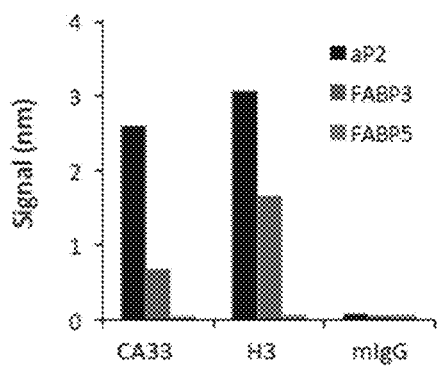
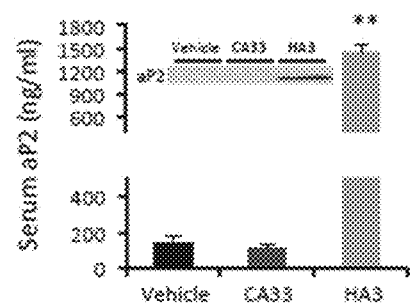
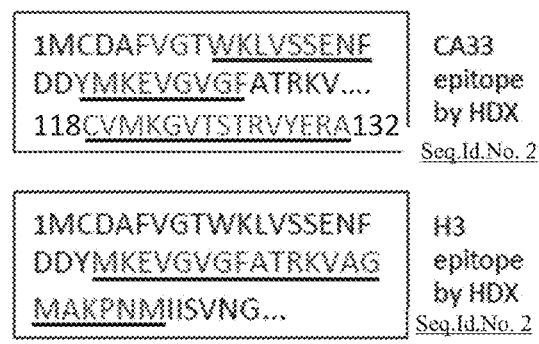
FIG. 2A
FIG. 2B
FIG. 2C
FIG. 2D

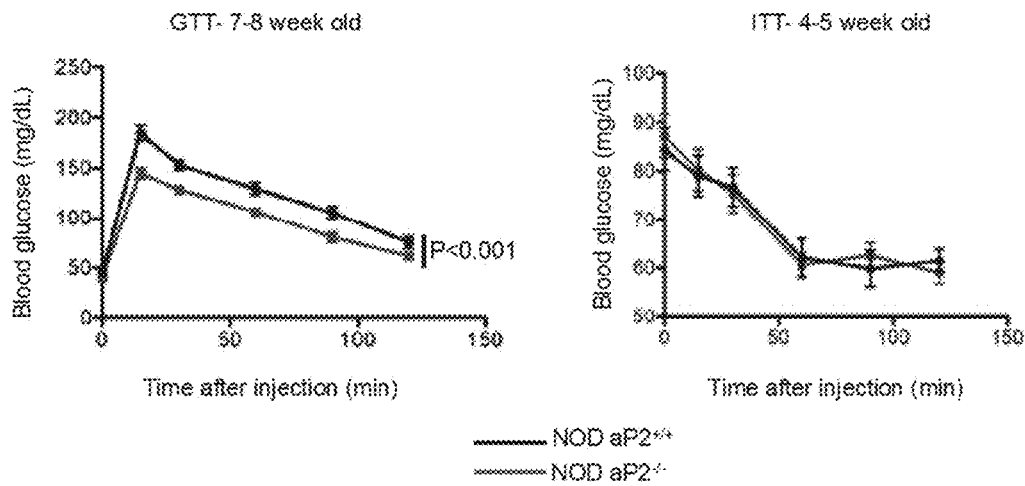
FIG.11A   FIG.11B
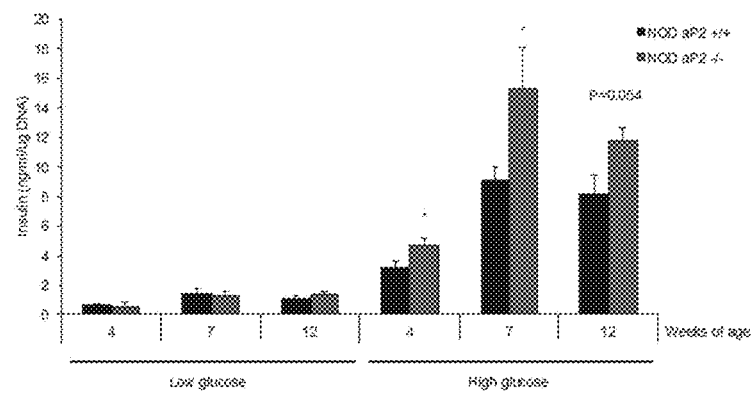
FIG. 12A
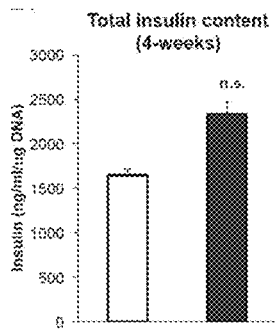 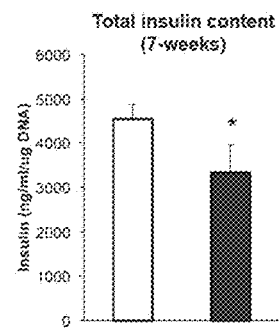
FIG. 12B   FIG. 12C

| Age (wks) | 5 | 6 | 7 | 8 | 9 | 10 | 11 | 12 | 13 | 14 | 15 | 16 | 17 | 18 |
|---|---|---|---|---|---|---|---|---|---|---|---|---|---|---|
| | | | | | | Average Body Weight (g) | | | | | | | | |
| PBS | 19.8 | 22.0 | 24.7 | 25.6 | 27.8 | 29.0 | 29.6 | 30.7 | 30.8 | 32.0 | 32.8 | 33.5 | 33.6 | 33.7 |
| CA33 | 20.0 | 22.0 | 23.3 | 24.2 | 26.2 | 27.6 | 28.4 | 29.1 | 28.9 | 29.8 | 30.4 | 30.7 | 30.9 | 31.3 |
| CA15 | 20.1 | 22.1 | 24.3 | 25.3 | 27.1 | 28.3 | 29.3 | 30.3 | 29.9 | 31.1 | 31.8 | 32.7 | 32.7 | 33.0 |
| antibody dose (ug) | 660 | 728 | 795 | 826 | 892 | 934 | 960 | 991 | 986 | 1022 | 1045 | 1066 | 1070 | 1078 |
| Concentration | | | | | 5 mg/ml | | | | | | | 10 mg/ml | | |
| inj volume (ul) | 132 | 146 | 159 | 165 | 178 | 187 | 192 | 198 | 197 | 102 | 104 | 107 | 107 | 108 |

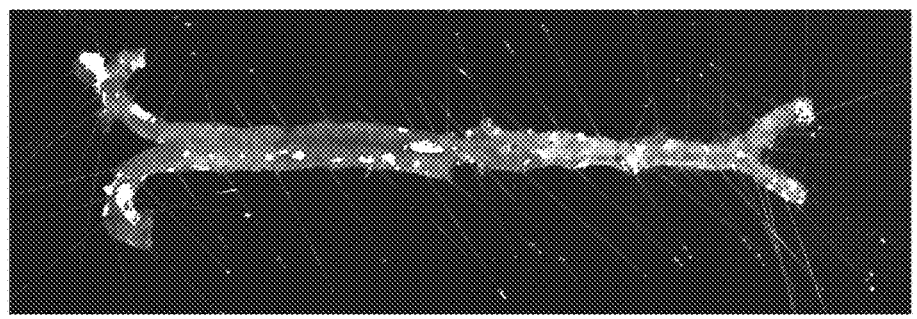
FIG. 22E CA15
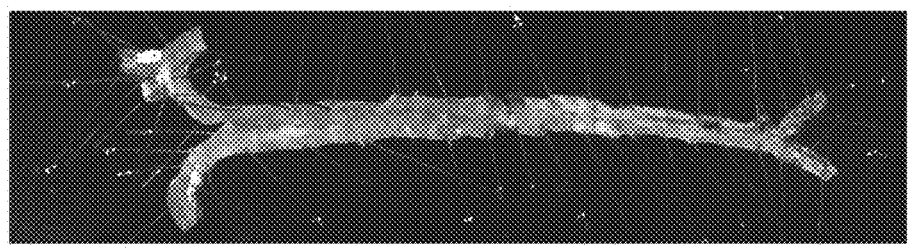
FIG. 22D CA33
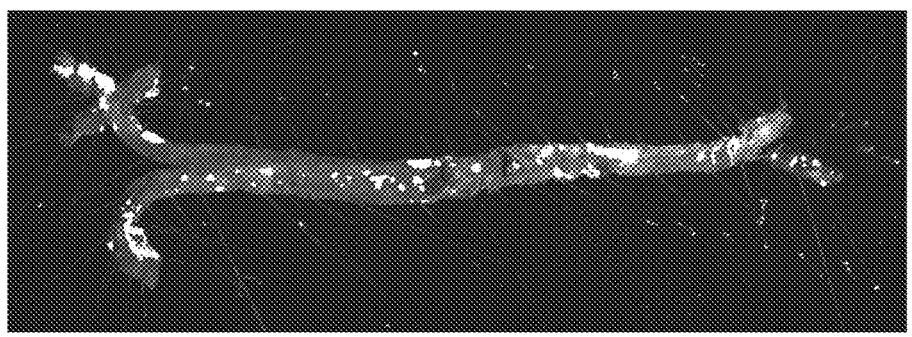
FIG. 22C PBS adipose tissue

|  | Light chain | Heavy chain | Affinity |
|---|---|---|---|
| CA33 |  |  | 6.5 µM |
| APP5168 | PPP4048 | g11 = W91A | g19 = W33A, Y52S | 6.03 µM |
| APP5169 | PPP4049 | g1 = parent | g20 = W33A, Y52S, Y98F | 5.82 µM |

| Anti-aP2 BSN | Human Binding Resp at 40uM | KD (M) | KD (μM) | Mouse Binding Resp at 40uM | KD (M) | KD (μM) |
|---|---|---|---|---|---|---|
| 5251.mIgG1.168 (PB1172) | 30.6 | 5.62E-06 | 5.62 | 31.4 | 4.14E-06 | 4.14 |
|  | 28.7 | 6.44E-06 | 6.44 | 32.7 | 4.99E-06 | 4.99 |
| Average |  |  | 6.03 |  |  | 4.57 |
| 5252.mIgG1.169 (PB1171) | 33.4 | 6.13E-06 | 6.13 | 36.5 | 5.53E-06 | 5.53 |
|  | 30.5 | 5.51E-06 | 5.51 | 35.5 | 4.71E-06 | 4.71 |
| Average |  |  | 5.82 |  |  | 5.12 |

FIG. 31

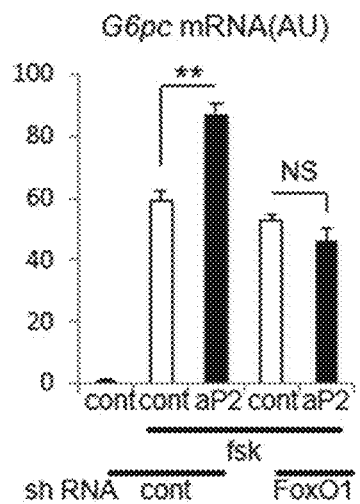
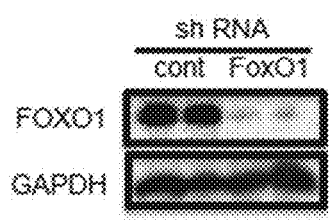
FIG. 32D
FIG. 32E
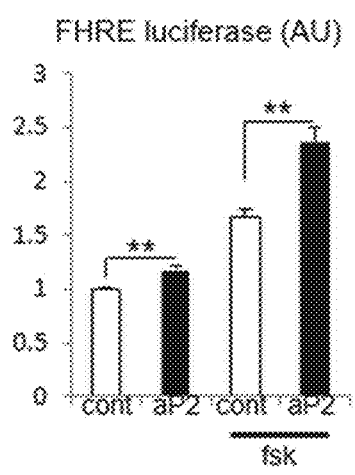
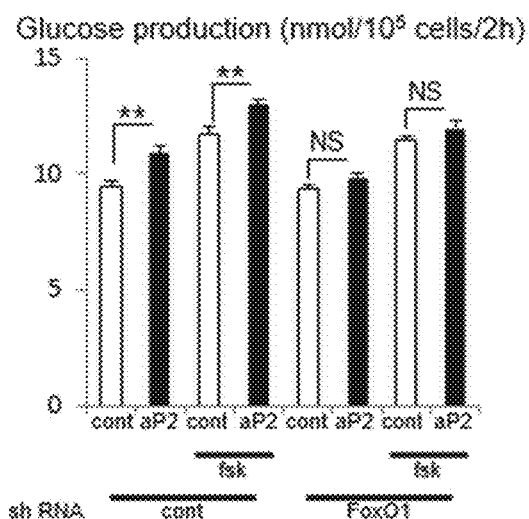
FIG. 32F
FIG. 32G

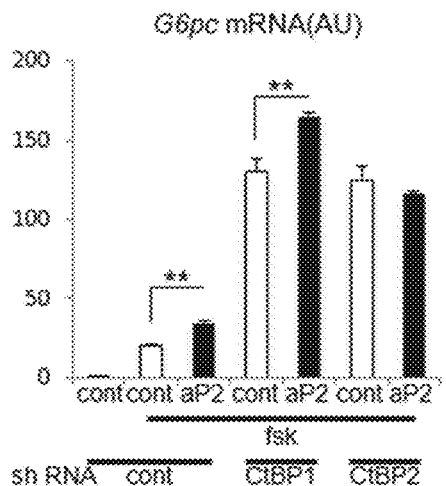
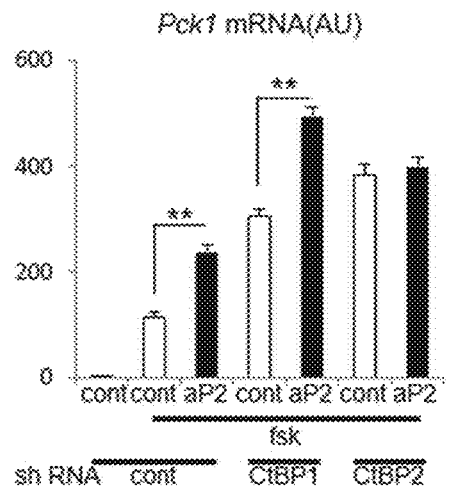

FIG. 34A          FIG. 34B

```
mouse FOXO1 571 algsyssvss cngygrmgvl hqek psdl  gmflerldcd mesiimdim 610    Seq. ID. No. 603
mouse FOXO3 581 tlsdslsgss lysasanlpv mghdk psdl  dnfngsle cdmesiirse 620    Seq. ID. No. 604
mouse FOXO4 441 magapipkvl gtpvlaspte dsshdm pdl l dmymenl ecdmdniisd 480    Seq. ID. No. 605
mouse FOXO6 481 lpgpyaaaaa gplgagpdrf padl d dnfs gslecdvesl lndfmdsde 520   Seq. ID. No. 606
human FOXO1 581 vsscngygm glfhqek ps dl gmflerl dcdmesiim dlmdgdldf 620      Seq. ID. No. 607
human FOXO3 591 slystsanlp vmghek psdl dnfngsl ecdmesiirs elmdadgldf 630     Seq. ID. No. 608
human FOXO4 451 tpvllpptea asqdm psdl d dmymenle cdmdniisdl mdegegldfn 490  Seq. ID. No. 609
human FOXO6 411 ldalpgpyaa aaagplgaap drf padl d mfsgslecdv esiilndfmd 451  Seq. ID. No. 610
```

FIG. 34C

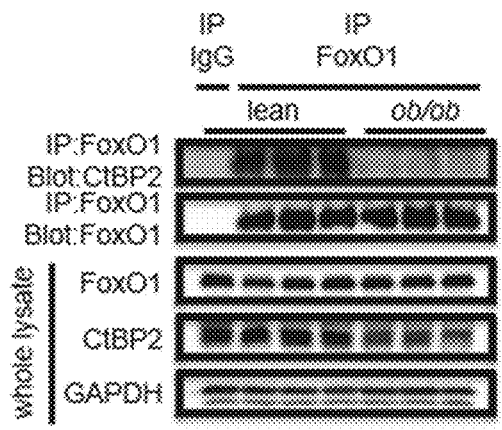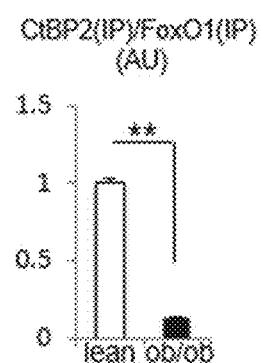
FIG. 36A　　　　　　　　　FIG. 36B
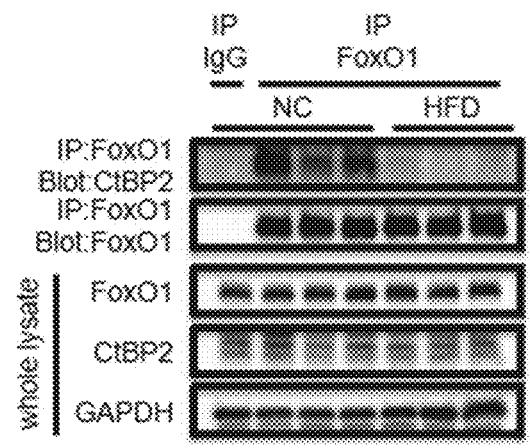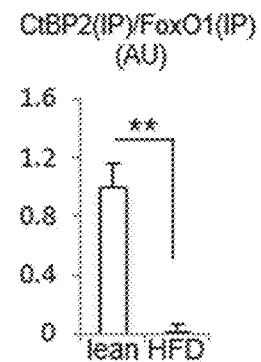
FIG. 36C　　　　　　　　　FIG. 36D

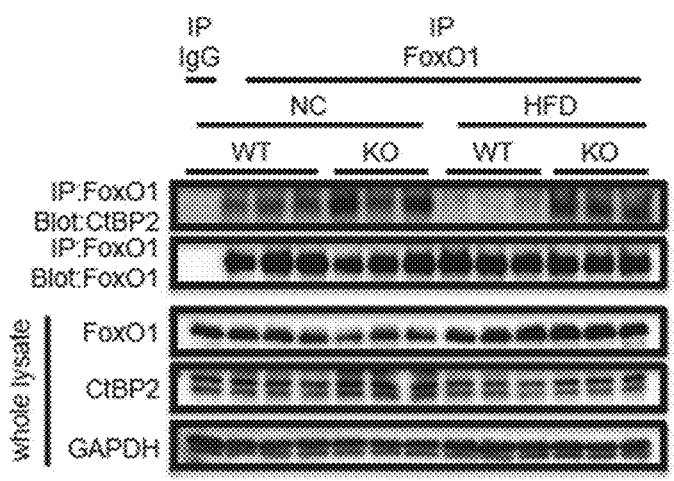
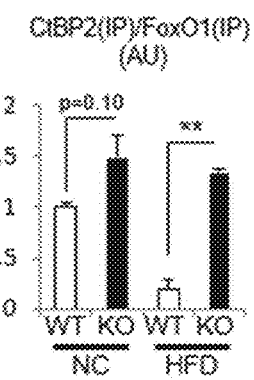
FIG. 36E
FIG. 36F
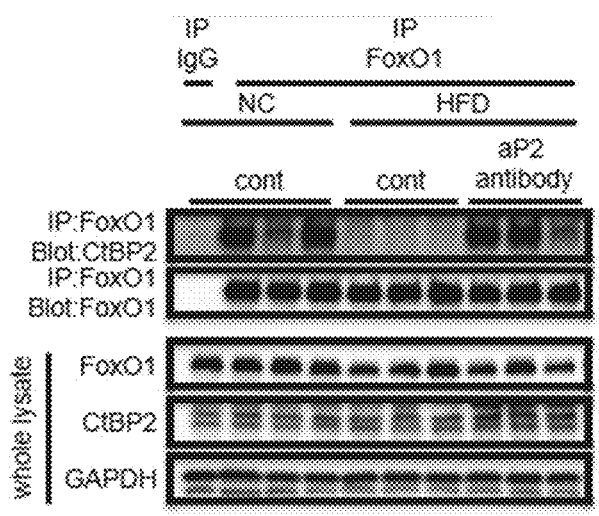
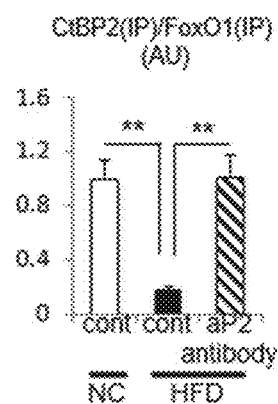
FIG. 36G
FIG. 36H

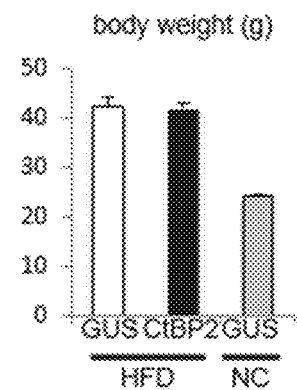
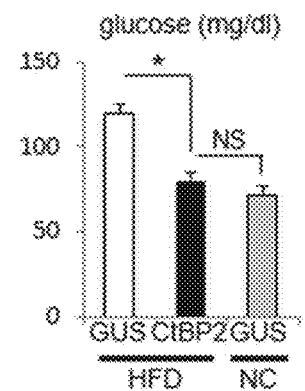
FIG. 37A
FIG. 37B
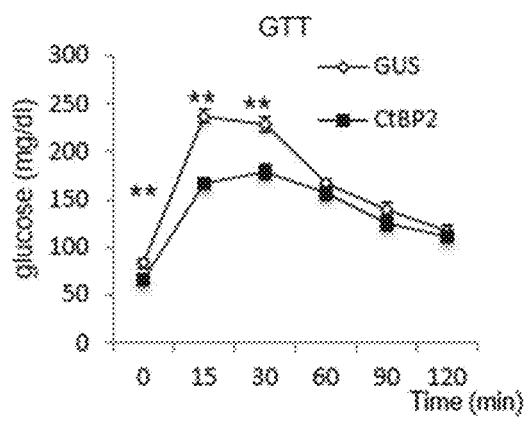
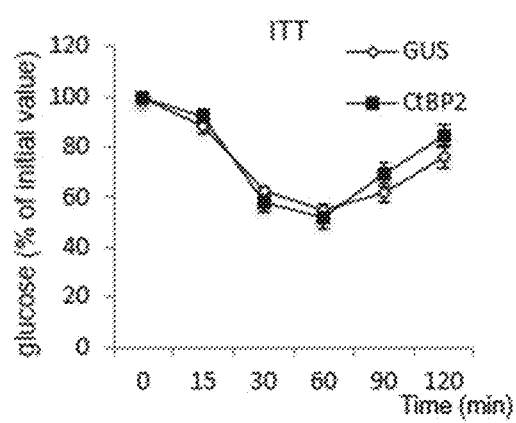
FIG. 37C
FIG. 37D

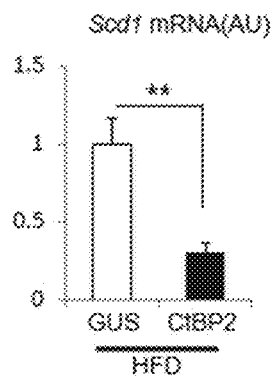
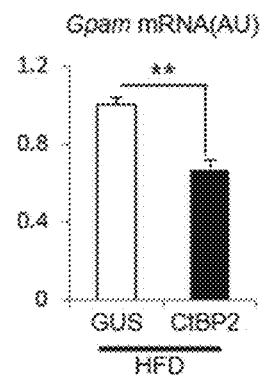
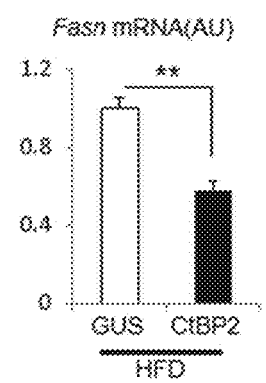
FIG. 37M          FIG. 37N          FIG. 37O
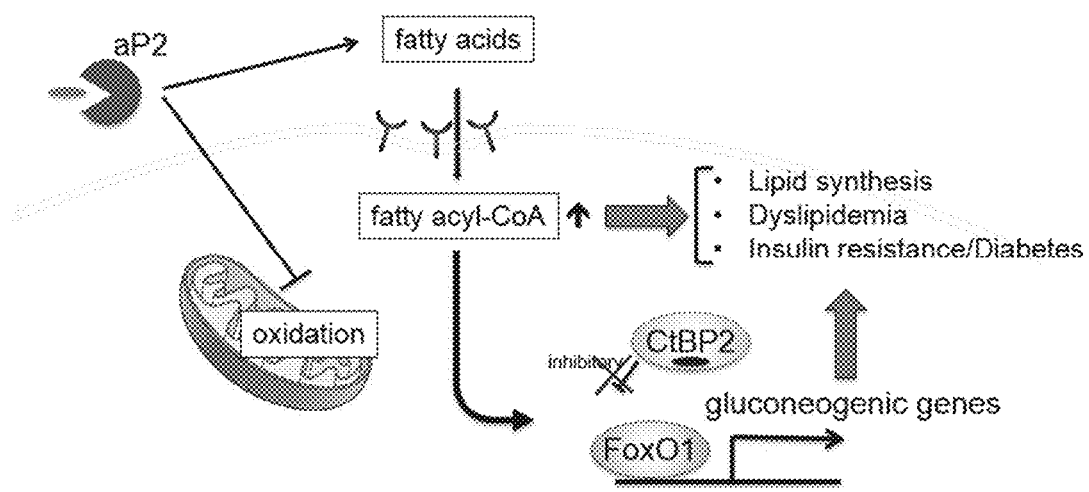
FIG. 37P

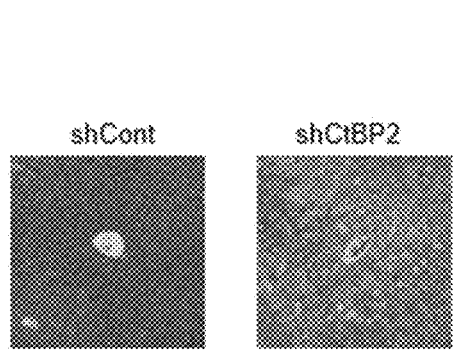
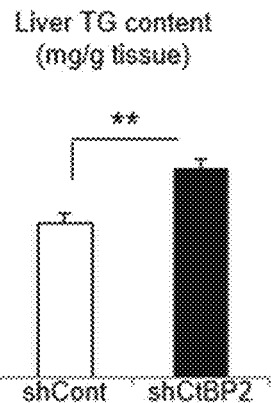
FIG. 45G
FIG. 45H
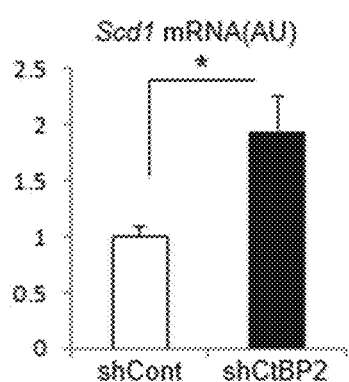
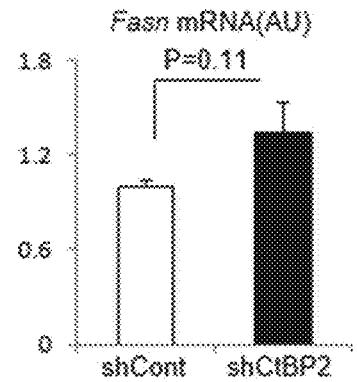
FIG. 45I
FIG. 45J

SEQUENCE LISTING

```
<160> NUMBER OF SEQ ID NOS: 610

<210> SEQ ID NO 1
<211> LENGTH: 70
<212> TYPE: PRT
<213> ORGANISM: Homo sapiens

<400> SEQUENCE: 1

Met Cys Asp Ala Phe Val Gly Thr Trp Lys Leu Val Ser Ser Glu Asn
1               5                   10                  15

Phe Asp Asp Tyr Met Lys Glu Val Gly Val Gly Phe Ala Thr Arg Lys
            20                  25                  30

Val Ala Gly Met Ala Lys Pro Asn Met Ile Ile Ser Val Asn Gly Asp
        35                  40                  45

Val Ile Thr Ile Lys Ser Glu Ser Thr Phe Lys Asn Thr Glu Ile Ser
    50                  55                  60

Phe Ile Leu Gly Gln Glu
65                  70

<210> SEQ ID NO 2
<211> LENGTH: 132
<212> TYPE: PRT
<213> ORGANISM: Mus musculus

<400> SEQUENCE: 2

Met Cys Asp Ala Phe Val Gly Thr Trp Lys Leu Val Ser Ser Glu Asn
1               5                   10                  15

Phe Asp Asp Tyr Met Lys Glu Val Gly Val Gly Phe Ala Thr Arg Lys
            20                  25                  30
```

```
Val Ala Gly Met Ala Lys Pro Asn Met Ile Ile Ser Val Asn Gly Asp
         35                  40                  45

Leu Val Thr Ile Arg Ser Glu Ser Thr Phe Lys Asn Thr Glu Ile Ser
 50                  55                  60

Phe Lys Leu Gly Val Glu Phe Asp Glu Ile Thr Ala Asp Asp Arg Lys
 65                  70                  75                  80

Val Lys Ser Ile Ile Thr Leu Asp Gly Gly Ala Leu Val Gln Val Gln
                 85                  90                  95

Lys Trp Asp Gly Lys Ser Thr Thr Ile Lys Arg Lys Arg Asp Gly Asp
             100                 105                 110

Lys Leu Val Val Glu Cys Val Met Lys Gly Val Thr Ser Thr Arg Val
             115                 120                 125

Tyr Glu Arg Ala
    130
```

<210> SEQ ID NO 3
<211> LENGTH: 11
<212> TYPE: PRT
<213> ORGANISM: Artificial Sequence
<220> FEATURE:
<223> OTHER INFORMATION: aP2 nuclear localization amino acid sequence

<400> SEQUENCE: 3

```
Lys Glu Val Gly Val Gly Phe Ala Thr Arg Lys
 1               5                  10
```

<210> SEQ ID NO 4
<211> LENGTH: 3
<212> TYPE: PRT
<213> ORGANISM: Artificial Sequence
<220> FEATURE:
<223> OTHER INFORMATION: aP2 fatty acid binding domain amino acid
      sequence

<400> SEQUENCE: 4

```
Arg Val Tyr
 1
```

<210> SEQ ID NO 5
<211> LENGTH: 399
<212> TYPE: DNA
<213> ORGANISM: Homo sapiens

<400> SEQUENCE: 5

```
atgtgtgatg cttttgtagg tacctggaaa cttgtctcca gtgaaaactt tgatgattat      60
atgaaagaag taggagtggg ctttgccacc aggaaagtgg ctggcatggc caaacctaac     120
atgatcatca gtgtgaatgg ggatgtgatc accattaaat ctgaaagtac ctttaaaaat     180
actgagattt ccttcatact gggccaggaa tttgacgaag tcactgcaga tgacaggaaa     240
gtcaagagca ccataacctt agatgggggt gtcctggtac atgtgcagaa atgggatgga     300
aaatcaacca cataaagag aaaacgagag gatgataaac tggtggtgga atgcgtcatg     360
aaaggcgtca cttccacgag agtttatgag agagcataa                            399
```

<210> SEQ ID NO 6
<211> LENGTH: 399
<212> TYPE: DNA
<213> ORGANISM: Mus musculus

<400> SEQUENCE: 6

```
atgtgtgatg cctttgtggg aacctggaag cttgtctcca gtgaaaactt cgatgattac      60
```

```
atgaaagaag tgggagtggg ctttgccaca aggaaagtgg caggcatggc caagcccaac    120
atgatcatca gcgtaaatgg ggatttggtc accatccggt cagagagtac ttttaaaaac    180
accgagattt ccttcaaact gggcgtggaa ttcgatgaaa tcaccgcaga cgacaggaag    240
gtgaagagca tcataaccct agatggcggg gccctggtgc aggtgcagaa gtgggatgga    300
aagtcgacca caataaagag aaaacgagat ggtgacaagc tggtggtgga atgtgttatg    360
aaaggcgtga cttccacaag agtttatgaa agggcatga                          399
```

<210> SEQ ID NO 7
<211> LENGTH: 11
<212> TYPE: PRT
<213> ORGANISM: Artificial Sequence
<220> FEATURE:
<223> OTHER INFORMATION: CDRL1

<400> SEQUENCE: 7

Gln Ala Ser Glu Asp Ile Ser Arg Tyr Leu Val
1               5                   10

<210> SEQ ID NO 8
<211> LENGTH: 7
<212> TYPE: PRT
<213> ORGANISM: Artificial Sequence
<220> FEATURE:
<223> OTHER INFORMATION: CDRL2

<400> SEQUENCE: 8

Lys Ala Ser Thr Leu Ala Ser
1               5

<210> SEQ ID NO 9
<211> LENGTH: 14
<212> TYPE: PRT
<213> ORGANISM: Artificial Sequence
<220> FEATURE:
<223> OTHER INFORMATION: CDRL3

<400> SEQUENCE: 9

Gln Cys Thr Tyr Gly Thr Tyr Ala Gly Ser Phe Phe Tyr Ser
1               5                   10

<210> SEQ ID NO 10
<211> LENGTH: 14
<212> TYPE: PRT
<213> ORGANISM: Artificial Sequence
<220> FEATURE:
<223> OTHER INFORMATION: CDRL3 variant 1

<400> SEQUENCE: 10

Gln Ala Thr Tyr Gly Thr Tyr Ala Gly Ser Phe Phe Tyr Ser
1               5                   10

<210> SEQ ID NO 11
<211> LENGTH: 14
<212> TYPE: PRT
<213> ORGANISM: Artificial Sequence
<220> FEATURE:
<223> OTHER INFORMATION: CDRL3 variant 2

<400> SEQUENCE: 11

Gln Gln Thr Tyr Gly Thr Tyr Ala Gly Ser Phe Phe Tyr Ser
1               5                   10

<210> SEQ ID NO 12
<211> LENGTH: 14
<212> TYPE: PRT
<213> ORGANISM: Artificial Sequence
<220> FEATURE:
<223> OTHER INFORMATION: CDRL3 variant 3

<400> SEQUENCE: 12

Gln His Thr Tyr Gly Thr Tyr Ala Gly Ser Phe Phe Tyr Ser
1               5                   10

<210> SEQ ID NO 13
<211> LENGTH: 9
<212> TYPE: PRT
<213> ORGANISM: Artificial Sequence
<220> FEATURE:
<223> OTHER INFORMATION: CDRL3 variant 4

<400> SEQUENCE: 13

Gln Gln Ala Ser His Tyr Pro Leu Thr
1               5

<210> SEQ ID NO 14
<211> LENGTH: 10
<212> TYPE: PRT
<213> ORGANISM: Artificial Sequence
<220> FEATURE:
<223> OTHER INFORMATION: CDRH1

<400> SEQUENCE: 14

Gly Phe Ser Leu Ser Thr Tyr Tyr Met Ser
1               5                   10

<210> SEQ ID NO 15
<211> LENGTH: 10
<212> TYPE: PRT
<213> ORGANISM: Artificial Sequence
<220> FEATURE:
<223> OTHER INFORMATION: CDRH1 variant 1

<400> SEQUENCE: 15

Gly Tyr Thr Phe Thr Ser Asn Ala Ile Thr
1               5                   10

<210> SEQ ID NO 16
<211> LENGTH: 16
<212> TYPE: PRT
<213> ORGANISM: Artificial Sequence
<220> FEATURE:
<223> OTHER INFORMATION: CDRH2

<400> SEQUENCE: 16

Ile Ile Tyr Pro Ser Gly Ser Thr Tyr Cys Ala Ser Trp Ala Lys Gly
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: CDRH2 variant 1

<400> SEQUENCE: 17

Ile Ile Tyr Pro Ser Gly Ser Thr Tyr Ser Ala Ser Trp Ala Lys Gly
1               5                   10                  15

<210> SEQ ID NO 18

```
<211> LENGTH: 17
<212> TYPE: PRT
<213> ORGANISM: Artificial Sequence
<220> FEATURE:
<223> OTHER INFORMATION: CDRH2 variant 2

<400> SEQUENCE: 18

Asp Ile Ser Pro Gly Ser Gly Ser Thr Thr Asn Asn Glu Lys Phe Lys
1               5                   10                  15
Ser

<210> SEQ ID NO 19
<211> LENGTH: 15
<212> TYPE: PRT
<213> ORGANISM: Artificial Sequence
<220> FEATURE:
<223> OTHER INFORMATION: CDHR3

<400> SEQUENCE: 19

Pro Asp Asn Asp Gly Thr Ser Gly Tyr Leu Ser Gly Phe Gly Leu
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: CDRH3 variant 1

<400> SEQUENCE: 20

Pro Asp Asn Glu Gly Thr Ser Gly Tyr Leu Ser Gly Phe Gly Leu
1               5                   10                  15

<210> SEQ ID NO 21
<211> LENGTH: 10
<212> TYPE: PRT
<213> ORGANISM: Artificial Sequence
<220> FEATURE:
<223> OTHER INFORMATION: CDRH3 variant 2

<400> SEQUENCE: 21

Leu Arg Gly Phe Tyr Asp Tyr Phe Asp Phe
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Epitope of the human aP2 protein

<400> SEQUENCE: 22

Trp Lys Leu Val Ser Ser Glu Asn Phe
1               5

<210> SEQ ID NO 23
<211> LENGTH: 9
<212> TYPE: PRT
<213> ORGANISM: Artificial Sequence
<220> FEATURE:
<223> OTHER INFORMATION: Epitope of human aP2 protein

<400> SEQUENCE: 23

Tyr Met Lys Glu Val Gly Val Gly Phe
1               5
```

```
<210> SEQ ID NO 24
<211> LENGTH: 15
<212> TYPE: PRT
<213> ORGANISM: Artificial Sequence
<220> FEATURE:
<223> OTHER INFORMATION: Epitope of human aP2 protein

<400> SEQUENCE: 24

Cys Val Met Lys Gly Val Thr Ser Thr Arg Val Tyr Glu Arg Ala
1               5                   10                  15

<210> SEQ ID NO 25
<211> LENGTH: 23
<212> TYPE: PRT
<213> ORGANISM: Artificial Sequence
<220> FEATURE:
<223> OTHER INFORMATION: O12 FR1

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 26
<211> LENGTH: 15
<212> TYPE: PRT
<213> ORGANISM: Artificial Sequence
<220> FEATURE:
<223> OTHER INFORMATION: O12 FR2

<400> SEQUENCE: 26

Trp Tyr Gln Gln Lys Pro Gly Lys Ala Pro Lys Leu Leu Ile Tyr
1               5                   10                  15

<210> SEQ ID NO 27
<211> LENGTH: 32
<212> TYPE: PRT
<213> ORGANISM: Artificial Sequence
<220> FEATURE:
<223> OTHER INFORMATION: O12 FR3

<400> SEQUENCE: 27

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 28
<211> LENGTH: 23
<212> TYPE: PRT
<213> ORGANISM: Artificial Sequence
<220> FEATURE:
<223> OTHER INFORMATION: O2 FR1

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 29
<211> LENGTH: 15
<212> TYPE: PRT
<213> ORGANISM: Artificial Sequence
<220> FEATURE:
```

```
<223> OTHER INFORMATION: O2 FR2

<400> SEQUENCE: 29

Trp Tyr Gln Gln Lys Pro Gly Lys Ala Pro Lys Leu Leu Ile Tyr
1               5                   10                  15

<210> SEQ ID NO 30
<211> LENGTH: 32
<212> TYPE: PRT
<213> ORGANISM: Artificial Sequence
<220> FEATURE:
<223> OTHER INFORMATION: O2 FR3

<400> SEQUENCE: 30

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 31
<211> LENGTH: 23
<212> TYPE: PRT
<213> ORGANISM: Artificial Sequence
<220> FEATURE:
<223> OTHER INFORMATION: O18 FR1

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 32
<211> LENGTH: 15
<212> TYPE: PRT
<213> ORGANISM: Artificial Sequence
<220> FEATURE:
<223> OTHER INFORMATION: O18 FR2

<400> SEQUENCE: 32

Trp Tyr Gln Gln Lys Pro Gly Lys Ala Pro Lys Leu Leu Ile Tyr
1               5                   10                  15

<210> SEQ ID NO 33
<211> LENGTH: 32
<212> TYPE: PRT
<213> ORGANISM: Artificial Sequence
<220> FEATURE:
<223> OTHER INFORMATION: O18 FR3

<400> SEQUENCE: 33

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 34
<211> LENGTH: 23
<212> TYPE: PRT
<213> ORGANISM: Artificial Sequence
<220> FEATURE:
<223> OTHER INFORMATION: O8 FR1

<400> SEQUENCE: 34

Asp Ile Gln Met Thr Gln Ser Pro Ser Ser Leu Ser Ala Ser Val Gly
```

```
                   1               5                  10                  15

Asp Arg Val Thr Ile Thr Cys
                20

<210> SEQ ID NO 35
<211> LENGTH: 15
<212> TYPE: PRT
<213> ORGANISM: Artificial Sequence
<220> FEATURE:
<223> OTHER INFORMATION: O8 FR2

<400> SEQUENCE: 35

Trp Tyr Gln Gln Lys Pro Gly Lys Ala Pro Lys Leu Leu Ile Tyr
1               5                  10                  15

<210> SEQ ID NO 36
<211> LENGTH: 32
<212> TYPE: PRT
<213> ORGANISM: Artificial Sequence
<220> FEATURE:
<223> OTHER INFORMATION: O8 FR3

<400> SEQUENCE: 36

Gly Val Pro Ser Arg Phe Ser Gly Ser Gly Ser Gly Thr Asp Phe Thr
1               5                  10                  15

Phe Thr Ile Ser Ser Leu Gln Pro Glu Asp Ile Ala Thr Tyr Tyr Cys
                20                  25                  30

<210> SEQ ID NO 37
<211> LENGTH: 23
<212> TYPE: PRT
<213> ORGANISM: Artificial Sequence
<220> FEATURE:
<223> OTHER INFORMATION: A20 FR1

<400> SEQUENCE: 37

Asp Ile Gln Met Thr Gln Ser Pro Ser Ser Leu Ser Ala Ser Val Gly
1               5                  10                  15

Asp Arg Val Thr Ile Thr Cys
                20

<210> SEQ ID NO 38
<211> LENGTH: 15
<212> TYPE: PRT
<213> ORGANISM: Artificial Sequence
<220> FEATURE:
<223> OTHER INFORMATION: A20 FR2

<400> SEQUENCE: 38

Trp Tyr Gln Gln Lys Pro Gly Lys Val Pro Lys Leu Leu Ile Tyr
1               5                  10                  15

<210> SEQ ID NO 39
<211> LENGTH: 32
<212> TYPE: PRT
<213> ORGANISM: Artificial Sequence
<220> FEATURE:
<223> OTHER INFORMATION: A20 FR3

<400> SEQUENCE: 39

Gly Val Pro Ser Arg Phe Ser Gly Ser Gly Ser Gly Thr Asp Phe Thr
1               5                  10                  15

Leu Thr Ile Ser Ser Leu Gln Pro Glu Asp Val Ala Thr Tyr Tyr Cys
                20                  25                  30
```

<210> SEQ ID NO 40
<211> LENGTH: 23
<212> TYPE: PRT
<213> ORGANISM: Artificial Sequence
<220> FEATURE:
<223> OTHER INFORMATION: A30 FR1

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 41
<211> LENGTH: 15
<212> TYPE: PRT
<213> ORGANISM: Artificial Sequence
<220> FEATURE:
<223> OTHER INFORMATION: A30 FR2

<400> SEQUENCE: 41

Trp Tyr Gln Gln Lys Pro Gly Lys Ala Pro Lys Arg Leu Ile Tyr
1               5                   10                  15

<210> SEQ ID NO 42
<211> LENGTH: 32
<212> TYPE: PRT
<213> ORGANISM: Artificial Sequence
<220> FEATURE:
<223> OTHER INFORMATION: A30 FR3

<400> SEQUENCE: 42

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 43
<211> LENGTH: 23
<212> TYPE: PRT
<213> ORGANISM: Artificial Sequence
<220> FEATURE:
<223> OTHER INFORMATION: L14 FR1

<400> SEQUENCE: 43

Asn Ile Gln Met Thr Gln Ser Pro Ser Ala Met Ser Ala Ser Val Gly
1               5                   10                  15

Asp Arg Val Thr Ile Thr Cys
            20

<210> SEQ ID NO 44
<211> LENGTH: 15
<212> TYPE: PRT
<213> ORGANISM: Artificial Sequence
<220> FEATURE:
<223> OTHER INFORMATION: L14 FR2

<400> SEQUENCE: 44

Trp Phe Gln Gln Lys Pro Gly Lys Val Pro Lys His Leu Ile Tyr
1               5                   10                  15

<210> SEQ ID NO 45
<211> LENGTH: 32
<212> TYPE: PRT
<213> ORGANISM: Artificial Sequence

```
<220> FEATURE:
<223> OTHER INFORMATION: L14 FR3

<400> SEQUENCE: 45

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 46
<211> LENGTH: 23
<212> TYPE: PRT
<213> ORGANISM: Artificial Sequence
<220> FEATURE:
<223> OTHER INFORMATION: L1 FR1

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 47
<211> LENGTH: 15
<212> TYPE: PRT
<213> ORGANISM: Artificial Sequence
<220> FEATURE:
<223> OTHER INFORMATION: L1 FR2

<400> SEQUENCE: 47

Trp Phe Gln Gln Lys Pro Gly Lys Ala Pro Lys Ser Leu Ile Tyr
1               5                   10                  15

<210> SEQ ID NO 48
<211> LENGTH: 32
<212> TYPE: PRT
<213> ORGANISM: Artificial Sequence
<220> FEATURE:
<223> OTHER INFORMATION: L1 FR3

<400> SEQUENCE: 48

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 49
<211> LENGTH: 23
<212> TYPE: PRT
<213> ORGANISM: Artificial Sequence
<220> FEATURE:
<223> OTHER INFORMATION: L15 FR1

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 50
<211> LENGTH: 15
<212> TYPE: PRT
<213> ORGANISM: Artificial Sequence
<220> FEATURE:
<223> OTHER INFORMATION: L15 FR2
```

<400> SEQUENCE: 50

Trp Tyr Gln Gln Lys Pro Glu Lys Ala Pro Lys Ser Leu Ile Tyr
1               5                   10                  15

<210> SEQ ID NO 51
<211> LENGTH: 32
<212> TYPE: PRT
<213> ORGANISM: Artificial Sequence
<220> FEATURE:
<223> OTHER INFORMATION: L15 FR3

<400> SEQUENCE: 51

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 52
<211> LENGTH: 23
<212> TYPE: PRT
<213> ORGANISM: Artificial Sequence
<220> FEATURE:
<223> OTHER INFORMATION: L4 FR1

<400> SEQUENCE: 52

Ala Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 53
<211> LENGTH: 15
<212> TYPE: PRT
<213> ORGANISM: Artificial Sequence
<220> FEATURE:
<223> OTHER INFORMATION: L4 FR2

<400> SEQUENCE: 53

Trp Tyr Gln Gln Lys Pro Gly Lys Ala Pro Lys Leu Leu Ile Tyr
1               5                   10                  15

<210> SEQ ID NO 54
<211> LENGTH: 32
<212> TYPE: PRT
<213> ORGANISM: Artificial Sequence
<220> FEATURE:
<223> OTHER INFORMATION: L4 FR3

<400> SEQUENCE: 54

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 55
<211> LENGTH: 23
<212> TYPE: PRT
<213> ORGANISM: Artificial Sequence
<220> FEATURE:
<223> OTHER INFORMATION: L18 FR1

<400> SEQUENCE: 55

Ala Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 56
<211> LENGTH: 15
<212> TYPE: PRT
<213> ORGANISM: Artificial Sequence
<220> FEATURE:
<223> OTHER INFORMATION: L18 FR2

<400> SEQUENCE: 56

Trp Tyr Gln Gln Lys Pro Gly Lys Ala Pro Lys Leu Leu Ile Tyr
1               5                   10                  15

<210> SEQ ID NO 57
<211> LENGTH: 32
<212> TYPE: PRT
<213> ORGANISM: Artificial Sequence
<220> FEATURE:
<223> OTHER INFORMATION: L18 FR3

<400> SEQUENCE: 57

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 58
<211> LENGTH: 23
<212> TYPE: PRT
<213> ORGANISM: Artificial Sequence
<220> FEATURE:
<223> OTHER INFORMATION: L5 FR1

<400> SEQUENCE: 58

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 59
<211> LENGTH: 15
<212> TYPE: PRT
<213> ORGANISM: Artificial Sequence
<220> FEATURE:
<223> OTHER INFORMATION: L5 FR2

<400> SEQUENCE: 59

Trp Tyr Gln Gln Lys Pro Gly Lys Ala Pro Lys Leu Leu Ile Tyr
1               5                   10                  15

<210> SEQ ID NO 60
<211> LENGTH: 32
<212> TYPE: PRT
<213> ORGANISM: Artificial Sequence
<220> FEATURE:
<223> OTHER INFORMATION: L5 FR3

<400> SEQUENCE: 60

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

```
<210> SEQ ID NO 61
<211> LENGTH: 23
<212> TYPE: PRT
<213> ORGANISM: Artificial Sequence
<220> FEATURE:
<223> OTHER INFORMATION: L19 FR1

<400> SEQUENCE: 61

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 62
<211> LENGTH: 15
<212> TYPE: PRT
<213> ORGANISM: Artificial Sequence
<220> FEATURE:
<223> OTHER INFORMATION: L19 FR2

<400> SEQUENCE: 62

Trp Tyr Gln Gln Lys Pro Gly Lys Ala Pro Lys Leu Leu Ile Tyr
1               5                   10                  15

<210> SEQ ID NO 63
<211> LENGTH: 32
<212> TYPE: PRT
<213> ORGANISM: Artificial Sequence
<220> FEATURE:
<223> OTHER INFORMATION: L19 FR3

<400> SEQUENCE: 63

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 64
<211> LENGTH: 23
<212> TYPE: PRT
<213> ORGANISM: Artificial Sequence
<220> FEATURE:
<223> OTHER INFORMATION: L8 FR1

<400> SEQUENCE: 64

Asp Ile Gln Leu Thr Gln Ser Pro Ser Phe Leu Ser Ala Ser Val Gly
1               5                   10                  15

Asp Arg Val Thr Ile Thr Cys
            20

<210> SEQ ID NO 65
<211> LENGTH: 15
<212> TYPE: PRT
<213> ORGANISM: Artificial Sequence
<220> FEATURE:
<223> OTHER INFORMATION: L8 FR2

<400> SEQUENCE: 65

Trp Tyr Gln Gln Lys Pro Gly Lys Ala Pro Lys Leu Leu Ile Tyr
1               5                   10                  15

<210> SEQ ID NO 66
<211> LENGTH: 32
<212> TYPE: PRT
<213> ORGANISM: Artificial Sequence
<220> FEATURE:
```

<223> OTHER INFORMATION: L8 FR3

<400> SEQUENCE: 66

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 67
<211> LENGTH: 23
<212> TYPE: PRT
<213> ORGANISM: Artificial Sequence
<220> FEATURE:
<223> OTHER INFORMATION: L23 FR1

<400> SEQUENCE: 67

Ala Ile Arg Met Thr Gln Ser Pro Phe Ser Leu Ser Ala Ser Val Gly
1               5                   10                  15

Asp Arg Val Thr Ile Thr Cys
            20

<210> SEQ ID NO 68
<211> LENGTH: 15
<212> TYPE: PRT
<213> ORGANISM: Artificial Sequence
<220> FEATURE:
<223> OTHER INFORMATION: L23 FR2

<400> SEQUENCE: 68

Trp Tyr Gln Gln Lys Pro Ala Lys Ala Pro Lys Leu Phe Ile Tyr
1               5                   10                  15

<210> SEQ ID NO 69
<211> LENGTH: 32
<212> TYPE: PRT
<213> ORGANISM: Artificial Sequence
<220> FEATURE:
<223> OTHER INFORMATION: L23 FR3

<400> SEQUENCE: 69

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 70
<211> LENGTH: 23
<212> TYPE: PRT
<213> ORGANISM: Artificial Sequence
<220> FEATURE:
<223> OTHER INFORMATION: L9 FR1

<400> SEQUENCE: 70

Ala Ile Arg Met Thr Gln Ser Pro Ser Ser Phe Ser Ala Ser Thr Gly
1               5                   10                  15

Asp Arg Val Thr Ile Thr Cys
            20

<210> SEQ ID NO 71
<211> LENGTH: 15
<212> TYPE: PRT
<213> ORGANISM: Artificial Sequence
<220> FEATURE:
<223> OTHER INFORMATION: L9 FR2

<400> SEQUENCE: 71

Trp Tyr Gln Gln Lys Pro Gly Lys Ala Pro Lys Leu Leu Ile Tyr
1               5                   10                  15

<210> SEQ ID NO 72
<211> LENGTH: 32
<212> TYPE: PRT
<213> ORGANISM: Artificial Sequence
<220> FEATURE:
<223> OTHER INFORMATION: L9 FR3

<400> SEQUENCE: 72

Gly Val Pro Ser Arg Phe Ser Gly Ser Gly Ser Gly Thr Asp Phe Thr
1               5                   10                  15

Leu Thr Ile Ser Cys Leu Gln Ser Glu Asp Phe Ala Thr Tyr Tyr Cys
            20                  25                  30

<210> SEQ ID NO 73
<211> LENGTH: 23
<212> TYPE: PRT
<213> ORGANISM: Artificial Sequence
<220> FEATURE:
<223> OTHER INFORMATION: L24 FR1

<400> SEQUENCE: 73

Val Ile Trp Met Thr Gln Ser Pro Ser Leu Leu Ser Ala Ser Thr Gly
1               5                   10                  15

Asp Arg Val Thr Ile Ser Cys
            20

<210> SEQ ID NO 74
<211> LENGTH: 15
<212> TYPE: PRT
<213> ORGANISM: Artificial Sequence
<220> FEATURE:
<223> OTHER INFORMATION: L24 FR2

<400> SEQUENCE: 74

Trp Tyr Gln Gln Lys Pro Gly Lys Ala Pro Glu Leu Leu Ile Tyr
1               5                   10                  15

<210> SEQ ID NO 75
<211> LENGTH: 32
<212> TYPE: PRT
<213> ORGANISM: Artificial Sequence
<220> FEATURE:
<223> OTHER INFORMATION: L24 FR3

<400> SEQUENCE: 75

Gly Val Pro Ser Arg Phe Ser Gly Ser Gly Ser Gly Thr Asp Phe Thr
1               5                   10                  15

Leu Thr Ile Ser Cys Leu Gln Ser Glu Asp Phe Ala Thr Tyr Tyr Cys
            20                  25                  30

<210> SEQ ID NO 76
<211> LENGTH: 23
<212> TYPE: PRT
<213> ORGANISM: Artificial Sequence
<220> FEATURE:
<223> OTHER INFORMATION: L11 FR1

<400> SEQUENCE: 76

Ala Ile Gln Met Thr Gln Ser Pro Ser Ser Leu Ser Ala Ser Val Gly
1               5                   10                  15

Asp Arg Val Thr Ile Thr Cys
        20

<210> SEQ ID NO 77
<211> LENGTH: 15
<212> TYPE: PRT
<213> ORGANISM: Artificial Sequence
<220> FEATURE:
<223> OTHER INFORMATION: L11 FR2

<400> SEQUENCE: 77

Trp Tyr Gln Gln Lys Pro Gly Lys Ala Pro Lys Leu Leu Ile Tyr
1               5                   10                  15

<210> SEQ ID NO 78
<211> LENGTH: 32
<212> TYPE: PRT
<213> ORGANISM: Artificial Sequence
<220> FEATURE:
<223> OTHER INFORMATION: L11 FR3

<400> SEQUENCE: 78

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 79
<211> LENGTH: 23
<212> TYPE: PRT
<213> ORGANISM: Artificial Sequence
<220> FEATURE:
<223> OTHER INFORMATION: L12 FR1

<400> SEQUENCE: 79

Asp Ile Gln Met Thr Gln Ser Pro Ser Thr Leu Ser Ala Ser Val Gly
1               5                   10                  15

Asp Arg Val Thr Ile Thr Cys
        20

<210> SEQ ID NO 80
<211> LENGTH: 15
<212> TYPE: PRT
<213> ORGANISM: Artificial Sequence
<220> FEATURE:
<223> OTHER INFORMATION: L12 FR2

<400> SEQUENCE: 80

Trp Tyr Gln Gln Lys Pro Gly Lys Ala Pro Lys Leu Leu Ile Tyr
1               5                   10                  15

<210> SEQ ID NO 81
<211> LENGTH: 32
<212> TYPE: PRT
<213> ORGANISM: Artificial Sequence
<220> FEATURE:
<223> OTHER INFORMATION: L12 FR3

<400> SEQUENCE: 81

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 82

```
<211> LENGTH: 23
<212> TYPE: PRT
<213> ORGANISM: Artificial Sequence
<220> FEATURE:
<223> OTHER INFORMATION: O11 FR1

<400> SEQUENCE: 82

Asp Ile Val Met Thr Gln Thr Pro Leu Ser Leu Pro Val Thr Pro Gly
1               5                   10                  15

Glu Pro Ala Ser Ile Ser Cys
            20

<210> SEQ ID NO 83
<211> LENGTH: 15
<212> TYPE: PRT
<213> ORGANISM: Artificial Sequence
<220> FEATURE:
<223> OTHER INFORMATION: O11 FR2

<400> SEQUENCE: 83

Trp Tyr Leu Gln Lys Pro Gly Gln Ser Pro Gln Leu Leu Ile Tyr
1               5                   10                  15

<210> SEQ ID NO 84
<211> LENGTH: 32
<212> TYPE: PRT
<213> ORGANISM: Artificial Sequence
<220> FEATURE:
<223> OTHER INFORMATION: O11 FR3

<400> SEQUENCE: 84

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 85
<211> LENGTH: 23
<212> TYPE: PRT
<213> ORGANISM: Artificial Sequence
<220> FEATURE:
<223> OTHER INFORMATION: O1 FR1

<400> SEQUENCE: 85

Asp Ile Val Met Thr Gln Thr Pro Leu Ser Leu Pro Val Thr Pro Gly
1               5                   10                  15

Glu Pro Ala Ser Ile Ser Cys
            20

<210> SEQ ID NO 86
<211> LENGTH: 15
<212> TYPE: PRT
<213> ORGANISM: Artificial Sequence
<220> FEATURE:
<223> OTHER INFORMATION: O1 FR2

<400> SEQUENCE: 86

Trp Tyr Leu Gln Lys Pro Gly Gln Ser Pro Gln Leu Leu Ile Tyr
1               5                   10                  15

<210> SEQ ID NO 87
<211> LENGTH: 32
<212> TYPE: PRT
<213> ORGANISM: Artificial Sequence
<220> FEATURE:
<223> OTHER INFORMATION: O1 FR3
```

<400> SEQUENCE: 87

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 88
<211> LENGTH: 23
<212> TYPE: PRT
<213> ORGANISM: Artificial Sequence
<220> FEATURE:
<223> OTHER INFORMATION: A17 FR1

<400> SEQUENCE: 88

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 89
<211> LENGTH: 15
<212> TYPE: PRT
<213> ORGANISM: Artificial Sequence
<220> FEATURE:
<223> OTHER INFORMATION: A17 FR2

<400> SEQUENCE: 89

Trp Phe Gln Gln Arg Pro Gly Gln Ser Pro Arg Arg Leu Ile Tyr
1               5                   10                  15

<210> SEQ ID NO 90
<211> LENGTH: 32
<212> TYPE: PRT
<213> ORGANISM: Artificial Sequence
<220> FEATURE:
<223> OTHER INFORMATION: A17 FR3

<400> SEQUENCE: 90

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 91
<211> LENGTH: 23
<212> TYPE: PRT
<213> ORGANISM: Artificial Sequence
<220> FEATURE:
<223> OTHER INFORMATION: A1 FR1

<400> SEQUENCE: 91

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 92
<211> LENGTH: 15
<212> TYPE: PRT
<213> ORGANISM: Artificial Sequence
<220> FEATURE:
<223> OTHER INFORMATION: A1 FR2

<400> SEQUENCE: 92

Trp Phe Gln Gln Arg Pro Gly Gln Ser Pro Arg Arg Leu Ile Tyr
1               5                   10                  15

<210> SEQ ID NO 93
<211> LENGTH: 32
<212> TYPE: PRT
<213> ORGANISM: Artificial Sequence
<220> FEATURE:
<223> OTHER INFORMATION: A1 FR3

<400> SEQUENCE: 93

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 94
<211> LENGTH: 23
<212> TYPE: PRT
<213> ORGANISM: Artificial Sequence
<220> FEATURE:
<223> OTHER INFORMATION: A18 FR1

<400> SEQUENCE: 94

Asp Ile Val Met Thr Gln Thr Pro Leu Ser Leu Ser Val Thr Pro Gly
1               5                   10                  15

Gln Pro Ala Ser Ile Ser Cys
            20

<210> SEQ ID NO 95
<211> LENGTH: 15
<212> TYPE: PRT
<213> ORGANISM: Artificial Sequence
<220> FEATURE:
<223> OTHER INFORMATION: A18 FR2

<400> SEQUENCE: 95

Trp Tyr Leu Gln Lys Pro Gly Gln Ser Pro Gln Leu Leu Ile Tyr
1               5                   10                  15

<210> SEQ ID NO 96
<211> LENGTH: 32
<212> TYPE: PRT
<213> ORGANISM: Artificial Sequence
<220> FEATURE:
<223> OTHER INFORMATION: A18 FR3

<400> SEQUENCE: 96

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 97
<211> LENGTH: 23
<212> TYPE: PRT
<213> ORGANISM: Artificial Sequence
<220> FEATURE:
<223> OTHER INFORMATION: A2 FR1

<400> SEQUENCE: 97

Asp Ile Val Met Thr Gln Thr Pro Leu Ser Leu Ser Val Thr Pro Gly
1               5                   10                  15

Gln Pro Ala Ser Ile Ser Cys

20

<210> SEQ ID NO 98
<211> LENGTH: 15
<212> TYPE: PRT
<213> ORGANISM: Artificial Sequence
<220> FEATURE:
<223> OTHER INFORMATION: A2 FR2

<400> SEQUENCE: 98

Trp Tyr Leu Gln Lys Pro Gly Gln Pro Pro Gln Leu Leu Ile Tyr
1               5                   10                  15

<210> SEQ ID NO 99
<211> LENGTH: 32
<212> TYPE: PRT
<213> ORGANISM: Artificial Sequence
<220> FEATURE:
<223> OTHER INFORMATION: A2 FR3

<400> SEQUENCE: 99

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 100
<211> LENGTH: 23
<212> TYPE: PRT
<213> ORGANISM: Artificial Sequence
<220> FEATURE:
<223> OTHER INFORMATION: A19 FR1

<400> SEQUENCE: 100

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 101
<211> LENGTH: 15
<212> TYPE: PRT
<213> ORGANISM: Artificial Sequence
<220> FEATURE:
<223> OTHER INFORMATION: A19 FR2

<400> SEQUENCE: 101

Trp Tyr Leu Gln Lys Pro Gly Gln Ser Pro Gln Leu Leu Ile Tyr
1               5                   10                  15

<210> SEQ ID NO 102
<211> LENGTH: 32
<212> TYPE: PRT
<213> ORGANISM: Artificial Sequence
<220> FEATURE:
<223> OTHER INFORMATION: A19 FR3

<400> SEQUENCE: 102

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 103
<211> LENGTH: 23

```
<212> TYPE: PRT
<213> ORGANISM: Artificial Sequence
<220> FEATURE:
<223> OTHER INFORMATION: A3 FR1

<400> SEQUENCE: 103

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 104
<211> LENGTH: 15
<212> TYPE: PRT
<213> ORGANISM: Artificial Sequence
<220> FEATURE:
<223> OTHER INFORMATION: A3 FR2

<400> SEQUENCE: 104

Trp Tyr Leu Gln Lys Pro Gly Gln Ser Pro Gln Leu Leu Ile Tyr
1               5                   10                  15

<210> SEQ ID NO 105
<211> LENGTH: 32
<212> TYPE: PRT
<213> ORGANISM: Artificial Sequence
<220> FEATURE:
<223> OTHER INFORMATION: A3 FR3

<400> SEQUENCE: 105

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 106
<211> LENGTH: 23
<212> TYPE: PRT
<213> ORGANISM: Artificial Sequence
<220> FEATURE:
<223> OTHER INFORMATION: A23 FR1

<400> SEQUENCE: 106

Asp Ile Val Met Thr Gln Thr Pro Leu Ser Ser Pro Val Thr Leu Gly
1               5                   10                  15

Gln Pro Ala Ser Ile Ser Cys
            20

<210> SEQ ID NO 107
<211> LENGTH: 15
<212> TYPE: PRT
<213> ORGANISM: Artificial Sequence
<220> FEATURE:
<223> OTHER INFORMATION: A23 FR2

<400> SEQUENCE: 107

Trp Leu Gln Gln Arg Pro Gly Gln Pro Pro Arg Leu Leu Ile Tyr
1               5                   10                  15

<210> SEQ ID NO 108
<211> LENGTH: 32
<212> TYPE: PRT
<213> ORGANISM: Artificial Sequence
<220> FEATURE:
<223> OTHER INFORMATION: A23 FR3
```

<400> SEQUENCE: 108

Gly Val Pro Asp Arg Phe Ser Gly Ser Gly Ala Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 109
<211> LENGTH: 23
<212> TYPE: PRT
<213> ORGANISM: Artificial Sequence
<220> FEATURE:
<223> OTHER INFORMATION: A27 FR1

<400> SEQUENCE: 109

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 110
<211> LENGTH: 15
<212> TYPE: PRT
<213> ORGANISM: Artificial Sequence
<220> FEATURE:
<223> OTHER INFORMATION: A27 FR2

<400> SEQUENCE: 110

Trp Tyr Gln Gln Lys Pro Gly Gln Ala Pro Arg Leu Leu Ile Tyr
1               5                   10                  15

<210> SEQ ID NO 111
<211> LENGTH: 32
<212> TYPE: PRT
<213> ORGANISM: Artificial Sequence
<220> FEATURE:
<223> OTHER INFORMATION: A27 FR3

<400> SEQUENCE: 111

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 112
<211> LENGTH: 23
<212> TYPE: PRT
<213> ORGANISM: Artificial Sequence
<220> FEATURE:
<223> OTHER INFORMATION: A11 FR1

<400> SEQUENCE: 112

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 113
<211> LENGTH: 15
<212> TYPE: PRT
<213> ORGANISM: Artificial Sequence
<220> FEATURE:
<223> OTHER INFORMATION: A11 FR2

<400> SEQUENCE: 113

Trp Tyr Gln Gln Lys Pro Gly Leu Ala Pro Arg Leu Leu Ile Tyr
1               5                   10                  15

<210> SEQ ID NO 114
<211> LENGTH: 32
<212> TYPE: PRT
<213> ORGANISM: Artificial Sequence
<220> FEATURE:
<223> OTHER INFORMATION: A11 FR3

<400> SEQUENCE: 114

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 115
<211> LENGTH: 23
<212> TYPE: PRT
<213> ORGANISM: Artificial Sequence
<220> FEATURE:
<223> OTHER INFORMATION: L2 FR1

<400> SEQUENCE: 115

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 116
<211> LENGTH: 15
<212> TYPE: PRT
<213> ORGANISM: Artificial Sequence
<220> FEATURE:
<223> OTHER INFORMATION: L2 FR2

<400> SEQUENCE: 116

Trp Tyr Gln Gln Lys Pro Gly Gln Ala Pro Arg Leu Leu Ile Tyr
1               5                   10                  15

<210> SEQ ID NO 117
<211> LENGTH: 32
<212> TYPE: PRT
<213> ORGANISM: Artificial Sequence
<220> FEATURE:
<223> OTHER INFORMATION: L2 FR3

<400> SEQUENCE: 117

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 118
<211> LENGTH: 23
<212> TYPE: PRT
<213> ORGANISM: Artificial Sequence
<220> FEATURE:
<223> OTHER INFORMATION: L16 FR1

<400> SEQUENCE: 118

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 119
<211> LENGTH: 15
<212> TYPE: PRT
<213> ORGANISM: Artificial Sequence
<220> FEATURE:
<223> OTHER INFORMATION: L16 FR2

<400> SEQUENCE: 119

Trp Tyr Gln Gln Lys Pro Gly Gln Ala Pro Arg Leu Leu Ile Tyr
1               5                   10                  15

<210> SEQ ID NO 120
<211> LENGTH: 32
<212> TYPE: PRT
<213> ORGANISM: Artificial Sequence
<220> FEATURE:
<223> OTHER INFORMATION: L16 FR3

<400> SEQUENCE: 120

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 121
<211> LENGTH: 23
<212> TYPE: PRT
<213> ORGANISM: Artificial Sequence
<220> FEATURE:
<223> OTHER INFORMATION: L6 FR1

<400> SEQUENCE: 121

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 122
<211> LENGTH: 15
<212> TYPE: PRT
<213> ORGANISM: Artificial Sequence
<220> FEATURE:
<223> OTHER INFORMATION: L6 FR2

<400> SEQUENCE: 122

Trp Tyr Gln Gln Lys Pro Gly Gln Ala Pro Arg Leu Leu Ile Tyr
1               5                   10                  15

<210> SEQ ID NO 123
<211> LENGTH: 32
<212> TYPE: PRT
<213> ORGANISM: Artificial Sequence
<220> FEATURE:
<223> OTHER INFORMATION: L6 FR3

<400> SEQUENCE: 123

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 124
<211> LENGTH: 23
<212> TYPE: PRT

<213> ORGANISM: Artificial Sequence
<220> FEATURE:
<223> OTHER INFORMATION: L20 FR1

<400> SEQUENCE: 124

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 125
<211> LENGTH: 15
<212> TYPE: PRT
<213> ORGANISM: Artificial Sequence
<220> FEATURE:
<223> OTHER INFORMATION: L20 FR2

<400> SEQUENCE: 125

Trp Tyr Gln Gln Lys Pro Gly Gln Ala Pro Arg Leu Leu Ile Tyr
1               5                   10                  15

<210> SEQ ID NO 126
<211> LENGTH: 32
<212> TYPE: PRT
<213> ORGANISM: Artificial Sequence
<220> FEATURE:
<223> OTHER INFORMATION: L20 FR3

<400> SEQUENCE: 126

Gly Ile Pro Ala Arg Phe Ser Gly Ser Gly Pro Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 127
<211> LENGTH: 23
<212> TYPE: PRT
<213> ORGANISM: Artificial Sequence
<220> FEATURE:
<223> OTHER INFORMATION: L25 FR1

<400> SEQUENCE: 127

Glu Ile Val Met Thr Gln Ser Pro Ala Thr Leu Ser Leu Ser Pro Gly
1               5                   10                  15

Glu Arg Ala Thr Leu Ser Cys
            20

<210> SEQ ID NO 128
<211> LENGTH: 15
<212> TYPE: PRT
<213> ORGANISM: Artificial Sequence
<220> FEATURE:
<223> OTHER INFORMATION: L25 FR2

<400> SEQUENCE: 128

Trp Tyr Gln Gln Lys Pro Gly Gln Ala Pro Arg Leu Leu Ile Tyr
1               5                   10                  15

<210> SEQ ID NO 129
<211> LENGTH: 32
<212> TYPE: PRT
<213> ORGANISM: Artificial Sequence
<220> FEATURE:
<223> OTHER INFORMATION: L25 FR3

<400> SEQUENCE: 129

```
Gly Ile Pro Ala Arg Phe Ser Gly Ser Gly Ser Gly Thr Asp Phe Thr
1               5                   10                  15

Leu Thr Ile Ser Ser Leu Gln Pro Glu Asp Phe Ala Val Tyr Tyr Cys
            20                  25                  30
```

<210> SEQ ID NO 130
<211> LENGTH: 23
<212> TYPE: PRT
<213> ORGANISM: Artificial Sequence
<220> FEATURE:
<223> OTHER INFORMATION: B3 FR1

<400> SEQUENCE: 130

```
Asp Ile Val Met Thr Gln Ser Pro Asp Ser Leu Ala Val Ser Leu Gly
1               5                   10                  15

Glu Arg Ala Thr Ile Asn Cys
            20
```

<210> SEQ ID NO 131
<211> LENGTH: 15
<212> TYPE: PRT
<213> ORGANISM: Artificial Sequence
<220> FEATURE:
<223> OTHER INFORMATION: B3 FR2

<400> SEQUENCE: 131

```
Trp Tyr Gln Gln Lys Pro Gly Gln Pro Pro Lys Leu Leu Ile Tyr
1               5                   10                  15
```

<210> SEQ ID NO 132
<211> LENGTH: 32
<212> TYPE: PRT
<213> ORGANISM: Artificial Sequence
<220> FEATURE:
<223> OTHER INFORMATION: B3 FR3

<400> SEQUENCE: 132

```
Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30
```

<210> SEQ ID NO 133
<211> LENGTH: 23
<212> TYPE: PRT
<213> ORGANISM: Artificial Sequence
<220> FEATURE:
<223> OTHER INFORMATION: B2 FR1

<400> SEQUENCE: 133

```
Glu Thr Thr Leu Thr Gln Ser Pro Ala Phe Met Ser Ala Thr Pro Gly
1               5                   10                  15

Asp Lys Val Asn Ile Ser Cys
            20
```

<210> SEQ ID NO 134
<211> LENGTH: 15
<212> TYPE: PRT
<213> ORGANISM: Artificial Sequence
<220> FEATURE:
<223> OTHER INFORMATION: B2 FR2

<400> SEQUENCE: 134

```
Trp Tyr Gln Gln Lys Pro Gly Glu Ala Ala Ile Phe Ile Ile Gln
```

<210> SEQ ID NO 135
<211> LENGTH: 32
<212> TYPE: PRT
<213> ORGANISM: Artificial Sequence
<220> FEATURE:
<223> OTHER INFORMATION: B2 FR3

<400> SEQUENCE: 135

Gly Ile Pro Pro Arg Phe Ser Gly Ser Gly Tyr Gly Thr Asp Phe Thr
1               5                   10                  15
Leu Thr Ile Asn Asn Ile Glu Ser Glu Asp Ala Ala Tyr Tyr Phe Cys
            20                  25                  30

<210> SEQ ID NO 136
<211> LENGTH: 23
<212> TYPE: PRT
<213> ORGANISM: Artificial Sequence
<220> FEATURE:
<223> OTHER INFORMATION: A26 FR1

<400> SEQUENCE: 136

Glu Ile Val Leu Thr Gln Ser Pro Asp Phe Gln Ser Val Thr Pro Lys
1               5                   10                  15
Glu Lys Val Thr Ile Thr Cys
            20

<210> SEQ ID NO 137
<211> LENGTH: 15
<212> TYPE: PRT
<213> ORGANISM: Artificial Sequence
<220> FEATURE:
<223> OTHER INFORMATION: A26 FR2

<400> SEQUENCE: 137

Trp Tyr Gln Gln Lys Pro Asp Gln Ser Pro Lys Leu Leu Ile Lys
1               5                   10                  15

<210> SEQ ID NO 138
<211> LENGTH: 32
<212> TYPE: PRT
<213> ORGANISM: Artificial Sequence
<220> FEATURE:
<223> OTHER INFORMATION: A26 FR3

<400> SEQUENCE: 138

Gly Val Pro Ser Arg Phe Ser Gly Ser Gly Ser Gly Thr Asp Phe Thr
1               5                   10                  15
Leu Thr Ile Asn Ser Leu Glu Ala Glu Asp Ala Ala Thr Tyr Tyr Cys
            20                  25                  30

<210> SEQ ID NO 139
<211> LENGTH: 23
<212> TYPE: PRT
<213> ORGANISM: Artificial Sequence
<220> FEATURE:
<223> OTHER INFORMATION: A10 FR1

<400> SEQUENCE: 139

Glu Ile Val Leu Thr Gln Ser Pro Asp Phe Gln Ser Val Thr Pro Lys
1               5                   10                  15
Glu Lys Val Thr Ile Thr Cys
            20

<210> SEQ ID NO 140
<211> LENGTH: 15
<212> TYPE: PRT
<213> ORGANISM: Artificial Sequence
<220> FEATURE:
<223> OTHER INFORMATION: A10 FR2

<400> SEQUENCE: 140

Trp Tyr Gln Gln Lys Pro Asp Gln Ser Pro Lys Leu Leu Ile Lys
1               5                   10                  15

<210> SEQ ID NO 141
<211> LENGTH: 32
<212> TYPE: PRT
<213> ORGANISM: Artificial Sequence
<220> FEATURE:
<223> OTHER INFORMATION: A10 FR3

<400> SEQUENCE: 141

Gly Val Pro Ser Arg Phe Ser Gly Ser Gly Ser Gly Thr Asp Phe Thr
1               5                   10                  15

Leu Thr Ile Asn Ser Leu Glu Ala Glu Asp Ala Ala Thr Tyr Tyr Cys
            20                  25                  30

<210> SEQ ID NO 142
<211> LENGTH: 23
<212> TYPE: PRT
<213> ORGANISM: Artificial Sequence
<220> FEATURE:
<223> OTHER INFORMATION: A14 FR1

<400> SEQUENCE: 142

Asp Val Val Met Thr Gln Ser Pro Ala Phe Leu Ser Val Thr Pro Gly
1               5                   10                  15

Glu Lys Val Thr Ile Thr Cys
            20

<210> SEQ ID NO 143
<211> LENGTH: 15
<212> TYPE: PRT
<213> ORGANISM: Artificial Sequence
<220> FEATURE:
<223> OTHER INFORMATION: A14 FR2

<400> SEQUENCE: 143

Trp Tyr Gln Gln Lys Pro Asp Gln Ala Pro Lys Leu Leu Ile Lys
1               5                   10                  15

<210> SEQ ID NO 144
<211> LENGTH: 32
<212> TYPE: PRT
<213> ORGANISM: Artificial Sequence
<220> FEATURE:
<223> OTHER INFORMATION: A14 FR3

<400> SEQUENCE: 144

Gly Val Pro Ser Arg Phe Ser Gly Ser Gly Ser Gly Thr Asp Phe Thr
1               5                   10                  15

Phe Thr Ile Ser Ser Leu Glu Ala Glu Asp Ala Ala Thr Tyr Tyr Cys
            20                  25                  30

<210> SEQ ID NO 145
<211> LENGTH: 10
<212> TYPE: PRT
<213> ORGANISM: Artificial Sequence

```
<220> FEATURE:
<223> OTHER INFORMATION: JK1 FR4

<400> SEQUENCE: 145

Phe Gly Gln Gly Thr Lys Val Glu Ile Lys
1               5                   10

<210> SEQ ID NO 146
<211> LENGTH: 10
<212> TYPE: PRT
<213> ORGANISM: Artificial Sequence
<220> FEATURE:
<223> OTHER INFORMATION: JK2 FR4

<400> SEQUENCE: 146

Phe Gly Gln Gly Thr Lys Leu Glu Ile Lys
1               5                   10

<210> SEQ ID NO 147
<211> LENGTH: 10
<212> TYPE: PRT
<213> ORGANISM: Artificial Sequence
<220> FEATURE:
<223> OTHER INFORMATION: JK3 FR4

<400> SEQUENCE: 147

Phe Gly Pro Gly Thr Lys Val Asp Ile Lys
1               5                   10

<210> SEQ ID NO 148
<211> LENGTH: 10
<212> TYPE: PRT
<213> ORGANISM: Artificial Sequence
<220> FEATURE:
<223> OTHER INFORMATION: JK4 FR4

<400> SEQUENCE: 148

Phe Gly Gly Gly Thr Lys Val Glu Ile Lys
1               5                   10

<210> SEQ ID NO 149
<211> LENGTH: 10
<212> TYPE: PRT
<213> ORGANISM: Artificial Sequence
<220> FEATURE:
<223> OTHER INFORMATION: JK5 FR4

<400> SEQUENCE: 149

Phe Gly Gln Gly Thr Arg Leu Glu Ile Lys
1               5                   10

<210> SEQ ID NO 150
<211> LENGTH: 22
<212> TYPE: PRT
<213> ORGANISM: Artificial Sequence
<220> FEATURE:
<223> OTHER INFORMATION: 1a FR1

<400> SEQUENCE: 150

Gln Ser Val Leu Thr Gln Pro Pro Ser Val Ser Glu Ala Pro Arg Gln
1               5                   10                  15

Arg Val Thr Ile Ser Cys
            20

<210> SEQ ID NO 151
<211> LENGTH: 15
```

```
<212> TYPE: PRT
<213> ORGANISM: Artificial Sequence
<220> FEATURE:
<223> OTHER INFORMATION: 1a FR2

<400> SEQUENCE: 151

Trp Tyr Gln Gln Leu Pro Gly Lys Ala Pro Lys Leu Leu Ile Tyr
1               5                   10                  15

<210> SEQ ID NO 152
<211> LENGTH: 32
<212> TYPE: PRT
<213> ORGANISM: Artificial Sequence
<220> FEATURE:
<223> OTHER INFORMATION: 1a FR3

<400> SEQUENCE: 152

Gly Val Ser Asp Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
            20                  25                  30

<210> SEQ ID NO 153
<211> LENGTH: 22
<212> TYPE: PRT
<213> ORGANISM: Artificial Sequence
<220> FEATURE:
<223> OTHER INFORMATION: 1e FR1

<400> SEQUENCE: 153

Gln Ser Val Leu Thr Gln Pro Pro Ser Val Ser Gly Ala Pro Gly Gln
1               5                   10                  15

Arg Val Thr Ile Ser Cys
            20

<210> SEQ ID NO 154
<211> LENGTH: 15
<212> TYPE: PRT
<213> ORGANISM: Artificial Sequence
<220> FEATURE:
<223> OTHER INFORMATION: 1e FR2

<400> SEQUENCE: 154

Trp Tyr Gln Gln Leu Pro Gly Thr Ala Pro Lys Leu Leu Ile Tyr
1               5                   10                  15

<210> SEQ ID NO 155
<211> LENGTH: 32
<212> TYPE: PRT
<213> ORGANISM: Artificial Sequence
<220> FEATURE:
<223> OTHER INFORMATION: 1e FR3

<400> SEQUENCE: 155

Gly Val Pro Asp Arg Phe Ser Gly Ser Lys Ser Gly Thr Ser Ala Ser
1               5                   10                  15

Leu Ala Ile Thr Gly Leu Gln Ala Glu Asp Glu Ala Asp Tyr Tyr Cys
            20                  25                  30

<210> SEQ ID NO 156
<211> LENGTH: 22
<212> TYPE: PRT
<213> ORGANISM: Artificial Sequence
<220> FEATURE:
<223> OTHER INFORMATION: 1c FR1
```

<400> SEQUENCE: 156

Gln Ser Val Leu Thr Gln Pro Pro Ser Ala Ser Gly Thr Pro Gly Gln
1               5                   10                  15

Arg Val Thr Ile Ser Cys
            20

<210> SEQ ID NO 157
<211> LENGTH: 15
<212> TYPE: PRT
<213> ORGANISM: Artificial Sequence
<220> FEATURE:
<223> OTHER INFORMATION: 1c FR2

<400> SEQUENCE: 157

Trp Tyr Gln Gln Leu Pro Gly Thr Ala Pro Lys Leu Leu Ile Tyr
1               5                   10                  15

<210> SEQ ID NO 158
<211> LENGTH: 32
<212> TYPE: PRT
<213> ORGANISM: Artificial Sequence
<220> FEATURE:
<223> OTHER INFORMATION: 1c FR3

<400> SEQUENCE: 158

Gly Val Pro Asp Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
            20                  25                  30

<210> SEQ ID NO 159
<211> LENGTH: 22
<212> TYPE: PRT
<213> ORGANISM: Artificial Sequence
<220> FEATURE:
<223> OTHER INFORMATION: 1g FR1

<400> SEQUENCE: 159

Gln Ser Val Leu Thr Gln Pro Pro Ser Ala Ser Gly Thr Pro Gly Gln
1               5                   10                  15

Arg Val Thr Ile Ser Cys
            20

<210> SEQ ID NO 160
<211> LENGTH: 15
<212> TYPE: PRT
<213> ORGANISM: Artificial Sequence
<220> FEATURE:
<223> OTHER INFORMATION: 1g FR2

<400> SEQUENCE: 160

Trp Tyr Gln Gln Leu Pro Gly Thr Ala Pro Lys Leu Leu Ile Tyr
1               5                   10                  15

<210> SEQ ID NO 161
<211> LENGTH: 32
<212> TYPE: PRT
<213> ORGANISM: Artificial Sequence
<220> FEATURE:
<223> OTHER INFORMATION: 1g FR3

<400> SEQUENCE: 161

Gly Val Pro Asp Arg Phe Ser Gly Ser Lys Ser Gly Thr Ser Ala Ser
1               5                   10                  15

Leu Ala Ile Ser Gly Leu Arg Ser Glu Asp Glu Ala Asp Tyr Tyr Cys
            20                  25                  30

<210> SEQ ID NO 162
<211> LENGTH: 22
<212> TYPE: PRT
<213> ORGANISM: Artificial Sequence
<220> FEATURE:
<223> OTHER INFORMATION: 1b FR1

<400> SEQUENCE: 162

Gln Ser Val Leu Thr Gln Pro Pro Ser Val Ser Ala Ala Pro Gly Gln
1               5                   10                  15

Lys Val Thr Ile Ser Cys
            20

<210> SEQ ID NO 163
<211> LENGTH: 15
<212> TYPE: PRT
<213> ORGANISM: Artificial Sequence
<220> FEATURE:
<223> OTHER INFORMATION: 1b FR2

<400> SEQUENCE: 163

Trp Tyr Gln Gln Leu Pro Gly Thr Ala Pro Lys Leu Leu Ile Tyr
1               5                   10                  15

<210> SEQ ID NO 164
<211> LENGTH: 32
<212> TYPE: PRT
<213> ORGANISM: Artificial Sequence
<220> FEATURE:
<223> OTHER INFORMATION: 1b FR3

<400> SEQUENCE: 164

Gly Ile Pro Asp Arg Phe Ser Gly Ser Lys Ser Gly Thr Ser Ala Thr
1               5                   10                  15

Leu Gly Ile Thr Gly Leu Gln Thr Gly Asp Glu Ala Asp Tyr Tyr Cys
            20                  25                  30

<210> SEQ ID NO 165
<211> LENGTH: 22
<212> TYPE: PRT
<213> ORGANISM: Artificial Sequence
<220> FEATURE:
<223> OTHER INFORMATION: 2c FR1

<400> SEQUENCE: 165

Gln Ser Ala Leu Thr Gln Pro Pro Ser Ala Ser Gly Ser Pro Gly Gln
1               5                   10                  15

Ser Val Thr Ile Ser Cys
            20

<210> SEQ ID NO 166
<211> LENGTH: 15
<212> TYPE: PRT
<213> ORGANISM: Artificial Sequence
<220> FEATURE:
<223> OTHER INFORMATION: 2c FR2

<400> SEQUENCE: 166

Trp Tyr Gln Gln His Pro Gly Lys Ala Pro Lys Leu Met Ile Tyr
1               5                   10                  15

<210> SEQ ID NO 167

```
<211> LENGTH: 32
<212> TYPE: PRT
<213> ORGANISM: Artificial Sequence
<220> FEATURE:
<223> OTHER INFORMATION: 2c FR3

<400> SEQUENCE: 167

Gly Val Pro Asp Arg Phe Ser Gly Ser Lys Ser Gly Asn Thr Ala Ser
1               5                   10                  15

Leu Thr Val Ser Gly Leu Gln Ala Glu Asp Glu Ala Asp Tyr Tyr Cys
            20                  25                  30

<210> SEQ ID NO 168
<211> LENGTH: 22
<212> TYPE: PRT
<213> ORGANISM: Artificial Sequence
<220> FEATURE:
<223> OTHER INFORMATION: 2e FR1

<400> SEQUENCE: 168

Gln Ser Ala Leu Thr Gln Pro Arg Ser Val Ser Gly Ser Pro Gly Gln
1               5                   10                  15

Ser Val Thr Ile Ser Cys
            20

<210> SEQ ID NO 169
<211> LENGTH: 15
<212> TYPE: PRT
<213> ORGANISM: Artificial Sequence
<220> FEATURE:
<223> OTHER INFORMATION: 2e FR2

<400> SEQUENCE: 169

Trp Tyr Gln Gln His Pro Gly Lys Ala Pro Lys Leu Met Ile Tyr
1               5                   10                  15

<210> SEQ ID NO 170
<211> LENGTH: 32
<212> TYPE: PRT
<213> ORGANISM: Artificial Sequence
<220> FEATURE:
<223> OTHER INFORMATION: 2e FR3

<400> SEQUENCE: 170

Gly Val Pro Asp Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 171
<211> LENGTH: 22
<212> TYPE: PRT
<213> ORGANISM: Artificial Sequence
<220> FEATURE:
<223> OTHER INFORMATION: 2a2 FR1

<400> SEQUENCE: 171

Gln Ser Ala Leu Thr Gln Pro Ala Ser Val Ser Gly Ser Pro Gly Gln
1               5                   10                  15

Ser Ile Thr Ile Ser Cys
            20

<210> SEQ ID NO 172
<211> LENGTH: 15
<212> TYPE: PRT
```

```
<213> ORGANISM: Artificial Sequence
<220> FEATURE:
<223> OTHER INFORMATION: 2a2 FR2

<400> SEQUENCE: 172

Trp Tyr Gln Gln His Pro Gly Lys Ala Pro Lys Leu Met Ile Tyr
1               5                   10                  15

<210> SEQ ID NO 173
<211> LENGTH: 32
<212> TYPE: PRT
<213> ORGANISM: Artificial Sequence
<220> FEATURE:
<223> OTHER INFORMATION: 2a2 FR3

<400> SEQUENCE: 173

Gly Val Ser Asn Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 174
<211> LENGTH: 22
<212> TYPE: PRT
<213> ORGANISM: Artificial Sequence
<220> FEATURE:
<223> OTHER INFORMATION: 2d FR1

<400> SEQUENCE: 174

Gln Ser Ala Leu Thr Gln Pro Pro Ser Val Ser Gly Ser Pro Gly Gln
1               5                   10                  15

Ser Val Thr Ile Ser Cys
            20

<210> SEQ ID NO 175
<211> LENGTH: 15
<212> TYPE: PRT
<213> ORGANISM: Artificial Sequence
<220> FEATURE:
<223> OTHER INFORMATION: 2d FR2

<400> SEQUENCE: 175

Trp Tyr Gln Gln Pro Pro Gly Thr Ala Pro Lys Leu Met Ile Tyr
1               5                   10                  15

<210> SEQ ID NO 176
<211> LENGTH: 32
<212> TYPE: PRT
<213> ORGANISM: Artificial Sequence
<220> FEATURE:
<223> OTHER INFORMATION: 2d FR3

<400> SEQUENCE: 176

Gly Val Pro Asp Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 177
<211> LENGTH: 22
<212> TYPE: PRT
<213> ORGANISM: Artificial Sequence
<220> FEATURE:
<223> OTHER INFORMATION: 2b2 FR1

<400> SEQUENCE: 177
```

Gln Ser Ala Leu Thr Gln Pro Ala Ser Val Ser Gly Ser Pro Gly Gln
1               5                   10                  15

Ser Ile Thr Ile Ser Cys
            20

<210> SEQ ID NO 178
<211> LENGTH: 15
<212> TYPE: PRT
<213> ORGANISM: Artificial Sequence
<220> FEATURE:
<223> OTHER INFORMATION: 2b2 FR2

<400> SEQUENCE: 178

Trp Tyr Gln Gln His Pro Gly Lys Ala Pro Lys Leu Met Ile Tyr
1               5                   10                  15

<210> SEQ ID NO 179
<211> LENGTH: 32
<212> TYPE: PRT
<213> ORGANISM: Artificial Sequence
<220> FEATURE:
<223> OTHER INFORMATION: 2b2 FR3

<400> SEQUENCE: 179

Gly Val Ser Asn Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 180
<211> LENGTH: 22
<212> TYPE: PRT
<213> ORGANISM: Artificial Sequence
<220> FEATURE:
<223> OTHER INFORMATION: 3r FR1

<400> SEQUENCE: 180

Ser Tyr Glu Leu Thr Gln Pro Pro Ser Val Ser Val Ser Pro Gly Gln
1               5                   10                  15

Thr Ala Ser Ile Thr Cys
            20

<210> SEQ ID NO 181
<211> LENGTH: 15
<212> TYPE: PRT
<213> ORGANISM: Artificial Sequence
<220> FEATURE:
<223> OTHER INFORMATION: 3r FR2

<400> SEQUENCE: 181

Trp Tyr Gln Gln Lys Pro Gly Gln Ser Pro Val Leu Val Ile Tyr
1               5                   10                  15

<210> SEQ ID NO 182
<211> LENGTH: 32
<212> TYPE: PRT
<213> ORGANISM: Artificial Sequence
<220> FEATURE:
<223> OTHER INFORMATION: 3r FR3

<400> SEQUENCE: 182

Gly Ile Pro Glu Arg Phe Ser Gly Ser Asn Ser Gly Asn Thr Ala Thr
1               5                   10                  15

Leu Thr Ile Ser Gly Thr Gln Ala Met Asp Glu Ala Asp Tyr Tyr Cys

-continued

```
                20                  25                  30
```

<210> SEQ ID NO 183
<211> LENGTH: 22
<212> TYPE: PRT
<213> ORGANISM: Artificial Sequence
<220> FEATURE:
<223> OTHER INFORMATION: 3j FR1

<400> SEQUENCE: 183

Ser Tyr Glu Leu Thr Gln Pro Leu Ser Val Ser Val Ala Leu Gly Gln
1               5                   10                  15

Thr Ala Arg Ile Thr Cys
            20

<210> SEQ ID NO 184
<211> LENGTH: 15
<212> TYPE: PRT
<213> ORGANISM: Artificial Sequence
<220> FEATURE:
<223> OTHER INFORMATION: 3j FR2

<400> SEQUENCE: 184

Trp Tyr Gln Gln Lys Pro Gly Gln Ala Pro Val Leu Val Ile Tyr
1               5                   10                  15

<210> SEQ ID NO 185
<211> LENGTH: 32
<212> TYPE: PRT
<213> ORGANISM: Artificial Sequence
<220> FEATURE:
<223> OTHER INFORMATION: 3j FR3

<400> SEQUENCE: 185

Gly Ile Pro Glu Arg Phe Ser Gly Ser Asn Ser Gly Asn Thr Ala Thr
1               5                   10                  15

Leu Thr Ile Ser Arg Ala Gln Ala Gly Asp Glu Ala Asp Tyr Tyr Cys
            20                  25                  30

<210> SEQ ID NO 186
<211> LENGTH: 22
<212> TYPE: PRT
<213> ORGANISM: Artificial Sequence
<220> FEATURE:
<223> OTHER INFORMATION: 3p FR1

<400> SEQUENCE: 186

Ser Tyr Glu Leu Thr Gln Pro Pro Ser Val Ser Val Ser Pro Gly Gln
1               5                   10                  15

Thr Ala Arg Ile Thr Cys
            20

<210> SEQ ID NO 187
<211> LENGTH: 15
<212> TYPE: PRT
<213> ORGANISM: Artificial Sequence
<220> FEATURE:
<223> OTHER INFORMATION: 3p FR2

<400> SEQUENCE: 187

Trp Tyr Gln Gln Lys Ser Gly Gln Ala Pro Val Leu Val Ile Tyr
1               5                   10                  15

<210> SEQ ID NO 188
<211> LENGTH: 32

```
<212> TYPE: PRT
<213> ORGANISM: Artificial Sequence
<220> FEATURE:
<223> OTHER INFORMATION: 3p FR3

<400> SEQUENCE: 188

Gly Ile Pro Glu Arg Phe Ser Gly Ser Ser Gly Thr Met Ala Thr
1               5                   10                  15

Leu Thr Ile Ser Gly Ala Gln Val Glu Asp Glu Ala Asp Tyr Tyr Cys
            20                  25                  30

<210> SEQ ID NO 189
<211> LENGTH: 22
<212> TYPE: PRT
<213> ORGANISM: Artificial Sequence
<220> FEATURE:
<223> OTHER INFORMATION: 3a FR1

<400> SEQUENCE: 189

Ser Tyr Glu Leu Thr Gln Pro Pro Ser Val Ser Val Ser Leu Gly Gln
1               5                   10                  15

Met Ala Arg Ile Thr Cys
            20

<210> SEQ ID NO 190
<211> LENGTH: 15
<212> TYPE: PRT
<213> ORGANISM: Artificial Sequence
<220> FEATURE:
<223> OTHER INFORMATION: 3a FR2

<400> SEQUENCE: 190

Trp Tyr Gln Gln Lys Pro Gly Gln Phe Pro Val Leu Val Ile Tyr
1               5                   10                  15

<210> SEQ ID NO 191
<211> LENGTH: 32
<212> TYPE: PRT
<213> ORGANISM: Artificial Sequence
<220> FEATURE:
<223> OTHER INFORMATION: 3a FR3

<400> SEQUENCE: 191

Gly Ile Pro Glu Arg Phe Ser Gly Ser Ser Gly Thr Ile Val Thr
1               5                   10                  15

Leu Thr Ile Ser Gly Val Gln Ala Glu Asp Glu Ala Asp Tyr Tyr Cys
            20                  25                  30

<210> SEQ ID NO 192
<211> LENGTH: 22
<212> TYPE: PRT
<213> ORGANISM: Artificial Sequence
<220> FEATURE:
<223> OTHER INFORMATION: 3l FR1

<400> SEQUENCE: 192

Ser Ser Glu Leu Thr Gln Asp Pro Ala Val Ser Val Ala Leu Gly Gln
1               5                   10                  15

Thr Val Arg Ile Thr Cys
            20

<210> SEQ ID NO 193
<211> LENGTH: 15
<212> TYPE: PRT
<213> ORGANISM: Artificial Sequence
```

```
<220> FEATURE:
<223> OTHER INFORMATION: 3l FR2

<400> SEQUENCE: 193

Trp Tyr Gln Gln Lys Pro Gly Gln Ala Pro Val Leu Val Ile Tyr
1               5                   10                  15

<210> SEQ ID NO 194
<211> LENGTH: 32
<212> TYPE: PRT
<213> ORGANISM: Artificial Sequence
<220> FEATURE:
<223> OTHER INFORMATION: 3l FR3

<400> SEQUENCE: 194

Gly Ile Pro Asp Arg Phe Ser Gly Ser Ser Gly Asn Thr Ala Ser
1               5                   10                  15

Leu Thr Ile Thr Gly Ala Gln Ala Glu Asp Glu Ala Asp Tyr Tyr Cys
            20                  25                  30

<210> SEQ ID NO 195
<211> LENGTH: 22
<212> TYPE: PRT
<213> ORGANISM: Artificial Sequence
<220> FEATURE:
<223> OTHER INFORMATION: 3h FR1

<400> SEQUENCE: 195

Ser Tyr Val Leu Thr Gln Pro Pro Ser Val Ser Val Ala Pro Gly Lys
1               5                   10                  15

Thr Ala Arg Ile Thr Cys
            20

<210> SEQ ID NO 196
<211> LENGTH: 15
<212> TYPE: PRT
<213> ORGANISM: Artificial Sequence
<220> FEATURE:
<223> OTHER INFORMATION: 3h FR2

<400> SEQUENCE: 196

Trp Tyr Gln Gln Lys Pro Gly Gln Ala Pro Val Leu Val Ile Tyr
1               5                   10                  15

<210> SEQ ID NO 197
<211> LENGTH: 32
<212> TYPE: PRT
<213> ORGANISM: Artificial Sequence
<220> FEATURE:
<223> OTHER INFORMATION: 3h FR3

<400> SEQUENCE: 197

Gly Ile Pro Glu Arg Phe Ser Gly Ser Asn Ser Gly Asn Thr Ala Thr
1               5                   10                  15

Leu Thr Ile Ser Arg Val Glu Ala Gly Asp Glu Ala Asp Tyr Tyr Cys
            20                  25                  30

<210> SEQ ID NO 198
<211> LENGTH: 22
<212> TYPE: PRT
<213> ORGANISM: Artificial Sequence
<220> FEATURE:
<223> OTHER INFORMATION: 3e FR1

<400> SEQUENCE: 198
```

Ser Tyr Glu Leu Thr Gln Leu Pro Ser Val Ser Val Ser Pro Gly Gln
1               5                   10                  15

Thr Ala Arg Ile Thr Cys
            20

<210> SEQ ID NO 199
<211> LENGTH: 15
<212> TYPE: PRT
<213> ORGANISM: Artificial Sequence
<220> FEATURE:
<223> OTHER INFORMATION: 3e FR2

<400> SEQUENCE: 199

Trp Tyr Gln Gln Lys Pro Gly Gln Ala Pro Glu Leu Val Ile Tyr
1               5                   10                  15

<210> SEQ ID NO 200
<211> LENGTH: 32
<212> TYPE: PRT
<213> ORGANISM: Artificial Sequence
<220> FEATURE:
<223> OTHER INFORMATION: 3e FR3

<400> SEQUENCE: 200

Gly Ile Pro Glu Arg Phe Ser Gly Ser Thr Ser Gly Asn Thr Thr Thr
1               5                   10                  15

Leu Thr Ile Ser Arg Val Leu Thr Glu Asp Glu Ala Asp Tyr Tyr Cys
            20                  25                  30

<210> SEQ ID NO 201
<211> LENGTH: 22
<212> TYPE: PRT
<213> ORGANISM: Artificial Sequence
<220> FEATURE:
<223> OTHER INFORMATION: 3m FR1

<400> SEQUENCE: 201

Ser Tyr Glu Leu Met Gln Pro Pro Ser Val Ser Val Ser Pro Gly Gln
1               5                   10                  15

Thr Ala Arg Ile Thr Cys
            20

<210> SEQ ID NO 202
<211> LENGTH: 15
<212> TYPE: PRT
<213> ORGANISM: Artificial Sequence
<220> FEATURE:
<223> OTHER INFORMATION: 3m FR2

<400> SEQUENCE: 202

Trp Tyr Gln Gln Lys Pro Gly Gln Ala Pro Val Leu Val Ile Tyr
1               5                   10                  15

<210> SEQ ID NO 203
<211> LENGTH: 32
<212> TYPE: PRT
<213> ORGANISM: Artificial Sequence
<220> FEATURE:
<223> OTHER INFORMATION: 3m FR3

<400> SEQUENCE: 203

Gly Ile Pro Glu Arg Phe Ser Gly Ser Ser Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 204
<211> LENGTH: 22
<212> TYPE: PRT
<213> ORGANISM: Artificial Sequence
<220> FEATURE:
<223> OTHER INFORMATION: 2-19 FR1

<400> SEQUENCE: 204

Ser Tyr Glu Leu Thr Gln Pro Ser Ser Val Ser Val Ser Pro Gly Gln
1               5                   10                  15

Thr Ala Arg Ile Thr Cys
            20

<210> SEQ ID NO 205
<211> LENGTH: 15
<212> TYPE: PRT
<213> ORGANISM: Artificial Sequence
<220> FEATURE:
<223> OTHER INFORMATION: 2-19 FR2

<400> SEQUENCE: 205

Trp Phe Gln Gln Lys Pro Gly Gln Ala Pro Val Leu Val Ile Tyr
1               5                   10                  15

<210> SEQ ID NO 206
<211> LENGTH: 32
<212> TYPE: PRT
<213> ORGANISM: Artificial Sequence
<220> FEATURE:
<223> OTHER INFORMATION: 2-19 FR3

<400> SEQUENCE: 206

Gly Ile Pro Glu Arg Phe Ser Gly Ser Ser Gly Thr Thr Val Thr
1               5                   10                  15

Leu Thr Ile Ser Gly Ala Gln Val Glu Asp Glu Ala Asp Tyr Tyr Cys
            20                  25                  30

<210> SEQ ID NO 207
<211> LENGTH: 22
<212> TYPE: PRT
<213> ORGANISM: Artificial Sequence
<220> FEATURE:
<223> OTHER INFORMATION: 4c FR1

<400> SEQUENCE: 207

Leu Pro Val Leu Thr Gln Pro Pro Ser Ala Ser Ala Leu Leu Gly Ala
1               5                   10                  15

Ser Ile Lys Leu Thr Cys
            20

<210> SEQ ID NO 208
<211> LENGTH: 15
<212> TYPE: PRT
<213> ORGANISM: Artificial Sequence
<220> FEATURE:
<223> OTHER INFORMATION: 4c FR2

<400> SEQUENCE: 208

Trp Tyr Gln Gln Arg Pro Gly Arg Ser Pro Gln Tyr Ile Met Lys
1               5                   10                  15

<210> SEQ ID NO 209
<211> LENGTH: 32
<212> TYPE: PRT

<213> ORGANISM: Artificial Sequence
<220> FEATURE:
<223> OTHER INFORMATION: 4c FR3

<400> SEQUENCE: 209

Gly Ile Pro Asp Arg Phe Met Gly Ser Ser Gly Ala Asp Arg Tyr
1               5                   10                  15

Leu Thr Phe Ser Asn Leu Gln Ser Asp Asp Glu Ala Glu Tyr His Cys
            20                  25                  30

<210> SEQ ID NO 210
<211> LENGTH: 22
<212> TYPE: PRT
<213> ORGANISM: Artificial Sequence
<220> FEATURE:
<223> OTHER INFORMATION: 4a FR1

<400> SEQUENCE: 210

Gln Pro Val Leu Thr Gln Ser Ser Ser Ala Ser Ala Ser Leu Gly Ser
1               5                   10                  15

Ser Val Lys Leu Thr Cys
            20

<210> SEQ ID NO 211
<211> LENGTH: 15
<212> TYPE: PRT
<213> ORGANISM: Artificial Sequence
<220> FEATURE:
<223> OTHER INFORMATION: 4a FR2

<400> SEQUENCE: 211

Trp His Gln Gln Gln Pro Gly Lys Ala Pro Arg Tyr Leu Met Lys
1               5                   10                  15

<210> SEQ ID NO 212
<211> LENGTH: 32
<212> TYPE: PRT
<213> ORGANISM: Artificial Sequence
<220> FEATURE:
<223> OTHER INFORMATION: 4a FR3

<400> SEQUENCE: 212

Gly Val Pro Asp Arg Phe Ser Gly Ser Ser Gly Ala Asp Arg Tyr
1               5                   10                  15

Leu Thr Ile Ser Asn Leu Gln Leu Glu Asp Glu Ala Asp Tyr Tyr Cys
            20                  25                  30

<210> SEQ ID NO 213
<211> LENGTH: 22
<212> TYPE: PRT
<213> ORGANISM: Artificial Sequence
<220> FEATURE:
<223> OTHER INFORMATION: 4b FR1

<400> SEQUENCE: 213

Gln Leu Val Leu Thr Gln Ser Pro Ser Ala Ser Ala Ser Leu Gly Ala
1               5                   10                  15

Ser Val Lys Leu Thr Cys
            20

<210> SEQ ID NO 214
<211> LENGTH: 15
<212> TYPE: PRT
<213> ORGANISM: Artificial Sequence
<220> FEATURE:

<223> OTHER INFORMATION: 4b FR2

<400> SEQUENCE: 214

Trp His Gln Gln Gln Pro Glu Lys Gly Pro Arg Tyr Leu Met Lys
1               5                   10                  15

<210> SEQ ID NO 215
<211> LENGTH: 32
<212> TYPE: PRT
<213> ORGANISM: Artificial Sequence
<220> FEATURE:
<223> OTHER INFORMATION: 4b FR3

<400> SEQUENCE: 215

Gly Ile Pro Asp Arg Phe Ser Gly Ser Ser Ser Gly Ala Glu Arg Tyr
1               5                   10                  15

Leu Thr Ile Ser Ser Leu Gln Ser Glu Asp Glu Ala Asp Tyr Tyr Cys
            20                  25                  30

<210> SEQ ID NO 216
<211> LENGTH: 22
<212> TYPE: PRT
<213> ORGANISM: Artificial Sequence
<220> FEATURE:
<223> OTHER INFORMATION: 5e FR1

<400> SEQUENCE: 216

Gln Pro Val Leu Thr Gln Pro Ser Ser Ser Ala Ser Pro Gly Glu
1               5                   10                  15

Ser Ala Arg Leu Thr Cys
            20

<210> SEQ ID NO 217
<211> LENGTH: 15
<212> TYPE: PRT
<213> ORGANISM: Artificial Sequence
<220> FEATURE:
<223> OTHER INFORMATION: 5e FR2

<400> SEQUENCE: 217

Trp Tyr Gln Gln Lys Pro Gly Ser Pro Arg Tyr Leu Leu Tyr
1               5                   10                  15

<210> SEQ ID NO 218
<211> LENGTH: 34
<212> TYPE: PRT
<213> ORGANISM: Artificial Sequence
<220> FEATURE:
<223> OTHER INFORMATION: 5e FR3

<400> SEQUENCE: 218

Gly Val Pro Ser Arg Phe Ser Gly Ser Lys Asp Ala Ser Ala Asn Thr
1               5                   10                  15

Gly Ile Leu Leu Ile Ser Gly Leu Gln Ser Glu Asp Glu Ala Asp Tyr
            20                  25                  30

Tyr Cys

<210> SEQ ID NO 219
<211> LENGTH: 22
<212> TYPE: PRT
<213> ORGANISM: Artificial Sequence
<220> FEATURE:
<223> OTHER INFORMATION: 5c FR1

<400> SEQUENCE: 219

Gln Ala Val Leu Thr Gln Pro Ala Ser Leu Ser Ala Ser Pro Gly Ala
1               5                   10                  15

Ser Ala Ser Leu Thr Cys
            20

<210> SEQ ID NO 220
<211> LENGTH: 15
<212> TYPE: PRT
<213> ORGANISM: Artificial Sequence
<220> FEATURE:
<223> OTHER INFORMATION: 5c FR2

<400> SEQUENCE: 220

Trp Tyr Gln Gln Lys Pro Gly Ser Pro Pro Gln Tyr Leu Leu Arg
1               5                   10                  15

<210> SEQ ID NO 221
<211> LENGTH: 34
<212> TYPE: PRT
<213> ORGANISM: Artificial Sequence
<220> FEATURE:
<223> OTHER INFORMATION: 5c FR3

<400> SEQUENCE: 221

Gly Val Pro Ser Arg Phe Ser Gly Ser Lys Asp Ala Ser Ala Asn Ala
1               5                   10                  15

Gly Ile Leu Leu Ile Ser Gly Leu Gln Ser Glu Asp Glu Ala Asp Tyr
            20                  25                  30

Tyr Cys

<210> SEQ ID NO 222
<211> LENGTH: 22
<212> TYPE: PRT
<213> ORGANISM: Artificial Sequence
<220> FEATURE:
<223> OTHER INFORMATION: 5b FR1

<400> SEQUENCE: 222

Gln Pro Val Leu Thr Gln Pro Ser Ser His Ser Ala Ser Ser Gly Ala
1               5                   10                  15

Ser Val Arg Leu Thr Cys
            20

<210> SEQ ID NO 223
<211> LENGTH: 15
<212> TYPE: PRT
<213> ORGANISM: Artificial Sequence
<220> FEATURE:
<223> OTHER INFORMATION: 5b FR2

<400> SEQUENCE: 223

Trp Tyr Gln Gln Lys Pro Gly Asn Pro Pro Arg Tyr Leu Leu Tyr
1               5                   10                  15

<210> SEQ ID NO 224
<211> LENGTH: 34
<212> TYPE: PRT
<213> ORGANISM: Artificial Sequence
<220> FEATURE:
<223> OTHER INFORMATION: 5b FR3

<400> SEQUENCE: 224

Gly Val Pro Ser Arg Phe Ser Gly Ser Asn Asp Ala Ser Ala Asn Ala
1               5                   10                  15

Gly Ile Leu Arg Ile Ser Gly Leu Gln Pro Glu Asp Glu Ala Asp Tyr
            20                  25                  30

Tyr Cys

<210> SEQ ID NO 225
<211> LENGTH: 22
<212> TYPE: PRT
<213> ORGANISM: Artificial Sequence
<220> FEATURE:
<223> OTHER INFORMATION: 6a FR1

<400> SEQUENCE: 225

Asn Phe Met Leu Thr Gln Pro His Ser Val Ser Glu Ser Pro Gly Lys
1               5                   10                  15

Thr Val Thr Ile Ser Cys
            20

<210> SEQ ID NO 226
<211> LENGTH: 15
<212> TYPE: PRT
<213> ORGANISM: Artificial Sequence
<220> FEATURE:
<223> OTHER INFORMATION: 6a FR2

<400> SEQUENCE: 226

Trp Tyr Gln Gln Arg Pro Gly Ser Ser Pro Thr Thr Val Ile Tyr
1               5                   10                  15

<210> SEQ ID NO 227
<211> LENGTH: 34
<212> TYPE: PRT
<213> ORGANISM: Artificial Sequence
<220> FEATURE:
<223> OTHER INFORMATION: 6a FR3

<400> SEQUENCE: 227

Gly Val Pro Asp Arg Phe Ser Gly Ser Ile Asp Ser Ser Ser Asn Ser
1               5                   10                  15

Ala Ser Leu Thr Ile Ser Gly Leu Lys Thr Glu Asp Glu Ala Asp Tyr
            20                  25                  30

Tyr Cys

<210> SEQ ID NO 228
<211> LENGTH: 22
<212> TYPE: PRT
<213> ORGANISM: Artificial Sequence
<220> FEATURE:
<223> OTHER INFORMATION: 7a FR1

<400> SEQUENCE: 228

Gln Thr Val Val Thr Gln Glu Pro Ser Leu Thr Val Ser Pro Gly Gly
1               5                   10                  15

Thr Val Thr Leu Thr Cys
            20

<210> SEQ ID NO 229
<211> LENGTH: 15
<212> TYPE: PRT
<213> ORGANISM: Artificial Sequence
<220> FEATURE:
<223> OTHER INFORMATION: 7a FR2

<400> SEQUENCE: 229

Trp Phe Gln Gln Lys Pro Gly Gln Ala Pro Arg Ala Leu Ile Tyr
1               5                   10                  15

<210> SEQ ID NO 230
<211> LENGTH: 32
<212> TYPE: PRT
<213> ORGANISM: Artificial Sequence
<220> FEATURE:
<223> OTHER INFORMATION: 7a FR3

<400> SEQUENCE: 230

Trp Thr Pro Ala Arg Phe Ser Gly Ser Leu Leu Gly Gly Lys Ala Ala
1               5                   10                  15

Leu Thr Leu Ser Gly Val Gln Pro Glu Asp Glu Ala Glu Tyr Tyr Cys
            20                  25                  30

<210> SEQ ID NO 231
<211> LENGTH: 22
<212> TYPE: PRT
<213> ORGANISM: Artificial Sequence
<220> FEATURE:
<223> OTHER INFORMATION: 7b FR1

<400> SEQUENCE: 231

Gln Ala Val Val Thr Gln Glu Pro Ser Leu Thr Val Ser Pro Gly Gly
1               5                   10                  15

Thr Val Thr Leu Thr Cys
            20

<210> SEQ ID NO 232
<211> LENGTH: 15
<212> TYPE: PRT
<213> ORGANISM: Artificial Sequence
<220> FEATURE:
<223> OTHER INFORMATION: 7b FR2

<400> SEQUENCE: 232

Trp Phe Gln Gln Lys Pro Gly Gln Ala Pro Arg Thr Leu Ile Tyr
1               5                   10                  15

<210> SEQ ID NO 233
<211> LENGTH: 32
<212> TYPE: PRT
<213> ORGANISM: Artificial Sequence
<220> FEATURE:
<223> OTHER INFORMATION: 7b FR3

<400> SEQUENCE: 233

Trp Thr Pro Ala Arg Phe Ser Gly Ser Leu Leu Gly Gly Lys Ala Ala
1               5                   10                  15

Leu Thr Leu Ser Gly Ala Gln Pro Glu Asp Glu Ala Glu Tyr Tyr Cys
            20                  25                  30

<210> SEQ ID NO 234
<211> LENGTH: 22
<212> TYPE: PRT
<213> ORGANISM: Artificial Sequence
<220> FEATURE:
<223> OTHER INFORMATION: 8a FR1

<400> SEQUENCE: 234

Gln Thr Val Val Thr Gln Glu Pro Ser Phe Ser Val Ser Pro Gly Gly
1               5                   10                  15

Thr Val Thr Leu Thr Cys
            20

<210> SEQ ID NO 235
<211> LENGTH: 15
<212> TYPE: PRT
<213> ORGANISM: Artificial Sequence
<220> FEATURE:
<223> OTHER INFORMATION: 8a FR2

<400> SEQUENCE: 235

Trp Tyr Gln Gln Thr Pro Gly Gln Ala Pro Arg Thr Leu Ile Tyr
1               5                   10                  15

<210> SEQ ID NO 236
<211> LENGTH: 32
<212> TYPE: PRT
<213> ORGANISM: Artificial Sequence
<220> FEATURE:
<223> OTHER INFORMATION: 8a FR3

<400> SEQUENCE: 236

Gly Val Pro Asp Arg Phe Ser Gly Ser Ile Leu Gly Asn Lys Ala Ala
1               5                   10                  15

Leu Thr Ile Thr Gly Ala Gln Ala Asp Asp Glu Ser Asp Tyr Tyr Cys
            20                  25                  30

<210> SEQ ID NO 237
<211> LENGTH: 22
<212> TYPE: PRT
<213> ORGANISM: Artificial Sequence
<220> FEATURE:
<223> OTHER INFORMATION: 9a FR1

<400> SEQUENCE: 237

Gln Pro Val Leu Thr Gln Pro Pro Ser Ala Ser Ala Ser Leu Gly Ala
1               5                   10                  15

Ser Val Thr Leu Thr Cys
            20

<210> SEQ ID NO 238
<211> LENGTH: 15
<212> TYPE: PRT
<213> ORGANISM: Artificial Sequence
<220> FEATURE:
<223> OTHER INFORMATION: 9a FR2

<400> SEQUENCE: 238

Trp Tyr Gln Gln Arg Pro Gly Lys Gly Pro Arg Phe Val Met Arg
1               5                   10                  15

<210> SEQ ID NO 239
<211> LENGTH: 32
<212> TYPE: PRT
<213> ORGANISM: Artificial Sequence
<220> FEATURE:
<223> OTHER INFORMATION: 9a FR3

<400> SEQUENCE: 239

Gly Ile Pro Asp Arg Phe Ser Val Leu Gly Ser Gly Leu Asn Arg Tyr
1               5                   10                  15

Leu Thr Ile Lys Asn Ile Gln Glu Glu Asp Glu Ser Asp Tyr His Cys
            20                  25                  30

<210> SEQ ID NO 240
<211> LENGTH: 22
<212> TYPE: PRT

```
<213> ORGANISM: Artificial Sequence
<220> FEATURE:
<223> OTHER INFORMATION: 10a FR1

<400> SEQUENCE: 240

Gln Ala Gly Leu Thr Gln Pro Pro Ser Val Ser Lys Gly Leu Arg Gln
1               5                   10                  15

Thr Ala Thr Leu Thr Cys
            20

<210> SEQ ID NO 241
<211> LENGTH: 15
<212> TYPE: PRT
<213> ORGANISM: Artificial Sequence
<220> FEATURE:
<223> OTHER INFORMATION: 10a FR2

<400> SEQUENCE: 241

Trp Leu Gln Gln His Gln Gly His Pro Pro Lys Leu Leu Ser Tyr
1               5                   10                  15

<210> SEQ ID NO 242
<211> LENGTH: 32
<212> TYPE: PRT
<213> ORGANISM: Artificial Sequence
<220> FEATURE:
<223> OTHER INFORMATION: 10a FR3

<400> SEQUENCE: 242

Gly Ile Ser Glu Arg Leu Ser Ala Ser Arg Ser Gly Asn Thr Ala Ser
1               5                   10                  15

Leu Thr Ile Thr Gly Leu Gln Pro Glu Asp Glu Ala Asp Tyr Tyr Cys
            20                  25                  30

<210> SEQ ID NO 243
<211> LENGTH: 10
<212> TYPE: PRT
<213> ORGANISM: Artificial Sequence
<220> FEATURE:
<223> OTHER INFORMATION: JL1 FR4

<400> SEQUENCE: 243

Phe Gly Thr Gly Thr Lys Val Thr Val Leu
1               5                   10

<210> SEQ ID NO 244
<211> LENGTH: 10
<212> TYPE: PRT
<213> ORGANISM: Artificial Sequence
<220> FEATURE:
<223> OTHER INFORMATION: JL2 FR4

<400> SEQUENCE: 244

Phe Gly Gly Gly Thr Lys Leu Thr Val Leu
1               5                   10

<210> SEQ ID NO 245
<211> LENGTH: 10
<212> TYPE: PRT
<213> ORGANISM: Artificial Sequence
<220> FEATURE:
<223> OTHER INFORMATION: JL3 FR4

<400> SEQUENCE: 245

Phe Gly Gly Gly Thr Lys Leu Thr Val Leu
1               5                   10
```

<210> SEQ ID NO 246
<211> LENGTH: 10
<212> TYPE: PRT
<213> ORGANISM: Artificial Sequence
<220> FEATURE:
<223> OTHER INFORMATION: JL7 FR4

<400> SEQUENCE: 246

Phe Gly Gly Gly Thr Gln Leu Thr Val Leu
1               5                   10

<210> SEQ ID NO 247
<211> LENGTH: 106
<212> TYPE: PRT
<213> ORGANISM: Artificial Sequence
<220> FEATURE:
<223> OTHER INFORMATION: Ig Kappa Constant Region (IGKC)

<400> SEQUENCE: 247

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 248
<211> LENGTH: 105
<212> TYPE: PRT
<213> ORGANISM: Artificial Sequence
<220> FEATURE:
<223> OTHER INFORMATION: Ig Lambda Constant Region (IGLC)

<400> SEQUENCE: 248

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 249
<211> LENGTH: 25

<212> TYPE: PRT
<213> ORGANISM: Artificial Sequence
<220> FEATURE:
<223> OTHER INFORMATION: 1-02 FR1

<400> SEQUENCE: 249

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 250
<211> LENGTH: 14
<212> TYPE: PRT
<213> ORGANISM: Artificial Sequence
<220> FEATURE:
<223> OTHER INFORMATION: 1-02 FR2

<400> SEQUENCE: 250

Trp Val Arg Gln Ala Pro Gly Gln Gly Leu Glu Trp Met Gly
1               5                   10

<210> SEQ ID NO 251
<211> LENGTH: 32
<212> TYPE: PRT
<213> ORGANISM: Artificial Sequence
<220> FEATURE:
<223> OTHER INFORMATION: 1-02 FR3

<400> SEQUENCE: 251

Arg Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 252
<211> LENGTH: 25
<212> TYPE: PRT
<213> ORGANISM: Artificial Sequence
<220> FEATURE:
<223> OTHER INFORMATION: 1-03 FR1

<400> SEQUENCE: 252

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 253
<211> LENGTH: 14
<212> TYPE: PRT
<213> ORGANISM: Artificial Sequence
<220> FEATURE:
<223> OTHER INFORMATION: 1-03 FR2

<400> SEQUENCE: 253

Trp Val Arg Gln Ala Pro Gly Gln Arg Leu Glu Trp Met Gly
1               5                   10

<210> SEQ ID NO 254
<211> LENGTH: 32
<212> TYPE: PRT
<213> ORGANISM: Artificial Sequence
<220> FEATURE:
<223> OTHER INFORMATION: 1-03 FR3

-continued

<400> SEQUENCE: 254

Arg Val Thr Ile Thr Arg Asp Thr Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 255
<211> LENGTH: 25
<212> TYPE: PRT
<213> ORGANISM: Artificial Sequence
<220> FEATURE:
<223> OTHER INFORMATION: 1-08 FR1

<400> SEQUENCE: 255

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 256
<211> LENGTH: 14
<212> TYPE: PRT
<213> ORGANISM: Artificial Sequence
<220> FEATURE:
<223> OTHER INFORMATION: 1-08 FR2

<400> SEQUENCE: 256

Trp Val Arg Gln Ala Thr Gly Gln Gly Leu Glu Trp Met Gly
1               5                   10

<210> SEQ ID NO 257
<211> LENGTH: 32
<212> TYPE: PRT
<213> ORGANISM: Artificial Sequence
<220> FEATURE:
<223> OTHER INFORMATION: 1-08 FR3

<400> SEQUENCE: 257

Arg Val Thr Met Thr Arg Asn Thr Ser Ile Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 258
<211> LENGTH: 25
<212> TYPE: PRT
<213> ORGANISM: Artificial Sequence
<220> FEATURE:
<223> OTHER INFORMATION: 1-18 FR1

<400> SEQUENCE: 258

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 259
<211> LENGTH: 14
<212> TYPE: PRT
<213> ORGANISM: Artificial Sequence
<220> FEATURE:
<223> OTHER INFORMATION: 1-18 FR2

<400> SEQUENCE: 259

```
Trp Val Arg Gln Ala Pro Gly Gln Gly Leu Glu Trp Met Gly
1               5                   10
```

<210> SEQ ID NO 260
<211> LENGTH: 32
<212> TYPE: PRT
<213> ORGANISM: Artificial Sequence
<220> FEATURE:
<223> OTHER INFORMATION: 1-18 FR3

<400> SEQUENCE: 260

```
Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30
```

<210> SEQ ID NO 261
<211> LENGTH: 25
<212> TYPE: PRT
<213> ORGANISM: Artificial Sequence
<220> FEATURE:
<223> OTHER INFORMATION: 1-24 FR1

<400> SEQUENCE: 261

```
Gln Val Gln Leu Val Gln Ser Gly Ala Glu Val Lys Lys Pro Gly Ala
1               5                   10                  15

Ser Val Lys Val Ser Cys Lys Val Ser
            20                  25
```

<210> SEQ ID NO 262
<211> LENGTH: 14
<212> TYPE: PRT
<213> ORGANISM: Artificial Sequence
<220> FEATURE:
<223> OTHER INFORMATION: 1-24 FR2

<400> SEQUENCE: 262

```
Trp Val Arg Gln Ala Pro Gly Lys Gly Leu Glu Trp Met Gly
1               5                   10
```

<210> SEQ ID NO 263
<211> LENGTH: 32
<212> TYPE: PRT
<213> ORGANISM: Artificial Sequence
<220> FEATURE:
<223> OTHER INFORMATION: 1-24 FR3

<400> SEQUENCE: 263

```
Arg Val Thr Met Thr Glu Asp Thr Ser Thr Asp Thr Ala Tyr Met Glu
1               5                   10                  15

Leu Ser Ser Leu Arg Ser Glu Asp Thr Ala Val Tyr Tyr Cys Ala Thr
            20                  25                  30
```

<210> SEQ ID NO 264
<211> LENGTH: 25
<212> TYPE: PRT
<213> ORGANISM: Artificial Sequence
<220> FEATURE:
<223> OTHER INFORMATION: 1-45 FR1

<400> SEQUENCE: 264

```
Gln Met Gln Leu Val Gln Ser Gly Ala Glu Val Lys Lys Thr Gly Ser
1               5                   10                  15

Ser Val Lys Val Ser Cys Lys Ala Ser
            20                  25
```

<210> SEQ ID NO 265
<211> LENGTH: 14
<212> TYPE: PRT
<213> ORGANISM: Artificial Sequence
<220> FEATURE:
<223> OTHER INFORMATION: 1-45 FR2

<400> SEQUENCE: 265

Trp Val Arg Gln Ala Pro Gly Gln Ala Leu Glu Trp Met Gly
1               5                   10

<210> SEQ ID NO 266
<211> LENGTH: 32
<212> TYPE: PRT
<213> ORGANISM: Artificial Sequence
<220> FEATURE:
<223> OTHER INFORMATION: 1-45 FR3

<400> SEQUENCE: 266

Arg Val Thr Ile Thr Arg Asp Arg Ser Met Ser Thr Ala Tyr Met Glu
1               5                   10                  15

Leu Ser Ser Leu Arg Ser Glu Asp Thr Ala Met Tyr Tyr Cys Ala Arg
            20                  25                  30

<210> SEQ ID NO 267
<211> LENGTH: 25
<212> TYPE: PRT
<213> ORGANISM: Artificial Sequence
<220> FEATURE:
<223> OTHER INFORMATION: 1-46 FR1

<400> SEQUENCE: 267

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 268
<211> LENGTH: 14
<212> TYPE: PRT
<213> ORGANISM: Artificial Sequence
<220> FEATURE:
<223> OTHER INFORMATION: 1-46 FR2

<400> SEQUENCE: 268

Trp Val Arg Gln Ala Pro Gly Gln Gly Leu Glu Trp Met Gly
1               5                   10

<210> SEQ ID NO 269
<211> LENGTH: 32
<212> TYPE: PRT
<213> ORGANISM: Artificial Sequence
<220> FEATURE:
<223> OTHER INFORMATION: 1-46 FR3

<400> SEQUENCE: 269

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 270
<211> LENGTH: 25
<212> TYPE: PRT

```
<213> ORGANISM: Artificial Sequence
<220> FEATURE:
<223> OTHER INFORMATION: 1-58 FR1

<400> SEQUENCE: 270

Gln Met Gln Leu Val Gln Ser Gly Pro Glu Val Lys Lys Pro Gly Thr
1               5                   10                  15

Ser Val Lys Val Ser Cys Lys Ala Ser
            20                  25

<210> SEQ ID NO 271
<211> LENGTH: 14
<212> TYPE: PRT
<213> ORGANISM: Artificial Sequence
<220> FEATURE:
<223> OTHER INFORMATION: 1-58 FR2

<400> SEQUENCE: 271

Trp Val Arg Gln Ala Arg Gly Gln Arg Leu Glu Trp Ile Gly
1               5                   10

<210> SEQ ID NO 272
<211> LENGTH: 32
<212> TYPE: PRT
<213> ORGANISM: Artificial Sequence
<220> FEATURE:
<223> OTHER INFORMATION: 1-58 FR3

<400> SEQUENCE: 272

Arg Val Thr Ile Thr Arg Asp Met Ser Thr Ser Thr Ala Tyr Met Glu
1               5                   10                  15

Leu Ser Ser Leu Arg Ser Glu Asp Thr Ala Val Tyr Tyr Cys Ala Ala
            20                  25                  30

<210> SEQ ID NO 273
<211> LENGTH: 25
<212> TYPE: PRT
<213> ORGANISM: Artificial Sequence
<220> FEATURE:
<223> OTHER INFORMATION: 1-69 FR1

<400> SEQUENCE: 273

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 274
<211> LENGTH: 14
<212> TYPE: PRT
<213> ORGANISM: Artificial Sequence
<220> FEATURE:
<223> OTHER INFORMATION: 1-69 FR2

<400> SEQUENCE: 274

Trp Val Arg Gln Ala Pro Gly Gln Gly Leu Glu Trp Met Gly
1               5                   10

<210> SEQ ID NO 275
<211> LENGTH: 32
<212> TYPE: PRT
<213> ORGANISM: Artificial Sequence
<220> FEATURE:
<223> OTHER INFORMATION: 1-69 FR3

<400> SEQUENCE: 275
```

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 276
<211> LENGTH: 25
<212> TYPE: PRT
<213> ORGANISM: Artificial Sequence
<220> FEATURE:
<223> OTHER INFORMATION: 1-e FR1

<400> SEQUENCE: 276

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 277
<211> LENGTH: 14
<212> TYPE: PRT
<213> ORGANISM: Artificial Sequence
<220> FEATURE:
<223> OTHER INFORMATION: 1-e FR2

<400> SEQUENCE: 277

Trp Val Arg Gln Ala Pro Gly Gln Gly Leu Glu Trp Met Gly
1               5                   10

<210> SEQ ID NO 278
<211> LENGTH: 32
<212> TYPE: PRT
<213> ORGANISM: Artificial Sequence
<220> FEATURE:
<223> OTHER INFORMATION: 1-e FR3

<400> SEQUENCE: 278

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 279
<211> LENGTH: 25
<212> TYPE: PRT
<213> ORGANISM: Artificial Sequence
<220> FEATURE:
<223> OTHER INFORMATION: 1-f FR1

<400> SEQUENCE: 279

Glu Val Gln Leu Val Gln Ser Gly Ala Glu Val Lys Lys Pro Gly Ala
1               5                   10                  15

Thr Val Lys Ile Ser Cys Lys Val Ser
            20                  25

<210> SEQ ID NO 280
<211> LENGTH: 14
<212> TYPE: PRT
<213> ORGANISM: Artificial Sequence
<220> FEATURE:
<223> OTHER INFORMATION: 1-f FR2

<400> SEQUENCE: 280

Trp Val Gln Gln Ala Pro Gly Lys Gly Leu Glu Trp Met Gly

<210> SEQ ID NO 281
<211> LENGTH: 32
<212> TYPE: PRT
<213> ORGANISM: Artificial Sequence
<220> FEATURE:
<223> OTHER INFORMATION: 1-f FR3'

<400> SEQUENCE: 281

Arg Val Thr Ile Thr Ala Asp Thr Ser Thr Asp Thr Ala Tyr Met Glu
1               5                   10                  15
Leu Ser Ser Leu Arg Ser Glu Asp Thr Ala Val Tyr Tyr Cys Ala Thr
                20                  25                  30

<210> SEQ ID NO 282
<211> LENGTH: 25
<212> TYPE: PRT
<213> ORGANISM: Artificial Sequence
<220> FEATURE:
<223> OTHER INFORMATION: 2-05 FR1

<400> SEQUENCE: 282

Gln Ile Thr Leu Lys Glu Ser Gly Pro Thr Leu Val Lys Pro Thr Gln
1               5                   10                  15
Thr Leu Thr Leu Thr Cys Thr Phe Ser
                20                  25

<210> SEQ ID NO 283
<211> LENGTH: 14
<212> TYPE: PRT
<213> ORGANISM: Artificial Sequence
<220> FEATURE:
<223> OTHER INFORMATION: 2-05 FR2

<400> SEQUENCE: 283

Trp Ile Arg Gln Pro Pro Gly Lys Ala Leu Glu Trp Leu Ala
1               5                   10

<210> SEQ ID NO 284
<211> LENGTH: 33
<212> TYPE: PRT
<213> ORGANISM: Artificial Sequence
<220> FEATURE:
<223> OTHER INFORMATION: 2-05 FR3

<400> SEQUENCE: 284

Arg Leu Thr Ile Thr Lys Asp Thr Ser Lys Asn Gln Val Val Leu Thr
1               5                   10                  15
Met Thr Asn Met Asp Pro Val Asp Thr Ala Thr Tyr Tyr Cys Ala His
                20                  25                  30
Arg

<210> SEQ ID NO 285
<211> LENGTH: 25
<212> TYPE: PRT
<213> ORGANISM: Artificial Sequence
<220> FEATURE:
<223> OTHER INFORMATION: 2-26 FR1

<400> SEQUENCE: 285

Gln Val Thr Leu Lys Glu Ser Gly Pro Val Leu Val Lys Pro Thr Glu
1               5                   10                  15
Thr Leu Thr Leu Thr Cys Thr Val Ser 20                  25

<210> SEQ ID NO 286
<211> LENGTH: 14
<212> TYPE: PRT
<213> ORGANISM: Artificial Sequence
<220> FEATURE:
<223> OTHER INFORMATION: 2-26 FR2

<400> SEQUENCE: 286

Trp Ile Arg Gln Pro Pro Gly Lys Ala Leu Glu Trp Leu Ala
1               5                   10

<210> SEQ ID NO 287
<211> LENGTH: 33
<212> TYPE: PRT
<213> ORGANISM: Artificial Sequence
<220> FEATURE:
<223> OTHER INFORMATION: 2-26 FR3

<400> SEQUENCE: 287

Arg Leu Thr Ile Ser Lys Asp Thr Ser Lys Ser Gln Val Val Leu Thr
1               5                   10                  15

Met Thr Asn Met Asp Pro Val Asp Thr Ala Thr Tyr Tyr Cys Ala Arg
            20                  25                  30

Ile

<210> SEQ ID NO 288
<211> LENGTH: 25
<212> TYPE: PRT
<213> ORGANISM: Artificial Sequence
<220> FEATURE:
<223> OTHER INFORMATION: 2-70 FR1

<400> SEQUENCE: 288

Gln Val Thr Leu Lys Glu Ser Gly Pro Ala Leu Val Lys Pro Thr Gln
1               5                   10                  15

Thr Leu Thr Leu Thr Cys Thr Phe Ser
            20                  25

<210> SEQ ID NO 289
<211> LENGTH: 14
<212> TYPE: PRT
<213> ORGANISM: Artificial Sequence
<220> FEATURE:
<223> OTHER INFORMATION: 2-70 FR2

<400> SEQUENCE: 289

Trp Ile Arg Gln Pro Pro Gly Lys Ala Leu Glu Trp Leu Ala
1               5                   10

<210> SEQ ID NO 290
<211> LENGTH: 33
<212> TYPE: PRT
<213> ORGANISM: Artificial Sequence
<220> FEATURE:
<223> OTHER INFORMATION: 2-70 FR3

<400> SEQUENCE: 290

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
            20                  25                  30

Ile

<210> SEQ ID NO 291
<211> LENGTH: 25
<212> TYPE: PRT
<213> ORGANISM: Artificial Sequence
<220> FEATURE:
<223> OTHER INFORMATION: 3-07 FR1

<400> SEQUENCE: 291

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 292
<211> LENGTH: 14
<212> TYPE: PRT
<213> ORGANISM: Artificial Sequence
<220> FEATURE:
<223> OTHER INFORMATION: 3-07 FR2

<400> SEQUENCE: 292

Trp Val Arg Gln Ala Pro Gly Lys Gly Leu Glu Trp Val Ala
1               5                   10

<210> SEQ ID NO 293
<211> LENGTH: 32
<212> TYPE: PRT
<213> ORGANISM: Artificial Sequence
<220> FEATURE:
<223> OTHER INFORMATION: 3-07 FR3

<400> SEQUENCE: 293

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 294
<211> LENGTH: 25
<212> TYPE: PRT
<213> ORGANISM: Artificial Sequence
<220> FEATURE:
<223> OTHER INFORMATION: 3-09 FR1

<400> SEQUENCE: 294

Glu Val Gln Leu Val Glu Ser Gly Gly Gly Leu Val Gln Pro Gly Arg
1               5                   10                  15

Ser Leu Arg Leu Ser Cys Ala Ala Ser
            20                  25

<210> SEQ ID NO 295
<211> LENGTH: 14
<212> TYPE: PRT
<213> ORGANISM: Artificial Sequence
<220> FEATURE:
<223> OTHER INFORMATION: 3-09 FR2

<400> SEQUENCE: 295

Trp Val Arg Gln Ala Pro Gly Lys Gly Leu Glu Trp Val Ser
1               5                   10

<210> SEQ ID NO 296
<211> LENGTH: 33
<212> TYPE: PRT

```
<213> ORGANISM: Artificial Sequence
<220> FEATURE:
<223> OTHER INFORMATION: 3-09 FR3

<400> SEQUENCE: 296

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Leu Tyr Tyr Cys Ala Lys
            20                  25                  30

Asp

<210> SEQ ID NO 297
<211> LENGTH: 25
<212> TYPE: PRT
<213> ORGANISM: Artificial Sequence
<220> FEATURE:
<223> OTHER INFORMATION: 3-11 FR1

<400> SEQUENCE: 297

Gln Val Gln Leu Val Glu Ser Gly Gly Gly Leu Val Lys Pro Gly Gly
1               5                   10                  15

Ser Leu Arg Leu Ser Cys Ala Ala Ser
            20                  25

<210> SEQ ID NO 298
<211> LENGTH: 14
<212> TYPE: PRT
<213> ORGANISM: Artificial Sequence
<220> FEATURE:
<223> OTHER INFORMATION: 3-11 FR2

<400> SEQUENCE: 298

Trp Ile Arg Gln Ala Pro Gly Lys Gly Leu Glu Trp Val Ser
1               5                   10

<210> SEQ ID NO 299
<211> LENGTH: 32
<212> TYPE: PRT
<213> ORGANISM: Artificial Sequence
<220> FEATURE:
<223> OTHER INFORMATION: 3-11 FR3

<400> SEQUENCE: 299

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 300
<211> LENGTH: 25
<212> TYPE: PRT
<213> ORGANISM: Artificial Sequence
<220> FEATURE:
<223> OTHER INFORMATION: 3-13 FR1

<400> SEQUENCE: 300

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 301
<211> LENGTH: 14
<212> TYPE: PRT
```

<213> ORGANISM: Artificial Sequence
<220> FEATURE:
<223> OTHER INFORMATION: 3-13 FR2

<400> SEQUENCE: 301

Trp Val Arg Gln Ala Thr Gly Lys Gly Leu Glu Trp Val Ser
1               5                   10

<210> SEQ ID NO 302
<211> LENGTH: 32
<212> TYPE: PRT
<213> ORGANISM: Artificial Sequence
<220> FEATURE:
<223> OTHER INFORMATION: 3-13 FR3

<400> SEQUENCE: 302

Arg Phe Thr Ile Ser Arg Glu Asn Ala Lys Asn Ser Leu Tyr Leu Gln
1               5                   10                  15

Met Asn Ser Leu Arg Ala Gly Asp Thr Ala Val Tyr Tyr Cys Ala Arg
            20                  25                  30

<210> SEQ ID NO 303
<211> LENGTH: 25
<212> TYPE: PRT
<213> ORGANISM: Artificial Sequence
<220> FEATURE:
<223> OTHER INFORMATION: 3-15 FR1

<400> SEQUENCE: 303

Glu Val Gln Leu Val Glu Ser Gly Gly Gly Leu Val Lys Pro Gly Gly
1               5                   10                  15

Ser Leu Arg Leu Ser Cys Ala Ala Ser
            20                  25

<210> SEQ ID NO 304
<211> LENGTH: 14
<212> TYPE: PRT
<213> ORGANISM: Artificial Sequence
<220> FEATURE:
<223> OTHER INFORMATION: 3-15 FR2

<400> SEQUENCE: 304

Trp Val Arg Gln Ala Pro Gly Lys Gly Leu Glu Trp Val Gly
1               5                   10

<210> SEQ ID NO 305
<211> LENGTH: 32
<212> TYPE: PRT
<213> ORGANISM: Artificial Sequence
<220> FEATURE:
<223> OTHER INFORMATION: 3-15 FR3

<400> SEQUENCE: 305

Arg Phe Thr Ile Ser Arg Asp Asp Ser Lys Asn Thr Leu Tyr Leu Gln
1               5                   10                  15

Met Asn Ser Leu Lys Thr Glu Asp Thr Ala Val Tyr Tyr Cys Thr Thr
            20                  25                  30

<210> SEQ ID NO 306
<211> LENGTH: 25
<212> TYPE: PRT
<213> ORGANISM: Artificial Sequence
<220> FEATURE:
<223> OTHER INFORMATION: 3-20 FR1

<400> SEQUENCE: 306

Glu Val Gln Leu Val Glu Ser Gly Gly Gly Val Val Arg Pro Gly Gly
1               5                   10                  15

Ser Leu Arg Leu Ser Cys Ala Ala Ser
            20                  25

<210> SEQ ID NO 307
<211> LENGTH: 14
<212> TYPE: PRT
<213> ORGANISM: Artificial Sequence
<220> FEATURE:
<223> OTHER INFORMATION: 3-20 FR2

<400> SEQUENCE: 307

Trp Val Arg Gln Ala Pro Gly Lys Gly Leu Glu Trp Val Ser
1               5                   10

<210> SEQ ID NO 308
<211> LENGTH: 32
<212> TYPE: PRT
<213> ORGANISM: Artificial Sequence
<220> FEATURE:
<223> OTHER INFORMATION: 3-20 FR3

<400> SEQUENCE: 308

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Leu Tyr His Cys Ala Arg
            20                  25                  30

<210> SEQ ID NO 309
<211> LENGTH: 25
<212> TYPE: PRT
<213> ORGANISM: Artificial Sequence
<220> FEATURE:
<223> OTHER INFORMATION: 3-21 FR1

<400> SEQUENCE: 309

Glu Val Gln Leu Val Glu Ser Gly Gly Gly Leu Val Lys Pro Gly Gly
1               5                   10                  15

Ser Leu Arg Leu Ser Cys Ala Ala Ser
            20                  25

<210> SEQ ID NO 310
<211> LENGTH: 14
<212> TYPE: PRT
<213> ORGANISM: Artificial Sequence
<220> FEATURE:
<223> OTHER INFORMATION: 3-21 FR2

<400> SEQUENCE: 310

Trp Val Arg Gln Ala Pro Gly Lys Gly Leu Glu Trp Val Ser
1               5                   10

<210> SEQ ID NO 311
<211> LENGTH: 32
<212> TYPE: PRT
<213> ORGANISM: Artificial Sequence
<220> FEATURE:
<223> OTHER INFORMATION: 3-21 FR3

<400> SEQUENCE: 311

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg

```
            20                  25                  30
```

<210> SEQ ID NO 312
<211> LENGTH: 25
<212> TYPE: PRT
<213> ORGANISM: Artificial Sequence
<220> FEATURE:
<223> OTHER INFORMATION: 3-23 FR1

<400> SEQUENCE: 312

```
Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25
```

<210> SEQ ID NO 313
<211> LENGTH: 14
<212> TYPE: PRT
<213> ORGANISM: Artificial Sequence
<220> FEATURE:
<223> OTHER INFORMATION: 3-23 FR2

<400> SEQUENCE: 313

```
Trp Val Arg Gln Ala Pro Gly Lys Gly Leu Glu Trp Val Ser
1               5                   10
```

<210> SEQ ID NO 314
<211> LENGTH: 32
<212> TYPE: PRT
<213> ORGANISM: Artificial Sequence
<220> FEATURE:
<223> OTHER INFORMATION: 3-23 FR3

<400> SEQUENCE: 314

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30
```

<210> SEQ ID NO 315
<211> LENGTH: 25
<212> TYPE: PRT
<213> ORGANISM: Artificial Sequence
<220> FEATURE:
<223> OTHER INFORMATION: 3-30 FR1

<400> SEQUENCE: 315

```
Gln Val Gln Leu Val Glu Ser Gly Gly Gly Val Val Gln Pro Gly Arg
1               5                   10                  15

Ser Leu Arg Leu Ser Cys Ala Ala Ser
            20                  25
```

<210> SEQ ID NO 316
<211> LENGTH: 14
<212> TYPE: PRT
<213> ORGANISM: Artificial Sequence
<220> FEATURE:
<223> OTHER INFORMATION: 3-30 FR2

<400> SEQUENCE: 316

```
Trp Val Arg Gln Ala Pro Gly Lys Gly Leu Glu Trp Val Ala
1               5                   10
```

<210> SEQ ID NO 317
<211> LENGTH: 32

```
<212> TYPE: PRT
<213> ORGANISM: Artificial Sequence
<220> FEATURE:
<223> OTHER INFORMATION: 3-30 FR3

<400> SEQUENCE: 317

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ala Lys
            20                  25                  30

<210> SEQ ID NO 318
<211> LENGTH: 25
<212> TYPE: PRT
<213> ORGANISM: Artificial Sequence
<220> FEATURE:
<223> OTHER INFORMATION: 3-30.3 FR1

<400> SEQUENCE: 318

Gln Val Gln Leu Val Glu Ser Gly Gly Gly Val Val Gln Pro Gly Arg
1               5                   10                  15
Ser Leu Arg Leu Ser Cys Ala Ala Ser
            20                  25

<210> SEQ ID NO 319
<211> LENGTH: 14
<212> TYPE: PRT
<213> ORGANISM: Artificial Sequence
<220> FEATURE:
<223> OTHER INFORMATION: 3-30.3 FR2

<400> SEQUENCE: 319

Trp Val Arg Gln Ala Pro Gly Lys Gly Leu Glu Trp Val Ala
1               5                   10

<210> SEQ ID NO 320
<211> LENGTH: 32
<212> TYPE: PRT
<213> ORGANISM: Artificial Sequence
<220> FEATURE:
<223> OTHER INFORMATION: 3-30.3 FR3

<400> SEQUENCE: 320

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ala Arg
            20                  25                  30

<210> SEQ ID NO 321
<211> LENGTH: 25
<212> TYPE: PRT
<213> ORGANISM: Artificial Sequence
<220> FEATURE:
<223> OTHER INFORMATION: 3-3 FR1

<400> SEQUENCE: 321

Gln Val Gln Leu Val Glu Ser Gly Gly Gly Val Val Gln Pro Gly Arg
1               5                   10                  15
Ser Leu Arg Leu Ser Cys Ala Ala Ser
            20                  25

<210> SEQ ID NO 322
<211> LENGTH: 14
<212> TYPE: PRT
<213> ORGANISM: Artificial Sequence
```

```
<220> FEATURE:
<223> OTHER INFORMATION: 3-30.5 FR2

<400> SEQUENCE: 322

Trp Val Arg Gln Ala Pro Gly Lys Gly Leu Glu Trp Val Ala
1               5                   10

<210> SEQ ID NO 323
<211> LENGTH: 32
<212> TYPE: PRT
<213> ORGANISM: Artificial Sequence
<220> FEATURE:
<223> OTHER INFORMATION: 3-30.5 FR3

<400> SEQUENCE: 323

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
                20                  25                  30

<210> SEQ ID NO 324
<211> LENGTH: 25
<212> TYPE: PRT
<213> ORGANISM: Artificial Sequence
<220> FEATURE:
<223> OTHER INFORMATION: 3-3 FR13

<400> SEQUENCE: 324

Gln Val Gln Leu Val Glu Ser Gly Gly Gly Val Val Gln Pro Gly Arg
1               5                   10                  15

Ser Leu Arg Leu Ser Cys Ala Ala Ser
                20                  25

<210> SEQ ID NO 325
<211> LENGTH: 14
<212> TYPE: PRT
<213> ORGANISM: Artificial Sequence
<220> FEATURE:
<223> OTHER INFORMATION: 3-33 FR2

<400> SEQUENCE: 325

Trp Val Arg Gln Ala Pro Gly Lys Gly Leu Glu Trp Val Ala
1               5                   10

<210> SEQ ID NO 326
<211> LENGTH: 32
<212> TYPE: PRT
<213> ORGANISM: Artificial Sequence
<220> FEATURE:
<223> OTHER INFORMATION: 3-33 FR3

<400> SEQUENCE: 326

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
                20                  25                  30

<210> SEQ ID NO 327
<211> LENGTH: 25
<212> TYPE: PRT
<213> ORGANISM: Artificial Sequence
<220> FEATURE:
<223> OTHER INFORMATION: 3-43 FR1

<400> SEQUENCE: 327
```

```
Glu Val Gln Leu Val Glu Ser Gly Gly Val Val Gln Pro Gly Gly
1               5                   10                  15

Ser Leu Arg Leu Ser Cys Ala Ala Ser
            20                  25
```

<210> SEQ ID NO 328
<211> LENGTH: 14
<212> TYPE: PRT
<213> ORGANISM: Artificial Sequence
<220> FEATURE:
<223> OTHER INFORMATION: 3-43 FR2

<400> SEQUENCE: 328

```
Trp Val Arg Gln Ala Pro Gly Lys Gly Leu Glu Trp Val Ser
1               5                   10
```

<210> SEQ ID NO 329
<211> LENGTH: 33
<212> TYPE: PRT
<213> ORGANISM: Artificial Sequence
<220> FEATURE:
<223> OTHER INFORMATION: 3-43 FR3

<400> SEQUENCE: 329

```
Arg Phe Thr Ile Ser Arg Asp Asn Ser Lys Asn Ser Leu Tyr Leu Gln
1               5                   10                  15

Met Asn Ser Leu Arg Thr Glu Asp Thr Ala Leu Tyr Tyr Cys Ala Lys
            20                  25                  30

Asp
```

<210> SEQ ID NO 330
<211> LENGTH: 25
<212> TYPE: PRT
<213> ORGANISM: Artificial Sequence
<220> FEATURE:
<223> OTHER INFORMATION: 3-48 FR1

<400> SEQUENCE: 330

```
Glu Val Gln Leu Val Glu Ser Gly Gly Gly Leu Val Gln Pro Gly Gly
1               5                   10                  15

Ser Leu Arg Leu Ser Cys Ala Ala Ser
            20                  25
```

<210> SEQ ID NO 331
<211> LENGTH: 14
<212> TYPE: PRT
<213> ORGANISM: Artificial Sequence
<220> FEATURE:
<223> OTHER INFORMATION: 3-48 FR2

<400> SEQUENCE: 331

```
Trp Val Arg Gln Ala Pro Gly Lys Gly Leu Glu Trp Val Ser
1               5                   10
```

<210> SEQ ID NO 332
<211> LENGTH: 32
<212> TYPE: PRT
<213> ORGANISM: Artificial Sequence
<220> FEATURE:
<223> OTHER INFORMATION: 3-48 FR3

<400> SEQUENCE: 332

```
Arg Phe Thr Ile Ser Arg Asp Asn Ala Lys Asn Ser Leu Tyr Leu Gln
1               5                   10                  15
```

Met Asn Ser Leu Arg Asp Glu Asp Thr Ala Val Tyr Tyr Cys Ala Arg
            20                  25                  30

<210> SEQ ID NO 333
<211> LENGTH: 25
<212> TYPE: PRT
<213> ORGANISM: Artificial Sequence
<220> FEATURE:
<223> OTHER INFORMATION: 3-49 FR1

<400> SEQUENCE: 333

Glu Val Gln Leu Val Glu Ser Gly Gly Gly Leu Val Gln Pro Gly Arg
1               5                   10                  15

Ser Leu Arg Leu Ser Cys Thr Ala Ser
            20                  25

<210> SEQ ID NO 334
<211> LENGTH: 14
<212> TYPE: PRT
<213> ORGANISM: Artificial Sequence
<220> FEATURE:
<223> OTHER INFORMATION: 3-49 FR2

<400> SEQUENCE: 334

Trp Phe Arg Gln Ala Pro Gly Lys Gly Leu Glu Trp Val Gly
1               5                   10

<210> SEQ ID NO 335
<211> LENGTH: 32
<212> TYPE: PRT
<213> ORGANISM: Artificial Sequence
<220> FEATURE:
<223> OTHER INFORMATION: 3-49 FR3

<400> SEQUENCE: 335

Arg Phe Thr Ile Ser Arg Asp Gly Ser Lys Ser Ile Ala Tyr Leu Gln
1               5                   10                  15

Met Asn Ser Leu Lys Thr Glu Asp Thr Ala Val Tyr Tyr Cys Thr Arg
            20                  25                  30

<210> SEQ ID NO 336
<211> LENGTH: 25
<212> TYPE: PRT
<213> ORGANISM: Artificial Sequence
<220> FEATURE:
<223> OTHER INFORMATION: 3-53 FR1

<400> SEQUENCE: 336

Glu Val Gln Leu Val Glu Thr Gly Gly Gly Leu Ile Gln Pro Gly Gly
1               5                   10                  15

Ser Leu Arg Leu Ser Cys Ala Ala Ser
            20                  25

<210> SEQ ID NO 337
<211> LENGTH: 14
<212> TYPE: PRT
<213> ORGANISM: Artificial Sequence
<220> FEATURE:
<223> OTHER INFORMATION: 3-53 FR2

<400> SEQUENCE: 337

Trp Val Arg Gln Ala Pro Gly Lys Gly Leu Glu Trp Val Ser
1               5                   10

<210> SEQ ID NO 338

```
<211> LENGTH: 32
<212> TYPE: PRT
<213> ORGANISM: Artificial Sequence
<220> FEATURE:
<223> OTHER INFORMATION: 3-53 FR3

<400> SEQUENCE: 338

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ala Arg
            20                  25                  30

<210> SEQ ID NO 339
<211> LENGTH: 25
<212> TYPE: PRT
<213> ORGANISM: Artificial Sequence
<220> FEATURE:
<223> OTHER INFORMATION: 3-64 FR1

<400> SEQUENCE: 339

Glu Val Gln Leu Val Glu Ser Gly Gly Gly Leu Val Gln Pro Gly Gly
1               5                   10                  15
Ser Leu Arg Leu Ser Cys Ala Ala Ser
            20                  25

<210> SEQ ID NO 340
<211> LENGTH: 14
<212> TYPE: PRT
<213> ORGANISM: Artificial Sequence
<220> FEATURE:
<223> OTHER INFORMATION: 3-64 FR2

<400> SEQUENCE: 340

Trp Val Arg Gln Ala Pro Gly Lys Gly Leu Glu Tyr Val Ser
1               5                   10

<210> SEQ ID NO 341
<211> LENGTH: 32
<212> TYPE: PRT
<213> ORGANISM: Artificial Sequence
<220> FEATURE:
<223> OTHER INFORMATION: 3-64 FR3

<400> SEQUENCE: 341

Arg Phe Thr Ile Ser Arg Asp Asn Ser Lys Asn Thr Leu Tyr Leu Gln
1               5                   10                  15
Met Gly Ser Leu Arg Ala Glu Asp Met Ala Val Tyr Tyr Cys Ala Arg
            20                  25                  30

<210> SEQ ID NO 342
<211> LENGTH: 25
<212> TYPE: PRT
<213> ORGANISM: Artificial Sequence
<220> FEATURE:
<223> OTHER INFORMATION: 3-66 FR1

<400> SEQUENCE: 342

Glu Val Gln Leu Val Glu Ser Gly Gly Gly Leu Val Gln Pro Gly Gly
1               5                   10                  15
Ser Leu Arg Leu Ser Cys Ala Ala Ser
            20                  25

<210> SEQ ID NO 343
<211> LENGTH: 14
<212> TYPE: PRT
```

```
<213> ORGANISM: Artificial Sequence
<220> FEATURE:
<223> OTHER INFORMATION: 3-66 FR2

<400> SEQUENCE: 343

Trp Val Arg Gln Ala Pro Gly Lys Gly Leu Glu Trp Val Ser
1               5                   10

<210> SEQ ID NO 344
<211> LENGTH: 32
<212> TYPE: PRT
<213> ORGANISM: Artificial Sequence
<220> FEATURE:
<223> OTHER INFORMATION: 3-66 FR3

<400> SEQUENCE: 344

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 345
<211> LENGTH: 25
<212> TYPE: PRT
<213> ORGANISM: Artificial Sequence
<220> FEATURE:
<223> OTHER INFORMATION: 3-72 FR1

<400> SEQUENCE: 345

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 346
<211> LENGTH: 14
<212> TYPE: PRT
<213> ORGANISM: Artificial Sequence
<220> FEATURE:
<223> OTHER INFORMATION: 3-72 FR2

<400> SEQUENCE: 346

Trp Val Arg Gln Ala Pro Gly Lys Gly Leu Glu Trp Val Gly
1               5                   10

<210> SEQ ID NO 347
<211> LENGTH: 32
<212> TYPE: PRT
<213> ORGANISM: Artificial Sequence
<220> FEATURE:
<223> OTHER INFORMATION: 3-72 FR3

<400> SEQUENCE: 347

Arg Phe Thr Ile Ser Arg Asp Asp Ser Lys Asn Ser Leu Tyr Leu Gln
1               5                   10                  15

Met Asn Ser Leu Lys Thr Glu Asp Thr Ala Val Tyr Tyr Cys Ala Arg
            20                  25                  30

<210> SEQ ID NO 348
<211> LENGTH: 25
<212> TYPE: PRT
<213> ORGANISM: Artificial Sequence
<220> FEATURE:
<223> OTHER INFORMATION: 3-73 FR1

<400> SEQUENCE: 348
```

```
Glu Val Gln Leu Val Glu Ser Gly Gly Gly Leu Val Gln Pro Gly Gly
1               5                   10                  15

Ser Leu Lys Leu Ser Cys Ala Ala Ser
            20                  25

<210> SEQ ID NO 349
<211> LENGTH: 14
<212> TYPE: PRT
<213> ORGANISM: Artificial Sequence
<220> FEATURE:
<223> OTHER INFORMATION: 3-73 FR2

<400> SEQUENCE: 349

Trp Val Arg Gln Ala Ser Gly Lys Gly Leu Glu Trp Val Gly
1               5                   10

<210> SEQ ID NO 350
<211> LENGTH: 32
<212> TYPE: PRT
<213> ORGANISM: Artificial Sequence
<220> FEATURE:
<223> OTHER INFORMATION: 3-73 FR3

<400> SEQUENCE: 350

Arg Phe Thr Ile Ser Arg Asp Asp Ser Lys Asn Thr Ala Tyr Leu Gln
1               5                   10                  15

Met Asn Ser Leu Lys Thr Glu Asp Thr Ala Val Tyr Tyr Cys Thr Arg
            20                  25                  30

<210> SEQ ID NO 351
<211> LENGTH: 25
<212> TYPE: PRT
<213> ORGANISM: Artificial Sequence
<220> FEATURE:
<223> OTHER INFORMATION: 3-74 FR1

<400> SEQUENCE: 351

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 352
<211> LENGTH: 14
<212> TYPE: PRT
<213> ORGANISM: Artificial Sequence
<220> FEATURE:
<223> OTHER INFORMATION: 3-74 FR2

<400> SEQUENCE: 352

Trp Val Arg Gln Ala Pro Gly Lys Gly Leu Val Trp Val Ser
1               5                   10

<210> SEQ ID NO 353
<211> LENGTH: 32
<212> TYPE: PRT
<213> ORGANISM: Artificial Sequence
<220> FEATURE:
<223> OTHER INFORMATION: 3-74 FR3

<400> SEQUENCE: 353

Arg Phe Thr Ile Ser Arg Asp Asn Ala Lys Asn Thr Leu Tyr Leu Gln
1               5                   10                  15

Met Asn Ser Leu Arg Ala Glu Asp Thr Ala Val Tyr Tyr Cys Ala Arg
```

<210> SEQ ID NO 354
<211> LENGTH: 25
<212> TYPE: PRT
<213> ORGANISM: Artificial Sequence
<220> FEATURE:
<223> OTHER INFORMATION: 3-d FR1

<400> SEQUENCE: 354

Glu Val Gln Leu Val Glu Ser Arg Gly Val Leu Val Gln Pro Gly Gly
1               5                   10                  15

Ser Leu Arg Leu Ser Cys Ala Ala Ser
            20                  25

<210> SEQ ID NO 355
<211> LENGTH: 14
<212> TYPE: PRT
<213> ORGANISM: Artificial Sequence
<220> FEATURE:
<223> OTHER INFORMATION: 3-d FR2

<400> SEQUENCE: 355

Trp Val Arg Gln Ala Pro Gly Lys Gly Leu Glu Trp Val Ser
1               5                   10

<210> SEQ ID NO 356
<211> LENGTH: 32
<212> TYPE: PRT
<213> ORGANISM: Artificial Sequence
<220> FEATURE:
<223> OTHER INFORMATION: 3-d FR3

<400> SEQUENCE: 356

Arg Phe Thr Ile Ser Arg Asp Asn Ser Lys Asn Thr Leu His Leu Gln
1               5                   10                  15

Met Asn Ser Leu Arg Ala Glu Asp Thr Ala Val Tyr Tyr Cys Lys Lys
            20                  25                  30

<210> SEQ ID NO 357
<211> LENGTH: 25
<212> TYPE: PRT
<213> ORGANISM: Artificial Sequence
<220> FEATURE:
<223> OTHER INFORMATION: 4-04 FR1

<400> SEQUENCE: 357

Gln Val Gln Leu Gln Glu Ser Gly Pro Gly Leu Val Lys Pro Ser Gly
1               5                   10                  15

Thr Leu Ser Leu Thr Cys Ala Val Ser
            20                  25

<210> SEQ ID NO 358
<211> LENGTH: 14
<212> TYPE: PRT
<213> ORGANISM: Artificial Sequence
<220> FEATURE:
<223> OTHER INFORMATION: 4-04 FR2

<400> SEQUENCE: 358

Trp Val Arg Gln Pro Pro Gly Lys Gly Leu Glu Trp Ile Gly
1               5                   10

<210> SEQ ID NO 359
<211> LENGTH: 32

```
<212> TYPE: PRT
<213> ORGANISM: Artificial Sequence
<220> FEATURE:
<223> OTHER INFORMATION: 4-04 FR3

<400> SEQUENCE: 359

Arg Val Thr Ile Ser Val Asp Lys Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 360
<211> LENGTH: 25
<212> TYPE: PRT
<213> ORGANISM: Artificial Sequence
<220> FEATURE:
<223> OTHER INFORMATION: 4-28 FR1

<400> SEQUENCE: 360

Gln Val Gln Leu Gln Glu Ser Gly Pro Gly Leu Val Lys Pro Ser Asp
1               5                   10                  15

Thr Leu Ser Leu Thr Cys Ala Val Ser
            20                  25

<210> SEQ ID NO 361
<211> LENGTH: 14
<212> TYPE: PRT
<213> ORGANISM: Artificial Sequence
<220> FEATURE:
<223> OTHER INFORMATION: 4-28 FR2

<400> SEQUENCE: 361

Trp Ile Arg Gln Pro Pro Gly Lys Gly Leu Glu Trp Ile Gly
1               5                   10

<210> SEQ ID NO 362
<211> LENGTH: 32
<212> TYPE: PRT
<213> ORGANISM: Artificial Sequence
<220> FEATURE:
<223> OTHER INFORMATION: 4-28 FR3

<400> SEQUENCE: 362

Arg Val Thr Met Ser Val Asp Thr Ser Lys Asn Gln Phe Ser Leu Lys
1               5                   10                  15

Leu Ser Ser Val Thr Ala Val Asp Thr Ala Val Tyr Tyr Cys Ala Arg
            20                  25                  30

<210> SEQ ID NO 363
<211> LENGTH: 25
<212> TYPE: PRT
<213> ORGANISM: Artificial Sequence
<220> FEATURE:
<223> OTHER INFORMATION: 4-30.1 FR1

<400> SEQUENCE: 363

Gln Val Gln Leu Gln Glu Ser Gly Pro Gly Leu Val Lys Pro Ser Gln
1               5                   10                  15

Thr Leu Ser Leu Thr Cys Thr Val Ser
            20                  25

<210> SEQ ID NO 364
<211> LENGTH: 14
<212> TYPE: PRT
<213> ORGANISM: Artificial Sequence
```

```
<220> FEATURE:
<223> OTHER INFORMATION: 4-30.1 FR2

<400> SEQUENCE: 364

Trp Ile Arg Gln His Pro Gly Lys Gly Leu Glu Trp Ile Gly
1               5                   10

<210> SEQ ID NO 365
<211> LENGTH: 32
<212> TYPE: PRT
<213> ORGANISM: Artificial Sequence
<220> FEATURE:
<223> OTHER INFORMATION: 4-30.1 FR3

<400> SEQUENCE: 365

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 366
<211> LENGTH: 25
<212> TYPE: PRT
<213> ORGANISM: Artificial Sequence
<220> FEATURE:
<223> OTHER INFORMATION: 4-3 FR1

<400> SEQUENCE: 366

Gln Leu Gln Leu Gln Glu Ser Gly Ser Gly Leu Val Lys Pro Ser Gln
1               5                   10                  15

Thr Leu Ser Leu Thr Cys Ala Val Ser
            20                  25

<210> SEQ ID NO 367
<211> LENGTH: 14
<212> TYPE: PRT
<213> ORGANISM: Artificial Sequence
<220> FEATURE:
<223> OTHER INFORMATION: 4-30.2 FR2

<400> SEQUENCE: 367

Trp Ile Arg Gln Pro Pro Gly Lys Gly Leu Glu Trp Ile Gly
1               5                   10

<210> SEQ ID NO 368
<211> LENGTH: 32
<212> TYPE: PRT
<213> ORGANISM: Artificial Sequence
<220> FEATURE:
<223> OTHER INFORMATION: 4-30.2 FR3

<400> SEQUENCE: 368

Arg Val Thr Ile Ser Val Asp Arg Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 369
<211> LENGTH: 25
<212> TYPE: PRT
<213> ORGANISM: Artificial Sequence
<220> FEATURE:
<223> OTHER INFORMATION: 4-3 FR10.4

<400> SEQUENCE: 369
```

Gln Val Gln Leu Gln Glu Ser Gly Pro Gly Leu Val Lys Pro Ser Gln
1               5                   10                  15

Thr Leu Ser Leu Thr Cys Thr Val Ser
            20                  25

<210> SEQ ID NO 370
<211> LENGTH: 14
<212> TYPE: PRT
<213> ORGANISM: Artificial Sequence
<220> FEATURE:
<223> OTHER INFORMATION: 4-30.4 FR2

<400> SEQUENCE: 370

Trp Ile Arg Gln Pro Pro Gly Lys Gly Leu Glu Trp Ile Gly
1               5                   10

<210> SEQ ID NO 371
<211> LENGTH: 32
<212> TYPE: PRT
<213> ORGANISM: Artificial Sequence
<220> FEATURE:
<223> OTHER INFORMATION: 4-30.4 FR3

<400> SEQUENCE: 371

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 372
<211> LENGTH: 25
<212> TYPE: PRT
<213> ORGANISM: Artificial Sequence
<220> FEATURE:
<223> OTHER INFORMATION: 4-3 FR1

<400> SEQUENCE: 372

Gln Val Gln Leu Gln Glu Ser Gly Pro Gly Leu Val Lys Pro Ser Gln
1               5                   10                  15

Thr Leu Ser Leu Thr Cys Thr Val Ser
            20                  25

<210> SEQ ID NO 373
<211> LENGTH: 14
<212> TYPE: PRT
<213> ORGANISM: Artificial Sequence
<220> FEATURE:
<223> OTHER INFORMATION: 4-31 FR2

<400> SEQUENCE: 373

Trp Ile Arg Gln His Pro Gly Lys Gly Leu Glu Trp Ile Gly
1               5                   10

<210> SEQ ID NO 374
<211> LENGTH: 32
<212> TYPE: PRT
<213> ORGANISM: Artificial Sequence
<220> FEATURE:
<223> OTHER INFORMATION: 4-31 FR3

<400> SEQUENCE: 374

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 375
<211> LENGTH: 25
<212> TYPE: PRT
<213> ORGANISM: Artificial Sequence
<220> FEATURE:
<223> OTHER INFORMATION: 4-34 FR1

<400> SEQUENCE: 375

Gln Val Gln Leu Gln Gln Trp Gly Ala Gly Leu Leu Lys Pro Ser Glu
1               5                   10                  15

Thr Leu Ser Leu Thr Cys Ala Val Tyr
            20                  25

<210> SEQ ID NO 376
<211> LENGTH: 14
<212> TYPE: PRT
<213> ORGANISM: Artificial Sequence
<220> FEATURE:
<223> OTHER INFORMATION: 4-34 FR2

<400> SEQUENCE: 376

Trp Ile Arg Gln Pro Pro Gly Lys Gly Leu Glu Trp Ile Gly
1               5                   10

<210> SEQ ID NO 377
<211> LENGTH: 32
<212> TYPE: PRT
<213> ORGANISM: Artificial Sequence
<220> FEATURE:
<223> OTHER INFORMATION: 4-34 FR3

<400> SEQUENCE: 377

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 378
<211> LENGTH: 25
<212> TYPE: PRT
<213> ORGANISM: Artificial Sequence
<220> FEATURE:
<223> OTHER INFORMATION: 4-39 FR1

<400> SEQUENCE: 378

Gln Leu Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 379
<211> LENGTH: 14
<212> TYPE: PRT
<213> ORGANISM: Artificial Sequence
<220> FEATURE:
<223> OTHER INFORMATION: 4-39 FR2

<400> SEQUENCE: 379

Trp Ile Arg Gln Pro Pro Gly Lys Gly Leu Glu Trp Ile Gly
1               5                   10

<210> SEQ ID NO 380
<211> LENGTH: 32
<212> TYPE: PRT

```
<213> ORGANISM: Artificial Sequence
<220> FEATURE:
<223> OTHER INFORMATION: 4-39 FR3

<400> SEQUENCE: 380

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 381
<211> LENGTH: 25
<212> TYPE: PRT
<213> ORGANISM: Artificial Sequence
<220> FEATURE:
<223> OTHER INFORMATION: 4-59 FR1

<400> SEQUENCE: 381

Gln Val Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 382
<211> LENGTH: 14
<212> TYPE: PRT
<213> ORGANISM: Artificial Sequence
<220> FEATURE:
<223> OTHER INFORMATION: 4-59 FR2

<400> SEQUENCE: 382

Trp Ile Arg Gln Pro Pro Gly Lys Gly Leu Glu Trp Ile Gly
1               5                   10

<210> SEQ ID NO 383
<211> LENGTH: 32
<212> TYPE: PRT
<213> ORGANISM: Artificial Sequence
<220> FEATURE:
<223> OTHER INFORMATION: 4-59 FR3

<400> SEQUENCE: 383

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 384
<211> LENGTH: 25
<212> TYPE: PRT
<213> ORGANISM: Artificial Sequence
<220> FEATURE:
<223> OTHER INFORMATION: 4-61 FR1

<400> SEQUENCE: 384

Gln Val Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 385
<211> LENGTH: 14
<212> TYPE: PRT
<213> ORGANISM: Artificial Sequence
<220> FEATURE:
```

<223> OTHER INFORMATION: 4-61 FR2

<400> SEQUENCE: 385

Trp Ile Arg Gln Pro Pro Gly Lys Gly Leu Glu Trp Ile Gly
1               5                   10

<210> SEQ ID NO 386
<211> LENGTH: 32
<212> TYPE: PRT
<213> ORGANISM: Artificial Sequence
<220> FEATURE:
<223> OTHER INFORMATION: 4-61 FR3

<400> SEQUENCE: 386

Arg Val Thr Ile Ser Val Asp Thr Ser Lys Asn Gln Phe Ser Leu Lys
1               5                   10                  15
Leu Ser Ser Val Thr Ala Ala Asp Thr Ala Val Tyr Tyr Cys Ala Arg
            20                  25                  30

<210> SEQ ID NO 387
<211> LENGTH: 25
<212> TYPE: PRT
<213> ORGANISM: Artificial Sequence
<220> FEATURE:
<223> OTHER INFORMATION: 4-b FR1

<400> SEQUENCE: 387

Gln Val Gln Leu Gln Glu Ser Gly Pro Gly Leu Val Lys Pro Ser Glu
1               5                   10                  15
Thr Leu Ser Leu Thr Cys Ala Val Ser
            20                  25

<210> SEQ ID NO 388
<211> LENGTH: 14
<212> TYPE: PRT
<213> ORGANISM: Artificial Sequence
<220> FEATURE:
<223> OTHER INFORMATION: 4-b FR2

<400> SEQUENCE: 388

Trp Ile Arg Gln Pro Pro Gly Lys Gly Leu Glu Trp Ile Gly
1               5                   10

<210> SEQ ID NO 389
<211> LENGTH: 32
<212> TYPE: PRT
<213> ORGANISM: Artificial Sequence
<220> FEATURE:
<223> OTHER INFORMATION: 4-b FR3

<400> SEQUENCE: 389

Arg Val Thr Ile Ser Val Asp Thr Ser Lys Asn Gln Phe Ser Leu Lys
1               5                   10                  15
Leu Ser Ser Val Thr Ala Ala Asp Thr Ala Val Tyr Tyr Cys Ala Arg
            20                  25                  30

<210> SEQ ID NO 390
<211> LENGTH: 25
<212> TYPE: PRT
<213> ORGANISM: Artificial Sequence
<220> FEATURE:
<223> OTHER INFORMATION: 5-51 FR1

<400> SEQUENCE: 390

Glu Val Gln Leu Val Gln Ser Gly Ala Glu Val Lys Lys Pro Gly Glu

```
                1               5                   10                  15
Ser Leu Lys Ile Ser Cys Lys Gly Ser
            20                  25

<210> SEQ ID NO 391
<211> LENGTH: 14
<212> TYPE: PRT
<213> ORGANISM: Artificial Sequence
<220> FEATURE:
<223> OTHER INFORMATION: 5-51 FR2

<400> SEQUENCE: 391

Trp Val Arg Gln Met Pro Gly Lys Gly Leu Glu Trp Met Gly
1               5                   10

<210> SEQ ID NO 392
<211> LENGTH: 32
<212> TYPE: PRT
<213> ORGANISM: Artificial Sequence
<220> FEATURE:
<223> OTHER INFORMATION: 5-51 FR3

<400> SEQUENCE: 392

Gln Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Arg
            20                  25                  30

<210> SEQ ID NO 393
<211> LENGTH: 25
<212> TYPE: PRT
<213> ORGANISM: Artificial Sequence
<220> FEATURE:
<223> OTHER INFORMATION: 5-a FR1

<400> SEQUENCE: 393

Glu Val Gln Leu Val Gln Ser Gly Ala Glu Val Lys Lys Pro Gly Glu
1               5                   10                  15

Ser Leu Arg Ile Ser Cys Lys Gly Ser
            20                  25

<210> SEQ ID NO 394
<211> LENGTH: 14
<212> TYPE: PRT
<213> ORGANISM: Artificial Sequence
<220> FEATURE:
<223> OTHER INFORMATION: 5-a FR2

<400> SEQUENCE: 394

Trp Val Arg Gln Met Pro Gly Lys Gly Leu Glu Trp Met Gly
1               5                   10

<210> SEQ ID NO 395
<211> LENGTH: 32
<212> TYPE: PRT
<213> ORGANISM: Artificial Sequence
<220> FEATURE:
<223> OTHER INFORMATION: 5-a FR3

<400> SEQUENCE: 395

His Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Arg
            20                  25                  30
```

<210> SEQ ID NO 396
<211> LENGTH: 25
<212> TYPE: PRT
<213> ORGANISM: Artificial Sequence
<220> FEATURE:
<223> OTHER INFORMATION: 6-01 FR1

<400> SEQUENCE: 396

Gln Val Gln Leu Gln Gln Ser Gly Pro Gly Leu Val Lys Pro Ser Gln
1               5                   10                  15

Thr Leu Ser Leu Thr Cys Ala Ile Ser
            20                  25

<210> SEQ ID NO 397
<211> LENGTH: 14
<212> TYPE: PRT
<213> ORGANISM: Artificial Sequence
<220> FEATURE:
<223> OTHER INFORMATION: 6-01 FR2

<400> SEQUENCE: 397

Trp Ile Arg Gln Ser Pro Ser Arg Gly Leu Glu Trp Leu Gly
1               5                   10

<210> SEQ ID NO 398
<211> LENGTH: 32
<212> TYPE: PRT
<213> ORGANISM: Artificial Sequence
<220> FEATURE:
<223> OTHER INFORMATION: 6-01 FR3

<400> SEQUENCE: 398

Arg Ile Thr Ile Asn Pro Asp Thr Ser Lys Asn Gln Phe Ser Leu Gln
1               5                   10                  15

Leu Asn Ser Val Thr Pro Glu Asp Thr Ala Val Tyr Tyr Cys Ala Arg
            20                  25                  30

<210> SEQ ID NO 399
<211> LENGTH: 25
<212> TYPE: PRT
<213> ORGANISM: Artificial Sequence
<220> FEATURE:
<223> OTHER INFORMATION: 7-4.1 FR1

<400> SEQUENCE: 399

Gln Val Gln Leu Val Gln Ser Gly Ser Glu Leu Lys Lys Pro Gly Ala
1               5                   10                  15

Ser Val Lys Val Ser Cys Lys Ala Ser
            20                  25

<210> SEQ ID NO 400
<211> LENGTH: 14
<212> TYPE: PRT
<213> ORGANISM: Artificial Sequence
<220> FEATURE:
<223> OTHER INFORMATION: 7-4.1 FR2

<400> SEQUENCE: 400

Trp Val Arg Gln Ala Pro Gly Gln Gly Leu Glu Trp Met Gly
1               5                   10

<210> SEQ ID NO 401
<211> LENGTH: 32
<212> TYPE: PRT
<213> ORGANISM: Artificial Sequence

```
<220> FEATURE:
<223> OTHER INFORMATION: 7-4.1 FR3

<400> SEQUENCE: 401

Arg Phe Val Phe Ser Leu Asp Thr Ser Val Ser Thr Ala Tyr Leu Gln
1               5                   10                  15
Ile Cys Ser Leu Lys Ala Glu Asp Thr Ala Val Tyr Tyr Cys Ala Arg
            20                  25                  30

<210> SEQ ID NO 402
<211> LENGTH: 11
<212> TYPE: PRT
<213> ORGANISM: Artificial Sequence
<220> FEATURE:
<223> OTHER INFORMATION: JH1 FR4

<400> SEQUENCE: 402

Trp Gly Gln Gly Thr Leu Val Thr Val Ser Ser
1               5                   10

<210> SEQ ID NO 403
<211> LENGTH: 11
<212> TYPE: PRT
<213> ORGANISM: Artificial Sequence
<220> FEATURE:
<223> OTHER INFORMATION: JH2 FR4

<400> SEQUENCE: 403

Trp Gly Arg Gly Thr Leu Val Thr Val Ser Ser
1               5                   10

<210> SEQ ID NO 404
<211> LENGTH: 11
<212> TYPE: PRT
<213> ORGANISM: Artificial Sequence
<220> FEATURE:
<223> OTHER INFORMATION: JH3 FR4

<400> SEQUENCE: 404

Trp Gly Gln Gly Thr Met Val Thr Val Ser Ser
1               5                   10

<210> SEQ ID NO 405
<211> LENGTH: 11
<212> TYPE: PRT
<213> ORGANISM: Artificial Sequence
<220> FEATURE:
<223> OTHER INFORMATION: JH4 FR4

<400> SEQUENCE: 405

Trp Gly Gln Gly Thr Leu Val Thr Val Ser Ser
1               5                   10

<210> SEQ ID NO 406
<211> LENGTH: 11
<212> TYPE: PRT
<213> ORGANISM: Artificial Sequence
<220> FEATURE:
<223> OTHER INFORMATION: JH5 FR4

<400> SEQUENCE: 406

Trp Gly Gln Gly Thr Leu Val Thr Val Ser Ser
1               5                   10

<210> SEQ ID NO 407
<211> LENGTH: 11
```

<212> TYPE: PRT
<213> ORGANISM: Artificial Sequence
<220> FEATURE:
<223> OTHER INFORMATION: JH6 FR4

<400> SEQUENCE: 407

Trp Gly Gln Gly Thr Thr Val Thr Val Ser Ser
1               5                   10

<210> SEQ ID NO 408
<211> LENGTH: 102
<212> TYPE: PRT
<213> ORGANISM: Artificial Sequence
<220> FEATURE:
<223> OTHER INFORMATION: IGAH1 CH1

<400> SEQUENCE: 408

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro
            100

<210> SEQ ID NO 409
<211> LENGTH: 18
<212> TYPE: PRT
<213> ORGANISM: Artificial Sequence
<220> FEATURE:
<223> OTHER INFORMATION: IGAH1 Hinge

<400> SEQUENCE: 409

Pro Ser Thr Pro Pro Thr Pro Ser Pro Ser Thr Pro Pro Thr Pro Ser
1               5                   10                  15

Pro Ser

<210> SEQ ID NO 410
<211> LENGTH: 101
<212> TYPE: PRT
<213> ORGANISM: Artificial Sequence
<220> FEATURE:
<223> OTHER INFORMATION: IGAH1 CH2

<400> SEQUENCE: 410

Cys Cys His Pro Arg Leu Ser Leu His Arg Pro Ala Leu Glu Asp Leu
1               5                   10                  15

Leu Leu Gly Ser Glu Ala Asn Leu Thr Cys Thr Leu Thr Gly Leu Arg
            20                  25                  30

Asp Ala Ser Gly Val Thr Phe Thr Trp Thr Pro Ser Ser Gly Lys Ser
        35                  40                  45

Ala Val Gln Gly Pro Pro Glu Arg Asp Leu Cys Gly Cys Tyr Ser Val
    50                  55                  60

Ser Ser Val Leu Pro Gly Cys Ala Glu Pro Trp Asn His Gly Lys Thr

```
                65                  70                  75                  80
            Phe Thr Cys Thr Ala Ala Tyr Pro Glu Ser Lys Thr Pro Leu Thr Ala
                                85                  90                  95

Thr Leu Ser Lys Ser
                        100

<210> SEQ ID NO 411
<211> LENGTH: 111
<212> TYPE: PRT
<213> ORGANISM: Artificial Sequence
<220> FEATURE:
<223> OTHER INFORMATION: IGAH1 CH3

<400> SEQUENCE: 411

Gly Asn Thr Phe Arg Pro Glu Val His Leu Leu Pro Pro Ser Glu
1               5                   10                  15

Glu Leu Ala Leu Asn Glu Leu Val Thr Leu Thr Cys Leu Ala Arg Gly
                20                  25                  30

Phe Ser Pro Lys Asp Val Leu Val Arg Trp Leu Gln Gly Ser Gln Glu
            35                  40                  45

Leu Pro Arg Glu Lys Tyr Leu Thr Trp Ala Ser Arg Gln Glu Pro Ser
50                  55                  60

Gln Gly Thr Thr Thr Phe Ala Val Thr Ser Ile Leu Arg Val Ala Ala
65                  70                  75                  80

Glu Asp Trp Lys Lys Gly Asp Thr Phe Ser Cys Met Val Gly His Glu
                85                  90                  95

Ala Leu Pro Leu Ala Phe Thr Gln Lys Thr Ile Asp Arg Leu Ala
            100                 105                 110

<210> SEQ ID NO 412
<211> LENGTH: 102
<212> TYPE: PRT
<213> ORGANISM: Artificial Sequence
<220> FEATURE:
<223> OTHER INFORMATION: IGAH2 CH1

<400> SEQUENCE: 412

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
                20                  25                  30

Pro Gln Glu Pro Leu Ser Val Thr Trp Ser Glu Ser Gly Gln Asn Val
            35                  40                  45

Thr Ala Arg Asn Phe Pro Pro Ser Gln Asp Ala Ser Gly Asp Leu Tyr
50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro
            100

<210> SEQ ID NO 413
<211> LENGTH: 5
<212> TYPE: PRT
<213> ORGANISM: Artificial Sequence
<220> FEATURE:
<223> OTHER INFORMATION: IGAH2 Hinge

<400> SEQUENCE: 413
```

Pro Pro Pro Pro Pro
1               5

<210> SEQ ID NO 414
<211> LENGTH: 101
<212> TYPE: PRT
<213> ORGANISM: Artificial Sequence
<220> FEATURE:
<223> OTHER INFORMATION: IGAH2 CH2

<400> SEQUENCE: 414

Cys Cys His Pro Arg Leu Ser Leu His Arg Pro Ala Leu Glu Asp Leu
1               5                   10                  15

Leu Leu Gly Ser Glu Ala Asn Leu Thr Cys Thr Leu Thr Gly Leu Arg
                20                  25                  30

Asp Ala Ser Gly Ala Thr Phe Thr Trp Thr Pro Ser Ser Gly Lys Ser
            35                  40                  45

Ala Val Gln Gly Pro Pro Glu Arg Asp Leu Cys Gly Cys Tyr Ser Val
        50                  55                  60

Ser Ser Val Leu Pro Gly Cys Ala Gln Pro Trp Asn His Gly Glu Thr
65                  70                  75                  80

Phe Thr Cys Thr Ala Ala His Pro Glu Leu Lys Thr Pro Leu Thr Ala
                85                  90                  95

Asn Ile Thr Lys Ser
            100

<210> SEQ ID NO 415
<211> LENGTH: 111
<212> TYPE: PRT
<213> ORGANISM: Artificial Sequence
<220> FEATURE:
<223> OTHER INFORMATION: IGAH2 CH3

<400> SEQUENCE: 415

Gly Asn Thr Phe Arg Pro Glu Val His Leu Leu Pro Pro Pro Ser Glu
1               5                   10                  15

Glu Leu Ala Leu Asn Glu Leu Val Thr Leu Thr Cys Leu Ala Arg Gly
                20                  25                  30

Phe Ser Pro Lys Asp Val Leu Val Arg Trp Leu Gln Gly Ser Gln Glu
            35                  40                  45

Leu Pro Arg Glu Lys Tyr Leu Thr Trp Ala Ser Arg Gln Glu Pro Ser
        50                  55                  60

Gln Gly Thr Thr Thr Phe Ala Val Thr Ser Ile Leu Arg Val Ala Ala
65                  70                  75                  80

Glu Asp Trp Lys Lys Gly Asp Thr Phe Ser Cys Met Val Gly His Glu
                85                  90                  95

Ala Leu Pro Leu Ala Phe Thr Gln Lys Thr Ile Asp Arg Leu Ala
            100                 105                 110

<210> SEQ ID NO 416
<211> LENGTH: 101
<212> TYPE: PRT
<213> ORGANISM: Artificial Sequence
<220> FEATURE:
<223> OTHER INFORMATION: IGDH CH1

<400> SEQUENCE: 416

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro
            100

<210> SEQ ID NO 417
<211> LENGTH: 58
<212> TYPE: PRT
<213> ORGANISM: Artificial Sequence
<220> FEATURE:
<223> OTHER INFORMATION: IGDH Hinge

<400> SEQUENCE: 417

Glu Ser Pro Lys Ala Gln Ala Ser Ser Val Pro Thr Ala Gln Pro Gln
1               5                   10                  15

Ala Glu Gly Ser Leu Ala Lys Ala Thr Thr Ala Pro Ala Thr Thr Arg
            20                  25                  30

Asn Thr Gly Arg Gly Gly Glu Glu Lys Lys Lys Glu Lys Glu Lys Glu
        35                  40                  45

Glu Gln Glu Glu Arg Glu Thr Lys Thr Pro
    50                  55

<210> SEQ ID NO 418
<211> LENGTH: 108
<212> TYPE: PRT
<213> ORGANISM: Artificial Sequence
<220> FEATURE:
<223> OTHER INFORMATION: IGDH CH2

<400> SEQUENCE: 418

Glu Cys Pro Ser His Thr Gln Pro Leu Gly Val Tyr Leu Leu Thr Pro
1               5                   10                  15

Ala Val Gln Asp Leu Trp Leu Arg Asp Lys Ala Thr Phe Thr Cys Phe
            20                  25                  30

Val Val Gly Ser Asp Leu Lys Asp Ala His Leu Thr Trp Glu Val Ala
        35                  40                  45

Gly Lys Val Pro Thr Gly Gly Val Glu Glu Gly Leu Leu Glu Arg His
    50                  55                  60

Ser Asn Gly Ser Gln Ser Gln His Ser Arg Leu Thr Leu Pro Arg Ser
65                  70                  75                  80

Leu Trp Asn Ala Gly Thr Ser Val Thr Cys Thr Leu Asn His Pro Ser
                85                  90                  95

Leu Pro Pro Gln Arg Leu Met Ala Leu Arg Glu Pro
            100                 105

<210> SEQ ID NO 419
<211> LENGTH: 108
<212> TYPE: PRT
<213> ORGANISM: Artificial Sequence
<220> FEATURE:
<223> OTHER INFORMATION: IGDH CH3

-continued

<400> SEQUENCE: 419

Ala Ala Gln Ala Pro Val Lys Leu Ser Leu Asn Leu Ala Ser Ser
1               5                   10                  15

Asp Pro Pro Glu Ala Ala Ser Trp Leu Leu Cys Glu Val Ser Gly Phe
            20                  25                  30

Ser Pro Pro Asn Ile Leu Leu Met Trp Leu Glu Asp Gln Arg Glu Val
        35                  40                  45

Asn Thr Ser Gly Phe Ala Pro Ala Arg Pro Pro Gln Pro Arg Ser
    50                  55                  60

Thr Thr Phe Trp Ala Trp Ser Val Leu Arg Val Pro Ala Pro Ser
65                  70                  75                  80

Pro Gln Pro Ala Thr Tyr Thr Cys Val Val Ser His Glu Asp Ser Arg
                85                  90                  95

Thr Leu Leu Asn Ala Ser Arg Ser Leu Glu Val Ser
            100                 105

<210> SEQ ID NO 420
<211> LENGTH: 103
<212> TYPE: PRT
<213> ORGANISM: Artificial Sequence
<220> FEATURE:
<223> OTHER INFORMATION: IGEH CH1

<400> SEQUENCE: 420

Ala Ser Thr Gln Ser Pro Ser Val Phe Pro Leu Thr Arg Cys Cys Lys
1               5                   10                  15

Asn Ile Pro Ser Asn Ala Thr Ser Val Thr Leu Gly Cys Leu Ala Thr
            20                  25                  30

Gly Tyr Phe Pro Glu Pro Val Met Val Thr Cys Asp Thr Gly Ser Leu
        35                  40                  45

Asn Gly Thr Thr Met Thr Leu Pro Ala Thr Thr Leu Thr Leu Ser Gly
    50                  55                  60

His Tyr Ala Thr Ile Ser Leu Leu Thr Val Ser Gly Ala Trp Ala Lys
65                  70                  75                  80

Gln Met Phe Thr Cys Arg Val Ala His Thr Pro Ser Ser Thr Asp Trp
                85                  90                  95

Val Asp Asn Lys Thr Phe Ser
            100

<210> SEQ ID NO 421
<211> LENGTH: 107
<212> TYPE: PRT
<213> ORGANISM: Artificial Sequence
<220> FEATURE:
<223> OTHER INFORMATION: IGEH CH2

<400> SEQUENCE: 421

Val Cys Ser Arg Asp Phe Thr Pro Pro Thr Val Lys Ile Leu Gln Ser
1               5                   10                  15

Ser Cys Asp Gly Gly Gly His Phe Pro Pro Thr Ile Gln Leu Leu Cys
            20                  25                  30

Leu Val Ser Gly Tyr Thr Pro Gly Thr Ile Asn Ile Thr Trp Leu Glu
        35                  40                  45

Asp Gly Gln Val Met Asp Val Asp Leu Ser Thr Ala Ser Thr Thr Gln
    50                  55                  60

Glu Gly Glu Leu Ala Ser Thr Gln Ser Glu Leu Thr Leu Ser Gln Lys
65                  70                  75                  80

His Trp Leu Ser Asp Arg Thr Tyr Thr Cys Gln Val Thr Tyr Gln Gly
            85                  90                  95

His Thr Phe Glu Asp Ser Thr Lys Lys Cys Ala
            100                 105

<210> SEQ ID NO 422
<211> LENGTH: 108
<212> TYPE: PRT
<213> ORGANISM: Artificial Sequence
<220> FEATURE:
<223> OTHER INFORMATION: IGEH CH3

<400> SEQUENCE: 422

Asp Ser Asn Pro Arg Gly Val Ser Ala Tyr Leu Ser Arg Pro Ser Pro
1               5                   10                  15

Phe Asp Leu Phe Ile Arg Lys Ser Pro Thr Ile Thr Cys Leu Val Val
            20                  25                  30

Asp Leu Ala Pro Ser Lys Gly Thr Val Asn Leu Thr Trp Ser Arg Ala
        35                  40                  45

Ser Gly Lys Pro Val Asn His Ser Thr Arg Lys Glu Glu Lys Gln Arg
    50                  55                  60

Asn Gly Thr Leu Thr Val Thr Ser Thr Leu Pro Val Gly Thr Arg Asp
65                  70                  75                  80

Trp Ile Glu Gly Glu Thr Tyr Gln Cys Arg Val Thr His Pro His Leu
                85                  90                  95

Pro Arg Ala Leu Met Arg Ser Thr Thr Lys Thr Ser
            100                 105

<210> SEQ ID NO 423
<211> LENGTH: 108
<212> TYPE: PRT
<213> ORGANISM: Artificial Sequence
<220> FEATURE:
<223> OTHER INFORMATION: IGEH CH4

<400> SEQUENCE: 423

Gly Pro Arg Ala Ala Pro Glu Val Tyr Ala Phe Ala Thr Pro Glu Trp
1               5                   10                  15

Pro Gly Ser Arg Asp Lys Arg Thr Leu Ala Cys Leu Ile Gln Asn Phe
            20                  25                  30

Met Pro Glu Asp Ile Ser Val Gln Trp Leu His Asn Glu Val Gln Leu
        35                  40                  45

Pro Asp Ala Arg His Ser Thr Thr Gln Pro Arg Lys Thr Lys Gly Ser
    50                  55                  60

Gly Phe Phe Val Phe Ser Arg Leu Glu Val Thr Arg Ala Glu Trp Glu
65                  70                  75                  80

Gln Lys Asp Glu Phe Ile Cys Arg Ala Val His Glu Ala Ala Ser Pro
                85                  90                  95

Ser Gln Thr Val Gln Arg Ala Val Ser Val Asn Pro
            100                 105

<210> SEQ ID NO 424
<211> LENGTH: 98
<212> TYPE: PRT
<213> ORGANISM: Artificial Sequence
<220> FEATURE:
<223> OTHER INFORMATION: IGGH1 CH1

<400> SEQUENCE: 424

Ala Ser Thr Lys Gly Pro Ser Val Phe Pro Leu Ala Pro Ser Ser Lys

```
                1               5                  10                 15
            Ser Thr Ser Gly Gly Thr Ala Ala Leu Gly Cys Leu Val Lys Asp Tyr
                            20                  25                  30

Phe Pro Glu Pro Val Thr Val Ser Trp Asn Ser Gly Ala Leu Thr Ser
                            35                  40                  45

Gly Val His Thr Phe Pro Ala Val Leu Gln Ser Ser Gly Leu Tyr Ser
                    50                  55                  60

Leu Ser Ser Val Val Thr Val Pro Ser Ser Leu Gly Thr Gln Thr
             65                 70                  75                  80

Tyr Ile Cys Asn Val Asn His Lys Pro Ser Asn Thr Lys Val Asp Lys
                            85                  90                  95

Lys Val

<210> SEQ ID NO 425
<211> LENGTH: 15
<212> TYPE: PRT
<213> ORGANISM: Artificial Sequence
<220> FEATURE:
<223> OTHER INFORMATION: IGGH1 Hinge

<400> SEQUENCE: 425

Glu Pro Lys Ser Cys Asp Lys Thr His Thr Cys Pro Pro Cys Pro
 1               5                  10                  15

<210> SEQ ID NO 426
<211> LENGTH: 110
<212> TYPE: PRT
<213> ORGANISM: Artificial Sequence
<220> FEATURE:
<223> OTHER INFORMATION: IGGH1 CH2

<400> SEQUENCE: 426

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
 65                 70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 427
<211> LENGTH: 105
<212> TYPE: PRT
<213> ORGANISM: Artificial Sequence
<220> FEATURE:
<223> OTHER INFORMATION: IGGH1 CH3

<400> SEQUENCE: 427

Gly Gln Pro Arg Glu Pro Gln Val Tyr Thr Leu Pro Pro Ser Arg Asp
 1               5                  10                  15

Glu Leu Thr Lys Asn Gln Val Ser Leu Thr Cys Leu Val Lys Gly Phe
                20                  25                  30
```

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro
            100                 105

<210> SEQ ID NO 428
<211> LENGTH: 98
<212> TYPE: PRT
<213> ORGANISM: Artificial Sequence
<220> FEATURE:
<223> OTHER INFORMATION: IGGH2 CH1

<400> SEQUENCE: 428

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val

<210> SEQ ID NO 429
<211> LENGTH: 12
<212> TYPE: PRT
<213> ORGANISM: Artificial Sequence
<220> FEATURE:
<223> OTHER INFORMATION: IGGH2 Hinge

<400> SEQUENCE: 429

Glu Arg Lys Cys Cys Val Glu Cys Pro Pro Cys Pro
1               5                   10

<210> SEQ ID NO 430
<211> LENGTH: 109
<212> TYPE: PRT
<213> ORGANISM: Artificial Sequence
<220> FEATURE:
<223> OTHER INFORMATION: IGGH2 CH2

<400> SEQUENCE: 430

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

```
Phe Asn Ser Thr Phe Arg Val Val Ser Val Leu Thr Val Val His Gln
 65                  70                  75                  80

Asp Trp Leu Asn Gly Lys Glu Tyr Lys Cys Lys Val Ser Asn Lys Gly
                 85                  90                  95

Leu Pro Ala Pro Ile Glu Lys Thr Ile Ser Lys Thr Lys
            100                 105
```

<210> SEQ ID NO 431
<211> LENGTH: 105
<212> TYPE: PRT
<213> ORGANISM: Artificial Sequence
<220> FEATURE:
<223> OTHER INFORMATION: IGGH2 CH3

<400> SEQUENCE: 431

```
Gly Gln Pro Arg Glu Pro Gln Val Tyr Thr Leu Pro Pro Ser Arg Glu
 1               5                  10                  15

Glu Met Thr Lys Asn Gln Val Ser Leu Thr Cys Leu Val Lys Gly Phe
             20                  25                  30

Tyr Pro Ser Asp Ile Ala Val Glu Trp Glu Ser Asn Gly Gln Pro Glu
         35                  40                  45

Asn Asn Tyr Lys Thr Thr Pro Pro Met Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro
            100                 105
```

<210> SEQ ID NO 432
<211> LENGTH: 98
<212> TYPE: PRT
<213> ORGANISM: Artificial Sequence
<220> FEATURE:
<223> OTHER INFORMATION: IGGH3 CH1

<400> SEQUENCE: 432

```
Ala Ser Thr Lys Gly Pro Ser Val Phe Pro Leu Ala Pro Cys Ser Arg
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Thr Cys Asn Val Asn His Lys Pro Ser Asn Thr Lys Val Asp Lys
                 85                  90                  95

Arg Val
```

<210> SEQ ID NO 433
<211> LENGTH: 62
<212> TYPE: PRT
<213> ORGANISM: Artificial Sequence
<220> FEATURE:
<223> OTHER INFORMATION: IGGH3 Hinge

<400> SEQUENCE: 433

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro
    50                  55                  60

<210> SEQ ID NO 434
<211> LENGTH: 110
<212> TYPE: PRT
<213> ORGANISM: Artificial Sequence
<220> FEATURE:
<223> OTHER INFORMATION: IGGH3 CH2

<400> SEQUENCE: 434

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
            100                 105                 110

<210> SEQ ID NO 435
<211> LENGTH: 105
<212> TYPE: PRT
<213> ORGANISM: Artificial Sequence
<220> FEATURE:
<223> OTHER INFORMATION: IGGH3 CH3

<400> SEQUENCE: 435

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Ser Gly Gln Pro Glu
        35                  40                  45

Asn Asn Tyr Asn Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn Arg Phe
                85                  90                  95

Thr Gln Lys Ser Leu Ser Leu Ser Pro
            100                 105

<210> SEQ ID NO 436
<211> LENGTH: 98

<212> TYPE: PRT
<213> ORGANISM: Artificial Sequence
<220> FEATURE:
<223> OTHER INFORMATION: IGGH4 CH1

<400> SEQUENCE: 436

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val
```

<210> SEQ ID NO 437
<211> LENGTH: 12
<212> TYPE: PRT
<213> ORGANISM: Artificial Sequence
<220> FEATURE:
<223> OTHER INFORMATION: IGGH4 Hinge

<400> SEQUENCE: 437

```
Glu Ser Lys Tyr Gly Pro Pro Cys Pro Ser Cys Pro
1               5                   10
```

<210> SEQ ID NO 438
<211> LENGTH: 110
<212> TYPE: PRT
<213> ORGANISM: Artificial Sequence
<220> FEATURE:
<223> OTHER INFORMATION: IGGH4 CH2

<400> SEQUENCE: 438

```
Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110
```

<210> SEQ ID NO 439
<211> LENGTH: 105
<212> TYPE: PRT
<213> ORGANISM: Artificial Sequence
<220> FEATURE:
<223> OTHER INFORMATION: IGGH4 CH3

<400> SEQUENCE: 439

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu
            100                 105

<210> SEQ ID NO 440
<211> LENGTH: 104
<212> TYPE: PRT
<213> ORGANISM: Artificial Sequence
<220> FEATURE:
<223> OTHER INFORMATION: IGMH CH1

<400> SEQUENCE: 440

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro
            100

<210> SEQ ID NO 441
<211> LENGTH: 112
<212> TYPE: PRT
<213> ORGANISM: Artificial Sequence
<220> FEATURE:
<223> OTHER INFORMATION: IGMH CH2

<400> SEQUENCE: 441

Val Ile Ala Glu Leu Pro Pro Lys Val Ser Val Phe Val Pro Pro Arg
1               5                   10                  15

Asp Gly Phe Phe Gly Asn Pro Arg Lys Ser Lys Leu Ile Cys Gln Ala
            20                  25                  30

Thr Gly Phe Ser Pro Arg Gln Ile Gln Val Ser Trp Leu Arg Glu Gly
        35                  40                  45

Lys Gln Val Gly Ser Gly Val Thr Thr Asp Gln Val Gln Ala Glu Ala
    50                  55                  60

Lys Glu Ser Gly Pro Thr Thr Tyr Lys Val Thr Ser Thr Leu Thr Ile
65                  70                  75                  80

```
Lys Glu Ser Asp Trp Leu Gly Gln Ser Met Phe Thr Cys Arg Val Asp
            85                  90                  95

His Arg Gly Leu Thr Phe Gln Asn Ala Ser Ser Met Cys Val Pro
            100                 105                 110

<210> SEQ ID NO 442
<211> LENGTH: 106
<212> TYPE: PRT
<213> ORGANISM: Artificial Sequence
<220> FEATURE:
<223> OTHER INFORMATION: IGMH CH3

<400> SEQUENCE: 442

Asp Gln Asp Thr Ala Ile Arg Val Phe Ala Ile Pro Pro Ser Phe Ala
1               5                   10                  15

Ser Ile Phe Leu Thr Lys Ser Thr Lys Leu Thr Cys Leu Val Thr Asp
            20                  25                  30

Leu Thr Thr Tyr Asp Ser Val Thr Ile Ser Trp Thr Arg Gln Asn Gly
            35                  40                  45

Glu Ala Val Lys Thr His Thr Asn Ile Ser Glu Ser His Pro Asn Ala
50                  55                  60

Thr Phe Ser Ala Val Gly Glu Ala Ser Ile Cys Glu Asp Asp Trp Asn
65                  70                  75                  80

Ser Gly Glu Arg Phe Thr Cys Thr Val Thr His Thr Asp Leu Pro Ser
                85                  90                  95

Pro Leu Lys Gln Thr Ile Ser Arg Pro Lys
            100                 105

<210> SEQ ID NO 443
<211> LENGTH: 110
<212> TYPE: PRT
<213> ORGANISM: Artificial Sequence
<220> FEATURE:
<223> OTHER INFORMATION: IGMH CH4

<400> SEQUENCE: 443

Gly Val Ala Leu His Arg Pro Asp Val Tyr Leu Leu Pro Pro Ala Arg
1               5                   10                  15

Glu Gln Leu Asn Leu Arg Glu Ser Ala Thr Ile Thr Cys Leu Val Thr
            20                  25                  30

Gly Phe Ser Pro Ala Asp Val Phe Val Gln Trp Met Gln Arg Gly Gln
            35                  40                  45

Pro Leu Ser Pro Glu Lys Tyr Val Thr Ser Ala Pro Met Pro Glu Pro
50                  55                  60

Gln Ala Pro Gly Arg Tyr Phe Ala His Ser Ile Leu Thr Val Ser Glu
65                  70                  75                  80

Glu Glu Trp Asn Thr Gly Glu Thr Tyr Thr Cys Val Ala His Glu Ala
                85                  90                  95

Leu Pro Asn Arg Val Thr Glu Arg Thr Val Asp Lys Ser Thr
            100                 105                 110

<210> SEQ ID NO 444
<211> LENGTH: 137
<212> TYPE: PRT
<213> ORGANISM: Artificial Sequence
<220> FEATURE:
<223> OTHER INFORMATION: Joining Polypeptide

<400> SEQUENCE: 444

Gln Glu Asp Glu Arg Ile Val Leu Val Asp Asn Lys Cys Lys Cys Ala
```

```
            1               5                   10                  15
        Arg Ile Thr Ser Arg Ile Ile Arg Ser Ser Glu Asp Pro Asn Glu Asp
                        20                  25                  30

Ile Val Glu Arg Asn Ile Arg Ile Val Pro Leu Asn Asn Arg Glu
                    35                  40                  45

Asn Ile Ser Asp Pro Thr Ser Pro Leu Arg Thr Arg Phe Val Tyr His
                    50                  55                  60

Leu Ser Asp Leu Cys Lys Lys Cys Asp Pro Thr Glu Val Glu Leu Asp
        65                  70                  75                  80

Asn Gln Ile Val Thr Ala Thr Gln Ser Asn Ile Cys Asp Glu Asp Ser
                        85                  90                  95

Ala Thr Glu Thr Cys Tyr Thr Tyr Asp Arg Asn Lys Cys Tyr Thr Ala
                        100                 105                 110

Val Val Pro Leu Val Tyr Gly Gly Glu Thr Lys Met Val Glu Thr Ala
                        115                 120                 125

Leu Thr Pro Asp Ala Cys Tyr Pro Asp
                    130                 135

<210> SEQ ID NO 445
<211> LENGTH: 112
<212> TYPE: PRT
<213> ORGANISM: Artificial Sequence
<220> FEATURE:
<223> OTHER INFORMATION: Rabbit Ab 909 VL-region

<400> SEQUENCE: 445

Asp Val Val Met Thr Gln Thr Pro Ala Ser Val Ser Glu Pro Val Gly
        1               5                   10                  15

Gly Thr Val Thr Ile Lys Cys Gln Ala Ser Glu Asp Ile Ser Arg Tyr
                        20                  25                  30

Leu Val Trp Tyr Gln Gln Lys Pro Gly Gln Pro Pro Lys Arg Leu Ile
                    35                  40                  45

Tyr Lys Ala Ser Thr Leu Ala Ser Gly Val Pro Ser Arg Phe Lys Gly
                    50                  55                  60

Ser Gly Ser Gly Thr Asp Phe Thr Leu Thr Ile Ser Asp Leu Glu Cys
        65                  70                  75                  80

Asp Asp Ala Ala Thr Tyr Tyr Cys Gln Cys Thr Tyr Gly Thr Tyr Ala
                        85                  90                  95

Gly Ser Phe Phe Tyr Ser Phe Gly Gly Gly Thr Glu Val Val Val Glu
                        100                 105                 110

<210> SEQ ID NO 446
<211> LENGTH: 112
<212> TYPE: PRT
<213> ORGANISM: Artificial Sequence
<220> FEATURE:
<223> OTHER INFORMATION: 909 gL1 VL-region

<400> SEQUENCE: 446

Asp Val Val Met Thr Gln Ser Pro Ser Ser Leu Ser Ala Ser Val Gly
        1               5                   10                  15

Asp Arg Val Thr Ile Thr Cys Gln Ala Ser Glu Asp Ile Ser Arg Tyr
                        20                  25                  30

Leu Val Trp Tyr Gln Gln Lys Pro Gly Lys Ala Pro Lys Arg Leu Ile
                    35                  40                  45

Tyr Lys Ala Ser Thr Leu Ala Ser Gly Val Pro Ser Arg Phe Lys Gly
                    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Cys Thr Tyr Gly Thr Tyr Ala
                 85                  90                  95

Gly Ser Phe Phe Tyr Ser Phe Gly Gly Gly Thr Lys Val Glu Ile Lys
                100                 105                 110
```

<210> SEQ ID NO 447
<211> LENGTH: 219
<212> TYPE: PRT
<213> ORGANISM: Artificial Sequence
<220> FEATURE:
<223> OTHER INFORMATION: 909 gL1 VL + CL-region

<400> SEQUENCE: 447

```
Asp Val Val Met Thr Gln Ser Pro Ser Ser Leu Ser Ala Ser Val Gly
  1               5                  10                  15

Asp Arg Val Thr Ile Thr Cys Gln Ala Ser Glu Asp Ile Ser Arg Tyr
                 20                  25                  30

Leu Val Trp Tyr Gln Gln Lys Pro Gly Lys Ala Pro Lys Arg Leu Ile
             35                  40                  45

Tyr Lys Ala Ser Thr Leu Ala Ser Gly Val Pro Ser Arg Phe Lys Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Cys Thr Tyr Gly Thr Tyr Ala
                 85                  90                  95

Gly Ser Phe Phe Tyr Ser Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 448
<211> LENGTH: 112
<212> TYPE: PRT
<213> ORGANISM: Artificial Sequence
<220> FEATURE:
<223> OTHER INFORMATION: 909 gL10 VL-region

<400> SEQUENCE: 448

```
Asp Val Val Met Thr Gln Ser Pro Ser Ser Leu Ser Ala Ser Val Gly
  1               5                  10                  15

Asp Arg Val Thr Ile Thr Cys Gln Ala Ser Glu Asp Ile Ser Arg Tyr
                 20                  25                  30

Leu Val Trp Tyr Gln Gln Lys Pro Gly Lys Ala Pro Lys Arg Leu Ile
             35                  40                  45
```

```
Tyr Lys Ala Ser Thr Leu Ala Ser Gly Val Pro Ser Arg Phe Lys Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Thr Tyr Gly Thr Tyr Ala
                85                  90                  95

Gly Ser Phe Phe Tyr Ser Phe Gly Gly Gly Thr Lys Val Glu Ile Lys
                100                 105                 110
```

<210> SEQ ID NO 449
<211> LENGTH: 219
<212> TYPE: PRT
<213> ORGANISM: Artificial Sequence
<220> FEATURE:
<223> OTHER INFORMATION: 909 gL10 VL + CL-region

<400> SEQUENCE: 449

```
Asp Val Val Met Thr Gln Ser Pro Ser Ser Leu Ser Ala Ser Val Gly
1               5                   10                  15

Asp Arg Val Thr Ile Thr Cys Gln Ala Ser Glu Asp Ile Ser Arg Tyr
                20                  25                  30

Leu Val Trp Tyr Gln Gln Lys Pro Gly Lys Ala Pro Lys Arg Leu Ile
            35                  40                  45

Tyr Lys Ala Ser Thr Leu Ala Ser Gly Val Pro Ser Arg Phe Lys Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Thr Tyr Gly Thr Tyr Ala
                85                  90                  95

Gly Ser Phe Phe Tyr Ser Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215
```

<210> SEQ ID NO 450
<211> LENGTH: 112
<212> TYPE: PRT
<213> ORGANISM: Artificial Sequence
<220> FEATURE:
<223> OTHER INFORMATION: 909 gL54 VL-region

<400> SEQUENCE: 450

```
Asp Val Val Met Thr Gln Ser Pro Ser Ser Leu Ser Ala Ser Val Gly
1               5                   10                  15

Asp Arg Val Thr Ile Thr Cys Gln Ala Ser Glu Asp Ile Ser Arg Tyr
```

```
                    20                  25                  30

Leu Val Trp Tyr Gln Gln Lys Pro Gly Lys Ala Pro Lys Arg Leu Ile
            35                  40                  45

Tyr Lys Ala Ser Thr Leu Ala Ser Gly Val Pro Ser Arg Phe Lys Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Gly Thr Tyr Ala
                85                  90                  95

Gly Ser Phe Phe Tyr Ser Phe Gly Gly Gly Thr Lys Val Glu Ile Lys
            100                 105                 110

<210> SEQ ID NO 451
<211> LENGTH: 219
<212> TYPE: PRT
<213> ORGANISM: Artificial Sequence
<220> FEATURE:
<223> OTHER INFORMATION: 909 gL54 VL + CL-region

<400> SEQUENCE: 451

Asp Val Val Met Thr Gln Ser Pro Ser Ser Leu Ser Ala Ser Val Gly
1               5                   10                  15

Asp Arg Val Thr Ile Thr Cys Gln Ala Ser Glu Asp Ile Ser Arg Tyr
            20                  25                  30

Leu Val Trp Tyr Gln Gln Lys Pro Gly Lys Ala Pro Lys Arg Leu Ile
        35                      40                  45

Tyr Lys Ala Ser Thr Leu Ala Ser Gly Val Pro Ser Arg Phe Lys Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Gly Thr Tyr Ala
                85                  90                  95

Gly Ser Phe Phe Tyr Ser Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 452
<211> LENGTH: 112
<212> TYPE: PRT
<213> ORGANISM: Artificial Sequence
<220> FEATURE:
<223> OTHER INFORMATION: 909 gL55 VL-region

<400> SEQUENCE: 452
```

Asp Val Val Met Thr Gln Ser Pro Ser Ser Leu Ser Ala Ser Val Gly
1               5                   10                  15

Asp Arg Val Thr Ile Thr Cys Gln Ala Ser Glu Asp Ile Ser Arg Tyr
            20                  25                  30

Leu Val Trp Tyr Gln Gln Lys Pro Gly Lys Ala Pro Lys Arg Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Thr Tyr Gly Thr Tyr Ala
                85                  90                  95

Gly Ser Phe Phe Tyr Ser Phe Gly Gly Gly Thr Lys Val Glu Ile Lys
            100                 105                 110

<210> SEQ ID NO 453
<211> LENGTH: 219
<212> TYPE: PRT
<213> ORGANISM: Artificial Sequence
<220> FEATURE:
<223> OTHER INFORMATION: 909 gL55 VL + CL-region

<400> SEQUENCE: 453

Asp Val Val Met Thr Gln Ser Pro Ser Ser Leu Ser Ala Ser Val Gly
1               5                   10                  15

Asp Arg Val Thr Ile Thr Cys Gln Ala Ser Glu Asp Ile Ser Arg Tyr
            20                  25                  30

Leu Val Trp Tyr Gln Gln Lys Pro Gly Lys Ala Pro Lys Arg Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Thr Tyr Gly Thr Tyr Ala
                85                  90                  95

Gly Ser Phe Phe Tyr Ser Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 454
<211> LENGTH: 120
<212> TYPE: PRT
<213> ORGANISM: Artificial Sequence
<220> FEATURE:

<223> OTHER INFORMATION: Rabbit Ab 909 VH region

<400> SEQUENCE: 454

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Tyr Tyr
            20                  25                  30

Met Ser Trp Val Arg Gln Ala Pro Gly Lys Gly Leu Glu Trp Ile Gly
        35                  40                  45

Ile Ile Tyr Pro Ser Gly Ser Thr Tyr Cys Ala Ser Trp Ala Lys Gly
    50                  55                  60

Arg Phe Thr Ile Ser Lys Ala Ser Thr Thr Val Asp Leu Lys Ile Thr
65                  70                  75                  80

Ser Pro Thr Thr Glu Asp Thr Ala Thr Tyr Phe Cys Ala Arg Pro Asp
                85                  90                  95

Asn Asp Gly Thr Ser Gly Tyr Leu Ser Gly Phe Gly Leu Trp Gly Gln
            100                 105                 110

Gly Thr Leu Val Thr Val Ser Ser
        115                 120

<210> SEQ ID NO 455
<211> LENGTH: 121
<212> TYPE: PRT
<213> ORGANISM: Artificial Sequence
<220> FEATURE:
<223> OTHER INFORMATION: 909gH1 VH region

<400> SEQUENCE: 455

Glu Val Gln Leu Gln Glu Ser Gly Pro Gly Leu Val Lys Pro Ser Gly
1               5                   10                  15

Thr Leu Ser Leu Thr Cys Thr Val Ser Gly Phe Ser Leu Ser Thr Tyr
            20                  25                  30

Tyr Met Ser Trp Val Arg Gln Pro Pro Gly Lys Gly Leu Glu Trp Ile
        35                  40                  45

Gly Ile Ile Tyr Pro Ser Gly Ser Thr Tyr Cys Ala Ser Trp Ala Lys
    50                  55                  60

Gly Arg Phe Thr Ile Ser Lys Ala Ser Thr Thr Val Asp Leu Lys Leu
65                  70                  75                  80

Ser Ser Val Thr Ala Ala Asp Thr Ala Thr Tyr Phe Cys Ala Arg Pro
                85                  90                  95

Asp Asn Asp Gly Thr Ser Gly Tyr Leu Ser Gly Phe Gly Leu Trp Gly
            100                 105                 110

Gln Gly Thr Leu Val Thr Val Ser Ser
        115                 120

<210> SEQ ID NO 456
<211> LENGTH: 448
<212> TYPE: PRT
<213> ORGANISM: Artificial Sequence
<220> FEATURE:
<223> OTHER INFORMATION: 909gH1 IgG4 VH + human ?-4P constant

<400> SEQUENCE: 456

Glu Val Gln Leu Gln Glu Ser Gly Pro Gly Leu Val Lys Pro Ser Gly
1               5                   10                  15

Thr Leu Ser Leu Thr Cys Thr Val Ser Gly Phe Ser Leu Ser Thr Tyr
            20                  25                  30

Tyr Met Ser Trp Val Arg Gln Pro Pro Gly Lys Gly Leu Glu Trp Ile

```
                   35                  40                  45
Gly Ile Ile Tyr Pro Ser Gly Ser Thr Tyr Cys Ala Ser Trp Ala Lys
 50                  55                  60

Gly Arg Phe Thr Ile Ser Lys Ala Ser Thr Thr Val Asp Leu Lys Leu
 65                  70                  75                  80

Ser Ser Val Thr Ala Ala Asp Thr Ala Thr Tyr Phe Cys Ala Arg Pro
                 85                  90                  95

Asp Asn Asp Gly Thr Ser Gly Tyr Leu Ser Gly Phe Gly Leu Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 457
```

```
<211> LENGTH: 123
<212> TYPE: PRT
<213> ORGANISM: Artificial Sequence
<220> FEATURE:
<223> OTHER INFORMATION: 909gH14 VH region

<400> SEQUENCE: 457

Glu Val Gln Leu Gln Glu Ser Gly Pro Gly Leu Val Lys Pro Ser Gly
1               5                   10                  15

Thr Leu Ser Leu Thr Cys Ala Val Ser Gly Phe Ser Leu Ser Thr Tyr
            20                  25                  30

Tyr Met Ser Trp Val Arg Gln Pro Pro Gly Lys Gly Leu Glu Trp Ile
        35                  40                  45

Gly Ile Ile Tyr Pro Ser Gly Ser Thr Tyr Cys Ala Ser Trp Ala Lys
50                  55                  60

Gly Arg Phe Thr Ile Ser Lys Ala Ser Thr Lys Asn Thr Val Asp Leu
65                  70                  75                  80

Lys Leu Ser Ser Val Thr Ala Ala Asp Thr Ala Thr Tyr Phe Cys Ala
                85                  90                  95

Arg Pro Asp Asn Asp Gly Thr Ser Gly Tyr Leu Ser Gly Phe Gly Leu
            100                 105                 110

Trp Gly Gln Gly Thr Leu Val Thr Val Ser Ser
        115                 120

<210> SEQ ID NO 458
<211> LENGTH: 450
<212> TYPE: PRT
<213> ORGANISM: Artificial Sequence
<220> FEATURE:
<223> OTHER INFORMATION: 909gH14 IgG4 VH + human ?-4P constant

<400> SEQUENCE: 458

Glu Val Gln Leu Gln Glu Ser Gly Pro Gly Leu Val Lys Pro Ser Gly
1               5                   10                  15

Thr Leu Ser Leu Thr Cys Ala Val Ser Gly Phe Ser Leu Ser Thr Tyr
            20                  25                  30

Tyr Met Ser Trp Val Arg Gln Pro Pro Gly Lys Gly Leu Glu Trp Ile
        35                  40                  45

Gly Ile Ile Tyr Pro Ser Gly Ser Thr Tyr Cys Ala Ser Trp Ala Lys
50                  55                  60

Gly Arg Phe Thr Ile Ser Lys Ala Ser Thr Lys Asn Thr Val Asp Leu
65                  70                  75                  80

Lys Leu Ser Ser Val Thr Ala Ala Asp Thr Ala Thr Tyr Phe Cys Ala
                85                  90                  95

Arg Pro Asp Asn Asp Gly Thr Ser Gly Tyr Leu Ser Gly Phe Gly Leu
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
```

```
            195                 200                 205
Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 459
<211> LENGTH: 123
<212> TYPE: PRT
<213> ORGANISM: Artificial Sequence
<220> FEATURE:
<223> OTHER INFORMATION: 909 gH15 VH region

<400> SEQUENCE: 459

Glu Val Gln Leu Gln Glu Ser Gly Pro Gly Leu Val Lys Pro Ser Gly
1               5                   10                  15

Thr Leu Ser Leu Thr Cys Thr Val Ser Gly Phe Ser Leu Ser Thr Tyr
            20                  25                  30

Tyr Met Ser Trp Val Arg Gln Pro Pro Gly Lys Gly Leu Glu Trp Ile
        35                  40                  45

Gly Ile Ile Tyr Pro Ser Gly Ser Thr Tyr Ser Ala Ser Trp Ala Lys
    50                  55                  60

Gly Arg Phe Thr Ile Ser Lys Ala Ser Thr Asn Thr Val Asp Leu
65                  70                  75                  80

Lys Leu Ser Ser Val Thr Ala Ala Asp Thr Ala Thr Tyr Phe Cys Ala
                85                  90                  95

Arg Pro Asp Asn Glu Gly Thr Ser Gly Tyr Leu Ser Gly Phe Gly Leu
```

```
                      100                 105                 110
Trp Gly Gln Gly Thr Leu Val Thr Val Ser Ser
            115                 120
```

<210> SEQ ID NO 460
<211> LENGTH: 450
<212> TYPE: PRT
<213> ORGANISM: Artificial Sequence
<220> FEATURE:
<223> OTHER INFORMATION: 909gH15 IgG4 VH + human ?-4P constant

<400> SEQUENCE: 460

```
Glu Val Gln Leu Gln Glu Ser Gly Pro Gly Leu Val Lys Pro Ser Gly
1               5                   10                  15

Thr Leu Ser Leu Thr Cys Thr Val Ser Gly Phe Ser Leu Ser Thr Tyr
            20                  25                  30

Tyr Met Ser Trp Val Arg Gln Pro Pro Gly Lys Gly Leu Glu Trp Ile
        35                  40                  45

Gly Ile Ile Tyr Pro Ser Gly Ser Thr Tyr Ser Ala Ser Trp Ala Lys
50                  55                  60

Gly Arg Phe Thr Ile Ser Lys Ala Ser Thr Lys Asn Thr Val Asp Leu
65                  70                  75                  80

Lys Leu Ser Ser Val Thr Ala Ala Asp Thr Ala Thr Tyr Phe Cys Ala
                85                  90                  95

Arg Pro Asp Asn Glu Gly Thr Ser Gly Tyr Leu Ser Gly Phe Gly Leu
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
```

```
                    340                 345                 350
Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
            435                 440                 445

Gly Lys
    450

<210> SEQ ID NO 461
<211> LENGTH: 123
<212> TYPE: PRT
<213> ORGANISM: Artificial Sequence
<220> FEATURE:
<223> OTHER INFORMATION: 909 gH61 VH region

<400> SEQUENCE: 461

Glu Val Gln Leu Gln Glu Ser Gly Pro Gly Leu Val Lys Pro Ser Gly
1               5                   10                  15

Thr Leu Ser Leu Thr Cys Ala Val Ser Gly Phe Ser Leu Ser Thr Tyr
            20                  25                  30

Tyr Met Ser Trp Val Arg Gln Pro Pro Gly Lys Gly Leu Glu Trp Ile
        35                  40                  45

Gly Ile Ile Tyr Pro Ser Gly Ser Thr Tyr Cys Ala Ser Trp Ala Lys
    50                  55                  60

Gly Arg Val Thr Ile Ser Lys Asp Ser Lys Asn Gln Val Ser Leu
65                  70                  75                  80

Lys Leu Ser Ser Val Thr Ala Ala Asp Thr Ala Val Tyr Tyr Cys Ala
            85                  90                  95

Arg Pro Asp Asn Asp Gly Thr Ser Gly Tyr Leu Ser Gly Phe Gly Leu
            100                 105                 110

Trp Gly Gln Gly Thr Leu Val Thr Val Ser Ser
        115                 120

<210> SEQ ID NO 462
<211> LENGTH: 450
<212> TYPE: PRT
<213> ORGANISM: Artificial Sequence
<220> FEATURE:
<223> OTHER INFORMATION: 909gH61 IgG4 VH + human ?-4P constant

<400> SEQUENCE: 462

Glu Val Gln Leu Gln Glu Ser Gly Pro Gly Leu Val Lys Pro Ser Gly
1               5                   10                  15

Thr Leu Ser Leu Thr Cys Ala Val Ser Gly Phe Ser Leu Ser Thr Tyr
            20                  25                  30

Tyr Met Ser Trp Val Arg Gln Pro Pro Gly Lys Gly Leu Glu Trp Ile
        35                  40                  45

Gly Ile Ile Tyr Pro Ser Gly Ser Thr Tyr Cys Ala Ser Trp Ala Lys
    50                  55                  60
```

Gly Arg Val Thr Ile Ser Lys Asp Ser Ser Lys Asn Gln Val Ser Leu
65                  70                  75                  80

Lys Leu Ser Ser Val Thr Ala Ala Asp Thr Ala Val Tyr Tyr Cys Ala
            85                  90                  95

Arg Pro Asp Asn Asp Gly Thr Ser Gly Tyr Leu Ser Gly Phe Gly Leu
        100                 105                 110

Trp Gly Gln Gly Thr Leu Val Thr Val Ser Ser Ala Ser Thr Lys Gly
    115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
450

<210> SEQ ID NO 463
<211> LENGTH: 123
<212> TYPE: PRT

<213> ORGANISM: Artificial Sequence
<220> FEATURE:
<223> OTHER INFORMATION: 909 gH62 VH region

<400> SEQUENCE: 463

Glu Val Gln Leu Gln Glu Ser Gly Pro Gly Leu Val Lys Pro Ser Gly
1               5                   10                  15

Thr Leu Ser Leu Thr Cys Ala Val Ser Gly Phe Ser Leu Ser Thr Tyr
            20                  25                  30

Tyr Met Ser Trp Val Arg Gln Pro Pro Gly Lys Gly Leu Glu Trp Ile
        35                  40                  45

Gly Ile Ile Tyr Pro Ser Gly Ser Thr Tyr Ser Ala Ser Trp Ala Lys
    50                  55                  60

Gly Arg Val Thr Ile Ser Lys Asp Ser Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Pro Asp Asn Glu Gly Thr Ser Gly Tyr Leu Ser Gly Phe Gly Leu
            100                 105                 110

Trp Gly Gln Gly Thr Leu Val Thr Val Ser Ser
        115                 120

<210> SEQ ID NO 464
<211> LENGTH: 450
<212> TYPE: PRT
<213> ORGANISM: Artificial Sequence
<220> FEATURE:
<223> OTHER INFORMATION: 909gH62 IgG4 VH + human ?-4P constant

<400> SEQUENCE: 464

Glu Val Gln Leu Gln Glu Ser Gly Pro Gly Leu Val Lys Pro Ser Gly
1               5                   10                  15

Thr Leu Ser Leu Thr Cys Ala Val Ser Gly Phe Ser Leu Ser Thr Tyr
            20                  25                  30

Tyr Met Ser Trp Val Arg Gln Pro Pro Gly Lys Gly Leu Glu Trp Ile
        35                  40                  45

Gly Ile Ile Tyr Pro Ser Gly Ser Thr Tyr Ser Ala Ser Trp Ala Lys
    50                  55                  60

Gly Arg Val Thr Ile Ser Lys Asp Ser Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Pro Asp Asn Glu Gly Thr Ser Gly Tyr Leu Ser Gly Phe Gly Leu
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 465
<211> LENGTH: 336
<212> TYPE: DNA
<213> ORGANISM: Artificial Sequence
<220> FEATURE:
<223> OTHER INFORMATION: Rabbit Ab 909 VL region (Seq. ID No. 445) cDNA

<400> SEQUENCE: 465
gacgtcgtga tgacccagac tccagcctcc gtgtctgaac ctgtgggagg cacagtcacc    60
atcaagtgcc aggccagtga ggatattagt aggtacttag tctggtatca gcagaaacca   120
gggcagcctc ccaagcgcct gatctacaag gcatccactc tggcatctgg ggtcccatcg   180
cggttcaaag gcagtggatc tgggacagat tcactctca ccatcagcga cctggagtgt    240
gacgatgctg ccacttacta ctgtcaatgc acttatggta cttatgctgg tagttttttt   300
tattctttcg gcggagggac cgaggtggtc gtcgaa                             336

<210> SEQ ID NO 466
<211> LENGTH: 360
<212> TYPE: DNA
<213> ORGANISM: Artificial Sequence
<220> FEATURE:
<223> OTHER INFORMATION: Rabbit Ab 909 VH region (Seq. ID No. 454) cDNA

<400> SEQUENCE: 466

```
cagtcggtgg aggagtccgg gggtcgcctg gtcacgcctg gacacccct gacactcacc      60 tgcacagtct ctggattctc cctcagtacc tactacatga gctgggtccg ccaggctcca    120
gggaaggggc tggaatggat cggaatcatt tatcctagtg gtagcacata ctgcgcgagc    180
tgggcgaaag gccgattcac catctccaaa gcctcaacca cggtggatct gaaaatcacc    240
agtccgacaa ccgaggacac ggccacctat ttctgtgcca gacctgataa tgatggtact    300
tctggttatt tgagtggttt cggcttgtgg ggccaaggca ccctcgtcac cgtctcgagc    360

<210> SEQ ID NO 467
<211> LENGTH: 336
<212> TYPE: DNA
<213> ORGANISM: Artificial Sequence
<220> FEATURE:
<223> OTHER INFORMATION: 909 gL1 V-region (Seq. ID No. 446) cDNA

<400> SEQUENCE: 467
gacgtcgtca tgacccagtc cccttcctcc ctttcagcca gcgtgggcga tagagtgact     60
atcacttgcc aagcgtcgga ggacatctcg cgctacctgg tgtggtatca acagaagcca    120
ggtaaagcgc ccaagcggct gatctacaag gcctcaactt tggcatccgg agtgccgtcg    180
aggttcaagg gcagcggatc gggaaccgac ttcactctca ccattagctc actgcagccg    240
gaagattttg ccacttacta ctgccagtgt acctacggga cctacgctgg gtcgttcttt    300
tacagcttcg gaggcggaac caaagtggaa atcaag                              336

<210> SEQ ID NO 468
<211> LENGTH: 657
<212> TYPE: DNA
<213> ORGANISM: Artificial Sequence
<220> FEATURE:
<223> OTHER INFORMATION: 909 gL1 light chain (V + constant) (Seq. ID No.
      447) cDNA

<400> SEQUENCE: 468
gacgtcgtca tgacccagtc cccttcctcc ctttcagcca gcgtgggcga tagagtgact     60
atcacttgcc aagcgtcgga ggacatctcg cgctacctgg tgtggtatca acagaagcca    120
ggtaaagcgc ccaagcggct gatctacaag gcctcaactt tggcatccgg agtgccgtcg    180
aggttcaagg gcagcggatc gggaaccgac ttcactctca ccattagctc actgcagccg    240
gaagattttg ccacttacta ctgccagtgt acctacggga cctacgctgg gtcgttcttt    300
tacagcttcg gaggcggaac caaagtggaa atcaagcgta cggtggccgc tcccctccgtg   360 ttcatcttcc caccctccga cgagcagctg aagtccggca ccgcctccgt cgtgtgcctg    420
ctgaacaact ctaccccccg cgaggccaag gtgcagtgga aggtggacaa cgccctgcag    480
tccggcaact cccaggaatc cgtcaccgag caggactcca aggacagcac ctactccctg    540
tcctccaccc tgaccctgtc caaggccgac tacgagaagc acaaggtgta cgcctgcgaa    600
gtgacccacc agggcctgtc cagccccgtg accaagtcct tcaaccgggg cgagtgc       657

<210> SEQ ID NO 469
<211> LENGTH: 336
<212> TYPE: DNA
<213> ORGANISM: Artificial Sequence
<220> FEATURE:
<223> OTHER INFORMATION: 909 gL10 V-region (Seq. ID No. 448) cDNA

<400> SEQUENCE: 469
gacgtcgtca tgacccagtc cccttcctcc ctttcagcca gcgtgggcga tagagtgact     60
```

```
atcacttgcc aagcgtcgga ggacatctcg cgctacctgg tgtggtatca acagaagcca    120
ggtaaagcgc ccaagcggct gatctacaag gcctcaactt tggcatccgg agtgccgtcg    180
aggttcaagg gcagcggatc gggaaccgac ttcactctca ccattagctc actgcagccg    240
gaagattttg ccacttacta ctgccaggct acctacggga cctacgctgg gtcgttcttt    300
tacagcttcg gaggcggaac caaagtggaa atcaag                              336
```

<210> SEQ ID NO 470
<211> LENGTH: 657
<212> TYPE: DNA
<213> ORGANISM: Artificial Sequence
<220> FEATURE:
<223> OTHER INFORMATION: 909 gL10 light chain (V + constant) (Seq. ID
      No. 449) cDNA

<400> SEQUENCE: 470

```
gacgtcgtca tgacccagtc cccttcctcc ctttcagcca gcgtgggcga tagagtgact    60
atcacttgcc aagcgtcgga ggacatctcg cgctacctgg tgtggtatca acagaagcca   120
ggtaaagcgc ccaagcggct gatctacaag gcctcaactt tggcatccgg agtgccgtcg   180
aggttcaagg gcagcggatc gggaaccgac ttcactctca ccattagctc actgcagccg   240
gaagattttg ccacttacta ctgccaggct acctacggga cctacgctgg gtcgttcttt   300
tacagcttcg gaggcggaac caaagtggaa atcaagcgta cggtggccgc tcccccgtg    360 ttcatcttcc caccctccga cgagcagctg aagtccggca ccgcctccgt cgtgtgcctg   420
ctgaacaact ctaccccccg cgaggccaag gtgcagtgga aggtggacaa cgccctgcag   480
tccggcaact cccaggaatc cgtcaccgag caggactcca aggacagcac ctactccctg   540
tcctccaccc tgaccctgtc caaggccgac tacgagaagc acaaggtgta cgcctgcgaa   600
gtgacccacc agggcctgtc cagccccgtg accaagtcct caaccggggg cgagtgc      657
```

<210> SEQ ID NO 471
<211> LENGTH: 336
<212> TYPE: DNA
<213> ORGANISM: Artificial Sequence
<220> FEATURE:
<223> OTHER INFORMATION: 909 gL54 V-region (Seq. ID No. 450) cDNA

<400> SEQUENCE: 471

```
gacgtcgtca tgacccagtc cccttcctcc ctttcagcca gcgtgggcga tagagtgact    60
atcacttgcc aagcgtcgga ggacatctcg cgctacctgg tgtggtatca acagaagcca   120
ggtaaagcgc ccaagcggct gatctacaag gcctcaactt tggcatccgg agtgccgtcg   180
aggttcaagg gcagcggatc gggaaccgac ttcactctca ccattagctc actgcagccg   240
gaagattttg ccacttacta ctgccagcag acctacggga cctacgctgg gtcgttcttt   300
tacagcttcg gaggcggaac caaagtggaa atcaag                              336
```

<210> SEQ ID NO 472
<211> LENGTH: 657
<212> TYPE: DNA
<213> ORGANISM: Artificial Sequence
<220> FEATURE:
<223> OTHER INFORMATION: 909 gL54 light chain (V + constant) (Seq. ID
      No. 451) cDNA

<400> SEQUENCE: 472

```
gacgtcgtca tgacccagtc cccttcctcc ctttcagcca gcgtgggcga tagagtgact    60
```

```
atcacttgcc aagcgtcgga ggacatctcg cgctacctgg tgtggtatca acagaagcca    120
ggtaaagcgc ccaagcggct gatctacaag gcctcaactt tggcatccgg agtgccgtcg    180
aggttcaagg gcagcggatc gggaaccgac ttcactctca ccattagctc actgcagccg    240
gaagattttg ccacttacta ctgccagcag acctacggga cctacgctgg gtcgttcttt    300
tacagcttcg gaggcggaac caaagtggaa atcaagcgta cggtggccgc tcccteegtg    360 ttcatcttcc caccctccga cgagcagctg aagtccggca ccgcctccgt cgtgtgcctg    420
ctgaacaact tctacccccg cgaggccaag gtgcagtgga aggtggacaa cgccctgcag    480
tccggcaact cccaggaatc cgtcaccgag caggactcca aggacagcac ctactccctg    540
tcctccaccc tgaccctgtc caaggccgac tacgagaagc acaaggtgta cgcctgcgaa    600
gtgacccacc agggcctgtc cagccccgtg accaagtcct caaccgggg cgagtgc       657

<210> SEQ ID NO 473
<211> LENGTH: 336
<212> TYPE: DNA
<213> ORGANISM: Artificial Sequence
<220> FEATURE:
<223> OTHER INFORMATION: 909 gL55 V-region (Seq. ID No. 452) cDNA

<400> SEQUENCE: 473
gacgtcgtca tgacccagtc cccttcctcc ctttcagcca gcgtgggcga tagagtgact    60
atcacttgcc aagcgtcgga ggacatctcg cgctacctgg tgtggtatca acagaagcca    120
ggtaaagcgc ccaagcggct gatctacaag gcctcaactt tggcatccgg agtgccgtcg    180
aggttcaagg gcagcggatc gggaaccgac ttcactctca ccattagctc actgcagccg    240
gaagattttg ccacttacta ctgccagcat acctacggga cctacgctgg gtcgttcttt    300
tacagcttcg gaggcggaac caaagtggaa atcaag                              336

<210> SEQ ID NO 474
<211> LENGTH: 657
<212> TYPE: DNA
<213> ORGANISM: Artificial Sequence
<220> FEATURE:
<223> OTHER INFORMATION: 909 gL55 light chain (V + constant) (Seq. ID
      No. 453) cDNA

<400> SEQUENCE: 474
gacgtcgtca tgacccagtc cccttcctcc ctttcagcca gcgtgggcga tagagtgact    60
atcacttgcc aagcgtcgga ggacatctcg cgctacctgg tgtggtatca acagaagcca    120
ggtaaagcgc ccaagcggct gatctacaag gcctcaactt tggcatccgg agtgccgtcg    180
aggttcaagg gcagcggatc gggaaccgac ttcactctca ccattagctc actgcagccg    240
gaagattttg ccacttacta ctgccagcat acctacggga cctacgctgg gtcgttcttt    300
tacagcttcg gaggcggaac caaagtggaa atcaagcgta cggtggccgc tcccteegtg    360 ttcatcttcc caccctccga cgagcagctg aagtccggca ccgcctccgt cgtgtgcctg    420
ctgaacaact tctacccccg cgaggccaag gtgcagtgga aggtggacaa cgccctgcag    480
tccggcaact cccaggaatc cgtcaccgag caggactcca aggacagcac ctactccctg    540
tcctccaccc tgaccctgtc caaggccgac tacgagaagc acaaggtgta cgcctgcgaa    600
gtgacccacc agggcctgtc cagccccgtg accaagtcct caaccgggg cgagtgc       657

<210> SEQ ID NO 475
<211> LENGTH: 363
<212> TYPE: DNA
```

<213> ORGANISM: Artificial Sequence
<220> FEATURE:
<223> OTHER INFORMATION: 909gH1 V-region (Seq. ID No. 455) cDNA

<400> SEQUENCE: 475

```
gaagtccagc tgcaagaatc aggtccaggc ctcgtcaaac catcaggaac tttgtcattg      60
acttgcacgg tgagcgggtt ctcgctttcg acctactaca tgtcgtgggt gcgccagccg     120
cctgggaagg gactggagtg gatcggcatc atctacccgt ccggcagcac gtactgcgct     180
agctgggcca aggggcggtt caccatcagc aaggcgtcca ctactgtgga cctcaagctg     240
tcgtcagtta ctgcggccga cactgcaacc tactttgtg cccgcccgga taacgatgga      300
acctccggct acctgtccgg attcggactg tggggacagg gaacccttgt gactgtctcg     360
agc                                                                    363
```

<210> SEQ ID NO 476
<211> LENGTH: 1344
<212> TYPE: DNA
<213> ORGANISM: Artificial Sequence
<220> FEATURE:
<223> OTHER INFORMATION: 909 gH1 IgG4 heavy chain (V + human ?-4P constant) Seq. ID No. 456) cDNA

<400> SEQUENCE: 476

```
gaagtccagc tgcaagaatc aggtccaggc ctcgtcaaac catcaggaac tttgtcattg      60
acttgcacgg tgagcgggtt ctcgctttcg acctactaca tgtcgtgggt gcgccagccg     120
cctgggaagg gactggagtg gatcggcatc atctacccgt ccggcagcac gtactgcgct     180
agctgggcca aggggcggtt caccatcagc aaggcgtcca ctactgtgga cctcaagctg     240
tcgtcagtta ctgcggccga cactgcaacc tactttgtg cccgcccgga taacgatgga      300
acctccggct acctgtccgg attcggactg tggggacagg gaacccttgt gactgtctcg     360
agcgcctcca ccaagggccc ctccgtgttc cctctggccc cttgctcccg gtccacctcc     420
gagtctaccg ccgctctggg ctgcctggtc aaggactact ccccgagcc cgtgacagtg      480
tcctggaact ctggcgccct gaccccggc gtgcacacct ccctgccgt gctgcagtcc       540
tccggcctgt actccctgtc ctcgtcgtg accgtgccct cctccagcct gggcaccaag     600
acctacacct gtaacgtgga ccacaagccc tccaacacca aggtggacaa gcgggtggaa     660
tctaagtacg gccctcccctg ccccccctgc cctgccctg aatttctggg cggaccttcc     720
gtgttcctgt tccccccaaa gcccaaggac accctgatga tctcccggac ccccgaagtg     780
acctgcgtgt ggtggacgt gtcccaggaa gatcccgagg tccagttcaa ttggtacgtg     840
gacggcgtgg aagtgcacaa tgccaagacc aagcccagag aggaacagtt caactccacc     900
tacccgggtg tgtccgtgct gaccgtgctg caccaggact ggctgaacgg caaagagtac     960
aagtgcaagg tgtccaacaa gggcctgccc tccagcatcg aaaagaccat ctccaaggcc    1020
aagggccagc ccgcgagcc ccaggtgtac accctgcccc ctagccagga agagatgacc    1080
aagaaccagg tgtccctgac ctgtctggtc aagggcttct acccctccga cattgccgtg    1140
gaatgggagt ccaacggcca gcccgagaac aactacaaga ccacccccc tgtgctggac    1200
agcgacggct ccttcttcct gtactctcgg ctgaccgtgg acaagtcccg gtggcaggaa   1260
ggcaacgtct tctcctgctc cgtgatgcac gaggccctgc acaaccacta cacccagaag   1320
tccctgtccc tgagcctggg caag                                          1344
```

<210> SEQ ID NO 477

```
<211> LENGTH: 369
<212> TYPE: DNA
<213> ORGANISM: Artificial Sequence
<220> FEATURE:
<223> OTHER INFORMATION: 909gH15 V-region (Seq. ID. No. 457) cDNA

<400> SEQUENCE: 477
gaagtccagc tgcaagaatc aggtccaggc ctcgtcaaac catcaggaac tttgtcattg    60
acttgcacgg tgagcgggtt ctcgctttcg acctactaca tgtcgtgggt gcgccagccg   120
cctgggaagg gactggagtg gatcggcatc atctacccgt ccggcagcac gtactccgct   180
agctgggcca aggggcggtt caccatcagc aaggcgtcca ctaaaaatac tgtggacctc   240
aagctgtcgt cagttactgc ggccgacact gcaacctact tttgtgcccg cccggataac   300
gagggaacct ccggctacct gtccggattc ggactgtggg gacagggaac ccttgtgact   360
gtctcgagc                                                           369

<210> SEQ ID NO 478
<211> LENGTH: 1350
<212> TYPE: DNA
<213> ORGANISM: Artificial Sequence
<220> FEATURE:
<223> OTHER INFORMATION: 909 gH15 IgG4 heavy chain (V + human gamma-4P
      constant) (Seq. ID No. 458) cDNA

<400> SEQUENCE: 478
gaagtccagc tgcaagaatc aggtccaggc ctcgtcaaac catcaggaac tttgtcattg    60
acttgcacgg tgagcgggtt ctcgctttcg acctactaca tgtcgtgggt gcgccagccg   120
cctgggaagg gactggagtg gatcggcatc atctacccgt ccggcagcac gtactccgct   180
agctgggcca aggggcggtt caccatcagc aaggcgtcca ctaaaaatac tgtggacctc   240
aagctgtcgt cagttactgc ggccgacact gcaacctact tttgtgcccg cccggataac   300
gagggaacct ccggctacct gtccggattc ggactgtggg gacagggaac ccttgtgact   360
gtctcgagcg cctccaccaa gggcccctcc gtgttccctc tggccccttg ctcccggtcc   420
acctccgagt ctaccgccgc tctgggctgc ctggtcaagg actacttccc cgagcccgtg   480
acagtgtcct ggaactctgg cgccctgacc tccggcgtgc acaccttccc tgccgtgctg   540
cagtcctccg gcctgtactc cctgtcctcc gtcgtgaccg tgccctcctc agcctgggc   600
accaagacct acacctgtaa cgtggaccac aagccctcca acaccaaggt ggacaagcgg   660
gtggaatcta gtacggcccc tccctgcccc cctgccctg ccctgaatt tctgggcgga   720
ccttccgtgt tcctgttccc cccaaagccc aaggacaccc tgatgatctc ccggaccccc   780
gaagtgacct gcgtggtggt ggacgtgtcc caggaagatc ccgaggtcca gttcaattgg   840
tacgtgacg gcgtggaagt gcacaatgcc aagaccaagc cagagagga acagttcaac   900
tccacctacc gggtggtgtc cgtgctgacc gtgctgcacc aggactggct gaacggcaaa   960
gagtacaagt gcaaggtgtc caacaagggc ctgcccttca gcatcgaaaa gaccatctcc  1020
aaggccaagg gccagccccg cgagccccag gtgtacaccc tgccccctag ccaggaagag  1080
atgaccaaga accaggtgtc cctgacctgt ctggtcaagg gcttctaccc ctccgacatt  1140
gccgtggaat gggagtccaa cggccagccc gagaacaact acaagaccac cccccctgtg  1200
ctggacagcg acggctcctt cttcctgtac tctcggctga ccgtggacaa gtcccggtgg  1260
caggaaggca acgtcttctc ctgctccgtg atgcacgagg ccctgcacaa ccactacacc  1320
cagaagtccc tgtccctgag cctgggcaag                                   1350
```

<210> SEQ ID NO 479
<211> LENGTH: 320
<212> TYPE: DNA
<213> ORGANISM: Artificial Sequence
<220> FEATURE:
<223> OTHER INFORMATION: Human IGKV1-17 (A30)-JK4 acceptor framework cDNA

<400> SEQUENCE: 479

```
gacatccaga tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacag cataatagtt accctctcac tttcggcgga     300
gggaccaagg tggagatcaa                                                 320
```

<210> SEQ ID NO 480
<211> LENGTH: 339
<212> TYPE: DNA
<213> ORGANISM: Artificial Sequence
<220> FEATURE:
<223> OTHER INFORMATION: Human IGHV4-4 JH4 acceptor framework cDNA

<400> SEQUENCE: 480

```
caggtgcagc tgcaggagtc gggcccagga ctggtgaagc cttcagggac cctgtccctc      60
acctgcgctg tctctggtgg ctccatcagc agtagtaact ggtggagttg ggtccgccag     120
cccccaggga aggggctgga gtggattggg gaaatctatc atagtgggag caccaactac     180
aacccgtccc tcaagagtcg agtcaccata tcagtagaca gtccaagaa ccagttctcc      240
ctgaagctga gctctgtgac cgccgcggac acggccgtgt attactgtgc gagatacttt     300
gactactggg gccaaggaac cctggtcacc gtctcctca                            339
```

<210> SEQ ID NO 481
<211> LENGTH: 113
<212> TYPE: PRT
<213> ORGANISM: Artificial Sequence
<220> FEATURE:
<223> OTHER INFORMATION: IGHV4-4

<400> SEQUENCE: 481

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Tyr Phe Asp Tyr Trp Gly Gln Gly Thr Leu Val Thr Val Ser
            100                 105                 110

Ser
```

-continued

<210> SEQ ID NO 482
<211> LENGTH: 119
<212> TYPE: PRT
<213> ORGANISM: Artificial Sequence
<220> FEATURE:
<223> OTHER INFORMATION: H3 gH1 heavy chain variable region

<400> SEQUENCE: 482

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Asn
            20                  25                  30

Trp Ile Thr Trp Val Lys Gln Arg Pro Gly Gln Gly Leu Glu Trp Ile
        35                  40                  45

Gly Asp Ile Tyr Pro Gly Ser Gly Ser Thr Thr Asn Asn Glu Lys Phe
    50                  55                  60

Lys Ser Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Leu Arg Gly Tyr Tyr Asp Tyr Phe Asp Phe Trp Gly Gln Gly
            100                 105                 110

Thr Thr Leu Thr Val Ser Ser
        115

<210> SEQ ID NO 483
<211> LENGTH: 119
<212> TYPE: PRT
<213> ORGANISM: Artificial Sequence
<220> FEATURE:
<223> OTHER INFORMATION: H3 gH19 heavy chain variable region

<400> SEQUENCE: 483

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Asn
            20                  25                  30

Ala Ile Thr Trp Val Lys Gln Arg Pro Gly Gln Gly Leu Glu Trp Ile
        35                  40                  45

Gly Asp Ile Ser Pro Gly Ser Gly Ser Thr Thr Asn Asn Glu Lys Phe
    50                  55                  60

Lys Ser Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Leu Arg Gly Tyr Tyr Asp Tyr Phe Asp Phe Trp Gly Gln Gly
            100                 105                 110

Thr Thr Leu Thr Val Ser Ser
        115

<210> SEQ ID NO 484
<211> LENGTH: 119
<212> TYPE: PRT
<213> ORGANISM: Artificial Sequence
<220> FEATURE:
<223> OTHER INFORMATION: H3 gH20 heavy chain variable region

<400> SEQUENCE: 484

Gln Val Gln Leu Gln Gln Pro Gly Ala Glu Leu Val Lys Pro Gly Ala
1               5                   10                  15

```
Ser Val Lys Leu Ser Cys Lys Ala Ser Gly Tyr Thr Phe Thr Ser Asn
         20                  25                  30

Ala Ile Thr Trp Val Lys Gln Arg Pro Gly Gln Gly Leu Glu Trp Ile
         35                  40                  45

Gly Asp Ile Ser Pro Gly Ser Gly Ser Thr Thr Asn Asn Glu Lys Phe
50                   55                  60

Lys Ser Lys Ala Thr Leu Thr Val Asp Thr Ser Ser Ser Thr Ala Tyr
65                   70                  75                  80

Met Gln Leu Ser Ser Leu Thr Ser Glu Asp Ser Ala Val Tyr Tyr Cys
                 85                  90                  95

Ala Arg Leu Arg Gly Phe Tyr Asp Tyr Phe Asp Phe Trp Gly Gln Gly
             100                 105                 110

Thr Thr Leu Thr Val Ser Ser
            115

<210> SEQ ID NO 485
<211> LENGTH: 108
<212> TYPE: PRT
<213> ORGANISM: Artificial Sequence
<220> FEATURE:
<223> OTHER INFORMATION: H3 gL1 light chain variable region

<400> SEQUENCE: 485

Glu Val Val Leu Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Ser
            20                  25                  30

Asn Leu His Trp Tyr Gln Gln Lys Ser Glu Thr Ser Pro Lys Pro Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser His Tyr Pro
                85                  90                  95

Leu Thr Phe Gly Ala Gly Thr Lys Leu Glu Leu Lys
            100                 105

<210> SEQ ID NO 486
<211> LENGTH: 108
<212> TYPE: PRT
<213> ORGANISM: Artificial Sequence
<220> FEATURE:
<223> OTHER INFORMATION: H3 gL11 light chain variable region

<400> SEQUENCE: 486

Glu Val Val Leu Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Ser
            20                  25                  30

Asn Leu His Trp Tyr Gln Gln Lys Ser Glu Thr Ser Pro Lys Pro Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Ala Ser His Tyr Pro
```

```
                85                  90                  95

Leu Thr Phe Gly Ala Gly Thr Lys Leu Glu Leu Lys
            100                 105
```

<210> SEQ ID NO 487
<211> LENGTH: 112
<212> TYPE: PRT
<213> ORGANISM: Artificial Sequence
<220> FEATURE:
<223> OTHER INFORMATION: 909 gL13 VL-region

<400> SEQUENCE: 487

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Ser Arg Tyr
            20                  25                  30

Leu Val Trp Tyr Gln Gln Lys Pro Gly Lys Ala Pro Lys Arg Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Ala Thr Tyr Gly Thr Tyr Ala
                85                  90                  95

Gly Ser Phe Phe Tyr Ser Phe Gly Gly Gly Thr Lys Val Glu Ile Lys
            100                 105                 110
```

<210> SEQ ID NO 488
<211> LENGTH: 112
<212> TYPE: PRT
<213> ORGANISM: Artificial Sequence
<220> FEATURE:
<223> OTHER INFORMATION: 909 gL50 VL-region

<400> SEQUENCE: 488

```
Asp Val Val Met Thr Gln Ser Pro Ser Ser Leu Ser Ala Ser Val Gly
1               5                   10                  15

Asp Arg Val Thr Ile Thr Cys Gln Ala Ser Glu Asp Ile Ser Arg Tyr
            20                  25                  30

Leu Val Trp Tyr Gln Gln Lys Pro Gly Lys Ala Pro Lys Arg Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Ala Gln Ala Thr Tyr Gly Thr Tyr Ala
                85                  90                  95

Gly Ser Phe Phe Tyr Ser Phe Gly Gly Gly Thr Lys Val Glu Ile Lys
            100                 105                 110
```

<210> SEQ ID NO 489
<211> LENGTH: 219
<212> TYPE: PRT
<213> ORGANISM: Artificial Sequence
<220> FEATURE:
<223> OTHER INFORMATION: 909 gL13 VL + CL-region

<400> SEQUENCE: 489

```
Asp Ile Gln Met Thr Gln Ser Pro Ser Ser Leu Ser Ala Ser Val Gly
1               5                   10                  15
```

Asp Arg Val Thr Ile Thr Cys Gln Ala Ser Glu Asp Ile Ser Arg Tyr
                20                  25                  30

Leu Val Trp Tyr Gln Gln Lys Pro Gly Lys Ala Pro Lys Arg Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Ala Thr Tyr Gly Thr Tyr Ala
                85                  90                  95

Gly Ser Phe Phe Tyr Ser Phe Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 490
<211> LENGTH: 219
<212> TYPE: PRT
<213> ORGANISM: Artificial Sequence
<220> FEATURE:
<223> OTHER INFORMATION: 909 gL50 VL + CL-region

<400> SEQUENCE: 490

Asp Val Val Met Thr Gln Ser Pro Ser Ser Leu Ser Ala Ser Val Gly
1               5                   10                  15

Asp Arg Val Thr Ile Thr Cys Gln Ala Ser Glu Asp Ile Ser Arg Tyr
                20                  25                  30

Leu Val Trp Tyr Gln Gln Lys Pro Gly Lys Ala Pro Lys Arg Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Ala Gln Ala Thr Tyr Gly Thr Tyr Ala
                85                  90                  95

Gly Ser Phe Phe Tyr Ser Phe Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

```
Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys
    210                 215

<210> SEQ ID NO 491
<211> LENGTH: 336
<212> TYPE: DNA
<213> ORGANISM: Artificial Sequence
<220> FEATURE:
<223> OTHER INFORMATION: 909 gL13 V-region (Seq. ID No. 487) cDNA

<400> SEQUENCE: 491
gacatccaaa tgacccagtc cccttcctcc ctttcagcca gcgtgggcga tagagtgact    60
atcacttgcc aagcgtcgga ggacatctcg cgctacctgg tgtggtatca acagaagcca   120
ggtaaagcgc ccaagcggct gatctacaag gcctcaactt tggcatccgg agtgccgtcg   180
aggttctccg gcagcggatc gggaaccgag ttcactctca ccattagctc actgcagccg   240
gaagattttg ccacttacta ctgccaggct acctacggga cctacgctgg gtcgttcttt   300
tacagcttcg gaggcggaac caaagtggaa atcaag                             336

<210> SEQ ID NO 492
<211> LENGTH: 657
<212> TYPE: DNA
<213> ORGANISM: Artificial Sequence
<220> FEATURE:
<223> OTHER INFORMATION: 909 gL13 light chain (V + constant) (Seq. ID
      No. 489) cDNA

<400> SEQUENCE: 492
gacatccaaa tgacccagtc cccttcctcc ctttcagcca gcgtgggcga tagagtgact    60
atcacttgcc aagcgtcgga ggacatctcg cgctacctgg tgtggtatca acagaagcca   120
ggtaaagcgc ccaagcggct gatctacaag gcctcaactt tggcatccgg agtgccgtcg   180
aggttctccg gcagcggatc gggaaccgag ttcactctca ccattagctc actgcagccg   240
gaagattttg ccacttacta ctgccaggct acctacggga cctacgctgg gtcgttcttt   300
tacagcttcg gaggcggaac caaagtggaa atcaagcgta cggtggccgc tcccctccgtg  360 ttcatcttcc caccctccga cgagcagctg aagtccggca ccgcctccgt cgtgtgcctg   420
ctgaacaact tctaccccg cgaggccaag gtgcagtgga aggtggacaa cgccctgcag    480
tccggcaact cccaggaatc cgtcaccgag caggactcca aggacagcac ctactccctg   540
tcctccaccc tgaccctgtc aaggccgac tacgagaagc acaaggtgta cgcctgcgaa    600
gtgacccacc agggcctgtc cagccccgtg accaagtcct tcaaccgggg cgagtgc      657

<210> SEQ ID NO 493
<211> LENGTH: 336
<212> TYPE: DNA
<213> ORGANISM: Artificial Sequence
<220> FEATURE:
<223> OTHER INFORMATION: 909 gL50 V-region (Seq. ID No. 488) cDNA

<400> SEQUENCE: 493
gacgtcgtca tgacccagtc cccttcctcc ctttcagcca gcgtgggcga tagagtgact    60
```

```
atcacttgcc aagcgtcgga ggacatctcg cgctacctgg tgtggtatca acagaagcca    120
ggtaaagcgc ccaagcggct gatctacaag gcctcaactt tggcatccgg agtgccgtcg    180
aggttcaagg gcagcggatc gggaaccgac ttcactctca ccattagctc actgcagccg    240
gaagattttg ccacttacta cgcccaggct acctacggga cctacgctgg gtcgttcttt    300
tacagcttcg gaggcggaac caaagtggaa atcaag                              336
```

<210> SEQ ID NO 494
<211> LENGTH: 657
<212> TYPE: DNA
<213> ORGANISM: Artificial Sequence
<220> FEATURE:
<223> OTHER INFORMATION: 909 gL50 light chain (V + constant) (Seq. ID No. 490) cDNA

<400> SEQUENCE: 494

```
gacgtcgtca tgacccagtc cccttcctcc ctttcagcca gcgtgggcga tagagtgact    60
atcacttgcc aagcgtcgga ggacatctcg cgctacctgg tgtggtatca acagaagcca    120
ggtaaagcgc ccaagcggct gatctacaag gcctcaactt tggcatccgg agtgccgtcg    180
aggttcaagg gcagcggatc gggaaccgac ttcactctca ccattagctc actgcagccg    240
gaagattttg ccacttacta cgcccaggct acctacggga cctacgctgg gtcgttcttt    300
tacagcttcg gaggcggaac caaagtggaa atcaagcgta cggtggccgc tcccctccgtg   360 ttcatcttcc caccctccga cgagcagctg aagtccggca ccgcctccgt cgtgtgcctg    420
ctgaacaact ctaccccccg cgaggccaag gtgcagtgga aggtggacaa cgccctgcag    480
tccggcaact cccaggaatc cgtcaccgag caggactcca aggacagcac ctactccctg    540
tcctccaccc tgaccctgtc caaggccgac tacgagaagc acaaggtgta cgcctgcgaa    600
gtgacccacc agggcctgtc cagccccgtg accaagtcct caaccggggg cgagtgc      657
```

<210> SEQ ID NO 495
<211> LENGTH: 357
<212> TYPE: DNA
<213> ORGANISM: Artificial Sequence
<220> FEATURE:
<223> OTHER INFORMATION: H3 gH20 heavy chain variable region (Seq. ID No. 484) cDNA

<400> SEQUENCE: 495

```
caggtccaac tacagcagcc tggggctgaa cttgtgaagc ctggggcttc agtgaagctg    60
tcctgcaagg cttctggcta caccttcacc agcaacgcga taacctgggt gaagcagagg    120
cctggacaag gccttgagtg gattggagat atttctcctg gtagtggtag tactactaac    180
aatgagaagt tcaagagcaa ggccacactg actgtagaca catcctccag cacagcctac    240
atgcagctca gcagcctgac atctgaggac tctgcggtct attactgtgc aaggctaagg    300
ggcttctatg attactttga cttctggggc caaggcacca ctctcacagt ctcgagt      357
```

<210> SEQ ID NO 496
<211> LENGTH: 102
<212> TYPE: PRT
<213> ORGANISM: Artificial Sequence
<220> FEATURE:
<223> OTHER INFORMATION: Heavy chain Fab gamma 1 constant region

<400> SEQUENCE: 496

```
Ala Lys Thr Thr Pro Pro Ser Val Tyr Pro Leu Ala Pro Gly Ser Ala
1               5                   10                  15
```

```
Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
         35                  40                  45

Gly Val His Thr Phe Pro Ala Val Leu Gln Ser Asp Leu Tyr Thr Leu
 50                  55                  60

Ser Ser Val Thr Val Pro Ser Ser Thr Trp Pro Ser Glu Thr Val
 65                  70                  75                  80

Thr Cys Asn Val Ala His Pro Ala Ser Ser Thr Lys Val Asp Lys Lys
                 85                  90                  95

Ile Val Pro Arg Asp Cys
            100
```

<210> SEQ ID NO 497
<211> LENGTH: 306
<212> TYPE: DNA
<213> ORGANISM: Artificial Sequence
<220> FEATURE:
<223> OTHER INFORMATION: Heavy chain Fab gamma 1 constant region (Seq. ID No. 496) cDNA

<400> SEQUENCE: 497

```
gccaaaacga caccccatc  tgtctatcca  ctggcccctg  gatctgctgc  ccaaactaac    60
tccatggtga ccctgggatg cctggtcaag ggctatttcc ctgagccagt gacagtgacc   120
tggaactctg gatccctgtc cagcggtgtg cacaccttcc cggctgtcct gcaatctgac   180
ctctacactc tgagcagctc agtgactgtc ccctccagca cctggcccag cgagaccgtc   240
acctgcaacg ttgcccaccc ggccagcagc accaaggtgg acaagaaaat tgtgcccagg   300
gattgt                                                              306
```

<210> SEQ ID NO 498
<211> LENGTH: 324
<212> TYPE: PRT
<213> ORGANISM: Artificial Sequence
<220> FEATURE:
<223> OTHER INFORMATION: Heavy chain full length gamma 1 constant region

<400> SEQUENCE: 498

```
Ala Lys Thr Thr Pro Pro Ser Val Tyr Pro Leu Ala Pro Gly Ser Ala
 1               5                  10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
         35                  40                  45

Gly Val His Thr Phe Pro Ala Val Leu Gln Ser Asp Leu Tyr Thr Leu
 50                  55                  60

Ser Ser Val Thr Val Pro Ser Ser Thr Trp Pro Ser Glu Thr Val
 65                  70                  75                  80

Thr Cys Asn Val Ala His Pro Ala Ser Ser Thr Lys Val Asp Lys Lys
                 85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140
```

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
            165                 170                 175

Phe Arg Ser Val Ser Glu Leu Pro Ile Met His Gln Asp Trp Leu Asn
        180                 185                 190

Gly Lys Glu Phe Lys Cys Arg Val Asn Ser Ala Ala Phe Pro Ala Pro
    195                 200                 205

Ile Glu Lys Thr Ile Ser Lys Thr Lys Gly Arg Pro Lys Ala Pro Gln
210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 499
<211> LENGTH: 1044
<212> TYPE: DNA
<213> ORGANISM: Artificial Sequence
<220> FEATURE:
<223> OTHER INFORMATION: Heavy chain full length gamma 1 constant region
      (Seq. ID No. 498) cDNA

<400> SEQUENCE: 499
gccaaaacga cacccccatc tgtctatcca ctggcccctg gatctgctgc ccaaactaac    60
tccatggtga ccctgggatg cctggtcaag ggctatttcc ctgagccagt gacagtgacc   120
tggaactctg gatccctgtc cagcggtgtg cacaccttcc cagctgtcct gcagtctgac   180
ctctacactc tgagcagctc agtgactgtc cctccagca cctggcccag cgagaccgtc   240
acctgcaacg ttgcccaccc ggccagcagc accaaggtgg acaagaaaat tgtgcccagg   300
gattgtggtt gtaagccttg catatgtaca gtcccagaag tatcatctgt cttcatcttc   360
cccccaaagc ccaaggatgt gctcaccatt actctgactc ctaaggtcac gtgtgttgtg   420
gtagacatca gcaaggatga tcccgaggtc cagttcagct ggtttgtaga tgatgtggag   480
gtgcacacag ctcagacgca accccgggag gagcagttca acagcacttt ccgctcagtc   540
agtgaacttc ccatcatgca ccaggactgg ctcaatggca aggagttcaa atgcagggtc   600
aacagtgcag ctttccctgc ccccatcgag aaaaccatct ccaaaaccaa aggcagaccg   660
aaggctccac aggtgtacac cattccacct cccaaggagc agatggccaa ggataaagtc   720
agtctgacct gcatgataac agacttcttc cctgaagaca ttactgtgga gtggcagtgg   780
aatgggcagc cagcggagaa ctacaagaac actcagccca tcatggacac agatggctct   840
tacttcgtct acagcaagct caatgtgcag aagagcaact gggaggcagg aaatactttc   900
acctgctctg tgttacatga gggcctgcac aaccaccata ctgagaagag cctctcccac   960

```
tctcctggta aatgatccca gtgtccttgg agccctctgg tcctacagga ctctgacacc   1020
tacctccacc cctccctgta taaa                                          1044
```

<210> SEQ ID NO 500
<211> LENGTH: 107
<212> TYPE: PRT
<213> ORGANISM: Artificial Sequence
<220> FEATURE:
<223> OTHER INFORMATION: Light chain kappa constant

<400> SEQUENCE: 500

```
Arg Thr Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105
```

<210> SEQ ID NO 501
<211> LENGTH: 321
<212> TYPE: DNA
<213> ORGANISM: Artificial Sequence
<220> FEATURE:
<223> OTHER INFORMATION: Light chain kappa constant (Seq. ID No. 500)
      cDNA

<400> SEQUENCE: 501

```
cgtacggatg ctgcaccaac tgtatccatc ttcccaccat ccagtgagca gttaacatct   60
ggaggtgcct cagtcgtgtg cttcttgaac aacttctacc caaagacat caatgtcaag   120 tggaagattg atggcagtga acgacaaaat ggcgtcctga cagttggac tgatcaggac   180 agcaaagaca gcacctacag catgagcagc accctcacgt tgaccaagga cgagtatgaa   240
cgacataaca gctatacctg tgaggccact cacaagacat caacttcacc cattgtcaag   300
agcttcaaca ggaatgagtg t                                             321
```

<210> SEQ ID NO 502
<211> LENGTH: 324
<212> TYPE: DNA
<213> ORGANISM: Artificial Sequence
<220> FEATURE:
<223> OTHER INFORMATION: H3 gL1 light chain variable region (Seq. ID No.
      485) cDNA

<400> SEQUENCE: 502

```
gaagttgtgc tcacccagtc tccagcactc atggctgcat ctccagggga aaggtcacc   60 atcacctgca gtgtcagctc aagtataagt tccagcaact gcactggta ccagcagaag   120 tcagaaacct cccccaaaac ctggatttat ggcacatcca acctggcttc tggagtccct   180
gttcgcttca gtggcagtgg atctgggacc tcttattctc tcacaatcag cagcatggag   240
gctgaagatg ctgccactta ttactgtcaa cagtggagtc attacccgct cacgttcggt   300
```

```
<210> SEQ ID NO 503
<211> LENGTH: 324
<212> TYPE: DNA
<213> ORGANISM: Artificial Sequence
<220> FEATURE:
<223> OTHER INFORMATION: H3 gL11 light chain variable region (Seq. ID
      No. 486) cDNA

<400> SEQUENCE: 503
gaagttgtgc tcacccagtc tccagcactc atggctgcat ctccagggga gaaggtcacc    60
atcacctgca gtgtcagctc aagtataagt tccagcaact tgcactgtta ccagcagaag   120
tcagaaaacct cccccaaacc ctggatttat ggcacatcca acctggcttc tggagtccct  180
gttcgcttca gtggcagtgg atctgggacc tcttattctc tcacaatcag cagcatggag   240
gctgaagatg ctgccactta ttactgtcaa caggcgagtc attacccgct cacgttcggt   300
gctgggacca agctggagct gaaa                                           324

<210> SEQ ID NO 504
<211> LENGTH: 357
<212> TYPE: DNA
<213> ORGANISM: Artificial Sequence
<220> FEATURE:
<223> OTHER INFORMATION: H3 gH1 heavy chain variable region (Seq. ID No.
      482) cDNA

<400> SEQUENCE: 504
caggtccaac tacagcagcc tggggctgaa cttgtgaagc ctggggcttc agtgaagctg    60
tcctgcaagg cttctggcta caccttcacc agcaactgga taacctgggt gaagcagagg   120
cctggacaag gccttgagtg gattggagat atttatcctg gtagtggtag tactactaac   180
aatgagaagt tcaagagcaa ggccacactg actgtagaca tcctccag cacagcctac     240
atgcagctca gcagcctgac atctgaggac tctgcggtct attactgtgc aaggctaagg   300
ggctactatg attactttga cttctggggc caaggcacca ctctcacagt ctcgagt      357

<210> SEQ ID NO 505
<211> LENGTH: 357
<212> TYPE: DNA
<213> ORGANISM: Artificial Sequence
<220> FEATURE:
<223> OTHER INFORMATION: H3 gH19 heavy chain variable region (Seq. ID
      No. 483) cDNA

<400> SEQUENCE: 505
caggtccaac tacagcagcc tggggctgaa cttgtgaagc ctggggcttc agtgaagctg    60
tcctgcaagg cttctggcta caccttcacc agcaacgcga taacctgggt gaagcagagg   120
cctggacaag gccttgagtg gattggagat atttctcctg gtagtggtag tactactaac   180
aatgagaagt tcaagagcaa ggccacactg actgtagaca tcctccag cacagcctac     240
atgcagctca gcagcctgac atctgaggac tctgcggtct attactgtgc aaggctaagg   300
ggctactatg attactttga cttctggggc caaggcacca ctctcacagt ctcgagt      357

<210> SEQ ID NO 506
<211> LENGTH: 107
<212> TYPE: PRT
<213> ORGANISM: Artificial Sequence
<220> FEATURE:
<223> OTHER INFORMATION: IGKV1-17
```

<400> SEQUENCE: 506

Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65              70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Leu Glu Ile Lys
            100                 105

<210> SEQ ID NO 507
<211> LENGTH: 369
<212> TYPE: DNA
<213> ORGANISM: Artificial Sequence
<220> FEATURE:
<223> OTHER INFORMATION: 909gH14 V-region (Seq. ID No. 457) cDNA

<400> SEQUENCE: 507

```
gaagtccagc tgcaagaatc aggtccaggc ctcgtcaaac catcaggaac tttgtcattg      60
acttgcgccg tgagcgggtt ctcgctttcg acctactaca gtcgtgggt gcgccagccg     120
cctgggaagg gactggagtg gatcggcatc atctacccgt ccggcagcac gtactgcgct    180
agctgggcca aggggcggtt caccatcagc aaggcgtcca ctaaaaatac tgtggacctc    240
aagctgtcgt cagttactgc ggccgacact gcaacctact tttgtgcccg cccggataac    300
gatggaacct ccggctacct gtccggattc ggactgtggg acagggaac ccttgtgact    360
gtctcgagc                                                            369
```

<210> SEQ ID NO 508
<211> LENGTH: 1350
<212> TYPE: DNA
<213> ORGANISM: Artificial Sequence
<220> FEATURE:
<223> OTHER INFORMATION: 909 gH14 IgG4 heavy chain (V + human gamma-4P constant) (Seq. ID No. 457) cDNA

<400> SEQUENCE: 508

```
gaagtccagc tgcaagaatc aggtccaggc ctcgtcaaac catcaggaac tttgtcattg      60
acttgcgccg tgagcgggtt ctcgctttcg acctactaca gtcgtgggt gcgccagccg     120
cctgggaagg gactggagtg gatcggcatc atctacccgt ccggcagcac gtactgcgct    180
agctgggcca aggggcggtt caccatcagc aaggcgtcca ctaaaaatac tgtggacctc    240
aagctgtcgt cagttactgc ggccgacact gcaacctact tttgtgcccg cccggataac    300
gatggaacct ccggctacct gtccggattc ggactgtggg acagggaac ccttgtgact    360
gtctcgagcg cctccaccaa gggcccctcc gtgttccctc tggccccttg ctccggtcc    420
acctccgagt ctaccgccgc tctgggctgc ctggtcaagg actacttccc cgagcccgtg    480
acagtgtcct ggaactctgg cgccctgacc tccggcgtgc acaccttccc tgccgtgctg    540
cagtcctccg gcctgtactc cctgtcctcc gtcgtgaccg tgccctcctc agcctgggc     600
accaagacct acacctgtaa cgtggaccac aagccctcca acaccaaggt ggacaagcgg    660
```

```
gtggaatcta agtacggccc tccctgcccc cctgccctg ccctgaatt tctgggcgga      720 ccttccgtgt tcctgttccc cccaaagccc aaggacaccc tgatgatctc cggaccccc     780 gaagtgacct gcgtggtggt ggacgtgtcc aggaagatc ccgaggtcca gttcaattgg     840
tacgtggacg gcgtggaagt gcacaatgcc aagaccaagc ccagagagga acagttcaac    900
tccacctacc gggtggtgtc cgtgctgacc gtgctgcacc aggactggct gaacggcaaa    960
gagtacaagt gcaaggtgtc caacaagggc ctgcccctcca gcatcgaaaa gaccatctcc   1020
aaggccaagg gccagccccg cgagcccag gtgtacaccc tgcccctag ccaggaagag      1080 atgaccaaga accaggtgtc cctgacctgt ctggtcaagg gcttctaccc ctccgacatt    1140
gccgtggaat gggagtccaa cggccagccc gagaacaact acaagaccac ccccctgtg    1200 ctggacagcg acggctcctt cttcctgtac tctcggctga ccgtggacaa gtcccggtgg    1260
caggaaggca acgtcttctc ctgctccgtg atgcacgagg ccctgcacaa ccactacacc    1320
cagaagtccc tgtccctgag cctgggcaag                                    1350
```

<210> SEQ ID NO 509
<211> LENGTH: 369
<212> TYPE: DNA
<213> ORGANISM: Artificial Sequence
<220> FEATURE:
<223> OTHER INFORMATION: 909gH61 V-region (Seq. ID. No. 461) cDNA

<400> SEQUENCE: 509

```
gaagtccagc tgcaagaatc aggtccaggc ctcgtcaaac catcaggaac tttgtcattg     60
acttgcgccg tgagcgggtt ctcgctttcg acctactaca tgtcgtgggt gcgccagccg    120
cctgggaagg gactggagtg gatcggcatc atctacccgt ccggcagcac gtactgcgct    180
agctgggcca aggggcgggt gaccatcagc aaggactcca gcaaaaatca ggtgagcctc    240
aagctgtcgt cagttactgc ggccgacact gcagtgtact attgtgcccg cccggataac    300
gatggaacct ccggctacct gtccggattc ggactgtggg gacagggaac ccttgtgact    360
gtctcgagc                                                           369
```

<210> SEQ ID NO 510
<211> LENGTH: 1350
<212> TYPE: DNA
<213> ORGANISM: Artificial Sequence
<220> FEATURE:
<223> OTHER INFORMATION: 909 gH61 IgG4 heavy chain (V + human gamma-4P
      constant) (Seq. ID No. 462) cDNA

<400> SEQUENCE: 510

```
gaagtccagc tgcaagaatc aggtccaggc ctcgtcaaac catcaggaac tttgtcattg     60
acttgcgccg tgagcgggtt ctcgctttcg acctactaca tgtcgtgggt gcgccagccg    120
cctgggaagg gactggagtg gatcggcatc atctacccgt ccggcagcac gtactgcgct    180
agctgggcca aggggcgggt gaccatcagc aaggactcca gcaaaaatca ggtgagcctc    240
aagctgtcgt cagttactgc ggccgacact gcagtgtact attgtgcccg cccggataac    300
gatggaacct ccggctacct gtccggattc ggactgtggg gacagggaac ccttgtgact    360
gtctcgagcg cctccaccaa gggcccctcc gtgttccctc tggccccttg ctcccggtcc    420
acctccgagt ctaccgccgc tctgggctgc ctggtcaagg actacttccc cgagccgtg    480 acagtgtcct ggaactctgg cgccctgacc tccggcgtgc acaccttccc tgccgtgctg    540
cagtcctccg gcctgtactc cctgtcctcc gtcgtgaccg tgccctcctc cagcctgggc    600
```

```
accaagacct acacctgtaa cgtggaccac aagccctcca acaccaaggt ggacaagcgg    660
gtggaatcta agtacggccc tcccctgccc ccctgccctg ccctgaatt  ctgggcgga    720 ccttccgtgt tcctgttccc cccaaagccc aaggacaccc tgatgatctc ccggacccct    780
gaagtgacct gcgtggtggt ggacgtgtcc caggaagatc ccgaggtcca gttcaattgg    840
tacgtggacg gcgtggaagt gcacaatgcc aagaccaagc cagagagga  acagttcaac    900 tccacctacc gggtggtgtc cgtgctgacc gtgctgcacc aggactggct gaacggcaaa    960
gagtacaagt gcaaggtgtc caacaagggc ctgccctcca gcatcgaaaa gaccatctcc   1020
aaggccaagg gccagccccg cgagcccag  gtgtacaccc tgcccccta  ccaggaagag   1080 atgaccaaga accaggtgtc cctgacctgt ctggtcaagg gcttctaccc ctccgacatt   1140
gccgtggaat gggagtccaa cggccagccc gagaacaact acaagaccac ccccctgtg   1200 ctggacagcg acggctcctt cttcctgtac tctcggctga ccgtggacaa gtcccggtgg   1260
caggaaggca acgtcttctc ctgctccgtg atgcacgagg ccctgcacaa ccactacacc   1320
cagaagtccc tgtccctgag cctgggcaag                                    1350

<210> SEQ ID NO 511
<211> LENGTH: 369
<212> TYPE: DNA
<213> ORGANISM: Artificial Sequence
<220> FEATURE:
<223> OTHER INFORMATION: 909gH62 V-region (Seq. ID. No. 463) cDNA

<400> SEQUENCE: 511
gaagtccagc tgcaagaatc aggtccaggc ctcgtcaaac catcaggaac tttgtcattg     60
acttgcgccg tgagcggggtt ctcgctttcg acctactaca tgtcgtgggt gcgccagccg    120
cctgggaagg gactggagtg gatcggcatc atctacccgt ccggcagcac gtactccgct    180
agctgggcca aggggcgggt gaccatcagc aaggactcca gcaaaaatca ggtgagcctc    240
aagctgtcgt cagttactgc ggccgacact gcagtgtact attgtgcccg cccggataac    300
gagggaacct ccggctacct gtccggattc ggactgtggg gacagggaac ccttgtgact    360
gtctcgagc                                                            369

<210> SEQ ID NO 512
<211> LENGTH: 1350
<212> TYPE: DNA
<213> ORGANISM: Artificial Sequence
<220> FEATURE:
<223> OTHER INFORMATION: 909 gH62 IgG4 heavy chain (V + human gamma-4P
      constant) (Seq. ID No. 464) cDNA

<400> SEQUENCE: 512
gaagtccagc tgcaagaatc aggtccaggc ctcgtcaaac catcaggaac tttgtcattg     60
acttgcgccg tgagcggggtt ctcgctttcg acctactaca tgtcgtgggt gcgccagccg    120
cctgggaagg gactggagtg gatcggcatc atctacccgt ccggcagcac gtactccgct    180
agctgggcca aggggcgggt gaccatcagc aaggactcca gcaaaaatca ggtgagcctc    240
aagctgtcgt cagttactgc ggccgacact gcagtgtact attgtgcccg cccggataac    300
gagggaacct ccggctacct gtccggattc ggactgtggg gacagggaac ccttgtgact    360
gtctcgagcg cctccaccaa gggcccctcc gtgttccctc tggcccccttg ctcccggtcc    420 acctccgagt ctaccgccgc tctgggctgc ctggtcaagg actacttccc cgagcccgtg    480
acagtgtcct ggaactctgg cgccctgacc tccggcgtgc acaccttccc tgccgtgctg    540
```

```
cagtcctccg gcctgtactc cctgtcctcc gtcgtgaccg tgccctcctc cagcctgggc    600
accaagacct acacctgtaa cgtggaccac aagccctcca acaccaaggt ggacaagcgg    660
gtggaatcta agtacggccc tccctgcccc cctgccctg ccctgaatt tctgggcgga      720 ccttccgtgt tcctgttccc cccaaagccc aaggacaccc tgatgatctc ccggacccc    780 gaagtgacct gcgtggtggt ggacgtgtcc caggaagatc ccgaggtcca gttcaattgg    840
tacgtggacg gcgtggaagt gcacaatgcc aagaccaagc ccagagagga acagttcaac    900
tccacctacc gggtggtgtc cgtgctgacc gtgctgcacc aggactggct gaacggcaaa    960
gagtacaagt gcaaggtgtc caacaagggc ctgcccctcca gcatcgaaaa gaccatctcc    1020
aaggccaagg gccagccccg cgagcccag gtgtacaccc tgcccctag ccaggaagag     1080 atgaccaaga accaggtgtc cctgacctgt ctggtcaagg gcttctaccc ctccgacatt    1140
gccgtggaat gggagtccaa cggccagccc gagaacaact acaagaccac cccccctgtg    1200
ctggacagcg acggctcctt cttcctgtac tctcggctga ccgtggacaa gtcccggtgg    1260
caggaaggca acgtcttctc ctgctccgtg atgcacgagg ccctgcacaa ccactacacc    1320
cagaagtccc tgtccctgag cctgggcaag                                     1350
```

<210> SEQ ID NO 513
<211> LENGTH: 21
<212> TYPE: DNA
<213> ORGANISM: Artificial Sequence
<220> FEATURE:
<223> OTHER INFORMATION: 36B4 primer 1

<400> SEQUENCE: 513
cactggtcta ggacccgaga a    21

<210> SEQ ID NO 514
<211> LENGTH: 21
<212> TYPE: DNA
<213> ORGANISM: Artificial Sequence
<220> FEATURE:
<223> OTHER INFORMATION: 36B4 primer 2

<400> SEQUENCE: 514 aggggagat gttcagcatg t    21

<210> SEQ ID NO 515
<211> LENGTH: 21
<212> TYPE: DNA
<213> ORGANISM: Artificial Sequence
<220> FEATURE:
<223> OTHER INFORMATION: FAS primer 1

<400> SEQUENCE: 515
ggaggtggtg atagccggta t    21

<210> SEQ ID NO 516
<211> LENGTH: 21
<212> TYPE: DNA
<213> ORGANISM: Artificial Sequence
<220> FEATURE:
<223> OTHER INFORMATION: FAS primer 2

<400> SEQUENCE: 516
tgggtaatcc atagagccca g    21

<210> SEQ ID NO 517

```
<211> LENGTH: 22
<212> TYPE: DNA
<213> ORGANISM: Artificial Sequence
<220> FEATURE:
<223> OTHER INFORMATION: SCD1 primer 1

<400> SEQUENCE: 517
ttcttgcgat acactctggt gc                                              22

<210> SEQ ID NO 518
<211> LENGTH: 22
<212> TYPE: DNA
<213> ORGANISM: Artificial Sequence
<220> FEATURE:
<223> OTHER INFORMATION: SCD1 primer 2

<400> SEQUENCE: 518
cgggattgaa tgttcttgtc gt                                              22

<210> SEQ ID NO 519
<211> LENGTH: 21
<212> TYPE: DNA
<213> ORGANISM: Artificial Sequence
<220> FEATURE:
<223> OTHER INFORMATION: Pck1 primer 1

<400> SEQUENCE: 519
ctgcataacg gtctggactt c                                               21

<210> SEQ ID NO 520
<211> LENGTH: 19
<212> TYPE: DNA
<213> ORGANISM: Artificial Sequence
<220> FEATURE:
<223> OTHER INFORMATION: Pck1 primer 2

<400> SEQUENCE: 520
cagcaactgc ccgtactcc                                                  19

<210> SEQ ID NO 521
<211> LENGTH: 21
<212> TYPE: DNA
<213> ORGANISM: Artificial Sequence
<220> FEATURE:
<223> OTHER INFORMATION: G6pc primer 1

<400> SEQUENCE: 521
cgactcgcta tctccaagtg a                                               21

<210> SEQ ID NO 522
<211> LENGTH: 20
<212> TYPE: DNA
<213> ORGANISM: Artificial Sequence
<220> FEATURE:
<223> OTHER INFORMATION: G6pc primer 2

<400> SEQUENCE: 522
gttgaaccag tctccgacca                                                 20

<210> SEQ ID NO 523
<211> LENGTH: 21
<212> TYPE: DNA
<213> ORGANISM: Artificial Sequence
<220> FEATURE:
<223> OTHER INFORMATION: ACC1 primer 1

<400> SEQUENCE: 523
```
atgtctggct tgcacctagt a                                    21

<210> SEQ ID NO 524
<211> LENGTH: 23
<212> TYPE: DNA
<213> ORGANISM: Artificial Sequence
<220> FEATURE:
<223> OTHER INFORMATION: ACC1 primer 2

<400> SEQUENCE: 524
ccccaaagcg agtaacaaat tct                                  23

<210> SEQ ID NO 525
<211> LENGTH: 23
<212> TYPE: DNA
<213> ORGANISM: Artificial Sequence
<220> FEATURE:
<223> OTHER INFORMATION: TNF primer 1

<400> SEQUENCE: 525
ccctcacact cagatcatct tct                                  23

<210> SEQ ID NO 526
<211> LENGTH: 19
<212> TYPE: DNA
<213> ORGANISM: Artificial Sequence
<220> FEATURE:
<223> OTHER INFORMATION: TNF primer 2

<400> SEQUENCE: 526
gctacgacgt gggctacag                                       19

<210> SEQ ID NO 527
<211> LENGTH: 22
<212> TYPE: DNA
<213> ORGANISM: Artificial Sequence
<220> FEATURE:
<223> OTHER INFORMATION: IL-1beta primer 1

<400> SEQUENCE: 527
gcaactgttc ctgaactcaa ct                                   22

<210> SEQ ID NO 528
<211> LENGTH: 21
<212> TYPE: DNA
<213> ORGANISM: Artificial Sequence
<220> FEATURE:
<223> OTHER INFORMATION: IL-1beta primer 2

<400> SEQUENCE: 528
atcttttggg gtccgtcaac t                                    21

<210> SEQ ID NO 529
<211> LENGTH: 22
<212> TYPE: DNA
<213> ORGANISM: Artificial Sequence
<220> FEATURE:
<223> OTHER INFORMATION: IL-6 primer 1

<400> SEQUENCE: 529
acaaccacgg ccttccctac tt                                   22

<210> SEQ ID NO 530
<211> LENGTH: 23
<212> TYPE: DNA

```
<213> ORGANISM: Artificial Sequence
<220> FEATURE:
<223> OTHER INFORMATION: IL-6 primer 2

<400> SEQUENCE: 530
cacgatttcc cagagaacat gtg                                             23

<210> SEQ ID NO 531
<211> LENGTH: 18
<212> TYPE: DNA
<213> ORGANISM: Artificial Sequence
<220> FEATURE:
<223> OTHER INFORMATION: CCL2 primer 1

<400> SEQUENCE: 531
catccacgtg ttggctca                                                   18

<210> SEQ ID NO 532
<211> LENGTH: 23
<212> TYPE: DNA
<213> ORGANISM: Artificial Sequence
<220> FEATURE:
<223> OTHER INFORMATION: CCL2 primer 2

<400> SEQUENCE: 532
gatcatcttg ctggtgaatg agt                                             23

<210> SEQ ID NO 533
<211> LENGTH: 20
<212> TYPE: DNA
<213> ORGANISM: Artificial Sequence
<220> FEATURE:
<223> OTHER INFORMATION: CXCL1 primer 1

<400> SEQUENCE: 533
gactccagcc acactccaac                                                 20

<210> SEQ ID NO 534
<211> LENGTH: 18
<212> TYPE: DNA
<213> ORGANISM: Artificial Sequence
<220> FEATURE:
<223> OTHER INFORMATION: CXCL1 primer 2

<400> SEQUENCE: 534
tgacagcgca gctcattg                                                   18

<210> SEQ ID NO 535
<211> LENGTH: 21
<212> TYPE: DNA
<213> ORGANISM: Artificial Sequence
<220> FEATURE:
<223> OTHER INFORMATION: F4/80 primer 1

<400> SEQUENCE: 535
tgactcacct tgtggtccta a                                               21

<210> SEQ ID NO 536
<211> LENGTH: 22
<212> TYPE: DNA
<213> ORGANISM: Artificial Sequence
<220> FEATURE:
<223> OTHER INFORMATION: F4/80 primer 2

<400> SEQUENCE: 536
cttcccagaa tccagtcttt cc                                              22
```

<210> SEQ ID NO 537
<211> LENGTH: 21
<212> TYPE: DNA
<213> ORGANISM: Artificial Sequence
<220> FEATURE:
<223> OTHER INFORMATION: CD68 primer 1

<400> SEQUENCE: 537
tgtctgatct tgctaggacc g                                          21

<210> SEQ ID NO 538
<211> LENGTH: 22
<212> TYPE: DNA
<213> ORGANISM: Artificial Sequence
<220> FEATURE:
<223> OTHER INFORMATION: CD68 primer 2

<400> SEQUENCE: 538
gagagtaacg gccttttttgt ga                                        22

<210> SEQ ID NO 539
<211> LENGTH: 22
<212> TYPE: DNA
<213> ORGANISM: Artificial Sequence
<220> FEATURE:
<223> OTHER INFORMATION: TBP primer 1

<400> SEQUENCE: 539
agaacaatcc agactagcag ca                                         22

<210> SEQ ID NO 540
<211> LENGTH: 21
<212> TYPE: DNA
<213> ORGANISM: Artificial Sequence
<220> FEATURE:
<223> OTHER INFORMATION: TBP primer 2

<400> SEQUENCE: 540
gggaacttca catcacagct c                                          21

<210> SEQ ID NO 541
<211> LENGTH: 21
<212> TYPE: DNA
<213> ORGANISM: Artificial Sequence
<220> FEATURE:
<223> OTHER INFORMATION: Control target sequence

<400> SEQUENCE: 541
gtctccacgc gcagtacatt t                                          21

<210> SEQ ID NO 542
<211> LENGTH: 21
<212> TYPE: DNA
<213> ORGANISM: Artificial Sequence
<220> FEATURE:
<223> OTHER INFORMATION: Foxo1 target sequence

<400> SEQUENCE: 542
gcatgtttat tgagcgcttg g                                          21

<210> SEQ ID NO 543
<211> LENGTH: 21
<212> TYPE: DNA
<213> ORGANISM: Artificial Sequence
<220> FEATURE:

<223> OTHER INFORMATION: CtBP1 target sequence

<400> SEQUENCE: 543
gcagcgggtt tgacaatatc g                                    21

<210> SEQ ID NO 544
<211> LENGTH: 21
<212> TYPE: DNA
<213> ORGANISM: Artificial Sequence
<220> FEATURE:
<223> OTHER INFORMATION: CtBP2 target sequence 1

<400> SEQUENCE: 544
gggaagacta ggacgtgatt a                                    21

<210> SEQ ID NO 545
<211> LENGTH: 21
<212> TYPE: DNA
<213> ORGANISM: Artificial Sequence
<220> FEATURE:
<223> OTHER INFORMATION: CtBP2 target sequence 2

<400> SEQUENCE: 545
gccacattct caatctgtat c                                    21

<210> SEQ ID NO 546
<211> LENGTH: 21
<212> TYPE: DNA
<213> ORGANISM: Artificial Sequence
<220> FEATURE:
<223> OTHER INFORMATION: HNF4a target sequence

<400> SEQUENCE: 546
gctgcagatt gatgacaatg a                                    21

<210> SEQ ID NO 547
<211> LENGTH: 21
<212> TYPE: DNA
<213> ORGANISM: Artificial Sequence
<220> FEATURE:
<223> OTHER INFORMATION: Rplp0 forward primer

<400> SEQUENCE: 547
cactggtcta ggacccgaga a                                    21

<210> SEQ ID NO 548
<211> LENGTH: 21
<212> TYPE: DNA
<213> ORGANISM: Artificial Sequence
<220> FEATURE:
<223> OTHER INFORMATION: Rplp0 reverse primer

<400> SEQUENCE: 548 aggggagat gttcagcatg t                                     21

<210> SEQ ID NO 549
<211> LENGTH: 21
<212> TYPE: DNA
<213> ORGANISM: Artificial Sequence
<220> FEATURE:
<223> OTHER INFORMATION: Pck1 forward primer

<400> SEQUENCE: 549
ctgcataacg gtctggactt c                                    21

-continued

```
<210> SEQ ID NO 550
<211> LENGTH: 19
<212> TYPE: DNA
<213> ORGANISM: Artificial Sequence
<220> FEATURE:
<223> OTHER INFORMATION: Pck1 reverse primer

<400> SEQUENCE: 550
cagcaactgc ccgtactcc                                                  19

<210> SEQ ID NO 551
<211> LENGTH: 21
<212> TYPE: DNA
<213> ORGANISM: Artificial Sequence
<220> FEATURE:
<223> OTHER INFORMATION: G6pc forward primer

<400> SEQUENCE: 551
cgactcgcta tctccaagtg a                                               21

<210> SEQ ID NO 552
<211> LENGTH: 20
<212> TYPE: DNA
<213> ORGANISM: Artificial Sequence
<220> FEATURE:
<223> OTHER INFORMATION: G6pc reverse primer

<400> SEQUENCE: 552
gttgaaccag tctccgacca                                                 20

<210> SEQ ID NO 553
<211> LENGTH: 21
<212> TYPE: DNA
<213> ORGANISM: Artificial Sequence
<220> FEATURE:
<223> OTHER INFORMATION: Foxo1 forward primer

<400> SEQUENCE: 553
aacacacagc tgggtgtcag g                                               21

<210> SEQ ID NO 554
<211> LENGTH: 23
<212> TYPE: DNA
<213> ORGANISM: Artificial Sequence
<220> FEATURE:
<223> OTHER INFORMATION: Foxo1 reverse primer

<400> SEQUENCE: 554
gcatctttgg actgctcctc agt                                             23

<210> SEQ ID NO 555
<211> LENGTH: 21
<212> TYPE: DNA
<213> ORGANISM: Artificial Sequence
<220> FEATURE:
<223> OTHER INFORMATION: Foxo3 forward primer

<400> SEQUENCE: 555
ctggtgctaa gcaggcctca t                                               21

<210> SEQ ID NO 556
<211> LENGTH: 24
<212> TYPE: DNA
<213> ORGANISM: Artificial Sequence
<220> FEATURE:
<223> OTHER INFORMATION: Foxo3 reverse primer
```

```
<400> SEQUENCE: 556
tgtaggtctt ccgtcagttt gagg                                              24

<210> SEQ ID NO 557
<211> LENGTH: 24
<212> TYPE: DNA
<213> ORGANISM: Artificial Sequence
<220> FEATURE:
<223> OTHER INFORMATION: Foxo4 forward primer

<400> SEQUENCE: 557
tgtatatgga gaacctggag tgcg                                              24

<210> SEQ ID NO 558
<211> LENGTH: 24
<212> TYPE: DNA
<213> ORGANISM: Artificial Sequence
<220> FEATURE:
<223> OTHER INFORMATION: Foxo4 reverse primer

<400> SEQUENCE: 558
caaagcttct tgctgtgact cagg                                              24

<210> SEQ ID NO 559
<211> LENGTH: 22
<212> TYPE: DNA
<213> ORGANISM: Artificial Sequence
<220> FEATURE:
<223> OTHER INFORMATION: Cebpa forward primer

<400> SEQUENCE: 559
caagaacagc aacgagtacc gg                                                22

<210> SEQ ID NO 560
<211> LENGTH: 22
<212> TYPE: DNA
<213> ORGANISM: Artificial Sequence
<220> FEATURE:
<223> OTHER INFORMATION: Cebpa reverse primer

<400> SEQUENCE: 560
tgtcactggt caactccagc ac                                                22

<210> SEQ ID NO 561
<211> LENGTH: 24
<212> TYPE: DNA
<213> ORGANISM: Artificial Sequence
<220> FEATURE:
<223> OTHER INFORMATION: Nr3c1 forward primer

<400> SEQUENCE: 561
ctgacgtgtg gaagctgtaa agtc                                              24

<210> SEQ ID NO 562
<211> LENGTH: 23
<212> TYPE: DNA
<213> ORGANISM: Artificial Sequence
<220> FEATURE:
<223> OTHER INFORMATION: Nr3c1 reverse primer

<400> SEQUENCE: 562
gatgcaatca tttcttccag cac                                               23

<210> SEQ ID NO 563
<211> LENGTH: 22
```

```
<212> TYPE: DNA
<213> ORGANISM: Artificial Sequence
<220> FEATURE:
<223> OTHER INFORMATION: CtBP1 forward primer

<400> SEQUENCE: 563
ttgggcatca ttggactagg tc                                              22

<210> SEQ ID NO 564
<211> LENGTH: 25
<212> TYPE: DNA
<213> ORGANISM: Artificial Sequence
<220> FEATURE:
<223> OTHER INFORMATION: CtBP1 reverse primer

<400> SEQUENCE: 564
gctcgattcc atcagatagg tatgg                                           25

<210> SEQ ID NO 565
<211> LENGTH: 24
<212> TYPE: DNA
<213> ORGANISM: Artificial Sequence
<220> FEATURE:
<223> OTHER INFORMATION: CtBP2 forward primer

<400> SEQUENCE: 565
gcaggacttg ctatatcaga gcga                                            24

<210> SEQ ID NO 566
<211> LENGTH: 21
<212> TYPE: DNA
<213> ORGANISM: Artificial Sequence
<220> FEATURE:
<223> OTHER INFORMATION: CtBP2 reverse primer

<400> SEQUENCE: 566
atgcaccttg cctcatctgc t                                               21

<210> SEQ ID NO 567
<211> LENGTH: 21
<212> TYPE: DNA
<213> ORGANISM: Artificial Sequence
<220> FEATURE:
<223> OTHER INFORMATION: Alb forward primer

<400> SEQUENCE: 567
agacgtgtgt tgccgatgag t                                               21

<210> SEQ ID NO 568
<211> LENGTH: 22
<212> TYPE: DNA
<213> ORGANISM: Artificial Sequence
<220> FEATURE:
<223> OTHER INFORMATION: Alb reverse primer

<400> SEQUENCE: 568
gttttcacgg aggtttggaa tg                                              22

<210> SEQ ID NO 569
<211> LENGTH: 22
<212> TYPE: DNA
<213> ORGANISM: Artificial Sequence
<220> FEATURE:
<223> OTHER INFORMATION: Gpam forward primer

<400> SEQUENCE: 569
```
acagttggca caatagacgt tt                                              22

<210> SEQ ID NO 570
<211> LENGTH: 22
<212> TYPE: DNA
<213> ORGANISM: Artificial Sequence
<220> FEATURE:
<223> OTHER INFORMATION: Gpam reverse primer

<400> SEQUENCE: 570
ccttccattt cagtgttgca ga                                              22

<210> SEQ ID NO 571
<211> LENGTH: 20
<212> TYPE: DNA
<213> ORGANISM: Artificial Sequence
<220> FEATURE:
<223> OTHER INFORMATION: Fasn forward primer

<400> SEQUENCE: 571
agagatcccg agacgcttct                                                 20

<210> SEQ ID NO 572
<211> LENGTH: 21
<212> TYPE: DNA
<213> ORGANISM: Artificial Sequence
<220> FEATURE:
<223> OTHER INFORMATION: Fasn reverse primer

<400> SEQUENCE: 572
gcctggtagg cattctgtag t                                               21

<210> SEQ ID NO 573
<211> LENGTH: 21
<212> TYPE: DNA
<213> ORGANISM: Artificial Sequence
<220> FEATURE:
<223> OTHER INFORMATION: Scd1 forward primer

<400> SEQUENCE: 573
cccgggagaa tatcctggtt t                                               21

<210> SEQ ID NO 574
<211> LENGTH: 22
<212> TYPE: DNA
<213> ORGANISM: Artificial Sequence
<220> FEATURE:
<223> OTHER INFORMATION: Scd1 reverse primer

<400> SEQUENCE: 574
tcgatgaaga acgtggtgaa gt                                              22

<210> SEQ ID NO 575
<211> LENGTH: 22
<212> TYPE: DNA
<213> ORGANISM: Artificial Sequence
<220> FEATURE:
<223> OTHER INFORMATION: Hif1a forward primer

<400> SEQUENCE: 575
atgaagtgca ccctaacaag cc                                              22

<210> SEQ ID NO 576
<211> LENGTH: 24
<212> TYPE: DNA
<213> ORGANISM: Artificial Sequence

```
<220> FEATURE:
<223> OTHER INFORMATION: Hif1a reverse primer

<400> SEQUENCE: 576
cacactgagg ttggttactg ttgg                                              24

<210> SEQ ID NO 577
<211> LENGTH: 21
<212> TYPE: DNA
<213> ORGANISM: Artificial Sequence
<220> FEATURE:
<223> OTHER INFORMATION: Ppargc1a forward primer

<400> SEQUENCE: 577
gaagtggtgt agcgaccaat c                                                 21

<210> SEQ ID NO 578
<211> LENGTH: 21
<212> TYPE: DNA
<213> ORGANISM: Artificial Sequence
<220> FEATURE:
<223> OTHER INFORMATION: Ppargc1a reverse primer

<400> SEQUENCE: 578
aatgagggca atccgtcttc a                                                 21

<210> SEQ ID NO 579
<211> LENGTH: 20
<212> TYPE: DNA
<213> ORGANISM: Artificial Sequence
<220> FEATURE:
<223> OTHER INFORMATION: Stat3 forward primer

<400> SEQUENCE: 579
accattgacc tgccgatgtc                                                   20

<210> SEQ ID NO 580
<211> LENGTH: 20
<212> TYPE: DNA
<213> ORGANISM: Artificial Sequence
<220> FEATURE:
<223> OTHER INFORMATION: Stat3 reverse primer

<400> SEQUENCE: 580
tgagcgactc aaactgccct                                                   20

<210> SEQ ID NO 581
<211> LENGTH: 20
<212> TYPE: DNA
<213> ORGANISM: Artificial Sequence
<220> FEATURE:
<223> OTHER INFORMATION: Srebf1c forward primer

<400> SEQUENCE: 581
ggagccatgg attgcacatt                                                   20

<210> SEQ ID NO 582
<211> LENGTH: 18
<212> TYPE: DNA
<213> ORGANISM: Artificial Sequence
<220> FEATURE:
<223> OTHER INFORMATION: Srebf1c reverse primer

<400> SEQUENCE: 582
ggcccgggaa gtcactgt                                                     18
```

<210> SEQ ID NO 583
<211> LENGTH: 22
<212> TYPE: DNA
<213> ORGANISM: Artificial Sequence
<220> FEATURE:
<223> OTHER INFORMATION: Mlxip1 forward primer

<400> SEQUENCE: 583
cactcaggga atacacgcct ac                                              22

<210> SEQ ID NO 584
<211> LENGTH: 23
<212> TYPE: DNA
<213> ORGANISM: Artificial Sequence
<220> FEATURE:
<223> OTHER INFORMATION: Mlxip1 reverse primer

<400> SEQUENCE: 584
atcttggtct tagggtcttc agg                                             23

<210> SEQ ID NO 585
<211> LENGTH: 21
<212> TYPE: DNA
<213> ORGANISM: Artificial Sequence
<220> FEATURE:
<223> OTHER INFORMATION: Pklr forward primer

<400> SEQUENCE: 585
tcaaggcagg gatgaacatt g                                               21

<210> SEQ ID NO 586
<211> LENGTH: 21
<212> TYPE: DNA
<213> ORGANISM: Artificial Sequence
<220> FEATURE:
<223> OTHER INFORMATION: Pklr reverse primer

<400> SEQUENCE: 586
cacgggtctg tagctgagtg g                                               21

<210> SEQ ID NO 587
<211> LENGTH: 21
<212> TYPE: DNA
<213> ORGANISM: Artificial Sequence
<220> FEATURE:
<223> OTHER INFORMATION: Acly forward primer

<400> SEQUENCE: 587 acccttttcac tggggatcac a                                              21

<210> SEQ ID NO 588
<211> LENGTH: 22
<212> TYPE: DNA
<213> ORGANISM: Artificial Sequence
<220> FEATURE:
<223> OTHER INFORMATION: Acly reverse primer

<400> SEQUENCE: 588
gacagggatc aggatttcct tg                                              22

<210> SEQ ID NO 589
<211> LENGTH: 22
<212> TYPE: DNA
<213> ORGANISM: Artificial Sequence
<220> FEATURE:
<223> OTHER INFORMATION: Crp forward primer

<400> SEQUENCE: 589
atggagaagc tactctggtg cc                                                22

<210> SEQ ID NO 590
<211> LENGTH: 25
<212> TYPE: DNA
<213> ORGANISM: Artificial Sequence
<220> FEATURE:
<223> OTHER INFORMATION: Crp reverse primer

<400> SEQUENCE: 590
acacacagta aaggtgttca gtggc                                             25

<210> SEQ ID NO 591
<211> LENGTH: 25
<212> TYPE: DNA
<213> ORGANISM: Artificial Sequence
<220> FEATURE:
<223> OTHER INFORMATION: Apcs forward primer

<400> SEQUENCE: 591
gtcagacaga cctcaagagg aaagt                                             25

<210> SEQ ID NO 592
<211> LENGTH: 25
<212> TYPE: DNA
<213> ORGANISM: Artificial Sequence
<220> FEATURE:
<223> OTHER INFORMATION: Apcs reverse primer

<400> SEQUENCE: 592
aggttcggaa acacagtgta aaatt                                             25

<210> SEQ ID NO 593
<211> LENGTH: 21
<212> TYPE: DNA
<213> ORGANISM: Artificial Sequence
<220> FEATURE:
<223> OTHER INFORMATION: CD36 forward primer

<400> SEQUENCE: 593
agatgacgtg gcaaagaaca g                                                 21

<210> SEQ ID NO 594
<211> LENGTH: 23
<212> TYPE: DNA
<213> ORGANISM: Artificial Sequence
<220> FEATURE:
<223> OTHER INFORMATION: CD36 reverse primer

<400> SEQUENCE: 594
ccttggctag ataacgaact ctg                                               23

<210> SEQ ID NO 595
<211> LENGTH: 23
<212> TYPE: DNA
<213> ORGANISM: Artificial Sequence
<220> FEATURE:
<223> OTHER INFORMATION: Acadm forward primer

<400> SEQUENCE: 595
agggtttagt tttgagttga cgg                                               23

<210> SEQ ID NO 596

```
<211> LENGTH: 21
<212> TYPE: DNA
<213> ORGANISM: Artificial Sequence
<220> FEATURE:
<223> OTHER INFORMATION: Acadm reverse primer

<400> SEQUENCE: 596
ccccgctttt gtcatattcc g                                              21

<210> SEQ ID NO 597
<211> LENGTH: 12
<212> TYPE: PRT
<213> ORGANISM: Artificial Sequence
<220> FEATURE:
<223> OTHER INFORMATION: CDRL1 variant 1

<400> SEQUENCE: 597

Ser Val Ser Ser Ser Ile Ser Ser Ser Asn Leu His
1               5                   10

<210> SEQ ID NO 598
<211> LENGTH: 7
<212> TYPE: PRT
<213> ORGANISM: Artificial Sequence
<220> FEATURE:
<223> OTHER INFORMATION: CDRL2 variant 1

<400> SEQUENCE: 598

Gly Thr Ser Asn Leu Ala Ser
1               5

<210> SEQ ID NO 599
<211> LENGTH: 9
<212> TYPE: PRT
<213> ORGANISM: Artificial Sequence
<220> FEATURE:
<223> OTHER INFORMATION: CDRL3 variant 5

<400> SEQUENCE: 599

Gln Gln Trp Ser His Tyr Pro Leu Thr
1               5

<210> SEQ ID NO 600
<211> LENGTH: 10
<212> TYPE: PRT
<213> ORGANISM: Artificial Sequence
<220> FEATURE:
<223> OTHER INFORMATION: CDRH1 variant 2

<400> SEQUENCE: 600

Gly Tyr Thr Phe Thr Ser Asn Trp Ile Thr
1               5                   10

<210> SEQ ID NO 601
<211> LENGTH: 17
<212> TYPE: PRT
<213> ORGANISM: Artificial Sequence
<220> FEATURE:
<223> OTHER INFORMATION: CDRH2 variant 3

<400> SEQUENCE: 601

Asp Ile Tyr Pro Gly Ser Gly Ser Thr Thr Asn Asn Glu Lys Phe Lys
1               5                   10                  15

Ser

<210> SEQ ID NO 602
```

```
<211> LENGTH: 10
<212> TYPE: PRT
<213> ORGANISM: Artificial Sequence
<220> FEATURE:
<223> OTHER INFORMATION: CDRH3 variant 3

<400> SEQUENCE: 602

Leu Arg Gly Tyr Tyr Asp Tyr Phe Asp Phe
1               5                   10

<210> SEQ ID NO 603
<211> LENGTH: 50
<212> TYPE: PRT
<213> ORGANISM: Mus musculus

<400> SEQUENCE: 603

Ala Leu Gly Ser Tyr Ser Ser Val Ser Cys Asn Gly Tyr Gly Arg
1               5                   10                  15

Met Gly Val Leu His Gln Glu Lys Leu Pro Ser Asp Leu Asp Gly Met
                20                  25                  30

Phe Ile Glu Arg Leu Asp Cys Asp Met Glu Ser Ile Ile Arg Asn Asp
            35                  40                  45

Leu Met
    50

<210> SEQ ID NO 604
<211> LENGTH: 50
<212> TYPE: PRT
<213> ORGANISM: Mus musculus

<400> SEQUENCE: 604

Thr Leu Ser Asp Ser Leu Ser Gly Ser Ser Leu Tyr Ser Ala Ser Ala
1               5                   10                  15

Asn Leu Pro Val Met Gly His Asp Lys Phe Pro Ser Asp Leu Asp Leu
                20                  25                  30

Asp Met Phe Asn Gly Ser Leu Glu Cys Asp Met Glu Ser Ile Ile Arg
            35                  40                  45

Ser Glu
    50

<210> SEQ ID NO 605
<211> LENGTH: 50
<212> TYPE: PRT
<213> ORGANISM: Mus musculus

<400> SEQUENCE: 605

Met Ala Gly Ala Pro Ile Pro Lys Val Leu Gly Thr Pro Val Leu Ala
1               5                   10                  15

Ser Pro Thr Glu Asp Ser Ser His Asp Arg Met Pro Gln Asp Leu Asp
                20                  25                  30

Leu Asp Met Tyr Met Glu Asn Leu Glu Cys Asp Met Asp Asn Ile Ile
            35                  40                  45

Ser Asp
    50

<210> SEQ ID NO 606
<211> LENGTH: 50
<212> TYPE: PRT
<213> ORGANISM: Mus musculus

<400> SEQUENCE: 606
```

```
Leu Pro Gly Pro Tyr Ala Ala Ala Ala Gly Pro Leu Gly Ala Gly
1               5                   10                  15

Pro Asp Arg Phe Pro Ala Asp Leu Asp Leu Asp Met Phe Ser Gly Ser
            20                  25                  30

Leu Glu Cys Asp Val Glu Ser Ile Ile Leu Asn Asp Phe Met Asp Ser
        35                  40                  45

Asp Glu
    50
```

<210> SEQ ID NO 607
<211> LENGTH: 50
<212> TYPE: PRT
<213> ORGANISM: Homo sapiens

<400> SEQUENCE: 607

```
Val Ser Ser Cys Asn Gly Tyr Gly Arg Met Gly Leu Leu His Gln Glu
1               5                   10                  15

Lys Leu Pro Ser Asp Leu Asp Gly Met Phe Ile Glu Arg Leu Asp Cys
            20                  25                  30

Asp Met Glu Ser Ile Ile Arg Asn Asp Leu Met Asp Gly Gly Thr Leu
        35                  40                  45

Asp Phe
    50
```

<210> SEQ ID NO 608
<211> LENGTH: 50
<212> TYPE: PRT
<213> ORGANISM: Homo sapiens

<400> SEQUENCE: 608

```
Ser Leu Tyr Ser Thr Ser Ala Asn Leu Pro Val Met Gly His Glu Lys
1               5                   10                  15

Leu Pro Ser Asp Leu Gly Leu Asp Met Phe Asn Gly Ser Leu Glu Cys
            20                  25                  30

Asp Met Glu Ser Ile Ile Arg Ser Glu Leu Met Asp Ala Asp Gly Leu
        35                  40                  45

Asp Phe
    50
```

<210> SEQ ID NO 609
<211> LENGTH: 50
<212> TYPE: PRT
<213> ORGANISM: Homo sapiens

<400> SEQUENCE: 609

```
Thr Pro Val Leu Thr Pro Pro Thr Glu Ala Ala Ser Gln Asp Arg Met
1               5                   10                  15

Pro Gln Asp Leu Asp Leu Asp Met Tyr Met Glu Asn Leu Glu Cys Asp
            20                  25                  30

Met Asp Asn Ile Ile Ser Asp Leu Met Asp Glu Gly Glu Gly Leu Asp
        35                  40                  45

Phe Asn
    50
```

<210> SEQ ID NO 610
<211> LENGTH: 50
<212> TYPE: PRT
<213> ORGANISM: Homo sapiens

```
<400> SEQUENCE: 610

Leu Asp Ala Leu Pro Gly Pro Tyr Ala Ala Ala Ala Gly Pro Leu
1               5                   10                  15

Gly Ala Ala Pro Asp Arg Phe Pro Ala Asp Leu Asp Leu Asp Met Phe
                20                  25                  30

Ser Gly Ser Leu Glu Cys Asp Val Glu Ser Ile Ile Leu Asn Asp Phe
            35                  40                  45

Met Asp
    50
```

ANTI-AP2 ANTIBODIES AND ANTIGEN BINDING AGENTS TO TREAT METABOLIC DISORDERS

RELATED APPLICATIONS

This application is related to and claims the benefit of provisional U.S. Application No. 62/155,217, filed Apr. 30, 2015, provisional U.S. Application No. 62/232,148, filed Sep. 24, 2015, and provisional U.S. Application No. 62/268,257, filed Dec. 16, 2015. The entirety of these provisional applications are hereby incorporated by reference for all purposes.

FIELD OF THE INVENTION

This invention is in the area of improved anti-aP2 antibodies and antigen binding agents, and compositions thereof, which target the lipid chaperone aP2/FABP4 (referred to as "aP2") for use in treating disorders such as diabetes, obesity, cardiovascular disease, fatty liver disease, and/or cancer, among others. In one aspect, improved treatments for aP2 mediated disorders are disclosed in which serum aP2 is targeted and the biological activity of aP2 is neutralized or modulated using low-binding affinity aP2 monoclonal antibodies, providing lower fasting blood glucose levels, improved systemic glucose metabolism, increased systemic insulin sensitivity, reduced fat mass, reduced liver steatosis, reduced cardiovascular disease and/or a reduced risk of developing cardiovascular disease.

INCORPORATION BY REFERENCE

The contents of the text file named "15020-001US1_2018-03-12_SequenceListing_ST25.txt" which was created on Mar. 12, 2018, and is 263 KB in size, are hereby incorporated by reference in their entirety.

BACKGROUND OF THE INVENTION

Human adipocyte lipid-binding protein (aP2) belongs to a family of intracellular lipid-binding proteins involved in the transport and storage of lipids (Banzszak et al., (1994) Adv. Protein Chem. 45, 89-151). The aP2 protein is involved in lipolysis and lipogenesis and has been indicated in diseases of lipid and energy metabolism such as diabetes, atherosclerosis, and metabolic syndromes. aP2 has also been indicated in the integration of metabolic and inflammatory response systems. (Ozcan et al., (2006) Science 313(5790):1137-40; Makowski et al., (2005) J Biol Chem. 280(13):12888-95; and Erbay et al., (2009) Nat Med. 15(12):1383-91). More recently, aP2 has been shown to be differentially expressed in certain soft tissue tumors such as certain liposarcomas (Kashima et al., (2013) Virchows Arch. 462, 465-472).

aP2 is highly expressed in adipocytes and regulated by peroxisome-proliferator-activated receptor-γ (PPARγ) agonists, insulin, and fatty acids (Hertzel et al., (2000) Trends Endocrinol. Metab. 11, 175-180; Hunt et al., (1986) PNAS USA 83, 3786-3790; Melki et al., (1993) J. Lipid Res. 34, 1527-1534; Distel et al., (1992) J. Biol. Chem. 267, 5937-5941). Studies in aP2 deficient mice (aP2-/-) indicate protection against the development of insulin resistance associated with genetic or diet-induced obesity and improved lipid profile in adipose tissue with increased levels of C16:1n7-palmitoleate, reduced hepatosteatosis, and improved control of hepatic glucose production and peripheral glucose disposal (Hotamisligil et al., (1996) Science 274, 1377-1379; Uysal et al., (2000) Endocrinol. 141, 3388-3396; Cao et al., (2008) Cell 134, 933-944).

In addition, genetic deficiency or pharmacological blockade of aP2 reduces both early and advanced atherosclerotic lesions in the apolipoprotein E-deficient (ApoE-/-) mouse model (Furuhashi et al., (2007) Nature, June 21; 447(7147): 959-65; Makowski et al., (2001) Nature Med. 7, 699-705; Layne et al., (2001) FASEB 15, 2733-2735; Boord et al., (2002) Arteriosclerosis, Thrombosis, and Vas. Bio. 22, 1686-1691). Furthermore, aP2-deficiency leads to a marked protection against early and advanced atherosclerosis in apolipoprotein E-deficient (ApoE-/-) mice (Makowski et al., (2001) Nature Med. 7, 699-705; Fu et al., (2000) J. Lipid Res. 41, 2017-2023). Hence, aP2 plays a critical role in many aspects of development of metabolic disease in preclinical models.

In the past two decades, the biological functions of FABPs in general and aP2 in particular have primarily been attributed to their action as intracellular proteins. Since the abundance of aP2 protein in the adipocytes is extremely high, accounting for up to few percent of the total cellular protein (Cao et al., (2013) Cell Metab. 17(5):768-78), therapeutically targeting aP2 with traditional approaches has been challenging, and the promising success obtained in preclinical models (Furuhashi et al., (2007) Nature 447, 959-965; Won et al., (2014) Nature Mat. 13, 1157-1164; Cai et al., (2013) Acta Pharm. Sinica 34, 1397-1402; Hoo et al., (2013) J. of Hepat. 58, 358-364) has been slow to progress toward clinical translation.

In addition to its presence in the cytoplasm, it has recently been shown that aP2 is actively secreted from adipose tissue through a non-classical regulated pathway (Cao et al., (2013) Cell Metab. 17(5), 768-778; Ertunc et al., (2015) J. Lipid Res. 56, 423-424). The secreted form of aP2 acts as a novel adipokine and regulates hepatic glucose production and systemic glucose homeostasis in mice in response to fasting and fasting-related signals. Serum aP2 levels are significantly elevated in obese mice, and blocking circulating aP2 improves glucose homeostasis in mice with diet-induced obesity (Cao et al., (2013) Cell Metab. 17(5):768-78). Importantly, the same patterns are also observed in human populations where secreted aP2 levels are increased in obesity and strongly correlate with metabolic and cardiovascular diseases in multiple independent human studies (Xu et al., (2006) Clin. Chem. 53, 405-413; Yoo et al., (2011) J. Clin. Endocrin. & Metab. 96, E488-492; von Eynatten et al., (2012) Arteriosclerosis, Thrombosis, and Vas. Bio. 32, 2327-2335; Suh et al., (2014) Scandinavian J. Gastro. 49, 979-985; Furuhashi et al., (2011) PloS One 6, e27356; Ishimura et al., (2013) PloS One 8, e81318; Karakas et al., (2009) Metabolism: Clinical and Experimental 58, 1002-1007; Kaess et al., (2012) J. Endocrin. & Metab. 97, E1943-1947; Cabre et al., (2007) Atherosclerosis 195, e150-158). Finally, humans carrying a haploinsufficiency allele which results in reduced aP2 expression are protected against diabetes and cardiovascular disease (Tuncman et al., (2006) PNAS USA 103, 6970-6975; Saksi et al., (2014) Circulation, Cardiovascular Genetics 7, 588-598).

Cao et al. used a rabbit anti-mouse aP2 polyclonal antibody to show a reduction in plasma aP2 levels in obese antibody-treated mice, which occurred without any alteration in aP2 protein levels in the adipose tissue (Cao et al., (2013) Cell Metab. 17(5): 768-778; PCT Publication WO 2010/102171). Administration of the antibody in obese mice did not alter the body weight, but did cause a significant decrease in fasting blood glucose levels within two weeks of treatment compared to controls treated with a pre-immune IgG. In a glucose tolerance test, mice receiving the aP2 polyclonal antibody exhibited significantly improved glucose disposal curves compared to control animals.

Miao et al. reported the use of a high affinity mouse anti-human aP2 monoclonal antibody (identified as mAb 2E4) to achieve improved high-fat diet (HFD) induced inflammation in antibody treated mice receiving a high-fat diet (Miao et al., (2015) Molecular and Cellular Endocrinology 403, 1-9). Treatment with the high affinity mAb 2E4, however, resulted in drastically increased body weights compared with control animals, and no notable change was observed in basal glucose levels after six weeks of treatment. Furthermore, mAb 2E4 treatment failed to affect HFD-induced insulin tolerance.

It is an object of the invention to identify new compounds, methods, and compositions for the treatment of metabolic disorders.

It is in particular an object of the invention to identify new compounds, methods, and compositions for the reduction of fasting blood glucose levels, the improvement of systemic glucose metabolism, the improvement of glucose tolerance, the increase in systemic insulin sensitivity, the reduction in fat mass, the reduction in fat cell lipolysis, the reduction in hepatic glucose production, the reduction in hyperinsulinemia, and/or the reduction in liver steatosis.

It is also an object of the invention to identify new compounds, methods, and compositions for the treatment of diabetes, obesity, and dyslipidemia.

It is further object of the invention to identify new compounds, methods, and compositions for the treatment of inflammatory induced disorders, for example atherosclerosis.

It is another object of the invention to identify new compounds, methods, and compositions for the treatment of a tumor, cancer, or other neoplasm.

SUMMARY OF THE INVENTION

Anti-aP2 monoclonal antibodies and antigen binding agents are provided that have superior and unexpected activity for the treatment of aP2-mediated disorders. In one embodiment, anti-aP2 monoclonal antibodies and antigen binding agents are provided that contain a light chain or light chain fragment having a variable region, wherein said variable region comprises one, two, or three complementarity determining regions (CDRs) independently selected from Seq. ID No. 7, Seq. ID No. 8, and Seq. ID No. 9. In another embodiment, anti-aP2 monoclonal antibodies and antigen binding agents are provided that comprise a light chain or light chain fragment having a variable region, wherein said variable region comprises one, two, or three CDRs independently selected from Seq. ID No. 10, Seq. ID No. 11, Seq. ID No. 12, Seq. ID No. 13, Seq. ID No. 597, Seq. ID No. 598, or Seq. ID No. 599. In still another embodiment, anti-aP2 monoclonal antibodies and antigen binding agents are provided that comprise a light chain or light chain fragment having a variable region, wherein said variable region comprises one, two, or three CDRs independently selected from Seq. ID No. 7, Seq. ID No. 8 and Seq. ID No. 9, Seq. ID No. 10, Seq. ID No. 11, Seq. ID No. 12, Seq. ID No. 13, Seq. ID No. 597, Seq. ID No. 598, or Seq. ID No. 599. In one embodiment, anti-aP2 monoclonal antibodies and antigen binding agents are provided that comprise a light chain or light chain fragment having a variable region, wherein said variable region comprises Seq. ID No. 7, Seq. ID. No. 8, and at least one CDR selected from Seq. ID. No. 9, Seq. ID No. 10, Seq. ID No. 11, Seq. ID No. 12, Seq. ID No. 13, Seq. ID No. 597, Seq. ID No. 598, or Seq. ID No. 599. Alternatively, one or more of the disclosed and selected CDRs can be altered by substitution of one or more amino acids that do not adversely affect or that improve the properties of the antibody or antigen binding agent, as further described herein. In one embodiment, the selected CDR(s) is/are placed in a human immunoglobulin framework. In one embodiment, the human immunoglobulin framework is further modified or altered to maintain the binding affinity specificity of the grafted CDR region.

One of the unexpected discoveries disclosed herein is that the described antibodies and antigen binding agents do not tightly bind aP2 protein. Typically, antibodies and antigen binding agents are sought that have tight binding affinity (very low KD), as was reported by Miao, et al. (See Background of the Invention). It has been discovered that an antibody or antigen binding agent that binds to aP2 protein in its secreted (non-cytosolic) state with a weaker binding affinity having a KD of about $\geq 10^{-7}$ M, has an improved ability to neutralize secreted aP2 and cause a significant inhibitory effect on aP2-mediated disorders. In certain embodiments, the anti-aP2 monoclonal antibody or antigen binding agent has a KD for human aP2 of between about $10^{-4}$ to $10^{-6}$ M. In other examples, the anti-aP2 monoclonal antibody or antigen binding agent has a KD for human aP2 of about >500 nM, for example, about 500 nM to about 10 μM. In another embodiment, the anti-aP2 monoclonal antibody or antigen binding agent has a KD for human aP2 of about 1 μM to about 7 μM, or 2 μM to about 5 μM. In an alternative embodiment, the anti-aP2 monoclonal antibody has a low binding affinity for mouse aP2 in its native, conformational form, for example, in the ranges specified above.

The inventors have also surprisingly found that mice treated with the antibodies described herein maintained total circulating aP2 levels at a level similar to or slightly lower than that seen in control-treated animals. These findings are in contrast to those observed with higher affinity antibodies, including H3, where treatment of mice with this high affinity antibody leads to a dramatic 10-fold increase in total circulating aP2 levels. The dramatic increase in aP2 levels seen in mice treated with high affinity antibodies may be due to the increased half-life of the aP2 protein, which generally has a short-half life, when complexed with a high-affinity aP2 antibody.

When administered to a host in need thereof, these anti-aP2 antibodies and antigen binding agents neutralize the activity of secreted aP2 and provide lower fasting blood glucose levels, improved systemic glucose metabolism, increased systemic insulin sensitivity, reduced fat mass, liver steatosis, improved serum lipid profiles, and reduced atherogenic plaque formation in a host when compared to anti-aP2 monoclonal antibodies having higher binding affinities. Therefore, the anti-aP2 antibodies and antigen binding agents described herein are particularly useful to treat metabolic disorders including, but not limited to, diabetes (both type 1 and type 2), hyperglycemia, obesity, fatty liver disease, dyslipidemia, polycystic ovary syndrome (POS), a proliferative disorder such as a tumor or neoplasm, (including, but not limited to, for example, transitional bladder cancer, ovarian cancer, and liposarcoma), atherosclerosis, and other cardiovascular disorders by administering an effective amount to a host, typically a human, in need thereof.

Without wishing to be bound by any one theory, it is believed that various tissues contribute to circulating aP2 levels. For example, it is believed that adipose tissue contributes to levels of circulating aP2. In addition, it is believed that other tissues, for example macrophages, contribute to circulating levels of aP2. In one embodiment, a host is administered an anti-aP2 antibody or antigen binding agent described herein to treat an aP2 mediated disorder. In one embodiment, a host is administered an anti-aP2 antibody or antigen binding agent described herein to treat an aP2 mediated disorder wherein the disorder is mediated by adipose tissue-contributed circulating aP2. In one embodiment, a host is administered an anti-aP2 antibody or antigen binding agent described herein to treat an aP2 mediated disorder wherein the disorder is mediate by macrophage-contributed circulating aP2.

In one embodiment, the anti-aP2 antibody or antigen binding agent includes at least one CDR selected from Seq. ID Nos. 7-13 or Seq. ID Nos. 597-599, and at least one CDR selected from CDRH1 (Seq. ID NO. 14), CDRH1 variant 1 (Seq. ID No. 15), CDRH1 variant 2 (Seq. ID No. 600), CDRH2 (Seq. ID No. 16), CDRH2 variant 1 (Seq. ID No. 17), CDRH2 variant 2 (Seq. ID No. 18), CDRH2 variant 3 (Seq. ID No. 601), CDHR3 (Seq. ID No. 19), CDHR3 variant 1 (Seq. ID No. 20), CDRH3 variant 2 (Seq. ID No. 21), or CDRH3 variant 3 (Seq. ID No. 602), wherein the CDR sequences are grafted into a human immunoglobulin framework. In one embodiment, the human immunoglobulin framework is further modified or altered to maintain the binding affinity specificity of the grafted CDR region.

In certain embodiments, the anti-aP2 antibody or antigen binding agent includes at least the light chain variable sequence 909 gL1 (Seq. ID No. 446), the light chain sequence 909 gL1 VL+CL (Seq. ID No. 447), the light chain variable sequence 909 gL10 (Seq. ID No. 448), the light chain sequence 909 gL10 VL+CL (Seq. ID No. 449), the light chain variable sequence 909 gL13 (Seq. ID No. 487), the light chain sequence 909 gL13 VL+CL (Seq. ID No. 489), the light chain variable sequence 909 gL50 (Seq. ID No. 488), the light chain sequence 909 gL50 VL+CL (Seq. ID No. 490), the light chain variable sequence 909 gL54 (Seq. ID No. 450), the light chain sequence 909 gL54 VL+CL (Seq. ID No. 451), the light chain variable sequence 909 gL55 (Seq. ID No. 452) or the light chain sequence 909 gL55 VL+CL (Seq. ID No. 453).

In other embodiments, the anti-aP2 antibody or antigen binding agent includes a light chain variable sequence selected from 909 gL1 (Seq. ID No. 446), 909 gL10 (Seq. ID No. 448), 909 gL13 (Seq. ID No. 487), 909 gL50 (Seq. ID No. 488), 909 gL54 (Seq. ID No. 450), or 909 gL55 (Seq. ID No. 452), and a heavy chain variable sequence selected from 909 gH1 (Seq. ID No. 455), 909 gH14 (Seq. ID No. 457), 909 gH15 (Seq. ID No. 459), 909 gH61 (Seq. ID No. 461), and 909 gH62 (Seq. ID No. 463). For example, the antibody or antigen binding agent can include at least the light chain variable sequence 909 gL1 (Seq. ID No. 446) and the heavy chain variable sequence 909 gH1 (Seq. ID. No. 455). In one embodiment, the anti-aP2 antibody or antigen binding agent includes at least the light chain variable sequence 909 gL10 (Seq. ID No. 448) and the heavy chain variable sequence 909 gH1 (Seq. ID No. 455). In one embodiment, the anti-aP2 antibody or antigen binding agent includes at least the light chain variable sequence 909 gL10 (Seq. ID No. 448) and the heavy chain variable sequence 909 gH15 (Seq. ID No. 459). In one embodiment, the anti-aP2 antibody or antigen binding agent includes at least the light chain variable sequence 909 gL1 (Seq. ID No. 446) and the heavy chain variable sequence 909 gH15 (Seq. ID No. 459). In one embodiment, the anti-aP2 antibody or antigen binding agent includes at least the light chain variable sequence 909 gL13 (Seq. ID No. 487) and the heavy chain variable sequence 909 gH1 (Seq. ID No. 455). In one embodiment, the anti-aP2 antibody or antigen binding agent includes at least the light chain variable sequence 909 gL13 (Seq. ID No. 487) and the heavy chain variable sequence 909 gH15 (Seq. ID No. 459). In one embodiment, the anti-aP2 antibody or antigen binding agent includes at least the light chain variable sequence 909 gL50 (Seq. ID No. 488) and the heavy chain variable sequence 909 gH1 (Seq. ID No. 455). In one embodiment, the anti-aP2 antibody or antigen binding agent includes at least the light chain variable sequence 909 gL50 (Seq. ID No. 488) and the heavy chain variable sequence 909 gH15 (Seq. ID No. 459). In one embodiment, the anti-aP2 antibody or antigen binding agent includes at least the light chain variable sequence 909 gL54 (Seq. ID No. 450) and the heavy chain variable sequence 909 gH1 (Seq. ID No. 455). In one embodiment, the anti-aP2 antibody or antigen binding agent includes at least the light chain variable sequence 909 gL54 (Seq. ID No. 450) and the heavy chain variable sequence 909 gH15 (Seq. ID No. 459). In one embodiment, the anti-aP2 antibody or antigen binding agent includes at least the light chain variable sequence 909 gL55 (Seq. ID No. 452) and the heavy chain variable sequence 909 gH1 (Seq. ID No. 455). In one embodiment, the anti-aP2 antibody or antigen binding agent includes at least the light chain variable sequence 909 gL55 (Seq. ID No. 452) and the heavy chain variable sequence 909 gH15 (Seq. ID No. 459). In one embodiment, the anti-aP2 antibody or antigen binding agent can include at least the light chain variable sequence 909 gL1 (Seq. ID No. 446) and the heavy chain variable sequence 909 gH14 (Seq. ID. No. 457). In one embodiment, the anti-aP2 antibody or antigen binding agent includes at least the light chain variable sequence 909 gL10 (Seq. ID No. 448) and the heavy chain variable sequence 909 gH14 (Seq. ID No. 457). In one embodiment, the anti-aP2 antibody or antigen binding agent includes at least the light chain variable sequence 909 gL13 (Seq. ID No. 487) and the heavy chain variable sequence 909 gH4 (Seq. ID No. 457). In one embodiment, the anti-aP2 antibody or antigen binding agent includes at least the light chain variable sequence 909 gL50 (Seq. ID No. 488) and the heavy chain variable sequence 909 gH4 (Seq. ID No. 457). In one embodiment, the anti-aP2 antibody or antigen binding agent includes at least the light chain variable sequence 909 gL54 (Seq. ID No. 450) and the heavy chain variable sequence 909 gH14 (Seq. ID No. 457). In one embodiment, the anti-aP2 antibody or antigen binding agent includes at least the light chain variable sequence 909 gL55 (Seq. ID No. 452) and the heavy chain variable sequence 909 gH14 (Seq. ID No. 457). In one embodiment, the anti-aP2 antibody or antigen binding agent can include at least the light chain variable sequence 909 gL1 (Seq. ID No. 446) and the heavy chain variable sequence 909 gH61 (Seq. ID. No. 461). In one embodiment, the anti-aP2 antibody or antigen binding agent includes at least the light chain variable sequence 909 gL10 (Seq. ID No. 448) and the heavy chain variable sequence 909 gH61 (Seq. ID No. 461). In one embodiment, the anti-aP2 antibody or antigen binding agent includes at least the light chain variable sequence 909 gL13 (Seq. ID No. 487) and the heavy chain variable sequence 909 gH61 (Seq. ID No. 461). In one embodiment, the anti-aP2 antibody or antigen binding agent includes at least the light chain variable sequence 909 gL50 (Seq. ID No. 488) and the heavy chain variable sequence 909 gH61 (Seq. ID No. 461). In one embodiment, the anti-aP2 antibody or antigen binding agent includes at least the light chain variable sequence 909 gL54 (Seq. ID No. 450) and the heavy chain variable sequence 909 gH61 (Seq. ID No. 461). In one embodiment, the anti-aP2 antibody or antigen binding agent includes at least the light chain variable sequence 909 gL55 (Seq. ID No. 452) and the heavy chain variable sequence 909 gH61 (Seq. ID No. 461). In one embodiment, the anti-aP2 antibody or antigen binding agent can include at least the light chain variable sequence 909 gL1 (Seq. ID No. 446) and the heavy chain variable sequence 909 gH62 (Seq. ID. No. 463). In one embodiment, the anti-aP2 antibody or antigen binding agent includes at least the light chain variable sequence 909 gL10 (Seq. ID No. 448) and the heavy chain variable sequence 909 gH62 (Seq. ID No. 463). In one embodiment, the anti-aP2 antibody or antigen binding agent includes at least the light chain variable sequence 909 gL13 (Seq. ID No. 487) and the heavy chain variable sequence 909 gH62 (Seq. ID No. 463). In one embodiment, the anti-aP2 antibody or antigen binding agent includes at least the light chain variable sequence 909 gL50 (Seq. ID No. 488) and the heavy chain variable sequence 909 gH62 (Seq. ID No. 463). In one embodiment, the anti-aP2 antibody or antigen binding agent includes at least the light chain variable sequence 909 gL54 (Seq. ID No. 450) and the heavy chain variable sequence 909 gH62 (Seq. ID No. 463). In one embodiment, the anti-aP2 antibody or antigen binding agent includes at least the light chain variable sequence 909 gL55 (Seq. ID No. 452) and the heavy chain variable sequence 909 gH62 (Seq. ID No. 463). The anti-aP2 monoclonal antibodies, and where relevant the antigen binding agents, described herein containing the variable light and/or variable heavy chain sequences containing the CDRs described herein may further comprise constant region domains selected having regard to the proposed function of the antibody molecule, and in particular the effector functions which may be required. For example, the constant region domains may be human IgA, IgD, IgE, IgG, or IgM domains. In particular, human IgG constant region domains may be used, especially for example the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. It will be appreciated that sequence variants of these constant region domains may also be used. For example IgG4 molecules in which the serine at position 241 (IgG4P) has been changed to proline as described in Angal et al., Molecular Immunology, 1993, 30 (1), 105-108 may be used, and are contemplated herein.

In one embodiment, the anti-aP2 antibody comprises a light chain variable sequence Rabbit Ab 909 VL region (Seq. ID No. 445), and further optionally comprises a heavy chain variable sequence Rabbit Ab 909 VH region (Seq. ID No. 454).

In one embodiment, a low binding affinity monoclonal anti-aP2 antibody CA33, a rabbit-mouse hybrid anti-aP2 monoclonal antibody, which includes Rabbit 909 VH (Seq. ID No. 454) and 909 VL (Seq. ID No. 445), is described that lowers fasting blood glucose levels, improves systemic glucose metabolism, increases systemic insulin sensitivity and reduces fat mass and liver steatosis in obese mice.

It has been found that CA33 binds to both lipid-bound and lipid-free aP2 at similar affinities (See FIGS. 2H and 2I, respectively). These data suggest that the efficacy of CA33 is not mediated by its binding only apo-aP2 or only aP2 molecules that carry a specific lipid. It has also been found that the CA33 epitope does not overlap with the hinge region (which contains E15, N16, and F17) and it does not appear that CA33 binding alters ligand access to the hydrophobic pocket of aP2. In fact, at neutral pH, paranaric acid binding to aP2 is similar in the presence or absence of CA33, supporting the conclusion that antibody binding to aP2 does not block overall lipid binding (See FIG. 2G).

Furthermore, it has been discovered that exogenous aP2 treatment leads to the disassociation of a novel transcriptional holocomplex composed of Forkhead box protein O1 (FoxO1) and the transcriptional corepressor C-terminal binding protein 2 (CtBP2) in hepatocytes, leading to expression of gluconeogenic genes. In vivo, the FoxO1/CtBP2 interaction is readily detectable in the liver of lean mice, but markedly decreased in the context of obesity, a setting in which the level of circulating aP2 is markedly increased. It is shown herein that administration of recombinant aP2 decreases the FoxO1/CtBP2 interaction while the interaction increases in the setting of aP2 genetic deficiency and antibody-mediated neutralization. It has further been shown herein that CtBP2 overexpression in the liver of obese mice dramatically ameliorates glucose intolerance as well as hepatic steatosis through repression of gluconeogenic and lipogenic gene expression. In one embodiment of the invention, an anti-aP2 antibody is administered for the treatment of a disorder in a host, including a human, associated with the misregulation of the FoxO1/CtBP2 pathway. In one embodiment, improved treatments for FoxO1-mediated disorders or CtBP2-mediated disorders are disclosed in which serum aP2 is targeted and the biological activity of aP2 is neutralized or modulated using a low-binding affinity aP2 monoclonal antibody described herein, wherein the expression level of one or more FoxO1-regulated or CtBP2-regulated genes is reduced. In one embodiment, provided herein is a method of modulating the expression of a FoxO1 and/or CtBP2-regulated gene comprising administering to a host a low-binding affinity aP2 monoclonal antibody described herein. See Jack et al. "C-terminal binding protein: A metabolic sensor implicated in regulating adipogenesis." *Int J Biochem Cell Biol.* 2011 May; 43(5):693-6; Vernochet C, et al. "C/EBPalpha and the corepressors CtBP1 and CtBP2 regulate repression of select visceral white adipose genes during induction of the brown phenotype in white adipocytes by peroxisome proliferator-activated receptor gamma agonists." *Mol Cell Biol.* 2009 September; 29(17):4714-28; Kajimura, S. et al. "Regulation of the brown and white fat gene programs through a PRDM16/CtBP transcriptional complex." *Genes Dev.* 2008 May 15; 22 (10): 1397-409.

Antigen binding agents may be in any form that provides the desired results. As non-limiting examples, the form of the binding agent may include a single chain fragment, Fab fragment, Fab' fragment, F(ab')2 fragment, a scFv, a scAb, single domain light chain, a single domain heavy chain, a synthetic antigen binding agent that includes a naturally occurring or non-naturally occurring linking moiety between two or more fragments (for example a compound that links two or more of the light chain CDRs described herein or a variant thereof with one or more amino acid substitutions), an antigen binding agent conjugated for targeted delivery, as well as any peptide obtained from or derived from such an antibody.

In one aspect, the present invention provides a polynucleotide, such as DNA, encoding an antibody or fragment as described herein, for example as provided in Table 12. Also provided is a host cell comprising said polynucleotide.

Specifically, the invention includes administering an effective amount of an anti-aP2 antibody described herein, or a pharmaceutically acceptable composition thereof, capable of reducing the activity of secreted aP2 (i.e., extracellular aP2) in a body fluid of a host, for example blood or serum, which results in the attenuation of the severity of, for example, aP2 mediated disorders, including but not limited to a metabolic, cardiovascular, inflammatory, liver, or neoplastic disorder or symptom.

In one aspect of the invention, the purified anti-aP2 monoclonal antibody or antigen binding agent binds to human aP2 protein (Seq. ID. No. 1) with a unique pattern of contact points within 3-4 Angstroms.

In one embodiment, the anti-aP2 monoclonal antibody binds human aP2 having the amino acid sequence:

```
                                         (Seq. ID No. 1)
MCDAFVGTWKLVSSENFDDYMKEVGVGFAT RKVAGMAKPN

MIISVNGDVI TIKSESTFKN TEISFILGQE FDEVTADDRK

VKSTITLDGG VLVHVQKWDG KSTTIKRKRE DDKLVVECVM

KGVTSTRVYERA,
``` or a naturally occurring variant thereof. In an alternative embodiment, the anti-aP2 monoclonal antibody binds to a human aP2 protein having an amino acid sequence that is at least 95%, 96%, 97%, 98%, or 99% identical to Seq. ID No. 1. In one embodiment, the anti-aP2 monoclonal antibody binds to a human aP2 protein having an amino acid sequence that has one or more (for example 1, 2, 3 or 4) amino acid substitutions, additions and/or deletions as compared to Seq. ID No. 1.

In one embodiment, the anti-aP2 monoclonal antibody or antigen binding agent binds to an epitope selected from an amino acid sequence underlined in Seq. ID No. 1 above. In one embodiment, the anti-aP2 monoclonal antibody directly interacts with one or more, for example 1, 2, 3, 4, 5, 6, 7, 8, or 9, amino acids bolded in Seq. ID No. 1 above. In one example, the anti-aP2 monoclonal antibody or antigen binding agent binds to an epitope of the human aP2 protein comprising at least one, for example 1, 2, 3, 4, 5, 6, 7, 8, 9, 10 or more, of amino acids 9-17, amino acids 20-28, or amino acids 118-132 of Seq. ID No. 1, and optionally has a KD of at least about $\geq 10^{-7}$ M.

In another example, the anti-aP2 monoclonal antibody or antigen binding agent thereof binds an epitope of human aP2 comprising one or more, for example 1, 2, 3, 4, 5, 6, 7, 8, or 9 or more, amino acid residues selected from 10K, 11L, 12V, 13S, 37A, 38K, 57T, 130E, 132A (bolded in Seq. ID No. 1, above), or an amino acid residue within about 4 angstroms of any of 10K, 11L, 12V, 13S, 37A, 38K, 57T, 130E, and 132A, optionally with a KD for secreted aP2 of about $\geq 10^{-7}$ M.

In one embodiment, the light chain of the antibody binds an epitope of human aP2 comprising one or more, for example 1, 2, 3, 4, 5, 6, 7, 8, or 9 or more, amino acid residues selected from 10K, 11L, 12V, 13S, 37A, 38K, 57T, 130E, or 132A, or an amino acid residue within about 4 angstroms thereof. In one embodiment, the light chain of the antibody binds an epitope of human aP2 comprising one or more, for example 1, 2, 3, 4, 5, 6, 7, 8, or 9 or more, amino acid residues selected from 10K, 11L, 12V, 13S, 37A, 38K, 57T, 130E, or 132A, or an amino acid residue within about 4 angstroms thereof, and has a KD of at least about $\geq 10^{-7}$ M.

In one embodiment, the anti-aP2 monoclonal antibody or antigen binding agent binds to aP2 only through, or primarily through, light chain CDRs. In an alternative embodiment, the anti-aP2 monoclonal antibody or antigen binding agent has light chain CDRs that bind to aP2 with a greater affinity than its heavy chain CDRs bind to aP2. As one example, the antibody or antigen binding agent specifically binds aP2, and does not specifically bind to FABP5/Mal1.

Methods of producing the disclosed anti-aP2 antibodies and antigen binding agents are provided herein as well as methods of conjugating the antibody or fragment to a polymer, such as PEG.

The present disclosure also includes pharmaceutical compositions comprising an effective amount of one of the anti-aP2 antibodies and/or antigen binding agents in combination with a pharmaceutically acceptable carrier. The anti-aP2 monoclonal antibody or antigen binding agent can be administered to the host by any desired route, including intravenous, systemic, topical transdermal, sublingual, buccal, oral, intra-aortal, topical, intranasal, intraocular, or via inhalation. In one embodiment, the anti-aP2 monoclonal antibody or antigen binding agent is administered to the host via controlled release delivery.

A method of preventing or attenuating the severity of an aP2 mediated disorder in a host, such as a human, is presented that includes administering an effective amount of a humanized antibody, for example, an anti-aP2 monoclonal antibody or antigen binding agent described herein, resulting in the reduction or attenuation of the biological activity of secreted aP2. Nonlimiting examples of uses of the described anti-aP2 antibodies and antigen binding agents by administering an effective amount to a host in need thereof include one or a combination of:

(i) Reduction of total cholesterol;
(ii) Reduction of high density lipoprotein (HDL), low density lipoprotein (LDL), very low density lipoprotein (VLDL), and/or triglycerides;
(iii) Reduction of fasting blood glucose levels;
(iv) Reduction of fat mass levels;
(v) Reduction of hepatic glucose production;
(vi) Reduction of fat cell lipolysis;
(vii) Reduction of hyperinsulinemia;
(viii) Reduction of liver steatosis;
(ix) Improvement in glucose metabolism;
(x) Increase in insulin sensitivity; and/or,
(xi) Preventing islet β-cell death, dysfunction, or loss.

Other features and advantages of the invention will be apparent from the following detailed description and claims.

BRIEF DESCRIPTION OF THE DRAWINGS

FIGS. 1-8 are further discussed in Example 1 below.

FIG. 1A is a table listing the binding affinities (KD(M)) of anti-aP2 monoclonal antibodies (CA33, CA13, CA15, CA23, and H3) to human and mouse aP2 as determined by biomolecular interaction analysis, using a Biacore T200 system.

FIG. 1B is a schematic describing the in vivo study design and antibody regimen for the treatment of obese mice (fed a high-fat diet (HFD)) with vehicle or anti-aP2 antibodies. Mice (21 weeks old) were fed HFD for 15 weeks prior to antibody administration (n=10 for each group). Anti-aP2 antibodies were administered by subcutaneous injection at a concentration of 33 mg/kg, twice per week.

FIG. 1C is a bar graph showing plasma insulin levels (ng/ml) at week 0 (open bars) or week 4 (solid bars) in mice treated with vehicle or anti-aP2 monoclonal antibodies CA33, CA13, CA15, CA23, or H3. * p<0.05.

FIG. 1D is bar graph showing blood glucose levels (mg/dl) at week 0 (open bars) or week 4 (solid bars) in obese mice on a high-fat diet (HFD) treated with vehicle or anti-aP2 monoclonal antibodies CA33, CA13, CA15, CA23, or H3. Blood glucose levels were measured after 6 hours of day-time food withdrawal. * p<0.05, ** p<0.01.

FIG. 1E is a line graph showing glucose levels (mg/dl) vs. time (minutes) during a glucose tolerance test (GTT). The test was performed after 2 weeks of treatment in obese mice on HFD with vehicle (diamonds) or anti-aP2 monoclonal antibodies (0.75 g/kg glucose)(CA33; squares)(CA15: triangles). * p<0.05.

FIG. 1F is a line graph showing insulin levels (mg/dl) vs. time (minutes) during an insulin tolerance test (ITT). This test was performed after 3 weeks of treatment in obese mice on HFD with vehicle (diamonds) or anti-aP2 monoclonal antibodies (0.75 IU/kg insulin) (CA33; squares) (CA15; triangles). ** p<0.01.

FIG. 1G is a bar graph showing body weight (g) at week 0 (open bars) or week 4 (solid bars) in mice treated with vehicle or anti-aP2 monoclonal antibodies CA33, CA13, CA15, CA23, or H3. Weight was measured in the fed state. * p<0.05.

FIG. 2A is a bar graph of the signal interaction (nm) as determined by octet analysis for the anti-aP2 antibodies CA33 and H3 against aP2 (black bars) compared to the related proteins FABP3 (gray bars) and FABP5/Mal1 (light gray bars).

FIG. 2B is a bar graph of plasma aP2 levels (ng/ml) as determined by ELISA in HFD-fed mice treated with vehicle, CA33, or H3 for 3 weeks (n=10 mice per group). Mice had been on HFD for 12 weeks before the experiment was initiated. A Western blot to detect aP2 in serum from three mice from each group (vehicle, CA33, or H3) is shown in the inset. ** p<0.01.

FIG. 2C is a table of antibody crossblocking of H3 vs. CA33, CA13, CA15, and CA23 as determined by Biacore analysis. ++=complete blocking; +=partial blocking; -=no crossblocking.

FIG. 2D shows the epitope sequence of aP2 residues involved in the interaction with CA33 and H3, as identified by hydrogen-deuterium exchange mass spectrometry (HDX). Interacting residues are underlined. The indicated interaction of CA33 with first alpha helix and the first beta sheet of aP2 on residues 9-17, 20-28 and 118-132 of Seq. ID. No. 2, which partially overlapped with the aP2 epitope on residues 21-41 of Seq. ID. No. 2 identified for H3.

FIGS. 9-16 are further discussed in Example 2 below.

FIG. 9 is a line graph illustrating diabetes incidence (%) vs. time (weeks of treatment) in the NOD mouse model for Type 1 Diabetes. NOD mice were treated with vehicle (diamonds) or the aP2 monoclonal antibody CA33 (squares).

FIGS. 11A and 11B: NOD aP2$^{+/+}$ and NOD aP2$^{-/-}$ mice were subjected to glucose tolerance test (GTT) (FIG. 11A) and insulin tolerance test (ITT) (FIG. 11B).

FIG. 12A is a bar graph showing insulin (ng/ml/ug DNA) secretion from NOD aP2$^{+/+}$ and NOD aP2$^{-/-}$ mice islets after stimulation with either low or high glucose.

FIGS. 12B and 12C: illustrates bar graphs showing total insulin (ng/ml/ug DNA) content from isolated islets of four (FIG. 12B) and seven (FIG. 12C) week old NOD aP2$^{+/+}$ (left bar) and NOD aP2$^{-/-}$ mice (right bar).

FIG. 13 illustrates the number of islets visible in NOD aP2$^{-/-}$ mice compared to NOD aP2$^{+/+}$ mice following pancreatic dissection.

FIG. 16 is a diagram of an inducible model of Type 1 diabetes in mice (rat insulin promoter-lymphocytic choriomeningitis virus-glycoprotein, or RIP-LCMV-GP, mice). Mice are injected with LCMV, which leads to destruction of β-cells and the development of diabetes.

FIGS. 22-26 are further discussed in Example 3 below.

FIG. 22C is a representative image of an en face pinned aorta from an ApoE knockout mouse fed western diet and treated with vehicle for twelve weeks.

FIG. 22D is a representative image of an en face pinned aorta from an ApoE knockout mouse fed western diet and treated with CA33 (33 mg/kg) for twelve weeks.

FIG. 22E is a representative image of an en face pinned aorta from an ApoE knockout mouse fed western diet and treated with CA15 (33 mg/kg) for twelve weeks.

FIGS. 27-28 are further discussed in Example 4 below.

FIG. 27 provides anti-human aP2 humanized kappa light chain variable region antibody fragments, wherein the 909 sequence (Seq. ID. No. 445) is rabbit variable light chain sequence, and the 909 gL1 (Seq. ID. No. 446), gL10 (Seq. ID. 448), gL13 (Seq. ID. No. 487), gL50 (Seq. ID. No. 488), gL54 (Seq. ID. No. 450), and gL55 (Seq. ID. No. 452) sequences are humanized grafts of 909 variable light chain using IGKV1-17 (Seq. ID. No. 506) human germline as the acceptor framework. The CDRs are shown in bold/underlined, while the applicable donor residues are shown in bold/italic and are highlighted: 2V, 3V, 63K and 70D. The mutation in CDRL3 to remove a Cysteine residue is shown in bold/underlined and is highlighted: 90A.

FIG. 28 provides anti-human aP2 humanized heavy chain variable region antibody fragments, wherein the 909 sequence (Seq. ID. No. 454) is rabbit variable heavy chain sequence, and the 909gH1 Seq. ID. No. 455), gH14 Seq. ID. No. 457), gH15 Seq. ID. No. 459), gH61 (Seq. ID. No. 461), and gH62 (Seq. ID. No. 463) sequences are humanized grafts of 909 variable heavy chain using IGHV4-4 (Seq. ID. No. 481) human germline as the acceptor framework. The CDRs are shown in bold/underlined. The two residue gap in framework 3, in the loop between beta sheet strands D and E, is highlighted in gH1: 75 and 76. Applicable donor residues are shown in bold/italic and are highlighted: 23T, 67F, 71K, 72A, 73S, 74T, 77T, 78V, 79D, 89T, and 91F. The mutation in CDRH2 to remove a Cysteine residue is shown in bold/underlined and is highlighted: 59S. The mutation in CDRH3 to remove a potential Aspartate isomerization site is shown in bold/underlined and is highlighted: 98E. The N-terminal Glutamine residue is replaced with Glutamic acid, and is shown in bold and highlighted: 1E.

FIGS. 29-31 are further discussed in Example 5 below.

FIG. 29 is an illustration representing key contact points between aP2 and a murine derived anti-aP2 antibody. As is shown in the figure, substitution of particular amino acid residues with CDR regions of the heavy and light chains resulted in a reduction in the affinity of the altered antibodies in comparison with the parent antibody H3.

FIG. 30A provides amino acid substitutions for inducing a re

FHRE luciferase activity following CtBP2 knockdown (n=8).

FIG. 36 shows the regulation of the endogenous FoxO1/CtBP2 complex in vivo. FIGS. 36A, 36C, 36E, 36G, and 36J: liver homogenates from the following groups of mice were subjected to co-immunoprecipitaton to assay the endogenous FoxO1/CtBP2 complex. All mice were sacrificed after 4-6 h fasting. The densitometric quantification is shown to the right of each blot; see FIGS. 36B, 36D, 36F, 36H and 36K. FIGS. 36A and 36B: genetically obese ob/ob mice and their control lean mice. FIGS. 36C and 36D: diet-induced obese mice (high fat diet (HFD) for 16 weeks) and their control lean mice (normal chow (NC)). FIGS. 36E and 36F: aP2 knockout (KO) or their control wild-type (WT) mice on normal chow (NC) or high fat diet (HFD) for 16 weeks. FIGS. 36G and 36H: diet-induced obese mice (HFD) treated with monoclonal aP2 antibody (CA33) or vehicle, and control lean mice (NC). FIGS. 36I, 36J, 36K, 36L, and 36M: recombinant aP2 was administered into wild-type lean mice for 5 days. Serum aP2 levels (FIG. 36I) and FoxO1/CtBP2 complex (FIGS. 36J and 36K), gene expression in liver (FIGS. 36L and 36M) were analyzed (n=4).

FIG. 37: CtBP2 gain of function in liver improves glucose tolerance and ameliorates steatosis in obese mice. CtBP2 was overexpressed in the liver of diet-induced obese mice (14 weeks on the diet) by adenoviral transduction. HFD: high fat diet, NC: normal chow. FIGS. 37A and 37B tabulate the measurement of body weights and blood glucose levels, respectively, after overnight fasting (n=4-5). FIGS. 37C, 37D, and 37Q: Dietary induced obese mice transduced with AdGUS or AdCtBP2 were subjected to glucose tolerance test (GTT, FIG. 37C), insulin tolerance test (ITT, FIG. 37D), and pyruvate tolerance test (PTT, FIG. 37Q) (n=10-12). FIGS. 37K, 37L, 37M, 37N, and 37O show Mlxipl/Srebf1c expression (FIGS. 37K and 37L) and lipogenic gene expression (FIGS. 37M, 37N and 37O) in the liver (n=10). Mice were sacrificed after overnight fasting. FIG. 37P is a schematic diagram showing a potential regulatory mechanism. ACSL; acyl-CoA synthetase. Data are expressed as the mean±SEM. *, ** and NS denote $p<0.05$, $p<0.01$ and no significant difference, respectively, determined by Student's t-test.

FIG. 38: cAMP stimuli amplify aP2-induced gluconeogenic gene expression. FIGS. 38A and 38B show the G6pc mRNA and Pck1 mRNA levels, respectively, from when primary hepatocytes were stimulated with or without 50 μg/ml of aP2 in the absence or presence of 2 μM forskolin (fsk) for 3 h (n=4). The y-axis scale is expanded in the inset to show the data in the absence of fsk more clearly. In FIGS. 38C and 38D, primary hepatocytes were treated in the same way as in FIG. 38A with or without PKA inhibitor (H89, 20 μM) (n=4); G6pc mRNA and Pck1 mRNA levels were measured and tabulated. Data are expressed as the mean±SEM. ** denotes $p<0.01$ determined by Student's t-test.

Figure 32A:
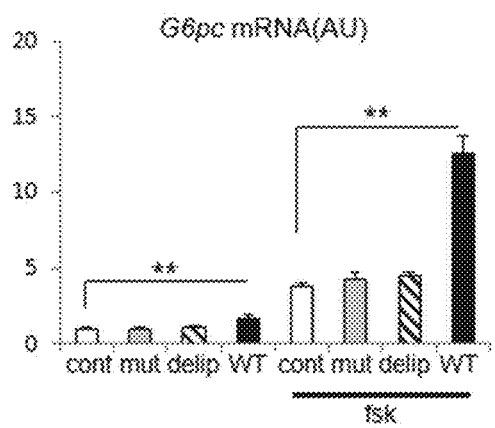
Figure 32B:
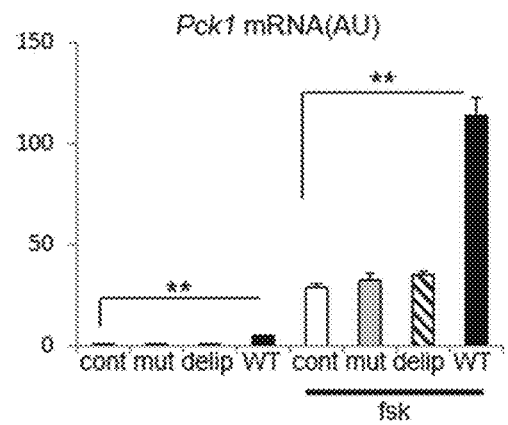
Figure 32C:
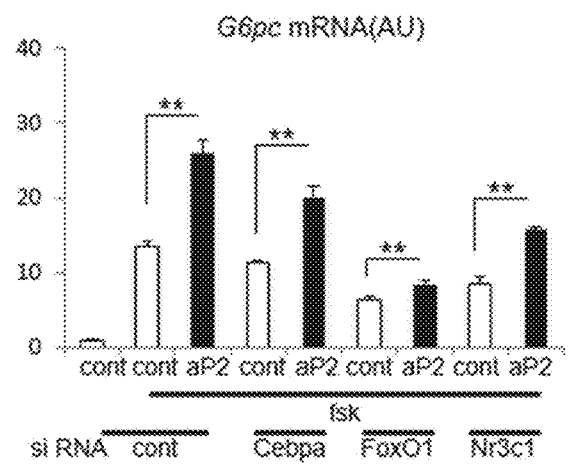

FIG. 39 shows the screening of transcription factor(s) responsible for aP2-mediated upregulation of gluconeogenic genes. FIGS. 39A, 39B and 39C show the knockdown efficiency at the mRNA level, corresponding to the experiment shown in FIG. 32C (n=4). FIGS. 39D, 39E, 39F and 39G show the screening of the transcription factor(s) responsible for aP2-dependent upregulation of gluconeogenic genes. Primary hepatocytes were treated in the same way as FIG. 32A after knockdown of Hif1a, Ppargc1a or Stat3 (n=4). FIG. 39H shows Foxo1 expression levels as in FIG. 32 (n=4). Data are expressed as the mean±SEM. * and ** denote $p<0.05$ and $p<0.01$, respectively, determined by Student's t-test.

FIG. 40: CtBP2-dependent transcriptional activation by aP2. FIGS. 40A, 40B, 40C and 40D show the knockdown efficiency at mRNA and protein levels corresponding to FIG. 34 (n=4). FIGS. 40E, 40F and 40G show the gluconeogenic gene expression in primary hepatocytes after adenoviral mediated knockdown of HNF4α (n=4). Gene expression profiles for G6pc and Pck1 are shown in FIGS. 40E and 40F, respectively, and knockdown efficiency at protein levels is shown in FIG. 40G. Data are expressed as the mean±SEM. * and ** denote $p<0.05$ and $p<0.01$, respectively, determined by Student's t-test.

FIG. 41: Characterization of the FoxO1/CtBP complex. FIGS. 41A and 41B show the results of mutagenesis studies for FoxO1/CtBP1 interaction. HEK293 cells transfected with wild-type FLAG FoxO1 (WT) or mutant FoxO1 (Mut: PSDL>PSAS, Δpsdl: PxDL motif deletion) along with CtBP1 expression plasmid were lysed and subjected to co-immunoprecipitation. FIG. 41C shows the results of incubating primary hepatocytes with 50 μg/ml aP2 in the presence or absence of forskolin (fsk, 2 μM) for 2 h and the native FoxO1/CtBP2 complex was immunoprecipitated. FIG. 41D shows the cellular lactate/pyruvate ratio. Primary hepatocytes were treated as in FIG. 33E. FIG. 41E shows immunocytochemistry corresponding to FIG. 34L. FIG. 41F shows levels of phosphorylation and acetylation of FoxO1. Primary hepatocytes were treated with forskolin (fsk, 2 μM) and/or 50 μg/ml aP2 for 30 min.

Figure 42:
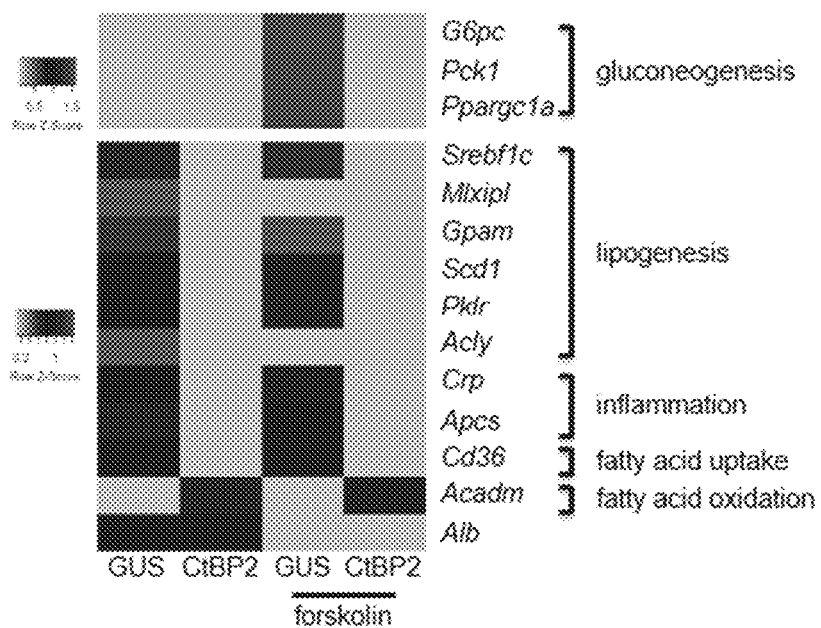
Figures 43A, 43B, 43C:
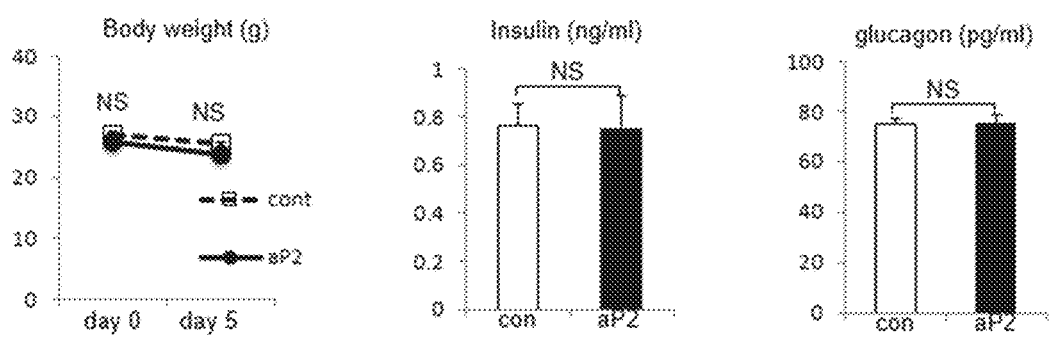
Figure 43D:
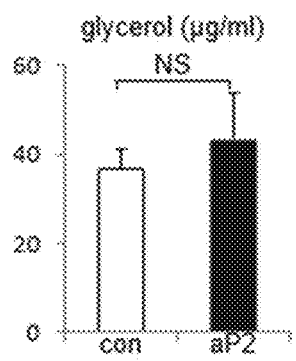
Figure 43E:
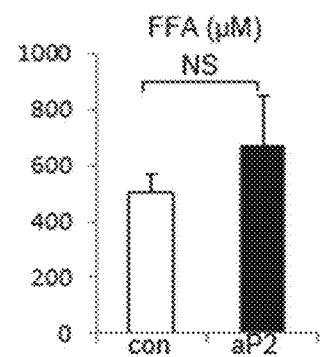
Figure 43F:
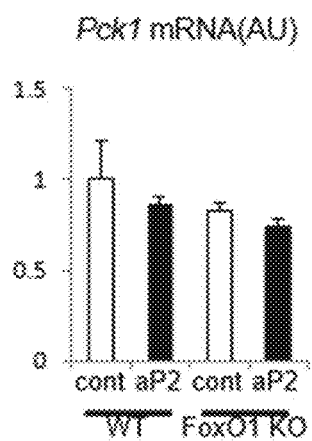
Figure 43G:
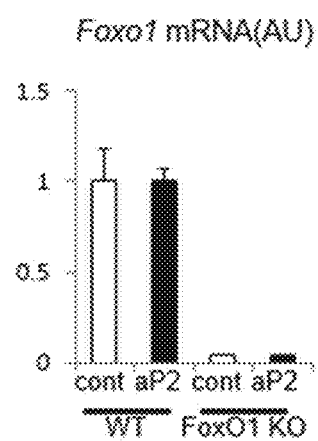

FIG. 42 shows the effect of CtBP2 overexpression on the expression of particular genes. Primary hepatocytes were treated as in FIG. 35D and the gene expression profile was analyzed.

FIG. 43 illustrates the results of the in vivo administration of recombinant aP2. Recombinant aP2 was administered into wild-type lean mice for 5 days (n=4). FIGS. 43A, 43B, 43C, 43D and 43E show results for body weights before (day 0) and after intraperitoneal injections (day 5) of aP2, serum levels of insulin, glucagon, glycerol, and free fatty acids (FFA), respectively. FIGS. 43F and 43G show the mRNA levels for Pck1 and Foxo1, respectively, in wild-type or liver specific FoxO1 KO mice treated with recombinant aP2 (n=7-8). Data are expressed as the mean±SEM. NS denotes no significant difference determined by Student's t-test.

Figure 44A:
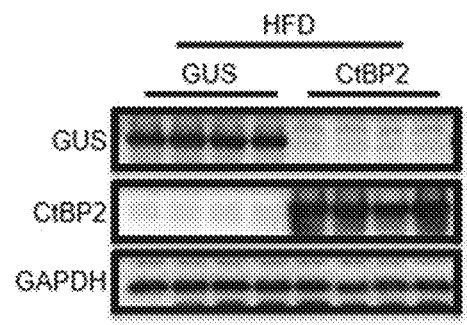
Figure 44B:
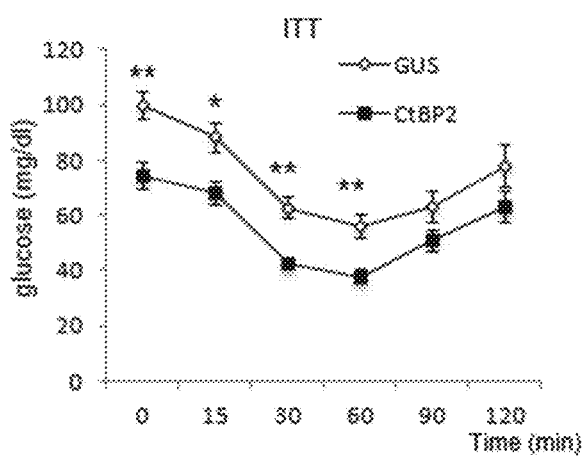
Figure 44C:
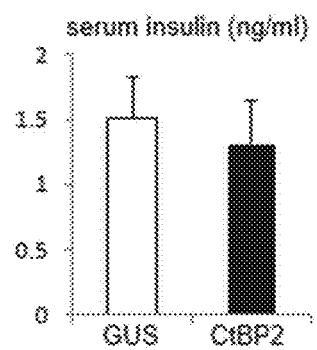

FIG. 44: CtBP2 overexpression in vivo. FIG. 44A illustrates the protein levels of overexpression of GUS and CtBP2 in liver. FIG. 44B illustrates the blood glucose levels without normalization to the baseline in the ITT study (FIG. 37D, n=10-12). FIG. 44C shows the serum insulin levels in GUS or CtBP2 overexpressed liver. Data are expressed as the mean±SEM. * and ** denote p<0.05 and p<0.01, respectively, determined by Student's t-test.

FIG. 45: Involvement of CtBP2 in the pathogenesis of hepatic steatosis. FIGS. 45A, 45B, 45C, 45D, 45E, and 45F show the effect of CtBP2 overexpression on lipogenic gene expression in wild-type primary hepatocytes (FIGS. 45A, 45B, 45C, and 45D, n=4) or FoxO1 knockout hepatocytes (FIGS. 45E and 45F, n=5). FIGS. 45G, 45H, 45I, and 45J show results from liver samples analyzed after 14 days of Ad/shCtBP2 transduction in wild-type lean mice. FIG. 45G shows representative Hematoxylin and Eosin stained liver sections. FIG. 45H shows liver triglyceride content (n=6). FIGS. 45I and 45J show liver Stearyol-CoA desaturase-1 (Scd1) and Fatty acid synthase (Fasn) expression (n=6), respectively. Mice were sacrificed after overnight fasting. Data are expressed as the mean±SEM. * and ** denote p<0.05 and p<0.01, respectively, determined by Student's t-test.

Figure 46A:
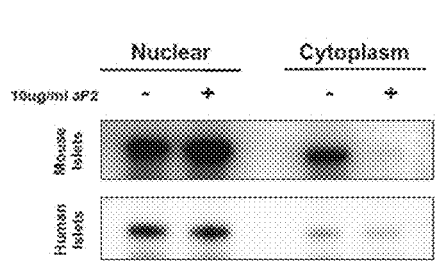
Figure 46B:
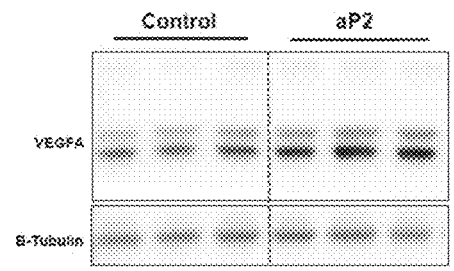
Figure 46C:
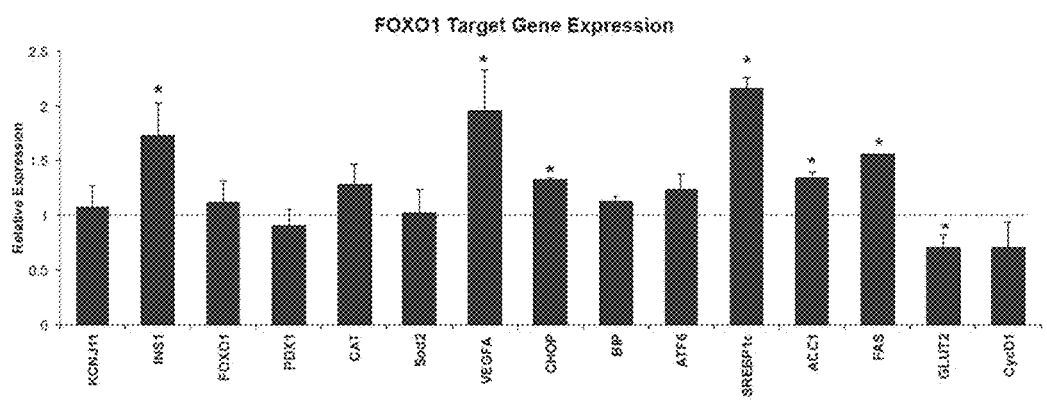

FIG. 46: Illustrates that the addition of recombinant aP2 activates FOXO1 translocation and activity. FIG. 46A illustrates nuclear translocation of FOXO1 in mouse and human islets treated with 10 ug/ml aP2 for 20 minutes (N=3 mouse islets, N=1 human islets). FIG. 46B illustrates gene expression changes of FOXO1 target genes in INS1 cells treated with 10 ug/ml aP2 for 24 hrs (N=4/group). FIG. 46C illustrates validation of change in FOXO1 target gene expression showing increased VEGFA protein after 24 hr of 10 ug/ml aP2 treatment (N=3/group).

Figure 47:
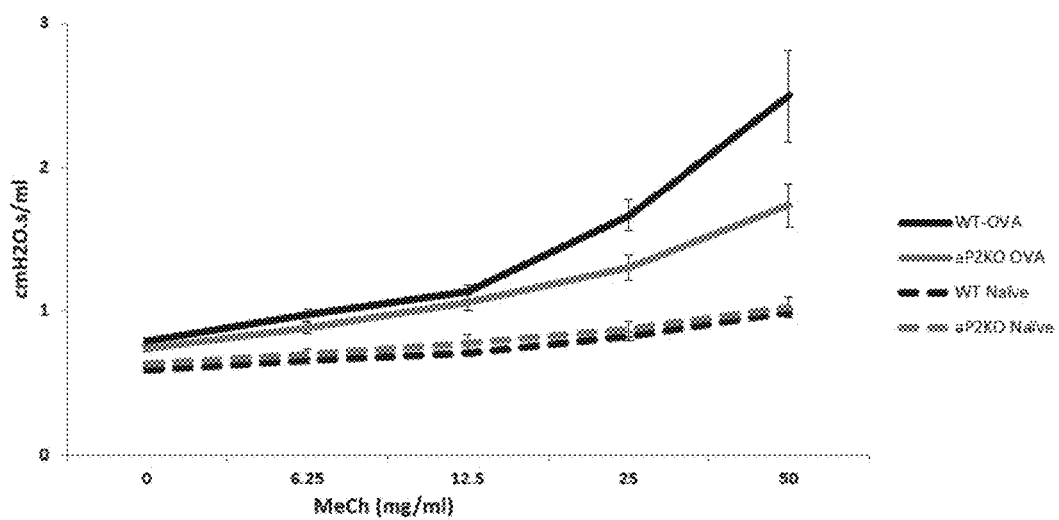

FIG. 47 is a line graph of airway resistance (cmH2O·s/ml) vs. methacholine (mg/ml) during a methacholine challenge test in wild type and aP2 knockout mice treated with either ovalbumin or vehicle.

DETAILED DESCRIPTION OF THE INVENTION

Anti-aP2 monoclonal antibodies and antigen binding agents are provided that have superior and unexpected activity for the treatment of aP2-mediated disorders. For example, anti-aP2 monoclonal antibodies and antigen binding agents are provided that comprise a light chain or light chain fragment having a variable region, wherein said variable region comprises one, two, or three CDRs independently selected from Seq. ID No. 7, Seq. ID No. 8 and Seq. ID No. 9, Seq. ID No. 10, Seq. ID No. 11, Seq. ID No. 12, and Seq. ID No. 13. Alternatively, one or more of the disclosed and selected CDRs can be altered by substitution of one or more amino acids that do not adversely affect or that improve the properties of the antibody or antigen binding agent, as further described herein. In one embodiment, the selected CDR(s) is/are placed in a human immunoglobulin framework. In one embodiment, the human immunoglobulin framework is further modified or altered to maintain the binding affinity specificity of the grafted CDR region.

One of the unexpected discoveries disclosed herein is that the described antibodies and antigen binding agents do not tightly bind aP2 protein. Typically, antibodies and other antigen binding agents are sought that have tight binding affinity (very low KD), as was reported by Miao, et al. (See Background of the Invention).

Therefore, in another embodiment, it has been discovered that an antibody or antigen binding agent that binds to aP2 protein in its secreted (non-cytosolic) state with a weaker binding *▯ affinity of KD about ≥$10^{-7}$ M, has an improved ability to neutralize secreted aP2 and cause a significant inhibitory effect on aP2-mediated disorders when provided in an effective amount to a host in need thereof. Furthermore, it has been discovered that the use of a low-affinity binding anti-aP2 antibody reduces the undesirable effects seen with the use of high affinity anti-aP2 antibodies, for example, weight gain and increased aP2 serum levels.

The anti-aP2 antibodies and antigen binding agents of the present invention can alternatively be described by contact points between the antibody or antigen binding agent with the epitope(s) of the aP2 protein. aP2 is known to have a discontinuous epitope, in which the amino acids are in close proximity in the folded protein but not close when the protein is unfolded or stretched out (see WO 2010/102171). Thus, in one embodiment, the anti-aP2 monoclonal antibody or antigen binding agent thereof binds an epitope of human aP2 comprising one or more, for example 1, 2, 3, 4, 5, 6, 7, 8, or 9, amino acid residues selected from 10K, 11L, 12V, 13S, 37A, 38K, 57T, 130E, 132A (bolded in Seq. ID No. 1, above), or an amino acid residue within about 3 or 4 angstroms of any of 10K, 11L, 12V, 13S, 37A, 38K, 57T, 130E, and 132A, optionally with a KD for secreted aP2 of about ≥$10^{-7}$ M. In a particular embodiment, the antibody has contact with each of these amino acids within a 3 or 4 Angstrom range. In another embodiment, the antibody or antigen binding agent of the present invention has 3 or 4 Angstrom range contact with at least 6, 7, or 8 of the listed amino acid residues.

In one embodiment, the anti-aP2 monoclonal antibody or antigen binding agent binds to aP2 only through, or primarily through, light chain complementarity determining regions (CDRs). In an alternative embodiment, the anti-aP2 monoclonal antibody or antigen binding agent has light chain CDRs that bind to aP2 with a greater affinity than its heavy chain CDRs bind to aP2. As one example, the antibody or antigen binding agent specifically binds aP2, and does not specifically bind to FABP5/Mal1.

When administered to a host in need thereof, these anti-aP2 antibodies and antigen binding agents neutralize the activity of aP2 and provide lower fasting blood glucose levels, improved systemic glucose metabolism, increased systemic insulin sensitivity, reduced fat mass, liver steatosis, improved serum lipid profiles, and/or reduced atherogenic plaque formation in a host when compared to anti-aP2 monoclonal antibodies having higher binding affinities. Therefore, the anti-aP2 antibodies and antigen binding agents described herein are particularly useful to treat metabolic disorders including, but not limited to, diabetes (both type 1 and type 2), hyperglycemia, obesity, fatty liver disease, dyslipidemia, polycystic ovary syndrome (POS), a proliferative disorder such as a tumor or neoplasm, (including, for example, transitional bladder cancer, ovarian cancer and liposarcoma), atherosclerosis and other cardiovascular disorders by administering an effective amount to a host, typically a human, in need thereof.

The present invention thus provides at least the following:
(a) A monoclonal anti-aP2 antibody or antigenic binding agent, as described herein, or a described variant or conjugate thereof.
(b) A humanized monoclonal anti-aP2 antibody or antigenic binding agent, as described herein, or a described variant or conjugate thereof.
(c) A monoclonal anti-aP2 antibody or antigenic binding agent, as described herein, or a described variant or conjugate thereof, wherein the antibody or antibody conjugate is characterized by at least one of:
  i. Structural inclusion of one or more CDRs described in Seq. IDs 7-13 or a variant thereof with amino acid substitutions that do not adversely affect the binding properties of the CDR region as described in Seq. IDs 7-13;
ii. KD binding affinity for human aP2 of ≥10$^{-7}$ M; and/or iii. Contact points with a human or mouse aP2 protein within 3 or 4 Angstroms as further specified herein.
(d) A monoclonal anti-aP2 antibody or antigenic binding agent, as described herein, or a described variant or conjugate thereof for use to treat a host, and in particular a human, with an aP2-mediated disorder.
(e) Use of a monoclonal anti-aP2 antibody or antigenic binding agent, as described herein, or a variant or conjugate thereof, to treat a host, and in particular a human, with an aP2-mediated disorder.
(f) Use of a monoclonal anti-aP2 antibody or antigenic binding agent, as described herein, or a variant or conjugate thereof, in the manufacture of a medicament to treat a host, and in particular a human, with an aP2-mediated disorder.
(g) A process for manufacturing a medicament intended for the therapeutic use in treating an aP2-mediated disorder, characterized in that a monoclonal anti-aP2 antibody or antigenic binding agent, as described herein, or a variant or conjugate thereof is used in the manufacture.
(h) A pharmaceutical composition that includes an effective amount of a monoclonal anti-aP2 antibody or antigenic binding agent, as described herein, or a described variant or conjugate thereof.

General Definitions

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics, and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques may be performed according to manufacturer's specifications, as commonly accomplished in the art or as described herein. The nomenclatures used in connection with, and the laboratory procedures and techniques of, analytical chemistry, synthetic organic chemistry, and medicinal, and pharmaceutical chemistry described herein are those well known and commonly used in the art. Standard techniques are used for chemical syntheses, chemical analyses, pharmaceutical preparation, formulation, and delivery, and treatment of patients.

That the present invention may be more readily understood, selected terms are defined below.

The term "host" as used herein, typically refers to a human subject, and in particular where a human or humanized framework is used as an acceptor structure. Where another host is treated, it is understood by those of skill in the art that the antibody or antigen binding agent may need to be tailored to that host to avoid rejection or to make more compatible. It is known how to use the CDRs in the present invention and engineer them into the proper framework or peptide sequence for desired delivery and function for a range of hosts. Other hosts may include other mammals or vertebrate species. The term "host," therefore, can alternatively refer to animals such as mice, monkeys, dogs, pigs, rabbits, domesticated swine (pigs and hogs), ruminants, equine, poultry, felines, murines, bovines, canines, and the like, where the antibody or antigen binding agent, if necessary is suitably designed for compatibility with the host.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments, and polypeptide analogs of a protein sequence. A polypeptide may be monomeric or polymeric.

The term "recovering" as used herein, refers to the process of rendering a chemical species such as a polypeptide substantially free of naturally associated components by isolation, e.g., using protein purification techniques well known in the art.

The term "human aP2 protein" or "human FABP4/aP2 protein", as used herein refers to the protein encoded by Seq. ID. No. 1, and natural variants thereof, as described by Baxa, C. A., Sha, R. S., Buelt, M. K., Smith, A. J., Matarese, V., Chinander, L. L., Boundy, K. L., Bernlohr, A. Human adipocyte lipid-binding protein: purification of the protein and cloning of its complementary DNA. Biochemistry 28: 8683-8690, 1989.

The term "mouse aP2 protein" or "mouse FAB4P/aP2 protein", as used herein, refers to the protein encoded by Seq. ID. No. 2, and natural variants thereof. The mouse protein is registered in Swiss-Prot under the number P04117.

The terms "specific binding" or "specifically binding", as used herein, in reference to the interaction of an antibody, a protein, or a peptide with a second chemical species, mean that the interaction is dependent upon the presence of a particular structure (e.g., an "antigenic determinant" or "epitope" as defined below) on the chemical species, for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains at least some portion of the epitope binding features of an Ig molecule allowing it to specifically bind to aP2. Such mutant, variant, or derivative antibody formats are known in the art and described below. Nonlimiting embodiments of which are discussed below. An antibody is said to be "capable of binding" a molecule if it is capable of specifically reacting with the molecule to thereby bind the molecule to the antibody.

A "monoclonal antibody" as used herein is intended to refer to a preparation of antibody molecules, which share a common heavy chain and common light chain amino acid sequence, or any functional fragment, mutant, variant, or derivation thereof which retains at least the light chain epitope binding features of an Ig molecule, in contrast with "polyclonal" antibody preparations that contain a mixture of different antibodies. Monoclonal antibodies can be generated by several known technologies like phage, bacteria, yeast or ribosomal display, as well as classical methods exemplified by hybridoma-derived antibodies (e.g., an antibody secreted by a hybridoma prepared by hybridoma technology, such as the standard Kohler and Milstein hybridoma methodology ((1975) Nature 256:495-497).

In a full-length antibody, each heavy chain is comprised of a heavy chain variable region (abbreviated herein as HCVR or VH) and a heavy chain constant region (CH). The heavy chain constant region is comprised of four domains—either CH1, Hinge, CH2, and CH3 (heavy chains γ, α and δ), or CH1, CH2, CH3, and CH4 (heavy chains μ and ε). Each light chain is comprised of a light chain variable region (abbreviated herein as LCVR or VL) and a light chain constant region (CL). The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The term "antigen binding agent" or "antigenic binding agent" as used herein, refers to one or more fragments or portions of an antibody that retain the ability to specifically bind to an antigen (e.g., aP2), or synthetic modifications of antibody fragments that retain the desired binding ability to the antigen. It has been shown that the antigen-binding function of an antibody can be performed by fragments or certain portions of a full-length antibody, or modifications thereof. Embodiments include bispecific, dual specific and multi-specific formats which may specifically bind to two or more different antigens or to several epitopes or discontinuous epitope regions of an antigen. Nonlimiting examples of antigen binding agents include (i) a Fab fragment, a monovalent fragment consisting of the VL, VH, CL, and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546, Winter et al., PCT publication WO 90/05144 A1 herein incorporated by reference), which comprises a single variable domain; (vi) an isolated complementarity determining region (CDR), (vii) fusions of antibody fragments such as those that are immunoglobulin in character, for example, diabodies, scab, bispecific, triabody, Fab-Fv, Fab-Fv-Fv, tribody, (Fab-Fv)2-Fc, and (viii) antibody portions such as CDRs or antibody loops grafted onto non-immunoglobulin frameworks such as fibronectin or leucine zippers (see Binz et al. (2005) Nat. Biotech. 23:1257-1268, incorporated herein). Furthermore, although the two domains of the Fv fragment, VL and VH, are coded for by separate genes, they can be joined, using recombinant or other methods, by a synthetic or naturally occurring linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term antigen binding agent. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5).

The term "antibody construct" as used herein refers to a polypeptide comprising one or more of the antigen binding portions of the invention linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, P., et al. (1993) Proc. Natl. Acad. Sci. USA 90:6444-6448; Poljak, R. J., et al. (1994) Structure 2:1121-1123). An immunoglobulin constant domain refers to a heavy or light chain constant domain, for example a human IgA, IgD, IgE, IgG or IgM constant domains. Heavy chain and light chain constant domain amino acid sequences are known in the art. Non-limiting examples of Ig heavy chain γ1 constant region and Ig light chain λ and κ chains are provided for in Tables 8 and 6, respectively.

Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds aP2 is substantially free of antibodies that specifically bind antigens other than aP2). An isolated antibody that specifically binds, for example, human aP2 may, however, have cross-reactivity to other antigens, such as aP2 molecules from other species. Moreover, an isolated antibody may be substantially free of other cellular material and/or chemicals.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having human heavy and light chain variable regions in which one or more of the human CDRs (e.g., CDR3) has been replaced with murine CDR sequences.

The terms "Kabat numbering", "Kabat definitions" and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) *Ann. NY Acad, Sci.* 190:382-391 and, Kabat, E. A., et al. (1991) *Sequences of Proteins of Immunological Interest, Fifth Edition*, U.S. Department of Health and Human Services, NIH Publication No. 91-3242). For the heavy chain variable region, the hypervariable region ranges from amino acid positions 31-35 (CDR-H1), residues 50-65 (CDR-H2) and residues 95-102 (CDR-H3) according to the Kabat numbering system. However, according to Chothia (Chothia et al., (1987) J. Mol. Biol., 196, 901-917 (1987)), the loop equivalent to CDR-H1 extends from residue 26 to residue 32. Thus unless indicated otherwise "CDR-H1" as employed herein is intended to refer to residues 26 to 35, as described by a combination of the Kabat numbering system and Chothia's topological loop definition. For the light chain variable region, the hypervariable region ranges from amino acid positions 24 to 34 for CDRL1, amino acid positions 50 to 56 for CDRL2, and amino acid positions 89 to 97 for CDRL3.

As used herein, the terms "acceptor" and "acceptor antibody" refer to the antibody or nucleic acid sequence providing or encoding at least 80%, at least 85%, at least 90%, at least 95%, at least 98% or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "CDR" refers to the complementarity determining region within antibody variable sequences. There are three CDRs in each of the variable regions of the heavy chain and the light chain, which are designated CDRH1, CDRH2 and CDRH3 for the heavy chain CDRs, and CDRL1, CDRL2, and CDRL3 for the light chain CDRs. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia, or a mixture thereof, defined CDRs.

As used herein, the term "canonical" residue refers to a residue in a CDR or framework that defines a particular canonical CDR structure as defined by Chothia et al. (J. Mol. Biol. 196:901-907 (1987), Chothia et al., J. Mol. Biol. 227:799 (1992), both are incorporated herein by reference). According to Chothia et al., critical portions of the CDRs of many antibodies have nearly identical peptide backbone conformations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In a preferred embodiment, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

Human heavy chain and light chain acceptor sequences are known in the art. In one embodiment of the invention the human light chain and heavy chain acceptor sequences are selected from the sequences described in Tables 4, 5, and 7. Different combinations for human framework sequences FR1 to FR4 are described in said tables.

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. See, e.g., Shapiro et al., Crit. Rev. Immunol. 22(3): 183-200 (2002); Marchalonis et al., Adv Exp Med Biol. 484:13-30 (2001). One of the advantages provided by various embodiments of the present invention takes advantage of the recognition that germline antibody genes are more likely than mature antibody genes to conserve essential amino acid sequence structures characteristic of individuals in the species, hence less likely to be recognized as from a foreign source when used therapeutically in that species.

As used herein, the term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

The term "humanized antibody" generally refers to antibodies which comprise heavy and light chain variable region sequences from a non-human species (e.g., a rabbit, mouse, etc.) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. Another type of humanized antibody is a CDR-grafted antibody, in which at least one non-human CDR is inserted into a human framework. The latter is typically the focus of the present invention.

In particular, the term "humanized antibody" as used herein, is an antibody or a variant, derivative, analog or fragment thereof which immuno-specifically binds to an antigen of interest and which comprises a framework (FR) region having substantially the amino acid sequence of a human antibody and a complementarity determining region (CDR) having substantially the amino acid sequence of a non-human antibody. As used herein, the term "substantially" in the context of a CDR refers to a CDR having an amino acid sequence at least 50, 55, 60, 65, 70, 75 or 80%, preferably at least 85%, at least 90%, at least 95%, at least 98% or at least 99% identical to the amino acid sequence of a non-human antibody CDR. In one embodiment, the humanized antibody has a CDR region having one or more (for example 1, 2, 3 or 4) amino acid substitutions, additions and/or deletions in comparison to the non-human antibody CDR. Further, the non-human CDR can be engineered to be more "human-like" or compatible with the human body, using known techniques. A humanized antibody comprises substantially all of at least one, and typically two, variable domains (Fab, Fab', F(ab')2, F(ab')c, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, and CH3, or CH1, CH2, CH3, and CH4 of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgY, IgM, IgG, IgD, IgA and IgE, and any isotype, including without limitation IgA1, IgA2, IgG1, IgG2, IgG3 and IgG4. The humanized antibody may comprise sequences from more than one class or isotype, and particular constant domains may be selected to optimize desired effector functions using techniques well known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond exactly to either the donor antibody or the consensus framework. In a preferred embodiment, such mutations, however, will not be extensive. Usually, at least 50, 55, 60, 65, 70, 75 or 80%, preferably at least 85%, more preferably at least 90%, and most preferably at least 95%, 98% or 99% of the humanized antibody residues will correspond to those of the parental FR and CDR sequences. In one embodiment, one or more (for example 1, 2, 3 or 4) amino acid substitutions, additions and/or deletions may be present in the humanized antibody compared to the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

As used herein, "Vernier" zone refers to a subset of framework residues that may adjust CDR structure and fine-tune the fit to antigen as described by Foote and Winter (1992, J. Mol. Biol. 224:487-499, which is incorporated herein by reference). Vernier zone residues form a layer underlying the CDRs and may impact on the structure of CDRs and the affinity of the antibody.

As used herein, the term "neutralizing" refers to neutralization of biological activity of aP2 protein, for example, secreted aP2 protein, when an antibody described herein specifically binds the aP2 protein. Neutralizing may be the result of different ways of binding of said antibody to aP2.

Preferably a neutralizing antibody is an antibody whose binding to aP2 results in neutralization of a biological activity of aP2. Preferably the neutralizing binding protein binds aP2 and decreases a biologically activity of aP2 by at least about 5%, 10%, 15%, 20%, 25%, 30%, 35%, 40%, 50%, 60%, 80%, 85%, or more. Neutralization of a biological activity of aP2 by a neutralizing antibody can be assessed by measuring one or more indicators of aP2 biological activity described herein.

A "neutralizing monoclonal antibody" as used herein is intended to refer to a preparation of antibody molecules, which upon binding to aP2 are able to inhibit or reduce the biological activity of aP2 either partially or fully.

As used herein, the term "attenuation," "attenuate," and the like refers to the lessening or reduction in the severity of a symptom or condition caused by elevated serum aP2 levels.

The term "epitope" or "antigenic determinant" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

The term "$K_{on}$", as used herein, is intended to refer to the on rate constant for association of an antibody to the antigen to form the antibody/antigen complex as is known in the art.

The term "$K_{off}$", as used herein, is intended to refer to the off rate constant for dissociation of an antibody from the antibody/antigen complex as is known in the art.

The term "$K_d$", as used herein, is intended to refer to the dissociation constant of a particular antibody-antigen interaction as is known in the art.

The strength, or affinity of immunological binding interactions can be expressed in terms of the dissociation constant ($K_d$) of the interaction, wherein a smaller $k_d$ represents a greater or higher affinity. Immunological binding properties of selected polypeptides can be quantified using methods well known in the art. One such method involves measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ("$K_{on}$") and the "off rate constant" ("$K_{off}$") can be determined by calculation of the concentrations and the actual rates of association and dissociation. (Nature 361:186-87 (1993)). The ratio of $K_{off}/K_{on}$ enables the cancellation of all parameters not related to affinity, and is equal to the dissociation constant $K_d$. Davies et al. (1990) Annual Rev Biochem 59:439-473.

The term "KD", as used herein, is intended to refer to the Affinity (or Affinity constant), which is a measure of the rate of binding (association and dissociation) between the antibody and antigen, determining the intrinsic binding strength of the antibody binding reaction.

The term "antibody conjugate" refers to a binding protein, such as an antibody or antibody fragment or binding portion thereof, chemically linked to a second chemical moiety, such as a therapeutic or cytotoxic agent. The term "agent" is used herein to denote a chemical compound, a mixture of chemical compounds, a biological macromolecule, or an extract made from biological materials.

The terms "crystal", and "crystallized" as used herein, refer to an antibody, or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and Proteins, a Practical Approach, 2nd ea., pp. 20 1-16, Oxford University Press, New York, N.Y., (1999)."

The term "polynucleotide" as referred to herein means a polymeric form of two or more nucleotides, either ribonucleotides or deoxynucleotides or a modified form of either type of nucleotide. The term includes single and double stranded forms of DNA but preferably is double-stranded DNA.

The term "isolated polynucleotide" as used herein means a polynucleotide (e.g., of genomic, cDNA, or synthetic origin, or some combination thereof) that, by virtue of its origin, the "isolated polynucleotide" is not associated with all or a portion of a polynucleotide with which the "isolated polynucleotide" is found in nature; is operably linked to a polynucleotide that it is not linked to in nature; or does not occur in nature as part of a larger sequence.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences, which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences.

"Transformation," as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells, which transiently express the inserted DNA or RNA for limited periods of time.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the Kingdoms of life. Preferred eukaryotic cells include protist, fungal, plant and animal cells. Most preferably host cells include but are not limited to the prokaryotic cell line *E. coli*; mammalian cell lines CHO, HEK 293 and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

As used herein, the term "effective amount" refers to the amount of a therapy which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g. prophylactic or therapeutic agent).

aP2 Protein

Fatty acid-binding proteins (FABPs) are members of the superfamily of lipid-binding proteins (LBP). Nine different FABPs have to date been identified, each showing relative tissue enrichment: L (liver), I (intestinal), H (muscle and heart), A (adipocyte), E (epidermal), Il (ileal), B (brain), M (myelin) and T (testis). The primary role of all the FABP family members is regulation of fatty acid uptake and intracellular transport. The structure of all FABPs is similar—the basic motif characterizing these proteins is β-barrel, and a single ligand (e.g. a fatty acid, cholesterol, or retinoid) is bound in its internal water-filled cavity.

The adipocyte fatty acid-binding protein aP2 regulates systemic glucose and lipid metabolism, and has been implicated in the pathology of many immunometabolic diseases, such as diabetes and atherosclerosis. While aP2 has classically been considered a cytosolic protein, it has been found to be an active adipokine that contributes to hyperglycemia by promoting hepatic gluconeogenesis. Serum aP2 levels have been found to be markedly elevated in mouse and human obesity.

The human aP2 protein is a 14.7 kDa intracellular and extracellular (secreted) lipid binding protein that consists of 132 amino acids comprising the amino acid sequence (Seq. ID No. 1) of Table 1. The cDNA sequence of human aP2 was previously described in Baxa, C. A., Sha, R. S., Buelt, M. K., Smith, A. J., Matarese, V., Chinander, L. L., Boundy, K. L., Bernlohr, A. Human adipocyte lipid-binding protein: purification of the protein and cloning of its complementary DNA. Biochemistry 28: 8683-8690, 1989, and is provided in Seq. ID No. 5. The human protein is registered in Swiss-Prot under the number P15090.

The mouse aP2 protein sequence comprises the amino acid sequence of Seq. ID No. 2 of Table 1. The cDNA sequence of mouse aP2 is provided in Seq. ID No. 6. The mouse protein is registered in Swiss-Prot under the number P04117.

Both the human and mouse aP2 protein include at least two major conserved domains: an 11 amino acid nuclear localization signal (aa22-32: kevgvgfatrk (Seq. ID No. 3)); and a three amino acid fatty acid binding region (aa127-129: rvy (Seq. ID No. 4)).

TABLE 1 aP2 Protein and cDNA Sequences

| Protein or cDNA | Seq. ID No. | SEQUENCE |
|---|---|---|
| Fatty acid-binding protein, adipocyte (FABP4/aP2)[H. sapiens] | 1 | MCDAFVGTWKLVSSENFDDYMKEVGVGFATRKV AGMAKPNMIISVNGDVITIKSESTFKNTEISFILGQE FDEVTADDRKVKSTITLDGGVLVHVQKWDGKSTT IKRKREDDKLVVECVMKGVTSTRVYERA |
| Fatty acid-binding protein, adipocyte (FABP4/aP2 [M. musculus]) | 2 | MCDAFVGTWKLVSSENFDDYMKEVGVGFATRKV AGMAKPNMIISVNGDL VTIRSESTFKNTEISFKLGV EFDEITADDRKVKSIITLDGGALVQVQKWDGKSTTI KRKRDGDKLVVECVMKGVTSTRVYERA |
| aP2 nuclear localization amino acid sequence | 3 | KEVGVGFATRK |
| aP2 fatty acid binding domain amino acid sequence | 4 | RVY |
| Fatty acid-binding protein, adipocyte (FABP4/aP2)[H. sapiens] cDNA | 5 | ATGTGTGATGCTTTTGTAGGTACCTGGAAACTTG TCTCCAGTGAAAACTTTGATGATTATATGAAAGA AGTAGGAGTGGGCTTTGCCACCAGGAAAGTGGC TGGCATGGCCAAACCTAACATGATCATCAGTGTG AATGGGATGTGATCACCATTAAATCTGAAAGT ACCTTTAAAAATACTGAGATTTCCTTCATACTGG GCCAGGAATTTGACGAAGTCACTGCAGATGACA GGAAAGTCAAGAGCACCATAACCTTAGATGGGG GTGTCCTGGTACATGTGCAGAAATGGGATGG AAAATCAACCACCATAAAGAGAAAACGAGAGG ATGATAAACTGGTGGTGGAATGCGTCATGAAAG GCGTCACTTCCACGAGAGTTTATGAGAGAGCAT AA |
| Fatty acid-binding protein, adipocyte (FABP4/aP2 [M. musculus]) cDNA | 6 | ATGTGTGATGCCTTTGTGGGAACCTGGAAGCTTG TCTCCAGTGAAAACTTCGATGATTACATGAAAGA AGTGGGAGTGGGCTTTGCCACAAGGAAAGTGGC AGGCATGGCCAAGCCCAACATGATCATCAGCGT AAATGGGGATTTGGTCACCATCCGGTCAGAGAG TACTTTTAAAAACACCGAGATTTCCTTCAAACTG GGCGTGGAATTCGATGAAATCACCGCAGACGAC AGGAAGGTGAAGAGCATCATAACCCTAGATGGC GGGGCCCTGGTGCAGGTGCAGAAGTGGGATGGA AAGTCGACCACAATAAAGAGAAAACGAGATGGT GACAAGCTGGTGGTGGAATGTGTTATGAAAGGC GTGACTTCCACAAGAGTTTATGAAAGGGCATGA | aP2-Binding Epitopes

In one aspect of the invention, anti-aP2 monoclonal antibody molecules, including humanized monoclonal antibodies, and antigen binding agents are provided, that specifically bind to human aP2 or mouse aP2 at specific, identified amino acids within the aP2 molecule while folded in its native, conformational form or complexed with its natural binding partner.

In one embodiment, the anti-aP2 monoclonal antibody binds human aP2 having the amino acid sequence:

(Seq. ID. No 1)
MCDAFVGTWKLVSSENFDDYMKEVGVGFAT RKVAGMAKPN

MIISVNGDVI TIKSESTFKN TEISFILGQE FDEVTADDRK

VKSTITLDGG VLVHVQKWDG KSTTIKRKRE DDKLVVECVM

KGVTSTRVYERA, or a naturally occurring variant thereof.

In an alternative embodiment, the anti-aP2 monoclonal antibody or antigen binding agent binds to a human aP2 having an amino acid sequence that is at least 80%, 85%, 90%, 95%, 96%, 97%, 98%, or 99% identical to Seq. ID No. 1. In one embodiment, the antibody has a KD for aP2 of $\geq 10^{-7}$ M. In one embodiment, the antibody binds to an epitope selected from an amino acid sequence underlined in Seq. ID No. 1 above and has a KD for aP2 of about $\geq 10^{-7}$ M. In one embodiment, the antibody binds to an epitope that has one or more (for example, 1, 2, 3, or 4) amino acid substitutions, additions, or deletions as compared to Seq. ID. No. 1.

aP2-Binding Epitopes as Determined by X-Ray Crystallography

In one embodiment, the anti-aP2 antibody or antigen binding agent directly interacts with one or more, for example 1, 2, 3, 4, 5, 6, 7, 8, or 9, amino acids bolded in Seq. ID No. 1 above within a 3 or 4 Angstrom distance. In another embodiment, the anti-aP2 monoclonal antibody or antigen binding agent contacts all nine of the bolded amino acids in Seq. ID No. 1 above within a 3 or 4 Angstrom distance.

In one embodiment, the purified anti-aP2 monoclonal antibody binds a non-contiguous epitope of human and/or mouse aP2 comprising at least one or more, for example 1, 2, 3, 4, 5, 6, 7, 8, or 9 amino acid residues selected from 10K, 11L, 12V, 13S, 37A, 38K, 57T, 130E, and 132A (bolded in Seq. ID No. 1, above), or an amino acid residue within about 4 angstroms of any of 10K, 11L, 12V, 13S, 37A, 38K, 57T, 130E, and 132A. In one embodiment, the purified anti-aP2 monoclonal antibody binds an epitope of human aP2 comprising at least one or more, for example 1, 2, 3, 4, 5, 6, 7, 8, or 9, amino acid residues selected from 10K, 11L, 12V, 13S, 37A, 38K, 57T, 130E, and 132A (bolded in Seq. ID No. 1, above), or an amino acid residue within about 4 angstroms of any of 10K, 11L, 12V, 13S, 37A, 38K, 57T, 130E, and 132A and has a KD for aP2 of $\geq 10^{-7}$ M.

In an alternative embodiment, the purified anti-aP2 monoclonal antibody binds an epitope of human and/or mouse aP2 comprising at least one or more, for example 1, 2, 3, 4, 5, 6, or 7, amino acid residues selected from 10K, 11L, 12V, 13S, 38K, 130E, or 132A (bolded in Seq. ID No. 1, above), or an amino acid residue within about 4 angstroms of any of 10K, 11L, 12V, 13S, 38K, 130E, or 132A. In one embodiment, the purified anti-aP2 monoclonal antibody binds an epitope of human aP2 comprising at least one or more, for example 1, 2, 3, 4, 5, 6, or 7, amino acid residues selected from 10K, 11L, 12V, 13S, 38K, 130E, or 132A (bolded in Seq. ID No. 1, above), or an amino acid residue within about 4 angstroms of any of 10K, 11L, 12V, 13S, 38K, 130E, or 132A and has a KD for aP2 of $\geq 10^{-7}$ M. In one embodiment, the antibody further binds 37A and/or 57T.

In one embodiment, the light chain of the antibody binds an epitope of human aP2 comprising at least one or more, for example 1, 2, 3, 4, 5, 6, 7, 8, or 9, amino acid residues selected from 10K, 11L, 12V, 13S, 37A, 38K, 57T, 130E, or 132A, or an amino acid residue within about 4 angstroms thereof, and has a KD of at least about $\geq 10^{-7}$ M. In one embodiment, the light chain of the antibody binds an epitope of human aP2 comprising at least one or more, for example 1, 2, 3, 4, 5, 6, or 7, amino acid residues selected from 10K, 11L, 12V, 13S, 37A, 38K, 57T, 130E, or 132A, or an amino acid residue within about 4 angstroms thereof, and has a KD of at least about $\geq 10^{7-7}$ M.

In one embodiment, the light chain of the antibody binds an epitope of human aP2 comprising at least one or more, for example 1, 2, 3, 4, 5, 6, 7, 8, or 9, amino acid residues selected from 10K, 11L, 12V, 13S, 37A, 38K, 57T, 130E, or 132A, or an amino acid residue within about 4 angstroms thereof, and the heavy chain of the antibody binds an epitope of human aP2 comprising at least one of 10K and 132A, or an amino acid within about 4 angstroms thereof. In one embodiment, the antibody has a KD of at least about $\geq 10^{-7}$ M.

In one embodiment, the light chain of the antibody binds an epitope of human aP2 comprising at least one or more, for example 1, 2, 3, 4, 5, 6, or 7, amino acid residues selected from 10K, 11L, 12V, 13S, 38K, 130E, or 132A, or an amino acid residue within about 4 angstroms thereof, and the heavy chain of the antibody binds an epitope of human aP2 comprising at least one of 10K and 132A, or an amino acid within about 4 angstroms thereof, and has a KD of at least about $\geq 10^{-7}$ M.

In one embodiment, the antibody binds to the human aP2 protein in its native confirmation at least at 10K. In one embodiment, the antibody binds to the human aP2 protein in its native confirmation at least at 38K. In one embodiment, the antibody binds to the human aP2 protein in its native confirmation at least at 12V. In one embodiment, the antibody binds to the human aP2 protein in its native confirmation at least at 11L. In one embodiment, the antibody binds to the human aP2 protein in its native confirmation at least at 130E. In one embodiment, the antibody binds to the human aP2 protein in its native confirmation at least at 132A. In one embodiment, the antibody binds to the human aP2 protein in its native confirmation at least at 13S. In one embodiment, the antibody binds to the human aP2 protein in its native confirmation at least at 11L and 12V. In one embodiment, the antibody binds to the human aP2 protein in its native confirmation at least at 130E and 132A. In one embodiment, the antibody binds to the human aP2 protein in its native confirmation at a specific amino acid described above and has a KD of about $\geq 10^{-7}$ M.

In one embodiment, the antibody binds to the human aP2 protein in its native confirmation at least at 10K and 38K. In one embodiment, the antibody binds to the human aP2 protein in its native confirmation at least at 10K, 38K, and 12V. In one embodiment, the antibody binds to the human aP2 protein in its native confirmation at least at 10K, 38K, 12V, and 11L. In one embodiment, the antibody binds to the human aP2 protein in its native confirmation at least at 10K, 38K, 12V, 11L, and 57T. In one embodiment, the antibody binds to the human aP2 protein in its native confirmation at least at 10K, 38K, 12V, 11L, 57T, and 37A. In one embodiment, the antibody binds to the human aP2 protein in its native confirmation at least at 10K, 38K, 12V, 11L, 57T, 37A, and 130E. In one embodiment, the antibody binds to the human aP2 protein in its native confirmation at least at 10K, 38K, 12V, 11L, 57T, 37A, 130E, and 132A. In one embodiment, the antibody binds to the human aP2 protein in its native confirmation at least at 10K, 38K, 12V, 11L, 57T, 37A, 130E, 132A, and 13S.

Also provided herein is a specific region or epitope of human aP2 which is bound by an antibody provided by the present invention, in particular an epitope bound by the antibody comprising the light chain variable sequence 909gL1 (Seq. ID No. 446), 909gL10 (Seq. ID No. 448), 909gL13 (Seq. ID No. 487), 909gL50 (Seq. ID No. 488), 909gL54 (Seq. ID No. 450), or 909gL55 (Seq. ID No. 452), and/or heavy chain variable sequence 909gH1 (Seq. ID No. 455), 909gH14 (Seq. ID No. 457), 909gH15 (Seq. ID No. 459), 909gH61 (Seq. ID No. 461), or 909gH62 (Seq. ID No. 463).

This specific region or epitope of the human aP2 protein provided herein can be identified by any suitable epitope mapping method known in the art in combination with any one of the antibodies provided by the present invention. Examples of such methods include screening peptides of varying lengths derived from aP2 for binding to the antibody of the present invention with the smallest fragment that can specifically bind to the antibody containing the sequence of the epitope recognized by the antibody. The aP2 peptides may be produced synthetically or by proteolytic digestion of the aP2 protein. Peptides that bind the antibody can be identified by, for example, mass spectrometric analysis. In another example, NMR spectroscopy or X-ray crystallography can be used to identify the epitope bound by an antibody of the present invention. Crystallization and X-ray crystallography techniques for determining the structure of aP2 and specific interactions of the aP2 protein with its natural binding partners, for example medium chain and long chain fatty acids, are described in Marr et al., Expression, purification, crystallization and structure of human adipocyte lipid-binding protein (aP2), Acta Cryst. (2006), F62, 1058-1060. Once identified, the epitopic fragment which binds an antibody of the present invention can be used, if desired, as an immunogen to obtain additional antibodies which bind the same epitope.

In one example the epitope of the antibody molecule is determined by X-ray crystallography using the aP2 protein (Seq. ID No. 1).

In one embodiment, the antibody of the present invention comprises at least one or more specific amino acids within a CDR domain as defined in Table 2 that interact with a mouse or human aP2 protein in its native conformation at the amino acid contact point defined in Table 2.

TABLE 2

Anti-aP2 antibody/aP2 protein Contact Points

| Ab Chain | Ab CDR | Ab Amino Acid | Ab Source Atom | aP2 Amino Acid | aP2 Target Atom | Distance (angstroms) |
|---|---|---|---|---|---|---|
| Light | CDRL3 | 92Tyr | C | 10Lys | C | 3.72 |
| Light | CDRL3 | 92Tyr | C | 10Lys | C | 3.92 |
| Light | CDRL3 | 92Tyr | O | 10Lys | C | 3.66 |
| Light | CDRL3 | 93Gly | N | 10Lys | C | 3.30 |
| Light | CDRL3 | 93Gly | C | 10Lys | C | 3.65 |
| Light | CDRL3 | 93Gly | C | 10Lys | C | 3.67 |
| Light | CDRL3 | 94Thr | N | 10Lys | C | 3.74 |
| Light | CDRL3 | 92Tyr | C | 10Lys | C | 3.25 |
| Light | CDRL3 | 92Tyr | C | 10Lys | C | 3.85 |
| Light | CDRL3 | 92Tyr | C | 10Lys | C | 3.14 |
| Light | CDRL3 | 94Thr | O | 10Lys | C | 3.31 |
| Heavy |  | 104Leu* | C | 10Lys | N | 3.06 |
| Light | CDRL3 | 93Gly | N | 10Lys | N | 2.74 |
| Light | CDRL3 | 93Gly | C | 10Lys | N | 3.64 |
| Light | CDRL3 | 92Tyr | C | 10Lys | N | 3.37 |
| Light | CDRL3 | 92Tyr | C | 10Lys | N | 3.32 |
| Light | CDRL3 | 92Tyr | C | 10Lys | N | 3.02 |
| Light | CDRL3 | 92Tyr | C | 10Lys | N | 3.87 |
| Light | CDRL3 | 92Tyr | C | 10Lys | N | 3.35 |
| Light | CDRL3 | 92Tyr | C | 10Lys | N | 3.88 |
| Light | CDRL3 | 92Tyr | C | 10Lys | N | 3.29 |
| Light | CDRL3 | 92Tyr | C | 10Lys | N | 3.82 |
| Light | CDRL3 | 92Tyr | O | 11Leu | N | 3.77 |
| Light | CDRL3 |  |  | 11Leu | C | 3.93 |
| Light | CDRL3 |  |  | 11Leu | C | 3.95 |
| Light | CDRL3 |  |  | 11Leu | C | 3.46 |
| Light | CDRL3 | 92Tyr | C | 11Leu | O | 3.51 |
| Light | CDRL3 | 92Tyr | C | 11Leu | O | 3.82 |
| Light | CDRL3 | 92Tyr | O | 11Leu | O | 2.40 |
| Light | CDRL3 | 95Tyr | C | 11Leu | O | 3.60 |
| Light | CDRL3 |  |  | 12Val | C | 3.88 |
| Light | CDRL3 |  |  | 12Val | C | 3.52 |
| Light | CDRL3 | 96Ala | N | 12Val | C | 3.92 |
| Light | CDRL3 | 95Tyr | C | 12Val | C | 3.88 |
| Light | CDRL3 | 95Tyr | C | 12Val | O | 3.25 |
| Light | CDRL3 | 95Tyr | C | 12Val | O | 3.43 |
| Light | CDRL3 | 95Tyr | C | 12Val | O | 3.45 |
| Light | CDRL3 | 96Ala | N | 12Val | O | 2.72 |
| Light | CDRL3 | 96Ala | C | 12Val | O | 3.77 |
| Light | CDRL3 | 95Tyr | C | 12Val | O | 3.90 |
| Light | CDRL3 | 95Tyr | C | 12Val | O | 3.97 |
| Light | CDRL3 |  |  | 13Ser | N | 3.93 |
| Light | CDRL1 | 28Asp | C | 37Ala | C | 3.94 |
| Light | CDRL1 | 28Asp | C | 37Ala | C | 3.68 |
| Light | CDRL1 | 28Asp | O | 37Ala | C | 3.83 |
| Light | CDRL1 | 28Asp | O | 37Ala | C | 4.00 |
| Light | CDRL1 | 28Asp | C | 38Lys | N | 3.88 |
| Light | CDRL1 | 28Asp | C | 38Lys | N | 3.60 |
| Light | CDRL1 | 28Asp | O | 38Lys | N | 3.20 |
| Light | CDRL1 |  |  | 38Lys | C | 3.93 |
| Light | CDRL1 | 28Asp | O | 38Lys | C | 3.40 |
| Light | CDRL1 |  |  | 38Lys | C | 3.40 |
| Light | CDRL1 | 27Glu | O | 38Lys | C | 3.50 |
| Light | CDRL3 | 95Tyr | C | 38Lys | C | 3.80 |
| Light | CDRL3 | 95Tyr | C | 38Lys | C | 3.83 |
| Light | CDRL3 | 95Tyr | C | 38Lys | N | 3.99 |
| Light | CDRL1 | 28Asp | O | 38Lys | N | 3.56 |
| Light | CDRL1 | 27Glu | C | 38Lys | N | 2.96 |
| Light | CDRL3 | 95Tyr | C | 38Lys | N | 3.54 |
| Light | CDRL3 | 95Tyr | C | 38Lys | N | 3.28 |
| Light | CDRL3 | 95Tyr | C | 38Lys | N | 3.54 |
| Light |  | 100Phe* | C | 38Lys | N | 3.23 |
| Light |  | 100Phe* | C | 38Lys | N | 3.95 |
| Light | CDRL1 | 28Asp | O | 38Lys | O | 3.89 |
| Light | CDRL1 | 30Ser | O | 38Lys | O | 3.37 |
| Light | CDRL1 | 28Asp | O | 57Thr | C | 3.57 |
| Light | CDRL1 | 28Asp | C | 57Thr | O | 3.25 |
| Light | CDRL1 | 28Asp | O | 57Thr | O | 2.61 |
| Light | CDRL1 | 28Asp | O | 57Thr | O | 3.15 |
| Light | CDRL1 | 28Asp | O | 57Thr | C | 3.95 |
| Light | CDRL3 | 94Thr | O | 130Glu | C | 3.88 |
| Light | CDRL3 | 94Thr | C | 130Glu | O | 3.84 |
| Light | CDRL3 | 94Thr | O | 130Glu | O | 2.81 |
| Heavy | CDRH3 | 104Leu* | C | 132Ala | C | 3.95 |

TABLE 2-continued

Anti-aP2 antibody/aP2 protein Contact Points

| Ab Chain | Ab CDR | Ab Amino Acid | Ab Source Atom | aP2 Amino Acid | aP2 Target Atom | Distance (angstroms) |
|---|---|---|---|---|---|---|
| Heavy | CDRH3 | | | 132Ala | C | 3.97 |
| Light | CDRL1 | 32Tyr | O | 132Ala | C | 3.59 |

*indicates contact points outside of CDR regions as determined by Kabat numbering The anti-aP2 monoclonal antibodies of the present invention can further be defined by specific amino acids within the CDRs that contact the aP2 protein in its native, conformational form during binding. In one embodiment, provided is a purified anti-aP2 monoclonal antibody comprising a light chain comprising the following amino acids at the identified specific position: CDRL1—27Glu, 28Asp, 30Ser; CDRL3—92Tyr, 93Gly, 94Thr, 95Tyr, 96Ala; and 100Phe. In one embodiment, the antibody binds to the human aP2 protein in its native confirmation and has a KD of about $\geq 10^{-7}$ M. In one embodiment, the anti-aP2 monoclonal antibody is humanized.

In one embodiment, provided is a purified anti-aP2 monoclonal antibody comprising a light chain comprising the following amino acids at the identified position: CDRL1—27Glu, 28Asp, 30Ser; CDRL3—92Tyr, 93Gly, 94Thr, 95Tyr, 96Ala; and 100Phe; and a heavy chain comprising the following amino acid at the identified position: 104Leu. In one embodiment, the antibody binds to the human aP2 protein in its native confirmation and has a KD of about $\geq 10^{-7}$ M. In one embodiment, the anti-aP2 monoclonal antibody is humanized.

In one embodiment, provided is a purified anti-aP2 monoclonal antibody comprising a light chain comprising the following amino acid at the identified position: CDRL3—91Ala; and a heavy chain comprising the following amino acids at the identified positions: CDRH1—33Ala; CDRH2—52Ser. In one embodiment, the heavy chain further comprises the following amino acid at the identified position: CDRH3—98Phe. In one embodiment, the antibody binds to the human aP2 protein in its native confirmation and has a KD of about $\geq 10^{-7}$ M. In one embodiment, the anti-aP2 monoclonal antibody is humanized.

In one embodiment, the purified anti-aP2 monoclonal antibody binds to aP2 only through, or primarily through, its light chain CDRs. In an alternative embodiment, the purified anti-aP2 monoclonal antibody has light chain CDRs that bind to aP2 with a greater affinity than its heavy chain CDRs bind to aP2.

In one embodiment, the purified anti-aP2 monoclonal antibody is characterized by having a low affinity for human aP2 in its native, conformational form. In one embodiment, the purified anti-aP2 monoclonal antibody has a KD for human aP2 of about $\geq 10^{-7}$ M. In one embodiment, the purified anti-aP2 monoclonal antibody has a KD for human aP2 of between about $10^{-4}$ to $10^{-6}$ M. In one embodiment, the purified anti-aP2 monoclonal antibody has a KD for human aP2 of about >500 nM. In one embodiment, the purified anti-aP2 monoclonal antibody has a KD for human aP2 of about 500 nM to about 10 μM. In one embodiment, the purified anti-aP2 monoclonal antibody has a KD for human aP2 of about 1 μM to about 7 μM. In one embodiment, the purified anti-aP2 monoclonal antibody has a KD for human aP2 of about 2 μM to about 5 μM.

In an alternative embodiment, the purified anti-aP2 monoclonal antibody has a low binding affinity for mouse aP2 in its native, conformational form. In one embodiment, the purified anti-aP2 monoclonal antibody has a KD for mouse aP2 of $\geq 10^{-7}$ M. In one embodiment, the purified anti-aP2 monoclonal antibody has a KD for mouse aP2 of between about $10^{-4}$ to $10^{-6}$ M. In one embodiment, the purified anti-aP2 monoclonal antibody has a KD for mouse aP2 of about >500 nM. In one embodiment, the purified anti-aP2 monoclonal antibody has a KD for mouse aP2 of about 500 nM to about 10 μM. In one embodiment, the purified anti-aP2 monoclonal antibody has a KD for mouse aP2 of about 1 μM to about 7 μM. In one embodiment, the purified anti-aP2 monoclonal antibody has a KD for mouse aP2 of about 2 μM to about 5 μM.

In one embodiment, the antibody specifically binds aP2, and does not specifically bind to FABP5/Mal1.

In one embodiment, provided is a purified anti-aP2 monoclonal antibody, and a process of making same, wherein the affinity for aP2 has been reduced by identifying an anti-aP2 antibody having a KD for aP2 of at least <10-7 M, altering at least one amino acid in either a CDR region or a FR region of the anti-aP2 antibody, wherein the alteration results in an anti-aP2 antibody with a KD of at least about $\geq 10^{-7}$ M. In one embodiment, the altered antibody is capable of binding to human aP2 in its native conformational form. In an alternative embodiment, the altered antibody is capable of binding to mouse aP2 in its native conformation form. In one embodiment, provided is a method of reducing the affinity for an anti-aP2 antibody having a KD of $<10^{-7}$ M comprising 1) identifying a monoclonal antibody having an affinity of at least $<10^{-7}$ M for an aP2 protein, 2) identifying an amino acid within a CDR region that contacts the aP2 protein in its native conformational form, and 3) substituting one or more contact amino acids with an amino acid selected from alanine, phenylalanine, and serine, wherein the substitutions result in a reduction in the affinity of the antibody to a KD of about $\geq 10^{-7}$ M. In one embodiment, a cysteine residue in CDRL3 is substituted. In one embodiment, the cysteine residue is substituted with an amino acid selected from alanine, glutamine, and histidine.

aP2-Binding Epitopes as Determined by Hydrogen-Deuterium Exchange

In one aspect of the invention, the purified monoclonal antibody binds to an epitope of the human aP2 protein as determined by hydrogen-deuterium exchange (HDX) comprising at least one, for example 1, 2, 3, 4, 5, 6, 7, 8, 9, or 10, or more, of amino acids 9-17, amino acids 20-28, or amino acids 118-132 of Seq. ID No. 1. In one embodiment, the purified monoclonal antibody binds to an epitope of the human aP2 protein comprising at least one, for example 1, 2, 3, 4, 5, 6, 7, 8, 9, 10 or more, of amino acids 9-17 (WKLVSSENF) (Seq. ID No. 22), amino acids 20-28 (YM-KEVGVGF) (Seq. ID No. 23), or amino acids 118-132 (CVMKGVTSTRVYERA) (Seq. ID No. 24) of Seq. ID No. 1, and has a KD of at least about $\geq 10^{-7}$ M. In one embodiment, the purified anti-aP2 monoclonal antibody binds to an epitope of the human aP2 protein within 3-4 angstrom contact points of at least one, for example 1, 2, 3, 4, 5, 6, 7, 8, 9, 10 or more, of amino acids 9-17, amino acids 20-28, or amino acids 118-132 of Seq. ID No. 1 when the human aP2 protein is in its native, conformational form. In one embodiment, the purified anti-aP2 monoclonal antibody binds to an epitope of the human aP2 protein within 3-4 angstrom contact points of at least one of, for example 1, 2, 3, 4, 5, 6, 7, 8, 9, 10 or more, amino acids 9-17, amino acids 20-28, or amino acids 118-132 of Seq. ID No. 1 when the human aP2 protein is in its native, conformational form and has a KD of at least about $\geq 10^{-7}$ M. Hydrogen-deuterium exchange (HDX) to determine binding interactions and antibody-epitope maps are well known in the art, for example, as described by Pandit et al. (2012) J. Mol. Recognit. March; 25(3): 114-24 (incorporated herein by reference)).

Anti-aP2 Antibodies and Antigen Binding Agent Structures

Anti-aP2 monoclonal antibodies and antigen binding agents have been discovered that have superior and unexpected activity for the treatment of aP2-mediated disorders. In one embodiment, anti-aP2 monoclonal antibodies and fragments are provided that contain a light chain or light chain fragment having a variable region, wherein said variable region comprises one, two or three CDRs independently selected from Seq. ID No. 7, Seq. ID No. 8, and Seq. ID No. 9, Seq. ID No. 10, Seq. ID No. 11, Seq. ID No. 12 and Seq. ID No. 13. Alternatively, one or more of the disclosed and selected CDRs can be altered by substitution of one or more amino acids (for example, 1, 2, 3, 4, 5, 6, 7 or 8 amino acids) that do not adversely affect or that improve the properties of the antibody or antigen binding agent, as further described herein. In one embodiment, the selected CDR(s) is/are placed in a human immunoglobulin framework. In one embodiment, the human immunoglobulin framework is further modified or altered to maintain the binding affinity specificity of the grafted CDR region.

Therefore, in another embodiment, it has been discovered that an antibody or antigen binding agent that binds to aP2 protein in its secreted (non-cytosolic) state with a weaker binding affinity of KD about $\geq 10^{-7}$ M, has an improved ability to neutralize secreted aP2 and cause a significant inhibitory effect on aP2-mediated disorders when provided to in an effective amount to a host in need thereof.

In an antibody molecule, there are two heavy chains and two light chains. Each heavy chain and each light chain has at its N-terminal end a variable domain. Each variable domain is composed of four framework regions (FRs) alternating with three complementarity determining regions (CDRs). The residues in the variable domains are conventionally numbered according to a system devised by Kabat et al (supra), or a combination of Kabat and Chothia as described above for CDR-H1. This numbering system is used in the present specification except where otherwise indicated.

Immunoglobulins (Ig) are the antigen recognition molecules of B cells. An Ig molecule is made up of 2 identical heavy chains and 2 identical light chains, either kappa or lambda, joined by disulfide bonds so that each heavy chain is linked to a light chain and the 2 heavy chains are linked together. The kappa and lambda light chains have no apparent functional differences. Each Ig kappa and lambda light chain has an N-terminal variable (V) region containing the antigen-binding site and a C-terminal constant (C) region, encoded by the C region gene (IGKC or IGLC), that provides signaling functions. The kappa and lambda light chain V regions are encoded by 2 types of genes: V genes and joining (J) genes. Random selection of just 1 gene of each type to assemble a V region accounts for the great diversity of V regions among Ig molecules. The kappa light chain locus on human chromosome 2 contains approximately 40 functional V genes, followed by approximately 5 functional J genes. The lambda light chain locus on human chromosome 22 contains approximately 30 functional V genes, followed by approximately 4 functional J genes. Due to polymorphism, the numbers of functional V and J genes differ among individuals.

Each Ig heavy chain has an N-terminal variable (V) region containing the antigen-binding site and a C-terminal constant (C) region, encoded by a C region gene, that provides effector or signaling functions. The heavy chain V region is encoded by 3 types of genes: V genes, joining (J) genes, and diversity (D) genes. Random selection of just 1 gene of each type to assemble a V region accounts for the great diversity of V regions among Ig molecules. The heavy chain locus on human chromosome 14 contains approximately 40 functional V genes, followed by approximately 25 functional D genes and approximately 6 functional J genes. Due to polymorphism, the numbers of functional V, J, and D genes differ among individuals. There are five types of mammalian immunoglobulin heavy chains: γ, δ, α, μ and ε. They define classes of immunoglobulins: IgG, IgD, IgA, IgM and IgE, respectively. Heavy chains γ, α and δ have a constant region composed of three tandem (in a line next to each other) immunoglobulin domains but also have a hinge region between CH1 and CH2 regions for added flexibility. Heavy chains μ and ε have a constant region composed of four domains.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or CDR, of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDRH1), residues 50-65 (CDRH2) and residues 95-102 (CDRH3) according to the Kabat numbering. However, according to Chothia (Chothia et al., (1987) J. Mol. Biol., 196, 901-917), the loop equivalent to CDR-H1 extends from residue 26 to residue 32. Thus unless indicated otherwise, "CDR-H1" as employed herein is intended to refer to residues 26 to 35, as described by a combination of the Kabat numbering system and Chothia's topological loop definition.

The CDRs of the light chain variable domain are located at residues 24-34 (CDRL1), residues 50-56 (CDRL2) and residues 89-97 (CDRL3) according to the Kabat numbering. Antibodies for use in the present disclosure may be obtained using any suitable method known in the art. The aP2 protein including fusion proteins, or cells (recombinantly or naturally) expressing the protein, can be used to produce antibodies, which specifically recognize aP2. The aP2 protein used can be the full biologically active protein or a fragment or derivative thereof.

aP2 proteins or peptides, for use to immunize a host, may be prepared by processes well known in the art from genetically engineered host cells comprising expression systems or they may be recovered from natural biological sources. The aP2 protein may in some instances be part of a larger protein such as a fusion protein for example fused to an affinity tag or similar, or complexed with its naturally occurring biological partner.

Antibodies generated against the aP2 protein may be obtained, where immunization of an animal is necessary, by administering the protein to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable. Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., 1996, Proc. Natl. Acad. Sci. USA 93(15):7843-78481; WO92/02551; WO2004/051268 and International Patent Application number WO2004/106377. Screening for antibodies can be performed using assays to measure binding to human aP2 and/or assays to measure the ability to block aP2 binding to its natural receptor. An example of a binding assay is an ELISA, in particular, using a fusion protein of human aP2 and human Fc, which is immobilized on plates, and employing a secondary antibody to detect anti-aP2 antibody bound to the fusion protein. Examples of suitable antagonistic and blocking assays are described in the Examples herein.

Humanized antibodies (which include CDR-grafted antibodies) are antibody molecules having one or more complementarity determining regions (CDRs) from a non-human species (e.g., a rabbit or mouse) and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanized antibodies may optionally further comprise one or more framework residues derived from the non-human species from which the CDRs were derived. The latter are often referred to as donor residues. The antibody molecules of the present invention suitably have a binding affinity of about $\geq 10^{-7}$ M, in particular in the micromolar (μM) range. Affinity may be measured using any suitable method known in the art, including BIAcore, as described in the Examples herein, using isolated natural or recombinant aP2 or a suitable fusion protein/polypeptide. In one embodiment described herein, the binding affinities of the anti-aP2 monoclonal antibody described herein may include antibodies having a KD of about $\geq 10^{-7}$ M. In one embodiment, the purified anti-aP2 monoclonal antibody has a KD for human aP2 of between about $10^{-4}$ to $10^{-6}$ M. In one embodiment, the purified anti-aP2 monoclonal antibody has a KD for human aP2 of about 2 to about 5 μM.

In one example the antibody of the present invention does not bind FABP5/Mal1. In one example the antibody of the present invention binds aP2 in its natural non-linear structural conformation.

The affinity of an antibody or antigen binding agent of the present invention, as well as the extent to which a binding agent (such as an antibody) inhibits binding, can be determined by one of ordinary skill in the art using conventional techniques, for example those described by Scatchard et al. (Ann. KY. Acad. Sci. 51:660-672 (1949)) or by surface plasmon resonance (SPR) using systems such as BIAcore. For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analysed to yield apparent rate constants for the association and dissociation phases of the binding reaction. The ratio of these values gives the apparent equilibrium constant (affinity) (see, e.g., Wolff et al, Cancer Res. 53:2560-65 (1993)).

In the present invention affinity of the test antibody molecule is typically determined using SPR as follows. The test antibody molecule is captured on the solid phase and human aP2 is run over the captured antibody in the mobile phase and affinity of the test antibody molecule for human aP2 is determined. The test antibody molecule may be captured on the solid phase chip surface using any appropriate method, for example using an anti-Fc or anti Fab' specific capture agent. In one example the affinity is determined at pH 6. In one example the affinity is determined at pH 7.4.

It will be appreciated that the affinity of antibodies provided by the present invention may be altered using any suitable method known in the art. The present invention therefore also relates to variants of the antibody molecules of the present invention, which have an improved affinity for aP2. Also contemplated, as described further herein, is the modification of high affinity anti-human aP2 antibodies in order to reduce the KD to at least about $\geq 10^{-7}$ M. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

CDR Regions

In one aspect of the present invention, an anti-aP2 monoclonal antibody or antigen binding agent is provided that binds to aP2 protein in its native conformation wherein the antibody comprises at least one, or more than one, of the CDR regions provided in Table 3.

TABLE 3

Anti-aP2 Antibody Complementarity Determining Regions (CDRs)

| Protein | Seq. ID No. | SEQUENCE |
|---|---|---|
| CDRL1 | 7 | QASEDISRYLV |
| CDRL1 variant 1 | 597 | SVSSSISSSNLH |
| CDRL2 | 8 | KASTLAS |

TABLE 3-continued

Anti-aP2 Antibody Complementarity Determining Regions (CDRs)

| Protein | Seq. ID No. | SEQUENCE |
| --- | --- | --- |
| CDRL2 variant 1 | 598 | GTSNLAS |
| CDRL3 | 9 | QCTYGTYAGSFFYS |
| CDRL3 variant 1 | 10 | QATYGTYAGSFFYS |
| CDRL3 variant 2 | 11 | QQTYGTYAGSFFYS |
| CDRL3 variant 3 | 12 | QHTYGTYAGSFFYS |
| CDRL3 variant 4 | 13 | QASHYPLT |
| CDRL3 variant 5 | 599 | QQWSHYPLT |
| CDRH1 | 14 | GFSLSTYYMS |
| CDRH1 variant 1 | 15 | GYTFTSNAIT |
| CDRH1 variant 2 | 600 | GYTFTSNWIT |
| CDRH2 | 16 | IIYPSGSTYCASWAKG |
| CDRH2 variant 1 | 17 | IIYPSGSTYSASWAKG |
| CDRH2 variant 2 | 18 | DISPGSGSTTNNEKFKS |
| CDRH2 variant 3 | 601 | DIYPGSGSTTNNEKFKS |
| CDRH3 | 19 | PDNDGTSGYLSGFGL |
| CDRH3 variant 1 | 20 | PDNEGTSGYLSGFGL |
| CDRH3 variant 2 | 21 | LRGFYDYFDF |
| CDRH3 variant 3 | 602 | LRGYYDYFDF |

In one aspect, provided is a purified anti-aP2 monoclonal antibody or antigen binding fragment comprising a light chain wherein the variable domain comprises one, two, or three CDRs independently selected from CDRL1 (QASEDISRYLV) (Seq. ID No. 7), CDRL1 variant 1 (SVSSSISSSNLH) (Seq. ID No. 597), CDRL2 (KASTLAS) (Seq. ID No. 8), CDRL2 variant 1 (GTSNLAS) (Seq. ID No. 598), CDRL3 (QCTYGTYAGSFFYS) (Seq. ID. No. 9), CDRL3 variant 1 (QATYGTYAGSFFYS) (Seq. ID No. 10), CDRL3 variant 2 (QQTYGTYAGSFFYS) (Seq. ID No. 11), CDRL3 variant 3 (QHTYGTYAGSFFYS) (Seq. ID No. 12), CDRL3 variant 4 (QQASHYPLT) (Seq. ID No. 13), or CDRL3 variant 5 (QQWSHYPLT) (Seq. ID No. 599). In one embodiment, provided herein is an antibody or antigen binding agent comprising a light chain variable region comprising CDRL1 (Seq. ID No. 7), CDRL2 (Seq. ID No. 8), and CDRL3 (Seq. ID No. 9). In one embodiment, provided herein is an antibody or antigen binding agent comprising a light chain variable region comprising CDRL1 (Seq. ID No. 7), CDRL2 (Seq. ID No. 8), and CDRL3 variant 1 (Seq. ID No. 10). In one embodiment, provided herein is an antibody or antigen binding agent comprising a light chain variable region comprising CDRL1 (Seq. ID No. 7), CDRL2 (Seq. ID No. 8), and CDRL3 variant 2 (Seq. ID No. 11). In one embodiment, provided herein is an antibody or antigen binding agent comprising a light chain variable region comprising CDRL1 (Seq. ID No. 7), CDRL2 (Seq. ID No. 8), and CDRL3 variant 3 (Seq. ID No. 12). In one embodiment, provided herein is an antibody or antigen binding agent comprising a light chain variable region comprising CDRL3 variant 4 (Seq. ID No. 13), wherein the antibody has a KD of about $\geq 10^{-7}$ M. In one embodiment, provided herein is an antibody or antigen binding agent comprising a light chain variable region comprising CDRL1 variant 1 (Seq. ID No. 597), CDRL2 variant 1 (Seq. ID No. 598), and CDRL3 variant 4 (Seq. ID No. 13). In one embodiment, provided herein is an antibody or antigen binding agent comprising a light chain variable region comprising CDRL3 variant 4 (Seq. ID No. 13) and a heavy chain variable region comprising CDHR1 variant 1 (GYTFTSNAIT) (Seq. ID No. 15), CDRH2 variant 2 (DISPGSGSTTNNEKFKS) (Seq. ID No. 18), and, in one embodiment, CDRH3 variant 2 (LRGFYDYFDF) (Seq. ID No. 21).

In one embodiment, the antibody or antigen binding agent comprises one, two, or three CDRs selected from CDRL1 (Seq. ID No. 7), CDRL2 (Seq. ID No. 8), CDRL3 (Seq. ID No. 9), CDRL3 variant 1 (Seq. ID No. 10), CDRL3 variant 2 (Seq. ID No. 11), CDRL3 variant 3 (Seq. ID No. 12), and CDRL3 variant 4 (Seq. ID No. 13), and has a KD of about $\geq 10^{-7}$ M. In one embodiment, the CDR sequences identified above are grafted into a human immunoglobulin framework. In one embodiment, the human immunoglobulin framework is further modified or altered, for example within the Vernier zone, to maintain the binding affinity specificity of the grafted CDR region.

In one embodiment, a purified anti-aP2 monoclonal antibody or antigen binding agent is provided comprising a light chain wherein the variable domain comprises one, two, or three CDRs independently selected from an amino acid sequence that is at least 80%, 85%, 90%, or 95% homologous with CDRL1 (Seq. ID No. 7), CDRL2 (Seq. ID No. 8), CDRL3 (Seq. ID No. 9), CDRL3 variant 1 (Seq. ID No. 10), CDRL3 variant 2 (Seq. ID No. 11), CDRL3 variant 3 (Seq. ID No. 12), or CDRL3 variant 4 (Seq. ID No. 13). In one embodiment, the antibody or antigen binding agent has a KD of about $\geq 10^{-7}$ M. In one embodiment, the CDR sequences identified above are grafted into a human immunoglobulin framework. In one embodiment, the human immunoglobulin framework is further modified or altered, for example within the Vernier zone, to maintain the binding affinity specificity of the grafted CDR region. In one embodiment, a purified anti-aP2 monoclonal antibody or antigen binding agent is provided comprising a light chain wherein the variable domain comprises one, two, or three CDRs independently selected from an amino acid sequence that has one or more (for example, 1, 2, 3, or 4) amino acid substitutions, additions, or deletions as compared with CDRL1 (Seq. ID No. 7), CDRL2 (Seq. ID No. 8), CDRL3 (Seq. ID No. 9), CDRL3 variant 1 (Seq. ID No. 10), CDRL3 variant 2 (Seq. ID No. 11), CDRL3 variant 3 (Seq. ID No. 12), or CDRL3 variant 4 (Seq. ID No. 13).

In one aspect, provided is a purified anti-aP2 monoclonal antibody or antigen binding agent comprising a light chain wherein the variable domain comprises one, two, or three CDRs selected from CDRL1 (Seq. ID No. 7), CDRL2 (Seq. ID No. 8), CDRL3 (Seq. ID No. 9), CDRL3 variant 1 (Seq. ID No. 10), CDRL3 variant 2 (Seq. ID No. 11), CDRL3 variant 3 (Seq. ID No. 12), or CDRL3 variant 4 (Seq. ID No. 13), and one, two, or three CDRs selected from CDRH1 (GFSLSTYYMS) (Seq. ID NO. 14), CDRH1 variant 1 (Seq. ID No. 15), CDRH1 variant 2 (GYTFTSNWIT) (Seq. ID No. 600), CDRH2 (IIYPSGSTYCASWAKG) (Seq. ID No. 16), CDRH2 variant 1 (IIYPSGSTYSASWAKG) (Seq. ID No. 17), CDRH2 variant 2 (Seq. ID No. 18), CDRH2 variant 3 (DIYPGSGSTTNNEKFKS) (Seq. ID No. 601), CDHR3 (PDNDGTSGYLSGFGL) (Seq. ID No. 19), CDRH3 variant 1 (PDNEGTSGYLSGFGL) (Seq. ID No. 20), CDRH3 variant 2 (Seq. ID No. 21), or CDRH3 variant 3 (LRGYY-DYFDFW) (Seq. ID No. 602). In one embodiment, provided herein is an antibody or antigen binding agent comprising a heavy chain variable region comprising CDRH1 variant 1 (Seq. ID No. 15), CDRH2 variant 2 (Seq. ID No. 18), and CDRH3 variant 3 (Seq. ID No. 602). In one embodiment, provided herein is an antibody or antigen binding agent comprising a heavy chain variable region comprising CDRH1 variant 1 (Seq. ID No. 15), CDRH2 variant 2 (Seq. ID No. 18), and CDRH3 variant 2 (Seq. ID No. 21). In one embodiment, the antibody or antigen binding agent has a KD of about $\geq 10^{-7}$ M. In one embodiment, the CDR sequences identified above are grafted into a human immunoglobulin framework. In one embodiment, the human immunoglobulin framework is further modified or altered, for example within the Vernier zone, to maintain the binding affinity specificity of the grafted CDR region.

In one embodiment, the antibody or antigen binding agent comprises one, two, or three CDRs selected from CDRH1 (Seq. ID NO. 14), CDRH1 variant 1 (Seq. ID No. 15), CDRH2 (Seq. ID No. 16), CDRH2 variant 1 (Seq. ID No. 17), CDRH2 variant 2 (Seq. ID No. 18), CDRH3 (Seq. ID No. 19), CDRH3 variant 1 (Seq. ID No. 20), or CDRH3 variant 2 (Seq. ID No. 21), and has a KD of about $\geq 10^{-7}$ M. In one embodiment, the antibody or antigen binding agent comprises CDRs CDRH1 (Seq. ID No. 14), CDRH2 (Seq. ID No. 16), and CDRH3 (Seq. ID No. 19). In one embodiment, the antibody or antigen binding agent comprises CDRs CDRH1 (Seq. ID No. 14), CDRH2 variant 1 (Seq. ID No. 17), and CDHR3 variant 1 (Seq. ID No. 20). In one embodiment, the antibody comprises CDRs CDRH1 variant 1 (Seq. ID No. 15) and CDRH2 variant 2 (Seq. ID No. 18). In one embodiment, the antibody comprises CDRs CDRH1 variant 1 (Seq. ID No. 15), and CDRH2 variant 2 (Seq. ID No. 18), and CDRH3 variant 2 (Seq. ID No. 21). In one embodiment, the CDR sequences identified above are grafted into a human immunoglobulin framework. In one embodiment, the human immunoglobulin framework is further modified or altered, for example within the Vernier zone, to maintain the binding affinity specificity of the grafted CDR region. In one embodiment, the antibody or antigen binding agent comprises one, two, or three CDRs selected from an amino acid sequence that has one or more (for example, 1, 2, 3, or 4) amino acid substitutions, additions, or deletions as compared to CDRH1 (Seq. ID NO. 14), CDRH1 variant 1 (Seq. ID No. 15), CDRH2 (Seq. ID No. 16), CDRH2 variant 1 (Seq. ID No. 17), CDRH2 variant 2 (Seq. ID No. 18), CDRH3 (Seq. ID No. 19), CDRH3 variant 1 (Seq. ID No. 20), or CDRH3 variant 2 (Seq. ID No. 21).

In one embodiment, a purified anti-aP2 monoclonal antibody or antigen binding agent is provided comprising a heavy chain wherein the variable domain comprises one, two, or three CDRs selected from an amino acid sequence that is at least 80%, 85%, 90%, or 95% homologous with CDRH1 (Seq. ID No. 14), CDRH1 variant 1 (Seq. ID No. 15), CDRH2 (Seq. ID No. 16), CDRH2 variant 1 (Seq. ID No. 17), CDRH2 variant 2 (Seq. ID No. 18), CDRH3 (Seq. ID No. 19), CDRH3 variant 1 (Seq. ID No. 20), or CDRH3 variant 2 (Seq. ID No. 21). In one embodiment, the antibody or antigen binding agent has a KD of about $\geq 10^{-7}$ M. In one embodiment, the CDR sequences identified above are grafted into a human immunoglobulin framework. In one embodiment, the human immunoglobulin framework is further modified or altered, for example within the Vernier zone, to maintain the binding affinity specificity of the grafted CDR region.

CDRs can be altered or modified to provide for improved binding affinity, minimize loss of binding affinity when grafted into a different backbone, or to decrease unwanted interactions between the CDR and the hybrid framework as described further below.

Humanized Antibodies and Antigen Binding Agents

In one aspect of the present invention, provided herein are humanized anti-aP2 monoclonal antibodies and antigen binding agents. Humanized antibodies are antibodies wherein the heavy and/or light chain contains one or more CDRs (including, if desired, one or more modified CDRs) from a donor antibody (e.g. a non-human antibody such as a murine or rabbit monoclonal antibody) grafted into a heavy and/or light chain variable region framework of an acceptor antibody (e.g. a human antibody). For a review, see Vaughan et al, Nature Biotechnology, 16, 535-539, 1998.

In one embodiment, rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein are transferred to the human antibody framework. In another embodiment only the specificity determining residues from each of the CDRs described herein are transferred to the human antibody framework.

When the CDRs or specificity determining residues are grafted, any appropriate acceptor variable region framework sequence may be used having regard to the class/type of the donor antibody from which the CDRs are derived, including mouse, rabbit, primate and human framework regions.

Suitably, the humanized antibody according to the present invention has a variable domain comprising human acceptor framework regions as well as one or more of the CDRs provided specifically herein. Thus, provided in one embodiment is a humanized monoclonal antibody which binds human aP2 wherein the variable domain comprises human acceptor framework regions and non-human donor CDRs.

Construction of CDR-grafted antibodies is generally described in European Patent Application EP-A-0239400, which discloses a process in which the CDRs of a mouse monoclonal antibody are grafted onto the framework regions of the variable domains of a human immunoglobulin by site directed mutagenesis using long oligonucleotides, and is incorporated herein. The CDRs determine the antigen binding specificity of antibodies and are relatively short peptide sequences carried on the framework regions of the variable domains.

The earliest work on humanizing monoclonal antibodies by CDR-grafting was carried out on monoclonal antibodies recognizing synthetic antigens, such as NP. However, examples in which a mouse monoclonal antibody recognizing lysozyme and a rat monoclonal antibody recognizing an antigen on human T-cells were humanized by CDR-grafting have been described by Verhoeyen et al. (Science, 239, 1534-1536, 1988) and Riechmann et al (Nature, 332, 323-324, 1988), respectively. Antibody humanization is achieved by grafting CDRs of a non-human antibody, such as a mouse, rat, goat, or rabbit antibody, onto a "similar" human framework (acceptor) and selecting minimal number of key framework residues (back-mutations) that are manually selected from the donor monoclonal antibody and incorporated into human acceptor framework in order to maintain the original CDR conformation. Such methods are known in the art, and include those described in Jones et al., Nature 321:522 (1986); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), Padlan, Molecular Immunology 28(4/5): 489-498 (1991); Studnicka et al., Protein Engineering 7(6): 805-814 (1994); Roguska. et al., PNAS 91:969-973 (1994); PCT publication WO 91/09967, PCT/: US98/16280, US96/18978, US91/09630, US91/05939, US94/01234, GB89/01334, GB91/01134, GB92/01755; WO90/14443, WO90/14424, WO90/14430, EP 229246, EP 592,106; EP 519,596, EP 239,400, U.S. Pat. Nos. 5,565,332, 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, which are incorporated herein.

The human variable heavy and light chain germline subfamily classification can be derived from the Kabat germline subgroup designations: VH1, VH2, VH3, VH4, VH5, VH6 or VH7 for a particular VH sequence and JH1, JH2, JH3, JH4, JH5, and JH6 for a for a particular variable heavy joining group for framework 4; VK1, VK2, VK3, VK4, VK5 or VK6 for a particular VL kappa sequence for framework 1, 2, and 3, and JK1, JK2, JK3, JK4, or JK5 for a particular kappa joining group for framework 4; or VL1, VL2, VL3, VL4, VL5, VL6, VL7, VL8, VL9, or VL10 for a particular VL lambda sequence for framework 1, 2, and 3, and JL1, JL2, JL3, or JL7 for a particular lambda joining group for framework 4.

In one embodiment, the general framework of the light chain contemplated herein comprises the structures selected from FR1-CDRL1-FR2-CDRL2-FR3-CDRL3-FR4 and FR1-CDRL1-FR2-CDRL2-FR3-CDRL3-FR4-CL, and variations thereof, wherein the CDR regions are selected from at least one variable light chain CDR selected from Seq. ID Nos. 7-13, the framework regions are selected from either an immunoglobulin kappa light chain variable framework region, for example as provided in Table 4 (Seq. ID Nos. 25-149), or an immunoglobulin lambda light chain variable framework region, for example as provided in Table 5 (Seq. ID Nos. 150-246), and an immunoglobulin light chain constant region from either a kappa light chain constant region (Seq. ID No. 247) when the framework region is a kappa light chain variable framework region, or a lambda light chain constant region (Seq. ID No. 248) when the framework region is a lambda light chain variable framework region.

In one embodiment, the general framework of the heavy chain regions contemplated herein comprises the structures selected from FR1-CDRH1-FR2-CDRH2-FR3-CDRH3-FR4, FR1-CDRH1-FR2-CDRH2-FR3-CDRH3-FR4-CH1, FR1-CDRH1-FR2-CDRH2-FR3-CDRH3-FR4-CH1-Hinge-CH2 for IgG, IgD, and IgA immunoglobulin classes and FR1-CDRH1-FR2-CDRH2-FR3-CDRH3-FR4-CH1-CH2 for IgM and IgE immunoglobulin classes, FR1-CDRH1-FR2-CDRH2-FR3-CDRH3-FR4-CH1-Hinge-CH2-CH3 for IgG, IgD, and IgA immunoglobulin classes, FR1-CDRH1-FR2-CDRH2-FR3-CDRH3-FR4-CH1-CH2-CH3 for IgM and IgE immunoglobulin classes, and FR1-CDRH1-FR2-CDRH2-FR3-CDRH3-FR4-CH1-CH2-CH3-CH4 for IgM and IgE immunoglobulin classes, and variations thereof, wherein the CDR regions are selected from at least one variable heavy chain CDR selected from Seq. ID Nos. 14-21, and the framework regions are selected from the heavy chain variable framework regions described in Table 7 (Seq. ID Nos. 249-407), and the heavy chain constant regions are selected from, for example, those provided in Table 8 (Seq. ID Nos. 408-443). IgA and IgM classes can further comprise a joining polypeptide (Seq. ID No. 444) provided in Table 9 that serves to link two monomer units of IgM or IgA together, respectively. In the case of IgM, the J chain-joined dimer is a nucleating unit for the IgM pentamer, and in the case of IgA it induces larger polymers.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular embodiments, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. It will be appreciated that sequence variants of these constant region domains may also be used. For example IgG4 molecules in which the serine at position 241 has been changed to proline as described in Angal et al., Molecular Immunology, 1993, 30 (1), 105-108 may be used. It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705: 129-134, 1995). Accordingly, the C-terminal lysine of the antibody heavy chain may be absent.

In one embodiment, the anti-aP2 monoclonal antibody comprises at least one light chain CDR selected from CDRL1 (Seq. ID No. 7), CDRL2 (Seq. ID No. 8), CDRL3 (Seq. ID No. 9), or CDRL3 variant 1 (Seq. ID No. 10), CDRL3 variant 2 (Seq. ID No. 11), CDRL3 variant 3 (Seq. ID NO. 12), and CDRL3 variant 4 (Seq. ID No. 13), and/or at least one heavy chain CDR selected from CDRH1 (Seq. ID No. 14), CDRH1 variant 1 (Seq. ID No. 15), CDRH2 (Seq. ID No. 16), CDRH2 variant 1 (Seq. ID No. 17), CDRH2 variant 2 (Seq. ID No. 18), CDRH3 (Seq. ID No. 19), CDRH3 variant 1 (Seq. ID No 20), or CDRH3 variant 2 (Seq. ID No. 21), or a combination or variant thereof, wherein the CDR is grafted into a human light or heavy chain variable framework, respectively.

In one embodiment, the anti-aP2 monoclonal antibody comprises one, two, or three light chain CDRs selected from CDRL1 (Seq. ID No. 7), CDRL2 (Seq. ID No. 8), CDRL3 (Seq. ID No. 9), CDRL3 variant 1 (Seq. ID No. 10), CDRL3 variant 2 (Seq. ID No. 11), CDRL3 variant 3 (Seq. ID NO. 12), and CDRL3 variant 4 (Seq. ID No. 13), or a combination or variant thereof, grafted into a human acceptor light chain framework. In one embodiment, the anti-aP2 monoclonal antibody comprises a variable light chain comprising CDRL1 (Seq. ID No. 7), CDRL2 (Seq. ID No. 8), and CDRL3 (Seq. ID No. 9) or CDRL3 variant 1 (Seq. ID No. 10) or CDRL3 variant 2 (Seq. ID No. 11) or CDRL3 variant 3 (Seq. ID No. 12), or a combination or variant thereof, grafted into a human acceptor light chain framework. In one embodiment, the human acceptor light chain framework is derived from an amino acid sequence encoded by a human IGKV (VL kappa) gene for framework 1, 2, and 3, and an IGKJ gene for framework 4. In one embodiment, the human acceptor light chain framework is derived from an amino acid sequence encoded by a human IGLV (VL lambda) gene for framework 1, 2, and 3, and an IGLJ gene for framework 4. Non-limiting examples of human light chain IGKV and IGKJ acceptor framework regions are provided, for example, in Table 4, and non-limiting examples of human light chain IGLV and IGLJ acceptor framework regions are provide, for example, Table 5.

TABLE 4

Human IGKV and IGKJ Framework Regions

| Variable Light κ Chain FR Region | Seq. ID No. | Sequence |
| --- | --- | --- |
| O12 FR1 | 25 | DIQMTQSPSSLSASVGDRVTITC |
| O12 FR2 | 26 | WYQQKPGKAPKLLIY |
| O12 FR3 | 27 | GVPSRFSGSGSGTDFTLTISSLQPEDFATYYC |
| O2 FR1 | 28 | DIQMTQSPSSLSASVGDRVTITC |
| O2 FR2 | 29 | WYQQKPGKAPKLLIY |
| O2 FR3 | 30 | GVPSRFSGSGSGTDFTLTISSLQPEDFATYYC |
| O18 FR1 | 31 | DIQMTQSPSSLSASVGDRVTITC |
| O18 FR2 | 32 | WYQQKPGKAPKLLIY |
| O18 FR3 | 33 | GVPSRFSGSGSGTDFTFTISSLQPEDIATYYC |
| O8 FR1 | 34 | DIQMTQSPSSLSASVGDRVTITC |
| O8 FR2 | 35 | WYQQKPGKAPKLLIY |
| O8 FR3 | 36 | GVPSRFSGSGSGTDFTFTISSLQPEDIATYYC |
| A20 FR1 | 37 | DIQMTQSPSSLSASVGDRVTITC |
| A20 FR2 | 38 | WYQQKPGKVPKLLIY |
| A20 FR3 | 39 | GVPSRFSGSGSGTDFTLTISSLQPEDVATYYC |
| A30 FR1 | 40 | DIQMTQSPSSLSASVGDRVTITC |
| A30 FR2 | 41 | WYQQKPGKAPKRLIY |
| A30 FR3 | 42 | GVPSRFSGSGSGTEFTLTISSLQPEDFATYYC |
| L14 FR1 | 43 | NIQMTQSPSAMSASVGDRVTITC |
| L14 FR2 | 44 | WFQQKPGKVPKHLIY |
| L14 FR3 | 45 | GVPSRFSGSGSGTEFTLTISSLQPEDFATYYC |
| L1 FR1 | 46 | DIQMTQSPSSLSASVGDRVTITC |
| L1 FR2 | 47 | WFQQKPGKAPKSLIY |
| L1 FR3 | 48 | GVPSRFSGSGSGTDFTLTISSLQPEDFATYYC |
| L15 FR1 | 49 | DIQMTQSPSSLSASVGDRVTITC |
| L15 FR2 | 50 | WYQQKPEKAPKSLIY |
| L15 FR3 | 51 | GVPSRFSGSGSGTDFTLTISSLQPEDFATYYC |
| L4 FR1 | 52 | AIQLTQSPSSLSASVGDRVTITC |
| L4 FR2 | 53 | WYQQKPGKAPKLLIY |
| L4 FR3 | 54 | GVPSRFSGSGSGTDFTLTISSLQPEDFATYYC |
| L18 FR1 | 55 | AIQLTQSPSSLSASVGDRVTITC |
| L18 FR2 | 56 | WYQQKPGKAPKLLIY |
| L18 FR3 | 57 | GVPSRFSGSGSGTDFTLTISSLQPEDFATYYC |
| L5 FR1 | 58 | DIQMTQSPSSVSASVGDRVTITC |

TABLE 4-continued

Human IGKV and IGKJ Framework Regions

| Variable Light κ Chain FR Region | Seq. ID No. | Sequence |
|---|---|---|
| L5 FR2 | 59 | WYQQKPGKAPKLLIY |
| L5 FR3 | 60 | GVPSRFSGSGSGTDFTLTISSLQPEDFATYYC |
| L19 FR1 | 61 | DIQMTQSPSSVSASVGDRVTITC |
| L19 FR2 | 62 | WYQQKPGKAPKLLIY |
| L19 FR3 | 63 | GVPSRFSGSGSGTDFTLTISSLQPEDFATYYC |
| L8 FR1 | 64 | DIQLTQSPSFLSASVGDRVTITC |
| L8 FR2 | 65 | WYQQKPGKAPKLLIY |
| L8 FR3 | 66 | GVPSRFSGSGSGTEFTLTISSLQPEDFATYYC |
| L23 FR1 | 67 | AIRMTQSPFSLSASVGDRVTITC |
| L23 FR2 | 68 | WYQQKPAKAPKLFIY |
| L23 FR3 | 69 | GVPSRFSGSGSGTDYTLTTSSLQPEDFATYYC |
| L9 FR1 | 70 | AIRMTQSPSSFSASTGDRVTITC |
| L9 FR2 | 71 | WYQQKPGKAPKLLIY |
| L9 FR3 | 72 | GVPSRFSGSGSGTDFTLTTSCLQSEDFATYYC |
| L24 FR1 | 73 | VIWMTQSPSLLSASTGDRVTISC |
| L24 FR2 | 74 | WYQQKPGKAPELLTY |
| L24 FR3 | 75 | GVPSRFSGSGSGTDFTLTISCLQSEDFATYYC |
| L11 FR1 | 76 | AIQMTQSPSSLSASVGDRVTITC |
| L11 FR2 | 77 | WYQQKPGKAPKLLIY |
| L11 FR3 | 78 | GVPSRFSGSGSGTDFTLTISSLQPEDFATYYC |
| L12 FR1 | 79 | DIQMTQSPSTLSASVGDRVTITC |
| L12 FR2 | 80 | WYQQKPGKAPKLLIY |
| L12 FR3 | 81 | GVPSRFSGSGSGTEFTLTISSLQPDDFATYYC |
| O11 FR1 | 82 | DIVMTQTPLSLPVTPGEPASISC |
| O11 FR2 | 83 | WYLQKPGQSPQLLIY |
| O11 FR3 | 84 | GVPDRFSGSGSGTDFTLKISRVEAEDVGVYYC |
| O1 FR1 | 85 | DIVMTQTPLSLPVTPGEPASISC |
| O1 FR2 | 86 | WYLQKPGQSPQLLIY |
| O1 FR3 | 87 | GVPDRFSGSGSGTDFTLKISRVEAEDVGVYYC |
| A17 FR1 | 88 | DVVMTQSPLSLPVTLGQPASISC |
| A17 FR2 | 89 | WFQQRPGQSPRRLIY |
| A17 FR3 | 90 | GVPDRFSGSGSGTDFTLKISRVEAEDVGVYYC |
| A1 FR1 | 91 | DVVMTQSPLSLPVTLGQPASISC |
| A1 FR2 | 92 | WFQQRPGQSPRRLIY |
| A1 FR3 | 93 | GVPDRFSGSGSGTDFTLKISRVEAEDVGVYYC |
| A18 FR1 | 94 | DIVMTQTPLSLSVTPGQPASISC |
| A18 FR2 | 95 | WYLQKPGQSPQLLIY |

TABLE 4-continued

Human IGKV and IGKJ Framework Regions

| Variable Light κ Chain FR Region | Seq. ID No. | Sequence |
|---|---|---|
| A18 FR3 | 96 | GVPDRFSGSGSGTDFTLKISRVEAEDVGVYYC |
| A2 FR1 | 97 | DIVMTQTPLSLSVTPGQPASISC |
| A2 FR2 | 98 | WYLQKPGQPPQLLIY |
| A2 FR3 | 99 | GVPDRFSGSGSGTDFTLKISRVEAEDVGVYYC |
| A19 FR1 | 100 | DIVMTQSPLSLPVTPGEPASISC |
| A19 FR2 | 101 | WYLQKPGQSPQLLIY |
| A19 FR3 | 102 | GVPDRFSGSGSGTDFTLKISRVEAEDVGVYYC |
| A3 FR1 | 103 | DIVMTQSPLSLPVTPGEPASISC |
| A3 FR2 | 104 | WYLQKPGQSPQLLIY |
| A3 FR3 | 105 | GVPDRFSGSGSGTDFTLKISRVEAEDVGVYYC |
| A23 FR1 | 106 | DIVMTQTPLSSPVTLGQPASISC |
| A23 FR2 | 107 | WLQQRPGQPPRLLIY |
| A23 FR3 | 108 | GVPDRFSGSGSGAGTDFTLKISRVEAEDVGVYYC |
| A27 FR1 | 109 | EIVLTQSPGTLSLSPGERATLSE |
| A27 FR2 | 110 | WYQQKPGQAPRLLIY |
| A27 FR3 | 111 | GIPDRFSGSGSGTDFTLTISRLEPEDFAVYYC |
| A11 FR1 | 112 | EIVLTQSPATLSLSPGERATLSC |
| A11 FR2 | 113 | WYQQKPGLAPRLLIY |
| A11 FR3 | 114 | GIPDRFSGSGSGTDFTLTISRLEPEDFAVYYC |
| L2 FR1 | 115 | EIVMTQSPATLSVSPGERATLSC |
| L2 FR2 | 116 | WYQQKPGQAPRLLIY |
| L2 FR3 | 117 | GIPARFSGSGSGTEFTLTISSLQSEDFAVYYC |
| L16 FR1 | 118 | EIVMTQSPATLSVSPGERATLSC |
| L16 FR2 | 119 | WYQQKPGQAPRLLIY |
| L16 FR3 | 120 | GIPARFSGSGSGTEFTLTISSLQSEDFAVYYC |
| L6 FR1 | 121 | EIVLTQSPATLSLSPGERATLSC |
| L6 FR2 | 122 | WYQQKPGQAPRLLIY |
| L6 FR3 | 123 | GIPARFSGSGSGTDFTLTISSLEPEDFAVYYC |
| L20 FR1 | 124 | EIVLTQSPATLSLSPGERATLSC |
| L20 FR2 | 125 | WYQQKPGQAPRLLIY |
| L20 FR3 | 126 | GIPARFSGSGPGTDFTLTISSLEPEDFAVYYC |
| L25 FR1 | 127 | EIVMTQSPATLSLSPGERATLSC |
| L25 FR2 | 128 | WYQQKPGQAPRLLIY |
| L25 FR3 | 129 | GIPARFSGSGSGTDFTLTISSLQPEDFAVYYC |
| B3 FR1 | 130 | DIVMTQSPDSLAVSLGERATINC |
| B3 FR2 | 131 | WYQQKPGQPPKLLIY |
| B3 FR3 | 132 | GVPDRFSGSGSGTDFTLTISSLQAEDVAVYYC |

TABLE 4-continued

Human IGKV and IGKJ Framework Regions

| Variable Light κ Chain FR Region | Seq. ID No. | Sequence |
|---|---|---|
| B2 FR1 | 133 | ETTLTQSPAFMSATPGDKVNISC |
| B2 FR2 | 134 | WYQQKPGEAAIFIIQ |
| B2 FR3 | 135 | GIPPRFSGSGYGTDFTLTINNIESEDAAYYFC |
| A26 FR1 | 136 | EIVLTQSPDFQSVTPKEKVTITC |
| A26 FR2 | 137 | WYQQKPDQSPKLLIK |
| A26 FR3 | 138 | GVPSRFSGSGSGTDFTLTINSLEAEDAATYYC |
| A10 FR1 | 139 | EIVLTQSPDFQSVTPKEKVTITC |
| A10 FR2 | 140 | WYQQKPDQSPKLLIK |
| A10 FR3 | 141 | GVPSRFSGSGSGTDFTLTINSLEAEDAATYYC |
| A14 FR1 | 142 | DvvMTQSPAFLSVTPGEKVTITC |
| A14 FR2 | 143 | WYQQKPDQAPKLLIK |
| A14 FR3 | 144 | GVPSRFSGSGSGTDFTFTISSLEAEDAATYYC |
| JK1 FR4 | 145 | FGQGTKVEIK |
| JK2 FR4 | 146 | FGQGTKLEIK |
| JK3 FR4 | 147 | FGPGTKVDIK |
| JK4 FR4 | 148 | FGGGTKVEIK |
| JK5 FR4 | 149 | FGQGTRLEIK |

TABLE 5

Human IGLV and IGLJ Framework Regions

| Variable Light λ Chain FR Region | Seq. ID No. | Sequence |
|---|---|---|
| 1a FR1 | 150 | QSVLTQPPSVSEAPRQRVTISC |
| 1a FR2 | 151 | WYQQLPGKAPKLLIY |
| 1a FR3 | 152 | GVSDRFSGSKSG-TSASLAISGLQSEDEADYYC |
| 1e FR1 | 153 | QSVLTQPPSVSGAPGQRVTISC |
| 1e FR2 | 154 | WYQQLPGTAPKLLIY |
| 1e FR3 | 155 | GVPDRFSGSKSG-TSASLAITGLQAEDEADYYC |
| 1c FR1 | 156 | QSVLTQPPSASGTPGQRVTISC |
| 1c FR2 | 157 | WYQQLPGTAPKLLIY |
| 1c FR3 | 158 | GVPDRFSGSKSG-TSASLAISGLQSEDEADYYC |
| 1g FR1 | 159 | QSVLTQPPSASGTPGQRVTISC |
| 1g FR2 | 160 | WYQQLPGTAPKLLIY |
| 1g FR3 | 161 | GVPDRFSGSKSG-TSASLAISGLRSEDEADYYC |
| 1b FR1 | 162 | QSVLTQPPSVSAAPGQKVTISC |
| 1b FR2 | 163 | WYQQLPGTAPKLLIY |
| 1b FR3 | 164 | GIPDRFSGSKSG-TSATLGITGLQTGDEADYYC |

TABLE 5-continued

Human IGLV and IGLJ Framework Regions

| Variable Light λ Chain FR Region | Seq. ID No. | Sequence |
|---|---|---|
| 2c FR1 | 165 | QSALTQPPSASGSPGQSVTISC |
| 2c FR2 | 166 | WYQQHPGKAPKLMIY |
| 2c FR3 | 167 | GVPDRFSGSKSG-NTASLTVSGLQAEDEADYYC |
| 2e FR1 | 168 | QSALTQPRSVSGSPGQSVTISC |
| 2e FR2 | 169 | WYQQHPGKAPKLMIY |
| 2e FR3 | 170 | GVPDRFSGSKSG-NTASLTISGLQAEDEADYYC |
| 2a2 FR1 | 171 | QSALTQPASVSGSPGQSITISC |
| 2a2 FR2 | 172 | WYQQHPGKAPKLMIY |
| 2a2 FR3 | 173 | GVSNRFSGSKSG-NTASLTISGLQAEDEADYYC |
| 2d FR1 | 174 | QSALTQPPSVSGSPGQSVTISC |
| 2d FR2 | 175 | WYQQPPGTAPKLMIY |
| 2d FR3 | 176 | GVPDRFSGSKSG-NTASLTISGLQAEDEADYYC |
| 2b2 FR1 | 177 | QSALTQPASVSGSPGQSITISC |
| 2b2 FR2 | 178 | WYQQHPGKAPKLMIY |
| 2b2 FR3 | 179 | GVSNRFSGSKSG-NTASLTISGLQAEDEADYYC |
| 3r FR1 | 180 | SYELTQPPSVSVSPGQTASITC |
| 3r FR2 | 181 | WYQQKPGQSPVLVIY |
| 3r FR3 | 182 | GIPERFSGSNSG-NTATLTISGTQAMDEADYYC |
| 3j FR1 | 183 | SYELTQPLSVSVALGQTARITC |
| 3j FR2 | 184 | WYQQKPGQAPVLVIY |
| 3j FR3 | 185 | GIPERFSGSNSG-NTATLTISRAQAGDEADYYC |
| 3p FR1 | 186 | SYELTQPPSVSVSPGQTARITC |
| 3p FR2 | 187 | WYQQKSGQAPVLVIY |
| 3p FR3 | 188 | GIPERFSGSSSG-TMATLTISGAQVEDEADYYC |
| 3a FR1 | 189 | SYELTQPPSVSVSLGQMARITC |
| 3a FR2 | 190 | WYQQKPGQFPVLVIY |
| 3a FR3 | 191 | GIPERFSGSSSG-TIVTLTISGVQAEDEADYYC |
| 3l FR1 | 192 | SSELTQDPAVSVALGQTVRITC |
| 3l FR2 | 193 | WYQQKPGQAPVLVIY |
| 3l FR3 | 194 | GIPDRFSGSSSG-NTASLTITGAQAEDEADYYC |
| 3h FR1 | 195 | SYVLTQPPSVSVAPGKTARITC |
| 3h FR2 | 196 | WYQQKPGQAPVLVIY |
| 3h FR3 | 197 | GIPERFSGSNSG-NTATLTISRVEAGDEADYYC |
| 3e FR1 | 198 | SYELTQLPSVSVSPGQTARITC |
| 3e FR2 | 199 | WYQQKPGQAPELVIY |
| 3e FR3 | 200 | GIPERFSGSTSG-NTTTLTISRVLTEDEADYYC |
| 3m FR1 | 201 | SYELMQPPSVSVSPGQTARITC |
| 3m FR2 | 202 | WYQQKPGQAPVLVIY |

TABLE 5-continued

Human IGLV and IGLJ Framework Regions

Variable Light λ
Chain FR Region    Seq. ID No.    Sequence

| Chain FR Region | Seq. ID No. | Sequence |
|---|---|---|
| 3m FR3 | 203 | GIPERFSGSSSG-TTVTLTISGVQAEDEADYYC |
| 2-19 FR1 | 204 | SYELTQPSSVSVSPGQTARITC |
| 2-19 FR2 | 205 | WFQQKPGQAPVLVIY |
| 2-19 FR3 | 206 | GIPERFSGSSSG-TTVTLTISGAQVEDEADYYC |
| 4c FR1 | 207 | LPVLTQPPSASALLGASIKLTC |
| 4c FR2 | 208 | WYQQRPGRSPQYIMK |
| 4c FR3 | 209 | GIPDRFMGSSSG-ADRYLTFSNLQSDDENEYHC |
| 4a FR1 | 210 | QPVLTQSSSASASLGSSVKLTC |
| 4a FR2 | 211 | WHQQQPGKAPRYLMK |
| 4a FR3 | 212 | GVPDRFSGSSSG-ADRYLTISNLQLEDEADYYC |
| 4b FR1 | 213 | QLVLTQSPSASASLGASVKLTC |
| 4h FR2 | 214 | WHQQQPEKGPRYLMK |
| 4b FR3 | 215 | GIPDRFSGSSSG-AERYLTISSLQSEDEADYYC |
| 5e FR1 | 216 | QPVLTQPPSSSASPGESARLTC |
| 5e FR2 | 217 | WYQQKPGSPPRYLLY |
| 5e FR3 | 218 | GVPSRFSGSKDASANTGILLISGLQSEDEADYYC |
| 5c FR1 | 219 | QAVLTQPASLSASPGASASLTC |
| 5c FR2 | 220 | WYQQKPGSPPQYLLR |
| 5c FR3 | 221 | GVPSRFSGSKDASANAGILLISGLQSEDEADYYC |
| 5b FR1 | 222 | QPVLTQPSSHSASSGASVRLTC |
| 5b FR2 | 223 | WYQQKPGNPPRYLLY |
| 5b FR3 | 224 | GVPSRFSGSNDASANAGILRISGLQPEDEADYYC |
| 6a FR1 | 225 | NFMLTQPHSVSESPGKTVTISC |
| 6a FR2 | 226 | WYQQRPGSSPTTVIY |
| 6a FR3 | 227 | GVPDRFSGSIDSSSNSASLTISGLKTEDEADYYC |
| 7a FR1 | 228 | QTVVTQEPSLTVSPGGTVTLTC |
| 7a FR2 | 229 | WFQQKPGQAPRALIY |
| 7a FR3 | 230 | WTPARFSGSLLG-GKAALTLSGVQPEDEAEYYC |
| 7b FR1 | 231 | QAVVTQEPSLTVSPGGTVTLTC |
| 7b FR2 | 232 | WFQQKPGQAPRTLIY |
| 7b FR3 | 233 | WTPARFSGSLLG-GKAALTLSGAQPEDEAEYYC |
| 8a FR1 | 234 | QTVVTQEPSFSVSPGGTVTLTC |
| 8a FR2 | 235 | WYQQTPGQAPRTLIY |
| 8a FR3 | 236 | GVPDRFSGSILG-NKAALTITGAQADDESDYYC |
| 9a FR1 | 237 | QPVLTQPPSASASLGASVTLTC |
| 9a FR2 | 238 | WYQQRPGKGPRFVMR |
| 9a FR3 | 239 | GIPDRFSVLGSG-LNRYLTIKNIQEEDESDYHC |
| 10a FR1 | 240 | QAGLTQPPSVSKGLRQTATLTC |

TABLE 5-continued

Human IGLV and IGLJ Framework Regions

| Variable Light λ Chain FR Region | Seq. ID No. | Sequence |
|---|---|---|
| 10a FR2 | 241 | WLQQHQGHPPKLLSY |
| 10a FR3 | 242 | GISERLSASRSG-NTASLTITGLQPEDEADYYC |
| JL1 FR4 | 243 | FGTGTKVTVL |
| JL2 FR4 | 244 | FGGGTKLTVL |
| JL3 FR4 | 245 | FGGGTKLTVL |
| JL7 FR4 | 246 | FGGGTQLTVL |

The immunoglobulin constant light chain region for use in the present invention is determined by the variable light chain the CDRs are grafted into. For example, if the variable light chain FR regions are derived from the immunoglobulin kappa light chain variable region, then a constant light chain region from an immunoglobulin kappa light chain constant region (IGKC) can be used to produce a light chain VL-CL chain. An IGKC that may be used in the present invention includes Seq. ID No. 247 in Table 6 below. Conversely, when the framework region is immunoglobulin lambda light chain variable region, then an immunoglobulin lambda light chain constant region (IGLC) may be used to produce a lambda VL-CL light chain. An immunoglobulin lambda light chain constant region that may be used in the present invention includes (Seq. ID No. 248) in Table 6 below, and allelic variants thereof, which are generally known in the art, for example as identified in OMIM entry 147200 for IGKC variants and 147220 for IGLC variants.

TABLE 6

Sequence of Human Immunoglobulin Light Chain Constant Regions

| Ig Light Chain Constant Region | Seq. ID No. | Sequence |
|---|---|---|
| Ig Kappa Constant Region (IGKC) | 247 | TVAAPSVFIFPPSDEQLKSGTASVVCLLNN FYPREAKVQWKVDNALQSGNSQESVTEQDS KDSTYSLSSTLTLSKADYEKHKVYACEVTH QGLSSPVTKSFNRGEC |
| Ig Lambda Constant Region (IGLC) | 248 | QPKAAPSVTLFPPSSEELQANKATLVCLIS DFYPGAVTVAWKADSSPVKAGVETTTPSKQ SNNKYAASSYLSLTPEQWKSHRSYSCQVTH EGSTVEKTVAPTECS |

In one embodiment, the anti-aP2 monoclonal antibody has at least one heavy chain CDR selected from CDRH1 (Seq. ID No. 14), CDRH1 variant 1 (Seq. ID No. 15), CDRH2 (Seq. ID No. 16), CDRH2 variant 1 (Seq. ID No. 17), CDRH2 variant 2 (Seq. ID No. 18), CDRH3 (Seq. ID No 19), CDRH3 variant 1 (Seq. ID No. 20), CHRH3 variant 2 (Seq. ID No. 21), or a combination or variant thereof, grafted into a human acceptor heavy chain framework. In one embodiment, the anti-aP2 monoclonal antibody comprises CDRs CDRH1 (Seq. ID No. 14), CDRH2 (Seq. ID No. 16), CDRH3 (Seq. ID No. 19), or variant thereof, grafted into a human acceptor heavy chain framework. In one embodiment, the anti-aP2 monoclonal antibody comprises CDRs CDRH1 (Seq. ID No. 14), CDRH2 variant 1 (Seq. ID No. 17), or CDRH3 variant 1 (Seq. ID No 20), or a variant thereof, grafted into a human acceptor heavy chain framework. In one embodiment, the anti-aP2 monoclonal antibody comprises CDRs CDRH1 variant 1 (Seq. ID No. 15) and CDRH2 variant 2 (Seq. ID No. 18), or a variant thereof, grafted into a human acceptor heavy chain framework. In one embodiment, the anti-aP2 monoclonal antibody comprises CDRs CDRH1 variant 1 (Seq. ID No. 15), CDRH2 variant 2 (Seq. ID No. 18), or CDRH3 variant 2 (Seq. ID No 21), or a variant thereof, grafted into a human acceptor heavy chain framework. In one embodiment, the human acceptor heavy chain framework is derived from an amino acid sequence encoded by a human IGHV gene for framework 1, 2, and 3, and an IGHJ gene for framework 4. Non-limiting examples of human heavy chain IGHV and IGHJ acceptor framework regions are provided, for example, in Table 7.

TABLE 7

Sequences of Human Immunoglobulin Heavy Chain Variable Regions

| Heavy Chain Variable FR Regions | Seq. ID No. | Sequence |
|---|---|---|
| 1-02 FR1 | 249 | QVQLVQSGAEVKKPGASVKVSCKAS |
| 1-02 FR2 | 250 | WVRQAPGQGLEWMG |
| 1-02 FR3 | 251 | RVTMTRDTSISTAYMELSRLRSDDTAVYYCAR |
| 1-03 FR1 | 252 | QVQLVQSGAEVKKPGASVKVSCKAS |

TABLE 7-continued

Sequences of Human Immunoglobulin Heavy Chain Variable Regions

| Heavy Chain Variable FR Regions | Seq. ID No. | Sequence |
|---|---|---|
| 1-03 FR2 | 253 | WVRQAPGQRLEWMG |
| 1-03 FR3 | 254 | RVTITRDTSASTAYMELSSLRSEDTAVYYCAR |
| 1-08 FR1 | 255 | QVQLVQSGAEVKKPGASVKVSCKAS |
| 1-08 FR2 | 256 | WVRQATGQGLEWMG |
| 1-08 FR3 | 257 | RVTMTRNTSISTAYMELSSLRSEDTAVYYCAR |
| 1-18 FR1 | 258 | QVQLVQSGAEVKKPGASVKVSCKAS |
| 1-18 FR2 | 259 | WVRQAPGQGLEWMG |
| 1-18 FR3 | 260 | RVTMTTDTSTSTAYMELRSLRSDDTAVYYCAR |
| 1-24 FR1 | 261 | QVQLVQSGAEVKKPGASVKVSCKVS |
| 1-24 FR2 | 262 | WVRQAPGKGLEWMG |
| 1-24 FR3 | 263 | RVTMTEDTSTDTAYMELSSLRSEDTAVYYCAT |
| 1-45 FR1 | 264 | QMQLVQSGAEVKKTGSSVKVSCKAS |
| 1-45 FR2 | 265 | WVRQAPGQALEWMG |
| 1-45 FR3 | 266 | RVTITRDRSMSTAYMELSSLRSEDTAMYYCAR |
| 1-46 FR1 | 267 | QVQLVQSGAEVKKPGASVKVSCKAS |
| 1-46 FR2 | 268 | WVRQAPGQGLEWMG |
| 1-46 FR3 | 269 | RVTMTRDTSTSTVYMELSSLRSEDTAVYYCAR |
| 1-58 FR1 | 270 | QMQLVQSGPEVKKPGTSVKVSCKAS |
| 1-58 FR2 | 271 | WVRQARGQRLEWIG |
| 1-58 FR3 | 272 | RVTITRDMSTSTAYMELSSLRSEDTAVYYCAA |
| 1-69 FR1 | 273 | QVQLVQSGAEVKKPGSSVKVSCKAS |
| 1-69 FR2 | 274 | WVRQAPGQGLEWMG |
| 1-69 FR3 | 275 | RVTITADESTSTAYMELSSLRSEDTAVYYCAR |
| 1-e FR1 | 276 | QVQLVQSGAEVKKPGSSVKVSCKAS |
| 1-e FR2 | 277 | WVRQAPGQGLEWMG |
| 1-e FR3 | 278 | RVTITADKSTSTAYMELSSLRSEDTAVYYCAR |
| 1-f FR1 | 279 | EVQLVQSGAEVKKPGATVKISCKVS |
| 1-f FR2 | 280 | WVQQAPGKGLEWMG |
| 1-f FR3 | 281 | RVTITADTSTDTAYMELSSLRSEDTAVYYCAT |
| 2-05 FR1 | 282 | QITLKESGPTLVKPTQTLTLTCTFS |
| 2-05 FR2 | 283 | WIRQPPGKALEWLA |
| 2-05 FR3 | 284 | RLTITKDTSKNQVVLTMTNMDPVDTATYYCAHR |
| 2-26 FR1 | 285 | QVTLKESGPVLVKPTETLTLTCTVS |
| 2-26 FR2 | 286 | WIRQPPGKALEWLA |
| 2-26 FR3 | 287 | RLTISKDTSKSQVVLTMTNMDPVDTATYYCARI |
| 2-70 FR1 | 288 | QVTLKESGPALVKPTQTLTLTCTFS |
| 2-70 FR2 | 289 | WIRQPPGKALEWLA |
| 2-70 FR3 | 290 | RLTISKDTSKNQVVLTMTNMDPVDTATYYCARI |
| 3-07 FR1 | 291 | EVQLVESGGGLVQPGGSLRLSCAAS |
| 3-07 FR2 | 292 | WVRQAPGKGLEWVA |
| 3-07 FR3 | 293 | RFTISRDNAKNSLYLQMNSLRAEDTAVYYCAR |
| 3-09 FR1 | 294 | EVQLVESGGGLVQPGRSLRLSCAAS |
| 3-09 FR2 | 295 | WVRQAPGKGLEWVS |
| 3-09 FR3 | 296 | RFTISRDNAKNSLYLQMNSLRAEDTALYYCAKD |
| 3-11 FR1 | 297 | QVQLVESGGGLVKPGGSLRLSCAAS |
| 3-11 FR2 | 298 | WIRQAPGKGLEWVS |
| 3-11 FR3 | 299 | RFTISRDNAKNSLYLQMNSLRAEDTAVYYCAR |
| 3-13 FR1 | 300 | EVQLVESGGGLVQPGGSLRLSCAAS |
| 3-13 FR2 | 301 | WVRQATGKGLEWVS |
| 3-13 FR3 | 302 | RFTISRENAKNSLYLQMNSLRAGDTAVYYCAR |
| 3-15 FR1 | 303 | EVQLVESGGGLVKPGGSLRLSCAAS |
| 3-15 FR2 | 304 | WVRQAPGKGLEWVG |
| 3-15 FR3 | 305 | RFTISRDDSKNTLYLQMNSLKTEDTAVYYCTT |
| 3-20 FR1 | 306 | EVQLVESGGGVVRPGGSLRLSCAAS |
| 3-20 FR2 | 307 | WVRQAPGKGLEWVS |
| 3-20 FR3 | 308 | RFTISRDNAKNSLYLQMNSLRAEDTALYHCAR |
| 3-21 FR1 | 309 | EVQLVESGGGLVKPGGSLRLSCAAS |
| 3-21 FR2 | 310 | WVRQAPGKGLEWVS |
| 3-21 FR3 | 311 | RFTISRDNAKNSLYLQMNSLRAEDTAVYYCAR |
| 3-23 FR1 | 312 | EVQLLESGGGLVQPGGSLRLSCAAS |
| 3-23 FR2 | 313 | WVRQAPGKGLEWVS |
| 3-23 FR3 | 314 | RFTISRDNSKNTLYLQMNSLRAEDTAVYYCAK |
| 3-30 FR1 | 315 | QVQLVESGGGVVQPGRSLRLSCAAS |
| 3-30 FR2 | 316 | WVRQAPGKGLEWVA |
| 3-30 FR3 | 317 | RFTISRDNSKNTLYLQMNSLRAEDTAVYYCAK |
| 3-30.3 FR1 | 318 | QVQLVESGGGVVQPGRSLRLSCAAS |
| 3-30.3 FR2 | 319 | WVRQAPGKGLEWVA |
| 3-30.3 FR3 | 320 | RFTISRDNSKNTLYLQMNSLRAEDTAVYYCAR |
| 3-3 FR1 | 321 | QVQLVESGGGVVQPGRSLRLSCAAS |
| 3-30.5 FR2 | 322 | WVRQAPGKGLEWVA |
| 3-30.5 FR3 | 323 | RFFISRDNSKNTLYLQMNSLRAEDTAVYYCAK |
| 3-3 FR13 | 324 | QVQLVESGGGVVQPGRSLRLSCAAS |

TABLE 7-continued

Sequences of Human Immunoglobulin Heavy Chain Variable Regions

| Heavy Chain Variable FR Regions | Seq. ID No. | Sequence |
|---|---|---|
| 3-33 FR2 | 325 | WVRQAPGKGLEWVA |
| 3-33 FR3 | 326 | RFTISRDNSKNTLYLQMNSLRAEDTAVYYCAR |
| 3-43 FR1 | 327 | EVQLVESGGVVVQPGGSLRLSCAAS |
| 3-43 FR2 | 328 | WVRQAPGKGLEWVS |
| 3-43 FR3 | 329 | RFTISRDNSKNSLYLQMNSLRTEDTALYYCAKD |
| 3-48 FR1 | 330 | EVQLVESGGGLVQPGGSLRLSCAAS |
| 3-48 FR2 | 331 | WVRQAPGKGLEWVS |
| 3-48 FR3 | 332 | RFTISRDNAKNSLYLQMNSLRDEDTAVYYCAR |
| 3-49 FR1 | 333 | EVQLVESGGGLVQPGRSLRLSCTAS |
| 3-49 FR2 | 334 | WFRQAPGKGLEWVG |
| 3-49 FR3 | 335 | RFTISRDGSKSIAYLQMNSLKTEDTAVYYCTR |
| 3-53 FR1 | 336 | EVQLVETGGGLIQPGGSLRLSCAAS |
| 3-53 FR2 | 337 | WVRQAPGKGLEWVS |
| 3-53 FR3 | 338 | RFFISRDNSKNTLYLQMNSLRAEDTAVYYCAR |
| 3-64 FR1 | 339 | EVQLVESGGGLVQPGGSLRLSCAAS |
| 3-64 FR2 | 340 | WVRQAPGKGLEYVS |
| 3-64 FR3 | 341 | RFTISRDNSKNTLYLQMGSLRAEDMAVYYCAR |
| 3-66 FR1 | 342 | EVQLVESGGGLVQPGGSLRLSCAAS |
| 3-66 FR2 | 343 | WVRQAPGKGLEWVS |
| 3-66 FR3 | 344 | RFTISRDNSKNTLYLQMNSLRAEDTAVYYCAR |
| 3-72 FR1 | 345 | EVQLVESGGGLVQPGGSLRLSCAAS |
| 3-72 FR2 | 346 | WVRQAPGKGLEWVG |
| 3-72 FR3 | 347 | RFTISRDDSKNSLYLQMNSLKTEDTAVYYCAR |
| 3-73 FR1 | 348 | EVQLVESGGGLVQPGGSLKLSCAAS |
| 3-73 FR2 | 349 | WVRQASGKGLEWVG |
| 3-73 FR3 | 350 | RFTISRDDSKNTAYLQMNSLKTEDTAVYYCTR |
| 3-74 FR1 | 351 | EVQLVESGGGLVQPGGSLRLSCAAS |
| 3-74 FR2 | 352 | WVRQAPGKGLVWVS |
| 3-74 FR3 | 353 | RFTISRDNAKNTLYLQMNSLRAEDTAVYYCAR |
| 3-d FR1 | 354 | EVQLVESRGVLVQPGGSLRLSCAAS |
| 3-d FR2 | 355 | WVRQAPGKGLEWVS |
| 3-d FR3 | 356 | RFTISRDNSKNTLHLQMNSLRAEDTAVYYCKK |
| 4-04 FR1 | 357 | QVQLQESGPGLVKPSGTLSLTCAVS |
| 4-04 FR2 | 358 | WVRQPPGKGLEWIG |
| 4-04 FR3 | 359 | RVTISVDKSKNQFSLKLSSVTAADTAVYYCAR |
| 4-28 FR1 | 360 | QVQLQESGPGLVKPSDTLSLTCAVS |
| 4-28 FR2 | 361 | WIRQPPGKGLEWIG |
| 4-28 FR3 | 362 | RVTMSVDTSKNQFSLKLSSVTAVDTAVYYCAR |
| 4-30.1 FR1 | 363 | QVQLQESGPGLVKPSQTLSLTCTVS |
| 4-30.1 FR2 | 364 | WIRQHPGKGLEWIG |
| 4-30.1 FR3 | 365 | RVTISVDTSKNQFSLKLSSVTAADTAVYYCAR |
| 4-3 FR1 | 366 | QLQLQESGSGLVKPSQTLSLTCAVS |
| 4-30.2 FR2 | 367 | WIRQPPGKGLEWIG |
| 4-30.2 FR3 | 368 | RVTISVDRSKNQFSLKLSSVTAADTAVYYCAR |
| 4-3 FR10.4 | 369 | QVQLQESGPGLVKPSQTLSLTCTVS |
| 4-30.4 FR2 | 370 | WIRQPPGKGLEWIG |
| 4-30.4 FR3 | 371 | RVTISVDTSKNQFSLKLSSVTAADTAVYYCAR |
| 4-3 FR1 | 372 | QVQLQESGPGLVKPSQTLSLTCTVS |
| 4-31 FR2 | 373 | WIRQHPGKGLEWIG |
| 4-31 FR3 | 374 | RVTISVDTSKNQFSLKLSSVTAADTAVYYCAR |
| 4-34 FR1 | 375 | QVQLQQWGAGLLKPSETLSLTCAVY |
| 4-34 FR2 | 376 | WIRQPPGKGLEWIG |
| 4-34 FR3 | 377 | RVTISVDTSKNQFSLKLSSVTAADTAVYYCAR |
| 4-39 FR1 | 378 | QLQLQESGPGLVKPSETLSLTCTVS |
| 4-39 FR2 | 379 | WIRQPPGKGLEWIG |
| 4-39 FR3 | 380 | RVTISVDTSKNQFSLKLSSVTAADTAVYYCAR |
| 4-59 FR1 | 381 | QVQLQESGPGLVKPSETLSLTCTVS |
| 4-59 FR2 | 382 | WIRQPPGKGLEWIG |
| 4-59 FR3 | 383 | RVTISVDTSKNQFSLKLSSVTAADTAVYYCAR |
| 4-61 FR1 | 384 | QVQLQESGPGLVKPSETLSLTCTVS |
| 4-61 FR2 | 385 | WIRQPPGKGLEWIG |
| 4-61 FR3 | 386 | RVTISVDTSKNQFSLKLSSVTAADTAVYYCAR |
| 4-b FR1 | 387 | QVQLQESGPGLVKPSETLSLTCAVS |
| 4-b FR2 | 388 | WIRQPPGKGLEWIG |
| 4-b FR3 | 389 | RVTISVDTSKNQFSLKLSSVTAADTAVYYCAR |
| 5-51 FR1 | 390 | EVQLVQSGAEVKKPGESLKISCKGS |
| 5-51 FR2 | 391 | WVRQMPGKGLEWMG |
| 5-51 FR3 | 392 | QVTISADKSISTAYLQWSSLKASDTAMYYCAR |
| 5-a FR1 | 393 | EVQLVQSGAEVKKPGESLRISCKGS |
| 5-a FR2 | 394 | WVRQMPGKGLEWMG |
| 5-a FR3 | 395 | HVTISADKSISTAYLQWSSLKASDTAMYYCAR |
| 6-01 FR1 | 396 | QVQLQQSGPGLVKPSQTLSLTCAIS |

TABLE 7-continued

Sequences of Human Immunoglobulin Heavy Chain Variable Regions

| Heavy Chain Variable FR Regions | Seq. ID No. | Sequence |
|---|---|---|
| 6-01 FR2 | 397 | WIRQSPSRGLEWLG |
| 6-01 FR3 | 398 | RITINPDTSKNQFSLQLNSVTPEDTAVYYCAR |
| 7-4.1 FR1 | 399 | QVQLVQSGSELKKPGASVKVSCKAS |
| 7-4.1 FR2 | 400 | WVRQAPGQGLEWMG |
| 7-4.1 FR3 | 401 | RFVFSLDTSVSTAYLQICSLKAEDTAVYYCAR |
| JH1 FR4 | 402 | WGQGTLVTVSS |
| JH2 FR4 | 403 | WGRGTLVTVSS |
| JH3 FR4 | 404 | WGQGTMVTVSS |
| JH4 FR4 | 405 | WGQGTLVTVSS |
| JH5 FR4 | 406 | WGQGTLVTVSS |
| JH6 FR4 | 407 | WGQGTTVTVSS |

The immunoglobulin heavy chain constant region for use in the present invention is determinant on the immunoglobulin class desired. All classes of immunoglobulins—IgG, IgD, IgA, IgM and IgE—are herein contemplated. For example, if the desired immunoglobulin is IgG, then the amino acid sequence encoding the IgG heavy chain constant region (IGGH) may be used. Immunoglobulin heavy chain constant regions that may be used in the present invention include those of IGGH, IGDH, IGAH, IGMH, and IGEH (Seq. ID Nos. 408-443) provided in Table 8 below, and allelic variants thereof, which are generally known in the art, for example as identified in OMIM entry 147100 for IGGH1 variants, 147110 for IGGH2 variants, 147120 for IGGH3 variants, 147130 for IGGH4 variants, 146900 for IGAH1 variants, 147000 for IGAH2 variants, 147180 for IGEH variants, 147020 for IGMH variants, 147170 for IGDH variants, all of which are incorporated by reference herein. In certain embodiment, the hinge region of a particular immunoglobulin class may be used in constructing the antibody contemplated herein. In one embodiment, the hinge region can be derived from a natural hinge region amino acid sequence as described in Table 8 (Seq. ID Nos. 409, 413, 417, 425, 429, 433, and 437), or a variant thereof. In one embodiment, the hinge region can be synthetically generated. Further contemplated herein are antibodies of immunoglobulin class IgA and IgM, which, in one embodiment, may be complexed with a joining polypeptide described in Table 9, or a variant thereof.

TABLE 8

Immunoglobulin Heavy Chain Constant Region

| Heavy Chain Constant Region | Seq. ID No. | Sequence |
|---|---|---|
| IGAH1 CH1 | 408 | ASPTSPKVFPLSLCSTQPDGNVVIACLVQGFFPQEPLSVTWSESGQG VTARNFPPSQDASGDLYTTSSQLTLPATQCLAGKSVTCHVKHYTNP SQDVTVPCP |
| IGAH1 Hinge | 409 | PSTPPTPSPSTPPTPSPS |
| IGAH1 CH2 | 410 | CCHPRLSLHRPALEDLLLGSEANLTCTLTGLRDASGVTFTWTPSSG KSAVQGPPERDLCGCYSVSSVLPGCAEPWNHGKTFTCTAAYTPESKT PLTATLSKS |
| IGAH1 CH3 | 411 | GNTFRPEVHLLPPPSEELALNELVTLTCLARGFSPKDVLVRWLQGS QELPREKYLTWASRQEPSQGTTTFAVTSILRVAAEDWKKGDTFSC MVGHEALPLAFTQKTIDRLA |
| IGAH2 CH1 | 412 | ASPTSPKVFPLSLDSTPQDGNVVVACLVQGFFPQEPLSVTWSESGQ NVTARNFPPSQDASGDLYTTSSQLTLPATQCPDGKSVTCHVKHYTN PSQDVTVPCP |
| IGAH2 Hinge | 413 | PPPPP |
| IGAH2 CH2 | 414 | CCHPRLSLHRPALEDLLLGSEANLTCTLTGLRDASGATFTWTPSSG KSAVQGPPERDLCGCYSVSSVLPGCAQPWNHGETFTCTAAHPELK TPLTANITKS |
| IGAH2 CH3 | 415 | GNTFRPEVHLLPPPSEELALNELVTLTCLARGFSPKDVLVRWLQGS QELPREKYLTWASRQEPSQGTTTFAVTSILRVAAEDWKKGDTFSC MVGHEALPLAFTQKTIDRLA |
| IGDH CH1 | 416 | APTKAPDVFPIISGCRHPKDNSPVVLACLITGYHPTSVTVTWYMGT QSQPQRTFPEIQRRDSYYIVITSSQLSTPLQQWRQGEYKCVVQHTAS KSKKEIFRWP |
| IGDH Hinge | 417 | ESPKAQASSVPTAQPQAEGSLAKATTAPATTRNTGRGGEEKKKEKE KEEQEERETKTP |
| IGDH CH2 | 418 | ECPSHTQPLGVYLLTPAVQDLWLRDKATFTCFVVGSDLKDAHLTW EVAGKVPTGGVEEGLLERHSNGSQSQHSRLTLPRSLWNAGTSVTCT LNHPSLPPQRLMALREP |

TABLE 8-continued

Immunoglobulin Heavy Chain Constant Region

| Heavy Chain Constant Region | Seq. ID No. | Sequence |
|---|---|---|
| IGDH CH3 | 419 | AAQAPVKLSLNLLASSDPPEAASWLLCEVSGFSPPNILLMWLEDQR EVNTSGFAPARPPPQPRSTTFWAWSVLRVPAPPSPQPATYTCVVSH EDSRTLLNASRSLEVS |
| IGEH CH1 | 420 | ASTQSPSVFPLTRCCKNIPSNATSVTLGCLATGYFPEPVMVTCDTGS LNGTTMTLPATTLTLSGHYATISLLTVSGAWAKQMFTCRVAHTPSS TDWVDNKTFS |
| IGEH CH2 | 421 | VCSRDFTPPTVKILQSSCDGGGHFPPTIQLLCLVSGYTPGTINITWLE DGQVMDVDLSTASTTQEGELASTQSELTLSQKHWLSDRTYTCQVT YQGHTFEDSTKKCA |
| IGEH CH3 | 422 | DSNPRGVSAYLSRPSPFTDLFIRKSPTITCLVVDLAPSKGTVNLTWSR ASGKPVNHSTRKEEKQRNGTLTVTSTLPVGTRDWIEGETYQCRVT HPHLPRALMRSTTKTS |
| IGEH CH4 | 423 | GPRAAPEVYAFATPEWPGSRDKRTLACLIQNFMPEDISVQWLHNEV QLPDARHSTTQPRKTKGSGFFVFSRLEVTRAEWEQKDEFICRAVHE AASPSQTVQRAVSVNP |
| IGGH1 CH1 | 424 | ASTKGPSVFPLAPSSKSTSGGTAALGCLVKDYFPEPVTVSWNSGAL TSGVHTFPAVXQSSGLYSLSSVVTVPSSSLGTQTYICNVNHKPSNTK VDKKV |
| IGGH1 Hinge | 425 | EPKSCDKTHTCPPCP |
| IGGH1 CH2 | 426 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAK |
| IGGH1 CH3 | 427 | GQPREPQVYTLPPSRDELTKNQVSLTCLVKGFYPSDIAVEWESNGQ PENNYKTTPPVLDSDGSFFLYSKLTVDKSRWQQGNVFSCSVMHEA LHNHYTQKSLSLSP |
| IGGH2 CH1 | 428 | ASTKGPSVFPLAPCSRSTSESTAALGCLVKDYFPEPVTVSWNSGALT SGVHTFPAVLQSSGLYSLSSVVTVPSSNFGTQTYTCNVDHKPSNTK VDKTV |
| IGGH2 Hinge | 429 | ERKCCVECPPCP |
| IGGH2 CH2 | 430 | APPVAGPSVFLFPPKPKDTLMISRTPEVTCVVVDVSHEDPEVQFNW YVDGVEVHNAKTKPREEQFNSTFRVVSVLTVVHQDWLNGKEYKC KVSNKGLPAPIEKTISKTK |
| IGGH2 CH3 | 431 | GQPREPQVYTLPPSREEMTKNQVSLTCLVKGFYPSDIAVEWESNGQ PENNYKTTPPMLDSDGSFFLYSKLTVDKSRWQOGNVFSCSVMHEA LHNHYTQKSLSLSP |
| IGGH3 CH1 | 432 | ASTKGPSVFPLAPCSRSTSGGTAALGCLVKDYFPEPVTVSWNSGAL TSGVHTFPAVLQSSGLYSLSSVVTVPSSSLGTQTYTCNVNHKPSNTK VDKRV |
| IGGH3 Hinge | 433 | ELKTPLGDTTHTCPRCPEPKSCDTPPPCPRCPEPKSCDTPPPCPRCPE PKSCDTPPPCPRCP |
| IGGH3 CH2 | 434 | APELLGGPSVFLFPPKPKDTLMISRTPEVTCVVVDVSHEDPEVQFK WYVDGVEVHNAKTKPREEQYNSTFRVVSVLTVLHQDWLNGKEYK CKVSNKALPAPIEKTISKTK |
| IGGH3 CH3 | 435 | GQPREPQVYTLPPSREEMTKNQVSLTCLVKGFYPSDIAVEWSSGQ PENNYNTTPPMLDSDGSFFLYSKLTVDKSRWQQGNIFSCSVMHEAL HNRFTQKSLSLSP |
| IGGH4 CH1 | 436 | ASTKGPSVFPLAPCSRSTSESTAALGCLVKDYFPEPVTVSVVNSGALT SGVHTFPAVLQSSGLYSLSSVVTWSSSLGTKTYTCNVDHKPSNTK VDKRV |
| IGGH4 Hinge | 437 | ESKYGPPCPSCP |
| IGGH4 CH2 | 438 | APEFLGGPSVFLFPPKPKDTLMISRTPEVTCVWDVSQEDPEVQFN WYVDGVEVHNAKTKPREEQFNSTYRVVSVLTVLHQDWLNGKEYK CKVSNKGLPSSIEKTISKAK |

TABLE 8-continued

Immunoglobulin Heavy Chain Constant Region

| Heavy Chain Constant Region | Seq. ID No. | Sequence |
|---|---|---|
| IGGH4 CH3 | 439 | GQPREPQVYTLPPSQEEMTKNQVSLTCLVKGFYPSDIAVEWESNGQ PENNYKTTPPVLDSDGSFFLYSRLTVDKSRWQEGNVFSCSVMHEAL HNHYTQKSLSLSL |
| IGMH CH1 | 440 | GSASAPTLFPLVSCENSPSDTSSVAVGCLAQDFLPDSITLSWKYKNN SDISSTRGFPSVLRGGKYAATSQVLLPSKDWQGTDEHVVCKVQH PNGNKEKNVPLP |
| IGMH CH2 | 441 | VIAELPPKVSVFVPPRDGFFGNPRKSKLICQATGFSPRQIQVSWLRE GKQVGSGVTTDQVQAEAKESGPTTYKVTSTLTIKESDWLGQSMFT CRVDHRGLTFQQNASSMCVP |
| IGMH CH3 | 442 | DQDTAIRVFAIPPSFASIFLTKSTKLTCLVTDLTTYDSVTISWTRQNG EAVKTHTNISESHPNATFSAVGEASICEDDWNSGERFTCTVTHTDLP SPLKQTISRPK |
| IGMH CH4 | 443 | GVALHRPDVYLLPPAREQLNLRESATITCLVTGFSPADVFVQWMQ RGQPLSPEKYVTSAPMPEPQAPGRYFAHSILTVSEEEWNTGETYTC VAHEALPNRVTERTVDKST |

TABLE 9

Joining Polypeptide for IgA and IgM Class Antibodies

| Ig Protein | Seq. ID No. | Sequence |
|---|---|---|
| Joining Polypeptide | 444 | QEDERIVLVDNKCKCARITSRIIRS SEDPNEDIVERNIRIIVPLNNRENIS DPTSPLRTRFVYHLSDLCKKC DPTEVELDNQIVTATQSNICDE DSATETCYTYDRNKCYTAVVPL VYGGETKMVETALTPDACYPD |

CDR and Human Framework Modifications

Riechmann et al., found that the transfer of the CDRs alone (as defined by Kabat (Kabat et al. (supra) and Wu et al., J. Exp. Med., 132, 211-250, 1970)) was not sufficient to provide satisfactory antigen binding activity in the CDR-grafted product. It was found that a number of framework residues have to be altered so that they correspond to those of the donor framework region. Proposed criteria for selecting which framework residues need to be altered are described in International Patent Application WO 90/07861, which is incorporated herein.

The substitution of non-human CDRs into a human variable domain framework is most likely to result in retention of the CDR's correct spatial orientation if the human variable domain framework adopts the same or similar conformation to the non-human variable framework from which the CDRs originated. This is achieved by obtaining the human variable domains from human antibodies whose framework sequences exhibit a high degree of sequence identity with the non-human variable framework domains from which the CDRs were derived. As described above, the heavy and light chain variable framework regions can be derived from the same or different human antibody sequences. The human antibody sequences can be the sequences of naturally occurring human antibodies or can be consensus sequences of several human antibodies. See Kettleborough et al, Protein Engineering 4:773 (1991); Kolbinger et al., Protein Engineering 6:971 (1993) and Carter et al, WO 92/22653.

Having identified the complementarity determining regions of the non-human donor immunoglobulin and appropriate human acceptor immunoglobulins, the next step is to determine which, if any, residues from these components should be substituted to optimize the properties of the resulting humanized antibody. In general, substitution of human amino acid residues with non-human amino acid residues should be minimized, because introduction of non-human residues increases the risk of the antibody eliciting a human-anti-donor-antibody (HADA) response in humans. Art-recognized methods of determining immune response can be performed to monitor a HADA response in a particular host or during clinical trials. Hosts administered humanized antibodies can be given an immunogenicity assessment at the beginning and throughout the administration of said therapy. The HADA response is measured, for example, by detecting antibodies to the humanized therapeutic reagent, in serum samples from the host using a method known to one in the art, including surface plasmon resonance technology (BIACORE) and/or solid-phase ELISA analysis.

The selection of amino acid residues for substitution is determined, in part, by computer modeling. Computer hardware and software are described herein for producing three-dimensional images of immunoglobulin molecules. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 500% sequence identity are selected for modeling, and preferably those sharing at least 60%, 70%, 80%, 90%, sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

The selection of amino acid residues for substitution can also be determined, in part, by examination of the characteristics of the amino acids at particular locations, or empirical observation of the effects of substitution or mutagenesis of particular amino acids. For example, when an amino acid differs between a donor variable region framework residue and a selected human variable region framework residue, the human framework amino acid should usually be substituted by the equivalent framework amino acid from the donor antibody when it is reasonably expected that the amino acid:
(1) noncovalently binds antigen directly,
(2) is adjacent to a CDR region,
(3) otherwise interacts with a CDR region (e.g., is within about 3-6 Angstrom of a CDR region as determined by computer modeling), or
(4) participates in the VL-VH interface.

Residues which "noncovalently bind antigen directly" include amino acids in positions in framework regions which have a good probability of directly' interacting with amino acids on the antigen according to established chemical forces, for example, by hydrogen bonding, Van der Waals forces, hydrophobic interactions, and the like. CDR and framework regions are as defined by Kabat et al. or Chothia et al., supra. When framework residues, as defined by Kabat et al., supra, constitute structural loop residues as defined by Chothia et al., supra, the amino acids present in the donor antibody may be selected for substitution into the humanized antibody. Residues which are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk 1 MB 196:901 (1987)). These amino acids are particularly likely to interact with the amino acids in the CDRs and, if chosen from the acceptor, to distort the donor CDRs and reduce affinity. Moreover, the adjacent amino acids may interact directly with the antigen (Amit et al, Science, 233:747 (1986), which is incorporated herein by reference) and selecting these amino acids from the donor may be desirable to keep all the antigen contacts that provide affinity in the original antibody.

Residues that "otherwise interact with a CDR region" include those that are determined by secondary structural analysis to be in a spatial orientation sufficient to effect a CDR region. In one embodiment, residues that "otherwise interact with a CDR region" are identified by analyzing a three-dimensional model of the donor immunoglobulin (e.g., a computer-generated model). A three-dimensional model, typically of the original donor antibody, shows that certain amino acids outside of the CDRs are close to the CDRs and have a good probability of interacting with amino acids in the CDRs by hydrogen bonding, Van der Waals forces, hydrophobic interactions, etc. At those amino acid positions, the donor immunoglobulin amino acid rather than the acceptor immunoglobulin amino acid may be selected. Amino acids according to this criterion will generally have a side chain atom within about 3 angstrom units (A) of some atom in the CDRs and must contain an atom that could interact with the CDR atoms according to established chemical forces, such as those listed above. In the case of atoms that may form a hydrogen bond, the 3 Å is measured between their nuclei, but for atoms that do not form a bond, the 3 Å is measured between their Van der Waals surfaces. Hence, in the latter case, the nuclei must be within about 6 Å (3 Å plus the sum of the Van der Waals radii) for the atoms to be considered capable of interacting. In many cases the nuclei will be from 4 or 5 to 6 Å apart. In determining whether an amino acid can interact with the CDRs, it is preferred not to consider the last 8 amino acids of heavy chain CDR 2 as part of the CDRs, because from the viewpoint of structure, these 8 amino acids behave more as part of the framework.

Amino acids that are capable of interacting with amino acids in the CDRs, may be identified in yet another way. The solvent accessible surface area of each framework amino acid is calculated in two ways: (1) in the intact antibody, and (2) in a hypothetical molecule consisting of the antibody with its CDRs removed. A significant difference between these numbers of about 10 square angstroms or more shows that access of the framework amino acid to solvent is at least partly blocked by the CDRs, and therefore that the amino acid is making contact with the CDRs. Solvent accessible surface area of an amino acid may be calculated based on a three-dimensional model of an antibody, using algorithms known in the art (e.g., Connolly, J. Appl. Cryst. 16:548 (1983) and Lee and Richards, J. Mol. Biol. 55:379 (1971), both of which are incorporated herein by reference). Framework amino acids may also occasionally interact with the CDRs indirectly, by affecting the conformation of another framework amino acid that in turn contacts the CDRs.

Particular amino acids at several positions in the framework are known to be capable of interacting with the CDRs in many antibodies (Chothia and Lesk, supra, Chothia et al., supra and Tramontano et al., J. Mol. Biol. 215:175 (1990), all of which are incorporated herein by reference). Notably, the amino acids at positions 2, 48, 64, and 71 of the light chain and 71 and 94 of the heavy chain (numbering according to Kabat) are known to be capable of interacting with the CDRs in many antibodies. The amino acids at positions 35 in the light chain and 93 and 103 in the heavy chain are also likely to interact with the CDRs. At all these numbered positions, choice of the donor amino acid rather than the acceptor amino acid (when they differ) to be in the humanized immunoglobulin is preferred. On the other hand, certain residues capable of interacting with the CDR region, such as the first 5 amino acids of the light chain, may sometimes be chosen from the acceptor immunoglobulin without loss of affinity in the humanized immunoglobulin.

In one embodiment, a humanized antibody to aP2 is provided comprising at least one light chain CDR selected from Seq. ID Nos. 7-13, at least one heavy chain CDR selected from Seq. ID Nos. 14-21, and at least one substitution within a human acceptor framework, wherein the substitution is derived from a donor residue.

In one example a humanized antibody is provided, wherein at least the residues at one of positions 23, 67, 71, 72, 73, 74, 76, 77, 78, 79, 88, 89, 91, 93 and 94 of the variable domain of the heavy chain (Kabat numbering) are donor residues. In one embodiment, at least the residues at one of positions 23, 67, 71, 72, 73, 74, 77, 78, 79, 89, and 91 of the variable domain of the heavy chain (Kabat numbering) are donor residues. In one embodiment, at least the residues at one of positions 23, 67, 71, 72, 73, 74, 77, 78, 79, 88, 89, 91, 93, and 94 of the variable domain of the heavy chain (Kabat numbering) are donor residues, but optionally (and in any permutation) one or more of the residues at positions 23, 67, 71, 72, 73, 74, 77, 78, 79, 88, 89, 91, 93, and 94 may use the human acceptor sequence. See for example the sequence given in Seq. ID Nos. 455, 457, 459, 461, and 463.

In one embodiment, the CDRs are Seq. ID No. 14, Seq. ID No. 16 or Seq. ID No. 17, and Seq. ID No. 19 or Seq. ID No. 20, and residue 1 of the heavy chain variable domain is replaced with an alternative amino acid, for example glutamic acid.

In one embodiment, the CDRs are Seq. ID No. 14, Seq. ID No. 16 or Seq. ID No. 17, and Seq. ID No. 19 or Seq. ID No. 20, and residue 23 of the heavy chain variable domain is replaced with an alternative amino acid, for example threonine.

In one embodiment, the CDRs are Seq. ID No. 14, Seq. ID No. 16 or Seq. ID No. 17, and Seq. ID No. 19 or Seq. ID No. 20, and residue 23 of the heavy chain is alanine.

In one embodiment, the CDRs are Seq. ID No. 14, Seq. ID No. 16 or Seq. ID No. 17, and Seq. ID No. 19 or Seq. ID No. 20, and residue 67 of the heavy chain variable domain is replaced with an alternative amino acid, for example phenylalanine.

In one embodiment, the CDRs are Seq. ID No. 14, Seq. ID No. 16 or Seq. ID No. 17, and Seq. ID No. 19 or Seq. ID No. 20, and residue 67 of the heavy chain variable domain is valine.

In one embodiment, the CDRs are Seq. ID No. 14, Seq. ID No. 16 or Seq. ID No. 17, and Seq. ID No. 19 or Seq. ID No. 20, and residue 71 of the heavy chain variable domain is replaced with an alternative amino acid, for example lysine.

In one embodiment, the CDRs are Seq. ID No. 14, Seq. ID No. 16 or Seq. ID No. 17, and Seq. ID No. 19 or Seq. ID No. 20, and residue 71 of the heavy chain variable domain is valine.

In one embodiment, the CDRs are Seq. ID No. 14, Seq. ID No. 16 or Seq. ID No. 17, and Seq. ID. No 19 or Seq. ID No. 20, and residue 72 of the heavy chain variable domain is replaced with an alternative amino acid, for example alanine.

In one embodiment, the CDRs are Seq. ID No. 14, Seq. ID No. 16 or Seq. ID No. 17, and Seq. ID. No 19 or Seq. ID No. 20, and residue 72 of the heavy chain variable domain is aspartic acid.

In one embodiment, the CDRs are Seq. ID No. 14, Seq. ID No. 16 or Seq. ID No. 17, and Seq. ID No. 19 or Seq. ID No. 20, and residue 73 of the heavy chain variable domain is replaced with an alternative amino acid, for example serine.

In one embodiment, the CDRs are Seq. ID No. 14, Seq. ID No. 16 or Seq. ID No. 17, and Seq. ID No. 19 or Seq. ID No. 20, and residue 73 of the heavy chain variable domain is lysine.

In one embodiment, the CDRs are Seq. ID No. 14, Seq. ID No. 16 or Seq. ID No. 17, and Seq. ID No. 19 or Seq. ID No. 20, and residue 74 of the heavy chain variable domain is replaced with an alternative amino acid, for example threonine.

In one embodiment, the CDRs are Seq. ID No. 14, Seq. ID No. 16 or Seq. ID No. 17, and Seq. ID No. 19 or Seq. ID No. 20, and residue 74 of the heavy chain variable domain is serine.

In one embodiment, the CDRs are Seq. ID No. 14, Seq. ID No. 16 or Seq. ID No. 17, and Seq. ID No. 19 or Seq. ID No. 20, and residue 77 of the heavy chain variable domain is replaced with an alternative amino acid, for example threonine.

In one embodiment, the CDRs are Seq. ID No. 14, Seq. ID No. 16 or Seq. ID No. 17, and Seq. ID No. 19 or Seq. ID No. 20, and residue 77 of the heavy chain variable domain is glutamine.

In one embodiment, the CDRs are Seq. ID No. 14, Seq. ID No. 16 or Seq. ID No. 17, and Seq. ID No. 19 or Seq. ID No. 20, and residue 78 of the heavy chain variable domain is replaced with an alternative amino acid, for example valine.

In one embodiment, the CDRs are Seq. ID No. 14, Seq. ID No. 16 or Seq. ID No. 17, and Seq. ID No. 19 or Seq. ID No. 20, and residue 78 of the heavy chain variable domain is phenylalanine.

In one embodiment, the CDRs are Seq. ID No. 14, Seq. ID No. 16 or Seq. ID No. 17, and Seq. ID No. 19 or Seq. ID No. 20, and residue 79 of the heavy chain variable domain is replaced with an alternative amino acid, for example aspartic acid.

In one embodiment, the CDRs are Seq. ID No. 14, Seq. ID No. 16 or Seq. ID No. 17, and Seq. ID No. 19 or Seq. ID No. 20, and residue 79 of the heavy chain variable domain is serine.

In one embodiment, the CDRs are Seq. ID No. 14, Seq. ID No. 16 or Seq. ID No. 17, and Seq. ID No. 19 or Seq. ID No. 20, and residue 89 of the heavy chain variable domain is replaced with an alternative amino acid, for example threonine.

In one embodiment, the CDRs are Seq. ID No. 14, Seq. ID No. 16 or Seq. ID No. 17, and Seq. ID No. 19 or Seq. ID No. 20, and residue 89 of the heavy chain variable domain is valine.

In one embodiment, the CDRs are Seq. ID No. 14, Seq. ID No. 16 or Seq. ID No. 17, and Seq. ID No. 19 or Seq. ID No. 20, and residue 91 of the heavy chain variable domain is replaced with an alternative amino acid, for example phenylalanine.

In one embodiment, the CDRs are Seq. ID No. 14, Seq. ID No. 16 or Seq. ID No. 17, and Seq. ID No. 19 or Seq. ID No. 20, and residue 91 of the heavy chain variable domain is tyrosine.

In one embodiment, the CDRs are Seq. ID No. 14, Seq. ID No. 16 or Seq. ID No. 17, and Seq. ID No. 19 or Seq. ID No. 20, and residue 23 is alanine, residue 67 is valine, residue 71 is valine, residue 72 is aspartic acid, reside 73 is lysine, reside 74 is serine, residue 77 is glutamine, residue 78 is phenylalanine, residue 79 is serine, residue 89 is valine, and residue 91 is tyrosine.

Accordingly, in one example there is provided a humanized antibody, wherein at least the residues at one of positions 2, 3, 36, 37, 58, 63, or 70 of the variable domain of the light chain (Kabat numbering) are donor residues. In one embodiment, at least the residues at one of positions 2, 3, 63, or 70 of the variable domain of the light chain (Kabat numbering) are donor residues. See for example the sequence given in Seq. ID Nos. 446, 448, 450, and 452.

In one embodiment, the CDRs are Seq. ID No. 7, Seq. ID No. 8, and Seq. ID No. 9, Seq. ID No. 10, Seq. ID No. 11, or Seq. ID No. 12, and residue 2 of the light chain variable domain is replaced with an alternative amino acid, for example valine.

In one embodiment, the CDRs are Seq. ID No. 7, Seq. ID No. 8, and Seq. ID No. 9, Seq. ID No. 10, Seq. ID No. 11, or Seq. ID No. 12, and residue 2 of the light chain variable domain is isoleucine.

In one embodiment, the CDRs are Seq. ID No. 7, Seq. ID No. 8, and Seq. ID No. 9, Seq. ID No. 10, Seq. ID No. 11, or Seq. ID No. 12, and residue 3 of the light chain variable domain is replaced with an alternative amino acid, for example valine.

In one embodiment, the CDRs are Seq. ID No. 7, Seq. ID No. 8, and Seq. ID No. 9, Seq. ID No. 10, Seq. ID No. 11, or Seq. ID No. 12, and residue 3 of the light chain variable domain is glutamine.

In one embodiment, the CDRs are Seq. ID No. 7, Seq. ID No. 8, and Seq. ID No. 9, Seq. ID No. 10, Seq. ID No. 11, or Seq. ID No. 12, and residue 63 of the light chain variable domain is replaced with an alternative amino acid, for example lysine.

In one embodiment, the CDRs are Seq. ID No. 7, Seq. ID No. 8, and Seq. ID No. 9, Seq. ID No. 10, Seq. ID No. 11, or Seq. ID No. 12, and residue 63 of the light chain variable domain is serine.

In one embodiment, the CDRs are Seq. ID No. 7, Seq. ID No. 8, and Seq. ID No. 9, Seq. ID No. 10, Seq. ID No. 11, or Seq. ID No. 12, and residue 70 of the light chain variable domain is replaced with an alternative amino acid, for example aspartic acid.

In one embodiment, the CDRs are Seq. ID No. 7, Seq. ID No. 8, and Seq. ID No. 9, Seq. ID No. 10, Seq. ID No. 11, or Seq. ID No. 12, and residue 70 of the light chain variable domain is glutamic acid.

In one embodiment, the CDRs are Seq. ID No. 7, Seq. ID No. 8, and Seq. ID No. 9, Seq. ID No. 10, Seq. ID No. 11, or Seq. ID No. 12, and residue 2 is isoleucine, residue 3 is glutamine, residue 63 is serine, residue 70 is glutamic acid.

Residues which "participate in the VL-VH interface" or "packing residues" include those residues at the interface between VL and VH as defined, for example, by Novotny and Haber, Proc. Natl. Acad. Sci. USA, 82:4592-66 (1985) or Chothia et al, supra. Generally, unusual packing residues should be retained in the humanized antibody if they differ from those in the human frameworks.

In general, one or more of the amino acids fulfilling the above criteria is substituted. In some embodiments, all or most of the amino acids fulfilling the above criteria are substituted. Occasionally, there is some ambiguity about whether a particular amino acid meets the above criteria, and alternative variant immunoglobulins are produced, one of which has that particular substitution, the other of which does not. Alternative variant immunoglobulins so produced can be tested in any of the assays described herein for the desired activity, and the preferred immunoglobulin selected.

Usually the CDR regions in humanized antibodies are substantially identical, and more usually, identical to the corresponding CDR regions of the donor antibody. Although not usually desirable, it is sometimes possible to make one or more conservative amino acid substitutions of CDR residues without appreciably affecting the binding affinity of the resulting humanized immunoglobulin. By conservative or similar substitutions is intended combinations such as, for example, leucine being substituted for isoleucine or valine. Other amino acids, which can often be substituted for one another, include but are not limited to:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains); and, cysteine and methionine (amino acids having sulphur-containing side chains).

Additional candidates for substitution are acceptor human framework amino acids that are unusual or "rare" for a human immunoglobulin at that position. These amino acids can be substituted with amino acids from the equivalent position of the donor antibody or from the equivalent positions of more typical human immunoglobulins. For example, substitution may be desirable when the amino acid in a human framework region of the acceptor immunoglobulin is rare for that position and the corresponding amino acid in the donor immunoglobulin is common for that position in human immunoglobulin sequences; or when the amino acid in the acceptor immunoglobulin is rare for that position and the corresponding amino acid in the donor immunoglobulin is also rare, relative to other human sequences. These criterion help ensure that an atypical amino acid in the human framework does not disrupt the antibody structure. Moreover, by replacing an unusual human acceptor amino acid with an amino acid from the donor antibody that happens to be typical for human antibodies, the humanized antibody may be made less immunogenic.

The term "rare", as used herein, indicates an amino acid occurring at that position in less than about 20% but usually less than about 10% of sequences in a representative sample of sequences, and the term "common," as used herein, indicates an amino acid occurring in more than about 25% but usually more than about 50% of sequences in a representative sample. For example, all human light and heavy chain variable region sequences are respectively grouped into "subgroups" of sequences that are especially homologous to each other and have the same amino acids at certain critical positions (Kabat et al, supra). When deciding whether an amino acid in a human acceptor sequence is "rare" or "common" among human sequences, it will often be preferable to consider only those human sequences in the same subgroup as the acceptor sequence.

Additional candidates for substitution are acceptor human framework amino acids that would be identified as part of a CDR region under the alternative definition proposed by Chothia et al., supra. Additional candidates for substitution are acceptor human framework amino acids that would be identified as part of a CDR region under the CDRs of Seq. ID Nos. 7-21 as described herein and/or the contact definitions described herein.

Additional candidates for substitution are acceptor framework residues that correspond to a rare or unusual donor framework residue. Rare or unusual donor framework residues are those that are rare or unusual (as defined herein) for donor antibodies at that position. For donor antibodies, the subgroup can be determined according to Kabat and residue positions identified which differ from the consensus. These donor specific differences may point to somatic mutations in the donor sequence, which enhance activity. Unusual residues that are predicted to affect binding are retained, whereas residues predicted to be unimportant for binding could be substituted.

Additional candidates for substitution are non-germline residues occurring in an acceptor framework region. For example, when an acceptor antibody chain (i.e., a human antibody chain sharing significant sequence identity with the donor antibody chain) is aligned to a germline antibody chain (likewise sharing significant sequence identity with the donor chain), residues not matching between acceptor chain framework and the germline chain framework can be substituted with corresponding residues from the germline sequence.

Other than the specific amino acid substitutions discussed above, the framework regions of humanized immunoglobulins are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin. Thus, in one embodiment the variable framework region of the humanized immunoglobulin shares at least 85% sequence similarity or identity to a human variable framework region sequence or consensus of such sequences. In another embodiment, the variable framework region of the humanized immunoglobulin shares at least 90%, preferably 95%, more preferably 96%, 97%, 98%, or 99%, sequence similarity or identity to a human variable framework region sequence or consensus of such sequences. In general, however, such substitutions are undesirable.

As used herein, degrees of identity and similarity can be readily calculated, for example as described in Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656, which are incorporated by reference herein.

A number of reviews discussing CDR-grafted antibodies have been published, including Vaughan et al. (Nature Biotechnology, 16, 535-539, 1998), which is incorporated by reference herein.

The anti-aP2 antibodies of the present invention may include further additional binding domains for example as per the molecule DVD-Ig as disclosed in WO 2007/024715, or the so-called (FabFv)2Fc described in WO2011/030107. Thus antibody as employed herein includes bi, tri or tetra-valent full length antibodies.

Antigen Binding Agents

Antigen binding agents include single chain antibodies (i.e. a full length heavy chain and light chain); Fab, modified Fab, Fab', modified Fab', F(ab')2, Fv, Fab-Fv, Fab-dsFv, single domain antibodies (e.g. VH or VL or VHH) for example as described in WO 2001090190, scFv, bi, tri or tetra-valent antibodies. Bis-scFv, diabodies, tribodies, triabodies, tetrabodies and epitope-antigen binding agents of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). The Fab-Fv format was first disclosed in WO2009/040562 and the disulphide stabilised versions thereof, the Fab-dsFv was first disclosed in WO2010/035012. Other antibody fragments for use in the present invention include the Fab and Fab' fragments described in International patent applications WO2005/003169, WO2005/003170, and WO2005/003171. Multi-valent antibodies may comprise multiple specificities e.g. bispecific or may be monospecific (see for example WO 92/22583 and WO05/113605). One such example of the latter is a Tri-Fab (or TFM) as described in WO92/22583.

A typical Fab' molecule comprises a heavy and a light chain pair in which the heavy chain comprises a variable region VH, a constant domain CH1 and a natural or modified hinge region and the light chain comprises a variable region VL and a constant domain CL.

In one embodiment, there is provided a dimer of a Fab' according to the present disclosure to create a F(ab')2 for example dimerization may be through a natural hinge sequence described herein, or derivative thereof, or a synthetic hinge sequence.

An antibody binding domain will generally comprise 6 CDRs, three from a heavy chain and three from a light chain. In one embodiment, the CDRs are in a framework and together form a variable region. Thus in one embodiment, the antigen binding agent includes a binding domain specific for aP2 comprising a light chain variable region and a heavy chain variable region.

It will be appreciated that one or more (for example 1, 2, 3 or 4) amino acid substitutions, additions and/or deletions may be made to the CDRs or other sequences (e.g. variable domains) provided by the present invention, as described above or below, without significantly altering the ability of the antibody to bind to aP2. The effect of any amino acid substitutions, additions and/or deletions can be readily tested by one skilled in the art, for example by using the methods described herein, in particular in the Examples.

In one embodiment, one or more (for example 1, 2, 3 or 4) amino acid substitutions, additions and/or deletions may be made to the CDRs or framework region employed in the antibody or fragment provided by the present invention so that the binding affinity to aP2 is retained, increased, or decreased to an affinity of about $\geq 10^{-7}$ M. In one embodiment, provided is a modified humanized antibody wherein modifications have been made to either the CDRs, framework regions, or both, in order to decrease the binding affinity, for example, to about $\geq 10^{-7}$ M.

Rabbit Donor CDR/Human Acceptor Framework Anti-aP2 Monoclonal Antibodies

In one aspect of the present invention a humanized anti-aP2 monoclonal antibody derived from an anti-aP2 rabbit CDR/mouse framework hybrid donor monoclonal antibody is provided, wherein the CDRs from the anti-human aP2 protein monoclonal antibody are grafted into human light chain and heavy chain framework regions.

In one embodiment, the variable light chain Ab 909 VL (Seq. ID No. 445 (Table 10, below and FIG. 27)) is the donor light chain sequence used for subsequent grafting into a human framework, wherein subsequent CDR and framework modifications may be optionally performed. In one embodiment, the CDRs provided for in Seq. ID Nos. 7, 8, and 9 derived from the variable light chain provided in Seq. ID No. 445, are grafted into the human immunoglobulin kappa light chain variable domain of human immunoglobulin IGKVA30-JK4, resulting in a humanized light chain variable region comprising A30 FR1 (Seq. ID No. 40)-CDRL1 (Seq. ID. No. 7)-A30 FR2 (Seq. ID No. 41)-CDRL2 (Seq. ID No. 8)-A30 FR3 (Seq. ID No. 41)-CDRL3 (Seq. ID. No. 9)-JK4 (Seq. ID No. 148).

In one embodiment, the CDRs provided for in Seq. ID Nos. 7, 8, and 10 derived from the variable light chain provided in Seq. ID No. 445, are grafted into the human immunoglobulin kappa light chain variable domain of human immunoglobulin IGKVA30-JK4, resulting in a humanized light chain variable region comprising A30 FR1 (Seq. ID No. 40)-CDRL1 (Seq. ID. No. 7)-A30 FR2 (Seq. ID No. 41)-CDRL2 (Seq. ID No. 8)-A30 FR3 (Seq. ID No. 41)-CDRL3 (Seq. ID. No. 10)-JK4 (Seq. ID No. 148), resulting in Ab 909 gL13 (Seq. ID No. 487).

In one embodiment, provided is the humanized kappa light chain variable region 909 gL1 (Seq. ID No. 446 (Table 10, below and FIG. 27)) wherein light chain variable region donor residues 2V, 3V, 63K, and 70D from Ab 909 VL (Seq. ID No. 445) are used as amino acid substitutes for the IGKV30-JK4 amino acids 2I, 3Q, 63S, 70E, resulting in the humanized kappa light chain 909 gL1 (Seq. ID No. 446 (Table 10, below and FIG. 27)).

In one embodiment, provided is the humanized kappa light chain 909 gL1 VL+CL (Seq. ID. No. 447 (Table 10, below)), wherein the humanized kappa light chain variable region 909 gL1 (Seq. ID No. 446 (Table 10, below and FIG. 27)) further comprises a human kappa light chain constant region.

In one embodiment, provided is the humanized kappa light chain 909 gL10 (Seq. ID No. 448 (Table 10, below and FIG. 27)) wherein the light chain variable region donor residues 2V, 3V, 63K, and 70D from Ab 909 VL (Seq. ID No. 445) are used as amino acid substitutes for the IGKV30-JK4 amino acids 2I, 3Q, 63S, 70E, and a substitution of an alanine in place of cysteine in the second position of CDRL3 (CDRL3 variant 1 (Seq. ID No. 10)) is provided, resulting in the humanized kappa light chain 909 gL10 (Seq. ID No. 448 (Table 10, below and FIG. 27)). Alternatively, a further substitution comprising C88A in FR3 is provided, resulting in Ab 909 gL50 (Seq. ID No. 488).

In one embodiment, provided is the humanized kappa light chain 909 gL10 VL+CL (Seq. ID. No. 449 (Table 10, below)), wherein the humanized kappa light chain variable region 909 gL10 (Seq. ID No. 448 (Table 10, below and FIG. 27)) further comprises a human kappa light chain constant region. Alternatively, a further substitution comprising C88A in FR3 is provided, resulting in Ab909 gL50VL+CL (Seq. ID. No. 490).

In one embodiment, provided is the humanized kappa light chain 909 gL54 (Seq. ID No. 450 (Table 10, below)) wherein the light chain variable region donor residues 2V, 3V, 63K, and 70D from Ab 909 VL (Seq. ID No. 445) are used as amino acid substitutes for the IGKV30-JK4 amino acids 2I, 3Q, 63S, 70E, and a substitution of an glutamine in place of cysteine in the second position of CDRL3 (CDRL3 variant 2 (Seq. ID No. 11)) is provided, resulting in the humanized kappa light chain 909 gL54 (Seq. ID No. 450 (Table 10, below)).

In one embodiment, provided is the humanized kappa light chain 909 gL54 VL+CL (Seq. ID. No. 451 (Table 10, below)), wherein the humanized kappa light chain variable region 909 gL54 (Seq. ID No. 450 (Table 10, below)) further comprises a human kappa light chain constant region.

In one embodiment, provided is the humanized kappa light chain 909 gL55 (Seq. ID No. 452 (Table 10, below)) wherein the light chain variable region donor residues 2V, 3V, 63K, and 70D from Ab 909 VL (Seq. ID No. 445) are used as amino acid substitutes for the IGKV30-JK4 amino acids 2I, 3Q, 63S, 70E, and a substitution of an histidine in place of cysteine in the second position of CDRL3 (CDRL3 variant 2 (Seq. ID No. 12)) is provided, resulting in the humanized kappa light chain 909 gL55 (Seq. ID No. 452 (Table 10, below)).

In one embodiment, provided is the humanized kappa light chain 909 gL55 VL+CL (Seq. ID. No. 453 (Table 10, below)), wherein the humanized kappa light chain variable region 909 gL55 (Seq. ID No. 452 (Table 10, below)) further comprises a human kappa light chain constant region.

TABLE 10

Sequences of Humanized aP2 Light Chain Regions

| Protein | Seq. ID No. | Sequence |
| --- | --- | --- |
| Rabbit Ab 909 VL-region | 445 | DVVMTQTPASVSEPVGGTVTIKCQASEDTSRYLVWYQQKPGQPPK<br>RLIYKASTLASGVPSRFKGSGSGTDFTLTISDLECDDAATYYCQCT<br>YGTYAGSFFYSFGGGTEVVVE |
| 909 gL1 VL-region | 446 | DVVMTQSPSSLSASVGDRVTITCQASEDISRYLVWYQQKPGKAPK<br>RLIYKASTLASGVPSRFKGSGSGTDFTLTISSLQPEDFATYYCQCTY<br>GTYAGSFFYSFGGGTKVEIK |
| 909 gL1 VL + CL-region | 447 | DVVMTQSPSSLSASVGDRVTITCQASEDISRYLVWYQQKPGKAPK<br>RLIYKASTLASGVPSRFKGSGSGTDFTLTISSLQPEDFATYYCQCTY<br>GTYAGSFFYSFGGGTKVEIKRTVAAPSVFIFPPSDEQLKSGTASVV<br>CLLNNFYPREAKVQWKVDNALQSGNSQESVTEQDSKDSTYSLSST<br>LTLSKADYEKHKVYACEVTHQGLSSPVTKSFNRGEC |
| 909 gL10 VL-region | 448 | DVVMTQSPSSLSASVGDRVTITCQASEDISRYLVWYQQKPGKAPK<br>RLIYKASTLASGVPSRFKGSGSGTDFTLTISSLQPEDFATYYCQATY<br>GTYAGSFFYSFGGGTKVEIK |
| 909 gL10 VL + CL-region | 449 | DVVMTQSPSSLSASVGDRVTITCQASEDISRYLVWYQQKPGKAPK<br>RLIYKASTLASGVPSRFKGSGSGTDFTLTISSLQPEDFATYYCQATY<br>GTYAGSFFYSFGGGTKVEIKRTVAAPSVFIFPPSDEQLKSGTASVV<br>CLLNNFYPREAKVQWKVDNALQSGNSQESVTEQDSKDSTYSLSST<br>LTLSKADYEKHKVYACEVTHQGLSSPVTKSFNRGEC |
| 909 gL54 VL-region | 450 | DVVMTQSPSSLSASVGDRVTITCQASEDISRYLVWYQQKPGKAPK<br>RLIYKASTLASGVPSRFKGSGSGTDFTLTISSLQPEDFATYYCQQTY<br>GTYAGSFFYSFGGGTKVEIK |
| 909 gL54 VL + CL-region | 451 | DVVMTQSPSSLSASVGDRVTITCQASEDISRYLVWYQQKPGKAPK<br>RLIYKASTLASGVPSRFKGSGSGTDFTLTISSLQPEDFATYYCQQTY<br>GTYAGSFFYSFGGGTKVEIKRTVAAPSVFIFPPSDEQLKSGTASVV<br>CLLNNFYPREAKVQWKVDNALQSGNSQESVTEQDSKDSTYSLSST<br>LTLSKADYEKHKVYACEVTHQGLSSPVTKSFNRGEC |

TABLE 10-continued

Sequences of Humanized aP2 Light Chain Regions

| Protein | Seq. ID No. | Sequence |
|---|---|---|
| 909 gL55 VL-region | 452 | DVVMTQSPSSLSASVGDRVTITCQASEDTSRYLVWYQQKPGKAPK<br>RLIYKASTLASGVPSRFKGSGSGTDFTLTTSSLQPEDFATYYCQHTY<br>GTYAGSFFYSFGGGTKVEIK |
| 909 gL55 VL + CL-region | 453 | DVVMTQSPSSLSASVGDRVTITCQASEDISRYLVWYQQKPGKAPK<br>RLIYKASTLASGVPSRFKGSGSGTDFTLTISSLQPEDFATYYCQHTY<br>GTYAGSFFYSFGGGTKVEIKRTVAAPSVFIFPPSDEQLKSGTASVV<br>CLLNNFYPREAKVQWKVDNALQSGNSQESVTEQDSKDSTYSLSST<br>LTLSKADYEKHKVYACEVTHQGLSSPVTKSFNRGEC |
| 909 gL13 VL-region | 487 | DIQMTQSPSSLSASVGDRVTITCQASEDISRYLVWYQQKPGKAPK<br>RLIYKASTLASGVPSRFSGSGSGTEFTLTISSLQPEDFATYYCQATY<br>GTYAGSFFYSFGGGTKVEIK |
| 909 gL13 VL + CL-region | 489 | DIQMTQSPSSLSASVGDRVTITCQASEDISRYLVWYQQKPGKAPK<br>RLIYKASTLASGVPSRFSGSGSGTEFTLTISSLQPEDFATYYCQATY<br>GTYAGSFFYSFGGGTKVEIKRTVAAPSVFIFPPSDEQLKSGTASVV<br>CLLNNFYPREAKVQWKVDNALQSGNSQESVTEQDSKDSTYSLSST<br>LTLSKADYEKHKVYACEVTHQGLSSPVTKSFNRGEC |
| 909 gL50 VL-region | 488 | DVVMTQSPSSLSASVGDRVTITCQASEDISRYLVWYQQKPGKAPK<br>RLIYKASTLASGVPSRFKGSGSGTDFTLTISSLQPEDFATYYAQATY<br>GTYAGSFFYSFGGGTKVEIK |
| 909 gL50 VL + CL-region | 490 | DVVMTQSPSSLSASVGDRVTITCQASEDISRYLVWYQQKPGKAPK<br>RLIYKASTLASGVPSRFKGSGSGTDFTLTISSLQPEDFATYYAQATY<br>GTYAGSFFYSFGGGTKVEIKRTVAAPSVFIFPPSDEQLKSGTASVV<br>CLLNNFYPREAKVQWKVDNALQSGNSQESVTEQDSKDSTYSLSST<br>LTLSKADYEKHKVYACEVTHQGLSSPVTKSFNRGEC |

For example, the variable heavy chain Ab 909 VH (Seq. ID No. 454 (Table 11, below and FIG. 28)) is the donor heavy chain sequence used for subsequent grafting into a human framework, wherein subsequent CDR and framework modifications may be optionally performed. In one embodiment, the variable heavy CDRs provided for in Seq. ID. Nos. 14, 16, and 19 derived from the variable heavy chain provide in Seq. ID No. 454, are grafted into the human immunoglobulin heavy chain variable domain of human immunoglobulin IGHV4-04-JH4 (Seq. ID No. 481 (FIG. 28)), resulting in a humanized heavy chain variable region comprising 4-04 FR1 (Seq. ID No. 357)-CDRH1 (Seq. ID No. 14)-4-04 FR2 (Seq. ID No. 358)-CDRH2 (Seq. ID No. 16)-4-04 FR3 (Seq. ID No. 359)-CDRH3 (Seq. ID No. 19)-JH4 (Seq. ID No. 405).

In one embodiment, the humanized heavy chain variable region 909 gH1 variable region is provided (Seq. ID No. 455 (Table 11, below and FIG. 28)) wherein the heavy chain variable region donor residues 23T, 67F, 71K, 72A, 73S, 74T, 77T, 78V, 79D, 89T, 91F from Ab 909 VH (Seq. ID No. 454) are used as amino acid substitutes for the IGHV4-04-JK4 amino acids 23A, 67V, 71V, 72D, 73K, 74S, 77Q, 78F, 79S, 89V, 91Y, and 1E is substituted for the IGHV4-04-JK4 amino acid 1Q, and a two amino acid residue amino acid gap in framework 3, in the loop between beta sheet strands D and E at amino acids 75 and 76 is maintained, resulting in the humanized heavy chain 909 gH1 (Seq. ID No. 455 (Table 11, below and FIG. 28)).

In one embodiment, the humanized IgG4 heavy chain 909 gH1 VH+IgG4P Constant is provided (Seq. ID No. 456 (Table 11, below)), wherein the humanized heavy chain variable region 909 gH1 (Seq. ID No. 455 (Table 11, below and FIG. 28)) further comprises a human IgG4P constant region. IgG4P as employed herein is a mutation of the wild-type IgG4 isotype where amino acid 241 is replaced by proline see for example where serine at position 241 has been changed to proline as described in Angal et al., Molecular Immunology, 1993, 30 (1), 105-108.

In one embodiment, the humanized heavy chain variable region 909 gH14 variable region is provided (Seq. ID No. 457 (Table 11, below and FIG. 28)) wherein the heavy chain variable region donor residues 67F, 71K, 72A, 73S, 74T, 77T, 78V, 79D, 89T, 91F from Ab 909 VH (Seq. ID No. 454) are used as amino acid substitutes for the IGHV4-04-JK4 amino acids 67V, 71V, 72D, 73K, 74S, 77Q, 78F, 79S, 89V, 91Y, and 1E is substituted for the IGHV4-04-JK4 amino acid 1Q, resulting in the humanized heavy chain 909 gH4 (Seq. ID No. 457 (Table 11, below and FIG. 28)).

In one embodiment, the humanized IgG4 heavy chain 909 gH14 VH+IgG4P Constant is provided (Seq. ID No. 458 (Table 11, below)), wherein the humanized heavy chain variable region 909 gH14 (Seq. ID No. 457 (Table 11, below and FIG. 28)) further comprises a human IgG4P constant region. IgG4P as employed herein is a mutation of the wild-type IgG4 isotype where amino acid 241 is replaced by proline see for example where serine at position 241 has been changed to proline as described in Angal et al., Molecular Immunology, 1993, 30 (1), 105-108.

In one embodiment, the humanized heavy chain variable region 909 gH15 variable region (Seq. ID No. 459 (Table 11, below and FIG. 28)) is provided wherein the heavy chain variable region donor residues 23T, 67F, 71K, 72A, 73S, 74T, 77T, 78V, 79D, 89T, 91F from Rabbit Ab 909 VH (Seq. ID No. 454) are used as amino acid substitutes for the IGHV4-04-JK4 amino acids 23A, 67V, 71V, 72D, 73K, 74S, 77Q, 78F, 79S, 89V, 91Y, and 1E is substituted for the IGHV4-04-JK4 amino acid 1Q, and there is a substitution of a serine in place of cysteine in the tenth position of CDRH2 (CDRH2 variant 1 (Seq. ID No. 17)) and a substitution of a glutamic acid in place of aspartic acid in the fourth position of CDRH3 (CDRH3 variant 1 (Seq. ID No. 20), resulting in the humanized heavy chain 909 gH15 VH region (Seq. ID No. 459 (Table 11, below and FIG. 28)).

In one embodiment, the humanized IgG4 heavy chain 909 gH15 VH+IgG4P Constant (Seq. ID No. 460 (Table 11, below)) is provided, wherein the humanized heavy chain variable region 909 gH15 VH (Seq. ID No. 459 (Table 11, below and FIG. 28)) further comprises a human IgG4P constant region. IgG4P as employed herein is a mutation of the wild-type IgG4 isotype where amino acid 241 is replaced by proline see for example where serine at position 241 has been changed to proline as described in Angal et al., Molecular Immunology, 1993, 30 (1), 105-108.

In one embodiment, the humanized heavy chain variable region 909 gH61 variable region (Seq. ID No. 461 (Table 11, below and FIG. 28)) is provided wherein the heavy chain variable region donor residues 71K, 73S, 78V from Rabbit Ab 909 VH (Seq. ID No. 454) are used as amino acid substitutes for the IGHV4-04-JK4 amino acids 71V, 73K, 78F, and 1E is substituted for the IGHV4-04-JK4 amino acid 1Q, resulting in the humanized heavy chain 909 gH61 VH region (Seq. ID No. 461 (Table 11, below and FIG. 28)).

In one embodiment, the humanized IgG4 heavy chain 909 gH61 VH+IgG4P Constant (Seq. ID No. 462 (Table 11, below)) is provided, wherein the humanized heavy chain variable region 909 gH61 VH (Seq. ID No. 461 (Table 11, below and FIG. 28)) further comprises a human IgG4P constant region. IgG4P as employed herein is a mutation of the wild-type IgG4 isotype where amino acid 241 is replaced by proline see for example where serine at position 241 has been changed to proline as described in Angal et al., Molecular Immunology, 1993, 30 (1), 105-108.

In one embodiment, the humanized heavy chain variable region 909 gH62 variable region (Seq. ID No. 463 (Table 11, below and FIG. 28)) is provided wherein the heavy chain variable region donor residues 71K, 73S, 78V from Rabbit Ab 909 VH (Seq. ID No. 454) are used as amino acid substitutes for the IGHV4-04-JK4 amino acids 71V, 73K, 78F, and 1E is substituted for the IGHV4-04-JK4 amino acid 1Q, and there is a substitution of a serine in place of cysteine in the tenth position of CDRH2 (CDRH2 variant 1 (Seq. ID No. 17)) and a substitution of a glutamic acid in place of aspartic acid in the fourth position of CDRH3 (CDRH3 variant 1 (Seq. ID No. 20), resulting in the humanized heavy chain 909 gH62 VH region (Seq. ID No. 463 (Table 11, below and FIG. 28)).

In one embodiment, the humanized IgG4 heavy chain 909 gH62 VH+IgG4P Constant (Seq. ID No. 464 (Table 11, below)) is provided, wherein the humanized heavy chain variable region 909 gH62 VH (Seq. ID No. 463 (Table 11, below and FIG. 28)) further comprises a human IgG4P constant region. IgG4P as employed herein is a mutation of the wild-type IgG4 isotype where amino acid 241 is replaced by proline see for example where serine at position 241 has been changed to proline as described in Angal et al., Molecular Immunology, 1993, 30 (1), 105-108.

TABLE 11

Sequences of Humanized aP2 Heavy Chain Regions

| Protein | Seq. ID No. | Sequence |
|---|---|---|
| Rabbit Ab 909 VH region | 454 | QSVEESGGRLVTPGTPLTLTCTVSGFSLSTYYMSWVRQAPGKGLE WIGHYPSGSTYCASWAKGRFTISKASTTVDLKITSPTTEDTATYFC ARPDNDGTSGYLSGFGLWGQGTLVTVSS |
| 909gH1 VH region | 455 | EVQLQESGPGLVKPSGTLSLTCTVSGFSLSTYYMSWVRQPPGKGL EWIGIIYPSGSTYCASWAKGRFTISKASTTVDLKLSSVTAADTATY FCARPDNDGTSGYLSGFGLWGQGTLVTVSS |
| 909gH1 IgG4 VH + human γ-4P constant | 456 | EVQLQESGPGLVKPSGTLSLTCTVSGFSLSTYYMSWVRQPPGKGL EWIGIIYPSGSTYCASWAKGRFTISKASTTVDLKLSSVTAADTATY FCARPDNDGTSGYLSGFGLWGQGTLVTVSSASTKGPSVFPLAPCS RSTSESTAALGCLVKDYFPEPVTVSWNSGALTSGVHTFPAVLQSS GLYSLSSVVTVPSSSLGTKTYTCNVDHKPSNTKVDKRVESKYGPP CPPCPAPEFLGGPSVFLFPPKPKDTLMISRTPEVTCVVVDVSQEDPE VQFNWYVDGVEVHNAKTKPREEQFNSTYRVVSVLTVLHQDWLN GKEYKCKVSNKGLPSSIEKTISKAKGQPREPQVYTLPPSQEEMTKN QVSLTCLVKGFYPSDIAVEWESNGQPENNYKTTPPVLDSDGSFFL YSRLTVDKSRWQEGNVFSCSVMHEALHNHYTQK SLSLSLGK |
| 909gH14 VH region | 457 | EVQLQESGPG LVKPSGTLSLTCAVSGFSLSTYYMSWVRQP PGKGLEWIGIIYPSGSTYCASWAKGRFTISKASTKNTVDLKLSSVT AADTATYFCARPDNDGTSGYLSGFGLWGQGTLVTVSS |
| 909gH14 IgG4 VH + human γ-4P constant | 458 | EVQLQESGPGLVKPSGTLSLTCAVSGFSLSTYYMSWVRQPPGKGL EWIGIIYPSGSTYCASWAKGRFTISKASTKNTVDLKLSSVTAADTA TYFCARPDNDGTSGYLSGFGLWGQGTLVTVSSASTKGPSVFPLAP CSRSTSESTAALGCLVKDYFPEPVTVSWNSGALTSGVHTFPAVLQ SSGLYSLSSVVTVPSSSLGTKTYTCNVDHKPSNTKVDKRVESKYG PPCPPCPAPEFLGGPSVFLFPPKPKDTLMISRTPEVTCVVVDSQED PEVQFNWYVDGVEVHNAKTKPREEQFNSTYRVVSVLTVLHQDW LNGKEYKCKVSNKGLPSSIEKTISKAKGQPREPQVYTLPPSQEEMT KNQVSLTCLVKGFYPSDIAVEWESNGQPENNYKTTPPVLDSDGSF FLYSRLTVDKSRWQEGNVFSCSVMHEALHNHYTQKSLSLSLGK |
| 909 gH15 VH region | 459 | EVQLQESGPGLVKPSGTLSLTCTVSGFSLSTYYMSWVRQPPGKGL EWIGIIYPSGSTYSASWAKGRFTISKASTKNTVDLKLSSVTAADTA TYFCARPDNEGTSGYLSGFGLWGQGTLVTVSS |

TABLE 11-continued

Sequences of Humanized aP2 Heavy Chain Regions

| Protein | Seq. ID No. | Sequence |
|---|---|---|
| 909gH15 IgG4 VH + human γ-4P constant | 460 | EVQLQESGPGLVKPSGTLSLTCTVSGFSLSTYYMSWVRQPPGKGL EWIGIIYPSGSTYSASWAKGRFTISKASTKNTVDLKLSSVTAADTA TYFCARPDNEGTSGYLSGFGLWGQGTLVTVSSASTKGPSVFPLAP CSRSTSESTAALGCLVKDYFPEPVTVSWNSGALTSGVHTFPAVLQ SSGLYSLSSVVTVPSSSLGTKTYTCNVDHKPSNTKVDKRVESKYG PPCPPCPAPEFLGGPSVFLFPPKPKDTLMISRTPEVTCVVVDVSQED PEVQFNWYVDGVEVHNAKTKPREEQFNSTYRVVSVLTVLHQDW LNGKEYKCKVSNKGLPSSIEKTISKAKGQPREPQVYTLPPSQEEMT KNQVSLTCLVKGFYPSDIAVEWESNGQPENNYKTTPPVLDSDGSF FLYSRLTVDKSRWQEGNVFSCSVMHEALHNHYTQKSLSLSLGK |
| 909 gH61 VH region | 461 | EVQLQESGPGLVKPSGTLSLTCAVSGFSLSTYYMSWVRQPPGKGL EWIGIIYPSGSTYCASWAKGRVTISKDSSKNQVSLKLSSVTAADTA VYYCARPDNDGTSGYLSGFGLWGQGTLVTVSS |
| 909gH61 IgG4 VH + human γ-4P constant | 462 | EVQLQESGPGLVKPSGTLSLTCAVSGFSLSTYYMSWVRQPPGKGL EWIGIIYPSGSTYCASWAKGRVTISKDSSKNQVSLKLSSVTAADTA VYYCARPDNDGTSGYLSGFGLWGQGTLVTVSSASTKGPSVFPLAP CSRSTSESTAALGCLVKDYFPEPVTVSWNSGALTSGVHTFPAVLQ SSGLYSLSSVVTVPSSSLGTKTYTCNVDHKPSNTKVDKRVESKYG PPCPPCPAPEFLGGPSVFLFPPKPKDTLMISRTPEVTCVVVDVSQED PEVQFNWYVDGVEVHNAKTKPREEQFNSTYRVVSVLTVLHQDW LNGKEYKCKVSNKGLPSSIEKTISKAKGQPREPQVYTLPPSQEEMT KNQVSLTCLVKGFYPSDIAVEWESNGQPENNYKTTPPVLDSDGSF FLYSRLTVDKSRWQEGNVFSCSVMHEALHNHYTQKSLSLSLGK |
| 909 gH62 VH region | 463 | EVQLQESGPGLVKPSGTLSLTCAVSGFSLSTYYMSWVRQPPGKGL EWIGIIYPSGSTYSASWAKGRVTISKDSSKNQVSLKLSSVTAADTA VYYCARPDNEGTSGYLSGFGLWGQGTLVTVSS |
| 909gH62 IgG4 VH + human γ-4P constant | 464 | EVQLQESGPGLVKPSGTLSLTCAVSGFSLSTYYMSWVRQPPGKGL EWIGIIYPSGSTYSASWAKGRVTISKDSSKNQVSLKLSSVTAADTA VYYCARPDNEGTSGYLSGFGLWGQGTLVTVSSASTKGPSVFPLAP CSRSTSESTAALGCLVKDYFPEPVTVSWNSGALTSGVHTFPAVLQ SSGLYSLSSVVTVPSSSLGTKTYTCNVDHKPSNTKVDKRVESKYG PPCPPCPAPEFLGGPSVFLFPPKPKDTLMISRTPEVTCVVVDVSQED PEVQFNWYVDGVEVHNAKTKPREEQFNSTYRVVSVLTVLHQDW LNGKEYKCKVSNKGLPSSIEKTISKAKGQPREPQVYTLPPSQEEMT KNQVSLTCLVKGFYPSDIAVEWESNGQPENNYKTTPPVLDSDGSF FLYSRLTVDKSRWQEGNVFSCSVMHEALHNHYTQKSLSLSLGK |

In one embodiment the disclosure provides an antibody sequence which is 80% similar or identical to a sequence disclosed herein, for example 85%, 900/%, 91%, 92%, 93/%, 94%, 95% 96%, 97%, 98% or 99% over part or whole of the relevant sequence, for example a variable domain sequence, a CDR sequence or a variable domain sequence excluding the CDRs. In one embodiment the relevant sequence is selected from Seq. ID Nos. 446, 447, 448, 487, 488, 489, 490, 449, 450, 451, 452, 453, 455, 456, 457, 458, 459, 460, 461, 462, 463, or 464. In one embodiment the disclosure provides an antibody sequence which has one or more (for example, 1, 2, 3, or 4) amino acid substitutions, additions, or deletions in the relevant sequence, for example a variable domain sequence, a CDR sequence or a variable domain sequence excluding the CDRs selected from Seq. ID Nos. 446, 447, 448, 487, 488, 489, 490, 449, 450, 451, 452, 453, 455, 456, 457, 458, 459, 460, 461, 462, 463, or 464.

In one embodiment, the present invention provides an antibody molecule which binds human aP2 comprising a light chain, wherein the variable domain of the light chain comprises a sequence having at least 80%, 85%, 90%, 91%, 92%, 93%, 94%, 95% 96%, 97%, 98% or 99% identity or similarity to a sequence selected from Seq. ID Nos. 446, 448, 487, 488, 450, or 452. In one embodiment, the present invention provides an antibody molecule which binds human aP2 comprising a light chain, wherein the variable domain of the light chain comprises a sequence having one or more (for example, 1, 2, 3, or 4) amino acid substitutions, additions, or deletions in its sequence compared to Seq. ID Nos. 446, 448, 487, 488, 450, or 452.

In one embodiment the present invention provides an antibody molecule which binds human aP2 wherein the antibody has a heavy chain variable domain which is at least 80% 90%, 91%, 92%, 93%, 94%, 95% 96%, 97%, 98% or 99% similar or identical to a sequence selected from Seq. ID Nos. 455, 457, 459, 461 or 463. In one embodiment the present invention provides an antibody molecule which binds human aP2 wherein the antibody has a heavy chain variable domain which has one or more (for example, 1, 2, 3, or 4) amino acid substitutions, additions, or deletions in its sequence compared to Seq. ID Nos. 455, 467, 459, 461 or 463.

A suitable framework region for the light chain of the humanized antibody of the present invention is derived from the human germline sub-group IgKV1-17 (A30) (Seq. ID Nos. 40-42) together with JK4 (Seq. ID No. 148). Accordingly, in one example there is provided a humanized antibody comprising the sequence given in Seq. ID No. 7 for CDR-L1, the sequence given in Seq. ID No. 8 for CDR-L2 and the sequence selected from Seq. ID Nos. 9, 10, 11, or 12 for CDRL3, wherein the light chain framework region is derived from the human subgroup IGKV1-17 (A30) (Seq. ID Nos. 40-42) together with JK4 (Seq. ID No. 148). The JK4 sequence is as follows: FGGGTKVEIK (Seq. ID No.

148). In one example the light chain variable domain of the antibody comprises the sequence selected from Seq. ID Nos. 446, 448, 487, 488, 450, and 452.

A suitable framework region for the heavy chain variable region of the humanized antibody of the present invention is derived from the human germline sub-group IGHV 4-04 (Seq. ID Nos. 357, 358, and 359) together with JH4 (Seq. ID No. 405). Accordingly, in one example there is provided a humanized antibody comprising the sequence given in Seq. ID No. 14 for CDR-H1, a sequence selected from Seq. ID. Nos. 16 or 17 for CDR-H2 and the sequence selected from Seq. ID Nos. 19 or 20 for CDR-H3, wherein the heavy chain framework region is derived from the human subgroup IGHV 4-04 (Seq. ID Nos. 357, 358, and 359) together with JH4 (Seq. ID No. 405). The JH4 sequence is as follows: WGQGTLVTVSS (Seq. ID No. 405).

In one embodiment the antibody molecule of the present disclosure is a Fab, Fab', or F(ab')2 antibody fragment comprising a light chain variable region selected from Seq. ID Nos. 446, 448, 487, 488, 450, or 452, and a heavy chain variable region selected from Seq. ID Nos. 455, 457, 459, 461, or 463. In one embodiment the antibody molecule of the present disclosure is a Fab, Fab', or F(ab')2 antibody fragment comprising a light chain variable region given in Seq. ID No. 446, and a heavy chain variable region given in Seq. ID No. 455. In one embodiment the antibody molecule of the present disclosure is a Fab, Fab', or F(ab')2 antibody fragment comprising a light chain variable region given in Seq. ID No. 448, and a heavy chain variable region given in Seq. ID No. 455. In one embodiment the antibody molecule of the present disclosure is a Fab, Fab', or F(ab')2 antibody fragment comprising a light chain variable region given in Seq. ID No. 450, and a heavy chain variable region given in Seq. ID No. 455. In one embodiment the antibody molecule of the present disclosure is a Fab, Fab', or F(ab')2 antibody fragment comprising a light chain variable region given in Seq. ID No. 452, and a heavy chain variable region given in Seq. ID No. 455. In one embodiment the antibody molecule of the present disclosure is a Fab, Fab', or F(ab')2 antibody fragment comprising a light chain variable region given in Seq. ID No. 487, and a heavy chain variable region given in Seq. ID No. 455. In one embodiment the antibody molecule of the present disclosure is a Fab, Fab', or F(ab')2 antibody fragment comprising a light chain variable region given in Seq. ID No. 488, and a heavy chain variable region given in Seq. ID No. 455. In one embodiment, the antibody molecule of the present disclosure is a Fab, Fab', or F(ab')2 antibody fragment comprising a light chain variable region given in Seq. ID No. 446 and a heavy chain variable region given in Seq. ID No. 459. In one embodiment the antibody molecule of the present disclosure is a Fab, Fab', or F(ab')2 antibody fragment comprising a light chain variable region given in Seq. ID No. 448, and a heavy chain variable region given in Seq. ID No. 459. In one embodiment, the antibody molecule of the present disclosure is a Fab, Fab', or F(ab')2 antibody fragment comprising a light chain variable region given in Seq. ID No. 450 and a heavy chain variable region given in Seq. ID No. 459. In one embodiment, the antibody molecule of the present disclosure is a Fab, Fab', or F(ab')2 antibody fragment comprising a light chain variable region given in Seq. ID No. 452 and a heavy chain variable region given in Seq. ID No. 459. In one embodiment, the antibody molecule of the present disclosure is a Fab, Fab', or F(ab')2 antibody fragment comprising a light chain variable region given in Seq. ID No. 487 and a heavy chain variable region given in Seq. ID No. 459. In one embodiment, the antibody molecule of the present disclosure is a Fab, Fab', or F(ab')2 antibody fragment comprising a light chain variable region given in Seq. ID No. 488 and a heavy chain variable region given in Seq. ID No. 459. In one embodiment, the antibody molecule of the present disclosure is a Fab, Fab', or F(ab')2 antibody fragment comprising a light chain variable region given in Seq. ID No. 446 and a heavy chain variable region given in Seq. ID No. 457. In one embodiment the antibody molecule of the present disclosure is a Fab, Fab', or F(ab')2 antibody fragment comprising a light chain variable region given in Seq. ID No. 448, and a heavy chain variable region given in Seq. ID No. 457. In one embodiment, the antibody molecule of the present disclosure is a Fab, Fab', or F(ab')2 antibody fragment comprising a light chain variable region given in Seq. ID No. 450 and a heavy chain variable region given in Seq. ID No. 457. In one embodiment, the antibody molecule of the present disclosure is a Fab, Fab', or F(ab')2 antibody fragment comprising a light chain variable region given in Seq. ID No. 452 and a heavy chain variable region given in Seq. ID No. 457. In one embodiment, the antibody molecule of the present disclosure is a Fab, Fab', or F(ab')2 antibody fragment comprising a light chain variable region given in Seq. ID No. 487 and a heavy chain variable region given in Seq. ID No. 457. In one embodiment, the antibody molecule of the present disclosure is a Fab, Fab', or F(ab')2 antibody fragment comprising a light chain variable region given in Seq. ID No. 488 and a heavy chain variable region given in Seq. ID No. 457. In one embodiment, the antibody molecule of the present disclosure is a Fab, Fab', or F(ab')2 antibody fragment comprising a light chain variable region given in Seq. ID No. 446 and a heavy chain variable region given in Seq. ID No. 461. In one embodiment the antibody molecule of the present disclosure is a Fab, Fab', or F(ab')2 antibody fragment comprising a light chain variable region given in Seq. ID No. 448, and a heavy chain variable region given in Seq. ID No. 461. In one embodiment, the antibody molecule of the present disclosure is a Fab, Fab', or F(ab')2 antibody fragment comprising a light chain variable region given in Seq. ID No. 450 and a heavy chain variable region given in Seq. ID No. 461. In one embodiment, the antibody molecule of the present disclosure is a Fab, Fab', or F(ab')2 antibody fragment comprising a light chain variable region given in Seq. ID No. 452 and a heavy chain variable region given in Seq. ID No. 461. In one embodiment, the antibody molecule of the present disclosure is a Fab, Fab', or F(ab')2 antibody fragment comprising a light chain variable region given in Seq. ID No. 487 and a heavy chain variable region given in Seq. ID No. 461. In one embodiment, the antibody molecule of the present disclosure is a Fab, Fab', or F(ab')2 antibody fragment comprising a light chain variable region given in Seq. ID No. 488 and a heavy chain variable region given in Seq. ID No. 461. In one embodiment, the antibody molecule of the present disclosure is a Fab, Fab', or F(ab')2 antibody fragment comprising a light chain variable region given in Seq. ID No. 446 and a heavy chain variable region given in Seq. ID No. 463. In one embodiment the antibody molecule of the present disclosure is a Fab, Fab', or F(ab')2 antibody fragment comprising a light chain variable region given in Seq. ID No. 448, and a heavy chain variable region given in Seq. ID No. 463. In one embodiment, the antibody molecule of the present disclosure is a Fab, Fab', or F(ab')2 antibody fragment comprising a light chain variable region given in Seq. ID No. 450 and a heavy chain variable region given in Seq. ID No. 463. In one embodiment, the antibody molecule of the present disclosure is a Fab, Fab', or F(ab')2 antibody fragment comprising a light chain variable region given in Seq. ID No. 452 and a heavy chain variable region given in Seq. ID No. 463. In one embodiment, the antibody molecule of the present disclosure is a Fab, Fab', or F(ab')2 antibody fragment comprising a light chain variable region given in Seq. ID No. 487 and a heavy chain variable region given in Seq. ID No. 463. In one embodiment, the antibody molecule of the present disclosure is a Fab, Fab', or F(ab')2 antibody fragment comprising a light chain variable region given in Seq. ID No. 488 and a heavy chain variable region given in Seq. ID No. 463.

In one embodiment the antibody molecule of the present disclosure is a full length IgG1 antibody comprising the variable regions shown in Seq. ID Nos. 446, 448, 487, 488, 450, or 452 for the light chain and Seq. ID Nos. 455, 457, 459, 461, or 463 for the heavy chain.

In one embodiment the antibody molecule of the present disclosure is a full length IgG4 antibody comprising the variable regions shown in Seq. ID Nos. 446, 448, 487, 488, 450, or 452 for the light chain and Seq. ID Nos. 455, 457, 459, 461, or 463 for the heavy chain.

In one embodiment the antibody molecule of the present disclosure is a full length IgG4P antibody comprising the variable regions shown in Seq. ID Nos. 446, 448, 487, 488, 450, or 452 for the light chain and Seq. ID Nos. 455, 457, 459, 461, or 463 for the heavy chain. In one embodiment the antibody molecule has a light chain comprising a sequence selected from Seq. ID. Nos. 447, 449, 489, 490, 451, or 453 for the light chain and a sequence selected from Seq. ID Nos. 456, 458, 460, 462, or 464 for the heavy chain. In one embodiment the antibody according to the present disclosure is provided as aP2 binding antibody fusion protein which comprises an immunoglobulin moiety, for example a Fab or Fab' fragment, and one or two single domain antibodies (dAb) linked directly or indirectly thereto, for example as described in WO2009/040562, WO2010035012, WO2011/030107, WO2011/061492 and WO2011/086091 all incorporated herein by reference.

In one embodiment the fusion protein comprises two domain antibodies, for example as a variable heavy (VH) and variable light (VL) pairing, optionally linked by a disulphide bond.

The antibody fragment of the present invention includes Fab, Fab', F(ab')2, scFv, diabody, scFAb, dFv, single domain light chain antibodies, dsFv, a peptide comprising CDR, and the like.

An Fab is an antibody fragment having a molecular weight of about 50,000 and antigen binding activity, in which about a half of the N-terminal side of H chain and the entire L chain, among fragments obtained by treating IgG with a protease, papain (cut at an amino acid residue at position 224 of the H chain), are bound together through a disulfide bond.

The Fab of the present invention can be obtained by treating a human CDR-grafted antibody of the present invention, which specifically reacts with aP2, with a protease, papain. Also, the Fab can be produced by inserting DNA encoding Fab of the antibody into an expression vector for prokaryote or an expression vector for eukaryote, and introducing the vector into a prokaryote or eukaryote to express the Fab.

An F(ab')2 is an antibody fragment having a molecular weight of about 100,000 and antigen binding activity, which is slightly larger than the Fab bound via a disulfide bond of the hinge region, among fragments obtained by treating IgG with a protease, pepsin.

The F(ab')2 of the present invention can be obtained by treating a human CDR-grafted antibody which specifically reacts with aP2, with a protease, pepsin. Also, the F(ab')2 can be produced by binding Fab' described below via a thioether bond or a disulfide bond.

An Fab' is an antibody fragment having a molecular weight of about 50,000 and antigen binding activity, which is obtained by cutting a disulfide bond of the hinge region of the F(ab')2.

The Fab' of the present invention can be obtained by treating the F(ab')2 which specifically reacts with aP2, with a reducing agent, dithiothreitol. Also, the Fab' of the present invention can be produced by inserting DNA encoding an Fab' of a human CDR-grafted antibody of the present invention which specifically reacts with aP2 into an expression vector for prokaryote or an expression vector for eukaryote, and introducing the vector into a prokaryote or eukaryote to express the Fab'.

An scFv is a VH-P-VL or VL-P-VH polypeptide in which one chain VH and one chain VL are linked using an appropriate peptide linker (P) of 12 or more residues and which has an antigen-binding activity.

The scFv of the present invention can be produced by obtaining cDNAs encoding VH and VL of a human CDR-grafted antibody which specifically reacts with aP2 of the present invention, constructing DNA encoding scFv, inserting the DNA into an expression vector for prokaryote or an expression vector for eukaryote, and then introducing the expression vector into a prokaryote or eukaryote to express the scFv.

A diabody is an antibody fragment in which scFv's having the same or different antigen binding specificity forms a dimer, and has an divalent antigen binding activity to the same antigen or two specific antigen binding activities to different antigens.

The diabody of the present invention, for example, a divalent diabody which specifically reacts with aP2, can be produced by obtaining cDNAs encoding VH and VL of an antibody which specifically reacts with aP2, constructing DNA encoding scFv having a polypeptide linker of 3 to 10 residues, inserting the DNA into an expression vector for prokaryote or an expression vector for eukaryote, and then introducing the expression vector into a prokaryote or eukaryote to express the diabody.

A dsFv is obtained by binding polypeptides in which one amino acid residue of each of VH and VL is substituted with a cysteine residue via a disulfide bond between the cysteine residues. The amino acid residue, which is substituted with a cysteine residue, can be selected based on a three-dimensional structure estimation of the antibody in accordance with the method shown by Reiter et al. (Protein Engineering, 7, 697 (1994)).

The dsFv of the present invention can be produced by obtaining cDNAs encoding VH and VL of a human CDR-grafted antibody which specifically reacts with aP2 of the present invention, constructing DNA encoding dsFv, inserting the DNA into an expression vector for prokaryote or an expression vector for eukaryote, and then introducing the expression vector into a prokaryote or eukaryote to express the dsFv.

A peptide comprising CDR is constituted by including at least one region of H chain and L chain CDRs. Plural CDRs can be bound directly or via an appropriate peptide linker.

The peptide comprising CDR of the present invention can be produced by obtaining cDNA encoding CDR of VH and VL of a human CDR-grafted antibody which specifically reacts with aP2, constructing DNA encoding CDR, inserting the DNA into an expression vector for prokaryote or an expression vector for eukaryote, and then by introducing the expression vector into a prokaryote or eukaryote to express the peptide. Also, the peptide comprising CDR can also be produced by a chemical synthesis method such as an Fmoc method (fluorenylmethoxycarbonyl method), a tBoc method (t-butyloxycarbonyl method), or the like.

The antibody of the present invention includes antibody derivatives in which a radioisotope, a protein, an agent or the like is chemically or genetically conjugated to the antibody of the present invention.

The antibody derivatives of the present invention can be produced by chemically conjugating a radioisotope, a protein or an agent to the N-terminal side or C-terminal side of an H chain or an L chain of an antibody or antibody fragment which specifically reacts with aP2, to an appropriate substituent group or side chain of the antibody or antibody fragment or to a sugar chain in the antibody or antibody fragment (Antibody Engineering Handbook, edited by Osamu Kanemitsu, published by Chijin Shokan (1994)).

Also, it can be genetically produced by linking a DNA encoding the antibody or the antibody fragment of the present invention which specifically reacts with aP2 to other DNA encoding a protein to be bound, inserting the DNA into an expression vector, and introducing the expression vector into a host cell.

The radioisotope includes 131I, 125I and the like, and it can be conjugated to the antibody by, e.g., a chloramine T method.

The agent is preferably a low molecular weight compound. Examples include anticancer agents such as alkylating agents (e.g., nitrogen mustard, cyclophosphamide), metabolic antagonists (e.g., 5-fluorouracil, methotrexate), antibiotics (e.g., daunomycin, bleomycin, mitomycin C, daunorubicin, doxorubicin), plant alkaloids (e.g., vincristine, vinblastine, vindesine), hormone drugs (e.g., tamoxifen, dexamethasone), and the like (Clinical Oncology, edited by Japanese Society of Clinical Oncology, published by Cancer and Chemotherapy (1996)); anti-inflammatory agents such as steroid agents (e.g., hydrocortisone, prednisone), non-steroidal drugs (e.g., aspirin, indomethacin), immunomodulators (e.g., aurothiomalate, penicillamine), immunosuppressing agents (e.g., cyclophosphamide, azathioprine) and antihistaminic agents (e.g., chlorpheniramine maleate, clemastine) (Inflammation and Anti-inflammatory Therapy, Ishiyaku Shuppan (1982)); and the like. The method for conjugating daunomycin to an antibody includes a method in which daunomycin and an amino group of an antibody are conjugated via glutaraldehyde, a method in which an amino group of daunomycin and a carboxyl group of an antibody are conjugated via a water-soluble carbodiimide, and the like.

Also, in order to inhibit cancer cells directly, a toxin such as ricin, diphtheria toxin and the like, can be used. For example, a fusion antibody with a protein can be produced by linking a cDNA encoding an antibody or antibody fragment to other cDNA encoding the protein, constructing DNA encoding the fusion antibody, inserting the DNA into an expression vector for prokaryote or an expression vector for eukaryote, and then introducing it into a prokaryote or eukaryote to express the fusion antibody.

Further contemplated herein are antibody fragments or antigen binding agents including fusions of binding agents, for example immunoglobulin like fragments and agents such as diabodies, scAbs, bispecific fragments, triabodies, Fab-Fv-Fv, Fab-Fv, tribody, (Fab-Fv)2-Fc, and antibody fragments or portions, such as CDRs or antibody loops including CDRs, which are grafted onto non-Ig frameworks such as fibronectin or leucine zippers, as descried in Binz et al., (2005) Nat. Biotech. 23:1257-1268, incorporated in its entirety herein.

Conjugated Anti-aP2 Monoclonal Antibodies and Antigen Binding Agents

If desired, an antibody or antigen binding agent for use in the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO 03/031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, antigen binding agents, synthetic (including PEG) or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as 111In and 90Y, Lu177, Bismuth213, Californium252, Iridium192 and Tungsten188/Rhenium188; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumor necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions, which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include 125I, 131I, 111In and 99Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

In one embodiment a half-life provided by an effector molecule which is independent of aP2 or an anti-human aP2 antibody is advantageous.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents, which may be present on the above-mentioned synthetic polymers, include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Specific naturally occurring polymers include lactose, amylose, dextran, glycogen or derivatives thereof.

In one embodiment the polymer is albumin or a fragment thereof, such as human serum albumin or a fragment thereof. In one embodiment the polymer is a PEG molecule.

"Derivatives" as used herein in regard to conjugates is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the natural or synthetic polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. No. 5,219,996; U.S. Pat. No. 5,667,425; WO98/25971, WO2008/038024). In one example the antibody molecule of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above.

The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment, Fab' fragment or diFab which is PEGylated, i.e. has PEG (poly(ethyleneglycol)) covalently attached thereto, e.g. according to the method disclosed in EP 0948544 or EP1090037 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

Particular PEG molecules include 2-[3-(N-maleimido) propionamido]ethyl amide of N,N'-bis(methoxypoly(ethylene glycol) MW 20,000) modified lysine, also known as PEG2MAL40K (obtainable from Nektar, formerly Shearwater).

Alternative sources of PEG linkers include NOF who supply GL2-400MA3 (wherein m in the structure below is 5) and GL2-400MA (where m is 2) and n is approximately 450:

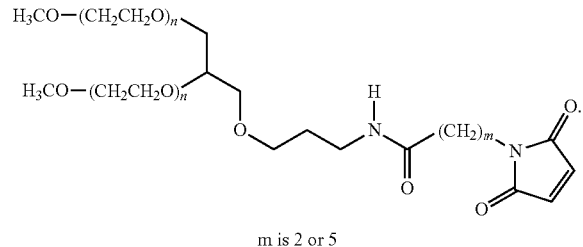

m is 2 or 5

That is to say each PEG is about 20,000 Da.

Thus in one embodiment the PEG is 2,3-Bis(methylpolyoxyethylene-oxy)-1-{[3-(6-maleimido-1-oxohexyl) amino]propyloxy} hexane (the 2 arm branched PEG, —CH2) 3NHCO(CH2)5-MAL, Mw 40,000 known as SUNBRIGHT GL2-400MA3.

Further alternative PEG effector molecules of the following type:

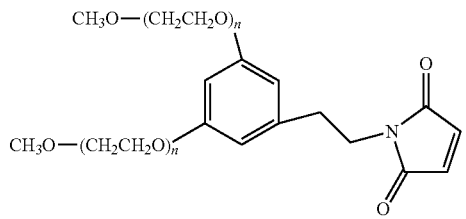

are available from Dr Reddy, NOF and Jenkem.

In one embodiment there is provided an antibody which is PEGylated (for example with a PEG described herein), attached through a cysteine amino acid residue at or about amino acid 229 in the chain, for example amino acid 229 of the heavy chain (by sequential numbering), for example amino acid 229 of Seq. ID No. 456, 460, 458, 462, or 464.

In one embodiment the present disclosure provides a Fab'PEG molecule comprising one or more PEG polymers, for example 1 or 2 polymers such as a 40 kDa polymer or polymers.

Fab'-PEG molecules according to the present disclosure may be particularly advantageous in that they have a half-life independent of the Fc fragment. In one example the present invention provides a method treating a disease ameliorated by modulating human aP2 biological activity comprising administering a therapeutically effective amount of an anti-aP2 antibody or antigen binding agent thereof wherein the antibody or antigen binding agent thereof has a half-life that is independent of Fc binding to aP2.

In one embodiment there is provided a Fab' conjugated to a polymer, such as a PEG molecule, a starch molecule or an albumin molecule.

In one embodiment there is provided a scFv conjugated to a polymer, such as a PEG molecule, a starch molecule or an albumin molecule.

In one embodiment the antibody or fragment is conjugated to a starch molecule, for example to increase the half-life. Methods of conjugating starch to a protein as described in U.S. Pat. No. 8,017,739 incorporated herein by reference.

Polynucleotides

The present invention also provides an isolated DNA sequence encoding the heavy and/or light chain(s) of an antibody molecule of the present invention. Suitably, the DNA sequence encodes the heavy or the light chain of an antibody molecule of the present invention. The DNA sequence of the present invention may comprise synthetic DNA, for instance produced by chemical processing, cDNA, genomic DNA or any combination thereof.

DNA sequences, which encode an antibody molecule of the present invention, can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesized completely or in part using oligonucleotide synthesis techniques. Site-directed mutagenesis and polymerase chain reaction (PCR) techniques may be used as appropriate.

Examples of suitable cDNA sequences are provided in Table 12 below.

Examples of suitable cDNA sequences encoding a humanized light chain variable region are provided in Seq. ID Nos. 467, 469, 491, 493, 471, and 473. Examples of suitable DNA sequences encoding the humanized heavy chain variable region are provided in Seq. ID No. 475, 507, 477, 509, and 511.

Examples of suitable cDNA sequences encoding the light chain (variable and constant) are provided in Seq. ID Nos. 468, 470, 492, 494, 472, and 474.

Examples of suitable cDNA sequences encoding the heavy chain (variable and constant) are provided in Seq. ID Nos. 476, 508, 478, 510, and 512.

TABLE 12

Examples of Suitable DNA sequences Encoding anti-aP2 Antibody Fragments

| cDNA Encoding Identifier | Seq. ID No. | Sequence |
| --- | --- | --- |
| Rabbit Ab 909 VL region (Seq. ID No. 445) cDNA | 465 | gacgtcgtgatgacccagactccagcctccgtgtctgaacctgtgggaggcacag tcaccatcaagtgccaggccagtgaggatattagtaggtacttagtctggtatcagc agaaaccagggcagcctcccaagcgcctgatctacaaggcatccactctggcatc tggggtcccatcgcggttcaaaggcagtggatctgggacagatttcactctcacca tcagcgacctggagtgtgacgatgctgccacttactactgtcaatgcacttatggta cttatgctggtagtttttttttattcttcggcggagggaccgaggtggtcgtcgaa |
| Rabbit Ab 909 VH region (Seq. ID No. 454) cDNA | 466 | cagtcggtggaggagtccgggggtcgcctggtcacgcctgggacaccctgac actcacctgcacagtctctggattctcctcagtacctactacatgagctgggtccg ccaggctccagggaaggggctggaatggatcggaatcatttatcctagtggtagc acatactgcgcgagctgggcgaaaggccgattcaccatctccaaagcctcaacca cggtggatctgaaaatcaccagtccgacaaccgaggacacggccacctatttctgt gccagacctgataatgatggtacttctggttatttgagtggtttcggcttgtggggcc aaggcaccctcgtcaccgtctcgagc |
| 909 gL1 V-region (Seq. ID No. 446) cDNA | 467 | gacgtcgtcatgacccagtcccccttcctcccctttcagccagcgtgggcgatagagt gactatcacttgccaagcgtcggaggacatctcgcgctacctggtgtggtatcaac agaagccaggtaaagcgcccaagcggctgatctacaaggcctcaactttggcatc cggagtgccgtcgaggttcaagggcagcggatcgggaaccgacttcactctcac cattagctcactgcagccggaagattttgccacttactactgccagtgtacctacgg gacctacgctgggtcgttcttttacagcttcggaggcggaaccaaagtggaaatca ag |
| 909 gL1 light chain (V + constant) (Seq. ID No. 447) cDNA | 468 | gacgtcgtcatgacccagtcccccttcctcccctttcagccagcgtgggcgatagagt gactatcacttgccaagcgtcggaggacatctcgcgctacctggtgtggtatcaac agaagccaggtaaagcgcccaagcggctgatctacaaggcctcaactttggcatc cggagtgccgtcgaggttcaagggcagcggatcgggaaccgacttcactctcac cattagctcactgcagccggaagattttgccacttactactgccagtgtacctacgg gacctacgctgggtcgttcttttacagcttcggaggcggaaccaaagtggaaatca agcgtacggtggccgctcccctccgtgttcatcttcccacccctccgacgagcagctg aagtccggcaccgcctccgtcgtgtgcctgctgaacaacttctaccccgcgagg ccaaggtgcagtggaaggtggacaacgccctgcagtccggcaactcccaggaat ccgtcaccgagcaggactccaaggacagcacctactccctgtcctccaccctgac cctgtccaaggccgactacgagaagcacaaggtgtacgcctgcgaagtgaccca ccagggcctgtccagccccgtgaccaagtccttcaaccggggcgagtgc |
| 909 gL10 V-region (Seq. ID No. 448) cDNA | 469 | gacgtcgtcatgacccagtcccccttcctcccctttcagccagcgtgggcgatagagt gactatcacttgccaagcgtcggaggacatctcgcgctacctggtgtggtatcaac agaagccaggtaaagcgcccaagcggctgatctacaaggcctcaactttggcatc cggagtgccgtcgaggttcaagggcagcggatcgggaaccgacttcactctcac cattagctcactgcagccggaagattttgccacttactactgccaggctacctacgg gacctacgctgggtcgttcttttacagcttcggaggcggaaccaaagtggaaatca ag |
| 909 gL10 light chain (V + constant) (Seq. ID No. 449) cDNA | 470 | gacgtcgtcatgacccagtcccccttcctcccctttcagccagcgtgggcgatagagt gactatcacttgccaagcgtcggaggacatctcgcgctacctggtgtggtatcaac agaagccaggtaaagcgcccaagcggctgatctacaaggcctcaactttggcatc cggagtgccgtcgaggttcaagggcagcggatcgggaaccgacttcactctcac cattagctcactgcagccggaagattttgccacttactactgccaggctacctacgg gacctacgctgggtcgttcttttacagcttcggaggcggaaccaaagtggaaatca agcgtacggtggccgctcccctccgtgttcatcttcccacccctccgacgagcagctg aagtccggcaccgcctccgtcgtgtgcctgctgaacaacttctaccccgcgagg ccaaggtgcagtggaaggtggacaacgccctgcagtccggcaactcccaggaat ccgtcaccgagcaggactccaaggacagcacctactccctgtcctccaccctgac cctgtccaaggccgactacgagaagcacaaggtgtacgcctgcgaagtgaccca ccagggcctgtccagccccgtgaccaagtccttcaaccggggcgagtgc |
| 909 gL13 V-region (Seq. ID No. 487) cDNA | 491 | gacatccaaatgacccagtcccccttcctcccctttcagccagcgtgggcgatagagt gactatcacttgccaagcgtcggaggacatctcgcgctacctggtgtggtatcaac agaagccaggtaaagcgcccaagcggctgatctacaaggcctcaactttggcatc cggagtgccgtcgaggttctccggcagcggatcgggaaccgagttcactctcacc attagctcactgcagccggaagattttgccacttactactgccaggctacctacggg acctacgctgggtcgttcttttacagcttcggaggcggaaccaaagtggaaatcaag |
| 909 gL13 light chain (V + constant) (Seq. ID No. 489) cDNA | 492 | gacatccaaatgacccagtcccccttcctcccctttcagccagcgtgggcgatagagt gactatcacttgccaagcgtcggaggacatctcgcgctacctggtgtggtatcaac agaagccaggtaaagcgcccaagcggctgatctacaaggcctcaactttggcatc cggagtgccgtcgaggttctccggcagcggatcgggaaccgagttcactctcacc attagctcactgcagccggaagattttgccacttactactgccaggctacctacggg |

TABLE 12-continued

Examples of Suitable DNA sequences Encoding anti-aP2 Antibody Fragments

| cDNA Encoding Identifier | Seq. ID No. | Sequence |
| --- | --- | --- |
| | | acctacgctgggtcgttcttttacagcttcggaggcggaaccaaagtggaaatcaa<br>gcgtacggtggccgctccctccgtgttcatcttcccacccctccgacgagcagctga<br>agtccggcaccgcctccgtcgtgtgcctgctgaacaacttctaccccgcgaggc<br>caaggtgcagtggaaggtggacaacgccctgcagtccggcaactcccaggaatc<br>cgtcaccgagcaggactccaaggacagcacctactccctgtcctccaccctgacc<br>ctgtccaaggccgactacgagaagcacaaggtgtacgcctgcgaagtgacccac<br>cagggcctgtccagcccgtgaccaagtccttcaaccggggcgagtgc |
| 909 gL50 V-region (Seq. ID No. 488) cDNA | 493 | gacgtcgtcatgacccagtccccttcctccctttcagccagcgtgggcgatagagt<br>gactatcacttgccaagcgtcggaggacatctcgcgctacctggtgtggtatcaac<br>agaagccaggtaaagcgcccaagcggctgatctacaaggcctcaactttggcatc<br>cggagtgccgtcgaggttcaagggcagcggatcgggaaccgacttcactctcac<br>cattagctcactgcagccggaagattttgccacttactacgcccaggctacctacg<br>ggacctacgctgggtcgttcttttacagcttcggaggcggaaccaaagtggaaatc<br>aag |
| 909 gL50 light chain (V + constant) (Seq. ID No. 490) cDNA | 494 | gacgtcgtcatgacccagtccccttcctccctttcagccagcgtgggcgatagagt<br>gactatcacttgccaagcgtcggaggacatctcgcgctacctggtgtggtatcaac<br>agaagccaggtaaagcgcccaagcggctgatctacaaggcctcaactttggcatc<br>cggagtgccgtcgaggttcaagggcagcggatcgggaaccgacttcactctcac<br>cattagctcactgcagccggaagattttgccacttactacgcccaggctacctacg<br>ggacctacgctgggtcgttcttttacagcttcggaggcggaaccaaagtggaaatc<br>aagcgtacggtggccgctcccctccgtgttcatcttcccaccctccgacgagcagct<br>gaagtccggcaccgcctccgtcgtgtgcctgctgaacaacttctaccccgcgag<br>gccaaggtgcagtggaaggtggacaacgccctgcagtccggcaactcccagga<br>atccgtcaccgagcaggactccaaggacagcacctactccctgtcctccaccctg<br>accctgtccaaggccgactacgagaagcacaaggtgtacgcctgcgaagtgacc<br>cacagggcctgtccagcccgtgaccaagtccttcaaccggggcgagtgc |
| 909 gL54 V-region (Seq. ID No. 450) cDNA | 471 | gacgtcgtcatgacccagtccccttcctccctttcagccagcgtgggcgatagagt<br>gactatcacttgccaagcgtcggaggacatctcgcgctacctggtgtggtatcaac<br>agaagccaggtaaagcgcccaagcggctgatctacaaggcctcaactttggcatc<br>cggagtgccgtcgaggttcaagggcagcggatcgggaaccgacttcactctcac<br>cattagctcactgcagccggaagattttgccacttactactgccagcagacctacg<br>ggacctacgctgggtcgttcttttacagcttcggaggcggaaccaaagtggaaatc<br>aag |
| 909 gL54 light chain (V + constant) (Seq. ID No. 451) cDNA | 472 | gacgtcgtcatgacccagtccccttcctccctttcagccagcgtgggcgatagagt<br>gactatcacttgccaagcgtcggaggacatctcgcgctcctggtgtggtatcaac<br>agaagccaggtaaagcgcccaagcggctgatctacaaggcctcaactttggcatc<br>cggagtgccgtcgaggttcaagggcagcggatcgggaaccgacttcactctcac<br>cattagctcactgcagccggaagattttgccacttactactgccagcagacctacg<br>ggacctacgctgggtcgttcttttacagcttcggaggcggaaccaaagtggaaatc<br>aagcgtacggtggccgctcccctccgtgttcatcttcccaccctccgacgagcagct<br>gaagtccggcaccgcctccgtcgtgtgcctgctgaacaacttctaccccgcgag<br>gccaaggtgcagtggaaggtggacaacgccctgcagtccggcaactcccagga<br>atccgtcaccgagcaggactccaaggacagcacctactccctgtcctccaccctg<br>accctgtccaaggccgactacgagaagcacaaggtgtacgcctgcgaagtgacc<br>cacagggcctgtccagcccgtgaccaagtccttcaaccggggcgagtgc |
| 909 gL55 V-region (Seq. ID No. 452) cDNA | 473 | gacgtcgtcatgacccagtccccttcctccctttcagccagcgtgggcgatagagt<br>gactatcacttgccaagcgtcggaggacatctcgcgctacctggtgtggtatcaac<br>agaagccaggtaaagcgcccaagcggctgatctacaaggcctcaactttggcatc<br>cggagtgccgtcgaggttcaagggcagcggatcgggaaccgacttcactctcac<br>cattagctcactgcagccggaagattttgccacttactactgccagcatacctacgg<br>gacctacgctgggtcgttcttttacagcttcggaggcggaaccaaagtggaaatca<br>ag |
| 909 gL55 light chain (V + constant) (Seq. ID No. 453) cDNA | 474 | gacgtcgtcatgacccagtccccttcctccctttcagccagcgtgggcgatagagt<br>gactatcacttgccaagcgtcggaggacatctcgcgctacctggtgtggtatcaac<br>agaagccaggtaaagcgcccaagcggctgatctacaaggcctcaactttggcatc<br>cggagtgccgtcgaggttcaagggcagcggatcgggaaccgacttcactctcac<br>cattagctcactgcagccggaagattttgccacttactactgccagcatacctacgg<br>gacctacgctgggtcgttcttttacagcttcggaggcggaaccaaagtggaaatca<br>agcgtacggtggccgctcccctccgtgttcatcttcccaccctccgacgagcagctg<br>aagtccggcaccgcctccgtcgtgtgcctgctgaacaacttctaccccgcgagg<br>ccaaggtgcagtggaaggtggacaacgccctgcagtccggcaactcccaggaat<br>ccgtcaccgagcaggactccaaggacagcacctactccctgtcctccaccctgac<br>cctgtccaaggccgactacgagaagcacaaggtgtacgcctgcgaagtgaccca<br>ccagggcctgtccagcccgtgaccaagtccttcaaccggggcgagtgc |
| 909gH1 V-region (Seq. ID No. 455) cDNA | 475 | gaagtccagctgcaagaatcaggtccaggcctcgtcaaaccatcaggaactttgtc<br>attgacttgcacggtgagcggttctcgctttcgacctactacatgtcgtgggtgcg<br>ccagccgcctgggaagggactggagtggatcggcatcatctacccgtccggcag |

TABLE 12-continued

Examples of Suitable DNA sequences Encoding anti-aP2 Antibody Fragments

| cDNA Encoding Identifier | Seq. ID No. | Sequence |
|---|---|---|
| | | cacgtactgcgctagctgggccaaggggcggttcaccatcagcaaggcgtccac<br>tactgtggacctcaagctgtcgtcagttactgcggccgacactgcaacctactttgt<br>gcccgcccggataacgatggaacctccggctacctgtccggattcggactgtggg<br>gacagggaaccctttgtgactgtctcgagc |
| 909 gH1 IgG4 heavy chain (V + human γ-4P constant) Seq. ID No. 456) cDNA | 476 | gaagtccagctgcaagaatcaggtccaggcctcgtcaaaccatcaggaactttgtc<br>attgacttgcacggtgagcgggttctcgcttttcgacctactacatgtcgtgggtgcg<br>ccagccgcctgggaagggactggagtggatcggcatcatctacccgtccggcag<br>cacgtactgcgctagctgggccaaggggcggttcaccatcagcaaggcgtccac<br>tactgtggacctcaagctgtcgtcagttactgcggccgacactgcaacctactttgt<br>gcccgcccggataacgatggaacctccggctacctgtccggattcggactgtggg<br>gacagggaaccctttgtgactgtctcgagcgcctccaccaagggcccctccgtgtt<br>ccctctggccccttgctcccggtccacctccgagtctaccgccgctctgggctgcc<br>tggtcaaggactacttccccgagcccgtgacagtgtcctggaactctggcgccctg<br>acctccggcgtgcacaccttccctgccgtgctgcagtcctccggcctgtactccct<br>gtcctccgtcgtgaccgtgccctcctccagcctgggcaccaagacctacacctgta<br>acgtggaccacaagccctccaacaccaaggtggacaagcgggtggaatctaagt<br>acggcccctccctgcccccctgccctgcccctgaatttctgggcggaccttccgtg<br>ttcctgttccccccaaagcccaaggacaccctgatgatctcccggaccccgaagt<br>gacctgcgtggtggtggacgtgtcccaggaagatcccgaggtccagttcaattgg<br>tacgtggacggcgtggaagtgcacaatgccaagaccaagcccagagaggaaca<br>gttcaactccacctaccgggtggtgtccgtgctgaccgtgctgcaccaggactgg<br>ctgaacggcaaagagtacaagtgcaaggtgtccaacaagggcctgcccctccagc<br>atcgaaaagaccatctccaaggccaagggccagccccgcgagccccaggtgta<br>caccctgccccctagccaggaagagatgaccaagaaccaggtgtccctgacctg<br>tctggtcaagggcttctaccccctccgacattgccgtggaatgggagtccaacggcc<br>agcccgagaacaactacaagaccacccccccctgtgctggacagcgacggctcct<br>tcttcctgtactctcggctgaccgtggacaagtcccggtggcaggaaggcaacgt<br>cttctcctgctccgtgatgcacgaggccctgcacaaccactacacccagaagtccc<br>tgtccctgagcctgggcaag |
| 909gH14 V-region (Seq. ID No. 457) cDNA | 507 | gaagtccagctgcaagaatcaggtccaggcctcgtcaaaccatcaggaactttgtc<br>attgacttgcgccgtgagcgggttctcgcttttcgacctactacatgtcgtgggtgcg<br>ccagccgcctgggaagggactggagtggatcggcatcatctacccgtccggcag<br>cacgtactgcgctagctgggccaaggggcggttcaccatcagcaaggcgtccac<br>taaaaatactgtggacctcaagctgtcgtcagttactgcggccgacactgcaacct<br>acttttgtgcccgcccggataacgatggaacctccggctacctgtccggattcgga<br>ctgtggggacagggaaccccttgtgactgtctcgagc |
| 909 gH14 IgG4 heavy chain (V + human gamma-4P constant) (Seq. ID No. 457) cDNA | 508 | gaagtccagctgcaagaatcaggtccaggcctcgtcaaaccatcaggaactttgtc<br>attgacttgcgccgtgagcgggttctcgcttttcgacctactacatgtcgtgggtgcg<br>ccagccgcctgggaagggactggagtggatcggcatcatctacccgtccggcag<br>cacgtactgcgctagctgggccaaggggcggttcaccatcagcaaggcgtccac<br>taaaaatactgtggacctcaagctgtcgtcagttactgcggccgacactgcaacct<br>acttttgtgcccgcccggataacgatggaacctccggctacctgtccggattcgga<br>ctgtggggacagggaaccccttgtgactgtctcgagcgcctccaccaagggcccct<br>ccgtgttccctctggccccttgctcccggtccacctccgagtctaccgccgctctgg<br>gctgcctggtcaaggactacttccccgagcccgtgacagtgtcctggaactctggc<br>gccctgacctccggcgtgcacaccttccctgccgtgctgcagtcctccggcctgta<br>ctccctgtcctccgtcgtgaccgtgccctcctccagcctgggcaccaagacctaca<br>cctgtaacgtggaccacaagccctccaacaccaaggtggacaagcgggtggaat<br>ctaagtacggcccctccctgcccccctgccctgcccctgaatttctgggcggacct<br>tccgtgttcctgttccccccaaagcccaaggacaccctgatgatctcccggacccc<br>cgaagtgacctgcgtggtggtggacgtgtcccaggaagatcccgaggtccagttc<br>aattggtacgtggacggcgtggaagtgcacaatgccaagaccaagcccagaga<br>ggaacagttcaactccacctaccgggtggtgtccgtgctgaccgtgctgcaccag<br>gactggctgaacggcaaagagtacaagtgcaaggtgtccaacaagggcctgccc<br>tccagcatcgaaaagaccatctccaaggccaagggccagccccgcgagccccag<br>gtgtacaccctgccccctagccaggaagagatgaccaagaaccaggtgtccct<br>gacctgtctggtcaagggcttctaccccctccgacattgccgtggaatgggagtcca<br>acggccagcccgagaacaactacaagaccaccccccctgtgctggacagcgac<br>ggctccttcttcctgtactctcggctgaccgtggacaagtcccggtggcaggaagg<br>caacgtcttctcctgctccgtgatgcacgaggccctgcacaaccactacacccaga<br>agtccctgtccctgagcctgggcaag |
| 909gH15 V-region (Seq. ID. No. 459) cDNA | 477 | gaagtccagctgcaagaatcaggtccaggcctcgtcaaaccatcaggaactttgtc<br>attgacttgcacggtgagcgggttctcgcttttcgacctactacatgtcgtgggtgcg<br>ccagccgcctgggaagggactggagtggatcggcatcatctacccgtccggcag<br>cacgtactccgctagctgggccaaggggcggttcaccatcagcaaggcgtccac<br>taaaaatactgtggacctcaagctgtcgtcagttactgcggccgacactgcaacct<br>acttttgtgcccgcccggataacgagggaacctccggctacctgtccggattcgga<br>ctgtggggacagggaaccccttgtgactgtctcgagc |

TABLE 12-continued

Examples of Suitable DNA sequences Encoding anti-aP2 Antibody Fragments

| cDNA Encoding Identifier | Seq. ID No. | Sequence |
| --- | --- | --- |
| 909 gH15 IgG4 heavy chain (V + human gamma-4P constant) (Seq. ID No. 460) cDNA | 478 | gaagtccagctgcaagaatcaggtccaggcctcgtcaaaccatcaggaactttgtc<br>attgacttgcacggtgagcgggttctcgctttcgacctactacatgtcgtgggtgcg<br>ccagccgcctgggaagggactggagtggatcggcatcatctacccgtccggcag<br>cacgtactccgctagctgggccaaggggcggttcaccatcagcaaggcgtccac<br>taaaaatactgtggacctcaagctgtcgtcagttactgcggccgacactgcaacct<br>acttttgtgcccgcccggataacgagggaacctccggctacctgtccggattcgga<br>ctgtggggacagggaaccccttgtgact<br>gtctcgagcgcctccaccaagggcccctccgtgttccctctggcccccttgctccccg<br>gtccacctccgagtctaccgccgctctgggctgcctggtcaaggactacttcccccg<br>agcccgtgacagtgtcctggaactctggcgccctgacctccggcgtgcacaccttt<br>ccctgcgctgctgcagtcctccggcctgtactccctgtcctccgtcgtgaccgtgcc<br>ctcctccagcctgggcaccaagacctacacctgtaacgtggaccacaagcccctcc<br>aacaccaaggtggacaagcgggtggaatctaagtacggccctccctgccccccc<br>tgccctgcccctgaatttctgggcggaccttccgtgttcctgttcccccaaagccc<br>aaggacaccctgatgatctcccggacccccgaagtgacctgcgtggtggtggac<br>gtgtcccaggaagatcccgaggtccagttcaattggtacgtggacggcgtggaag<br>tgcacaatgccaagaccaagcccagagaggaacagttcaactccacctaccggg<br>tggtgtccgtgctgaccgtgctgcaccaggactggctgaacggcaaagagtacaa<br>gtgcaaggtgtccaacaaggcctgcctccagcatcgaaaagaccatctccaa<br>ggccaagggccagccccgcgagccccaggtgtacaccctgcccctagccagg<br>aagagatgaccaagaaccaggtgtccctgacctgtctggtcaagggcttctaccc<br>ctccgacattgccgtggaatgggagtccaacgccagcccgagaacaactacaa<br>gaccacccccctgtgctggacagcgacggctccttcttcctgtactctcggctga<br>ccgtggacaagtcccggtggcaggaaggcaacgtcttctcctgctccgtgatgca<br>cgaggccctgcacaaccactacacccagaagtccctgtccctgagcctgggcaag |
| 909gH61 V-region (Seq. ID. No. 461) cDNA | 509 | gaagtccagctgcaagaatcaggtccaggcctcgtcaaaccatcaggaactttgtc<br>attgacttgcgccgtgagcgggttctcgctttcgacctactacatgtcgtgggtgcg<br>ccagccgcctgggaagggactggagtggatcggcatcatctacccgtccggcag<br>cacgtactgcgctagctgggccaaggggcgggtgaccatcagcaaggactcca<br>gcaaaaatcaggtgagcctcaagctgtcgtcagttactgcggccgacactgcagt<br>gtactattgtgcccgcccggataacgatggaacctccggctacctgtccggattcg<br>gactgtggggacagggaaccccttgtgactgtctcgagc |
| 909 gH61 IgG4 heavy chain (V + human gamma-4P constant) (Seq. ID No. 462) cDNA | 510 | gaagtccagctgcaagaatcaggtccaggcctcgtcaaaccatcaggaactttgtc<br>attgacttgcgccgtgagcgggttctcgctttcgacctactacatgtcgtgggtgcg<br>ccagccgcctgggaagggactggagtggatcggcatcatctacccgtccggcag<br>cacgtactgcgctagctgggccaaggggcgggtgaccatcagcaaggactcca<br>gcaaaaatcaggtgagcctcaagctgtcgtcagttactgcggccgacactgcagt<br>gtactattgtgcccgcccggataacgatggaacctccggctacctgtccggattc<br>ggactgtggggacagggaaccccttgtgactgtctcgagcgcctccaccaagggc<br>cctccgtgttccctctggcccccttgctcccggtccacctccgagtctaccgccgc<br>tctgggctgcctggtcaaggactacttccccgagcccgtgacagtgtcctggaact<br>ctggcgccctgacctccggcgtgcacaccttccctgccgtgctgcagtcctccg<br>cctgtactccctgtcctccgtcgtgaccgtgccctcctccagcctgggcaccaaga<br>cctacacctgtaacgtggaccacaagcccctccaacaccaaggtggacaagcgg<br>gtggaatctaagtacggcccctccctgccccccctgccctgcccctgaatttctggg<br>cggaccttccgtgttcctgttcccccaaagccaaggacaccctgatgatctccc<br>ggacccccgaagtgacctgcgtggtggtggacgtgtcccaggaagatcccgag<br>gtccagttcaattggtacgtggacggcgtggaagtgcacaatgccaagaccaagc<br>ccagagaggaacagttcaactccacctaccgggtggtgtccgtgctgaccgtgct<br>gcaccaggactggctgaacggcaaagagtacaagtgcaaggtgtccaacaagg<br>cctgcctccagcatcgaaaagaccatctccaagggcaagggccagccccg<br>cgagcccaggtgtacaccctgcccctagccaggaagagatgaccaagaacc<br>aggtgtccctgacctgtctggtcaagggcttctacccctccgacattgccgtggaat<br>gggagtccaacgccagcccgagaacaactacaagaccacccccctgtgctg<br>gacagcgacggctccttcttcctgtactctcggctgaccgtggacaagtcccggtg<br>gcaggaaggcaacgtcttctcctgctccgtgatgcacgaggccctgcacaaccac<br>tacacccagaagtccctgtccctgagcctgggcaag |
| 909gH62 V-region (Seq. ID. No. 463) cDNA | 511 | gaagtccagctgcaagaatcaggtccaggcctcgtcaaaccatcaggaactttgtc<br>attgacttgcgccgtgagcgggttctcgctttcgacctactacatgtcgtgggtgcg<br>ccagccgcctgggaagggactggagtggatcggcatcatctacccgtccggcag<br>cacgtactccgctagctgggccaaggggcgggtgaccatcagcaaggactcca<br>gcaaaaatcaggtgagcctcaagctgtcgtcagttactgcggccgacactgcagt<br>gtactattgtgcccgcccggataacgagggaacctccggctacctgtccggattcg<br>gactgtggggacagggaaccccttgtgactgtctcgagc |
| 909 gH62 IgG4 heavy chain (V + human gamma-4P constant) (Seq. ID No. 464) cDNA | 512 | gaagtccagctgcaagaatcaggtccaggcctcgtcaaaccatcaggaactttgtc<br>attgacttgcgccgtgagcgggttctcgctttcgacctactacatgtcgtgggtgcg<br>ccagccgcctgggaagggactggagtggatcggcatcatctacccgtccggcag<br>cacgtactccgctagctgggccaaggggcgggtgaccatcagcaaggactcca<br>gcaaaaatcaggtgagcctcaagctgtcgtcagttactgcggccgacactgcagt<br>gtactattgtgcccgcccggataacgagggaacctccggctacctgtccggattc |

TABLE 12-continued

Examples of Suitable DNA sequences Encoding anti-aP2 Antibody Fragments

| cDNA Encoding Identifier | Seq. ID No. | Sequence |
| --- | --- | --- |
| | | ggactgtggggacagggaacccttgtgactgtctcgagcgcctccaccaagggc ccctccgtgttccctctggcccttgctcccggtccacctccgagtctaccgccgct ctgggctgcctggtcaaggactacttccccgagcccgtgacagtgtcctggaactc tggcgccctgacctccggcgtgcacaccttccctgccgtgctgcagtcctccggc ctgtactccctgtcctccgtcgtgaccgtgccctcctccagcctgggcaccaagac ctacacctgtaacgtggaccacaagccctccaacaccaaggtggacaagcgggt ggaatctaagtacggccctccctgccccccctgccctgcccctgaatttctgggcg gaccttccgtgttcctgttcccccaaagcccaaggacaccctgatgatctcccgg accccgaagtgacctgcgtggtggtggacgtgtcccaggaagatcccgaggtc cagttcaattggtacgtggacggcgtggaagtgcacaatgccaagaccaagccc agagaggaacagttcaactccacctaccgggtggtgtccgtgctgaccgtgctgc accaggactggctgaacggcaaagagtacaagtgcaaggtgtccaacaagggc ctgccctccagcatcgaaaagaccatctccaaggccaagggccagccccgcga gccccaggtgtacacccctgcccctagccaggaagagatgaccaagaaccaggt gtccctgacctgtctggtcaagggcttctaccctccgacattgccgtggaatggg agtccaacggccagcccgagaacaactacaagaccacccccccctgtgctggaca gcgacggctccttcttcctgtactctcggctgaccgtggacaagtcccggtggcag gaaggcaacgtcttctcctgctccgtgatgcacgaggccctgcacaaccactaca cccagaagtccctgtccctgagcctgggcaag |
| Human IGKV1-17 (A30)-JK4 acceptor framework cDNA | 479 | gacatccagatgacccagtctccatcctccctgtctgcatctgtaggagacagagt caccatcacttgccgggcaagtcagggcattagaaatgatttaggctggtatcagc agaaaccagggaaagcccctaagcgcctgatctatgctgcatccagtttgcaaagt ggggtcccatcaaggttcagcggcagtggatctgggacagaattcactctcacaat cagcagcctgcagcctgaagattttgcaacttattactgtctacagcataatagttac cctctcactttcggcggagggaccaaggtggagatcaaa |
| Human IGHV4-4 JH4 acceptor framework cDNA | 480 | caggtgcagctgcaggagtcgggcccaggactggtgaagccttcagggaccct gtccctcacctgcgctgtctctggtggctccatcagcagtagtaactggtggagttg ggtccgccagcccccagggaaggggctggagtggattgggaaatctatcatag tgggagcaccaactacaacccgtccctcaagagtcgagtcaccatatcagtagac aagtccaagaaccagttctccctgaagctgagctctgtgaccgccgcggacacgg ccgtgtattactgtgcgagatactttgactactggggccaaggaaccctggtcacc gtctcctca |

The present invention also relates to a cloning or expression vector comprising one or more DNA sequences of the present invention. Accordingly, provided is a cloning or expression vector comprising one or more DNA sequences encoding an antibody of the present invention. Suitably, the cloning or expression vector comprises two DNA sequences, encoding the light chain and the heavy chain of the antibody molecule of the present invention, respectively and suitable signal sequences. In one example the vector comprises an intergenic sequence between the heavy and the light chains (see WO03/048208).

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbour Publishing.

Host Cells Expressing Anti-aP2 Antibodies or Fragments Thereof

Also provided is a host cell comprising one or more cloning or expression vectors comprising one or more DNA sequences encoding an antibody of the present invention. Any suitable host cell/vector system may be used for expression of the DNA sequences encoding the antibody molecule of the present invention. Bacterial, for example E. coli, and other microbial systems may be used or eukaryotic, for example mammalian, host cell expression systems may also be used. Suitable mammalian host cells include CHO, myeloma or hybridoma cells.

Suitable types of Chinese Hamster Ovary (CHO cells) for use in the present invention may include CHO and CHO-K1 cells including dhfr– CHO cells, such as CHO-DG44 cells and CHO-DXB11 cells and which may be used with a DHFR selectable marker or CHOK1-SV cells which may be used with a glutamine synthetase selectable marker. Other cell types of use in expressing antibodies include lymphocytic cell lines, e.g., NS0 myeloma cells and SP2 cells, COS cells. Other suitable cells may include human embryonic kidney (hek) fibroblasts, for example hek293F and ExpiHek cells, which are known in the art.

In one embodiment, provided is a host cell comprising a cloning or expression vector comprising a DNA sequence selected from Seq. ID Nos. 467, 469, 491, 493, 471, 473, 475, 507, 477, 509, 511, 468, 470, 492, 494, 472, 474, 476, 508, 478, 510, or 512.

Production of Anti-aP2 Antibodies or Fragments Thereof

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

There is a provided a process for culturing a host cell and expressing an antibody or fragment thereof, isolating the latter and optionally purifying the same to provide an isolated antibody or fragment. In one embodiment the process further comprises the step of conjugating an effector molecule to the isolated antibody or fragment, for example conjugating to a PEG polymer in particular as described herein.

In one embodiment there is provided a process for purifying an antibody (in particular an antibody or fragment according to the invention) comprising the steps: performing anion exchange chromatography in non-binding mode such that the impurities are retained on the column and the antibody is eluted.

In one embodiment the purification employs affinity capture on a Protein A column, and then titration. On one embodiment, the purification employs affinity capture on a Protein G column, and then HPLC titration. On one embodiment, the purification employs affinity capture on an aP2 column, and then titration.

In one embodiment the purification employs cibacron blue or similar for purification of albumin fusion or conjugate molecules.

Suitable ion exchange resins for use in the process include Q.FF resin (supplied by GE-Healthcare). The step may, for example be performed at a pH about 8.

The process may further comprise an initial capture step employing cation exchange chromatography, performed for example at a pH of about 4 to 5, such as 4.5. The cation exchange chromatography may, for example employ a resin such as CaptoS resin or SP sepharose FF (supplied by GE-Healthcare). The antibody or fragment can then be eluted from the resin employing an ionic salt solution such as sodium chloride, for example at a concentration of 200 mM.

Thus the chromatograph step or steps may include one or more washing steps, as appropriate.

The purification process may also comprise one or more filtration steps, such as a diafiltration step or HPLC filtration step.

Thus in one embodiment there is provided a purified anti-aP2 antibody or fragment, for example a humanised antibody or fragment, in particular an antibody or fragment according to the invention, in substantially purified from, in particular free or substantially free of endotoxin and/or host cell protein or DNA.

Purified from as used supra is intended to refer to at least 90% purity, such as 91, 92, 93, 94, 95, 96, 97, 98, 99% w/w or more pure.

Substantially free of endotoxin is generally intended to refer to an endotoxin content of 1 EU per mg antibody product or less such as 0.5 or 0.1 EU per mg product.

Substantially free of host cell protein or DNA is generally intended to refer to host cell protein and/or DNA content 400 µg per mg of antibody product or less such as 100 µg per mg or less, in particular 20 µg per mg, as appropriate.

Pharmaceutical Compositions

As the antibodies of the present invention are useful in the treatment and/or prophylaxis of a pathological condition, the present invention also provides a pharmaceutical or diagnostic composition comprising an antibody or antigen binding agent of the present invention in combination with one or more of a pharmaceutically acceptable excipient, diluent, or carrier. Accordingly, provided is the use of an antibody or antigen binding agent of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable excipient.

The present invention also provides a process for preparation of a pharmaceutical or diagnostic composition comprising adding and mixing the antibody or antigen binding agent of the present invention together with one or more of a pharmaceutically acceptable excipient, diluent, or carrier.

The antibody or antigen binding agent may be the sole active ingredient in the pharmaceutical or diagnostic composition or may be accompanied by other active ingredients including other antibody ingredients or non-antibody ingredients such as steroids or other drug molecules, in particular drug molecules whose half-life is independent of aP2 binding.

The pharmaceutical compositions suitably comprise a therapeutically effective amount of the antibody or antigen binding agent of the invention. The term "therapeutically effective amount" as used herein refers to an amount of a therapeutic agent needed to treat, ameliorate, or prevent a targeted disease or condition, or to exhibit a detectable therapeutic or preventative effect. For any disclosed antibody or antigen binding agent, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgment of the clinician. Generally, a therapeutically effective amount will be from 0.01 mg/kg to 500 mg/kg, for example 0.1 mg/kg to 200 mg/kg, such as 100 mg/Kg. Pharmaceutical compositions may be conveniently presented in unit dose forms containing a predetermined amount of an active agent of the invention per dose.

Therapeutic doses of the antibodies or antigen binding agents according to the present disclosure show no apparent toxicology effects in vivo.

Advantageously, the levels of aP2 activity in vivo may be maintained at an appropriately reduced level by administration of sequential doses of the antibody or binding agent according to the disclosure.

Compositions may be administered individually to a patient or may be administered in combination (e.g. simultaneously, sequentially, or separately) with other agents, drugs or hormones.

A pharmaceutical composition may also contain a pharmaceutically acceptable carrier for administration of the antibody or antigen binding agent. The carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Preferred forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, it is preferred that the compositions are adapted for administration to human subjects.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared. Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

In one embodiment, the anti-aP2 monoclonal antibodies described herein are administered as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are described by e.g., Sustained and Controlled Release Drug Delivery Systems, J. R. Robinson, ed., Marcel Dekker, Inc., New York, 1978. Pharmaceutical compositions are preferably manufactured under GMP conditions.

In one embodiment, the anti-aP2 monoclonal antibodies are administered continuously, for example, the antibody can be administered with a needleless hypodermic injection device, such as the devices disclosed in, e.g., U.S. Pat. Nos. 5,399,163, 5,383,851, 5,312,335, 5,064,413, 4,941,880, 4,790,824, or 4,596,556. Examples of implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known.

Therapeutic Applications

The anti-aP2 monoclonal antibody compounds described herein, including anti-human aP2 humanized antibody compounds, as well as the disclosed antigen binding agents target the lipid chaperone aP2/FABP4 protein and are useful in treating metabolic disorders, including, but not limited to, diabetes (for example type 2 diabetes), obesity, and fatty liver disease, cancer, including liposarcomas, bladder cancer, and ovarian cancer, and cardiovascular disorders. It has been surprisingly discovered that the anti-aP2 antibody compounds described herein are capable of binding to secreted aP2 at a low-binding affinity, which, when administered to a host in need thereof, neutralizes the activity of aP2 and provides lower fasting blood glucose levels, improved systemic glucose metabolism, increased systemic insulin sensitivity, reduced fat mass, liver steatosis, improved serum lipid profiles, and/or reduced atherogenic plaque formation in a host when compared to anti-aP2 monoclonal antibodies having higher binding affinities.

In one aspect of the present invention, a method is provided for treating an aP2 mediated disorder in a host by administering an effective amount of an anti-aP2 monoclonal antibody or antigen binding agent described herein. In one embodiment, the disorder is a metabolic disorder. In one embodiment, the disorder is diabetes. In one embodiment, the disorder is Type I diabetes. In one embodiment, the disorder is Type II diabetes. In one embodiment, the disorder is hyperglycemia. In one embodiment, the disorder is obesity. In one embodiment, the disorder is dyslipidemia. In one embodiment, the disorder is fatty liver disease. In one embodiment, the disorder is a cardiovascular disorder. In one embodiment, the disorder is atherosclerosis. In one embodiment, the disorder is an inflammatory disorder. In one embodiment, the disorder is asthma. In one embodiment, the disorder is a proliferative disorder, for example, a tumor or neoplasm. In one embodiment, the tumor is selected from transitional bladder cancer, ovarian cancer, and a liposarcoma. In one embodiment, the disorder is polycystic ovary syndrome (POS).

Metabolic Disorders

In one aspect of the present invention, a method is provided for treating metabolic disorder in a host by administering an effective amount of an anti-aP2 monoclonal antibody described herein. A metabolic disorder includes a disorder, disease, or condition, which is caused or characterized by an abnormal metabolism (i.e., the chemical changes in living cells by which energy is provided for vital processes and activities) in a subject. Metabolic disorders include diseases, disorders, or conditions associated with hyperglycemia or aberrant adipose cell (e.g., brown or white adipose cell) phenotype or function. Metabolic disorders can detrimentally affect cellular functions such as cellular proliferation, growth, differentiation, or migration, cellular regulation of homeostasis, inter- or intra-cellular communication; tissue function, such as liver function, renal function, or adipocyte function; systemic responses in an organism, such as hormonal responses (e.g., insulin response). Examples of metabolic disorders include obesity, diabetes, hyperphagia, endocrine abnormalities, triglyceride storage disease, Bardet-Biedl syndrome, Laurence-Moon syndrome, Prader-Labhart-Willi syndrome, and disorders of lipid metabolism.

Diabetes

Diabetes mellitus is the most common metabolic disease worldwide. Every day, 1700 new cases of diabetes are diagnosed in the United States, and at least one-third of the 16 million Americans with diabetes are unaware of it. Diabetes is the leading cause of blindness, renal failure, and lower limb amputations in adults and is a major risk factor for cardiovascular disease and stroke.

In one aspect of the present invention, a method is provided for treating diabetes by administering to a host an effective amount of an anti-aP2 monoclonal antibody described herein. In one embodiment, the disorder is Type I diabetes. In one embodiment, the disorder is Type II diabetes.

Type I diabetes results from autoimmune destruction of pancreatic beta cells causing insulin deficiency. Type II or non-insulin-dependent diabetes mellitus (NIDDM) accounts for >90% of cases and is characterized by a resistance to insulin action on glucose uptake in peripheral tissues, especially skeletal muscle and adipocytes, impaired insulin action to inhibit hepatic glucose production, and misregulated insulin secretion.

In one embodiment of the present invention, provided herein is a method of treating Type I diabetes in a host by administering to the host an effective amount of an anti-aP2 monoclonal antibody described herein in combination or alteration with insulin. In one embodiment of the present invention, provided herein is a method of treating Type I diabetes in a host by administering to the host an effective amount of an anti-aP2 monoclonal antibody described herein in combination or alteration with a synthetic insulin analog.

Some people who have Type II diabetes can achieve their target blood sugar levels with diet and exercise alone, but many also need diabetes medications or insulin therapy. In one embodiment of the present invention, provided herein is a method of treating Type II diabetes in a host by administering to the host an effective amount of an anti-aP2 monoclonal antibody described herein in combination or alteration with a compound selected from metformin (Glucophage, Glumetza); sulfonylureas, including glyburide (DiaBeta, Glynase), glipizide (Glucotrol) and glimepiride (Amaryl); Meglitinides, for example repaglinide (Prandin) and nateglinide (Starlix); thiazolidinediones, for example rosiglitazone (Avandia) and pioglitazone (Actos); DPP-4 inhibitors, for example, sitagliptin (Januvia), saxagliptin (Onglyza) and linagliptin (Tradjenta); GLP-1 receptor agonists, for example Exenatide (Byetta) and liraglutide (Victoza); SGLT2 inhibitors, for example canagliflozin (Invokana) and dapagliflozin (Farxiga); or insulin therapy. Nonlimiting examples of insulin include Insulin glulisine (Apidra); Insulin lispro (Humalog); Insulin aspart (Novolog); Insulin glargine (Lantus); Insulin detemir (Levemir); Insulin isophane (Humulin N, Novolin N).

In one embodiment, provided herein is a method of treating a disease or condition associated with diabetes by administering to a host an effective amount of an anti-aP2 monoclonal antibody described herein. Diseases and conditions associated with diabetes mellitus can include, but are not restricted to, hyperglycemia, hyperinsulinaemia, hyperlipidaemia, insulin resistance, impaired glucose metabolism, obesity, diabetic retinopathy, macular degeneration, cataracts, diabetic nephropathy, glomerulosclerosis, diabetic neuropathy, erectile dysfunction, premenstrual syndrome, vascular restenosis and ulcerative colitis. Furthermore, diseases and conditions associated with diabetes mellitus comprise, but are not restricted to: coronary heart disease, hypertension, angina pectoris, myocardial infarction, stroke, skin and connective tissue disorders, foot ulcerations, metabolic acidosis, arthritis, osteoporosis and in particular conditions of impaired glucose tolerance.

Body Weight Disorders

In one embodiment of the present invention, a method is provided for treating obesity in a host by administering an effective amount of an anti-aP2 monoclonal antibody described herein. Obesity represents the most prevalent of body weight disorders, affecting an estimated 30 to 50% of the middle-aged population in the western world.

In one embodiment of the present invention, a method is provided for treating obesity in a host by administering an effective amount of an anti-aP2 monoclonal antibody or antigen binding agent described herein in combination or alteration with a second therapeutic agent for treating obesity. Examples of treatments for obesity include, but are not limited to phentermine, Belviq (lorcaserin), diethylpropion, phendimetrazine tartrate, Xenical (orlistat), Contrave, orlistat, methamphetamine, Desoxyn, Didrex, Bontril PDM, Suprenza, benzphetamine, Qsymia (phentermine-topiramat), Regimex, naltrexone-bupropion, Evekeo, lorcaserin, and amphetamine sulfate.

In one embodiment, a method is provided for reducing or inhibiting weight gain in a host by administering an effective amount of an anti-aP2 monoclonal antibody or antigen binding agent described herein.

Fatty Liver Disease

There is a need for compositions and methods for the treatment and prevention of the development of fatty liver and conditions stemming from fatty liver, such as nonalcoholic steatohepatitis (NASH), liver inflammation, cirrhosis and liver failure. In one embodiment of the present invention, a method is provided for treating fatty liver disease in a host by administering an effective amount of an anti-aP2 monoclonal antibody or binding agent as described herein.

In one embodiment, the anti-aP2 monoclonal antibody or antigen binding agent described herein is administered in combination or alteration with omega-3 fatty acids or peroxisome proliferator-activated receptors (PPARs) agonists.

Omega-3 fatty acids are known to reduce serum triglycerides by inhibiting DGAT and by stimulating peroxisomal and mitochondrial beta-oxidation. Two omega-3 fatty acids, eicosapentaenoic acid (EPA) and docosahexaenoic acid (DHA), have been found to have high affinity for both PPAR-alpha and PPAR-gamma. Marine oils, e.g., fish oils, are a good source of EPA and DHA, which have been found to regulate lipid metabolism. Omega-3 fatty acids have been found to have beneficial effects on the risk factors for cardiovascular diseases, especially mild hypertension, hypertriglyceridemia and on the coagulation factor VII phospholipid complex activity. Omega-3 fatty acids lower serum triglycerides, increase serum HDL-cholesterol, lower systolic and diastolic blood pressure and the pulse rate, and lower the activity of the blood coagulation factor VII-phospholipid complex. Further, omega-3 fatty acids seem to be well tolerated, without giving rise to any severe side effects. One such form of omega-3 fatty acid is a concentrate of omega-3, long chain, polyunsaturated fatty acids from fish oil containing DHA and EPA and is sold under the trademark Omacor®. Such a form of omega-3 fatty acid is described, for example, in U.S. Pat. Nos. 5,502,077, 5,656, 667 and 5,698,594, the disclosures of which are incorporated herein by reference.

Peroxisome proliferator-activated receptors (PPARs) are members of the nuclear hormone receptor superfamily ligand-activated transcription factors that are related to retinoid, steroid and thyroid hormone receptors. There are three distinct PPAR subtypes that are the products of different genes and are commonly designated PPAR-alpha, PPAR-beta/delta (or merely, delta) and PPAR-gamma. General classes of pharmacological agents that stimulate peroxisomal activity are known as PPAR agonists, e.g., PPAR-alpha agonists, PPAR-gamma agonists and PPAR-delta agonists. Some pharmacological agents are combinations of PPAR agonists, such as alpha/gamma agonists, etc., and some other pharmacological agents have dual agonist/antagonist activity. Fibrates such as fenofibrate, bezafibrate, clofibrate and gemfibrozil, are PPAR-alpha agonists and are used in patients to decrease lipoproteins rich in triglycerides, to increase HDL and to decrease atherogenic-dense LDL. Fibrates are typically orally administered to such patients. Fenofibrate or 2-[4-(4-chlorobenzoyl)phenoxy]-2-methyl-propanoic acid, 1-methylethyl ester, has been known for many years as a medicinally active principle because of its efficacy in lowering blood triglyceride and cholesterol levels.

Cardiovascular Disease

In one embodiment of the present invention, a method is provided for treating cardiovascular disease in a host by administering an effective amount of an anti-aP2 monoclonal antibody described herein. The anti-aP2 antibodies of the present invention are useful in preventing, inhibiting or reducing risk of cardiovascular and cerebrovascular diseases resulting from atherosclerosis, such as cardiac and/or cerebral ischemia, myocardial infarction, angina, peripheral vascular disease and stroke.

In one embodiment, a method is provided for preventing, inhibiting or reducing risk of cardiovascular and cerebrovascular diseases resulting from atherosclerosis in a host by administering to the host an effective amount of an anti-aP2 monoclonal antibody described herein in combination or alteration with an anti-atherosclerotic agent.

Examples of anti-atherosclerotic agents include, but are not limited to, HMG CoA reductase inhibitors, microsomal triglyceride transfer protein (MTP) inhibitors, fibric acid derivatives, squalene synthetase inhibitors and other known cholesterol lowering agents, lipoxygenase inhibitors, ACAT inhibitors, and PPAR α/γ dual agonists as disclosed hereinafter.

The anti-atherosclerotic agent may be an HMG CoA reductase inhibitor, which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171, with pravastatin, lovastatin or simvastatin being preferred. Other HMG CoA reductase inhibitors, which may be employed herein, include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pyrazole analogs of mevalonolactone derivatives as disclosed in U.S. Pat. No. 4,613,610, indene analogs of mevalonolactone derivatives as disclosed in PCT application WO 86/03488, 6-(2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0142146A2, as well as other known HMG CoA reductase inhibitors. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869-1871, including isoprenoid (phosphinylmethyl)phosphonates as well as other squalene synthetase inhibitors as disclosed in U.S. Pat. Nos. 4,871,721 and 4,924,024. In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J.A.C.S., 1987, 109, 5544 and cyclopropanes reported by Capson, T. L., PhD dissertation, June 1987, Dept. Med. Chem. U of Utah, abstract, Table of Contents, pp 16, 17, 40-43, 48-51, Summary.

Other cholesterol lowering drugs suitable for use herein include, but are not limited to, antihyperlipoproteinemic agents such as fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred bile acid sequestrants such as cholestyramine, colestipol and DEAE-Sephadex (Secholex®, Polidexide®), as well as clofibrate, lipostabil (Rhone-Poulenc), Eisal E-5050 (an N-substituted ethanolamine derivatives, imanixii (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035. American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives such as disclosed in U.S. Pat. No. 4,759,923, quaternary amine poly(diallyldimethylarmonium chloride)

and ionenes such as disclosed in U.S. Pat. No. 4,027,009, and other known serum cholesterol lowering agents.

The antiatherosclerotic agent may also be a PPAR α/γ dual agonist such as disclosed by Murakami et al, "A Novel Insulin Sensitizer Acts As a Coligand for Peroxisome Proliferator-Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998).

The anti-atherosclerotic agent may be an ACAT inhibitor such as disclosed in, "The ACAT inhibitor, Cl-1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62.

The other anti-atherosclerotic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties, Brit. J. Pharmacology (1997) 120, 1199-1206, and Cornicelli et al, "15-Lipoxygenase and its Inhibition: A Novel Therapeutic Target for Vascular Disease", Current Pharmaceutical Design, 1999, 5, 11-20.

In one embodiment, provided herein is a method of preventing, attenuating or treating a cardiovascular disorder in a host, wherein the host is peri- or post-menopausal. aP2 is known to increase in peri- and post-menopausal women, who have a higher incidence of cardiovascular disease than pre-menopausal women. Accordingly, administering an anti-aP2 monoclonal antibody or antigen binding agent described herein may be used to attenuate, prevent, or treat peri- and post-menopausal women at risk for developing, or who have developed, cardiovascular disease associated with elevated levels of circulating aP2.

Inflammatory Disease

The anti-aP2 antibodies and antigen binding agents described herein may be administered for the treatment of an inflammatory disorder in a subject. Inflammation may arise as a response to an injury or abnormal stimulation caused by a physical, chemical, or biologic agent. An inflammation reaction may include the local reactions and resulting morphologic changes, destruction or removal of injurious material such as an infective organism, and responses that lead to repair and healing. The term "inflammatory" when used in reference to a disorder refers to a pathological process, which is caused by, resulting from, or resulting in inflammation that is inappropriate or which does not resolve in the normal manner. Inflammatory disorders may be systemic or localized to particular tissues or organs.

Inflammation is known to occur in many disorders which include, but are not limited to: Systemic Inflammatory Response (SIRS); Alzheimer's Disease (and associated conditions and symptoms including: chronic neuroinflammation, glial activation; increased microglia; neuritic plaque formation; Amyotrophic Lateral Sclerosis (ALS), arthritis (and associated conditions and symptoms including, but not limited to: acute joint inflammation, antigen-induced arthritis, arthritis associated with chronic lymphocytic thyroiditis, collagen-induced arthritis, juvenile arthritis, rheumatoid arthritis, osteoarthritis, prognosis and streptococcus-induced arthritis, spondyloarthropathies, and gouty arthritis), asthma (and associated conditions and symptoms, including: bronchial asthma; chronic obstructive airway disease, chronic obstructive pulmonary disease, juvenile asthma and occupational asthma); cardiovascular diseases (and associated conditions and symptoms, including atherosclerosis, autoimmune myocarditis, chronic cardiac hypoxia, congestive heart failure, coronary artery disease, cardiomyopathy and cardiac cell dysfunction, including: aortic smooth muscle cell activation, cardiac cell apoptosis and immunomodulation of cardiac cell function); diabetes (and associated conditions, including autoimmune diabetes, insulin-dependent (Type I) diabetes, diabetic periodontitis, diabetic retinopathy, and diabetic nephropathy); gastrointestinal inflammations (and related conditions and symptoms, including celiac disease, associated osteopenia, chronic colitis, Crohn's disease, inflammatory bowel disease and ulcerative colitis); gastric ulcers; hepatic inflammations such as viral and other types of hepatitis, cholesterol gallstones and hepatic fibrosis; HIV infection (and associated conditions, including—degenerative responses, neurodegenerative responses, and HIV associated Hodgkin's Disease); Kawasaki's Syndrome (and associated diseases and conditions, including mucocutaneous lymph node syndrome, cervical lymphadenopathy, coronary artery lesions, edema, fever, increased leukocytes, mild anemia, skin peeling, rash, conjunctiva redness, thrombocytosis); nephropathies (and associated diseases and conditions, including diabetic nephropathy, endstage renal disease, acute and chronic glomerulonephritis, acute and chronic interstitial nephritis, lupus nephritis, Goodpasture's syndrome, hemodialysis survival and renal ischemic reperfusion injury); neurodegenerative diseases or neuropathological conditions (and associated diseases and conditions, including acute neurodegeneration, induction of IL-I in aging and neurodegenerative disease, IL-I induced plasticity of hypothalamic neurons and chronic stress hyperresponsiveness, myelopathy); ophthalmopathies (and associated diseases and conditions, including diabetic retinopathy, Graves' ophthalmopathy, inflammation associated with corneal injury or infection including corneal ulceration, and uveitis), osteoporosis (and associated diseases and conditions, including alveolar, femoral, radial, vertebral or wrist bone loss or fracture incidence, postmenopausal bone loss, fracture incidence or rate of bone loss); otitis media (adult or pediatric); pancreatitis or pancreatic acinitis; periodontal disease (and associated diseases and conditions, including adult, early onset and diabetic); pulmonary diseases, including chronic lung disease, chronic sinusitis, hyaline membrane disease, hypoxia and pulmonary disease in SIDS; restenosis of coronary or other vascular grafts; rheumatism including rheumatoid arthritis, rheumatic Aschoff bodies, rheumatic diseases and rheumatic myocarditis; thyroiditis including chronic lymphocytic thyroiditis; urinary tract infections including chronic prostatitis, chronic pelvic pain syndrome and urolithiasis; immunological disorders, including autoimmune diseases, such as alopecia aerata, autoimmune myocarditis, Graves' disease, Graves ophthalmopathy, lichen sclerosis, multiple sclerosis, psoriasis, systemic lupus erythematosus, systemic sclerosis, thyroid diseases (e.g. goitre and struma lymphomatosa (Hashimoto's thyroiditis, lymphadenoid goitre); lung injury (acute hemorrhagic lung injury, Goodpasture's syndrome, acute ischemic reperfusion), myocardial dysfunction, caused by occupational and environmental pollutants (e.g. susceptibility to toxic oil syndrome silicosis), radiation trauma, and efficiency of wound healing responses (e.g. burn or thermal wounds, chronic wounds, surgical wounds and spinal cord injuries), septicaemia, acute phase response (e.g. febrile response), general inflammatory response, acute respiratory distress response, acute systemic inflammatory response, wound healing, adhesion, immunoinflammatory response, neuroendocrine response, fever development and resistance, acute-phase response, stress response, disease susceptibility, repetitive motion stress, tennis elbow, and pain management and response.

In one embodiment of the present invention, provided herein is a method of treating Type I diabetes in a host by administering to the host an effective amount of an anti-aP2 monoclonal antibody described herein in combination or alteration with an anti-inflammatory agent. The anti-inflammatory agent can be a steroidal anti-inflammatory agent, a nonsteroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

Cancers

The invention further provides a method of administering an anti-aP2 antibody or antigen binding agent disclosed herein to treat cancer. In one embodiment, the cancer is selected from liposarcoma, mesentery mixed-mullerian tumor, spinal schwannoma, gallbladder cancer, prostate cancer, brain astrocytoma, lung cancer, ovarian cancer, bladder cancer, colon cancer, esophageal cancer, post-menopausal breast cancer, endometrial cancer, kidney cancer, liver cancer, and pancreatic cancer In one embodiment of the present invention, a method is provided for treating a proliferative disorder, for example, a tumor or neoplasm, in a host by administering an effective amount of an anti-aP2 monoclonal antibody or antigen binding agent described herein. In one embodiment, the tumor is selected from transitional bladder cancer, ovarian cancer, and a liposarcoma.

In one embodiment, the cancer is bladder cancer. In one embodiment the cancer is transitional cell carcinoma of the bladder. In one embodiment of the present invention, provided herein is a method of treating bladder cancer in a host by administering to the host an effective amount of an anti-aP2 monoclonal antibody or antigen binding agent described herein.

In one embodiment of the present invention, a method is provided for treating bladder cancer in a host by administering an effective amount of an anti-aP2 monoclonal antibody or antigen binding agent described herein in combination or alteration with an additional chemotherapeutic agent. Additional chemotherapeutic agents for treatment of bladder cancer include, but are not limited to, methotrexate, vinblastine, doxorubicin, cisplatin, gemcitabine, carboplatin, paclitaxel, and epirubicin.

In one embodiment the cancer is ovarian cancer. In one embodiment of the present invention, provided herein is a method of treating ovarian cancer in a host by administering to the host an effective amount of an anti-aP2 monoclonal antibody or an antigen binding agent described herein.

In one embodiment of the present invention, a method is provided for treating ovarian cancer in a host by administering an effective amount of an anti-aP2 monoclonal antibody described herein in combination or alteration with an additional chemotherapeutic agent. Additional chemotherapeutic agents for treatment of ovarian cancer include, but are not limited to, cisplatin, carboplatin, paclitaxel, docetaxel, albumin bound paclitaxel, altretamine, capecitabine, cyclophosphamide, etoposide, gemcitabine, ifosfamide, irinotecan, liposomal doxorubicin, melphalan, pemetrexed, topotecan, and vinorelbine.

In one embodiment of the present invention, provided herein is a method of treating liposarcoma in a host by administering an effective amount of an anti-aP2 monoclonal antibody or antigen binding agent described herein. In one embodiment, the liposarcoma is well-differentiated liposarcoma, myxoid liposarcoma, pleomorphic liposarcoma, or dedifferentiated liposarcoma. In one embodiment, provided herein is a method of treating a sarcoma, for example, but not limited to, a fibrous histiocytoma, synovial sarcoma, or leiomyosarcoma. In one embodiment, the anti-aP2 monoclonal antibody or antigen binding agent is administered in combination with a chemotherapeutic agent and or radiative agent.

In one embodiment, the neoplasm is a benign lipoma, for example, an adenolipoma, angiolipoleiomyoma, angiolipoma, cerebellar pontine angle and internal auditory canal lipoma, chondroid lipoma, corpus callosum lipoma, hibernoma, intradermal spindle cell lipoma, neural fibrolipoma, pleomorphic lipoma, spindle-cell lipoma, and superficial subcutaneous lipoma.

Methods of Attenuating the Severity of an aP2-Mediated Disorder

A method of preventing or treating a disease or disorder caused by an aberrant level of aP2 in a host, typically a human, is provided by administering to the host a therapeutically effective amount of a monoclonal antibody or antigen binding agent as described herein. The monoclonal antibody or fragment is administered at a dose sufficient to inhibit or reduce the biological activity of aP2 either partially or fully.

In one aspect, a method of preventing or attenuating the severity of an aP2 mediated disorder in a host is provided by administering an effective amount of an anti-aP2 monoclonal antibody described herein, resulting in the reduction or attenuation of the biological activity of secreted aP2, and a reduction in the associated physiological effects of elevated aP2 serum levels, for example, a reduction in total cholesterol, high density lipoprotein (HDL), low density lipoprotein (LDL), very low density lipoprotein (VLDL), and/or triglyceride, fasting blood glucose levels, fat mass levels, hepatic glucose production, fat cell lipolysis, hyperinsulinemia, and/or liver steatosis. In one embodiment, the attenuation of the biological activity of secreted aP2 results in an increase in insulin sensitivity, glucose metabolism, and/or the prevention of islet β-cell death, dysfunction, or loss.

In one aspect of the present invention, a method of reducing total cholesterol in a host is provided by administering an effective amount of an anti-aP2 monoclonal antibody or antigen binding agent as described herein. In one embodiment, provided herein is a method of reducing total cholesterol, high density lipoprotein (HDL), low density lipoprotein (LDL), very low density lipoprotein (VLDL), and/or triglycerides in a host by administering an effective amount of an anti-aP2 monoclonal antibody described herein.

In other aspects of the present invention, methods are providing for:
  reducing fasting blood glucose levels;
  reducing fat mass levels;
  reducing hepatic glucose production;
  reducing fat cell lipolysis;
  reducing hyperinsulinemia;
  reducing liver steatosis;
  increasing glucose metabolism;
  increasing insulin sensitivity;
  preventing β-cell death, dysfunction, or loss; and/or
  determining circulating secreted aP2 levels in a host;
  comprising administering an effective amount of an anti-aP2 antibody or antigen binding agent described herein to a host, typically a human, in need thereof.

EXAMPLES

The lipid chaperone aP2/FABP4 has been implicated in the pathology of many immunometabolic diseases, such as diabetes and atherosclerosis. While multiple lines of evidence also support its involvement in human disease, targeting aP2 for therapeutic applications has not yet been accomplished. Recent studies have shown that aP2 is not simply an intracellular protein but also an active adipokine that contributes to hyperglycemia by promoting hepatic gluconeogenesis and interfering with peripheral insulin action. Serum aP2 levels are markedly elevated in mouse and human obesity, and strongly correlate with metabolic complications. As an illustrative embodiment, a low binding affinity monoclonal anti-aP2 antibody CA33, a rabbit-mouse hybrid anti-aP2 monoclonal antibody, which includes Rabbit 909 VH (Seq. ID No. 454) and 909 VL (Seq. ID No. 445), is described that lowers fasting blood glucose levels, improves systemic glucose metabolism, increases systemic insulin sensitivity and reduces fat mass and liver steatosis in obese mice. The structure of the aP2-CA33 complex was examined and the target epitope resolved by crystallographic studies in comparison to another monoclonal antibody that lacked efficacy in vivo (anti-aP2 monoclonal antibody H3). In hyperinsulinemic-euglycemic clamp studies, the antidiabetic effect of CA33 was predominantly linked to the regulation of hepatic glucose output and peripheral glucose utilization. Importantly, this antibody exhibited no biological effects in aP2-deficient mice, demonstrating its target specificity.

Example 1: Preparation of an Illustrative Monoclonal Antibody Targeting Secreted aP2

Animals

Animal care and experimental procedures were performed with approval from animal care committees of Harvard University. Male mice (leptin-deficient (ob/ob) and diet induced obese (DIO) mice with C57BL/6J background) were purchased from The Jackson Laboratory (Bar Harbor, Me.) and kept on a 12-hour light/dark cycle. DIO mice with C57BL/6J background were maintained on high-fat diet (60% kcal fat, Research Diets, Inc., D12492i) for 12 to 15 weeks before starting treatment except in clamp studies, for which they were on HFD for 20 weeks. Leptin-deficient (ob/ob) mice were maintained on regular chow diet (RD, PicoLab 5058 Lab Diet). Animals used were 18 to 31 weeks of age for dietary models and 9 to 12 weeks of age for the ob/ob model. In all experiments, at least 7 mice in each group were used, unless otherwise stated in the text. The mice were treated with 150 μl PBS (vehicle) or 1.5 mg/mouse (~33 mg/kg) anti-aP2 monoclonal antibody in 150 μl PBS by twice a week subcutaneous injections for 3 to 5 weeks (FIG. 1B). Before and after the treatment, blood samples were collected from the tail after 6 hours of daytime food withdrawal. Body weights were measured weekly in the fed state. Blood glucose levels were measured weekly after 6 hours of food withdrawal or after 16 hours overnight fast. After 2 weeks of treatment, glucose tolerance tests were performed by intraperitoneal glucose injections (0.75 g/kg for DIO, 0.5 g/kg for ob/ob mice). After 3 weeks of treatment, insulin tolerance tests were performed in DIO mice by intraperitoneal insulin injections (0.75 IU/kg). After 5 weeks of treatment, hyperinsulinemic-euglycemic clamp experiments were performed in DIO mice as previously described (Furuhashi et al., (2007) Nature 447, 959-965; Maeda et al., (2005) Cell metabolism 1, 107-119).

Metabolic cage (Oxymax, Columbus Instruments) and total body fat measurement by dual energy X-ray absorptiometry (DEXA; PIXImus) were performed as previously described (Furuhashi et al., (2007) Nature 447, 959-965).

Production and Administration of Anti-aP2 Antibodies

CA13, CA15, CA23 and CA33 (Rabbit Ab 909) were produced and purified by UCB. New Zealand White rabbits were immunized with a mixture containing recombinant human and mouse aP2 (generated in-house in *E. coli*: accession numbers CAG33184.1 and CAJ18597.1, respectively). Splenocytes, peripheral blood mononuclear cells (PBMCs) and bone marrow were harvested from immunized rabbits and subsequently stored at −80° C. B cell cultures from immunized animals were prepared using a method similar to that described by Zubler et al., ("Mutant EL-4 thymoma cells polyclonally activate murine and human B cells via direct cell interaction", J Immunol 134, 3662-3668 (1985)). After a 7 day incubation, antigen-specific antibody-containing wells were identified using a homogeneous fluorescence-linked immunosorbent assay with biotinylated mouse or human aP2 immobilized on Superavidin™ beads (Bangs Laboratories) and a goat anti-rabbit IgG Fcy-specific Cy-5 conjugate (Jackson ImmunoResearch). To identify, isolate and recover the antigen-specific B-cell from the wells of interest, we used the fluorescent foci method (Clargo et al., (2014) mAbs 6, 143-159). This method involved harvesting B cells from a positive well and mixing with paramagnetic streptavidin beads (New England Biolabs) coated with biotinylated mouse and human aP2 and goat anti-rabbit Fc fragment-specific FITC conjugate (Jackson ImmunoResearch). After static incubation at 37° C. for 1 h, antigen-specific B cells could be identified due to the presence of a fluorescent halo surrounding that B cell. Individual antigen-specific antibody secreting B cells were viewed using an Olympus IX70 microscope, and were picked with an Eppendorf micromanipulator and deposited into a PCR tube. Variable region genes from these single B-cells were recovered by RT-PCR, using primers that were specific to heavy- and light-chain variable regions. Two rounds of PCR were performed, with the nested 2° PCR incorporating restriction sites at the 3' and 5' ends allowing cloning of the variable region into a variety of expression vectors; mouse γ1 IgG, mouse Fab, rabbit γ1 IgG (VH) or mouse kappa and rabbit kappa (VL). Heavy- and light-chain constructs were transfected into HEK-293 cells using Fectin 293 (Invitrogen) and recombinant antibody expressed in 6-well plates. After 5 days' expression, supernatants were harvested and the antibody was subjected to further screening by biomolecular interaction analysis using the BiaCore system to determine affinity and epitope bin.

Mouse anti-aP2 monoclonal antibody H3 was produced by the Dana Farber Cancer Institute Antibody Core Facility. Female C57BL/6 aP2−/− mice, 4-6 weeks old, were immunized by injection of full-length human aP2/FABP4-Gst recombinant protein was suspended in Dulbecco's phosphate buffered saline (PBS; GIBCO, Grand Island, N.Y.) and emulsified with an equal volume of complete Freund's adjuvant (Sigma Chemical Co., St. Louis, Mo.). Spleens were harvested from immunized mice and cell suspensions were prepared and washed with PBS. The spleen cells were counted and mixed with SP 2/0 myeloma cells (ATCC No. CRL8-006, Rockville, Md.) that are incapable of secreting either heavy or light chain immunoglobulins (Kearney et al., (1979) Journal of Immunology 123, 1548-1550) at a spleen: myeloma ratio of 2:1. Cells were fused with polyethylene glycol 1450 (ATCC) in 12 96-well tissue culture plates in HAT selection medium according to standard procedures (Kohler et al., (1975) Nature 256, 495-497). Between 10 and 21 days after fusion, hybridoma colonies became visible and culture supernatants were harvested then screened by western blot on strep-His-human-aP2/FABP4. A secondary screen of 17 selected positive wells was done using high-protein binding 96-well EIA plates (Costar/Corning, Inc. Corning, N.Y.) coated with 50 µl/well of a 2 µg/ml solution (0.1 µg/well) of strep-His-human-aP2/FABP4 or an irrelevant Gst-protein and incubated overnight at 4° C.). Positive hybridomas were subcloned by limiting dilution and screened by ELISA. Supernatant fusions were isotyped with Isostrip kit (RocheDiagnostic Corp., Indianapolis, Ind.).

Large-scale transient transfections were carried out using UCB's proprietary CHOSXE cell line and electroporation expression platform. Cells were and maintained in logarithmic growth phase in CDCHO media (LifeTech) supplemented with 2 mM Glutamax at 140 rpm in a shaker incubator (Kuhner AG, Birsfelden, Switzerland) supplemented with 8% CO2 at 37° C. Prior to transfection, the cell numbers and viability were determined using CEDEX cell counter (Innovatis AG. Bielefeld, Germany) and 2×108 cells/ml were centrifuged at 1400 rpm for 10 minutes. The pelleted cells were washed in Hyclone MaxCyte buffer (Thermo Scientific) and respun for a further 10 minutes and the pellets were re-suspended at 2×108 cells/ml in fresh buffer. Plasmid DNA, purified using QIAGEN Plasmid Plus Giga Kit® was then added at 400 µg/ml. Following electroporation using a MAxcyte STX® flow electroporation instrument, the cells were transferred in ProCHO medium (Lonza) containing 2 mM Glutamax and antibiotic antimitotic solution and cultured in wave bag (Cell Bag, GE Healthcare) placed on Bioreactor platform set at 37° C. and 5% CO2 with wave motion induced by 25 rpm rocking.

Twenty-four hours post transfection a bolus feed was added and the temperature was reduced to 320 C and maintained for the duration of the culture period (12-14 days). At day 4 3 mM sodium butryrate (n-BUTRIC ACID sodium salt, Sigma B-5887) was added to the culture. At day 14, the cultures were centrifuged for 30 minutes at 4000 rpm and the retained supernatants were filtered through 0.22 µm SARTO BRAN-P (Millipore) followed by 0.22 µm Gamma gold filters. CHOSXE harvest expressing mouse monoclonal antibody (mAb) was conditioned by addition of NaCl (to 4M). The sample was loaded onto a protein A MabSelect Sure packed column (GE-healthcare) equilibrated with 0.1M Glycine+4M NaCl pH8.5 at 15 ml/min. The sample was washed with 0.1M Glycine+4M NaCl pH8.5 and an additional wash step was performed with 0.15M Na2HPO4 pH 9. The U.V absorbance peak at A280 nm was collected during elution from the column using 0.1M sodium citrate pH 3.4 elution buffer and then neutralized to pH 7.4 by addition of 2M Tris-HCl pH 8.5. The mAb pool from protein A was then concentrated to suitable volume using a minisette Tangential Flow Filtration device before being purified further on a HiLoad XK 50/60 Superdex 200 prep grade gel filtration column (GE-healthcare). Fractions collected were then analysed by analytical gel filtration technique for monomer peak and clean monomer fractions pooled as final product. The final product sample was then characterised by reducing and non-reduced SDS-PAGE and analytical gel filtration for final purity check. The sample was also tested and found to be negative for endotoxin using a LAL assay method for endotoxin measurements. The final buffer for all mAbs tested was PBS. For in vivo analysis, purified antibodies were diluted in saline to 10 mg/ml and injected at a dose of 1.5 mg/mouse (33 mg/kg) into ob/ob and WT mice on high-fat diet.

Measurement of Antibody Affinity

The affinity of anti-aP2 binding to aP2 (recombinantly generated in *E. coli* as described below) was determined by biomolecular interaction analysis, using a Biacore T200 system (GE Healthcare). Affinipure F(ab')2 fragment goat anti-mouse IgG, Fc fragment specific (Jackson ImmunoResearch Lab, Inc.) in 10 mM NaAc, pH 5 buffer was immobilized on a CM5 Sensor Chip via amine coupling chemistry to a capture level between 4500-6000 response units (RU) using HBS-EP+ (GE Healthcare) as the running buffer. Anti-aP2 IgG was diluted to between 1-10 µg/ml in running buffer. A 60 s injection of anti-aP2 IgG at 10 µl/min was used for capture by the immobilized anti-mouse IgG, Fc then aP2 was titrated from 25 nM to 3.13 nM over the captured anti-aP2 for 180 s at 30 µl/min followed by 300 s dissociation. The surface was regenerated by 2×60 s 40 mM HCl and 1×30 s 5 mM NaOH at 10 µl/min. The data were analyzed using Biacore T200 evaluation software (version 1.0) using the 1:1 binding model with local Rmax. For CA33, 60 s injection of the antibody at 10 µl/min was used for capture by the immobilized anti-mouse IgG, Fc then aP2 was titrated from 40 µM to 0.625 µM over the captured anti-aP2 for 180 s at 30 µl/min followed by 300 s dissociation. The surface was regenerated by 1×60 s 40 mM HCl, 1×30 s 5 mM NaOH and 1×60 s 40 mM HCl at 10 µl/min. Steady state fitting was used to determine affinity values.

Antibody Cross-Blocking

The assay was performed by injecting mouse aP2 in the presence or absence of mouse anti-aP2 IgG over captured rabbit anti-aP2 IgG. Biomolecular interaction analysis was performed using a Biacore T200 (GE Healthcare Bio-Sciences AB). Anti-aP2 rabbit IgG transient supernatants were captured on the immobilized anti-rabbit Fc surfaces (one supernatant per flowcell) using a flow rate of 10 µl/min and a 60 s injection to give response levels above 200RU. Then mouse aP2 at 100 nM, 0 nM or mouse aP2 at 100 nM plus mouse anti-aP2 IgG at 500 nM were passed over for 120 s followed by 120 s dissociation. The surfaces were regenerated with 2×60 s 40 mM HCl and 1×30 s 5 mM NaOH.

FABP Cross-Reactivity

The recombinant human proteins aP2 (generated at UCB in E. coli (see method below)), hFABP3 (Sino Biological Inc.) and hFABP5/hMal1 (Sino Biological Inc.) were biotinylated in a 5-fold molar excess of EZ-Link® Sulfo-NHS-LC-Biotin (Thermo Fisher Scientific) and purified from unbound biotin using a Zeba desalting column (Thermo Fisher Scientific). All binding studies were performed at 25° C. using a ForteBio Octet RED384 system (Pall ForteBio Corp.). After a 120 s baseline step in PBS containing 0.05% Tween 20, pH7.4 (PBS-T), Dip and Read™ streptavidin (SA) biosensors (Pall ForteBio Corp.) were loaded with biotinylated recombinant haP2, hFABP3 or hFABP5/hMal1 at 60 nM for 90 s. After a 60 s stabilisation step in PBS-T, each FABP-loaded biosensor was transferred to a sample of monoclonal antibody at 800 nM and association was measured for 5 min. Biosensors were then transferred back to PBS-T for 5 min to measure dissociation. Non-specific binding of antibodies was monitored using unloaded biosensor tips. Maximal association binding i.e., once signal had plateaued, minus background binding, was plotted for each antibody/FABP combination.

aP2 Expression and Purification

Mouse (or human) aP2 cDNA optimized for expression in E. coli was purchased from DNA 2.0 (Menlo Park, Calif.) and subcloned directly into a modified pET28a vector (Novagen) containing an in-frame N-terminal 10 His-tag followed by a Tobacco Etch Virus (TEV) protease site. Protein was expressed in the E. coli strain BL21DE3 and purified as follows. Typically, cells were lysed with a cooled cell disruptor (Constant Systems Ltd.) in 50 ml lysis buffer (PBS (pH 7.4) containing 20 mM imidazole) per liter of E. coli culture supplemented with a Complete protease inhibitor cocktail tablet, EDTA-free (Roche, Burgess Hill). Lysate was then clarified by high-speed centrifugation (60000 g, 30 minutes, 4° C.). 4 ml/Ni-NTA beads (Qiagen) were added per 100 ml cleared lysate and tumbled for 1 h at 4° C. Beads were packed in a Tri-Corn column (GE Healthcare) attached to an AKTA FPLC (GE Life Sciences) and protein eluted in a buffer containing 250 mM imidazole. Fractions containing protein of interest as judged by 4-12% Bis/Tris NuPage (Life Technologies Ltd.) gel electrophoresis were dialyzed to remove imidazole and treated with TEV protease at a ratio of 1 mg per 100 mg protein. After overnight incubation at 4° C. the sample was re-passed over the Ni/NTA beads in the Tri-Corn column. Untagged (i.e. TEV cleaved) aP2 protein did not bind to the beads and was collected in the column flow through. The protein was concentrated, and loaded onto an S75 26/60 gel filtration column (GE healthcare) pre-equilibrated in PBS, 1 mM DTT. Peak fractions were pooled and concentrated to 5 mg/ml. Six ml of this protein was then extracted and precipitated with acetonitrile at a ratio of 2:1 to remove any lipid. Following centrifugation at 16000 g for 15 mins the acetonitrile+buffer was removed for analysis of original lipid content. The pellet of denatured protein was then resuspended in 6 ml of 6 M GuHCl PBS+2 µMoles palmitic acid (5:1 ratio of palmitic acid to aP2) and then dialyzed two times against 5 L PBS for 20 hrs at 4° C. to allow refolding. Following centrifugation to remove precipitate (16000 g, 15 minutes) protein was gel filtered using a S75 26/20 column in PBS to remove aggregate. Peak fractions were pooled and concentrated to 13 mg/ml.

aP2 Crystallography

Purified mouse aP2 was complexed with CA33 and H3 Fab (generated at UCB by conventional methods) as follows. Complex was made by mixing 0.5 ml of aP2 at 13 mg/ml with either 0.8 ml of CA33 Fab at 21.8 mg/ml or 1.26 ml of H3 Fab at 13.6 mg/ml (aP2:Fab molar ratio of 1.2:1). Proteins were incubated at RT for 30 minutes then run on an S75 16/60 gel filtration column (GE Healthcare) in 50 mM Tris pH7.2, 150 mM NaCl+5% glycerol. Peak fractions were pooled and concentrated to 10 mg/ml for crystallography.

Sitting-drop crystallization trials were set up using commercially available screening kits (QIAGEN). Diffraction-quality crystals were obtained directly in primary crystallization screening without any need to optimize crystallization conditions. For the aP2/CA33 complex the well solution contained 0.1 M Hepes pH 7.5, 0.2 M $(NH_4)_2SO_4$, 16% PEG 4K and 10% isopropanol. For the aP2/H3 complex the well solution contained 0.1 M MES pH5.5, 0.15 M $(NH_4)_2SO_4$ and 24% PEG 4K. Data were collected at the Diamond Synchrotron on i02 (λ=0.97949) giving a 2.9 Å dataset for aP2/CA33 and a 2.3 Å dataset for aP2/H3. Structures were determined by molecular replacement using Phaser (44) (CCP4) with AP2 and a Fab domain starting models. Two complexes were found to be in the asymmetric unit for aP2/CA33 and one for aP2/H3. Cycles of refinement and model building were performed using CNS (Brunger et al., (2007) Nature Protocols 2, 2728-2733) and coot (Emsley et al., (2004) Acta crystallographica. Section D. Biological crystallography 60, 2126-2132) (CCP4) until all the refinement statistics converged for both models. Epitope information described above was derived by considering atoms within 4 Å distance at the aP2/Fab contact surface. The data collection and refinement statistics are shown below. Values in parenthesis refer to the high resolution shell.

| Structure | aP2-CA33 | aP2-H3 |
|---|---|---|
| Space group | P 1 2$_1$ 1 | P 1 2$_1$ 1 |
| Cell dimensions | | |
| a, b, c (Å) | 65.27, 101.95, 95.31 | 71.50, 66.04, 75.68 |
| α, β, γ (°) | 90.00, 90.03, 90.00 | 90.00, 111.67, 90.00 |

| | -continued | |
|---|---|---|
| Resolution (Å) | 54.97-2.95 (3.09-2.95) | 33.03-2.23 (2.37-2.23) |
| $R_{sym}$ or $R_{merge}$ | 0.18 (1.169) | 0.11 (0.352) |
| I/σI | 8.3 (2.9) | 6.8 (1.7) |
| Completeness (%) | 99.2 (98.9) | 98.6 (98.4) |
| Redundancy | 6.2 (6.3) | 2.6 (2.6) |
| Refinement | | |
| Resolution (Å) | 54.97-2.95 | 33.02-3.00 |
| No. reflections | 24898 | 13077 |
| $R_{work}/R_{free}$ | 0.21/0.28 | 0.22/0.27 |
| No. atoms | | |
| Protein | 8632 | 4331 |
| Water | 0 | 0 |
| B-factors | | |
| aP2 | (molecule 1) 58.3; (molecule 2) 64.6 | 27.5 |
| Fab | (molecule 1) 52.9; (molecule 2) 52.5 | 22.5 |
| R.m.s. deviations | | |
| Bond lengths (Å) | 0.009 | 0.011 |
| Bond angles (°) | 1.42 | 1.67 |

Values in parenthesis refer to the high resolution shell.
$R_{sym} = \Sigma|(I - <I>)|/\Sigma(I)$, where I is the observed Integrated intensity, <I> is the average integrated intensity obtained from multiple measurements, and the summation is over all observed reflections. $R_{work} = \Sigma||F_{obs}| - k|F_{calc}||/\Sigma|F_{obs}|$, where $F_{obs}$ and $F_{calc}$ are the observed and calculated structure factors, respectively. $R_{free}$ is calculated as $R_{work}$ using 5% of the reflection data chosen randomly and omitted from the refinement calculations. Epitope information was derived by considering atoms within 4 Å distance at the aP2/Fab contact surface.

Hyperinsulinemic-Euglycemic Clamp Studies and Hepatic Biochemical Assays

Hyperinsulinemic-euglycemic clamps were performed by a modification of a reported procedure (Cao et al., (2013) Cell Metab. 17, 768-778). Specifically, mice were clamped after 5 hours fasting and infused with 5 mU/kg/min insulin. Blood samples were collected at 10-min intervals for the immediate measurement of plasma glucose concentration, and 25% glucose was infused at variable rates to maintain plasma glucose at basal concentrations. Baseline whole-body glucose disposal was estimated with a continuous infusion of [3-3H]-glucose (0.05 µCi/min). This was followed by determination of insulin-stimulated whole-body glucose disposal whereby [3-3H]-glucose was infused at 0.1 µCi/min.

Total lipids in liver were extracted according to the Bligh-Dyer protocol (Bligh et al., (1959) Canadian J. Biochem. and Phys. 37, 911-917), and a colorimetric method used for triglyceride content measurement by a commercial kit according to manufacturer's instructions (Sigma Aldrich). Gluconeogenic enzyme Pck1 activity was measured by a modification of reported method (Petrescu et al., (1979) Analytical Biochem. 96, 279-281). Glucose-6-phosphatase (G6pc) activity was measured by a modification of Sigma protocol [EC 3.1.3.9]. Briefly, the livers were homogenized in lysis buffer containing 250 mM sucrose, Tris HCl and EDTA. Lysates were centrifuged at full speed for 15 min and the supernatant (predominantly cytoplasm) isolated. Then microsomal fractions were isolated by ultracentrifugation of cytoplasmic samples. Microsomal protein concentrations were measured by commercial BCA kit (Thermo Scientific Pierce). 200 mM glucose-6-phosphate (Sigma Aldrich) was pre-incubated in Bis-Tris. 150 µg microsomal protein or serial dilution of recombinant G6Pase were added and incubated in that solution for 20 min at 37° C. Then 20% TCA was added, mixed and incubated for 5 min at room temperature. Samples were centrifuged at full speed at 4° C. for 10 min, and the supernatant was transferred to a separate UV plate. Color reagent was added and absorbance at 660 nm was measured and normalized to standard curve prepared with serial dilution of recombinant glucose-6-phosphatase (G6pc) enzyme.

Plasma aP2, mal1, FABP3, Adiponectin, Glucagon, and Insulin ELISAs

Blood was collected from mice by tail bleeding after 6 hours daytime or 16 hours overnight food withdrawal. Terminal blood samples were collected by cardiac puncture or collected from tail vein. The samples were spun in a microcentrifuge at 3,000 rpm for 15 minutes at 4° C. Plasma aP2 (Biovendor R&D), mal1 (Circulex Mouse Mal1 ELISA, CycLex Co., Ltd., Japan), FABP3 (Hycult Biotech, Plymouth Meeting, Pa.) glucagon, adiponectin (Quantikine ELISA, R&D Systems, Minneapolis, Minn.), and insulin (insulin-mouse ultrasensitive ELISA, Alpco Diagnostics, Salem, N.H.) measurements were performed according to the manufacturer's instructions.

Quantitative Real Time PCR Analysis

Tissues were collected after 6 hours daytime food withdrawal, immediately frozen and stored at −80° C. RNA isolation was performed using Trizol (Invitrogen, Carlsbad, Calif.) according to the manufacturer's protocol. For first strand cDNA synthesis 0.5-1 ng RNA and 5× iScript RT Supermix were used (BioRad Laboratories, Herculus, Calif.). Quantitative real time PCR (Q-PCR) was performed using Power SYBR Green PCR master mix (Applied Biosystems, Life Technologies, Grand Island, N.Y.) and samples were analyzed using a ViiA7 PCR machine (Applied Biosystems, Life Technologies, Grand Island, N.Y.). Primers used for Q-PCR were as follows:

```
36B4   5'-cactggtctaggacccgagaa-3' Seq. ID No. 513; 5'-aggggagatgttcagcatgt-3'
       Seq. ID No. 514

FAS    5'-ggaggtggtgatag ccggtat-3' Seq. ID No. 515; 5'-tgggtaatccatagagcccag-3'
       Seq. ID No. 516

SCD1   5'-ttcttgcgatacactctggtgc-3' Seq. ID No. 517; 5'-cgggattgaatgacttgtcgt-3' Seq.
       ID No. 518

Pck1   5'-ctgcataacggtctggacttc-3' Seq. ID No. 519; 5'-cagcaactgcccgtactcc-3' Seq.
       ID No. 520

G6pc   5'-cgactcgctatctccaagtga-3' Seq. ID No. 521; 5'-gttgaaccagtctccgacca-3' Seq.
       ID No. 522

ACC1   5'-atgtctggcttgcacctagta-3' Seq. ID No. 523; 5'-ccccaaagcgagtaacaaattct-3'
       Seq. ID No. 524
```

-continued

| | | | |
|---|---|---|---|
| TNF | 5'-ccctcacactcagatcatcttct-3' Seq. ID No. 525; | 5'-gctacgacgtgggcta cag-3' Seq. ID No. 526 | |
| IL-1β | 5'-gcaactgttcctgaactcaact-3' Seq. ID No. 527; | 5'-atcttttggggtccgtcaact-3' Seq. ID No. 528 | |
| IL-6 | 5'-acaacc acggccttccctactt-3' Seq. ID No. 529; | 5'-cacgatttcccagagaacatgtg-3' Seq. ID No. 530 | |
| CCL2 | 5'-catccacgtgttggctca-3' Seq. ID No. 531; | 5'-gatcatcttgctggtgaatgagt-3' Seq. ID No. 532 | |
| CXCL1 | 5'-gactccagccacactccaac-3' Seq. ID No. 533; | 5'-tgacagcgcagctcattg-3' Seq. ID No. 534 | |
| F4/80 | 5'-tgactcaccttgtggtcctaa-3' Seq. ID No. 535; | 5'-cttcccagaatccagtctttcc-3' Seq. ID No. 536 | |
| CD68 | 5'-tgtctgatcttgctaggaccg-3' Seq. ID No. 537; | 5'-gagagtaacggccatttttgtga-3' Seq. ID No. 538 | |
| TBP | 5'-agaacaatccagactagcagca-3' Seq. ID No. 539; | 5'-gggaacttcacatcacagctc-3' Seq. ID No. 540 | |

Statistical Analysis

Results are presented as the mean±SEM. Statistical significance was determined by repeated measures ANOVA or student's t test. * denotes significance at p<0.05, **denotes significance at p<0.01.

Anti-aP2 Monoclonal Antibody Development and Screening

Obesity is associated with increased levels of circulating aP2, which contributes to the elevation of hepatic glucose production and reduced peripheral glucose disposal and insulin resistance, characteristics of type 2 diabetes. Therefore, neutralizing serum aP2 represents an efficient approach to treat diabetes and possibly other metabolic diseases.

Figure 7A:
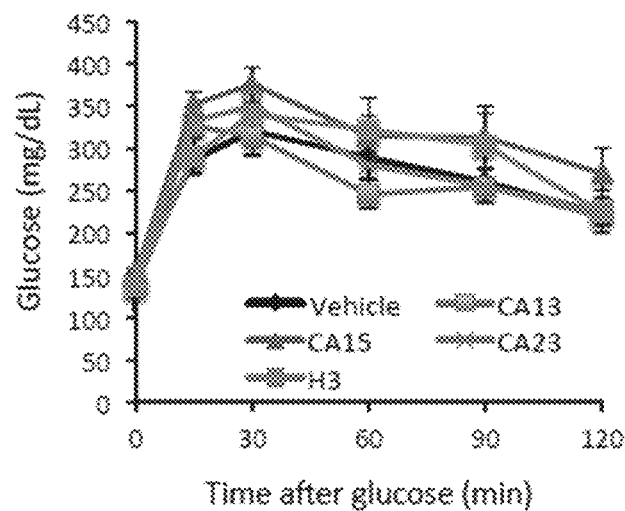
FIG. 7A is a line graph showing glucose levels (mg/dl) vs. time (minutes) in a glucose tolerance test (GTT) following two weeks of selective antibody treatment using high affinity antibodies (CA13, CA15, CA23, and H3) versus vehicle control.
Figure 7B:
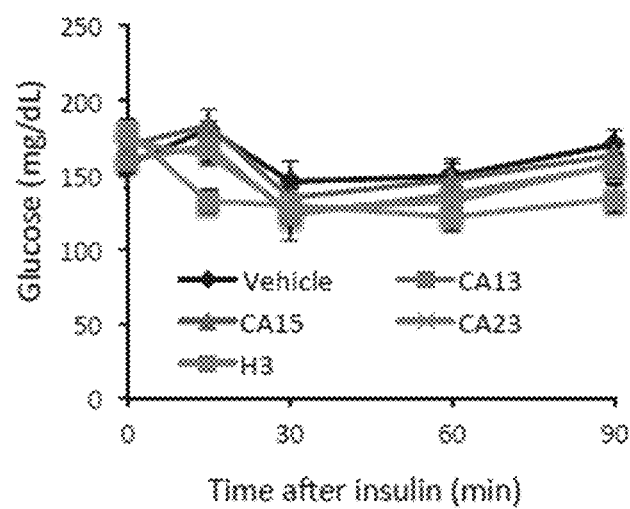
FIG. 7B is a line graph showing glucose levels (mg/dl) vs. time (minutes) in an insulin tolerance test (ITT) following three weeks of selective antibody treatment using high affinity antibodies (CA13, CA15, CA23, and H3) versus vehicle control.

Mouse and rabbit-mouse hybrid monoclonal antibodies raised against the human and mouse aP2 peptides were produced and screened. Assessment of binding affinity by biomolecular interaction analysis using a Biacore system demonstrated a wide range of affinities for these antibodies, from the micromolar to the low nanomolar range (FIG. 1A). As an initial test for the potential effects of these antibodies in vivo, the antibodies were administered subcutaneously for 4 weeks to mice with high fat diet (HFD)-induced obesity (FIG. 1B). The HFD-feeding resulted in a rise in serum insulin levels during the experiment, an effect that was blunted by treatment with the mouse antibody H3 and reversed by the hybrid antibody CA33, but unaltered by the other three hybrid antibodies tested (FIG. 1C). Interestingly, CA33 also significantly decreased fasting blood glucose (FIG. 1D), while the other antibodies tested did not improve glycemia, indicating that CA33 reduced insulin resistance associated with HFD and improved glucose metabolism. The systemic improvement in glucose metabolism was further verified using a glucose tolerance test (GTT). CA33 therapy resulted in significantly improved glucose tolerance (FIG. 1E), while the other antibodies did not improve glucose tolerance and glucose disposal curves were not different compared to vehicle (FIG. 7A). Furthermore, only CA33 treatment markedly improved insulin sensitivity as demonstrated in insulin tolerance tests, while other antibodies tested were similar to vehicle (FIG. 1F, FIG. 7B). There was a moderate reduction in weight gain in all but one of the antibody-treated groups (CA15) (FIG. 1G), although this did not correlate with improvement in glucose metabolism. Taken together, these results demonstrated that CA33 uniquely possessed anti-diabetic properties.

CA33 is a Low-Affinity Antibody that Neutralizes aP2

CA33 was further characterized to better understand its unique therapeutic properties. In an octet-binding assay, all of the antibodies tested demonstrated saturable binding to aP2. There was a measurable but low interaction with the related protein FABP3 (~25% of the aP2/FABP4 interaction), and only minor interaction with Mal1/FABP5 that was similar to control IgG (FIG. 2A). Interestingly, we also found that the improvement in glucose homeostasis in CA33-treated mice was related to a unique effect of this antibody on circulating aP2 levels. After 4 weeks of treatment, CA33 treated mice maintained circulating aP2 levels at a level similar to or slightly lower than that seen in control-treated animals, while all other antibodies including H3 resulted in a dramatic 10-fold increase in circulating aP2 levels (FIG. 2B). Indeed, circulating aP2 was undetectable by western blot in both control and CA-33-treated mice, but robustly evident in serum following H3 treatment (FIG. 2B, inset).

Figure 2E:
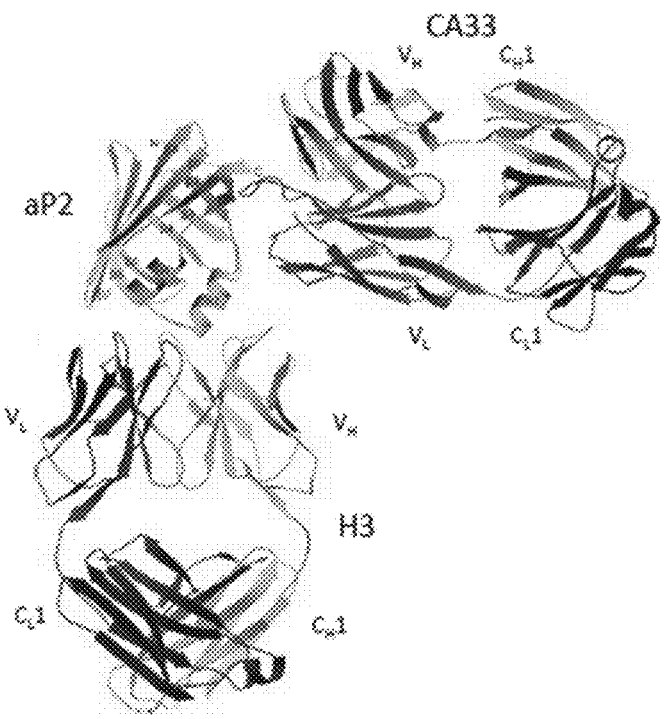
FIG. 2E is a superimposed image of the Fab of CA33 co-crystallized with aP2 and the Fab of H3 co-crystallized with aP2.
Figure 2F:
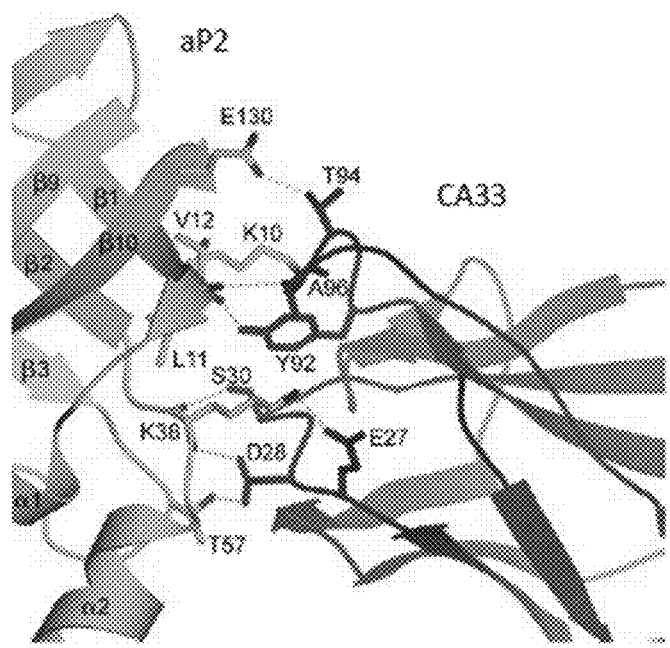
FIG. 2F is a high resolution mapping of CA33 epitope on aP2. Interacting residues in both molecules are indicated. Hydrogen bonds are shown as dashed lines. The side chain of K10 in aP2 forms a hydrophobic interaction with the phenyl side chain of Y92.
Figure 2G:
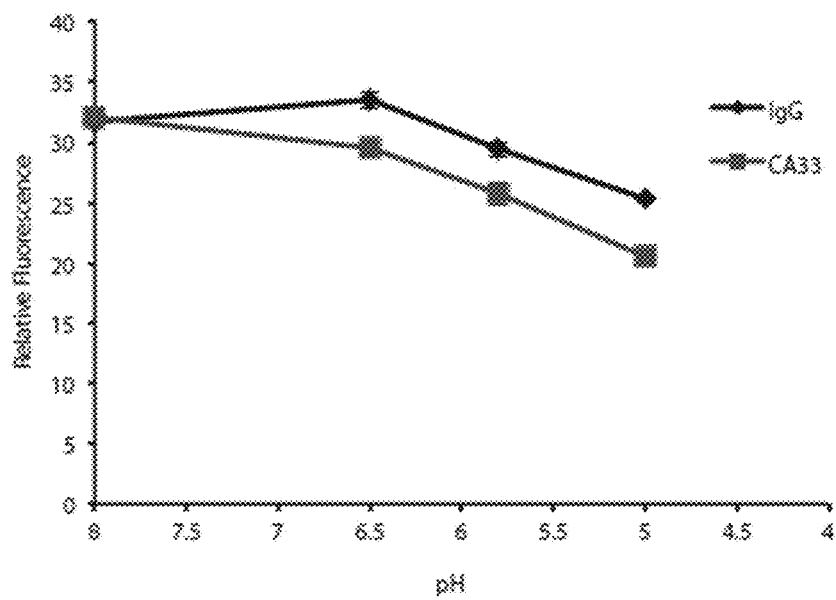
FIG. 2G is a line graph showing paranaric acid binding to aP2 (relative fluorescence) vs. pH in the presence of IgG control antibody (circles) or CA33 antibody (squares).
Figure 2H:
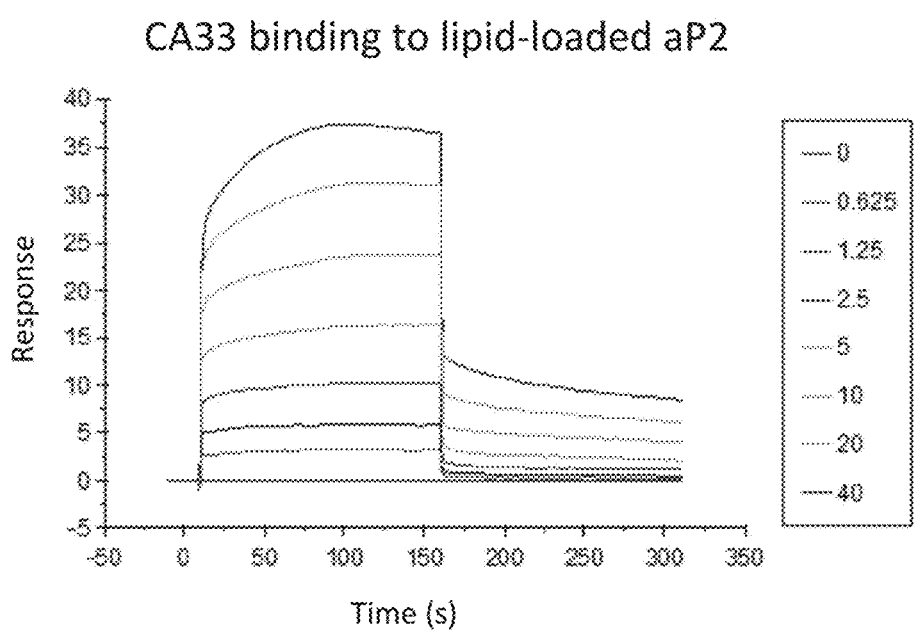
FIG. 2H is a graph showing CA33 binding to aP2 (resonance units) vs. time (seconds) in response to increasing concentrations of lipid-loaded aP2.
Figure 2I:
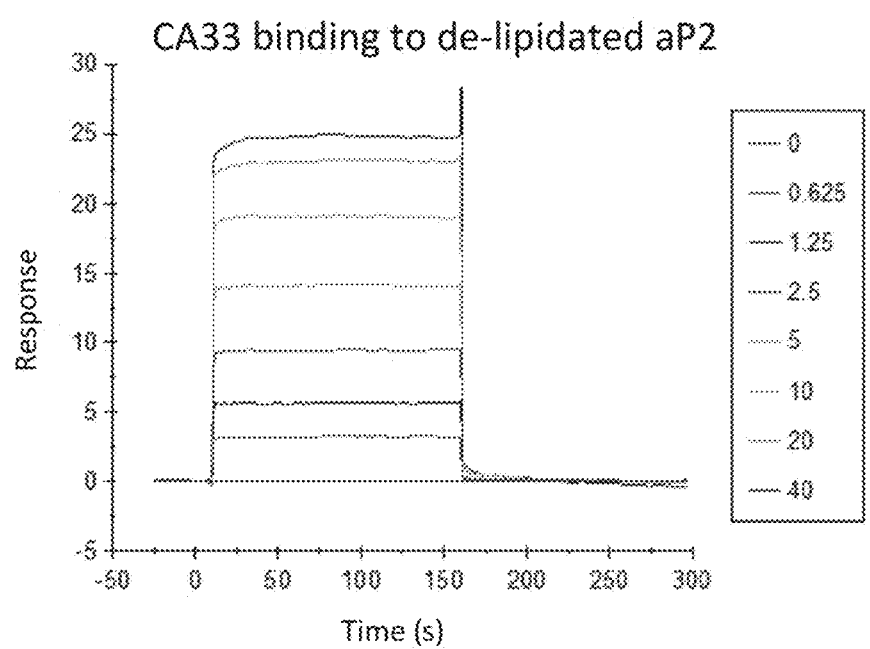
FIG. 2I is a graph showing CA33 binding to aP2 (resonance units) vs. time (seconds) in response to increasing concentrations of de-lipidated aP2.

In cross blocking experiments to begin characterizing the target sites, we found that CA33 partially blocked binding of the ineffective mouse antibody H3 to aP2, while H3 binding was completely blocked by the hybrid antibodies CA13 and CA15 (FIG. 2C). These data suggest that the epitope recognized by CA33 only partially overlaps with that recognized by H3. In further analysis, epitope identification based on hydrogen-deuterium exchange mass spectrometry experiments, for example, as described by Pandit et al. (2012) J. Mol. Recognit. March; 25(3):114-24 (incorporated herein by reference), indicated interaction of CA33 with first alpha helix and the first beta sheet of aP2 on residues 9-17, 20-28 and 118-132, which partially overlapped with the epitope identified for H3 (FIG. 2D). To understand these epitopes precisely, we then co-crystallized the Fab fragments of CA33 and H3 with aP2 (FIG. 2E). Analyses of the crystals showed that CA33 binds an epitope spread out over the secondary structure elements beta1 and beta10 and the random coil regions linking alpha2 to beta2 and beta3 to beta4, and includes the aP2 amino acids 57T, 38K, 11L, 12V, 10K and 130E (FIG. 2F). Despite the partial blocking of H3 by CA33, we observed that there is in fact no direct overlap of their epitopes. Instead, the significant movement of the region around aP2 Phe58 may partially block binding of one antibody by the other in the competition experiments. In addition, the low affinity of the CA33 Fab can be explained by the crystal structure. Unusually, only one amino acid in the heavy chain of CA33 makes a contact with aP2, and the majority of the contacts are through the light chain (FIG. 2E, F). In contrast, H3-aP2 contact is more conventional, with both Fab chains interacting with aP2. The structure also shows that CA33 does not bind to the 'lid' of the β-barrel (14S to 37A), which has been postulated to control access of lipids to the binding pocket or the 'hinge' which contains E15, N16, and F17. In addition, it was found that lipid binding (paranaric acid) to aP2 was not substantially altered by the presence of CA33 (FIG. 2G). H3 does bind directly to the 'lid' but has limited activity. Binding of CA33 to lipid-bound aP2 or lipid-free aP2 was also examined using biochemical analysis (Biacore). As seen in FIGS. 2H and 2I, CA33 binds to both lipid-bound aP2 and lipid-free aP2 with the following affinities:

| Mouse aP2 | KD |
|---|---|
| Lipid-loaded | 9.3 μM |
| De-lipidated | 4.7 μM |

Cumulatively, these results suggest that CA33 activity may be independent of aP2 lipid binding.

Figure 3A:
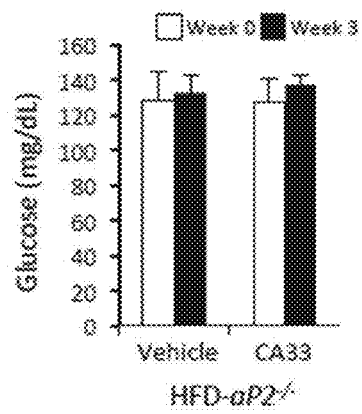
FIG. 3A is a bar graph showing fasting blood glucose (mg/dl) in HFD-induced obese aP2-/- mice before (open bars) and after CA33 antibody or vehicle treatment for three weeks (solid bars).
Figure 3B:
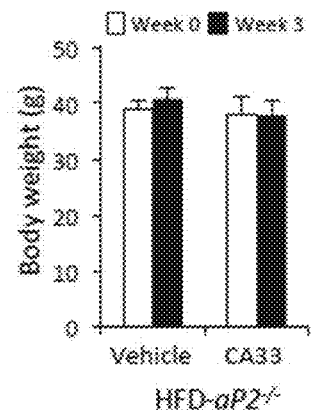
FIG. 3B is a bar graph showing body weight (g) in HFD-induced obese aP2-/- mice before (open bars) and after CA33 antibody or vehicle treatment for three weeks (solid bars).
Figure 3C:
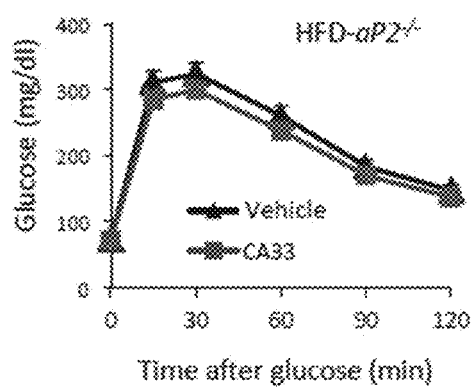
FIG. 3C is a line graph showing glucose levels (mg/dl) in HFD-induced obese aP2-/- mice vs. time (minutes) during a glucose tolerance test (GTT). The test was performed after 2 weeks of vehicle (triangles) or CA33 antibody treatment (squares) in aP2-/- mice.

Given the relatively low affinity of CA33 for aP2, off-target effects were examined. The effect of CA33 treatment in aP2−/− mice fed a HFD were tested. In these experiments, antibody therapy failed to induce any change in weight or fasting glucose in this model (FIG. 3A, 3B). Furthermore, CA33 did not affect glucose tolerance in obese aP2−/− mice (FIG. 3C), clearly demonstrating that the antibody's effects are due to targeting aP2.

Figure 3D:
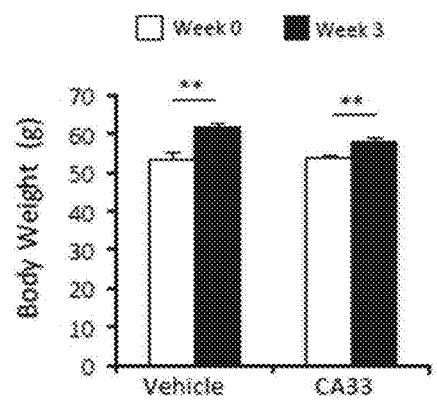
FIG. 3D is a bar graph showing body weight (g) in ob/ob mice before (open bars) and after (solid bars) 3 weeks of CA33 antibody or vehicle treatment (n=10 mice per group). ** p<0.01.
Figure 3E:
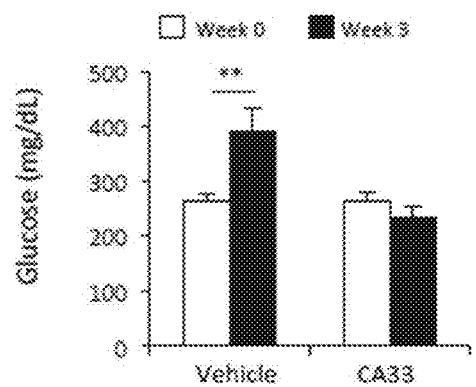
FIG. 3E is a bar graph showing fasting blood glucose levels (mg/dl) in ob/ob mice before (open bars) and after (solid bars) 3 weeks of CA33 antibody or vehicle treatment (n=10 mice per group). ** p<0.01.
Figure 3F:
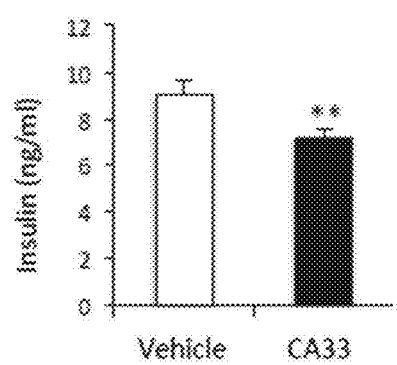
FIG. 3F is a bar graph showing plasma insulin levels (ng/ml) in ob/ob mice following three weeks of vehicle (open bar) or CA33 antibody treatment (solid bar). ** p<0.01.
Figure 3G:
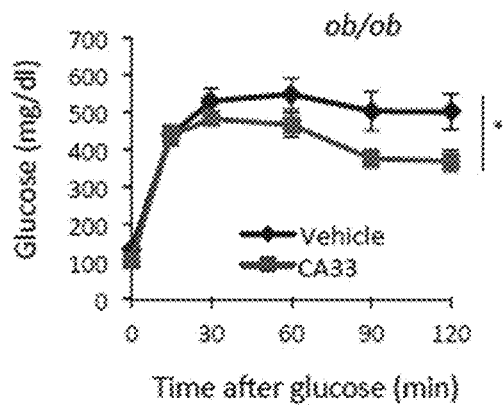
FIG. 3G is a line graph showing glucose levels (mg/dl) in ob/ob mice vs. time (minutes) during a glucose tolerance test (GTT). The test was performed after 2 weeks of vehicle (triangles) or CA33 antibody treatment (squares) in aP2-/- mice. * p<0.05.

Finally, the effect of CA33 in a second model of severe genetic obesity and insulin resistance using leptin-deficient ob/ob mice was examined. Over the course of 3 weeks of treatment, both the CA33 and vehicle-treated groups gained weight but the extent was less in the CA33-treated group (FIG. 3D). Strikingly, hyperglycemia in the ob/ob mice was normalized in CA33-treated mice compared to controls (FIG. 3E). The extent of hyperinsulinemia was also partially reduced in the CA33-treated animals (FIG. 3F). Normal glucose and lower insulin levels suggest improved glucose metabolism upon neutralization of aP2. Indeed, following administration of exogenous glucose, CA33 treated ob/ob mice also exhibited significantly improved glucose tolerance compared to vehicle treated mice despite the presence of massive obesity (FIG. 3G). These data underscore the broad applicability of aP2 neutralization to metabolic disease in independent preclinical models and are consistent with the results obtained in the context of dietary and genetic obesity.

Figure 4A:
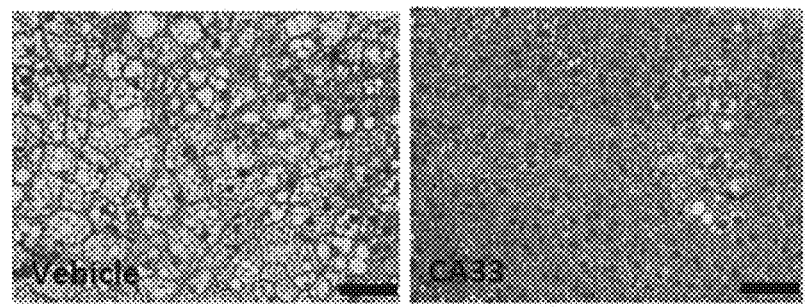
FIG. 4A is a representative image of hematoxylin and eosin (H&E) stained liver from HFD-induced obese mice after 5 weeks of treatment with vehicle or CA33. Scale bar is 50 µm.
Figure 4B:
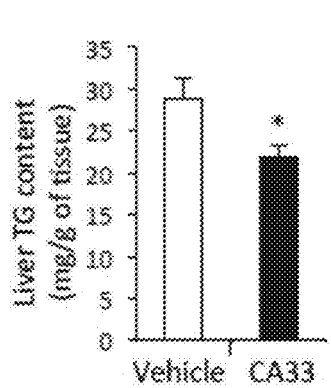
FIG. 4B is a bar graph of liver triglyceride (TG) content (mg/g of tissue) in HFD-induced obese mice after 5 weeks of treatment with vehicle (open bar) or CA33 antibody (solid bar). * p<0.05.
Figure 4C:
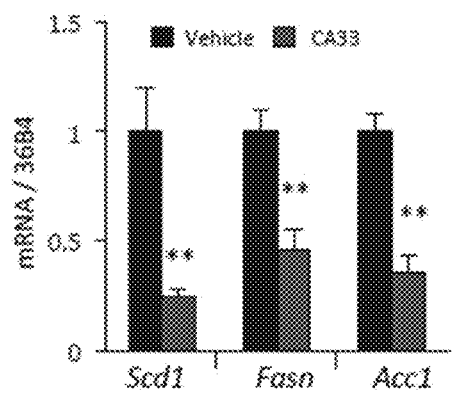
FIG. 4C is bar graph showing mRNA expression of lipogenic genes stearoyl-CoA desaturase (Scd1), fatty acid synthase (Fasn) and acetyl-CoA carboxylase (Acc1) in liver samples from HFD-induced obese mice after 5 weeks of vehicle (black bars) or CA33 treatment (gray bars). ** p<0.01.
Figure 4D:
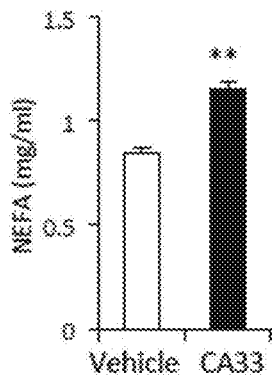
FIG. 4D is a bar graph showing levels of plasma nonesterified fatty acid (NEFA) (mg/ml) in HFD-induced obese mice after 5 weeks of vehicle (open bar) or CA33 treatment (solid bar). ** p<0.01.
Figure 4E:
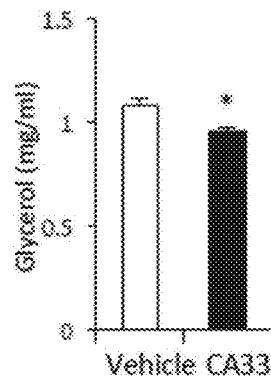
FIG. 4E is a bar graph showing levels of plasma glycerol (mg/ml) in HFD-induced obese mice after 5 weeks of vehicle (open bar) or CA33 treatment (solid bar). * p<0.05.
Figure 4F:
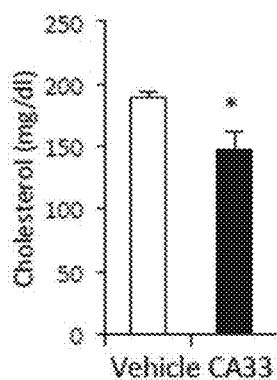
FIG. 4F is a bar graph showing levels of plasma total cholesterol (mg/dl) in HFD-induced obese mice after 5 weeks of vehicle (open bar) or CA33 treatment (solid bar).* p<0.05.
Figure 4G:
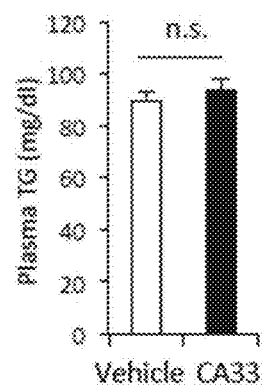
FIG. 4G is a bar graph showing levels of plasma triglycerides (mg/dl) in HFD-induced obese mice after 5 weeks of vehicle (open bar) or CA33 treatment (solid bar).
Figure 4H:
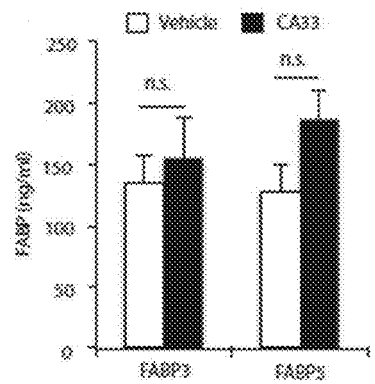
FIG. 4H is a bar graph showing levels of plasma FABP3 or FABP5 (Mal1) (ng/ml) in HFD-induced obese mice after 5 weeks of vehicle (open bar) or CA33 treatment (solid bar).
Figure 4I:
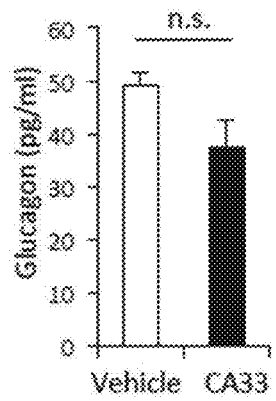
FIG. 4I is a bar graph showing levels of plasma glucagon (pg/ml) in HFD-induced obese mice after 5 weeks of vehicle (open bar) or CA33 treatment (solid bar).
Figure 4J:
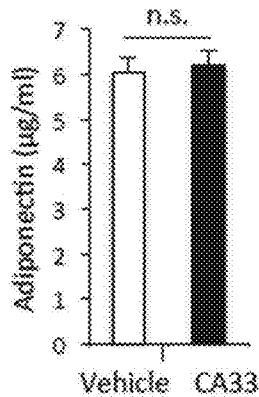
FIG. 4J is a bar graph showing levels of plasma adiponectin (µg/ml) in HFD-induced obese mice after 5 weeks of vehicle (open bar) or CA33 treatment (solid bar).

CA33 Treatment Improves Lipid Metabolism and Inhibits Hepatosteatosis in Obese Mice Having identified and physically characterized a candidate monoclonal antibody that could generate metabolic benefits, detailed functional studies in the HFD model were performed. To further explore the metabolic effects of CA33 treatment, we treated HFD-induced obese mice with CA33 or vehicle for five weeks and examined the effects on liver. As expected, long term high fat feeding induced steatosis and triglyceride accumulation in vehicle-treated mice, however, these effects were significantly ameliorated by CA33 treatment (FIG. 4A, B). In addition, the improvement in liver lipid homeostasis was accompanied by reduced hepatic expression of key genes involved in de novo lipogenesis (FIG. 4C). Similar to genetic aP2 deficiency, CA33 treated mice had moderately higher plasma free fatty acid levels (FIG. 4D) and lower glycerol levels (FIG. 4E). Total cholesterol levels were also lower in CA33 treated group (FIG. 4F), although there was no significant difference in plasma triglycerides (FIG. 4G). Notably, although complete whole body genetic aP2 deficiency is associated with a substantial upregulation of tissue mal1 (FABP5/Mal1) expression, significant changes in circulating mal1 levels upon CA33 treatment indicating lack of compensatory changes were not detected (FIG. 4H). In addition, CA33 treatment did not significantly alter the circulating levels of FABP3 protein (FIG. 4H). There was also no alteration in the serum levels of glucagon or adiponectin in CA33 treated mice (FIG. 4I-J).

Effects of CA33 Treatment on Adipose Tissue and Body Composition

Figure 5A:
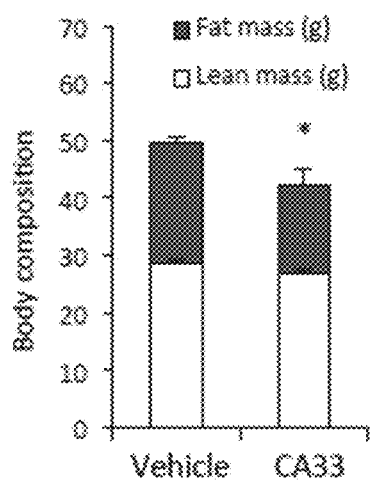
FIG. 5A is a bar graph of body fat mass (g) (open bar) and lean mass (g) (gray bar) as determined by dual-energy X-ray absorptiometry (DEXA) after 5 weeks of vehicle or CA33 treatment. (n=10 per group). * p<0.05.
Figure 5B:
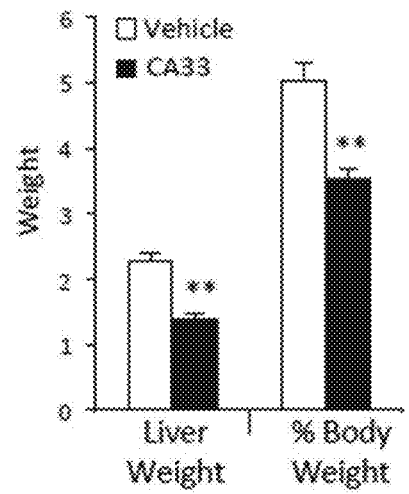
FIG. 5B is a bar graph showing liver weight (g) and % body weight of obese mice after 5 weeks of vehicle (open bars) or CA33 treatment (solid bars). ** p<0.01.
Figure 5C:
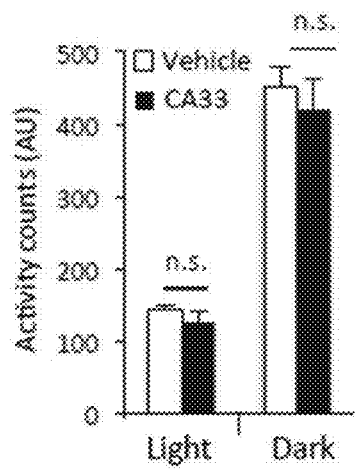
FIG. 5C is a bar graph showing physical activity (activity units—AU) for mice in the light or in the dark after 5 weeks of vehicle (open bars) or CA33 treatment (solid bars).
Figure 5D:
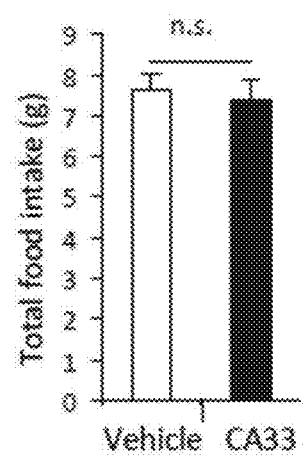
FIG. 5D is a bar graph showing total food intake (g) in obese mice after 5 weeks of vehicle (open bar) or CA33-treated mice (solid bar) on HFD (n=8 per group).

The impact of CA33 treatment on adipose tissue and body composition was also examined. Dual-energy X-ray absorptiometry (DEXA) scans showed that CA33-treatment significantly reduced fat mass (FIG. 5A); while lean mass was also slightly reduced, this likely reflects the reduced lipid accumulation in solid organs, especially liver (FIG. 4A, B). Indeed, CA33 treatment significantly decreased liver weight, and this reduction remained significant when expressed as percentage of body weight (FIG. 5B). The decrease in body weight in CA33-treated obese mice is reminiscent of the phenotype of mice with aP2-deficiency and combined aP2/mal1-deficiency on HFD, and raised the possibility that the antibody therapy directly altered metabolic parameters. In metabolic cage analysis, physical activity, food intake, and heat production were similar in vehicle and antibody-treated mice (FIG. 5C, D).

CA33 May Increase Fatty Acid Oxidation

Figure 5E:
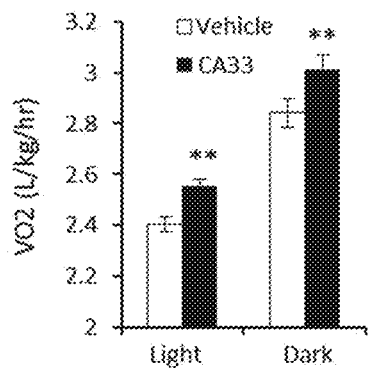
FIG. 5E is a bar graph showing VO2 concentrations by volume during the light and dark periods in mice treated with CA33 (solid bar) for eight weeks compared to vehicle (open bar).
Figure 5F:
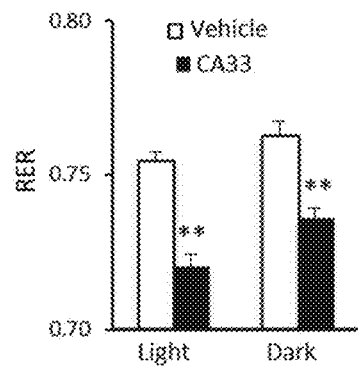
FIG. 5F is a bar graph showing calculated Respiratory Exchange Ratio (RER) during light and dark periods in mice treated with CA33 (solid bar) for eight weeks compared to vehicle (open bar).

For additional metabolic measurements, obese mice fed a HFD were placed in an indirect open circuit calorimeter (Oxymax System, Columbus Instruments). Oxygen and carbon dioxide concentrations by volume were monitored at the inlet and outlet parts of a partially sealed chamber, through which a known flow of ambient air was forcibly ventilated. The concentration difference measured between the parts was used to compute oxygen consumption (VO2) and carbon dioxide production (VCO2), and to calculate respiratory exchange rate (VCO2/VO2). In metabolic cage analysis, obese mice who were fed HFD and treated with CA33 for eight weeks showed increased VO2 Utilization compared to vehicle treated mice (FIG. 5E), resulting in a respiratory exchange ratio (RER) closer to 0.7 (FIG. 5F), suggesting that the antibody increased lipid utilization.

Figure 5G:
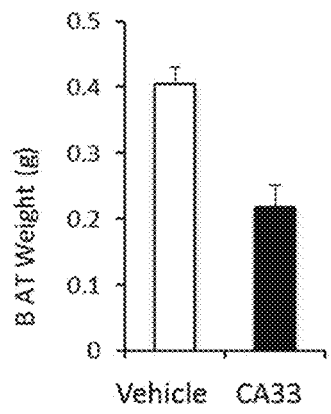
FIG. 5G is a bar graph showing the weight of brown adipose tissue (BAT) in mice treated with CA33 (solid bar) for eight weeks compared to vehicle (open bar).
Figure 5H:
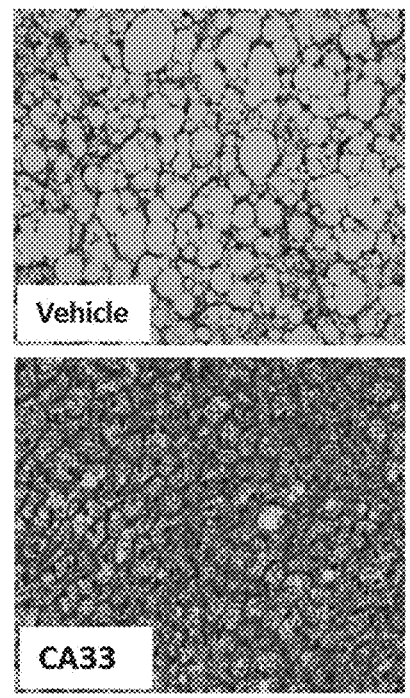
FIG. 5H shows representative H&E stained sections of BAT in mice following treatment with CA33 (solid bar) for eight weeks compared to vehicle (open bar).

Histological analysis revealed that, as expected, prolonged HFD-feeding resulted in abundant lipid accumulation in brown adipose tissue (BAT). However, treatment with CA33 resulted in a significant decrease in BAT tissue weight and dramatically decreased lipid droplet size (FIG. 5G, 5H).

Figure 5I:
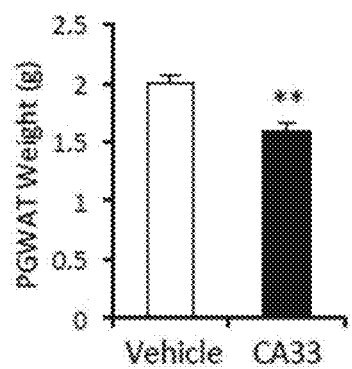
FIG. 5I is a bar graph showing the weight of perigonadal white adipose tissue (PGWAT) in obese mice after 5 weeks of vehicle (open bar) or CA33-treated mice (solid bar). ** p<0.01.
Figure 5J:
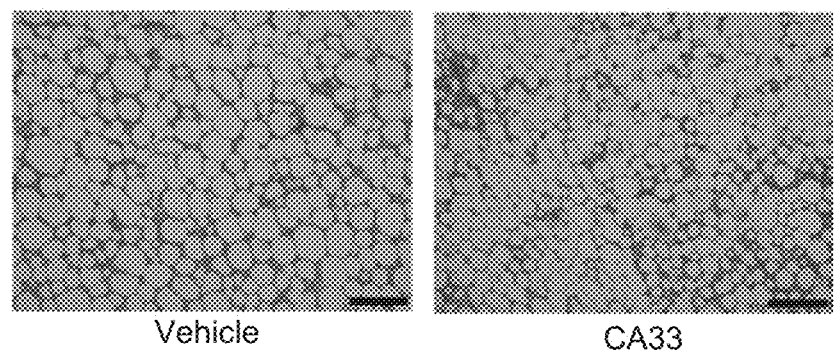
FIG. 5J is a representative image of hematoxylin and eosin (H&E) stained epididymal adipose tissue after 5 weeks of treatment with vehicle (left image) or CA33 (right image). Scale bar is 200 μm.
Figure 5K:
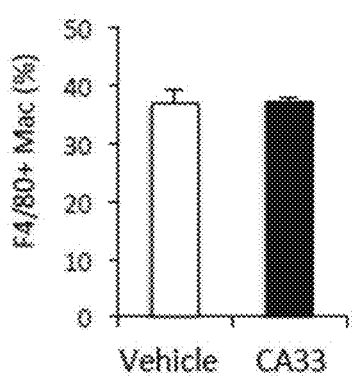
FIG. 5K is a bar graph showing F4/80+ Mac cells (%) in adipose tissue determined by FACS after 5 weeks of vehicle (open bar) or CA33-treated mice (solid bar).
Figure 5L:
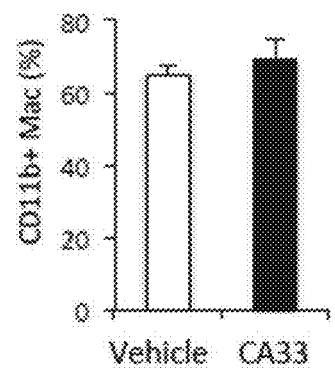
FIG. 5L is a bar graph showing CD11b+ cells (%) in adipose tissue determined by FACS analysis after 5 weeks of vehicle (open bar) or CA33-treated mice (solid bar).
Figure 5M:
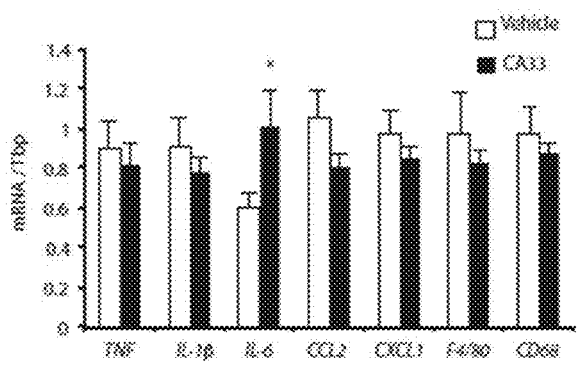
FIG. 5M is a bar graph showing mRNA levels (mRNA/Tbp) for TNF, IL-1β, IL-6, CCL2, CXCL1, F4/80 or CD68 in perigonadal white adipose tissue (PG-WAT) after 5 weeks of vehicle (open bar) or CA33-treated mice (solid bar).
Figure 5N:
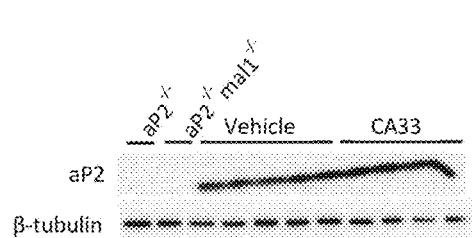
FIG. 5N is a Western blot showing adipose tissue aP2/FABP4 protein levels in mice treated with vehicle or CA33 for 3 weeks. Adipose tissue samples from aP2−/−, mal1−/−, and aP2/mal1−/− animals were included as protein controls. β-tubulin is shown as a loading control.
Figure 5O:
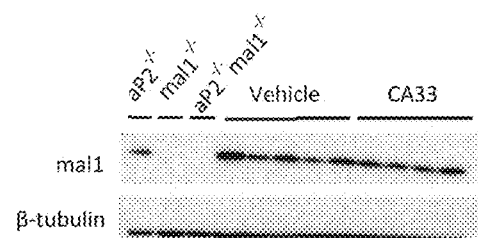
FIG. 5O is a Western blot showing adipose tissue Mal1/FABP5 protein levels in mice treated with vehicle or CA33 for 3 weeks. Adipose tissue samples from aP2−/−, mal1−/−, and aP2/mal1−/− animals were included as protein controls. β-tubulin is shown as a loading control.
Figure 5P:
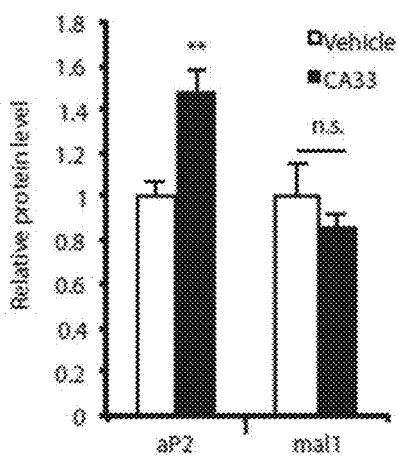
FIG. 5P is bar graph of relative protein levels for either aP2 or mal1 in mice treated with vehicle or CA33 for 3 weeks. The results shown in FIG. 5P quantify the Western blots shown in FIGS. 5N and 5O.

In general, adipose tissue depots appeared similar between antibody-treated and control groups; although there was a significant decrease in the size of the perigonadal fat pad (PGWAT; FIG. 5I). Analysis of H&E stained sections of PGWAT revealed a similar degree of inflammatory cell infiltration in CA33 and vehicle-treated mice. (FIG. 5J). Indeed, the infiltration of F4/80 and CD11b positive myeloid cells in adipose tissue preparations by FACS analysis indicated a similar number of these immune cells between the groups (FIG. 5K, L). In addition, there was no change observed in the expression of the inflammatory markers TNF, IL-1β, CCL2, CXCL1, F4/80 or CD68 in perigonadal white adipose tissue (PG-WAT) isolated from CA33-treated mice and only a modest increase in IL-6 mRNA levels (FIG. 5M). Adipose tissue aP2 protein levels showed a slight increase upon antibody treatment (FIG. 5N and FIG. 5P), and we did not observe compensatory regulation of mal1 (FIG. 5O and FIG. 5P), suggesting that neutralizing circulating aP2 in adult mice does not result in molecular compensation by other FABP isoforms, and in this way differs from genetic deficiency.

Figure 6A:
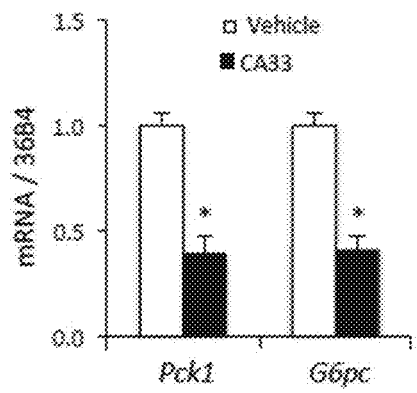
FIG. 6A is a bar graph showing mRNA expression of gluconeogenic genes phosphoenolpyruvate carboxykinase 1 (Pck1) and glucose-6-phosphatase (G6pc). Liver samples were collected after 6 hours of day-time food withdrawal from obese mice treated with vehicle (open bars) or CA33 (solid bars) (n=10 for each group) for 4 weeks. * p<0.05.
Figure 6B:
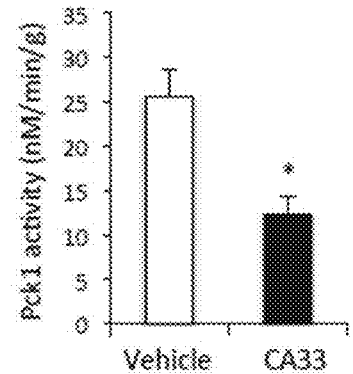
FIG. 6B is a bar graph showing enzymatic activity of Pck1 (nM/min/g) in liver samples. Liver samples were collected after 6 hours of day-time food withdrawal from obese mice treated with vehicle (open bars) or CA33 (solid bars) (n=10 for each group) for 4 weeks. * p<0.05.
Figure 6C:
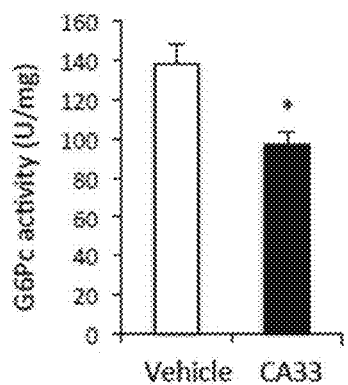
FIG. 6C is a bar graph showing enzymatic activity of glucose-6-phosphatase (G6pc) (U/mg) in liver microsomal fraction for mice treated with vehicle (open bars) or CA33 (solid bars) (n=10 for each group) for four weeks. * p<0.05.

CA33 Decreases Liver Glucose Production and Increases Peripheral Insulin Sensitivity Hepatic glucose production and peripheral glucose utilization are both critical in the maintenance of normoglycemia and adaptation to feeding and fasting responses. Recent studies demonstrated that hepatic glucose production and liver gluconeogenic activity were regulated by aP2 (Cao et al., (2013) Cell Metab. 17, 768-778), and suggested that this response, alone or in combination with peripheral effects, may be critical in mediating the anti-diabetic effect of aP2 blockade. To determine whether this underlies the therapeutic properties of CA33, livers from HFD-fed mice after 5 weeks of CA33 or vehicle treatment were collected. A marked reduction in expression of gluconeogenic genes phosphoenolpyruvate carboxykinase 1 (Pck1) and glucose-6-phosphatase (G6pc) in samples from the CA33-treated obese mice was observed (FIG. 6A). In addition, the enzymatic activities of cytoplasmic PCK1 and microsomal glucose-6-phosphatase were significantly reduced in samples from CA33-treated mice (FIG. 6B, C). These findings were consistent with earlier studies of aP2 function on liver (Cao et al., (2013) Cell Metab. 17, 768-778).

Figure 6D:
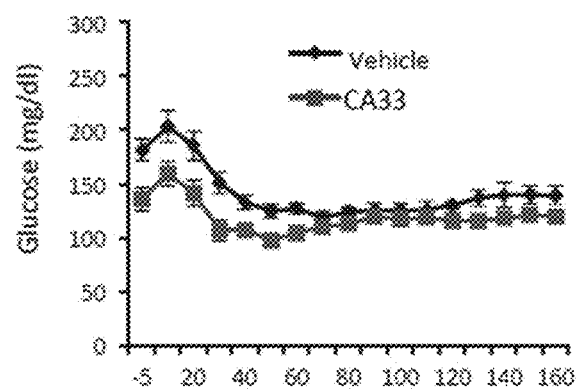
FIG. 6D is a line graph showing blood glucose (mg/dl) vs. time during hyperinsulinemic-euglycemic clamp. Clamp studies were performed in obese mice on a high-fat diet (HFD) after five weeks of treatment with vehicle (diamonds) or CA33 (squares) (n=7 for each group).
Figure 6E:
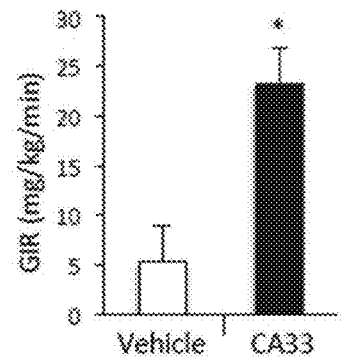
FIG. 6E is a bar graph showing glucose infusion rate (GIR) (mg/kg/min) in obese mice on a high-fat diet (HFD) after five weeks of treatment with vehicle (open bar) or CA33 (solid bar). * p<0.05.
Figure 6F:
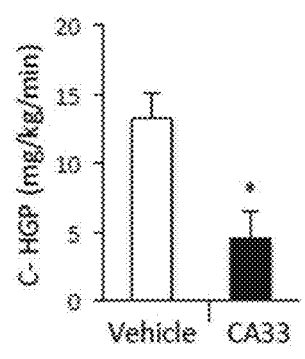
FIG. 6F is a bar graph showing clamp hepatic glucose production (c-HGP) (mg/kg/min) in obese mice on a high-fat diet (HFD) after five weeks of treatment with vehicle (open bar) or CA33 (solid bar).* p<0.05.
Figure 6G:
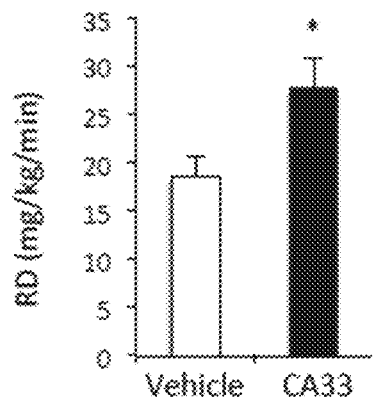
FIG. 6G is a bar graph showing the rate of whole body glucose disappearance (RD) (mg/kg/min) in obese mice on a high-fat diet (HFD) after five weeks of treatment with vehicle (open bar) or CA33 (solid bar). * p<0.05.
Figure 6H:
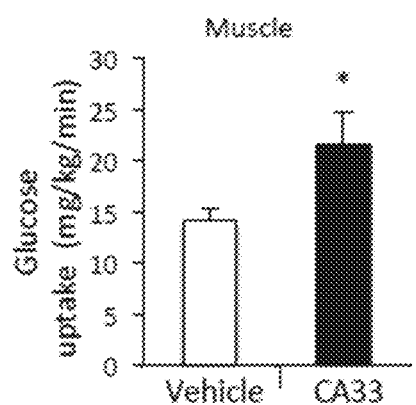
FIG. 6H is a bar graph showing glucose uptake in triceps surae muscle (mg/kg/min) in obese mice on HFD after five weeks of treatment with vehicle (open bar) or CA33 (solid bar). * p<0.05.
Figure 6I:
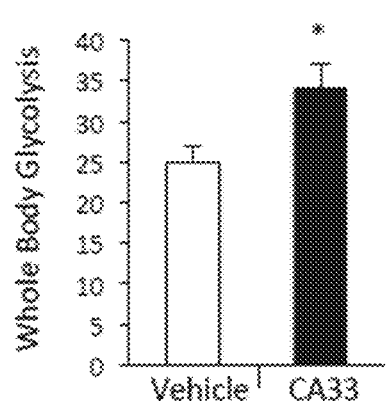
FIG. 6I is a bar graph showing whole body glycolysis in obese mice on a high-fat diet (HFD) after five weeks of treatment with vehicle (open bar) or CA33 (solid bar). * p<0.05.
Figure 8A:
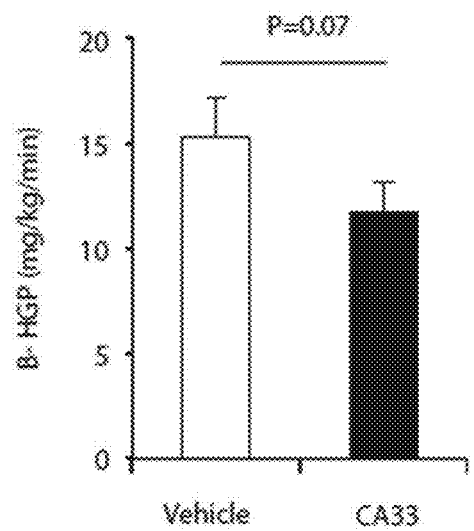
FIG. 8A is a bar graph showing basal hepatic glucose production (mg/kg/min) in vehicle control (open bar) or CA33 (solid bar) treated mice during hyperinsulinemic-euglycemic clamp of HFD-mice.
Figure 8B:
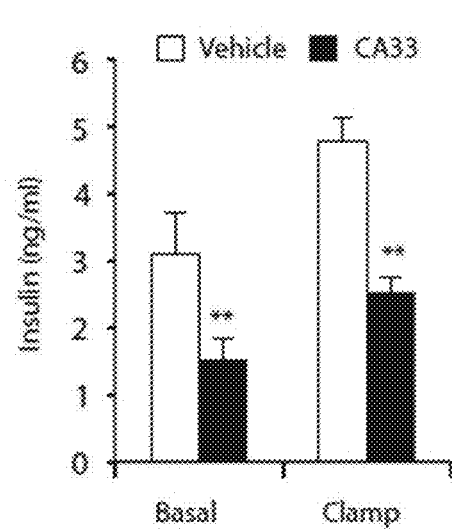
FIG. 8B is a bar graph showing serum insulin levels (ng/ml) in CA33 mice (solid bars) or vehicle control mice (open bars) during hyperinsulinemic-euglycemic clamp of HFD-mice. ** p<0.01.
Figure 8C:
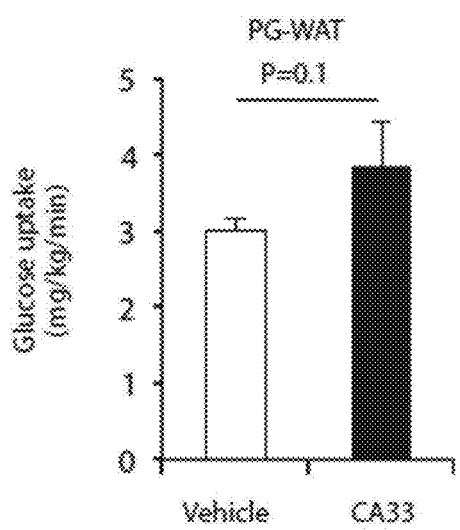
FIG. 8C is a bar graph showing glucose uptake (mg/kg/min) in gonadal white adipose tissue (GWAT) in vehicle control (open bar) or CA33 treated (solid bar) mice during hyperinsulinemic-euglycemic clamp of HFD-mice.

Next whole body glucose fluxes by hyperinsulinemic-euglycemic clamp studies were examined (FIG. 6D). For these experiments mice were kept on HFD for 20 weeks prior to antibody treatment, and clamp studies were performed after 5 weeks of antibody intervention. During the clamp study, CA33 treated obese mice required significantly higher glucose infusion rates to maintain euglycemia (FIG. 6E) and showed decreased clamp hepatic glucose production (FIG. 6F), as well as a non-significant trend towards a decrease basal hepatic glucose production (FIG. 8A, p=0.07). CA33 treatment also significantly increased whole body clamp glucose disposal rates (RD) (FIG. 6G), although plasma insulin levels were decreased compared to controls despite equivalent insulin infusion (5 mU/kg/min) (FIG. 8B). Taken together, these data indicate that CA33 also increased whole body systemic insulin sensitivity and increased insulin-stimulated glucose utilization. To further assess glucose utilization, we collected peripheral tissues after the clamp experiment and performed a 14C 2-deoxyglucose uptake assay. Insulin stimulated glucose uptake was significantly higher in muscle tissue isolated from CA33-treated obese mice (FIG. 4H), and there was a trend towards an increase in glucose uptake in perigonadal white adipose tissue (PGWAT) (FIG. 8C, p=0.1). Furthermore, whole body glycolysis, measured as the rate of increase in plasma [3H$_2$O] as a byproduct of glycolysis, was also increased by CA33 treatment (FIG. 6I). These data support the conclusion that the glucose-lowering effect of CA33 occurs predominantly through decreasing glucose production in liver and increasing glucose utilization in peripheral tissues such as muscle.

Example 2. Anti-aP2 Monoclonal Antibody (CA33) for the Treatment of Type 1 Diabetes CA33 Treatment is Protective Against Hyperglycemia and Mortality in the NOD Mouse Model of Type 1 Diabetes A model of Type 1 diabetes (T1D) in which diabetes onset is spontaneous, the NOD mouse (S. Makino, K. Kunimoto, Y. Murakoa, Y. Mizushima, K. Katagiri, Y. Tochino. Breeding of a non-obese, diabetic strain of mice. Jikken-dobutsu, Experimental animals 29, 1-13 (1980)), was used to examine the effects of CA33 treatment on diabetes incidence and mortality. Animal care and experimental procedures were performed with approval from animal care committees of Harvard University. Eight-week old female NOD mice were injected subcutaneously with either vehicle or CA33. For the first 6 weeks of treatment the CA33 treated mice were injected with 1 mg/injection, which corresponds to ~45 mg/kg dose, twice weekly. Starting at the seventh week of the study CA33 treated mice were injected with a 30 mg/kg dose of CA33 twice weekly. Six hour fasting blood glucose was measured weekly. Incidence of diabetes was defined as 2 consecutive weeks of 6 hour fasting blood glucose >200 mg/dL.

Figure 9:
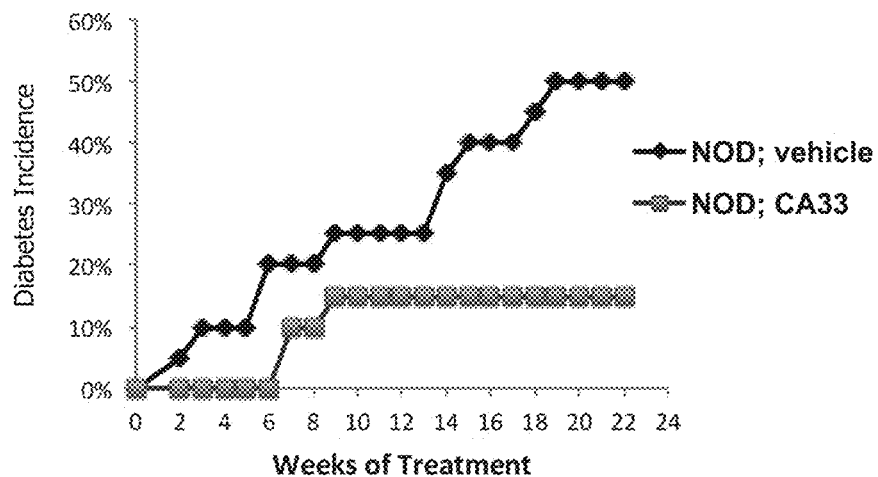
Figure 10A:
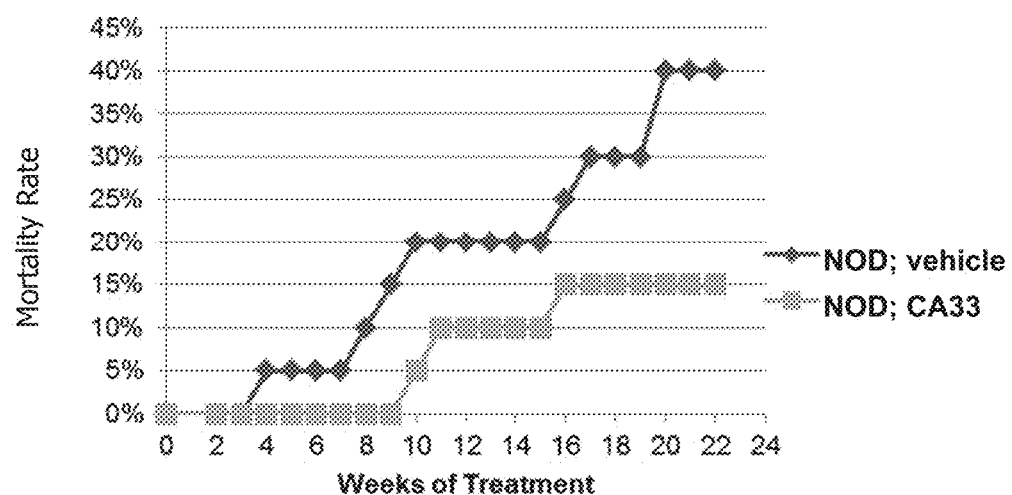
FIG. 10A is a line graph illustrating death rate (%) vs. time (weeks of treatment) in the NOD mouse model for Type 1 Diabetes. NOD mice were treated with vehicle (diamonds) or the aP2 monoclonal antibody CA33 (squares).
Figure 10B:
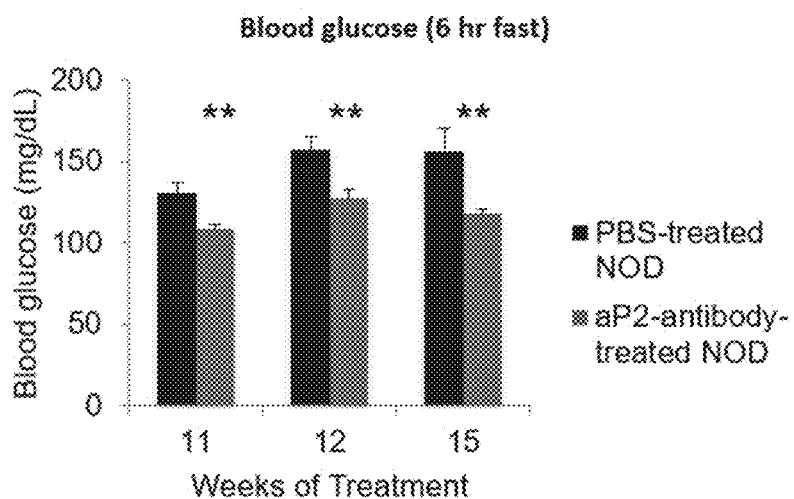
FIG. 10B is a bar graph illustrating blood glucose level (mg/dL) in PBS-treated or aP2-antibody treated NOD mice following a 6 hr fast.
Figure 10C:
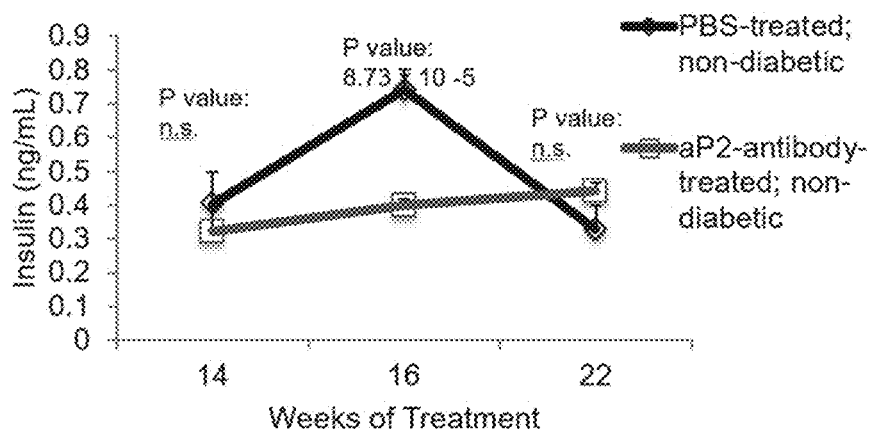
FIG. 10C is a line graph illustrating insulin level (ng/mL) in PBS-treated or aP2-antibody treated NOD mice following a 6 hr fast.

As seen in FIG. 9, treatment of NOD mice with anti-aP2 monoclonal antibody (CA33) was protective against the development of hyperglycemia. As a result, treatment with CA33 also reduced the mortality rate of NOD mice in this experiment (FIG. 10A). Furthermore, treatment of NOD mice with anti-aP2 antibody from 10 weeks of age for 22 weeks (until 32 weeks of age) reduced fasting glycemia (6 hr fast) at 11, 12, and 15 weeks of treatment (FIG. 10B) and reduced fasting insulin levels (6 hr fast) at 16 weeks of treatment (FIG. 10C), as compared to vehicle-treated NOD mice.

aP2 Deficiency Results in Improved Glucose Tolerance in NOD Mice Due to Enhanced Insulin Secretion and Expanded Beta-Cell Mass It has previously been reported that blocking aP2 function via genetic deletion, small molecule inhibition or antibody-mediated neutralization is protective in mouse models of obesity-induced glucose intolerance (Hotamisligil et al, 2006; Uysal et al., 1996; Furuhashi et al., 2007; Cao et al., 2013; Burak et al., 2015). aP2 deletion was explored to see if it would similarly confer improvements in glucose homeostasis in lean NOD mice. Indeed. NOD aP2$^{-/-}$ mice displayed significantly improved glucose tolerance compared to aP2$^{+/+}$ controls both at weaning (data not shown) and at 7-8 weeks of age (FIG. 11A). Notably, this effect on glucose homeostasis was lost by the time mice reached 11 weeks of age, in line with the predicted onset of insulitis in this model.

In the setting of obesity, blocking aP2 is associated with improved insulin sensitivity. However, altered insulin sensitivity in lean NOD aP2$^{-/-}$ mice compared to controls was not observed (FIG. 11B). This raised the possibility that improved glucose tolerance in NOD aP2$^{-/-}$ mice was related to a beta-cell intrinsic effect of aP2 deficiency. To evaluate the effect of aP2 genetic deletion on beta cell function, islets were isolated from NOD aP2$^{+/+}$ and NOD aP2$^{-/-}$ mice at 4, 7, and 12 weeks of age. At baseline, genotype was not associated with differences in insulin secretion. However, upon stimulation with high glucose, aP2$^{-/-}$ islets secreted significantly more insulin per cell than aP2$^{+/+}$ controls (FIG. 12A). Interestingly, this enhanced insulin secretion began to decline with age (FIG. 12B and FIG. 12C), and significant insulin secretion differences in islets isolated from 19 week old mice was not observed (data not shown). This is in line with the finding of a transient improvement in glucose tolerance in young NOD aP2$^{-/-}$ mice, and suggests that before the onset of insulitis, enhanced beta cell responsiveness at least in part underlies the glucose homeostasis phenotype in NOD aP2$^{-/-}$ mice.

Figure 13:
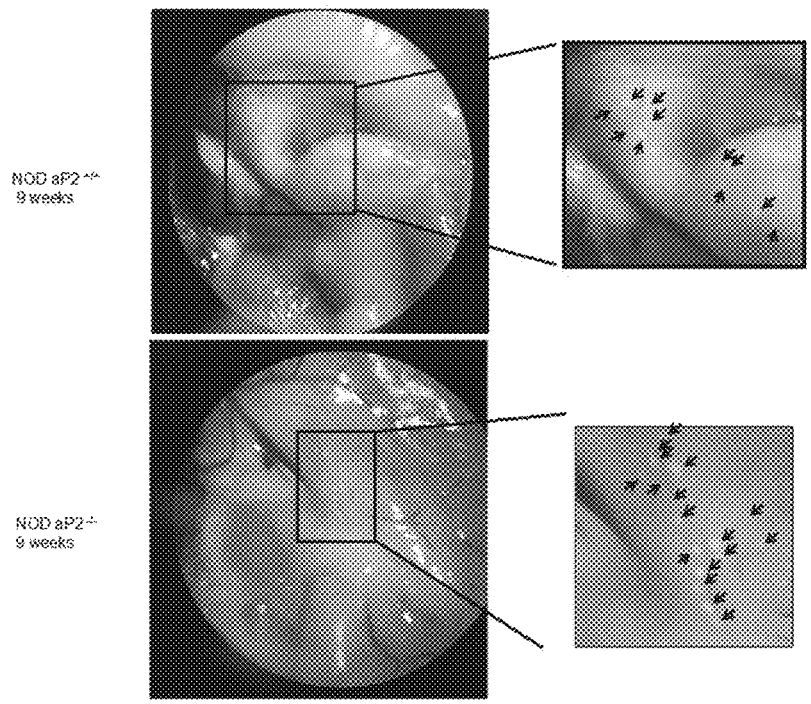
Figure 14A:
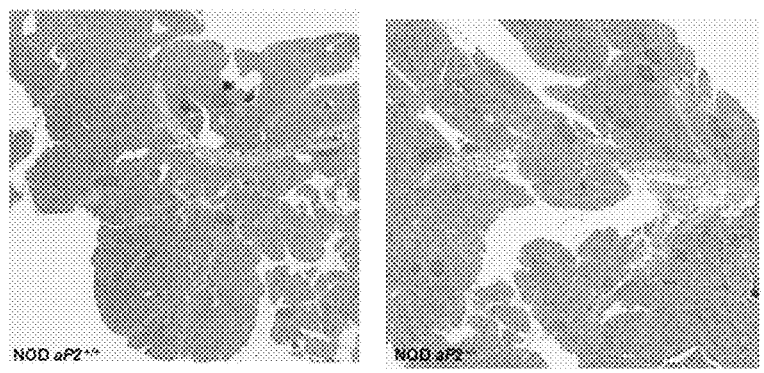
FIGS. 14A and 14B: illustrates stained beta cells (FIG. 14A), which were subsequently quantified (FIG. 14B) in NOD aP2$^{+/+}$ and NOD aP2$^{-/-}$ mice.
Figure 14B:
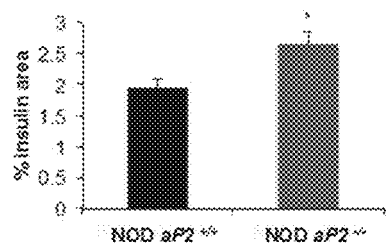

Improved glucose control observed in the setting of aP2 deficiency was also related to changes in beta cell mass. Remarkably, during pancreatic dissection more islets were visible in NOD aP2$^{-/-}$ mice than in aP2$^{+/+}$ controls (FIG. 13). This observation was further validated by quantifying beta-cell mass in NOD aP2$^{-/-}$ mice and controls. In 7-week old animals, aP2 deficiency was associated with a significant (~35%) increase in beta-cell mass (FIGS. 14A and 14B).

Hormonal aP2 Amplifies Glucose-Stimulated Insulin Secretion

Figure 15A:
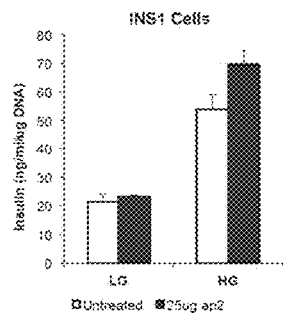
FIGS. 15A-15C: illustrates bar graphs showing glucose-stimulated insulin (ng/ml/ug DNA) secretion from either a rat insulinoma beta cell line (INS1) (FIG. 15A), aP2-deficient c57b/6 mice (Mouse Islets) (FIG. 15B), or human islets (FIG. 15C) after stimulation with either low or high glucose.
Figure 15B:
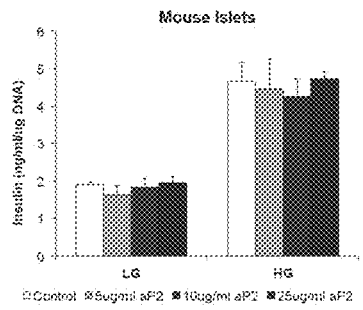
Figure 15C:
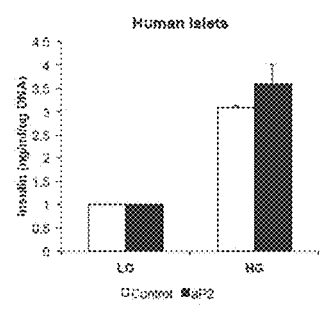
Figure 15D:
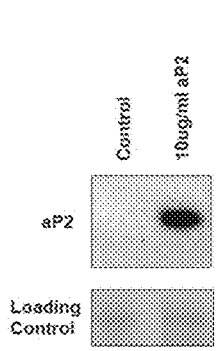
FIG. 15D illustrates that aP2 is taken up into mouse islets after 20 minutes of treatment with 10 ug/ml aP2 (n=5).
Figure 15E:
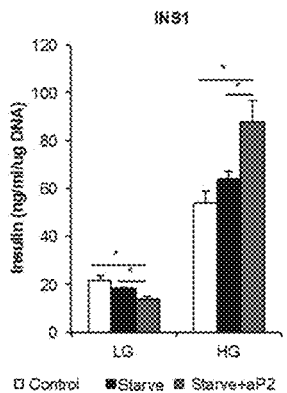
FIGS. 15E and 15F: bar graphs showing insulin (ng/ml/ug DNA) secretion following aP2 treatment for 24 hrs under "fasting" conditions from either INS1 beta cells (FIG. 15E) or primary islets isolated from aP2$^{-/-}$ mice (FIG. 15F) after stimulation with either low or high glucose.
Figure 15F:
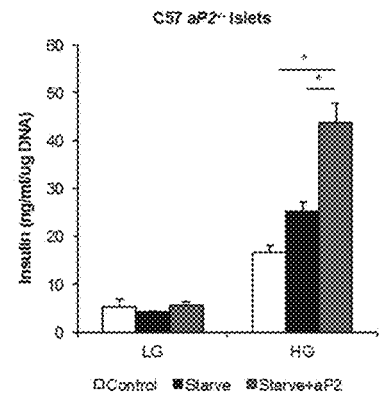

Given the recent discovery that aP2 is an actively secreted hormone and the finding that antibody-mediated aP2 neutralization is protective in models of Type 1 Diabetes, the circulating form of aP2 was further explored to try and understand whether this molecule acts directly on beta cells to regulate their function, survival, or proliferation. While addition of aP2 to primary islets under control, nutrient-abundant conditions had no effect on glucose-stimulated insulin secretion (GSIS) (FIG. 15A, FIG. 15B, and FIG. 15C), under starvation conditions (i.e., conditions where FOXO1 is activated), addition of aP2 acts to potentiate GSIS (FIG. 15E and FIG. 15F). A Western blot was run to confirm that aP2 is in fact taken up into mouse islets after 20 minutes of treatment with 10 ug/ml aP2 (FIG. 15D). This potentiation of glucose-responsive insulin secretion following prolonged starvation may be associated with increased stress-resistance in response to nutrient depletion. While this may be acutely beneficial, chronic activation of FOXO1 has been shown to be deleterious to beta cell function, resulting in loss of insulin expression, impaired GSIS, beta cell dedifferentiation, and increased susceptibility to apoptosis due to loss of PDX1 activity. Thus in the context of T1D, chronic activation of beta cell FOXO1 may increase susceptibility to immune destruction and accelerate diseases development.

Monoclonal Antibody Targeting aP2 (CA33) is Effective in Reducing the Incidence of Diabetes in the RIP-LCMV-GP Mouse Model of Type 1 Diabetes Neutralization of secreted aP2 provided beneficial effects in Type 1 diabetes, also referred to as juvenile diabetes. Monoclonal antibody targeting of aP2 with CA33 was effective in reducing the incidence of diabetes in an art-recognized rat insulin promoter-lymphocytic choriomeningitis virus-glycoprotein (RIP-LCMV-GP) model of type 1 diabetes.

Figure 16:
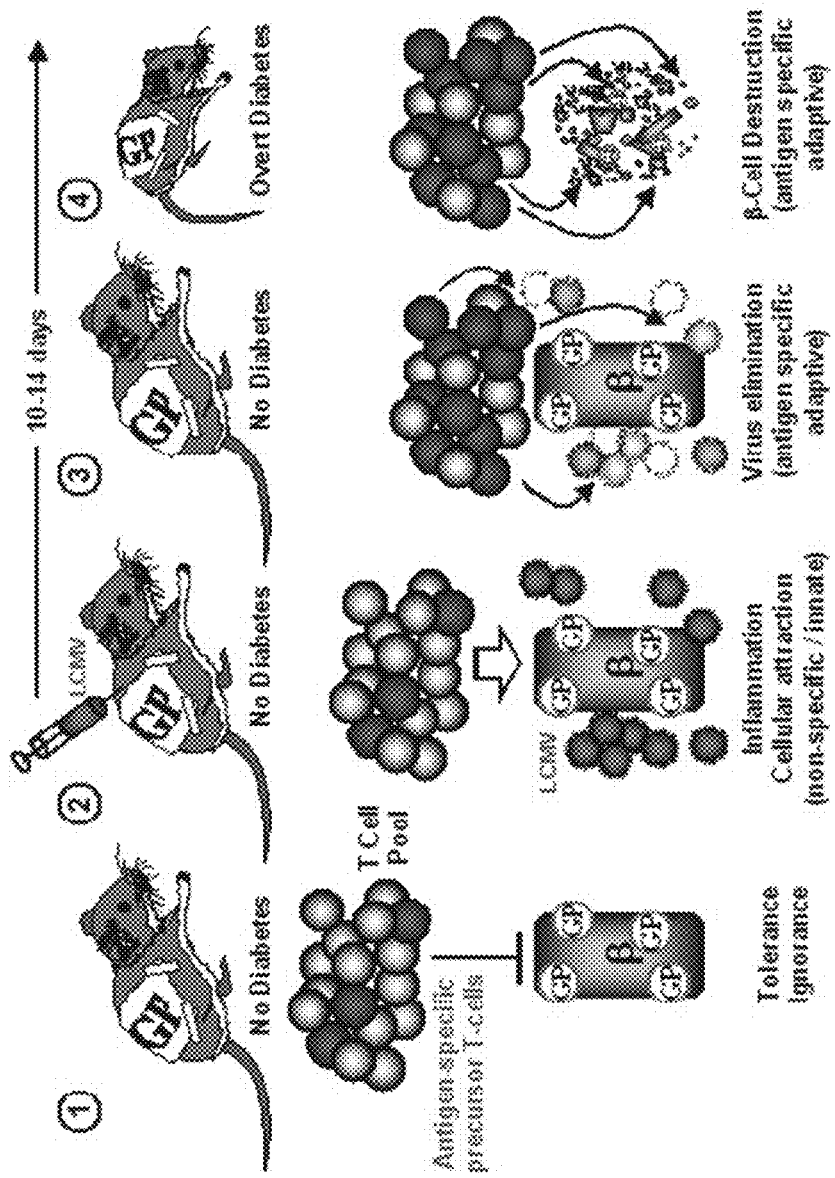

The RIP-LCMV-GP mouse model of type 1 diabetes is characterized by high penetrance and rapid onset of diabetes due to virally mediated β-cell destruction (FIG. 16) (Oldstone et al., (1991) Cell 65:319-331). The RIP-LCMV-GP mice were a gift from K. Bornfeldt's laboratory at Washington University in Seattle. The genetic backgrounds of all intercrossed mouse models were verified by congenic genotyping (288 loci for C57BL/6) with an ABI 3130 analyzer. In the RIP-LCMV-GP model, diabetes was induced with the administration of LCMV ($2 \times 10^3$ PFU/ml). Animal care and experimental procedures were performed with approval from animal care committees of Harvard University.

Figure 17:
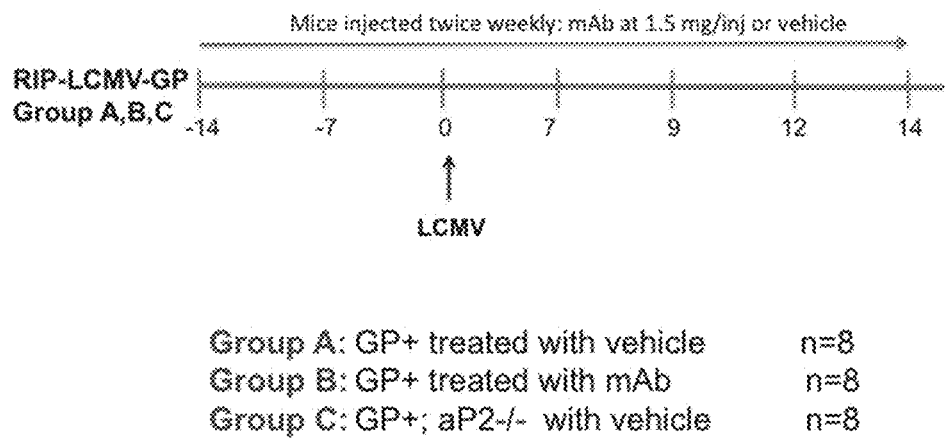
FIG. 17 is a schematic showing an aP2-antibody administration schedule in a Type 1 diabetes-induced mouse model (RIP-LCMV-GP mice) in a group of aP2−/− (Group C) and aP2-normal mice injected twice weekly with either 33 mg/kg of CA33 (Group B) or PBS control (Group A) and fed a normal chow diet.

The experiment was performed on three groups of mice (FIG. 17). Group A consisted of 8 RIP-LCMV-GP (GP+) mice that were injected intraperitoneally with vehicle (PBS) twice weekly starting at Day −14. Group B consisted of 8 RIP-LCMV-GP (GP+) mice that were injected intraperitoneally with CA33 at a dose of 1.5 mg/injection twice weekly starting at Day −14. Group C consisted of 8 RIP-LCMV-GP (GP+), aP2−/− mice that were injected intraperitoneally with vehicle twice weekly starting at Day −14. At Day 0, diabetes was induced with the administration of LCMV ($2 \times 10^3$ PFU/ml). Treatment with vehicle or CA33 was continued for two weeks after administration of LCMV (FIG. 17).

Figure 18:
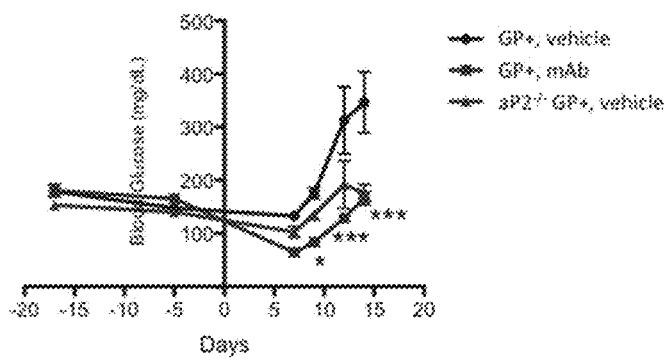
FIG. 18 is a line graph showing 6-hour fasting blood glucose measurements (mg/dl) vs. time (days) in a Type 1 diabetes-induced mouse model (RIP-LCMV-GP mice) in a group of aP2−/− (triangles) and aP2-normal mice injected twice weekly with either 33 mg/kg of CA33 (squares) or control (PBS) (circles) and fed a normal chow diet. CA33 treated and aP2 deficient animals had significantly lower fasting blood glucose after LCMV administration compared to vehicle treated animals. * p<0.05,  p<0.01, * p<0.005.
Figure 19:
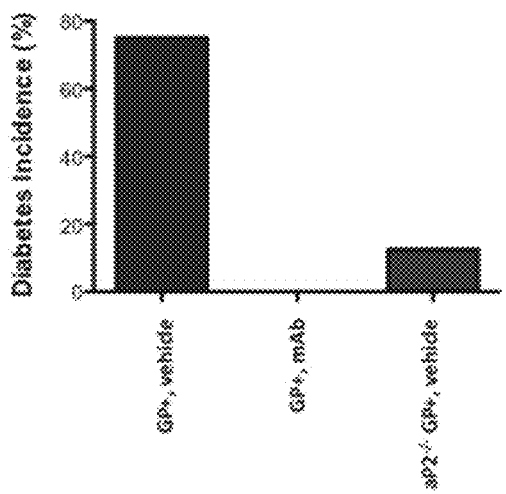
FIG. 19 is a bar graph showing incidence of Type 1 diabetes in a Type 1 diabetes-induced mouse model (RIP-LCMV-GP mice) in a group of aP2−/− (triangles) and aP2-normal mice injected twice weekly with either 33 mg/kg of CA33 (squares) or control (PBS) (circles) and fed a high fat diet. Diabetes was defined as a 6-hour fasting blood glucose measurement greater than 250 mg/dl. CA33 treatment provided protection against development of type 1 diabetes in the RIP-LCMV-GP model similar to that observed in aP2 genetically deficient animals.

Six-hour fasted blood glucose levels were measured periodically, and the onset of diabetes was defined as a 6-hour fasting blood glucose above 250 mg/dL. GP+ vehicle-treated animals showed a significant rise in fasting blood glucose levels (FIG. 18) and a greater than 75% incidence of diabetes within 14 days from LCMV treatment (FIG. 19). GP+, aP2−/− mice showed overall, significantly lower blood glucose levels than GP+ vehicle treated mice after LCMV treatment (FIG. 18). GP+, aP2−/− mice also experienced a much lower incidence of diabetes than the GP+ vehicle treated mice, 15% vs. 75% incidence (FIG. 19). Monoclonal antibody treated GP+ mice showed significantly lower blood glucose levels than the vehicle treated control mice (FIG. 18) and incidence of diabetic phenotype was not observed in the monoclonal antibody treated group (FIG. 19).

These results demonstrate that reduction in aP2 levels either through genetic deficiency or by monoclonal antibody neutralization has a strong anti-diabetic effect in this virally induced model of Type 1 diabetes.

Monoclonal Antibody Targeting aP2 (CA33) is Effective in Reducing Inflammation in the RIP-LCMV-GP Mouse Model of Type 1 Diabetes The RIP-LCMV-GP mouse model of type 1 diabetes is described above. Inflammation was examined by determining insulitis levels in three groups of mice. Group A consisted of 8 RIP-LCMV-GP (GP+) mice that were injected intraperitoneally with vehicle (PBS) twice weekly starting at Day −14. Group B consisted of 8 RIP-LCMV-GP (GP+) mice that were injected intraperitoneally with CA33 at a dose of 1.5 mg/injection twice weekly starting at Day −14. Group C consisted of 8 RIP-LCMV-GP (GP+), aP2−/− mice that were injected intraperitoneally with vehicle twice weekly starting at Day −14. At Day 0, diabetes was induced with the administration of LCMV ($2 \times 10^3$ PFU/ml). Treatment with vehicle or CA33 continued for two weeks after administration of LCMV.

Insulitis scoring was performed on hematoxylin and eosin (H&E) stained pancreatic sections. Each islet is scored as either "non-insulitis," "peri-insulitis," "mild insulitis" or "severe insulitis." The bar graph represents the percentage of each islet type in each animal analyzed (FIG. 20A).

For antibody staining, pancreata from RIP-LCMV-GP mice were formalin-fixed and paraffin-embedded. Then, 5-μm serial sections of the pancreata were generated, and staining was performed with antibodies against insulin (Linco), ATF6 (Santa Cruz Biotechnology); phospho-eIF2α (Biosource): sXBP1 (in house) and Alexa Fluor 488 and Alexa Fluor 568 (Invitrogen) according to established protocols.

After staining, image analysis was performed by using custom software developed in MATLAB (The MathWorks Inc.). Briefly, islet regions were identified as contiguous areas (connected pixels) of insulin staining (green channel) at or above a threshold intensity value optimized across multiple images. Mean fluorescence intensity for insulin (green channel) and for either sXBP1 or ATF6 (red channel) was calculated as the sum of intensities for all pixels divided by the number of pixels within the islet.

Figure 20A:
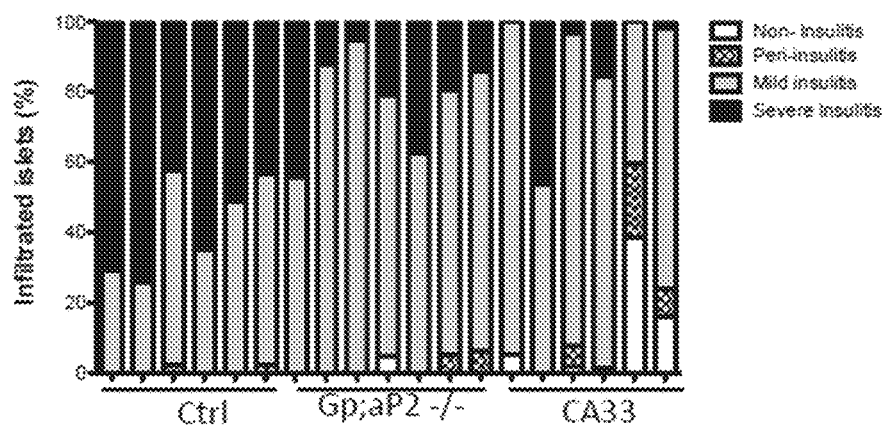
FIG. 20A is a bar graph showing islet infiltration (%; non-insulitis (open bars); peri-insulitis (checkered bars); mild insulitis (gray bars); severe insulitis (black bars)) in GP+ control mice, GP+ aP2−/− mice, or GP+ mice treated with CA33, 14 days after injection with LCMV. Mice were treated with 1.5 mg CA33 or vehicle by injection twice weekly, starting 14 days prior to LCMV infection. Insulitis scoring was performed on H&E stained pancreatic sections. Each islet was scored as either "non-insulitis," "peri-insulitis," "mild insulitis" or "severe insulitis." The bar graph represents the percentage of each islet type in each animal analyzed.
Figure 20B:
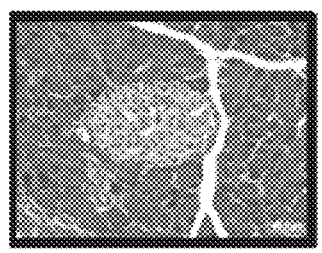
FIG. 20B is a representative picture of an islet showing little to no insulitis.
Figure 20C:
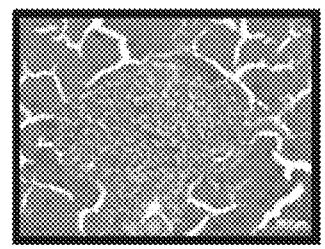
FIG. 20C is a representative picture of an islet showing severe insulitis.
Figure 20D:
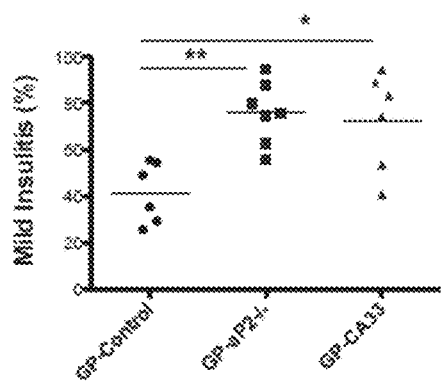
FIG. 20D is a bar graph showing islets with mild insulitis (%) in GP+ control mice, GP+aP2−/− mice, or GP+ mice treated with CA33, 14 days after injection with LCMV. Mice were treated with 1.5 mg CA33 or vehicle by injection twice weekly, starting 14 days prior to LCMV infection. * p<0.05; ** p<0.01.
Figure 20E:
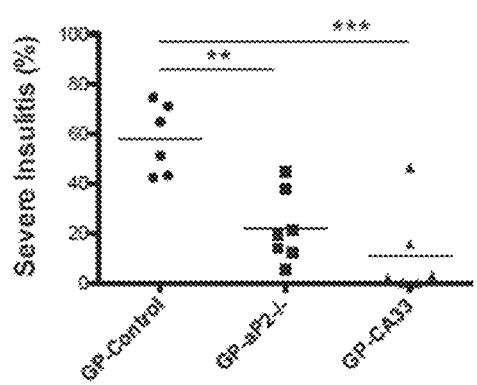
FIG. 20E is a bar graph showing islets with severe insulitis (%) in GP+ control mice, GP+ aP2−/− mice, or GP+ mice treated with CA33, 14 days after injection with LCMV. Mice were treated with 1.5 mg CA33 or vehicle by injection twice weekly, starting 14 days prior to LCMV infection.  p<0.01; * p<0.005.

As shown in FIG. 20A, GP+ vehicle-treated animals showed high levels inflammation with most islets showing either mild or severe insulitis. GP+, aP2−/− mice showed decreased levels of inflammation with most islets showing mild insulitis (FIGS. 20A and 20D). Monoclonal antibody (CA33) treated GP+ mice also showed decreased levels of inflammation with decreased numbers of islets showing severe insulitis (FIGS. 20A and 20E).

Figure 21A:
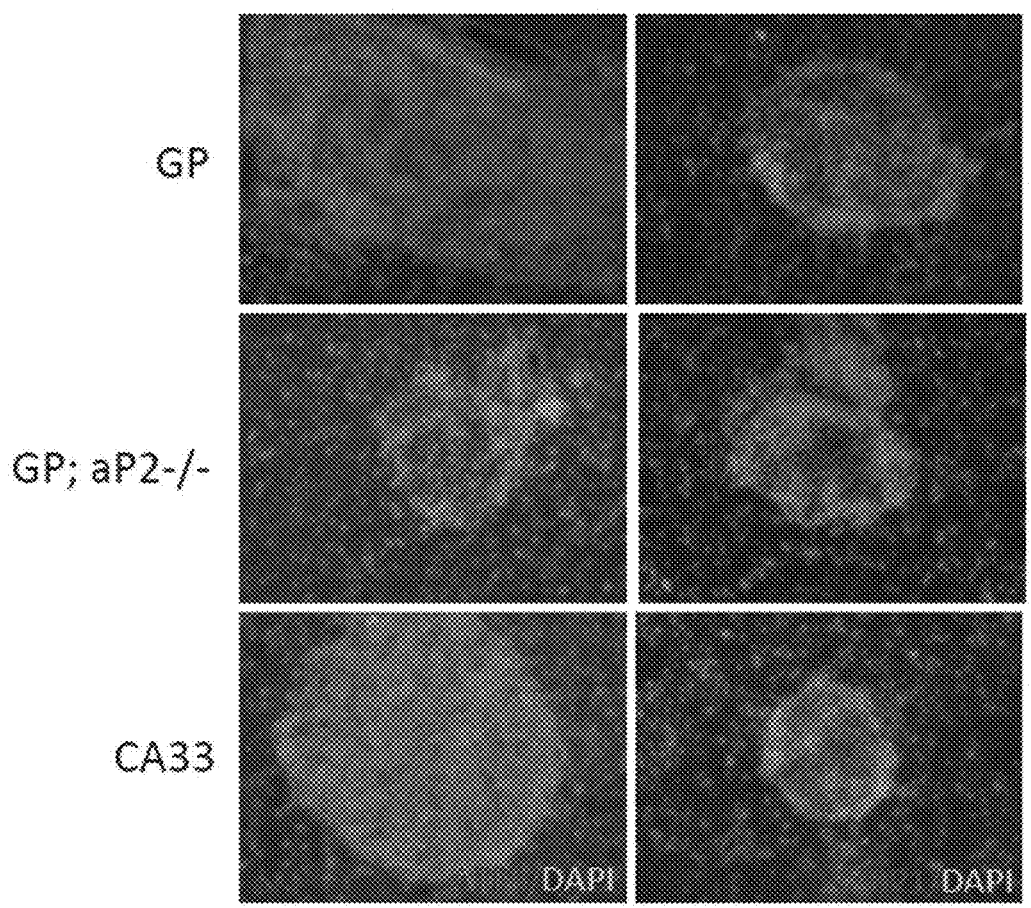
FIG. 21A is a series of representative images of islets stained for ATF6 (left column) or XBP1 (right column) in GP+ control mice, GP+ aP2−/− mice, or GP+ mice treated with CA33, 14 days after injection with LCMV. Mice were treated with 1.5 mg CA33 or vehicle by injection twice weekly, starting 14 days prior to LCMV infection.
Figure 21B:
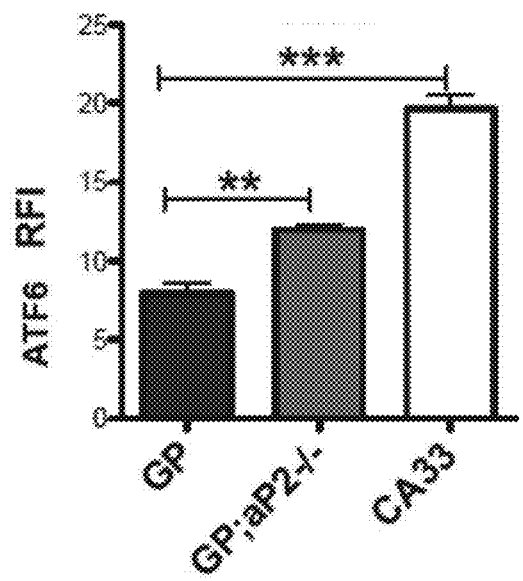
FIG. 21B is a bar graph showing ATF6 levels (relative fluorescence intensity, RFI) in pancreatic samples from GP+ control mice, GP+ aP2−/− mice, or GP+ mice treated with CA33, 14 days after injection with LCMV. Mice were treated with 1.5 mg CA33 or vehicle by injection twice weekly, starting 14 days prior to LCMV infection.  p<0.01; * p<0.005.
Figure 21C:
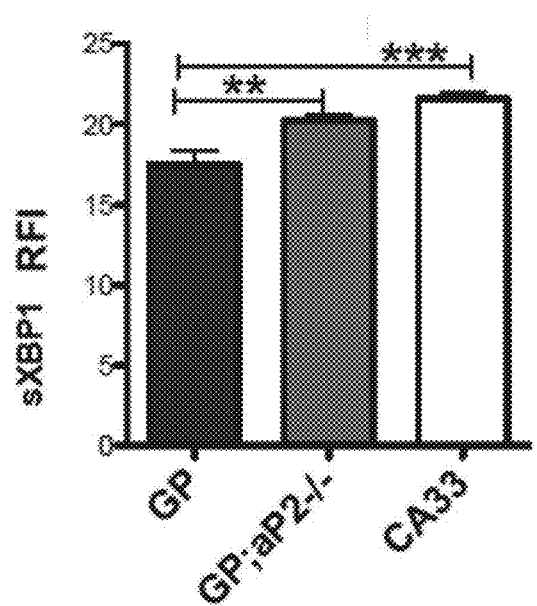
FIG. 21C is a bar graph showing sXBP1 levels (relative fluorescence intensity, RFI) in pancreatic samples from GP+ control mice, GP+ aP2−/− mice, or GP+ mice treated with CA33, 14 days after injection with LCMV. Mice were treated with 1.5 mg CA33 or vehicle by injection twice weekly, starting 14 days prior to LCMV infection.  p<0.01; * p<0.005.

As shown in the images in FIG. 21A, islet morphology and endoplasmic reticulum (ER) adaptive capacity was preserved in aP2 deficient and CA33-treated RIP-LCMV-GP mice, as shown by the increased levels of ATF6 and sXBP1 staining. ATF6 levels were significantly increased in both the GP+, aP2−/− mice and the monoclonal antibody (CA33) treated GP+ mice (FIG. 21B). In addition, sXBP1 levels were also significantly increased in both the GP+, aP2−/− mice and the monoclonal antibody (CA33) treated GP+ mice (FIG. 21C).

These results demonstrate that reduction in aP2 activity levels either through genetic deficiency or by monoclonal antibody neutralization reduces inflammation and preserves islet morphology in this virally induced model of Type 1 diabetes.

Example 3: Anti-aP2 Monoclonal Antibody for the Treatment, Reduction or Prevention of Atherosclerosis Animals Animal care and experimental procedures were performed with approval from animal care committees of Harvard University. Male ApoE−/− mice in the C57BL/6J background (Jackson Laboratory) were kept on a 12-h light cycle and were fed a high-cholesterol atherogenic western diet (D12079B: 21% fat, 0.21% cholesterol; Research Diets) ad libitum, beginning at 4-5 weeks of age. The mice were treated by subcutaneous administration of vehicle or antibody (33 mg/kg) for 12 weeks starting at 6-weeks of age.

Assessment of Atherosclerotic Lesions

Mice were sacrificed and flushed with saline and then 10% neutral buffered formalin solution by injection through the left ventricle. The aorta was dissected from the proximal aorta to the iliac bifurcation, and the aortae were pinned out in an en face preparation. En face pinned-out aortas were stained with Sudan IV.

Quantitation of lesion areas was achieved using ImageJ software developed at the NIH. The outer perimeter of the pinned out aorta was defined in the software to establish the total area of the aorta as a white background. The percent area of the lesions stained red with Sudan IV was then measured and calculated by the software.

Figures 22A, 22B:
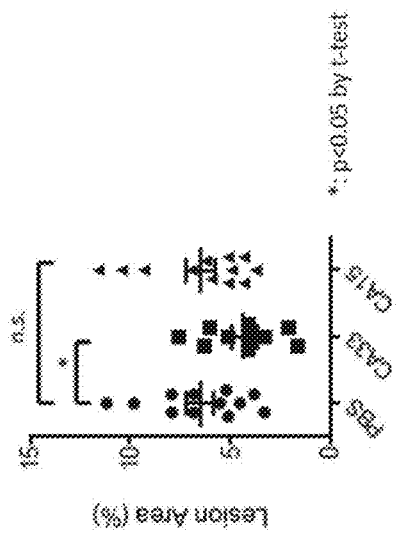
FIG. 22A is table providing the antibody dose (μg) and injection volume (μl) calculations to achieve a 33 mg/kg dosage based on average body weight of the ApoE knockout mice (atherosclerosis mouse model) at the indicated time points (weeks).
FIG. 22B is a graph showing atherosclerotic lesion area (%) in ApoE knockout mice treated with PBS (circles), CA33 (squares), or CA15 (triangles). Aortas from sacrificed ApoE knockout mice were dissected from the proximal aorta to the iliac bifurcation, and the aortae were pinned out in an en face preparation. En face pinned-out aortas were stained with Sudan IV. Quantitation of lesion areas was achieved using ImageJ software developed at the NIH. The outer perimeter of the pinned out aorta was defined in the software to establish the total area of the aorta as a white background. The percent area of the lesions stained red with Sudan IV was then measured and calculated by the software. * p<0.05.
Figure 22F:
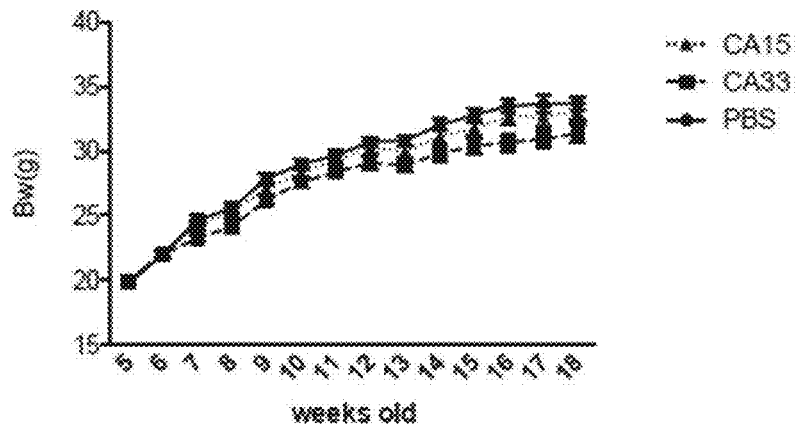
FIG. 22F is a line graph showing average body weight (g) of ApoE knockout mice vs. age (weeks old) in mice treated for twelve weeks with PBS (circles), CA33 (squares), or CA15 (triangles). ApoE knockout mice were fed western diet and treated with vehicle or antibody (33 mg/kg) for twelve weeks.

As shown in FIG. 22B, ApoE knockout mice treated with CA33 had decreased atherosclerotic lesion area. In contrast, ApoE knockout mice treated with CA15 showed no significant difference in atherosclerotic lesion area compared to controls. Representative images of en face pinned aortas from an ApoE knockout mice are shown in FIG. 22C (vehicle-treated mice), FIG. 22D (CA33-treated mice), and FIG. 22E (CA15-treated mice).

Figure 22G:
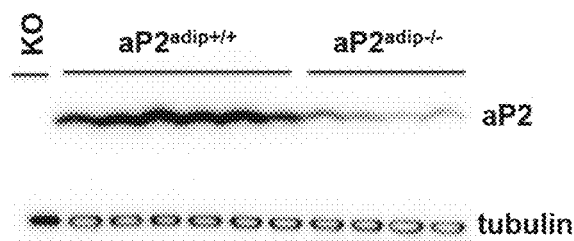
FIG. 22G illustrates aP2 protein expression in adipose tissue of aP2$^{adip-/-}$ mice.
Figure 22H:
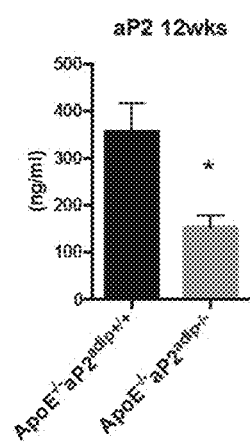
FIGS. 22H-22J: are bar graphs showing the level of aP2 (ng/ml) (FIG. 22H), triglyceride (mg/dl) (FIG. 22I), and cholesterol (mg/dl) (FIG. 22J) in ApoE$^{-/-}$aP2$^{adip+/+}$ and ApoE$^{-/-}$aP2$^{adip-/-}$ mice after 12 weeks of western diet.
Figure 22I:
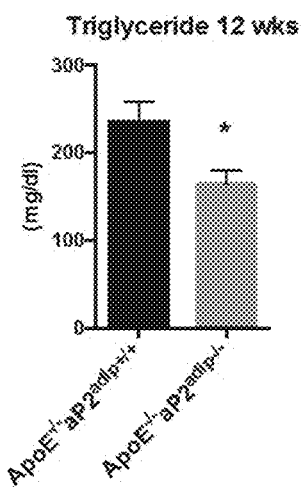
Figure 22J:
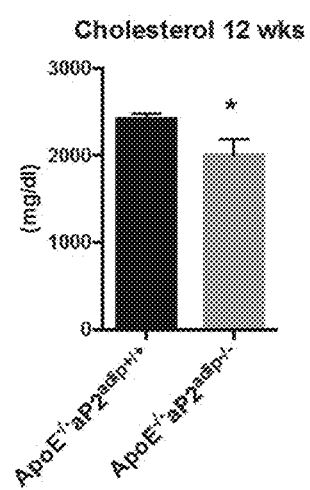
Figure 22K:
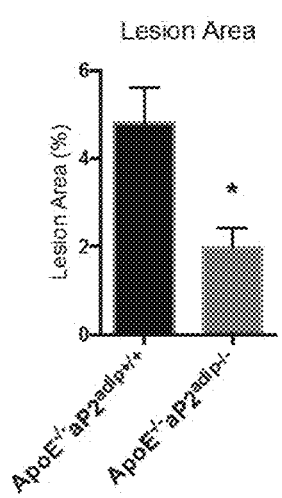
FIG. 22K is a bar graph showing the atherosclerotic lesion area in ApoE$^{-/-}$aP2$^{adip+/+}$ and ApoE$^{-/-}$aP2$^{adip-/-}$ mice.
Figure 22L:
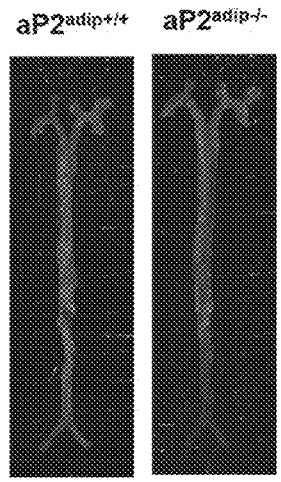
FIG. 22L is a representative image of an en face pinned aorta from ApoE$^{-/-}$aP2$^{adip+/+}$ and ApoE$^{-/-}$aP2$^{adip-/-}$ mice fed western diet for 12 weeks.

The deletion efficiency of mice that aP2 is specifically knocked out with the lox-P system in adipose tissue (aP2$^{adip-/-}$ mice) was analyzed by western blot (FIG. 22G). aP2$^{adip-/-}$ mice were crossed to ApoE$^{-/-}$ mice to generate ApoE$^{-/-}$aP2$^{adip-/-}$ mice. ApoE$^{-/-}$aP2$^{adip+/+}$ and ApoE$^{-/-}$aP2$^{adip-/-}$ mice fed western diet for 12 weeks were analyzed for serum aP2, TG, and cholesterol levels (FIG. 22H, FIG. 22I, and FIG. 22J). As shown in FIG. 22I and FIG. 22J, ApoE$^{-/-}$aP2$^{adip-/-}$ mice had lower triglyceride and cholesterol levels compared to ApoE$^{-/-}$aP2$^{adip+/+}$ mice. After sacrifice of these mice, atherosclerotic lesion area was analyzed by Sudan IV staining of en face aorta from these mice (FIG. 22K and FIG. 22L). As shown in FIG. 22K, ApoE$^{-/-}$aP2$^{adip-/-}$ mice had decreased atherosclerotic lesion area compared to ApoE$^{-/-}$aP2$_{adip+/+}$ mice. Overall, these results show that adipose tissue derived aP2 regulates dyslipidemia and atherosclerosis development in ApoE$^{-/-}$ mice.

Body Weight and Liver Weight

ApoE knockout mice were fed on western diet beginning at 4-5 weeks of age until mice were 18 weeks old. The mice were treated by subcutaneous administration of vehicle or antibody (33 mg/kg) for 12 weeks starting at 6-weeks of age. Body weight, lean mass, and fat mass were measured by dual X-ray absorbance (DXA) spectroscopy.

Figure 23A:
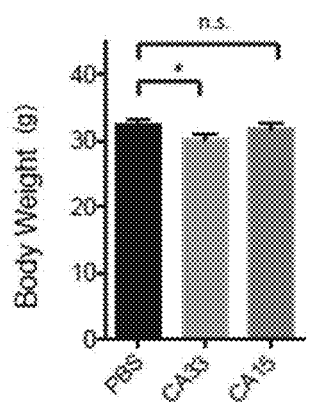
FIG. 23A is a bar graph showing average body weight (g) of ApoE knockout mice treated for twelve weeks with PBS (black bar), CA33 (light gray bar), or CA15 (gray bar). ApoE knockout mice were fed western diet and treated with vehicle or antibody (33 mg/kg) for twelve weeks. CA33-treated mice show a statistically significant lower average body weight than vehicle treated mice. * $p<0.05$.
Figure 23B:
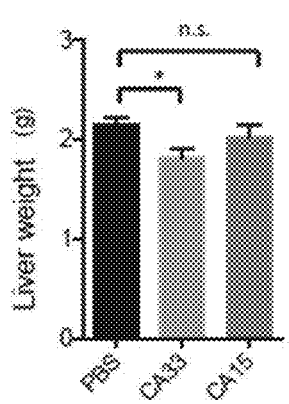
FIG. 23B is a bar graph showing liver weight (g) of ApoE knockout mice treated for twelve weeks with PBS (black bar), CA33 (light gray bar), or CA15 (gray bar). ApoE knockout mice were fed western diet and treated with vehicle or antibody (33 mg/kg) for twelve weeks. CA33 treated mice show a statistically significant lower average liver weight than vehicle treated mice. * $p<0.05$.
Figure 23C:
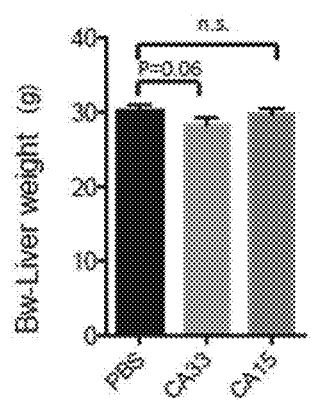
FIG. 23C is a bar graph showing body weight minus liver weight (g) of ApoE knockout mice treated for twelve weeks with PBS (black bar), CA33 (light gray bar), or CA15 (gray bar). ApoE knockout mice were fed western diet and treated with vehicle or antibody (33 mg/kg) for twelve weeks. CA33 treated mice show a lower average body weight minus liver weight than vehicle treated mice.

As shown in FIG. 23A, ApoE knockout mice treated with CA33 antibody showed a significant decrease in body weight. In addition, ApoE knockout mice treated with CA33 also showed a significant decrease in liver weight (FIG. 23B). In contrast, ApoE knockout mice treated with CA15 did not show any significant differences in body weight or liver weight (FIGS. 23A, 23B, and 23C).

Figure 23D:
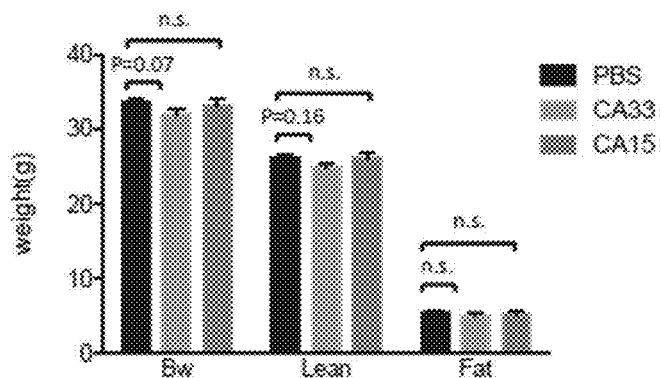
FIG. 23D is a bar graph showing average body weight, lean mass, or fat mass (g) of ApoE knockout mice treated for twelve weeks with PBS (black bar), CA33 (light gray bar), or CA15 (gray bar). ApoE knockout mice were fed western diet and treated with vehicle or antibody (33 mg/kg) for twelve weeks and body weight, lean mass, and fat mass were measured by dual X-ray absorbance (DEXA) spectroscopy.

As shown in FIG. 23D, ApoE knockout mice treated with CA33 antibody did not reveal any significant decreases in lean mass or fat mass. In addition, ApoE knockout mice treated with CA15 antibody did not show any significant differences in lean mass or fat mass (FIG. 23D).

Glucose Tolerance Test

The glucose tolerance test was performed by oral glucose administration (1.0 g/kg) on conscious mice after an overnight (16 h) fast. Particle size distribution of the lipoproteins was determined by fast-performance liquid chromatography (FPLC), using pooled samples of plasma after 6 or 12 weeks of vehicle or antibody treatment (33 mg/kg).

Figure 24A:
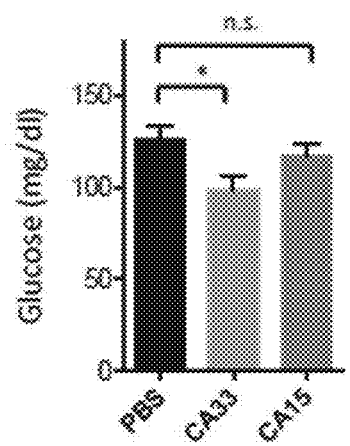
FIG. 24A is a bar graph of fasting basal glucose levels (mg/dl) prior to a glucose tolerance test in ApoE knockout mice treated with PBS (black bar), CA33 (light gray bar), or CA15 (gray bar). ApoE knockout mice were fed western diet and treated with vehicle or antibody (33 mg/kg) for twelve weeks. CA33-treated mice have statistically significant lower fasting blood glucose than vehicle treated mice. * $p<0.05$.
Figure 24B:
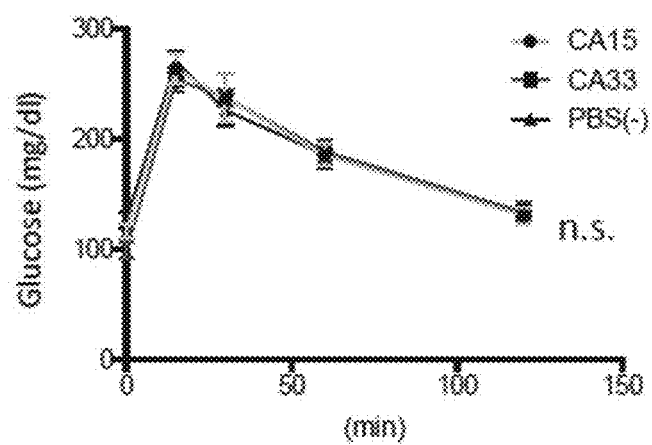
FIG. 24B is a line graph of glucose levels (mg/dl) vs. time (minutes) during a glucose tolerance test in ApoE knockout mice treated with PBS (triangles), CA33 (squares), or CA15 (circles). ApoE knockout mice were fed western diet and treated with vehicle or antibody (33 mg/kg) for twelve weeks. The glucose tolerance test was performed by oral glucose administration (1.0 g/kg) on conscious mice after an overnight (16 h) fast.

As shown in FIG. 24A, CA33 treated mice have a statistically significant lower fasting blood glucose than vehicle treated mice. However, CA33 treated mice did not show any difference in response to glucose in the glucose tolerance test (GTT) (FIG. 24B).

Measurement of Cholesterol and Triglycerides in Lipoprotein Fractions

Cholesterol and triglycerides were measured in lipoprotein fractions (total lipoprotein, very low-density lipoprotein (VLDL), low-density lipoprotein (LDL), or high-density lipoprotein (HDL)) in ApoE knockout mice treated with PBS, CA33 (33 mg/kg), or CA15 (33 mg/kg) for six weeks or twelve weeks. Particle size distribution of the lipoproteins was determined by fast-performance liquid chromatography (FPLC), using pooled samples of plasma.

Figure 25A:
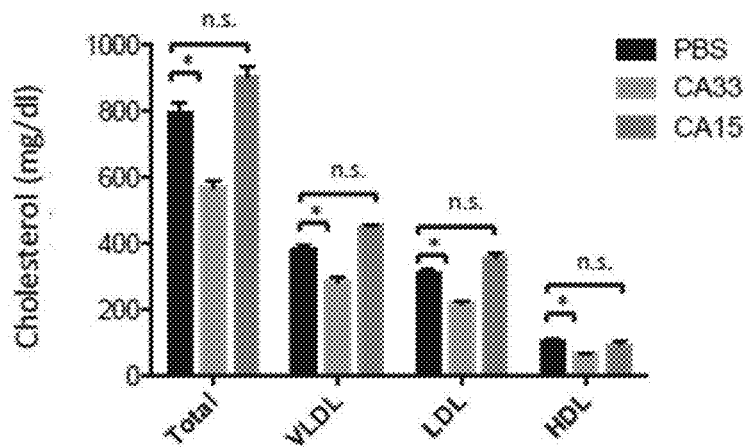
FIG. 25A is a bar graph of cholesterol in lipoprotein fractions (mg/dl) (total lipoprotein, very low-density lipoprotein (VLDL), low-density lipoprotein (LDL), or high-density lipoprotein (HDL)) in ApoE knockout mice treated with PBS (triangles), CA33 (squares), or CA15 (circles) for six weeks. Particle size distribution of the lipoproteins was determined by fast-performance liquid chromatography (FPLC), using pooled samples of plasma. * $p<0.05$.
Figure 25B:
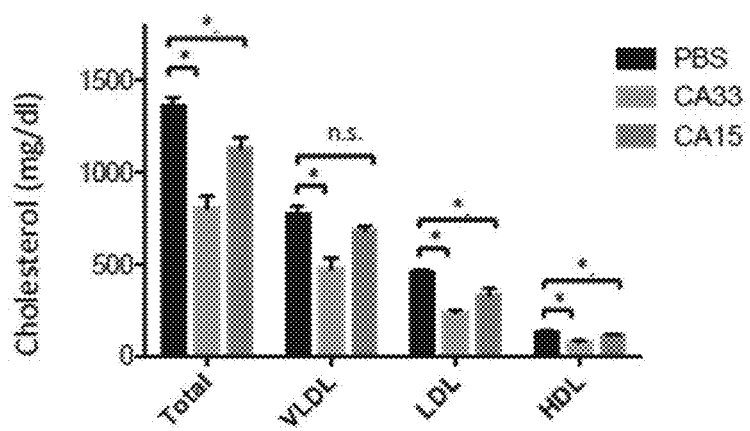
FIG. 25B is a bar graph of cholesterol in lipoprotein fractions (mg/dl) (total lipoprotein, very low-density lipoprotein (VLDL), low-density lipoprotein (LDL), or high-density lipoprotein (HDL)) in ApoE knockout mice treated with PBS (triangles), CA33 (squares), or CA15 (circles) for twelve weeks. Particle size distribution of the lipoproteins was determined by fast-performance liquid chromatography (FPLC), using pooled samples of plasma. * $p<0.05$.

As shown in FIG. 25A, ApoE knockout mice treated with CA33 for six weeks showed significant decreases in cholesterol levels in total lipoprotein, very low-density lipoprotein (VLDL), low-density lipoprotein (LDL), and high-density lipoprotein (HDL). In addition, ApoE knockout mice treated with CA33 for twelve weeks showed significant decreases in cholesterol levels in total lipoprotein, very low-density lipoprotein (VLDL), low-density lipoprotein (LDL), and high-density lipoprotein (HDL) (FIG. 25B). Treatment of ApoE knockout mice with CA15 for six weeks did not yield any significant differences in cholesterol levels (FIG. 25A), while treatment of ApoE knockout mice with CA15 for twelve weeks led to smaller decreases in cholesterol in total lipoprotein, low-density lipoprotein (LDL), and high-density lipoprotein (HDL), when compared to CA33-treated animals (FIG. 25B).

Figure 26A:
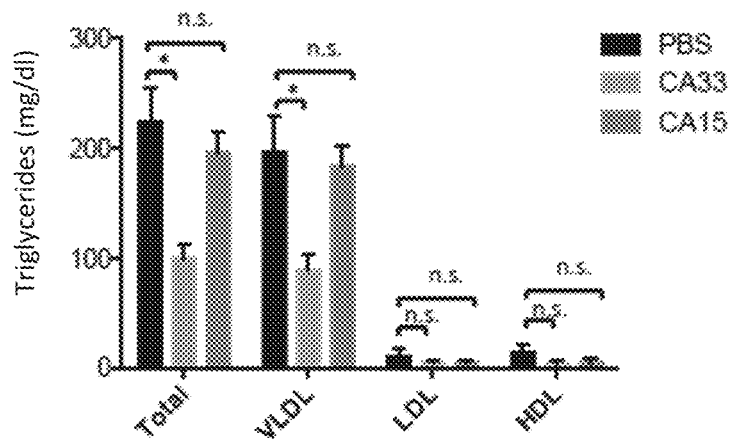
FIG. 26A is a bar graph of triglycerides in lipoprotein fractions (mg/dl) (total lipoprotein, very low-density lipoprotein (VLDL), low-density lipoprotein (LDL), or high-density lipoprotein (HDL)) in ApoE knockout mice treated with PBS (triangles), CA33 (squares), or CA15 (circles) for six weeks. Particle size distribution of the lipoproteins was determined by fast-performance liquid chromatography (FPLC), using pooled samples of plasma. * $p<0.05$.
Figure 26B:
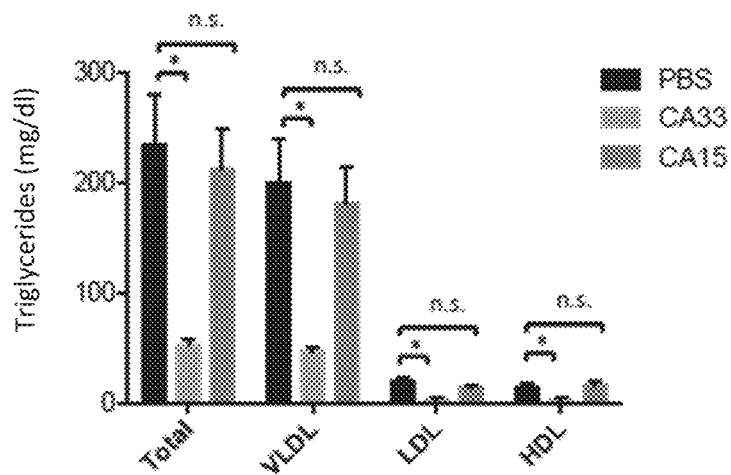
FIG. 26B is a bar graph of triglycerides in lipoprotein fractions (mg/dl) (total lipoprotein, very low-density lipoprotein (VLDL), low-density lipoprotein (LDL), or high-density lipoprotein (HDL)) in ApoE knockout mice treated with PBS (triangles), CA33 (squares), or CA15 (circles) for twelve weeks. Particle size distribution of the lipoproteins was determined by fast-performance liquid chromatography (FPLC), using pooled samples of plasma. * $p<0.05$.
Figure 29:
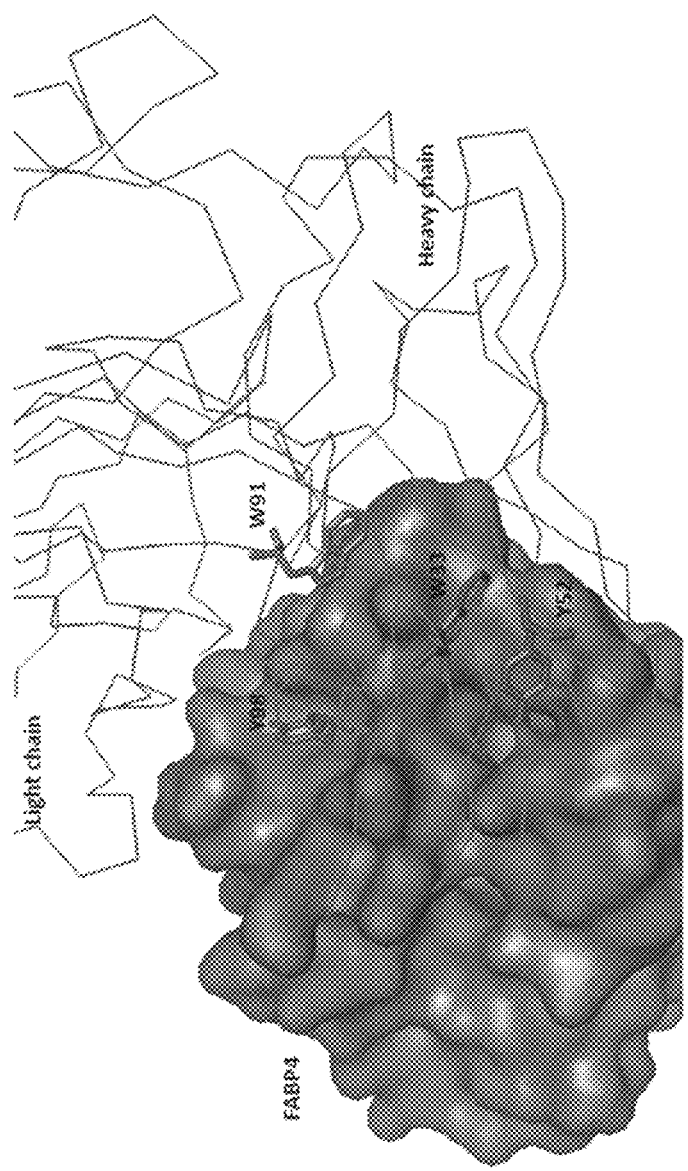

As shown in FIG. 26A, ApoE knockout mice treated with CA33 for six weeks showed significant decreases in triglyceride levels in total lipoprotein and very low-density lipoprotein (VLDL). In addition, ApoE knockout mice treated with CA33 for twelve weeks showed significant decreases in triglyceride levels in total lipoprotein, very low-density lipoprotein (VLDL), low-density lipoprotein (LDL), and high-density lipoprotein (HDL) (FIG. 26B). In contrast, treatment of ApoE knockout mice with CA15 for six weeks or twelve weeks did not yield any significant differences in triglyceride levels (FIGS. 26A and 26B), as compared to control animals treated with PBS.

Example 4: Humanization of CA33

Figures 27, 28:
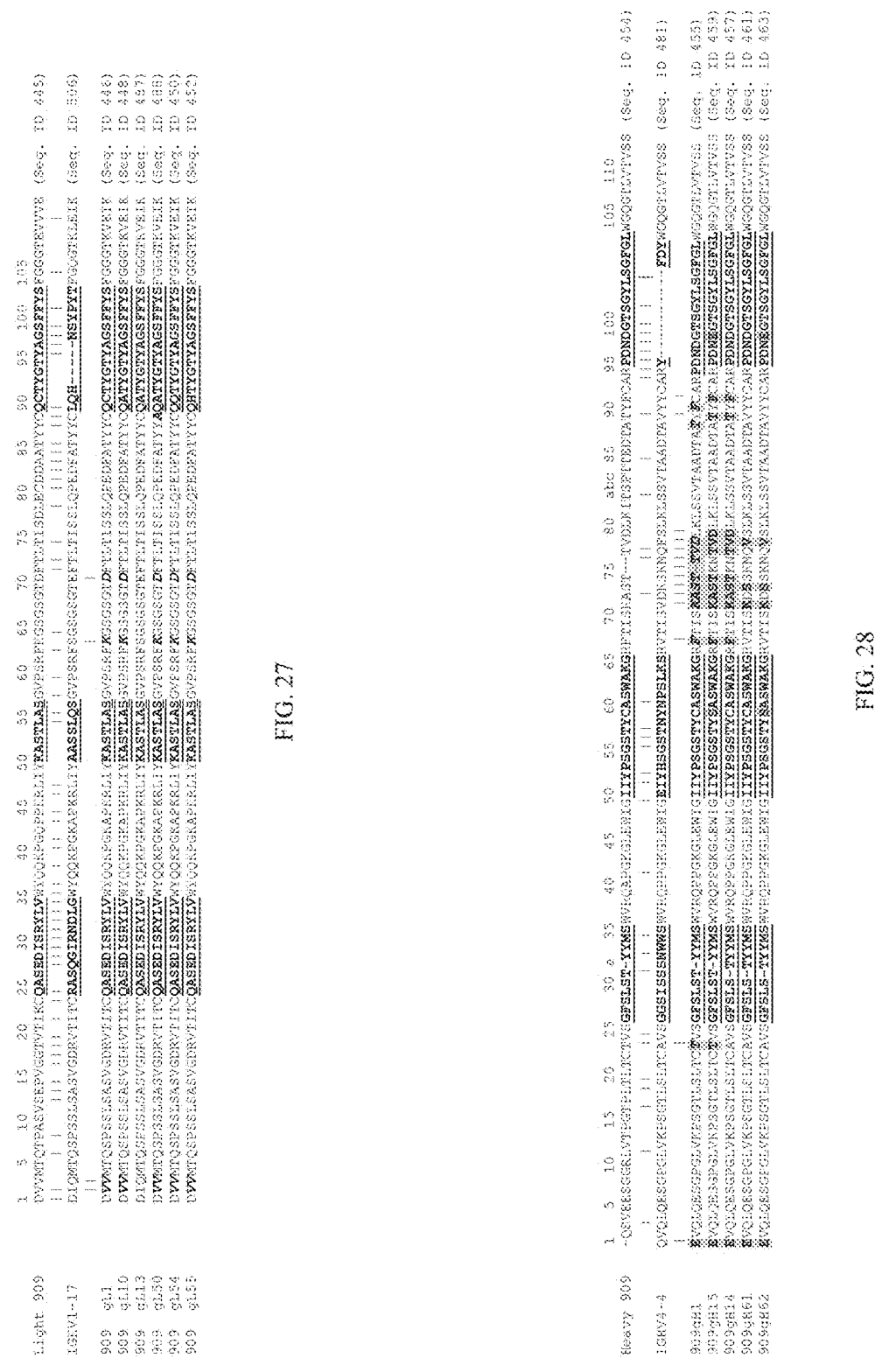

Rabbit Antibody 909 (CA33) was humanised by grafting the CDRs from the rabbit CDR/mouse framework hybrid antibody V-region CDRs onto human germline antibody V-region frameworks. In order to recover the activity of the antibody, a number of framework residues from the rabbit/mouse hybrid V-region were also retained in the humanized sequence. These residues were selected using the protocol outlined by Adair et al. (1991) (Humanised antibodies. WO91/09967). Alignments of the rabbit/mouse hybrid antibody (donor) V-region sequences with the human germline (acceptor) V-region sequences are shown in FIG. 27 (VL) and FIG. 28 (VH), together with the designed humanized sequences. The CDRs grafted from the donor to the acceptor sequence are as defined by Kabat (Kabat et al., 1987), with the exception of CDRH1 where the combined Chothia/Kabat definition is used (see Adair et al., 1991 Humanised antibodies. WO91/09967).

Genes encoding a number of variant heavy and light chain V-region sequences were designed and constructed by an automated synthesis approach by DNA 2.0 Inc. Further variants of both heavy and light chain V-regions were created by modifying the VH and VK genes by oligonucleotide-directed mutagenesis, including, in some cases, mutations within CDRs to modify potential aspartic acid isomerisation sites or remove unpaired Cysteine residues. These genes were cloned into vectors to enable expression of humanized 909 IgG4P (human IgG4 containing the hinge stabilising mutation S241P, Angal et al., Mol Immunol. 1993, 30(1):105-8) antibodies in mammalian cells.

The variant humanized antibody chains, and combinations thereof, were expressed and assessed for their potency relative to the parent antibody, their biophysical properties and suitability for downstream processing, leading to the selection of heavy and light chain grafts shown in FIGS. 27 and 28.

Human V-region IGKV1-17 (A30) plus JK4 J-region was chosen as the acceptor for antibody 909 light chain CDRs. The light chain framework residues in grafts gL1 (Seq. ID No. 446), gL10 (Seq. ID No. 448), gL54 (Seq. ID No. 450) and gL55 (Seq. ID No. 452) are all from the human germline gene, with the exception of residues 2, 3, 63 and 70 (Kabat numbering), where the donor residues Valine (2V), Valine (3V), Lysine (63K) and Aspartic acid (70D) were retained, respectively. Retention of residues 2, 3, 63 and 70 was essential for full potency of the humanized antibody. Residue 90 in CDRL3 of the gL10 graft, gL54 graft, and gL55 graft was mutated from a Cysteine (90C) to a Serine (90S), Glutamine (90Q), and Histidine (H90) residue, respectively, thus removing the unpaired Cysteine residue from the gL10, gL54, and gL55 sequence.

Human V-region IGHV4-4 plus JH4 J-region was chosen as the acceptor for the heavy chain CDRs of antibody 909. In common with many rabbit antibodies, the VH gene of antibody 909 is shorter than the selected human acceptor. When aligned with the human acceptor sequence, framework 1 of the VH region from antibody 909 (Seq. ID No. 454) lacks the N-terminal residue, which is retained in the humanised antibody (FIG. 28). Framework 3 of the 909 rabbit VH region also lacks two residues (75 and 76) in the loop between beta sheet strands D and E: in graft gH1 (Seq. ID No. 455) the gap in framework 3 is conserved, whilst in graft gH4 (Seq. ID No. 457), gH15 (Seq. ID No. 459), gH61 (Seq. ID No. 461), and gH62 (Seq. ID No. 463) the gap is filled with the corresponding residues (Lysine 75, 75K; Asparagine 76, 76N) from the selected human acceptor sequence (FIG. 28). The heavy chain framework residues in grafts gH1 and gH15 are all from the human germline gene, with the exception of residues 23, 67, 71, 72, 73, 74, 77, 78, 79, 89 and 91 (Kabat numbering), where the donor residues Threonine (23T), Phenylalanine (67F), Lysine (71K), Alanine (72A), Serine (73S), Threonine (74T), Threonine (77T), Valine (78V), Aspartic acid (79D), Threonine (89T) and Phenylalanine (91F) were retained, respectively. The heavy chain framework residues in graft gH14 are from the human germline gene, with the exception of residues 67, 71, 72, 73 74, 77, 78, 79, 89 and 91 (Kabat numbering), where the donor residues Threonine (23T), Phenylalanine (67F), Lysine (71K), Alanine (72A), Serine (73S), Threonine (74T), Threonine (77T), Valine (78V), Aspartic acid (79D), Threonine (89T) and Phenylalanine (91F) were retained, respectively. The heavy chain framework residues in grafts gH61 and gH62 are from the human germline gene, with the exception of residues 71, 73, and 78 (Kabat numbering), where the donor residues Lysine (71K), Serine (73S), and Valine (78V) were retained, respectively. The Glutamine residue at position 1 of the human framework was replaced with Glutamic acid (1E) to afford the expression and purification of a homogeneous product: the conversion of Glutamine to pyroGlutamate at the N-terminus of antibodies and antibody fragments is widely reported. Residue 59 in CDRH2 (Seq. ID No. 19) of the gH15 graft and gH62 graft was mutated from a Cysteine (59C) to a Serine (59S) residue, thus removing the unpaired Cysteine residue from the gH15 sequence. Residue 98 in CDRH3 (Seq. ID No. 20) of graft gH15 and graft gH62 was mutated from an Aspartic acid (98D) to a Glutamic acid (98E) residue, thus removing a potential Aspartic acid isomerization site from the gH15 sequence.

For expression of humanized Ab 909 in mammalian cells, the humanized light chain V-region gene was joined to a DNA sequence encoding the human C-kappa constant region (K1m3 allotype), to create a contiguous light chain gene. The humanized heavy chain V-region gene was joined to a DNA sequence encoding the human gamma-4 heavy chain constant region with the hinge stabilising mutation S241P (Angal et al., Mol Immunol. 1993, 30(1):105-8), to create a contiguous heavy chain gene. The heavy and light chain genes were cloned into the mammalian expression vector 1235-pGL3a(1)-SRHa(3)-SRLa(3)-DHFR(3) (Cellca GmbH).

Example 5. Reducing Affinity of a High Affinity Anti-aP2 Monoclonal Antibody

In light of the therapeutic activity of the low-affinity anti-aP2 monoclonal antibody CA33, amino acid residue substitutions were explored in the high-affinity anti-aP2 monoclonal murine antibody (H3 gL1/gH1) in order to develop low-affinity antibodies having potential aP2 modulating therapeutic activity. The original amino acid and cDNA sequences of H3 gL1/gH1, along with the mutated sequences thereof, are provided in Table 13 below.

TABLE 13

Modification of High Affinity H3 anti-aP2-antibody

| Protein/cDNA | Seq. ID No. | Sequence |
|---|---|---|
| H3 gL1 light chain variable region | 485 | EVVLTQSPALMAASPGEKVTITCSVSSSISSSNLHWYQQKSETSPKPWIYG TSNLASGVPVRFSGSGSGTSYSLTISSMEAEDAATYYCQQWSHYPLTFGAG TKLELK |
| H3 gL1 light chain variable region (Seq. ID No. 485) cDNA | 502 | GAAGTTGTGC TABLE 13-continued Modification of High Affinity H3 anti-aP2-antibody

| Protein/cDNA | Seq. ID No. | Sequence |
|---|---|---|
| Heavy chain full length gamma 1 constant region | 498 | AKTTPPSVYPLAPGSAAQTNSMVTLGCLVKGYFPEPVTVTWNSGSLSSGVHT FPAVLQSDLYTLSSSVTVPSSTWPSETVTCNVAHPASSTKVDKKIVPRDCGCK PCICTVPEVSSVFIFPPKDVLTITLTPKVTCVVVDISKDDPEVQFSWFVDDV EVHTAQTQPREEQFNSTFRSVSELPIMHQDWLNGKEFKCRVNSAAFPAPIEKT ISKTKGRPKAPQVYTIPPPKEQMAKDKVSLTCMITDFFPEDITVEWQWNGQPA ENYKNTQPIMDTDGSYFVYSKLNVQKSNWEAGNTFTCSVLHEGLHNHHTEKS LSHSPGK |
| Heavy chain full length gamma 1 constant region (Seq. ID No. 498) cDNA | 499 | GCCAAAACGACACCCCCATCTGTCTATCCACTGGCCCCTGGATCTGCTGCC CAAACTAACTCCATGGTGACCCTGGGATGCCTGGTCAAGGGCTATTTCCCT GAGCCAGTGACAGTGACCTGGAACTCTGGATCCCTGTCCAGCGGTGTGCAC ACCTTCCCAGCTGTCCTGCAGTCTGACCTCTACACTCTGAGCAGCTCAGTGA CTGTCCCCTCCAGCACCTGGCCCAGCGAGACCGTCACCTGCAACGTTGCCCA CCCGGCCAGCAGCACCAAGGTGGACAAGAAAATTGTGCCCAGGGATTGTGG TTGTAAGCCTTGCATATGTACAGTCCCAGAAGTATCATCTGTCTTCATCTTCCC CCCAAAGCCCAAGGATGTGCTCACCATTACTCTGACTCCTAAGGTCACGTGTG TTGTGGTAGACATCAGCAAGGATGATCCCGAGGTCCAGTTCAGCTGGTTTGTA GATGATGTGGAGGTGCACACAGCTCAGACGCAACCCCGGGAGGAGCAGTTCA ACAGCACTTTCCGCTCAGTCAGTGAACTTCCCATCATGCACCAGGACTGGCTC AATGGCAAGGAGTTCAAATGCAGGGTCAACAGTGCAGCTTTCCCTGCCCCCAT CGAGAAAACCATCTCCAAAACCAAAGGCAGACCGAAGGCTCCACAGGTGTAC ACCATTCCACCTCCCAAGGAGCAGATGGCCAAGGATAAAGTCAGTCTGACCTG CATGATAACAGACTTCTTCCCTGAAGACATTACTGTGGAGTGGCAGTGGAATG GGCAGCCAGCGGAGAACTACAAGAACACTCAGCCCATCATGGACACAGATGG CTCTTACTTCGTCTACAGCAAGCTCAATGTGCAGAAGAGCAACTGGGAGGCAG GAAATACTTTCACCTGCTCTGTGTTACATGAGGGCCTGCACAACCACCATACTG AGAAGAGCCTCTCCCACTCTCCTGGTAAATGATCCCAGTGTCCTTGGAGCCCTC TGGTCCTACAGGACTCTGACACCTACCTCCACCCCTCCCTGTATAAA |
| Light chain kappa constant | 500 | RTDAAPTVSIFPPSSEQLTSGGASVVCFLNNFYPKDINVKWKIDGSERQNGVL NSWTDQDSKDSTYSMSSTLTLTKDEYERHNSYTCEATHKTSTSPIVKSFNRNEC |
| Light chain kappa constant (Seq. ID No. 500) cDNA | 501 | CGTACGGATGCTGCACCAACTGTATCCATCTTCCCACCATCCAGTGAGCAGTT AACATCTGGAGGTGCCTCAGTCGTGTGCTTCTTGAACAACTTCTACCCCAAAG ACATCAATGTCAAGTGGAAGATTGATGGCAGTGAACGACAAAATGGCGTCCT GAACAGTTGGACTGATCAGGACAGCAAAGACAGCACCTACAGCATGAGCAGC ACCCTCACGTTGACCAAGGACGAGTATGAACGACATAACAGCTATACCTGTGA GGCCACTCACAAGACATCAACTTCACCCATTGTCAAGAGCTTCAACAGGAATG AGTGT |

To reduce the affinity of H3 (gL1/gH1) to that of CA33, H3 residues likely to form key contacts with murine aP2 were identified by visual inspection of the cr 2) Treatment of Diet-Induced Obese Mice with aP2 Antibody.

Wild-type mice were fed a high-fat diet for 12 weeks to induce dietary obesity and thereafter treated with either vehicle or monoclonal aP2 antibody (1.5 mg CA33/mouse) twice a week for 4 weeks on the same diet.

3) Recombinant aP2 Protein Injection Study.

Wild-type mice (10-12 weeks of age) received intraperitoneal injections of either vehicle or recombinant aP2 protein (100 µg/mouse) twice daily for 5 days. FoxO1$^{flox/flox}$ mice were generously provided by Domenico Accili (Columbia University, NY) and crossed with Albumin-Cre mice (Jackson Laboratories, Bar Harbor, Me.) to generate liver specific FoxO1 knockout mice. Either wild-type mice or FoxO1 liver specific knockout mice were treated with recombinant aP2 in the same way.

4) Adenovirus Transduction Study.

Recombinant adenovirus encoding either β-glucuronidase (AdGUS), CtBP2 (AdCtBP2), sh-control (Ad/shControl), sh-FoxO1 (Ad/shFoxO1) or sh-CtBP2 (Ad/shCtBP2) was delivered into mice at the titer of $1.5 \times 10^{11}$ particles/mouse. Glucose tolerance tests were performed by intraperitoneal glucose injection (0.75 g/kg) after an overnight fast, and insulin tolerance tests were performed by intraperitoneal injection of insulin (0.5 U/kg) after a 6 h-fast. Serum parameters were analyzed using the following systems: aP2; Mouse FABP4 ELISA (BioVendor), insulin; Mouse Ultrasensitive Insulin ELISA (ALPCO), glucagon; Glucagon Quantikine ELISA Kit (R&D Systems), FFA; NEFA-HR(2) (Wako Chemicals), glycerol; Free Glycerol Determination Kit (Sigma), Alanine aminotransferase (ALT); ALT activity assay kit (Sigma). Liver triglyceride was extracted by the chloroform-methanol method and determined by a colorimetric assay (Sigma).

Recombinant Protein Production and Purification

Mouse aP2 cDNA with an N-terminal polyhistidine tag followed by a TEV protease cleavage site was cloned into pET28 vector (EMD bioscience) and the plasmid was transformed into BL21AI strain of *E. coli* (Invitrogen). After the affinity purification and extensive endotoxin removal, the N-terminal His tag was removed by cleavage with TEV protease (Sigma). Lipid binding mutant (R126L, Y128F) was generated following the same strategy [see, Erbay, E., et al. Reducing endoplasmic reticulum stress through a macrophage lipid chaperone alleviates atherosclerosis. *Nature Medicine* 15, 1383-1391 (2009)]. To delipidate the recombinant protein, temperature-dependent binding of hydrophobic ligands to Lipidex1000 (Perkin-Elmer, Norwalk, Conn.), a 10% substituted hydroxyalkoxypropyl derivate of Sephadex G-25, was utilized. At 37° C., Lipidex 1000 removes both non-protein bound and protein associated lipids from an aqueous solution, whereas at 0° C. it only removes non-protein bound lipids [see, Glatz, J. F. & Veerkamp, J. H. Removal of fatty acids from serum albumin by Lipidex 1000 chromatography. *Journal of Biochemical and Biophysical Methods* 8, 57-61 (1983)]. Recombinant aP2 protein was delipidated with Lipidex1000 at 37° C. twice. Thereafter, the resultant proteins were further purified by gel filtration through Sephadex G-25 (PD-10, GE Healthcare).

Primary Hepatocyte Isolation, Screening of Transcription Factors, Subcellular Fractionation, and Adenovirus Transduction Primary mouse hepatocytes were isolated as described previously, see, Sekiya, M., et al. SREBP-1-independent regulation of lipogenic gene expression in adipocytes. *Journal of Lipid Research* 48, 1581-1591 (2007). After overnight serum starvation, cells were treated in William's medium E (Invitrogen) with 50 µg/ml of recombinant aP2 in the presence or absence of forskolin (2 µM, Sigma) for 3 h unless otherwise indicated. For the screening of transcription factors, on-target plus siRNAs were purchased from Dharmacon and transiently transfected into primary hepatocytes by RNAiFect (QIAGEN). For subcellular fractionation, cells were treated as indicated above for 90 min and fractionated utilizing NE-PER cell fractionation system (Pierce). For adenoviral transduction, shRNA oligonucleotides were cloned into pENTR/U6 vector followed by the recombination with pAd/BLOCK-it-DEST vector (Invitrogen). The targeted sequences of shRNAs were designed as follows. Control; 5'-GTCTCCACGCGCAGTACATTT-3', Seq. ID No. 541 Foxo1; 5'-GCATGTTTATTGAGCGCT-TGG-3', Seq. ID No. 542 CtBP1; 5'-GCAGCGGGTTT-GACAATATCG-3', Seq ID No. 543 CtBP2; 5'-GGGAAGACTAGGACGTGATTA-3' Seq. ID No. 544 and 5'-GCCACATTCTCAATCTGTATC-3', Seq. ID No. 545 HNF4a; 5'-GCTGCAGATTGATGACAATGA-3' Seq. ID No. 546. Forkhead response element (FHRE) luciferase (Addgene, Cambridge, Mass.) was cloned into pAd/PL-DEST vector (Invitrogen). Adenovirus encoding renilla luciferase was purchased from Vector Biolabs (Philadelphia, Pa.). Adenoviruses were amplified in HEK293A cells and purified by CsCl gradient centrifugation. To measure FoxO transcriptional activity, primary hepatocytes were infected with adenovirus expressing FHRE luciferase and renilla luciferase for 24 h. Thereafter, cells were serum starved overnight and incubated with 50 µg/ml of aP2 protein in the absence or presence of 2 µM forskolin for 6 h. Cells were lysed in passive lysis buffer and analyzed using Dual-Glo luciferase Reporter Systems (Promega). Firefly luciferase signal was normalized to Renilla luciferase.

Quantitative Real-Time RT-PCR

Total RNA was isolated using Trizol Reagent (Invitrogen) and cDNA was synthesized with iScript Reverse Transcription Supermix (Bio-Rad). Quantitative real-time PCR analysis was performed using SYBR Green in ViiA 7 Real-Time PCR systems (Applied Biosystems). Data were normalized to acidic ribosomal phosphoprotein P0 (Rplp0, 36B4) expression. Primers used for Q-PCR were as follows:

```
Rplp0   forward  5'-CACTGGTCTAGGACCCGAGAA-3'  Seq. ID No. 547
        reverse  5'-AGGGGGAGATGTTCAGCATGT-3'  Seq. ID No. 548

Pck1    forward  5'-CTGCATAACGGTCTGGACTTC-3'  Seq. ID No. 549
        reverse  5'-CAGCAACTGCCCGTACTCC-3'    Seq. ID No. 550

G6pc    forward  5'-CGACTCGCTATCTCCAAGTGA-3'  Seq. ID No. 551
        reverse  5'-GTTGAACCAGTCTCCGACCA-3'   Seq. ID No. 552

Foxo1   forward  5'-AACACACAGCTGGGTGTCAGG-3'  Seq. ID No. 553
        reverse  5'-GCATCTTTGGACTGCTCCTCAGT-3' Seq. ID No. 554
```

-continued

| Gene | Direction | Sequence | Seq. ID No. |
|---|---|---|---|
| Foxo3 | forward | 5'-CTGGTGCTAAGCAGGCCTCAT-3' | 555 |
| | reverse | 5'-TGTAGGTCTTCCGTCAGTTTGAGG-3' | 556 |
| Foxo4 | forward | 5'-TGTATATGGAGAACCTGGAGTGCG-3' | 557 |
| | reverse | 5'-CAAAGCTTCTTGCTGTGACTCAGG-3' | 558 |
| Cebpa | forward | 5'-CAAGAACAGCAACGAGTACCGG-3' | 559 |
| | reverse | 5'-TGTCACTGGTCAACTCCAGCAC-3' | 560 |
| Nr3c1 | forward | 5'-CTGACGTGTGGAAGCTGTAAAGTC-3' | 561 |
| | reverse | 5'-GATGCAATCATTTCTTCCAGCAC-3' | 562 |
| CtBP1 | forward | 5'-TTGGGCATCATTGGACTAGGTC-3' | 563 |
| | reverse | 5'-GCTCGATTCCATCAGATAGGTATGG-3' | 564 |
| CtBP2 | forward | 5'-GCAGGACTTGCTATATCAGAGCGA-3' | 565 |
| | reverse | 5'-ATGCACCTTGCCTCATCTGCT-3' | 566 |
| Alb | forward | 5'-AGACGTGTGTTGCCGATGAGT-3' | 567 |
| | reverse | 5'-GTTTTCACGGAGGTTTGGAATG-3' | 568 |
| Gpam | forward | 5'-ACAGTTGGCACAATAGACGTTT-3' | 569 |
| | reverse | 5'-CCTTCCATTTCAGTGTTGCAGA-3' | 570 |
| Fasn | forward | 5'-AGAGATCCCGAGACGCTTCT-3' | 571 |
| | reverse | 5'-GCCTGGTAGGCATTCTGTAGT-3' | 572 |
| Scd1 | forward | 5'-CCCGGGAGAATATCCTGGTTT-3' | 573 |
| | reverse | 5'-TCGATGAAGAACGTGGTGAAGT-3' | 574 |
| Hif1a | forward | 5'-ATGAAGTGCACCCTAACAAGCC-3' | 575 |
| | reverse | 5'-CACACTGAGGTTGGTTACTGTTGG-3' | 576 |
| Ppargc1a | forward | 5'-GAAGTGGTGTAGCGACCAATC-3' | 577 |
| | reverse | 5'-AATGAGGGCAATCCGTCTTCA-3' | 578 |
| Stat3 | forward | 5'-ACCATTGACCTGCCGATGTC-3' | 579 |
| | reverse | 5'-TGAGCGACTCAAACTGCCCT-3' | 580 |
| Srebf1c | forward | 5'-GGAGCCATGGATTGCACATT-3' | 581 |
| | reverse | 5'-GGCCCGGGAAGTCACTGT-3' | 582 |
| Mlxipl | forward | 5'-CACTCAGGGAATACACGCCTAC-3' | 583 |
| | reverse | 5'-ATCTTGGTCTTAGGGTCTTCAGG-3' | 584 |
| Pklr | forward | 5'-TCAAGGCAGGGATGAACATTG-3' | 585 |
| | reverse | 5'-CACGGGTCTGTAGCTGAGTGG-3' | 586 |
| Acly | forward | 5'-ACCCTTTCACTGGGGATCACA-3' | 587 |
| | reverse | 5'-GACAGGGATCAGGATTTCCTTG-3' | 588 |
| Crp | forward | 5'-ATGGAGAAGCTACTCTGGTGCC-3' | 589 |
| | reverse | 5'-ACACACAGTAAAGGTGTTCAGTGGC-3' | 590 |
| Apcs | forward | 5'-GTCAGACAGACCTCAAGAGGAAAGT-3' | 591 |
| | reverse | 5'-AGGTTCGGAAACACAGTGTAAAATT-3' | 592 |
| CD36 | forward | 5'-AGATGACGTGGCAAAGAACAG-3' | 593 |
| | reverse | 5'-CCTTGGCTAGATAACGAACTCTG-3' | 594 |
| Acadm | forward | 5'-AGGGTTTAGTTTTGAGTTGACGG-3' | 595 |
| | reverse | 5'-CCCCGCTTTTGTCATATTCCG-3' | 596 |

Nuclear Fatty Acyl-CoA Content

Primary hepatocytes ($6 \times 10^6$ cells per sample) were stimulated with 50 µg/ml of aP2 for 2 h. The cells were washed with PBS and nuclei were isolated without detergent as described previously in T. Nakamura et al., A critical role for PKR complexes with TRBP in Immunometabolic regulation and eIF2alpha phosphorylation in obesity. Cell Rep 11, 295-307 (2015). Thelipids in the isolated nuclei were extracted basically by Bligh-Dyer method using water acidified with acetic acid. Fatty acyl-CoA partitioned into methanol/water phase was collected. Fatty acyl-CoAs were oxidized by fatty acyl-CoA oxidase (Wako, Japan), yielding 2,3-trans-Enoyl-CoAs and hydrogen peroxide. The hydrogen peroxide was quantified by a fluorescent detection system (Enzo Life Sciences, NY).

Glucose Production Assay

Primary hepatocytes were infected with either Ad/shControl or Ad/shFoxO1 for 24 h and further incubated in fresh William's E medium with 5% FBS for 12 h. Thereafter, cells were serum starved overnight and incubated with either control or recombinant aP2 (50 µg/ml) in the presence or absence of forskolin (2 µM) for 5 h. Cells were washed twice with DMEM without glucose (Sigma) supplemented with 10 mM HEPES and incubated with the same DMEM without glucose with 20 mM glycerol in the presence of the same concentrations of vehicle, aP2 and/or forskolin for 2 h. The glucose concentrations in the media were determined by using the Amplex Red Glucose/Glucose Oxidase Assay Kit (Invitrogen).

Western Blot Analysis and Co-Immunoprecipitation Experiments

Proteins were extracted from cells or liver samples with buffer A (50 mM Tris-HCl pH 7.4, 150 mM NaCl, 1% Nonidet P-40, 1 mM EDTA, 10 mM NaF, 2 mM $Na_3VO_4$) with complete protease inhibitors (Sigma-Aldrich) and subjected to SDS-polyacrylamide gel electrophoresis. To detect acetylated FoxO1, 5 µM of trichostatin A (TSA) and 5 mM of nicotinamide were included in the buffer A to block deacetylation of FoxO1 protein. Membranes were incubated with anti-FoxO1 (Cell Signaling, C29H4), anti-CtBP (Santa Cruz, E-12), anti-CtBP1 (BD), anti-CtBP2 (BD), anti-FLAG (Clontech), anti-GAPDH (Santa Cruz, FL-335), anti-Lamin A/C (Cell Signaling, 4C11), anti-phospho PKA substrate (Cell signaling, #9621), anti-GUS (Invitrogen), anti-pAkt (Ser473, Cell Signaling, #9271), anti-Akt (Santa Cruz, H-136), anti-Ac-FKHR (Santa Cruz, D-19), anti-pFoxO1 (Ser 256, Cell Signaling, #9461) and anti-HNF4a (Santa Cruz, C-19). The membranes were incubated with the secondary antibody conjugated with horseradish peroxidase (Santa Cruz) and were visualized using the enhanced chemiluminescence system (Roche Diagnostics). To detect endogenous binding of FoxO1 and CtBPs, the anti-FoxO1 antibody (Santa Cruz, C-9), anti-CtBP antibody (Santa Cruz, E-12), anti-CtBP2 (Santa Cruz, E-16), control mouse IgG (generated in house) or control goat IgG (Santa Cruz) were cross-linked to Protein G dynabeads (Invitrogen) with 50 mM dimethyl pimelimidate (Sigma-Aldrich). Primary hepatocytes or liver samples were lysed with buffer A and the protein complex was immunoprecipitated in buffer A with reduced concentration of NP40 (0.5%) (50 mM Tris-HCl pH 7.4, 150 mM NaCl, 0.5% Nonidet P-40, 1 mM EDTA, 10 mM NaF, 2 mM $Na_3VO_4$) for 4 h at 4° C. The beads were washed with the buffer A with 0.5% NP40 without EDTA four times, eluted with SDS loading buffer and analyzed by Western blot analysis. FLAG-tag co-immunoprecipitation study was performed as follows. The plasmids encoding FLAG wild-type FoxO1 and CtBP1 are generous gifts from Domenico Accili (Columbia University, NY) and Pere Puigserver (Harvard Medical School, MA), respectively. CtBP2 cDNA was amplified by PCR and cloned into pcDNA3.1(+) (Invitrogen). The PSDL motif in FoxO1 was either mutated to PSAS or deleted by gene tailor site-directed mutagenesis system (Invitrogen). HEK293 cells were transiently transfected with control plasmid, FLAG wild-type FoxO1 or mutated FLAG FoxO1 along with either CtBP1 or CtBP2 using lipofectamine LTX (Invitrogen). Cells were lysed with buffer A with 1% NP40 and immunoprecipitated with FLAG M2 magnetic beads (Sigma) in buffer A with 0.5% NP40 for 4 h at 4° C. The beads were washed four times with buffer A, with 0.5% NP40 and eluted with 0.5 mg/ml of 3×FLAG peptide (Sigma). To evaluate the effect of oleoyl-CoA and NADH, the cell lysates were immunoprecipitated with FLAG M2 magnetic beads with increasing concentrations of oleoyl-CoA or NADH for 4 h at 4° C. Thereafter, the FoxO1/CtBP2 complex was eluted and analyzed in the same way.

Fatty Acid Uptake Assay

[1-$^{14}$C]oleate (59.0 mCi/mmol, PerkinElmer) was conjugated with BSA (fatty acid free, Sigma, BSA:oleate=1:6). Primary hepatocytes were incubated with recombinant aP2 (50 µg/ml) for 2 h and [1-$^{14}$C]oleate-BSA complex was added to give a final concentration of 150 µM. After the indicated period of time, cells were placed on ice, washed with cold PBS five times and lysed with 0.1N NaOH to measure the radioactivity and protein concentrations.

Fatty Acid Oxidation

Primary hepatocytes were seeded on type I collagen (Sigma)-coated XF96 cell culture microplates (Seahorse Bioscience) at a density of 7×10$^3$/well. Cells were treated with recombinant aP2 (50 µg/ml) for 2 h in Williams' E media without serum, thereafter the culture medium was changed to Krebs-Henseleit buffer (111 mM NaCl, 4.7 mM KCl, 1.25 mM $CaCl_2$, 2 mM $MgSO_4$, 1.2 mM $NaH_2PO_4$, 2.5 mM glucose, 0.5 mM carnitine, 5 mM HEPES pH 7.4) with the same concentrations of vehicle or recombinant aP2. Oxygen ($O_2$) consumption rates (OCR) were measured before and after the exposure to 150 µM of palmitate conjugated with BSA (Seahorse Bioscience).

Immunocytochemistry

Primary hepatocytes were incubated as described above for 90 min and fixed in 4% paraformaldehyde for 10 min at room temperature. Cells were permeabilized with 0.1% Triton X-100 for 10 min and blocked with 10% donkey serum (Sigma) for 1 hour. Primary antibodies employed to detect CtBP2 and FoxO1 were goat polyclonal CtBP2 antibody E-16 (Santa Cruz, 1:50) and a mixture of rabbit polyclonal FoxO1 antibodies containing ab39670 (Abcam®, 1:100), C29H4 (Cell Signaling, 1:100) and H-128 (Santa Cruz, 1:100), respectively. Alexa Fluor® 568-conjugated donkey anti-goat IgG and Alexa Fluor® 647-conjugated donkey anti-rabbit IgG were applied as secondary antibodies (Life Technologies, 1:200).

Chromatin Immunoprecipitation (ChIP)

Primary hepatocytes were incubated as described above for 90 min and fixed in 1% formaldehyde for 10 minutes at room temperature. Crosslinking was quenched by adding glycine to a final concentration of 125 mM. Thereafter, the ChIP assay was carried out using Magna ChIP HiSens Chromatin Immunoprecipitation Kit (EMD Millipore) with minor modifications: chromatin shearing was achieved by Micrococcal Nuclease (Cell Signaling). Chromatin was immunoprecipitated either with control IgG, anti-FoxO1 (Abcam®, ab39670) or anti-CtBP2 (Santa Cruz, E-16). Immunoprecipitated DNA and input DNA were quantified by real-time PCR with primers specific for G6pc gene promoter. See, Hall, J. A., Tabata, M., Rodgers, J. T. & Puigserver, P. USP7 attenuates hepatic gluconeogenesis through modulation of FoxO1 gene promoter occupancy. *Molecular endocrinology* 28, 912-924 (2014).

Cellular Lactate/Pyruvate Measurement

To estimate the cytosolic $NAD^+$/NADH ratio, cellular lactate and pyruvate contents were measured with a kit (Cayman Chemical). When the conversion between pyruvate/NADH and lactate/NAD is at equilibrium, the cytosolic $NAD^+$/NADH ratio could be estimated by the lactate/pyruvate ratio. See, Williamson, D. H., Lund, P. & Krebs, H. A. The redox state of free nicotinamide-adenine dinucleotide in the cytoplasm and mitochondria of rat liver. *The Biochemical Journal* 103, 514-527 (1967).

aP2 Upregulates Gluconeogenic Gene Expression in a FoxO1-Dependent Manner

Acting as an adipokine, aP2 directly upregulates expression of gluconeogenic genes both in liver in vivo, and in hepatocytes in vitro. See, Cao, H., et al. Adipocyte lipid chaperone AP2 is a secreted adipokine regulating hepatic glucose production. *Cell metabolism* 17, 768-778 (2013).

Figure 38A:
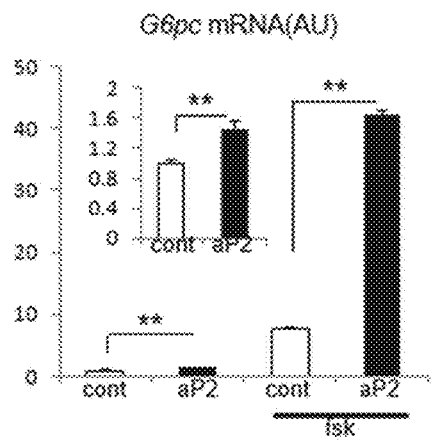
Figure 38B:
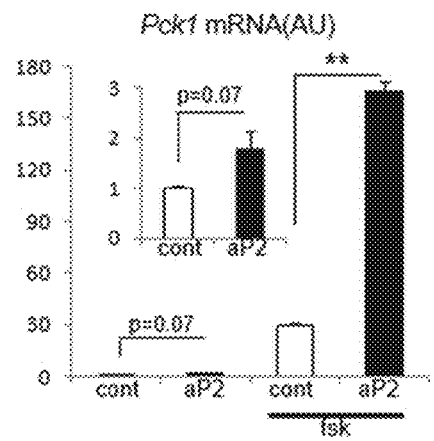
Figure 38C:
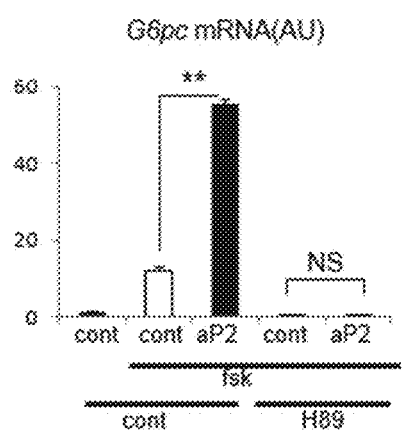
Figure 38D:
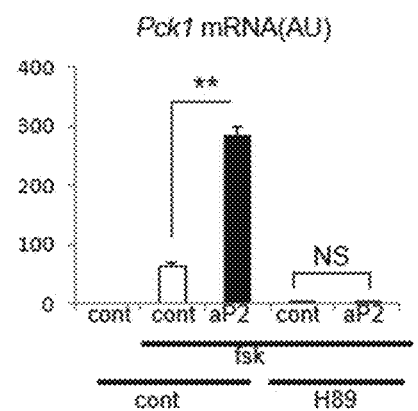

Since the extent of upregulation is modest in cell culture systems, additional experimental settings were examined to obtain more robust upregulation of these genes. It has been discovered that the presence of signals mimicking fasting increases the effect of aP2 on gene expression. For example, forskolin (an activator of adenylate cyclase) and glucagon (data not shown) enhanced the ability of aP2 to upregulate G6pc and Pck1 gene expression in primary hepatocytes (FIGS. 38A and 38B). Conversely, blocking cAMP-PKA signaling with H89 abolished the effect of aP2 (FIGS. 38C and 38D).

Further, the molecular basis of gluconeogenic gene regulation by aP2 in this setting has been identified as described herein. Both delipidated aP2 and a mutant form of aP2 that lacks lipid binding ability (R126L, Y128F) (Erbay, E., et al. Reducing endoplasmic reticulum stress through a macrophage lipid chaperone alleviates atherosclerosis. *Nature Medicine* 15, 1383-1391 (2009)) failed to upregulate gluconeogenic gene expression in the presence of forskolin, (FIGS. 32A and 32B), indicating that aP2 lipid cargo is an important mediator of this activity.

siRNA knockdown was used to screen several key hepatic transcription factors and cofactors, such as FoxO1, Hypoxia-inducible factor 1α (Hif1α), Signal transducer and activator of transcription 3 (Stat3), Peroxisome proliferator-activated receptor-gamma coactivator 1α (PGC-1α, Ppargc1a), CCAAT-enhancer-binding proteins α (C/EBPα, Cebpa) and Glucocorticoid Receptor (GR, Nuclear receptor subfamily 3 group C member 1, Nr3c1) for their ability to abrogate the effect of aP2 on gene expression. Among these, knockdown of FoxO1, which has previously been shown to play a critical role in the transcriptional regulation of gluconeogenic gene expression (see, Lin, H. V. & Accili, D. Hormonal regulation of hepatic glucose production in health and disease. *Cell metabolism* 14, 9-19 (2011)), most markedly blunted the effect of aP2 on G6pc expression (FIGS. 32C, 39A-39H).

Figure 39A:
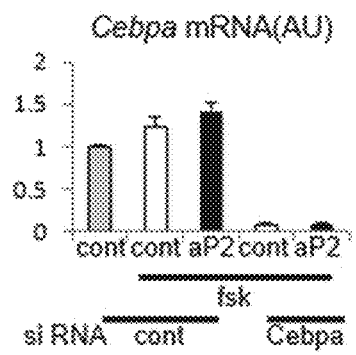
Figure 39B:
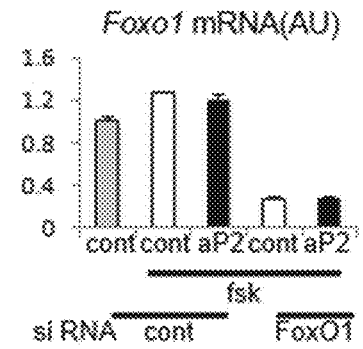
Figure 39C:
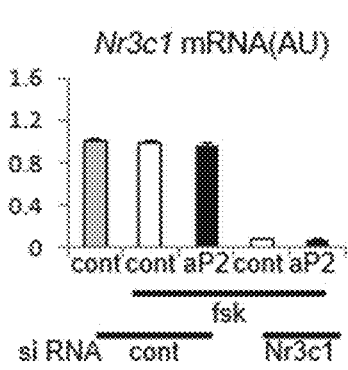
Figure 39D:
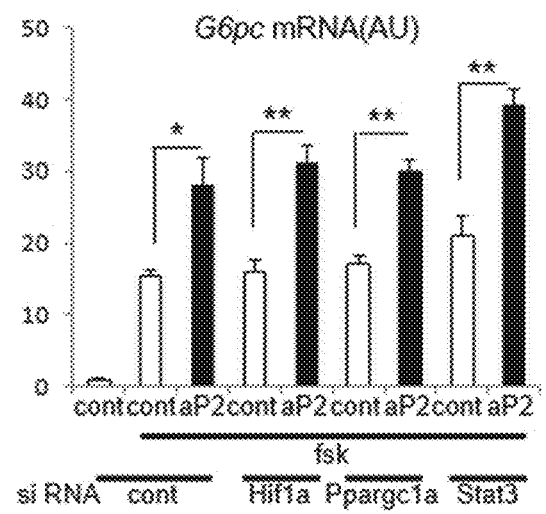
Figure 39E:
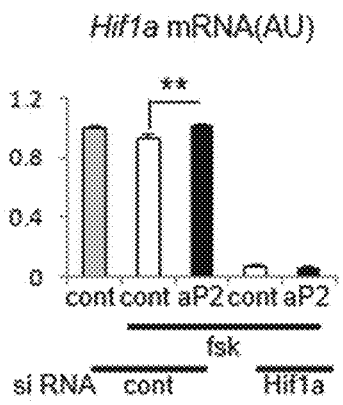
Figure 39F:
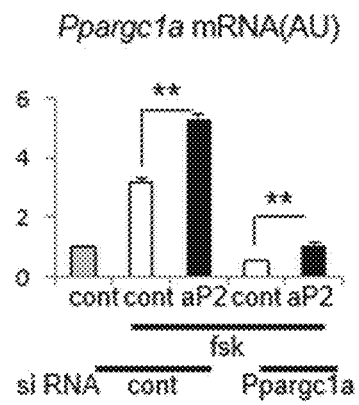
Figure 39G:
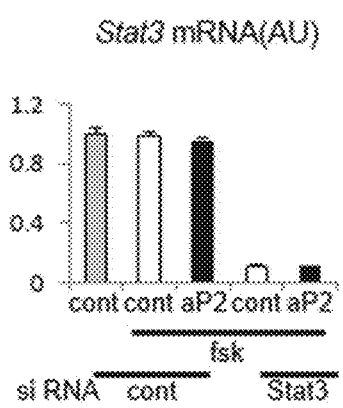
Figure 39H:
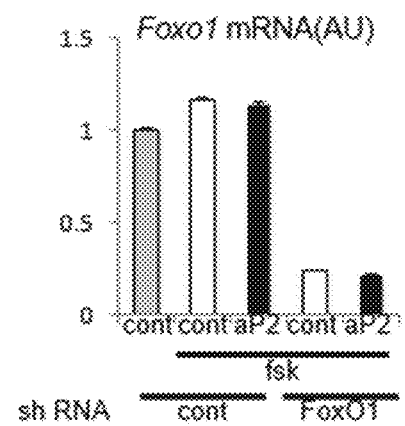

This finding was further validated by adenovirus-mediated shRNA delivery. Again adenovirus-mediated FoxO1 knockdown significantly diminished the upregulation of G6pc gene expression induced by aP2 (FIGS. 32D and 32E). Consistent with this finding, aP2 increased the activity of a FoxO-responsive luciferase reporter (FHRE) in primary hepatocytes, and this effect was more pronounced in the presence of forskolin (FIG. 32F). Treatment with aP2 did not influence the expression levels of Foxo1 (FIG. 39H). Furthermore, aP2 increased glucose production from hepatocytes in a FoxO1-dependent manner (FIG. 32G).

Extracellular aP2 Alters Fatty Acid Metabolism in Hepatocytes

Figure 33A:
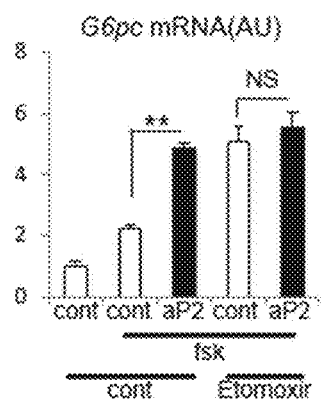
Figure 33B:
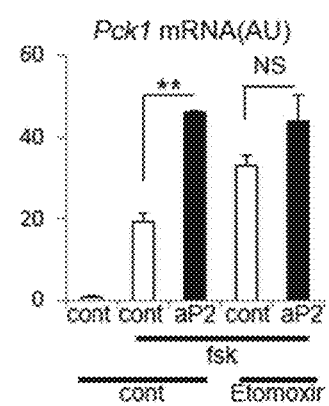
Figure 33C:
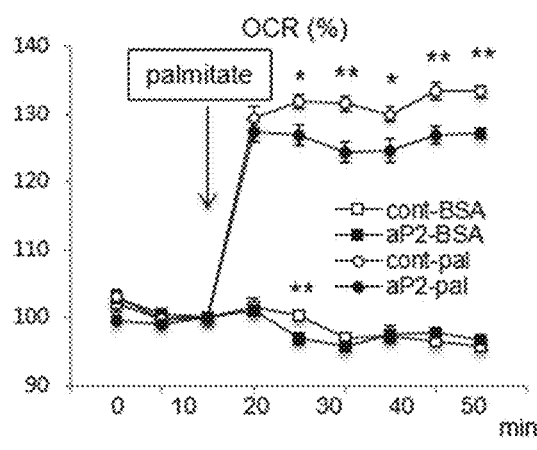
Figure 33D:
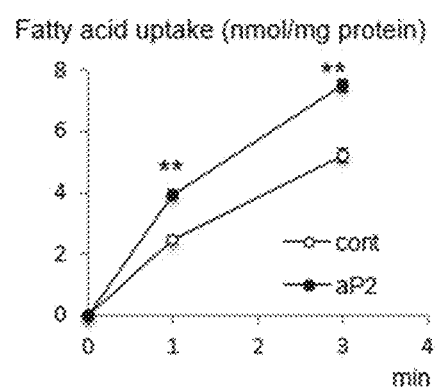
Figure 33E:
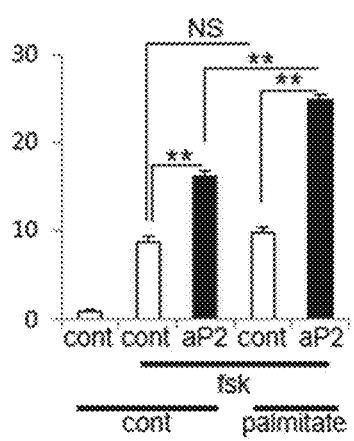
Figure 33F:
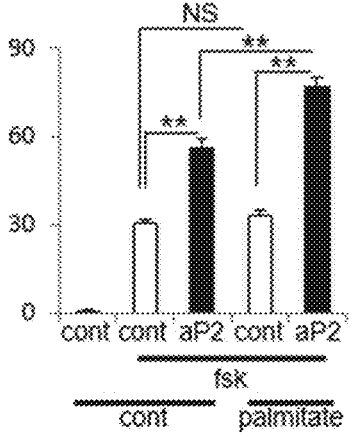

Since aP2 is a fatty acid binding protein and genetic deficiency and antibody-mediated neutralization of aP2 are known to alter systemic fatty acid metabolism (Hotamisligil, G. S., et al. Uncoupling of obesity from insulin resistance through a targeted mutation in aP2, the adipocyte fatty acid binding protein. *Science* (New York, N.Y.) 274, 1377-1379 (1996), Maeda, K., et al. Adipocyte/macrophage fatty acid binding proteins control integrated metabolic responses in obesity and diabetes. *Cell metabolism* 1, 107-119 (2005); Cao, H., et al. Regulation of metabolic responses by adipocyte/macrophage Fatty Acid-binding proteins in leptin-deficient mice. *Diabetes* 55, 1915-1922 (2006)), the effect of exogenous aP2 treatment on fatty acid metabolism in hepatocytes was assessed. The effect of aP2 was significantly diminished in the presence of etomoxir, a fatty acid oxidation inhibitor (FIGS. 33A and 33B). This data suggests that aP2 is regulating gluconeogenic gene expression by inhibiting fatty acid oxidation. Consistent with this finding, aP2 decreased the palmitate-stimulated increase in fatty acid oxidation, as measured by oxygen consumption rate after palmitate injection (FIG. 33C). Furthermore, aP2 robustly increased fatty acid uptake into hepatocytes (FIG. 33D) suggesting that the extent of inhibition of fatty acid oxidation by aP2 observed (FIG. 33C) may be an underestimation. Moreover, exogenously supplied palmitate increased the extent of gluconeogenic gene expression induced by aP2 (FIGS. 33E and 33F).

Figure 33G:
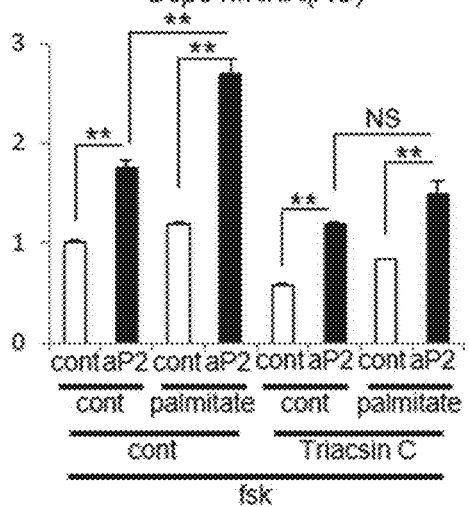
Figure 33H:
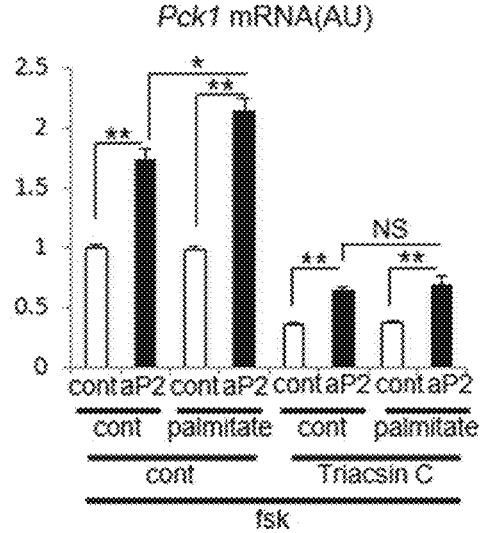
Figure 33I:
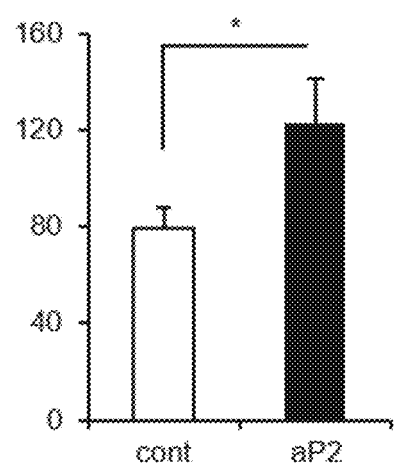

Once taken up into cells, fatty acids are esterified with CoA to form fatty acyl-CoA thioesters, and transported to organelles such as mitochondria and endoplasmic reticulum where they are utilized for oxidation and lipid synthesis. See, Mashek, D. G. & Coleman, R. A. Cellular fatty acid uptake: the contribution of metabolism. *Current opinion in lipidology* 17, 274-278 (2006) and Anderson, C. M. & Stahl, A. SLC27 fatty acid transport proteins. *Molecular aspects of medicine* 34, 516-528 (2013). Following aP2 treatment, an increase of fatty acid uptake with concomitant decline of fatty acid oxidation would presumably cause accumulation of cytosolic fatty acyl-CoAs, which has been shown to play regulatory roles in metabolic diseases. See, DeFronzo, R. A. Insulin resistance, lipotoxicity, type 2 diabetes and atherosclerosis: the missing links. The Claude Bernard Lecture 2009. *Diabetologia* 53, 1270-1287 (2010). To test whether the effect of palmitate on aP2-induced gluconeogenic gene expression involves cytosolic acyl-CoA, the acyl-CoA synthetase inhibitor, Triacsin C, was used. See, Mashek, D. G. & Coleman, R. A. Cellular fatty acid uptake: the contribution of metabolism. *Current opinion in lipidology* 17, 274-278 (2006). Chemical inhibition of acyl-CoA synthetase significantly diminished the ability of exogenous palmitate to enhance the aP2 effect on gene expression (FIGS. 33G and 33H). Furthermore, treating primary hepatocytes with aP2 induced a significant increase in the accumulation of nuclear fatty acyl-CoA (FIG. 33I). Taken together, these data indicate that both lipid flux and turnover in liver cells are modulated by aP2, and that this underlies the effect of aP2 on gluconeogenic gene expression.

A Novel Repressive Complex, FoxO1/CtBP2, is Modulated by aP2

Figure 40A:
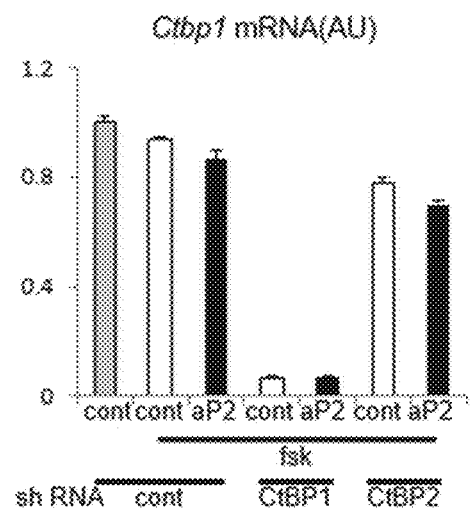
Figure 40B:
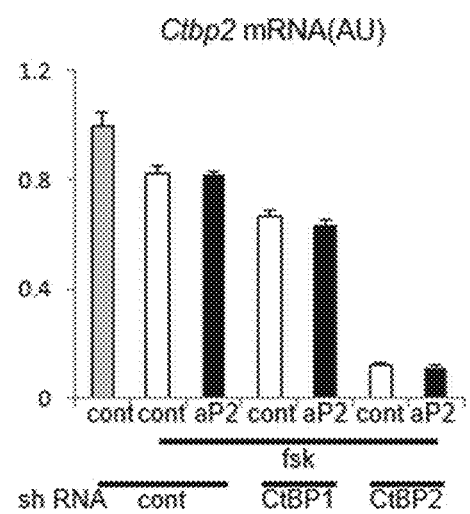
Figure 40C:
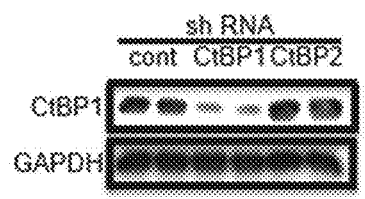
Figure 40D:
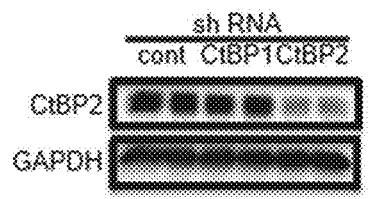
Figure 40E:
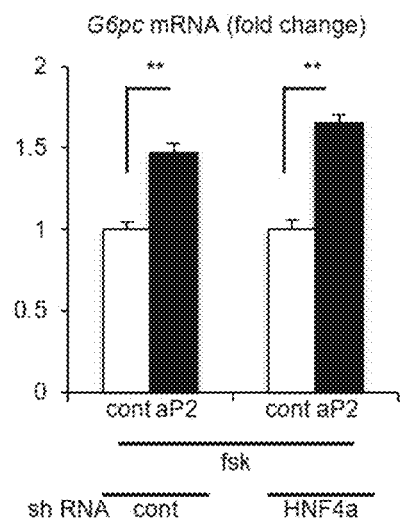
Figure 40F:
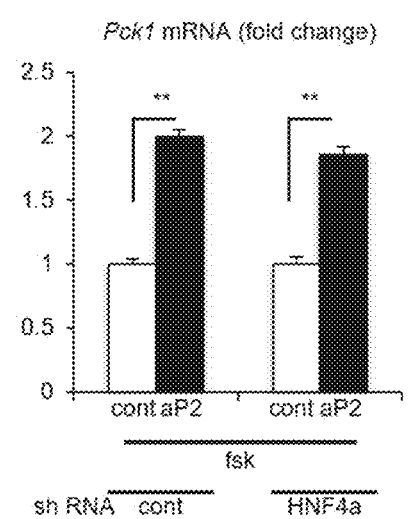
Figure 40G:
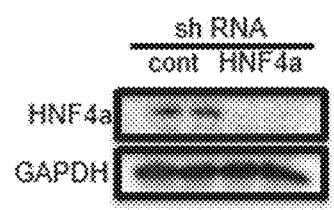
Figure 41A:
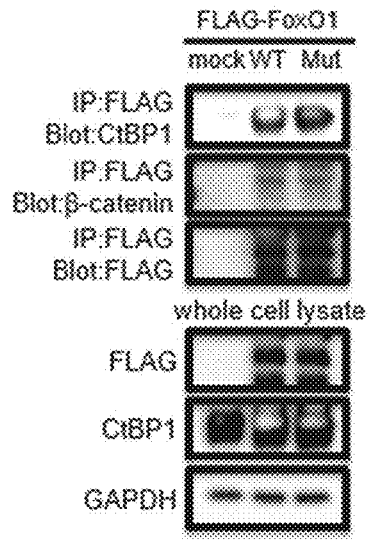
Figure 41B:
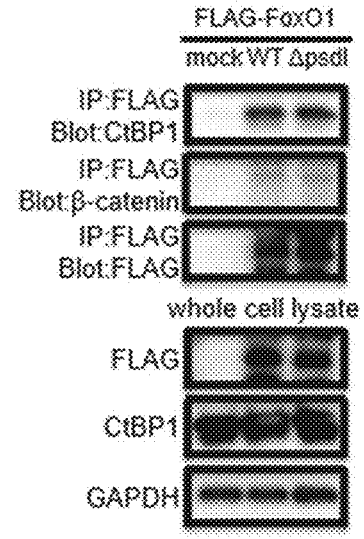
Figure 41C:
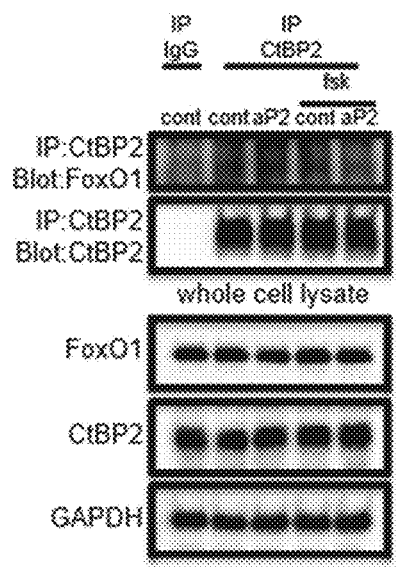
Figure 41D:
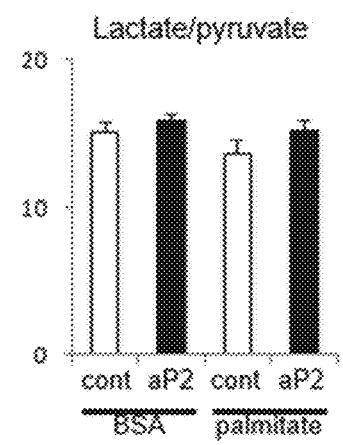
Figure 41E:
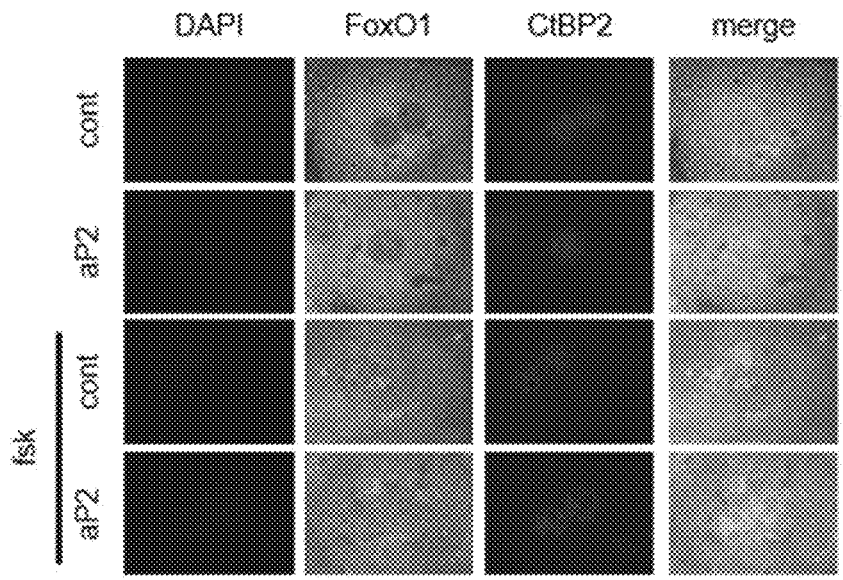
Figure 41F:
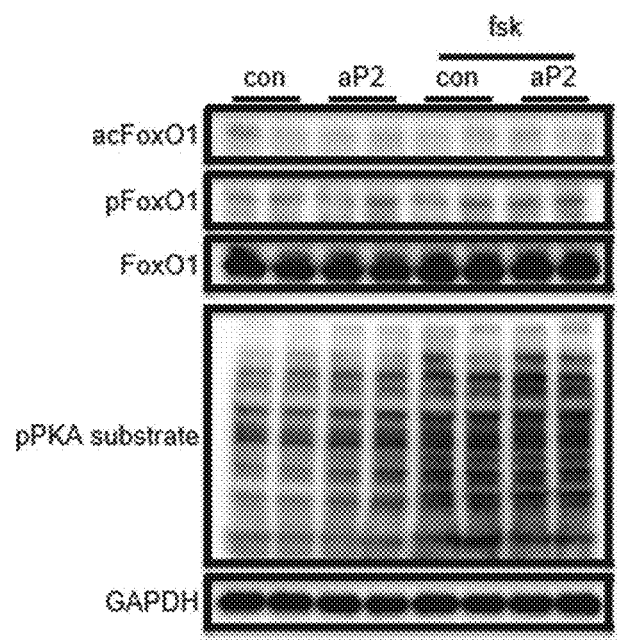

FoxO1 has not been previously shown to be regulated by the intracellular lipid milieu. Therefore, molecules which might link lipid signaling to FoxO1 activation were examined. C-terminal binding proteins (CtBPs) are transcriptional repressors that have been shown to bind to not only nicotinamide adenine dinucleotide ($NAD^+$/NADH) but also fatty acyl-CoAs. See, Nardini, M., et al. CtBP/BARS: a dual-function protein involved in transcription co-repression and Golgi membrane fission. *The EMBO journal* 22, 3122-3130 (2003). Importantly, $NAD^+$/NADH binding induces a conformational change of CtBPs and promotes homo-dimerization and formation of an active repressor form, while acyl-CoA binding induces monomeric conformation. See, Nardini, M., et al. CtBP/BARS: a dual-function protein involved in transcription co-repression and Golgi membrane fission. *The EMBO journal* 22, 3122-3130 (2003). In our experimental system, we examined the role of each of the two CtBP isoforms on aP2-mediated gene expression. While knockdown of CtBP1 had no impact on aP2-induced gene expression, CtBP2 knockdown blocked the effect of aP2 (See, FIGS. 34A, 34B, 40A, 40B, 40C and 40D). Notably, although Hepatocyte nuclear factor 4 α (HNF4α) is a well-known gluconeogenic transcription factor with binding affinity against long chain fatty acyl-CoAs (Hertz, R., Magenheim, J., Berman, I. & Bar-Tana, J. Fatty acyl-CoA thioesters are ligands of hepatic nuclear factor-4alpha. *Nature* 392, 512-516 (1998)) an effect of HNF4α knockdown on aP2-mediated gene expression was not observed (FIGS. 40E and 40F).

Figure 34D:
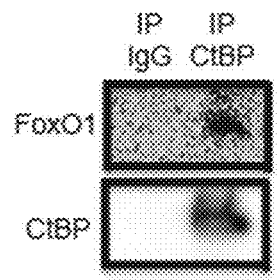
Figure 34E:
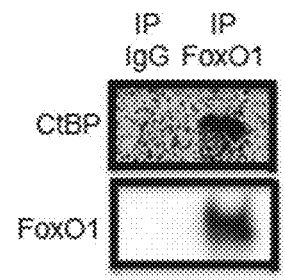
Figure 34F:
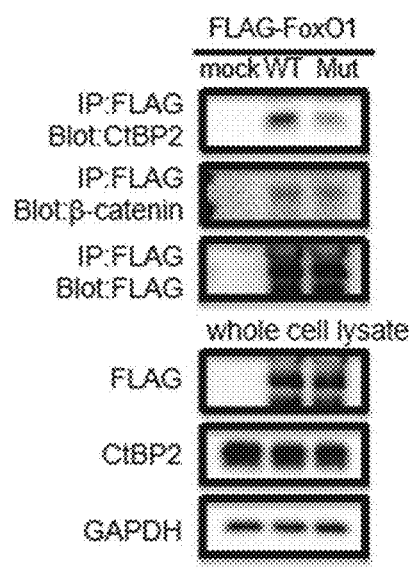
Figure 34G:
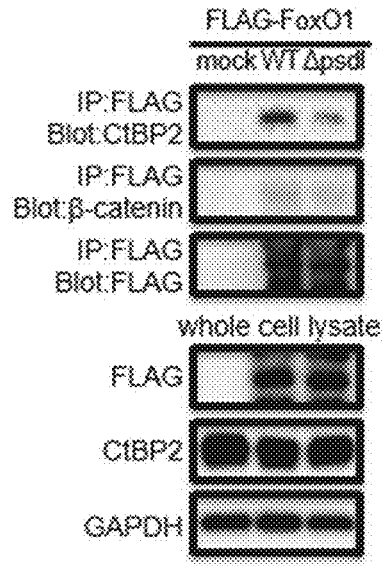
Figure 34H:
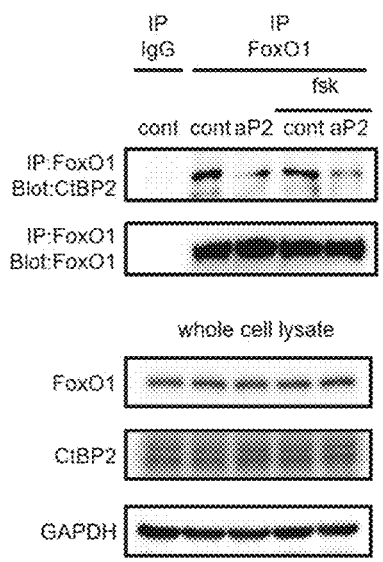

CtBPs bind PxDLx motifs in DNA-binding proteins. See, Chinnadurai, G. Transcriptional regulation by C-terminal binding proteins. *The international journal of biochemistry & cell biology* 39, 1593-1607 (2007) and Turner, J. & Crossley, M. The CtBP family: enigmatic and enzymatic transcriptional co-repressors. *BioEssays: news and reviews in molecular, cellular and developmental biology* 23, 683-690 (2001). Sequence analysis revealed PxDLx motifs in multiple mouse and human FoxO proteins (FIG. 34C), suggesting the potential for direct interaction between FoxOs and CtBPs. Co-immunoprecipitation experiments revealed an endogenous FoxO1/CtBP complex in primary hepatocytes (FIGS. 34D and 34E). Mutation or deletion of the PSDL motif in FoxO1 specifically reduced the interaction between FoxO1 and CtBP2, but did not diminish interaction between FoxO1 and CtBP1 or another binding partner, β-catenin (FIGS. 34F, 34G, 41A and 41B), indicating that CtBP2 directly binds to FoxO1 through its PxDLx motif whereas CtBP1 may bind to FoxO1 indirectly or through other interaction site(s). Remarkably, upon stimulation of primary hepatocytes with aP2, FoxO1 dissociated from CtBP2 (see FIGS. 34H, and 41C).

Figure 34I:
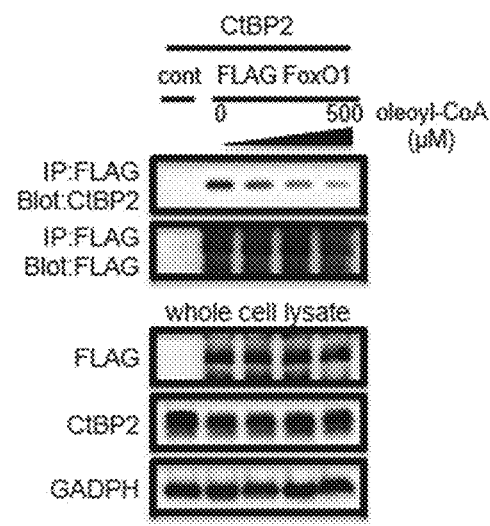
Figure 34J:
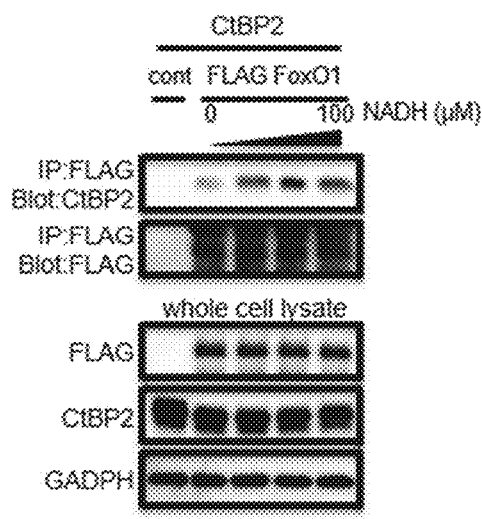
Figure 34K:
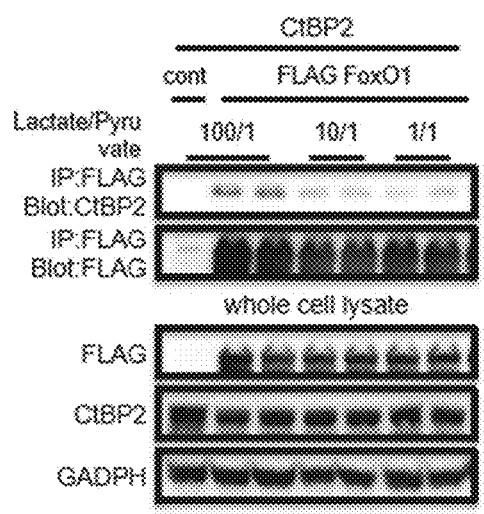
Figure 34L:
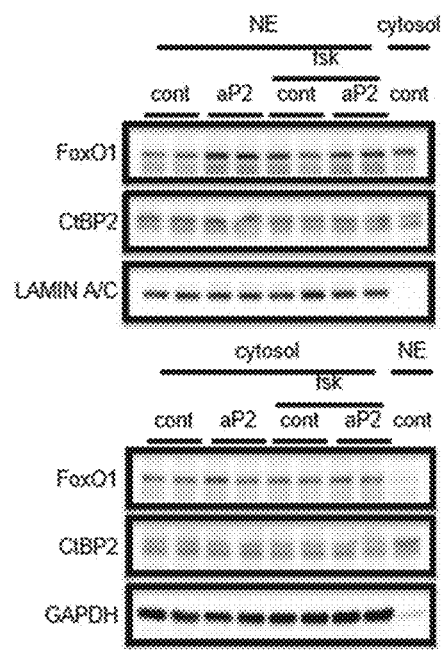

While the effect of NAD$^+$/NADH on transcriptional repression by CtBPs has been thoroughly investigated, [Zhang, Q., Piston, D. W. & Goodman, R. H. Regulation of corepressor function by nuclear NADH. *Science* (New York, N.Y.) 295, 1895-1897 (2002); Kumar, V., et al. Transcription corepressor CtBP is an NAD(+)-regulated dehydrogenase. *Molecular cell* 10, 857-869 (2002); Fjeld, C. C., Birdsong, W. T. & Goodman, R. H. Differential binding of NAD+ and NADH allows the transcriptional corepressor carboxyl-terminal binding protein to serve as a metabolic sensor. *Proceedings of the National Academy of Sciences of the United States of America* 100, 9202-9207 (2003); and Thio, S. S., Bonventre, J. V. & Hsu, S. I. The CtBP2 co-repressor is regulated by NADH-dependent dimerization and possesses a novel N-terminal repression domain. *Nucleic Acids Research* 32, 1836-1847 (2004)), the effect of fatty acyl-CoA on the transcriptional repressor activity of CtBPs has not been studied. See, Valente, C., Spano, S., Luini, A. & Corda, D. Purification and functional properties of the membrane fissioning protein CtBP3/BARS. *Methods In Enzymology* 404, 296-316 (2005). To elucidate this, increasing concentrations of oleoyl-CoA were added into cell lysates and it was found that this treatment resulted in dissociation of the FoxO1/CtBP2 complexes in a dose-dependent manner (FIG. 34I). In contrast, we also observed increased FoxO1/CtBP2 complex formation in the presence of exogenous NADH (see FIG. 34J). CtBPs have been reported to be a redox sensor that senses NAD$^+$/NADH ratio (Zhang, Q., Piston, D. W. & Goodman, R. H. Regulation of corepressor function by nuclear NADH. *Science* (New York, N.Y.) 295, 1895-1897 (2002); Chinnadurai, G. Transcriptional regulation by C-terminal binding proteins. *The International Journal Of Biochemistry & Cell Biology* 39, 1593-1607 (2007)), thus whether FoxO1/CtBP2 complex can respond to the cytosolic redox state or NAD$^+$/NADH ratio was examined. HEK293 cells transfected with FLAG-FoxO1 and CtBP2 were treated with different ratios of extracellular lactate/pyruvate to change the cytosolic redox state. Formation of the FoxO1/CtBP2 complex was enhanced in cells with a high extracellular lactate/pyruvate ratio (low cytosolic NAD$^+$/NADH ratio) (see FIG. 34K). These data suggest that the FoxO1/CtBP2 complex is regulated not only by fatty acyl-CoA but also by NAD$^+$/NADH. Therefore we next asked whether aP2 treatment directly alters the cytosolic NAD$^+$/NADH ratio. Since the cytosolic NAD$^+$/NADH ratio is reflected in the cellular pyruvate/lactate ratio assuming equilibrium of lactate dehydrogenase, we measured cellular lactate/pyruvate ratio in the same experimental setting as in FIGS. 33E and 33F. The lactate/pyruvate ratio tended to be increased by aP2 in the presence or absence of palmitate but the difference was not significant (see FIG. 41D). The inhibition of fatty acid oxidation was reported to increase lactate production. See, Pike, L. S., Smift, A. L., Croteau, N. J., Ferrick, D. A. & Wu, M. Inhibition of fatty acid oxidation by etomoxir impairs NADPH production and increases reactive oxygen species resulting in ATP depletion and cell death in human glioblastoma cells. *Biochimica Et Biophysica Acta* 1807, 726-734 (2011). Therefore, this trend toward an increase of lactate/pyruvate ratio could be secondary to the inhibition of fatty acid oxidation. Here we investigated direct action of aP2 in relatively acute experimental settings. Thus, aP2 regulates FoxO1/CtBP2 complex formation mainly by modulating cellular fatty acyl-CoA content although aP2 might influence NADH/NAD$^+$ ratio secondarily in a long term process. FoxO activity is regulated in part by nuclear cytoplasmic shuttling through posttranslational modifications such as phosphorylation and acetylation. See, Eijkelenboom, A. & Burgering, B. M. FOXOs: signalling integrators for homeostasis maintenance. *Nature Reviews. Molecular Cell Biology* 14, 83-97 (2013). It was found that aP2 treatment tended to increase the nuclear content of FoxO1 in hepatocytes, although the change of cytosolic content was negligible (see FIGS. 34L and 41E). In addition, nuclear cytoplasmic shuttling of CtBP2 by these stimuli were not observed. Interestingly, aP2 and forskolin treatment did not obviously alter the levels of FoxO1 phosphorylation and acetylation (see FIG. 41F), modifications, which are known to regulate nuclear-cytoplasmic shuttling of the protein.

Figure 34M:
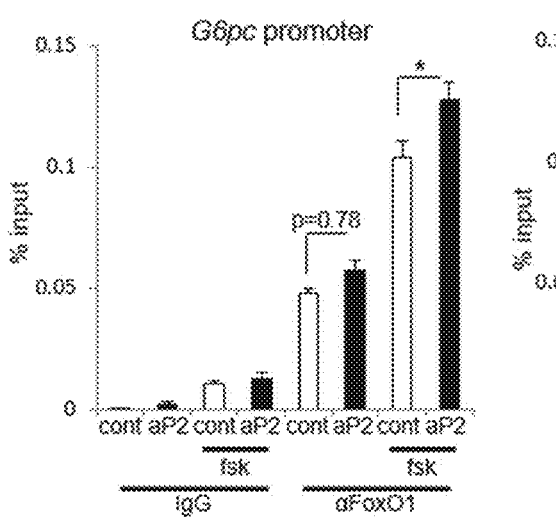
Figure 34N:
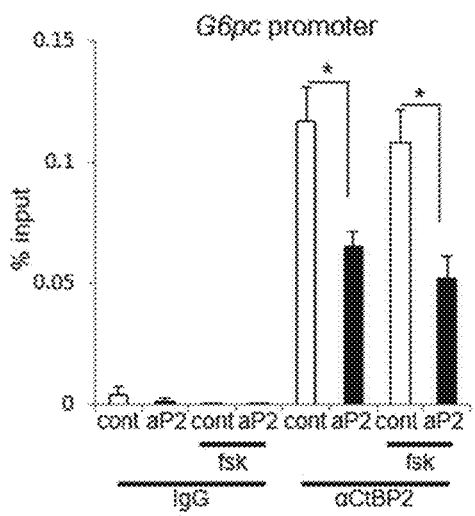

The promoter occupancy of CtBP2 as well as FoxO1 by chromatin immunoprecipitation (ChIP) assay were further investigated. Exposure to aP2 caused dissociation of CtBP2 from the G6pc promoter in the absence or presence of forskolin (FIGS. 34M and 34N). FoxO1 was recruited to G6pc promoter by aP2 treatment although the effect was marginal (FIGS. 34M and 34N).

CtBP2 Tightly Regulates Gluconeogenic Gene Expression

Figure 35A:
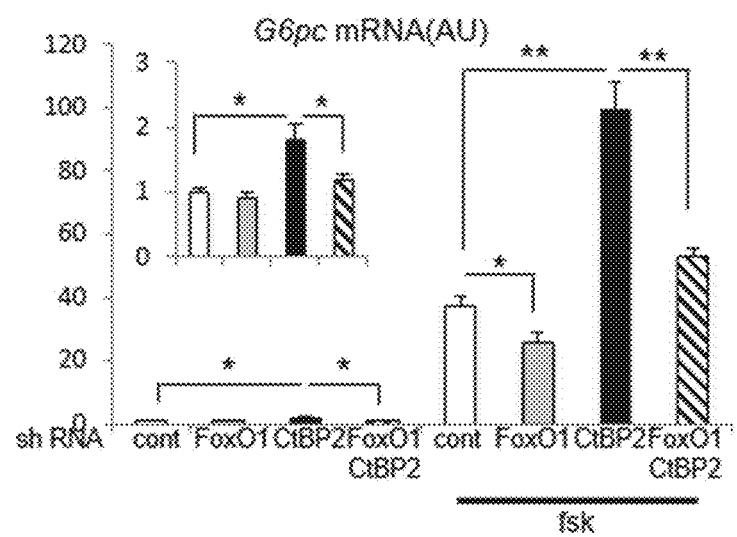
FIG. 35C shows GUS and CtBP2 overexpression in primary hepatocytes.
FIGS. 35D and 35E show the regulation of gluconeogenic gene expression by CtBP2 overexpression (n=4).
FIG. 35F shows FHRE luciferase activity following CtBP2 overexpression (n=8).
FIG. 35G shows the effect of acute activation of insulin and cAMP signaling on the FoxO1/CtBP2 complex. HEK293 cells transfected with FLAG-FoxO1 and CtBP2 were stimulated with either vehicle, 100 nM insulin (ins) or 50 μM of forskolin (fsk) for 30 min.
Figures 35B, 35C:
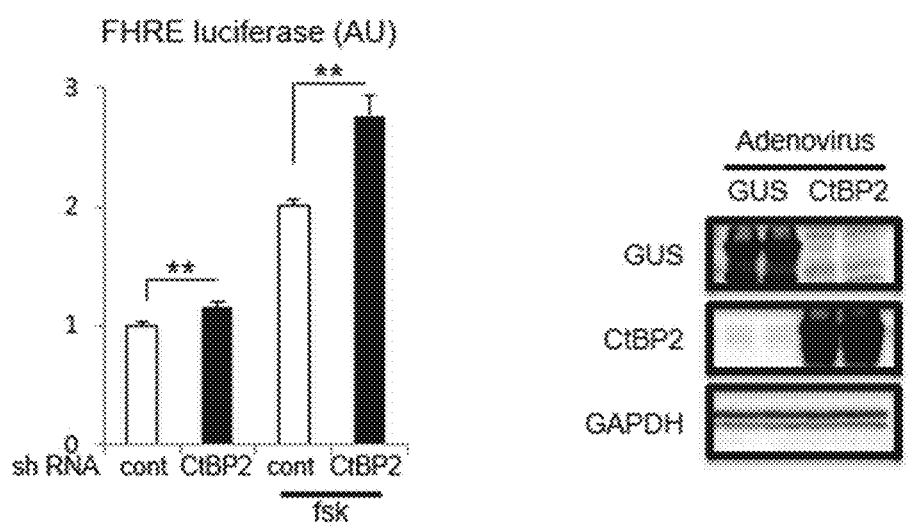
Figure 35D:
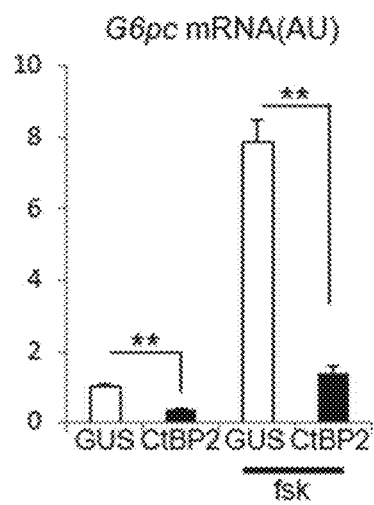
Figure 35E:
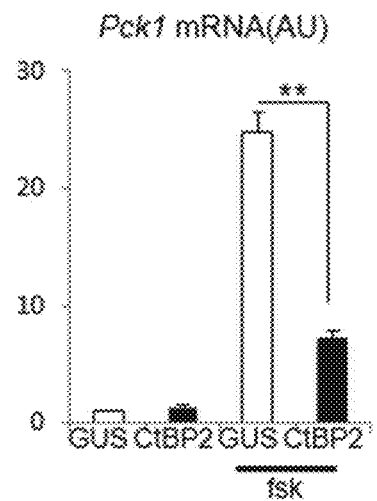
Figure 35F:
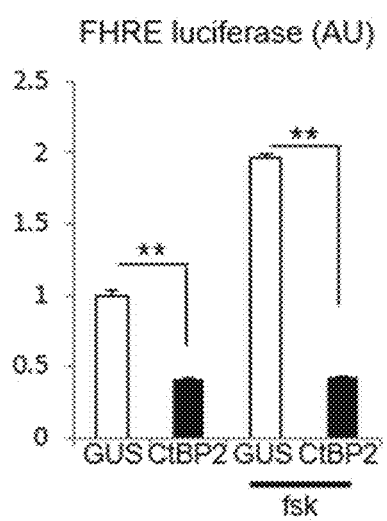
Figure 36I:
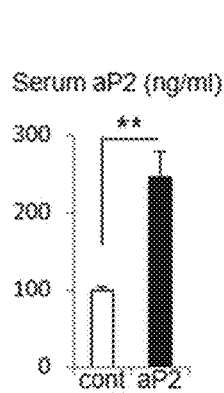
Figure 36J:
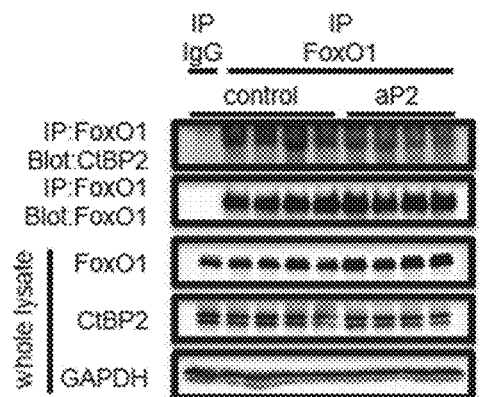
Figure 36K:
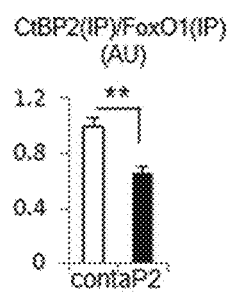

The characteristics of this newly identified transcriptional system were further investigated. CtBPs are known to be repressors, but they function as activators in some cases. See, Fang, M., et al. C-terminal-binding protein directly activates and represses Wnt transcriptional targets in *Drosophila*. *The EMBO journal* 25, 2735-2745 (2006). Therefore, the effects of CtBP2 on FoxO1-mediated gluconeogenic gene expression were verified. CtBP2 knockdown upregulated expression of G6pc (FIG. 35A) and Pck1 (data not shown) in primary hepatocytes, and this effect was enhanced in the presence of forskolin, which was also the case with aP2-mediated upregulation of these genes. Furthermore, the upregulation of these genes by CtBP2 knockdown was diminished by simultaneous knockdown of FoxO1 (FIG. 35A). CtBP2 knockdown also activated the FoxO-responsive luciferase reporter (FIG. 35B). Conversely, CtBP2 overexpression downregulated G6pc expression at baseline and forskolin-induced upregulation of G6pc and Pck1 were robustly suppressed by CtBP2 overexpression compared to β-glucuronidase (GUS) overexpression (see FIGS. 35C, 35D and 35E). To rule out the possibility of general transcriptional repression occurring upon overexpression of CtBP2, the expression of multiple hepatocyte genes was assessed. Some genes regulating cellular metabolism were upregulated (e.g. Acadm) others were unchanged (e.g. Alb, Creb1) (see FIGS. 36A-36N) and data not shown), suggesting a specific effect of CtBP2. Downregulation of FoxO1 target genes following CtBP2 overexpression was also verified by FoxO responsive luciferase reporter activity (FIG. 35F).

Figure 35G:
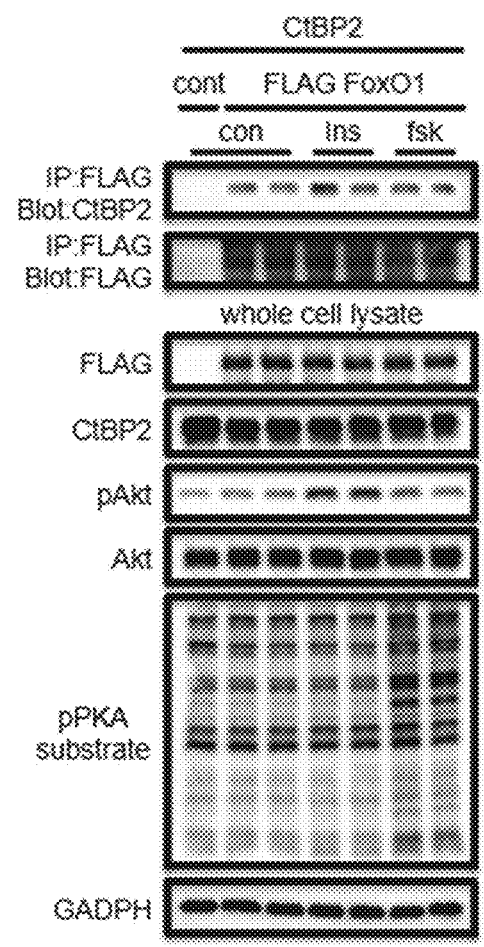

Whether insulin and cAMP signaling regulate the FoxO1/CtBP2 transcriptional complex, since these pathways have been previously shown to regulate FoxO1 transcriptional activity, was also investigated. See, Brunet, A., et al. Akt promotes cell survival by phosphorylating and inhibiting a Forkhead transcription factor. Cell 96, 857-868 (1999); Nakae, J., et al. Regulation of insulin action and pancreatic beta-cell function by mutated alleles of the gene encoding forkhead transcription factor Foxo1. Nature Genetics 32, 245-253 (2002); and Mihaylova, M. M., et al. Class IIa histone deacetylases are hormone-activated regulators of FOXO and mammalian glucose homeostasis. Cell 145, 607-621 (2011). As shown herein, acute activation of these pathways did not robustly alter the formation of the FoxO1/CtBP2 complex although a mild increase of FoxO1/CtBP2 complex by insulin treatment was observed (FIG. 35G), which may be caused by an increased NADH/NAD$^+$ ratio through enhanced glycolytic flux.

Circulating aP2 Activity Dissociates the FoxO1/CtBP2 Holocomplex In Vivo

To further explore the relevance of aP2 modulation of the FoxO1/CtBP2 complex, the transcriptional complex formation was analyzed in vivo. Since decreased NAD$^+$ and increased fatty acyl-CoA content in the liver of obese mice have been reported (Samuel, V. T., et al. Mechanism of hepatic insulin resistance in non-alcoholic fatty liver disease. The Journal of Biological Chemistry 279, 32345-32353 (2004); Hammond, L. E., et al. Mitochondrial glycerol-3-phosphate acyltransferase-1 is essential in liver for the metabolism of excess acyl-CoAs. The Journal of Biological Chemistry 280, 25629-25636 (2005); Cheng, Z., et al. Foxo1 integrates insulin signaling with mitochondrial function in the liver. Nature Medicine 15, 1307-1311 (2009); and Eckel-Mahan, K. L., et al. Reprogramming of the circadian clock by nutritional challenge. Cell 155, 1464-1478 (2013)) dysfunctional corepressor activity of CtBPs could underlie the unregulated hepatic gluconeogenesis in obesity. In the liver of both genetically-induced and diet-induced obese mice, which have elevated levels of circulating aP2 (Cao, H., et al. Adipocyte lipid chaperone aP2 is a secreted adipokine regulating hepatic glucose production. Cell Metabolism 17, 768-778 (2013)), FoxO1/CtBP2 association was dramatically reduced compared to lean controls (see FIGS. 36A, 36B, 36C and 36D). In addition, both genetic deficiency of aP2 and antibody-mediated neutralization of aP2 (using anti-aP2 monoclonal CA33) robustly enhanced formation of the FoxO1/CtBP2 complex (FIGS. 36E, 36F, 36G and 36H), consistent with the reduction in hepatic glucose production in these animals. See, Maeda, K., et al. Adipocyte/macrophage fatty acid binding proteins control integrated metabolic responses in obesity and diabetes. Cell Metabolism 1, 107-119 (2005); Cao, H., et al. Adipocyte lipid chaperone aP2 is a secreted adipokine regulating hepatic glucose production. Cell Metabolism 17, 768-778 (2013).

Figure 36L:
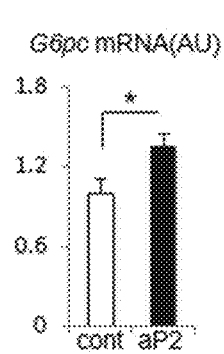
Figure 36M:
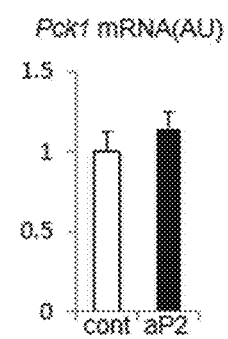
Figure 36N:
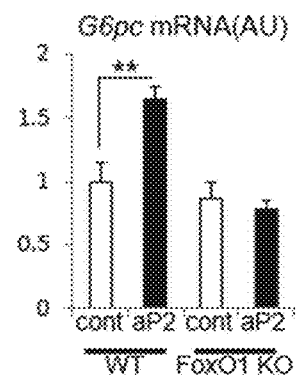
FIG. 36N shows the results from adenovirus-mediated knockdown of CtBP2 in the liver of wild-type lean mice 5 days after transduction (n=6). * and ** denote $p<0.05$ and $p<0.01$, respectively, determined by Student's t-test.

To determine whether elevated circulating aP2 was sufficient to disrupt the FoxO1/CtBP2 complex, recombinant aP2 by IP injection into wild-type lean mice for 5 days was administered, which resulted in a mild increase of serum aP2 levels (FIG. 36I), similar to the level observed in obese mice [Cao, H., et al. Adipocyte lipid chaperone aP2 is a secreted adipokine regulating hepatic glucose production. Cell Metabolism 17, 768-778 (2013)]. This short term increase in circulating aP2 resulted in significant reduction in FoxO1/CtBP2 interaction in the liver (FIGS. 36J and 36K), which led to a selective increase in G6pc expression (FIG. 36L). Importantly, this acute treatment did not affect body weight or serum metabolic parameters such as insulin, glucagon, free fatty acids or glycerol (FIGS. 43A, 43B, 43C, 43D, 43E, 43F and 43G).

Figure 37E:
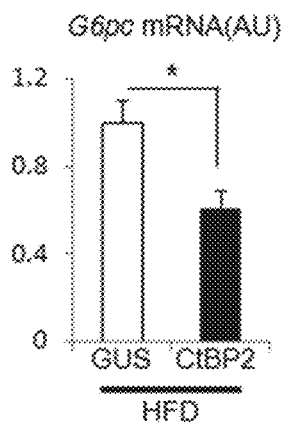
FIGS. 37E, 37F and 37G: Gene expression in liver (n=4-5) for G6pc, Pck1, or Alb mRNA, respectively.
Figure 37F:
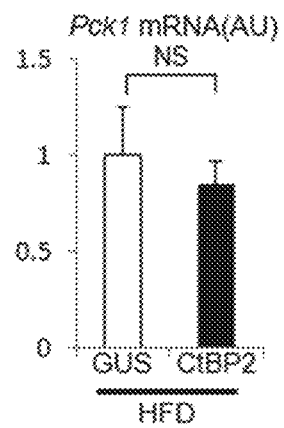
Figure 37G:
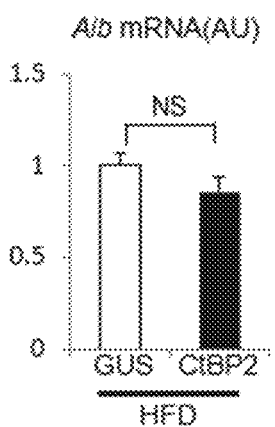
Figure 37H:
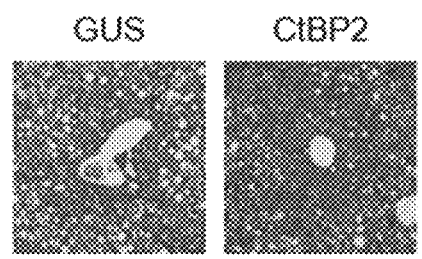
FIG. 37H illustrates representative hematoxylin and eosin stained sections of liver.
Figure 37I:
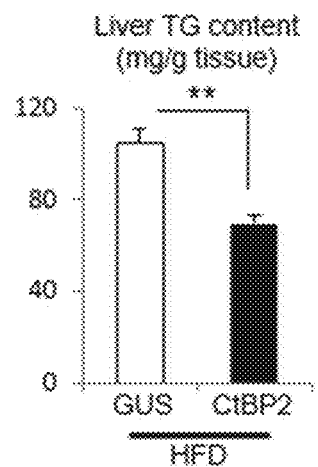
FIG. 37I shows tabulated liver triglyceride content (n=10).
Figure 37J:
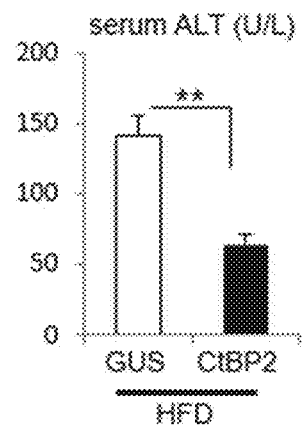
FIG. 37J shows tabulated serum ALT levels (n=10).
Figure 37K:
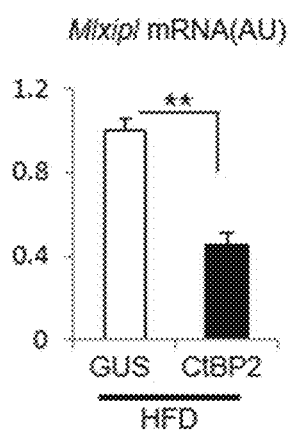
Figure 37L:
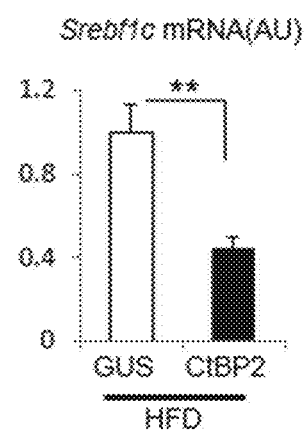
Figure 37Q:
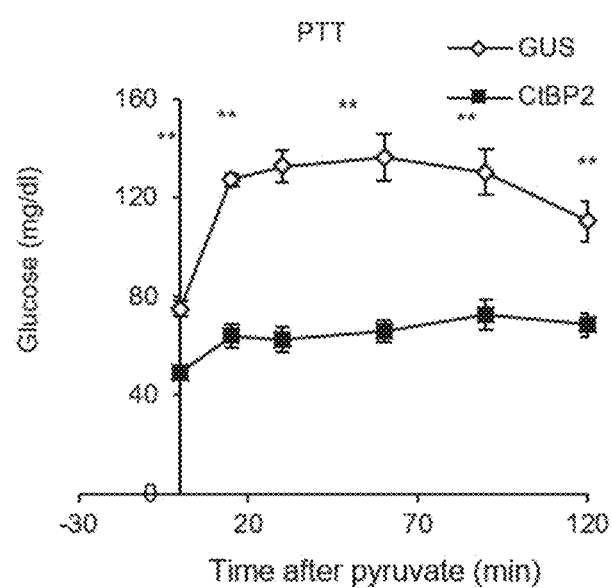
Figure 45A:
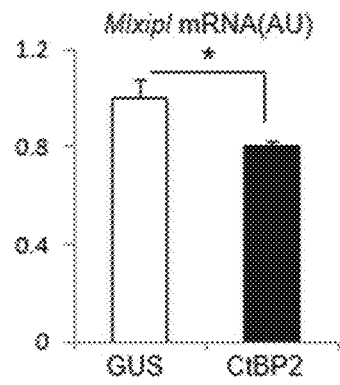
Figure 45B:
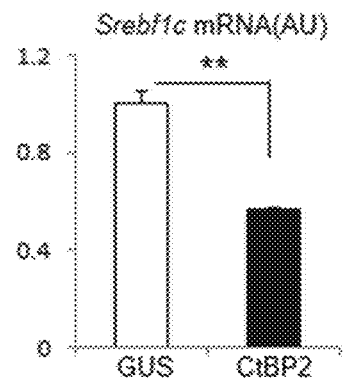
Figure 45C:
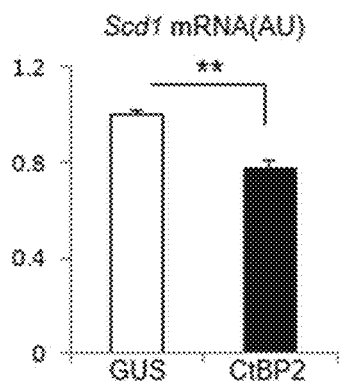
Figure 45D:
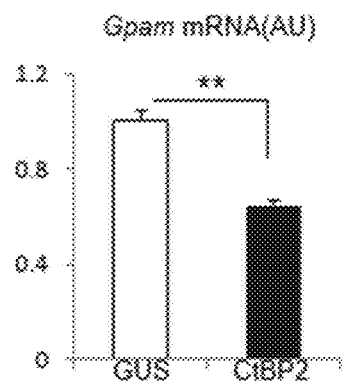
Figure 45E:
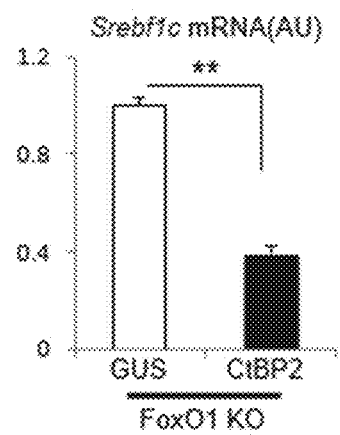
Figure 45F:
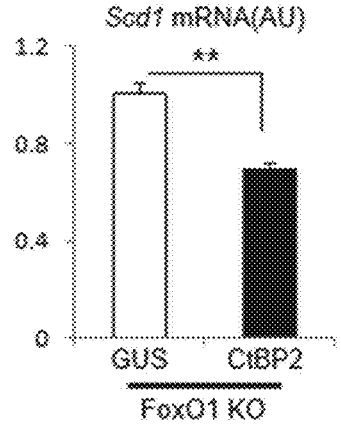

Since CtBP2 overexpression in hepatocytes robustly downregulated gluconeogenic gene expression (FIGS. 35D and 35E), the therapeutic potential of this signaling pathway was investigated in vivo by overexpressing CtBP2 in the liver of diet-induced obese mice by adenovirus-mediated gene delivery. Three days after adenovirus transduction, CtBP2 overexpression normalized fasting blood glucose levels in obese mice without inducing weight loss (FIGS. 37A, 37B, and 45A). In an independent cohort, 3 days of adenoviral CtBP2 overexpression in obese mice resulted in marked improvement in glucose tolerance (FIG. 37C). This improvement was not due to changes in insulin sensitivity, as determined by insulin tolerance test after 5 days of adenoviral transduction (FIGS. 37D, 45E and 45F). To more directly assess hepatic glucose production in this model, a pyruvate tolerance test was performed, and it was observed that CtBP2 overexpression resulted in a significantly blunted glucose excursion following pyruvate injection (FIG. 37Q). Consistent with this finding, G6pc expression in liver was robustly downregulated in CtBP2 overexpressing animals whereas Alb gene expression was not affected (FIGS. 37E, 37F and 37G).

Furthermore, a reduction of hepatic lipid accumulation in obese mice following 7 days of CtBP2 overexpression (FIG. 37H) was observed. Dramatic improvement of liver steatosis is another feature of genetic deletion and antibody-mediated neutralization of aP2. See, Maeda, K., et al. Adipocyte/macrophage fatty acid binding proteins control integrated metabolic responses in obesity and diabetes. Cell Metabolism 1, 107-119 (2005); Cao, H., et al. Regulation of metabolic responses by adipocyte/macrophage Fatty Acid-binding proteins in leptin-deficient mice. Diabetes 55, 1915-1922 (2006). The reduction of steatosis by CtBP2 overexpression was also verified by the measurement of liver triglycerides (FIG. 37I) and this was accompanied by a reduction of serum alanine aminotransferase (ALT) levels (FIG. 37J). Consistent with these findings, lipogenic gene expression was robustly downregulated by CtBP2 overexpression (FIGS. 37K, 37L, 37M, 37N and 37O). This expression profile was also observed in primary hepatocyte in a cell autonomous manner (FIGS. 45A, 45B, 45C and 45D). CtBP2 overexpression decreases the expression levels of these genes in FoxO1 knockout hepatocytes (FIGS. 45E and 45F), which suggests that CtBP2 regulates lipogenic gene expression in a FoxO1 independent manner. A role for CtBP2 in repressing hepatic steatosis was also shown by CtBP2 loss of function. Fourteen days after transduction of Ad/shCtBP2, CtBP2 knockdown resulted in an accumulation of triglyceride in the liver in lean mice on a normal chow diet (FIGS. 45G and 45H), which was accompanied by increased expression of lipogenic genes (FIGS. 45I and 45J).

In summary, the molecular mechanisms underlying the action of the circulating aP2 protein were investigated, and a novel transcriptional holocomplex composed of FoxO1 and CtBP2 was identified which senses cellular nutrients such as fatty acyl-CoA and $NAD^+/NADH$. By modulating fatty acid metabolism, aP2 mediates dissociation of the FoxO1/CtBP2 complex, liberating FoxO1 to drive gluconeogenic gene expression (FIG. 37P).

Furthermore, the adipokine aP2 is elevated under fasting conditions, where it acts to increase hepatic glucose production through modulation of FOXO1 activity. In the pancreatic beta cell, FOXO1 is a key regulator of beta cell function, acting as a counter-regulatory transcription factor to PDX1 (pancreatic and duodenal homeobox 1). Under stress conditions, such as prolonged fasting, FOXO1 translocates to the nucleus where it displaces PDX1 binding and activates the expression of stress-response genes including those for antioxidant and unfolded protein response (UPR) proteins. Addition of recombinant aP2 to primary mouse and human islets promoted the translocation of FOXO1 (FIG. 46A), suggesting that aP2 may act to modulate beta cell function through a FOXO1-dependent pathway. Further evidence of this is shown with increased expression of FOXO1 target genes and subsequent proteins after 24 hr treatment in INS1 cells (FIG. 46B and FIG. 46C).

In the absence of aP2, FOXO1 translocation is reduced, thus allowing for increased activity of PDX1. Enhanced PDX1 activity would correspond to increased insulin expression, enhanced glucose sensing due to up-regulation of glucose transporter and glucokinase, and reduced susceptibility to apoptosis. Thus, depletion of aP2 through genetic deletion or antibody treatment, may act to prevent T1D through a FOXO1-dependent mechanism.

Example 7: aP2 Deficiency Results in Improved Airway Function in aP2 Knockout Mice Upon Inhalation of a Bronchoconstrictor Agent (Methacholine)

Wild type and aP2 genetically deficient mice raised on regular diet until 11-13 weeks of age were sensitized with 100 micrograms of ovalbumin (OVA) injected intraperitoneally (IP) on experiment day 0 and 14. The animals were then nebulized with 1% OVA in PBS on days 28, 30, 32 and 33. Experimental measurements were collected on day 34. Airway resistance was measured during challenge using a bronchial constrictor, methacholine, at increasing concentrations. The mice were nebulized with methacholine for 20 minutes and repetitive measurements were taken for 3 minutes for a total of 12 consecutive measurements using the FlexiVent apparatus (Scireq, Scientific Respiratory Equipment, Canada). Results shown in FIG. 47 illustrate that ap2-deficient mice have improved airway function during methacholine challenge compared to wild type mice under the same conditions.

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

What is claimed is:

1. A humanized anti-adipocyte protein 2 (aP2) monoclonal antibody, or antigen binding agent, comprising:
   (a) a light chain variable region comprising:
      (i) a CDR-L1 complementarity determining region (CDR) comprising the amino acid sequence of Seq. ID No. 7;
      (ii) a CDR-L2 CDR comprising the amino acid sequence of Seq. ID No. 8; and
      (iii) a CDR-L3 CDR comprising an amino acid sequence selected from the group consisting of Seq. ID No. 9, Seq. ID No. 10, Seq. ID No. 11, and Seq. ID No. 12; and
   (b) a heavy chain variable region comprising:
      (i) a CDR-H1 CDR comprising the amino acid sequence of Seq. ID No. 14;
      (ii) a CDR-H2 CDR comprising an amino acid sequence selected from the group consisting of Seq. ID No. 16 and Seq. ID No. 17; and
      (iii) a CDR-H3 CDR comprising an amino acid sequence selected from the group consisting of Seq. ID No. 19 and Seq. ID No. 20.

2. The humanized anti-aP2 monoclonal antibody, or antigen binding agent, of claim 1, wherein the CDR-L3 CDR comprises the amino acid sequence of Seq. ID No. 9.

3. The humanized anti-aP2 monoclonal antibody, or antigen binding agent, of claim 1, wherein the CDR-L3 CDR comprises the amino acid sequence of Seq. ID No. 10.

4. The humanized anti-aP2 monoclonal antibody, or antigen binding agent, of claim 1, wherein the CDR-L3 CDR comprises the amino acid sequence of Seq. ID No. 11.

5. The humanized anti-aP2 monoclonal antibody, or antigen binding agent, of claim 1, wherein the CDR-L3 CDR comprises the amino acid sequence of Seq. ID No. 12.

6. The humanized anti-aP2 monoclonal antibody, or antigen binding agent, of claim 1, wherein the CDR-H2 CDR comprises the amino acid sequence of Seq. ID No. 16.

7. The humanized anti-aP2 monoclonal antibody, or antigen binding agent, of claim 1, wherein the CDR-H2 CDR comprises the amino acid sequence of Seq. ID No. 17.

8. The humanized anti-aP2 monoclonal antibody, or antigen binding agent, of claim 1, wherein the CDR-H3 CDR comprises the amino acid sequence of Seq. ID No. 19.

9. The humanized anti-aP2 monoclonal antibody, or antigen binding agent, of claim 1, wherein the CDR-H3 CDR comprises the amino acid sequence of Seq. ID No. 20.

10. The humanized anti-aP2 monoclonal antibody, or antigen binding agent, of claim 1, wherein the CDR-H1 CDR comprises the amino acid sequence of Seq. ID No. 14, the CDR-H2 CDR comprises the amino acid sequence of Seq. ID No. 16, and the CDR-H3 CDR comprises the amino acid sequence of Seq. ID No. 19.

11. The humanized anti-aP2 monoclonal antibody, or antigen binding agent, of claim 1, wherein the CDR-H1 CDR comprises the amino acid sequence of Seq. ID No. 14, the CDR-H2 CDR comprises the amino acid sequence of Seq. ID No. 17, and the CDR-H3 CDR comprises the amino acid sequence of Seq. ID No. 19.

12. The humanized anti-aP2 monoclonal antibody, or antigen binding agent, of claim 1, wherein the CDR-H1 CDR comprises the amino acid sequence of Seq. ID No. 14, the CDR-H2 CDR comprises the amino acid sequence of Seq. ID No. 16, and the CDR-H3 CDR comprises the amino acid sequence of Seq. ID No. 20.

13. The humanized anti-aP2 monoclonal antibody, or antigen binding agent, of claim 1, wherein the CDR-H1 CDR comprises the amino acid sequence of Seq. ID No. 14, the CDR-H2 CDR comprises the amino acid sequence of Seq. ID No. 17, and the CDR-H3 CDR comprises the amino acid sequence of Seq. ID No. 20.

14. The humanized anti-aP2 monoclonal antibody, or antigen binding agent, of claim 1, wherein the light chain variable region comprises an amino acid sequence selected from the group consisting of Seq. ID No. 446, Seq. ID No. 448, Seq. ID No. 487, Seq. ID No. 488, Seq. ID No. 450, and Seq. ID No. 452.

15. The humanized anti-aP2 monoclonal antibody, or antigen binding agent, of claim 1, wherein the heavy chain variable region comprises the amino acid sequence of Seq. ID No. 455.

16. The humanized anti-aP2 monoclonal antibody, or antigen binding agent, of claim 1, wherein the light chain variable region comprises the amino acid sequence of Seq. ID No. 446 and the heavy chain variable region comprises the amino acid sequence of Seq. ID No. 459.

17. The humanized anti-aP2 monoclonal antibody, or antigen binding agent, of claim 2, wherein the heavy chain variable region comprises the CDR-H2 CDR comprises the amino acid sequence of Seq. ID No. 16 and the CDR-H3 CDR comprises the amino acid sequence of Seq. ID No. 19.

18. The humanized anti-aP2 monoclonal antibody, or antigen binding agent, of claim 2, wherein the heavy chain variable region comprises the CDR-H2 CDR comprises the amino acid sequence of Seq. ID No. 17 and the CDR-H3 CDR comprises the amino acid sequence of Seq. ID No. 20.

19. The humanized anti-aP2 monoclonal antibody, or antigen binding agent, of claim 3, wherein the heavy chain variable region comprises the CDR-H2 CDR comprises the amino acid sequence of Seq. ID No. 16 and the CDR-H3 CDR comprises the amino acid sequence of Seq. ID No. 19.

20. The humanized anti-aP2 monoclonal antibody, or antigen binding agent, of claim 3, wherein the heavy chain variable region comprises the CDR-H2 CDR comprises the amino acid sequence of Seq. ID No. 17 and the CDR-H3 CDR comprises the amino acid sequence of Seq. ID No. 20.

21. The humanized anti-aP2 monoclonal antibody, or antigen binding agent, of claim 4, wherein the heavy chain variable region comprises the CDR-H2 CDR comprises the amino acid sequence of Seq. ID No. 16 and the CDR-H3 CDR comprises the amino acid sequence of Seq. ID No. 19.

22. The humanized anti-aP2 monoclonal antibody, or antigen binding agent, of claim 4, wherein the heavy chain variable region comprises the CDR-H2 CDR comprises the amino acid sequence of Seq. ID No. 17 and the CDR-H3 CDR comprises the amino acid sequence of Seq. ID No. 20.

23. The humanized anti-aP2 monoclonal antibody, or antigen binding agent, of claim 5, wherein the heavy chain variable region comprises the CDR-H2 CDR comprises the amino acid sequence of Seq. ID No. 16 and the CDR-H3 CDR comprises the amino acid sequence of Seq. ID No. 19.

24. The humanized anti-aP2 monoclonal antibody, or antigen binding agent, of claim 5, wherein the heavy chain variable region comprises the CDR-H2 CDR comprises the amino acid sequence of Seq. ID No. 17 and the CDR-H3 CDR comprises the amino acid sequence of Seq. ID No. 20.

25. The humanized anti-aP2 monoclonal antibody, or antigen binding agent, of claim 1, wherein the heavy chain variable region comprises the amino acid sequence of Seq. ID No. 459.

26. The humanized anti-aP2 monoclonal antibody, or antigen binding agent, of claim 1, wherein the heavy chain variable region comprises the amino acid sequence of Seq. ID No. 457.

27. The humanized anti-aP2 monoclonal antibody, or antigen binding agent, of claim 1, wherein the heavy chain variable region comprises the amino acid sequence of Seq. ID No. Seq. ID No. 461.

28. The humanized anti-aP2 monoclonal antibody, or antigen binding agent, of claim 1, wherein the heavy chain variable region comprises the amino acid sequence of Seq. ID No. 463.

29. The humanized anti-aP2 monoclonal antibody, or antigen binding agent, of claim 1, wherein the light chain variable region comprises the amino acid sequence of Seq. ID No. 446.

30. The humanized anti-aP2 monoclonal antibody, or antigen binding agent, of claim 25, wherein the light chain variable region comprises the amino acid sequence of Seq. ID No.446.

31. The humanized anti-aP2 monoclonal antibody, or antigen binding agent, of claim 26, wherein the light chain variable region comprises the amino acid sequence of Seq. ID No.446.

32. The humanized anti-aP2 monoclonal antibody, or antigen binding agent, of claim 27, wherein the light chain variable region comprises the amino acid sequence of Seq. ID No.446.

33. The humanized anti-aP2 monoclonal antibody, or antigen binding agent, of claim 28, wherein the light chain variable region comprises the amino acid sequence of Seq. ID No. 446.

34. The humanized anti-aP2 monoclonal antibody, or antigen binding agent, of claim 1, further comprising a human kappa light chain constant region.

35. The humanized anti-aP2 monoclonal antibody, or antigen binding agent, of claim 34, wherein the light chain variable region and human kappa light chain constant region amino acid sequence is selected from the group consisting of Seq. ID No. 447, Seq. ID No. 449, Seq. ID No. 489, Seq. ID No. 490, Seq. ID No. 451, and Seq. ID No. 453.

36. The humanized anti-aP2 monoclonal antibody, or antigen binding agent, of claim 1, further comprising a human IgG4 heavy chain constant region.

37. The humanized anti-aP2 monoclonal antibody, or antigen binding agent, of claim 36, wherein in the IgG4 heavy chain constant region comprises a proline substitution at amino acid 241.

38. The humanized anti-aP2 monoclonal antibody, or antigen binding agent, of claim 37, wherein the heavy chain variable region and human IgG4 heavy chain constant region amino acid sequence is selected from the group consisting of Seq. ID No. 456, Seq. ID No. 458, Seq. ID No. 460, Seq. ID No. 462, and Seq. ID No. 464.

39. The humanized anti-aP2 monoclonal antibody, or antigen binding agent, of claim 15, wherein the light chain variable region comprises Seq. ID No. 446.

40. The humanized anti-aP2 monoclonal antibody, or antigen binding agent, of claim 15, wherein the light chain variable region comprises Seq. ID No. 448.

41. The humanized anti-aP2 monoclonal antibody, or antigen binding agent, of claim 15, wherein the light chain variable region comprises Seq. ID No. 450.

42. The humanized anti-aP2 monoclonal antibody, or antigen binding agent, of claim 15, wherein the light chain variable region comprises Seq. ID No. 452.

43. The humanized anti-aP2 monoclonal antibody, or antigen binding agent, of claim 15, wherein the light chain variable region comprises Seq. ID No. 487.

44. The humanized anti-aP2 monoclonal antibody, or antigen binding agent, of claim 15, wherein the light chain variable region comprises Seq. ID No. 488.

45. The humanized anti-aP2 monoclonal antibody, or antigen binding agent, of claim 1, wherein the CDR-L1 CDR, CDR-L2 CDR, and CDR-L3 CDR are grafted into a human IGKV1-17 acceptor sequence comprising the amino acid sequence of Seq. ID No. 506.

46. The humanized anti-aP2 monoclonal antibody, or antigen binding agent, of claim 45, wherein the human IGKV1-17 acceptor sequence comprises one or more amino acid substitutions selected from the group consisting of valine at amino acid 2, valine at amino acid 3, lysine at amino acid 63, and aspartic acid at amino acid 70.

47. The humanized anti-aP2 monoclonal antibody, or antigen binding agent, of claim 1, wherein the CDR-H1 CDR, CDR-H2 CDR, and CDR-H3 CDR are grafted into a human IGHV4-4 acceptor sequence comprising the amino acid sequence of Seq. ID No. 481.

48. The humanized anti-aP2 monoclonal antibody, or antigen binding agent, of claim 47, wherein the human IGHV4-4 acceptor sequence comprises one or more amino acid substitutions selected from the group consisting of threonine at amino acid 23, phenylalanine at amino acid 67, lysine at amino acid 71, alanine at amino acid 72, serine at amino acid 73, threonine at amino acid 74, threonine at amino acid 77, valine at amino acid 78, aspartic acid at amino acid 79, threonine at amino acid 89, and phenylalanine at amino acid 91.

* * * * *